US012491217B2

(12) United States Patent
Hsiao et al.

(10) Patent No.: US 12,491,217 B2
(45) Date of Patent: Dec. 9, 2025

(54) COMPOSITIONS AND METHODS FOR PROMOTING HEALTHY NEURAL DEVELOPMENT IN AN UNBORN BABY

(71) Applicant: The Regents of the University of California, Oakland, CA (US)

(72) Inventors: Elaine Y. Hsiao, Los Angeles, CA (US); Helen E. Vuong, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1023 days.

(21) Appl. No.: 17/609,269

(22) PCT Filed: Oct. 31, 2019

(86) PCT No.: PCT/US2019/059157

§ 371 (c)(1),
(2) Date: Nov. 5, 2021

(87) PCT Pub. No.: WO2020/226683

PCT Pub. Date: Nov. 12, 2020

(65) Prior Publication Data

US 2022/0233611 A1 Jul. 28, 2022

Related U.S. Application Data

(60) Provisional application No. 62/844,503, filed on May 7, 2019.

(51) Int. Cl.

| | |
|---|---|
| ***A61P 25/28*** | (2006.01) |
| ***A61K 31/04*** | (2006.01) |
| ***A61K 31/197*** | (2006.01) |
| ***A61K 31/198*** | (2006.01) |
| ***A61K 31/4166*** | (2006.01) |
| ***A61K 35/741*** | (2015.01) |
| ***A61K 35/742*** | (2015.01) |

(52) U.S. Cl.

CPC ............ *A61K 35/742* (2013.01); *A61K 31/04* (2013.01); *A61K 31/197* (2013.01); *A61K 31/198* (2013.01); *A61K 31/4166* (2013.01); *A61K 35/741* (2013.01); *A61P 25/28* (2018.01)

(58) Field of Classification Search

CPC .... A61K 31/04; A61K 31/197; A61K 31/198; A61K 35/741; A61K 35/742; A61P 25/28

See application file for complete search history.

(56) References Cited

U.S. PATENT DOCUMENTS

| | | | |
|---|---|---|---|
| 2014/0065132 A1 | 3/2014 | Hsiao et al. | |
| 2022/0233611 A1 | 7/2022 | Hsiao et al. | |

FOREIGN PATENT DOCUMENTS

| | | | | |
|---|---|---|---|---|
| CA | 3018216 A1 * | 9/2017 | ....... A61K 39/39591 |
| WO | WO-2019/136214 A1 | 7/2019 | |
| WO | WO-2020/186161 A2 | 9/2020 | |
| WO | WO-2020/226683 A1 | 11/2020 | |

OTHER PUBLICATIONS

Of Imase et al. "Efficacy of Clostridium butyricum preparation concomitantly with Helicobacter pylor eradication therapy in relation to changes in the intestinal microbiota", Microbiology and Immunology, 2008, vol. 52, Issue 3, pp. 156-161. (Year: 2008).*

Cho et al. "Trimethylamine-N-Oxide: Friend, Foe or Simply Caught in the Cross-Fire?", Trends in Endocrinology & Metabolism, 2017, vol. 28, Issue 2, pp. 121-130. (Year: 2017).*

Appelman et al. "Sex differences in cardiovascular risk factors and disease prevention", Atherosclerosis, 2015, vol. 241, Issue 1, pp. 211-218. (Year: 2015).*

Taymourtash et al. Fetal development of functional thalamocortical and cortico-cortical connectivity, Cerebral Cortex, 2023, vol. 33 , pp. 5613-5624. (Year: 2023).*

Zhang et al. "Netrin-G1 regulates fear-like and anxiety-like behaviors indissociable neural circuits", Scientific Reports, 2016, vol. 6, Article 28750, 14 pages. (Year: 2016).*

Haikonen et al. "Diet- and microbiota-related metabolite, 5-aminovaleric acid betaine (5-AVAB), in health and disease", Trends in Endocrinology and Metabolism, 2022, vol. 33, Issue 7, pp. 463-480. (Year: 2022).*

Koh et al. "Microbially Produced Imidazole Propionate Impairs Insulin Signaling through mTORC1", Cell, 2018, vol. 175, Issue 4, pp. P947-961.E17. (Year: 2018).*

Alvogen Inc. "Methenamine Hippurate—methenamine hippurate tablet, Alvogen Inc.", revised Nov. 2024; available at https://dailymed.nlm.nih.gov/dailymed/fda/fdaDrugXsl.cfm?setid=bc95972d-3db2-122a-0d1c-d7080c251445 (Year: 2024).*

(Continued)

*Primary Examiner* — Louise W Humphrey
*Assistant Examiner* — Deepa Mishra
(74) *Attorney, Agent, or Firm* — Foley Hoag LLP; David P. Halstead; Allison L. Gilder

(57) ABSTRACT

Disclosed herein are methods for promoting healthy neural development in an unborn baby, which include administering to a maternal subject gestating the unborn baby a composition or a bacterial composition. Compositions can include trimethylamine N-oxide (TMAO), 5-aminovalerate (5-AV), imidazole propionate (IP), hippurate (HIP), or a combination thereof, and the bacterial compositions can include bacteria of the order Clostridiales. Also disclosed are methods for conditioning a female subject for bringing about offspring with healthy neural development. Additionally disclosed are methods for reducing adverse effects of antibiotic treatment on an unborn baby in a pregnant subject. Also disclosed are methods for selecting a female subject for conditioning to foster healthy neural development in offspring.

15 Claims, 47 Drawing Sheets

(56) References Cited

OTHER PUBLICATIONS

Dinicolantonio et al. "Association of moderately elevated trimethylamine N-oxide with cardiovascular risk: is TMAO serving as a marker for hepatic insulin resistance", Open Heart, 2019, vol. 6, Issue 1, article e000890. (Year: 2019).*
Rima et al. "Plasma trimethylamine N-oxide concentration is associated with choline, phospholipids, and methyl metabolism", The American Journal of Clinical Nutrition, 2016, vol. 103, Issue 3, pp. 703-711. (Year: 2016).*
Caudill Marie A. et al: "Maternal choline 1,5-9 supplementation during the third trimester A of pregnancy improves infant information processing speed: a randomized, double-blind, controlled feeding study", The FASEB Journal, vol. 32, No. 4 (2018).
Codagnone Martin G et al: "Programming Bugs: Microbiota and the Developmental Origins of Brain Health and Disease", Biological Psychiatry, vol. 85, No. 2:pp. 150-163 (2018).
Extended European Search Report for EP Application No. 19928129.6 dated Jan. 9, 2023.
Lebovitz Yeonwoo et al: "Emerging Developments in Microbiome and Microglia Research: Implications for Neurodevelopmental Disorders", Frontiers in Immunology, vol. 9: p. 1993 (2018).
Vogt Nicholas M. et al: "The gut microbiota-derived metabolite trimethylamine N-oxide is elevated in Alzheimer's disease", Alzheimer's Research & Therapy, vol. 10, No. 1, (2018).
Vuong Helen E et al: "The maternal microbiome modulates fetal neurodevelopment in mice", Nature vol. 586, No. 7828: pp. 281-286 (2020).
Yang N et al: "The effect of intestinal flora on the neural development of severe hyperbilirubinemia neonates", European Review for Medical and Pharmacological Sciences, vol. 23, No. 3: pp. 1291-1295 (2019).
Coley et al., "The maternal microbiome modifies adverse effects of protein undernutrition on offspring neurobehavioral impairment in mice." bioRxiv (2024).
International Search Report and Written Opinion for International Application No. PCT/US2019/059157 dated Dec. 19, 2019.

* cited by examiner

Fig. 1C
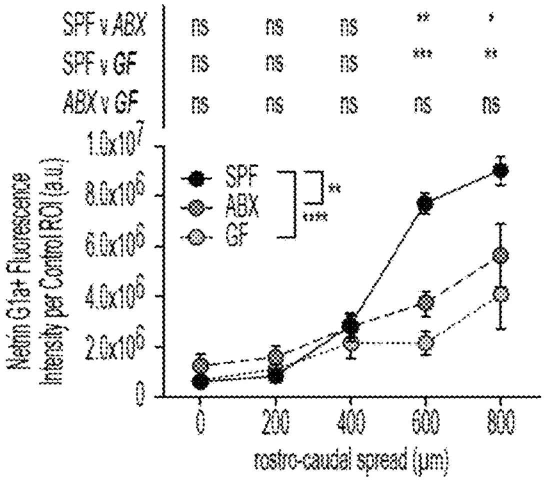
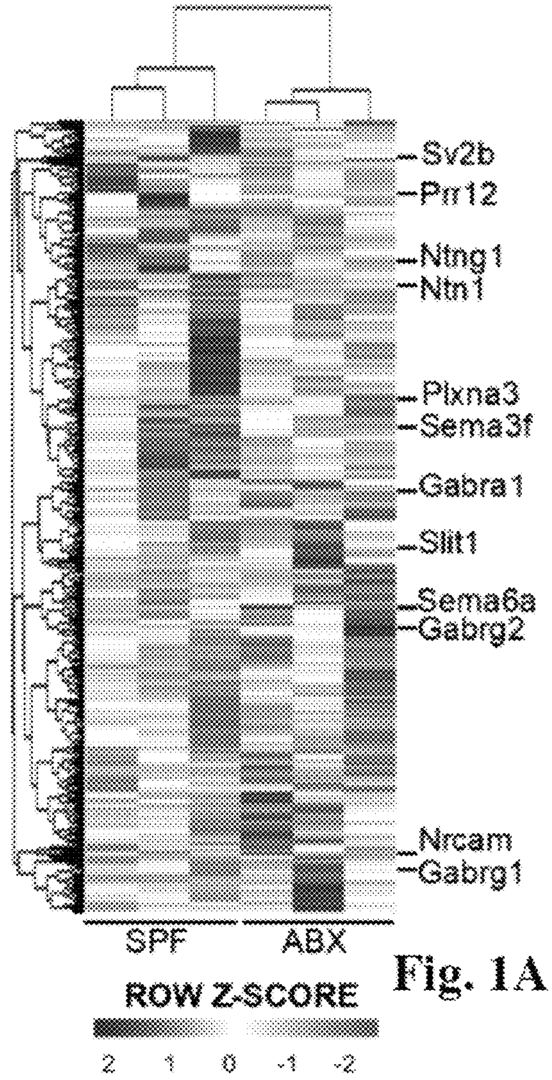
Fig. 1A
Fig. 1D
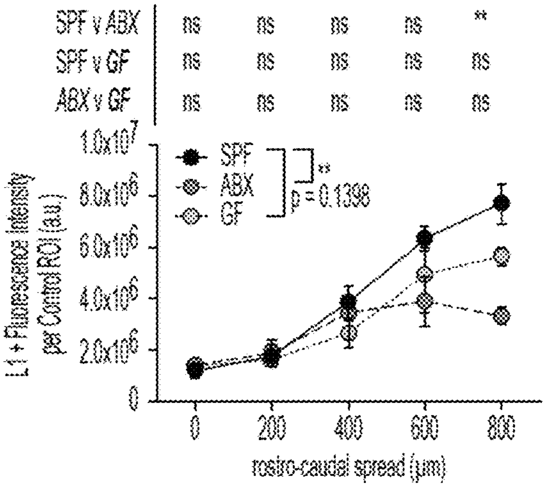
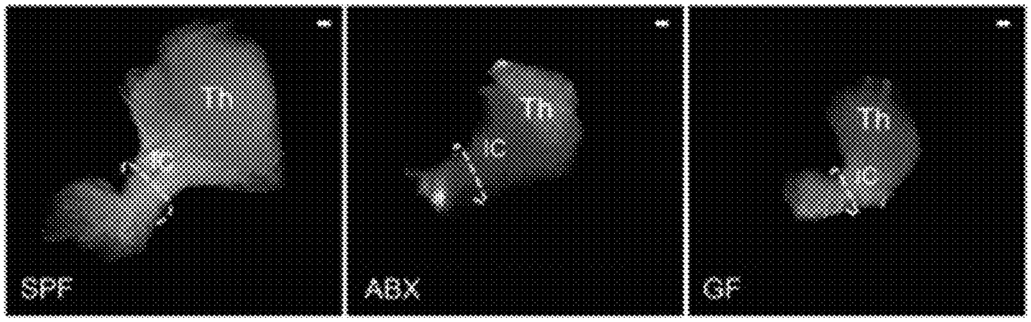
Fig. 1E

Fig. 4C
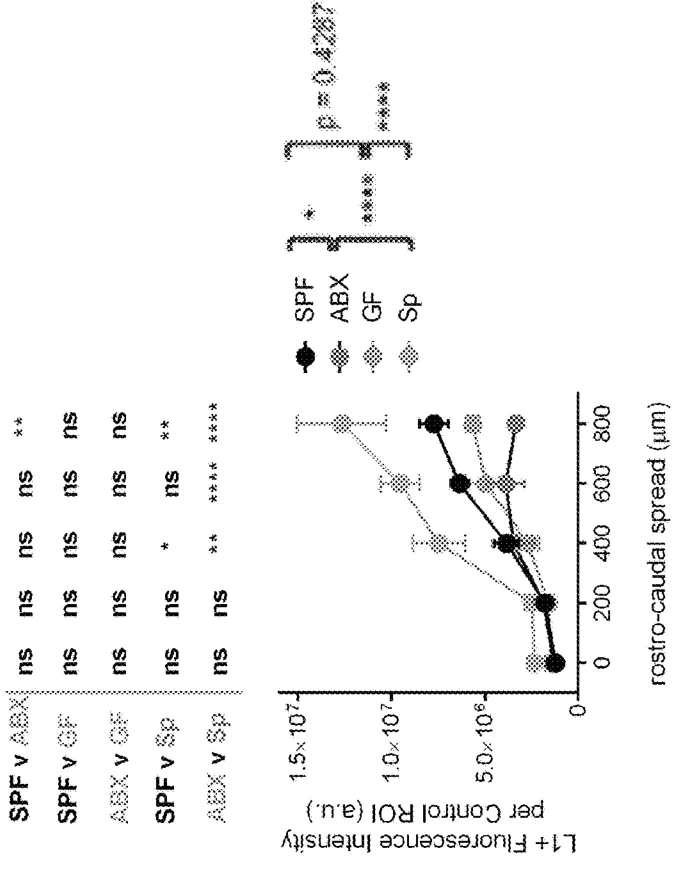
Fig. 4D
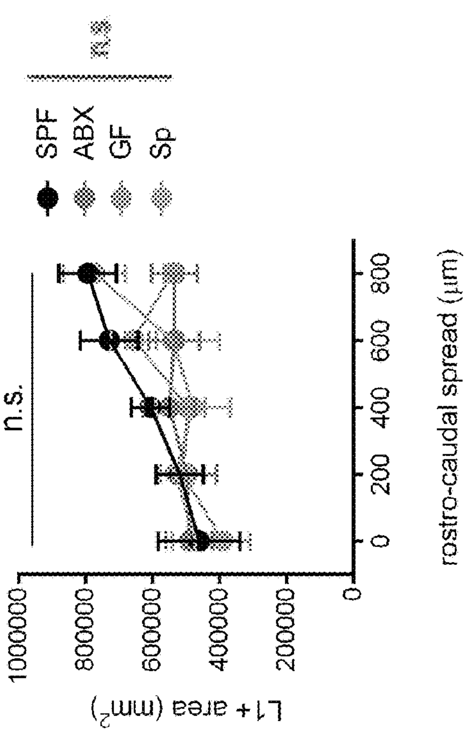
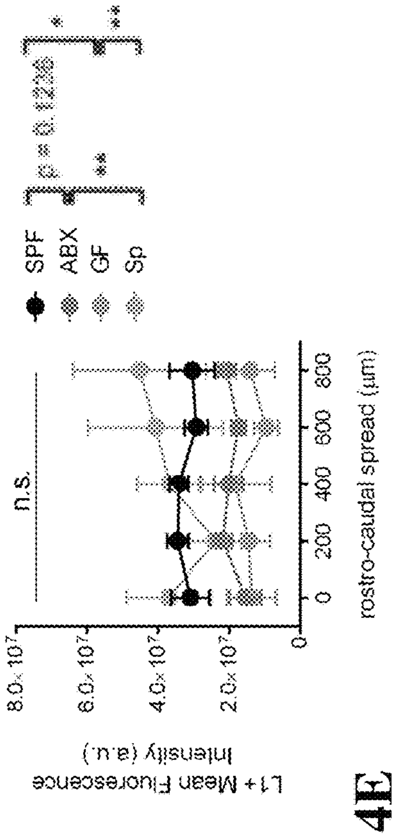
Fig. 4E

Fig. 9C
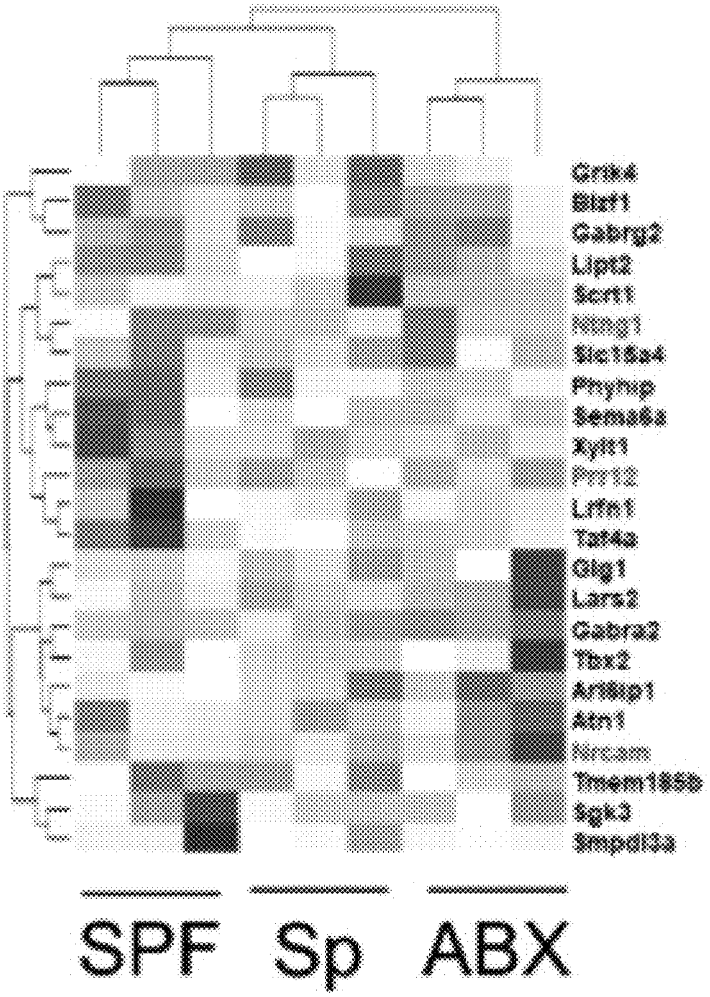
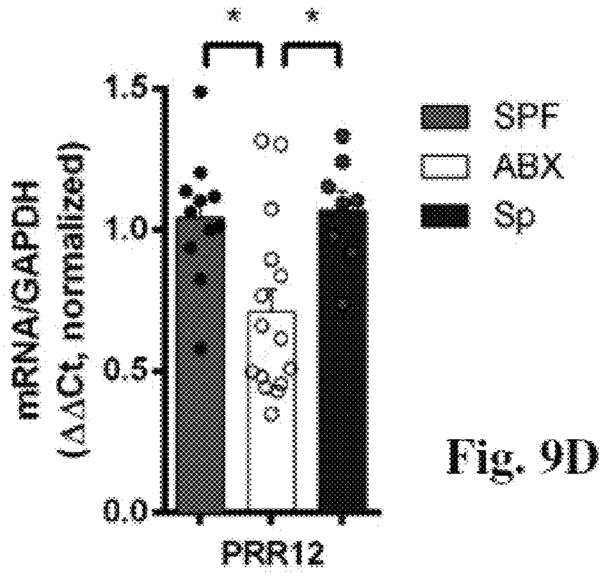
Fig. 9D

Th
Sp
Volume of Netrin G1a+ axons (mm³)
Length of Netrin G1a+ axons (mm)
Distance to Cortex (mm)
Circumference of Axon Bundle (mm)
SPF ABX Sp
n.s.
von Frey Filament Test
paw withdrawal threshold (g)
Adhesive Removal Test
latency to contact (s)
latency to remove (s)
time (s)
contact
removal
p > 0.9999
SPF
ABX
Sp FIG. 12D
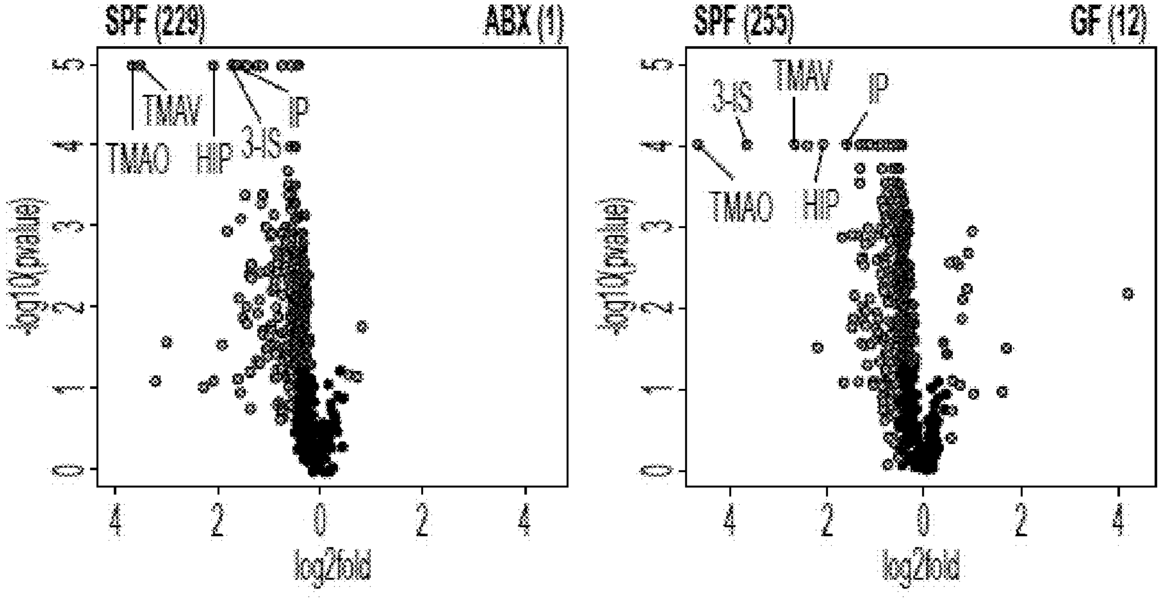
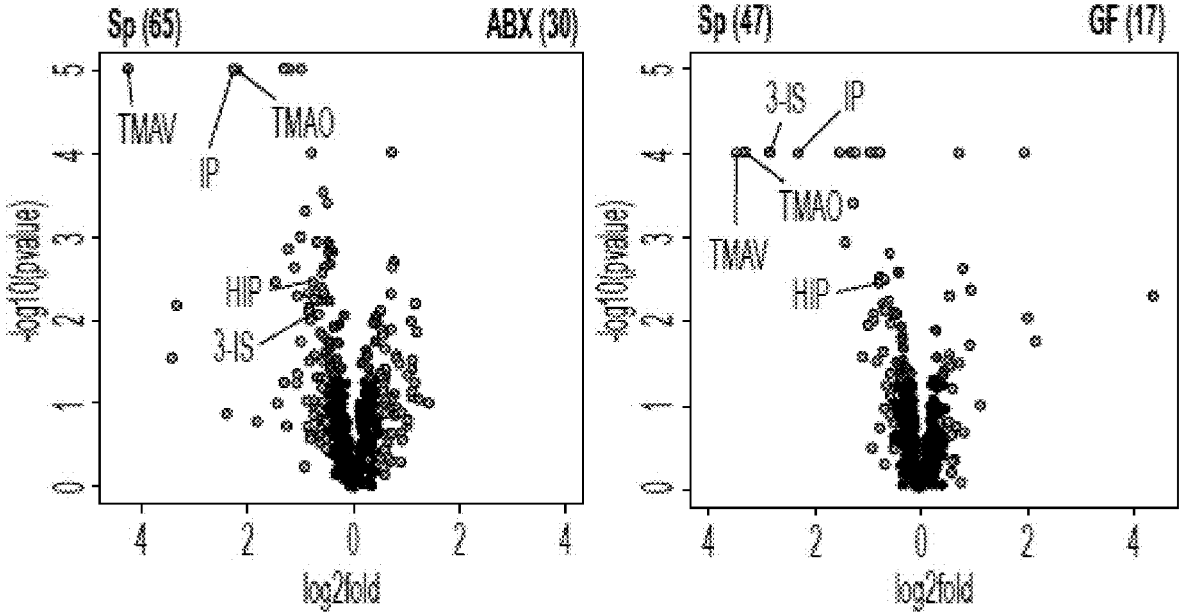
FIG. 12E Fig. 14G
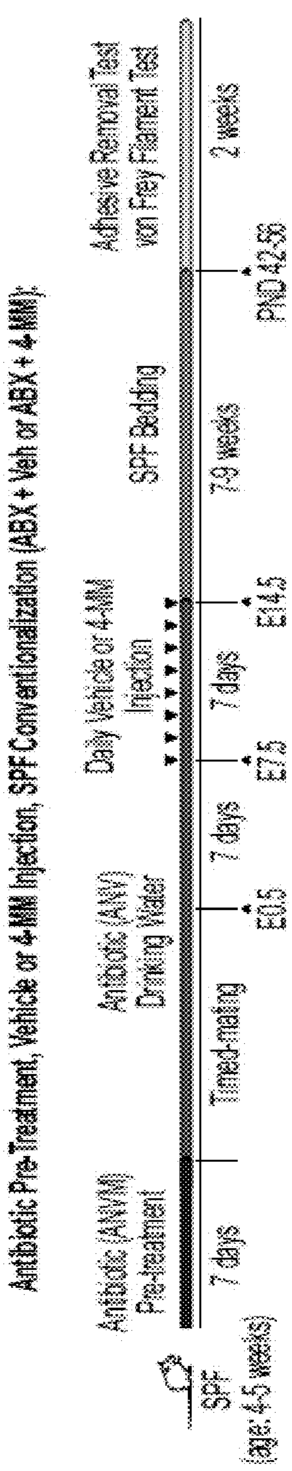
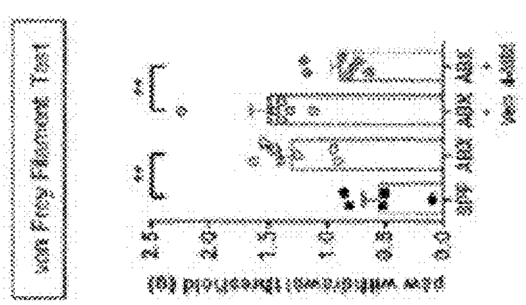
Fig. 14H
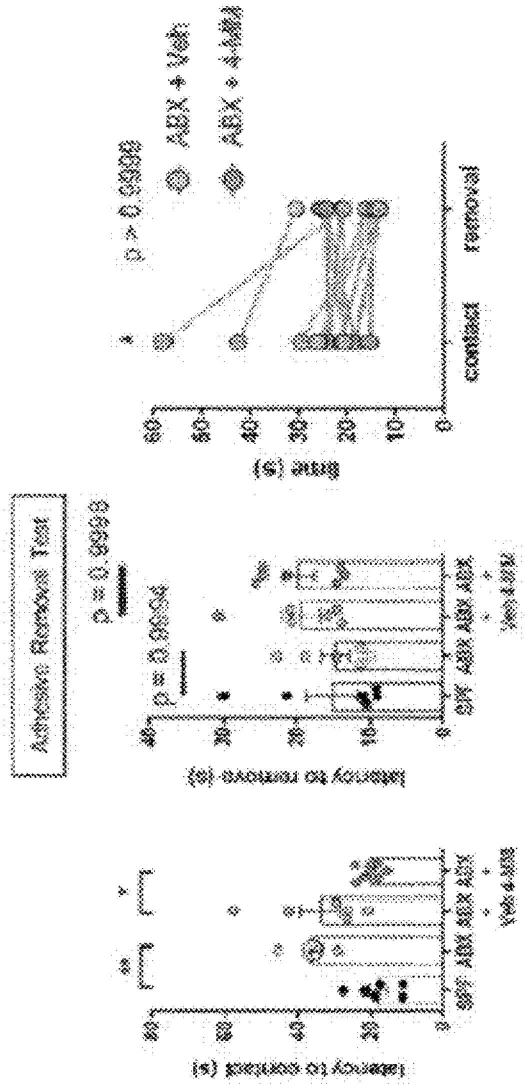
Fig. 14I

COMPOSITIONS AND METHODS FOR PROMOTING HEALTHY NEURAL DEVELOPMENT IN AN UNBORN BABY

RELATED APPLICATION APPLICATIONS

This application is the U.S. National Stage of International Patent Application No. PCT/US2019/059157, filed on Oct. 31, 2019, which claims a right of priority to and the benefit of U.S. Provisional Application No. 62/844,503, filed on May 7, 2019, which is hereby incorporated by reference herein in its entirety.

STATEMENT REGARDING FEDERALLY SPONSORED RESEARCH

This invention was made with government support under Grant Numbers AI007323, GM106996, and DE025172, awarded by the National Institutes of Health. The government has certain rights in the invention.

BACKGROUND

Dysbiosis of the maternal gut microbiome, in response to environmental challenges such as infection, altered diet, and stress during pregnancy has been increasingly associated with abnormalities in offspring brain function and behavior. However, whether the maternal gut microbiome begins to exert its influences during critical periods of embryonic brain development remains poorly understood.

The intestinal microbiota is an important modulator of brain function and behavior, but further research is necessary to resolve whether there are prenatal critical periods during which the microbiome impacts the development of the nervous system. Various model organisms reared devoid of microbial colonization (germ-free, GF) or depleted of the gut microbiome (antibiotic-treated, ABX) exhibit altered neurophysiology and behavior compared to conventionally-colonized (specific pathogen-free, SPF) controls. Only a subset of phenotypes can be corrected by postnatal restoration of the microbiome, suggesting a role for the early life microbiome in regulating developmental processes that impact brain function and behavior during adulthood. Thus, methods of modifying the maternal microbiome, for example to compensate for a depleted maternal microbiome, prenatally (i.e., during gestation) are needed.

SUMMARY

In some aspects, methods of promoting healthy neural development in an unborn baby include administering to a maternal subject gestating the unborn baby a composition that comprises trimethylamine N-oxide (TMAO), 5-aminovalerate (5-AV), imidazole propionate (IP), hippurate (HIP), or a combination thereof.

In certain aspects, methods of reducing adverse effects of antibiotic treatment on an unborn baby in a pregnant subject include administering to the pregnant subject, conjointly with the antibiotic treatment, a composition comprising trimethylamine N-oxide (TMAO), 5-aminovalerate (5-AV), imidazole propionate (IP), hippurate (HIP), or a combination thereof.

In some aspects, methods of conditioning a female subject for fostering healthy neural development in offspring are disclosed. These methods include administering to the female subject a composition comprising trimethylamine N-oxide (TMAO), 5-aminovalerate (5-AV), imidazole propionate (IP), hippurate (HIP), or a combination thereof, e.g., in which the composition is administered at least once during a period that runs from the first day of an expected-but-missed menstruation to a day that is two months after that first day. In some embodiments of these aspects, the composition is administered at least once during a period that runs from the second day of the expected-but-missed menstruation to a day that is 10 to 60 days (e.g., 10, 12, 14, 16, 18, 20, 22, 24, 26, 28, 30, 32, 34, 35, 36, 37, 38, 39, 40, 42, 44, 46, 48, 50, 52, 54, 56, 58, 60) after said second day.

These aspects have many embodiments. For example, in certain embodiments healthy neural development includes healthy tactile sensory development. In some embodiments, the composition includes 5-AV and IP. In certain embodiments, the composition includes TMAO. In certain embodiments, healthy neural development includes healthy thalamocortical axon growth. In some embodiments, healthy neural development includes healthy netrin-G1a+thalamocortical axogenesis. The maternal subject and the unborn baby are preferably mammals, most preferably primates, especially humans.

In particularly preferred embodiments, the maternal subject and the unborn baby are humans. In certain such embodiments, the method includes administering the composition at least once during the first trimester of the gestating maternal subject's gestation period. In some embodiments, the method includes administering the composition at least once during a period that runs from the start of the third week after conception to the end of the eighth week after conception. In certain embodiments, the method includes administering the composition at least once during a period that runs from the $17^{th}$ day post conception (dpc) to the $52^{nd}$ dpc. This period can be varied, for example, it can start from any of the following dpcs: 10, 11, 12, 13, 14, 15, 16, 17, 18, 19, 20, 21, 22, 23, 24, 25, 26, 27, 28, 29, 30 and end at any one of the following dpcs: 40, 41, 42, 43, 44, 45, 46, 47, 48, 49, 50, 51, 52, 53, 54, 55, 56, 57, 58, 59, 60, 70, 80, 90, 100, 150, 200, 250. In some embodiments, the method includes administering the composition at least once during the second trimester of the gestating maternal subject's gestation period. In certain embodiments, the method comprises administering the composition at least once during the third trimester of the gestating maternal subject's gestation period. In some embodiments, the unborn baby is an offspring of the maternal subject.

In some aspects, methods of promoting healthy neural development in an unborn baby include administering to a maternal subject gestating the unborn baby a bacterial composition comprising bacteria of the order Clostridiales. In some such embodiments (e.g., of any aspect involving the use of, as well as other embodiments relating to the use of bacteria of the order Clostridiales herein), the bacteria of the order Clostridiales include bacteria of the family Lachnospiraceae, family Ruminococcaceae, family Clostridiaceae, or a combination thereof. In certain embodiments, the bacteria of the order Clostridiales include bacteria of the genus *Clostridium*, genus Dehalobacterium, genus *Ruminococcus*, genus *Coprococcus*, genus *Dorea*, genus *Oscillospira*, or a combination thereof. In some embodiments, the bacteria of the order Clostridiales are spore-forming bacteria.

In certain embodiments (e.g., of any aspect involving the use of bacteria of the order Clostridiales), the method includes administering the bacterial composition at least once during the first trimester of the gestating maternal subject's gestation period. In some embodiments, the method further includes administering the bacterial composition at least once during the two-month period before said gestation period starts. In certain embodiments, the method further includes administering to the maternal subject a composition comprising trimethylamine N-oxide (TMAO), 5-aminovalerate (5-AV), imidazole propionate (IP), hippurate (HIP), or a combination thereof.

In certain aspects, methods of conditioning a female subject for bringing about offspring with healthy neural development are disclosed. These aspects include administering to the female subject a bacterial composition comprising spore-forming bacteria of the order Clostridiales, in which the bacterial composition is administered at least once during a two-month period that ends with the day of an expected or possible conception for the female subject.

In some aspects, methods of selecting a female subject for conditioning to foster healthy neural development in offspring are disclosed. These aspects include determining that a compound in a serum sample from the female subject, bacteria of the order Clostridiales in a fecal sample from the female subject, or both satisfy an applicable criterion, and selecting the female subject for conditioning to foster healthy neural development in offspring. The compound is 2-(4-hydroxyphenyl)propionate; 3-(3-hydroxyphenyl)propionate sulfate; 3-indoxyl sulfate; 3-phenylpropionate (hydrocinnamate); 7-ketodeoxycholate; alpha-ketoglutaramate; alpha-muricholate; beta-muricholate; biotin; deoxycholate; hippurate; imidazole propionate; indolepropionate; N,N,N-trimethyl-5-aminovalerate; p-cresol sulfate; phenylpropionylglycine; pyrraline; stachydrine; taurodeoxycholate; taurohyodeoxycholic acid; trimethylamine N-oxide; ursodeoxycholate; or a combination thereof. The applicable criterion for the compound (or a combination of compounds) is for the compound to have a level in a serum sample from the female subject that is at most 10%, 20%, 30%, 40%, 50%, 60%, or 70% of its level in a control serum sample representative of a healthy female subject. The applicable criterion for the bacteria of the order Clostridiales is for them to have a total level in a fecal sample from the female subject that is at most 0.5%, 1%, 2%, 3%, 4%, 5%, 6%, 7%, 8%, 9%, 10%, 12%, 14%, 16%, 18%, or 20% of their total level in a control fecal sample representative of a healthy female subject.

In some embodiments of these aspects related to selecting a female subject, the methods further include administering to the female subject a composition that comprises trimethylamine N-oxide (TMAO), 5-aminovalerate (5-AV), imidazole propionate (IP), hippurate (HIP), or a combination thereof; a bacterial composition that comprises spore-forming bacteria of the order Clostridiales; or a combination thereof.

In certain embodiments of these aspects related to selecting a female subject, the compound is 3-indoxyl sulfate; biotin; hippurate; imidazole propionate; N,N,N-trimethyl-5-aminovalerate; pyrraline; stachydrine; trimethylamine N-oxide; or a combination thereof; and the bacteria of the order Clostridiales are bacteria of the genus *Clostridium*, genus Dehalobacterium, genus *Ruminococcus*, genus *Coprococcus*, genus *Dorea*, genus *Oscillospira*, or a combination thereof. In some of these methods, liquid chromatography-mass spectrometry is used to determine a level for the compound. In some embodiments, 16S rDNA sequencing is used to determine a total level for the bacteria.

In certain embodiments disclosed herein, the unborn baby or offspring is a fetus more than eight weeks after conception.

In certain embodiments, the present invention provides methods comprising administering to a maternal subject gestating a fetus a composition comprising: a compound selected from trimethylamine-N-oxide (TMAO), N,N,N-trimethyl-5-aminovaleric acid (TMAV), imidazole propionic acid (IP), 3-indoxyl sulfuric acid (3-IS), hippuric acid (HIP), perfluorooctanesulfonic acid (PFOS), 3-sulfo-L-alanine, alpha-ketoglutaramic acid, 4-hydroxyglutamic acid, extoine, stachydrine, biotin, pyroglutamine, chiro-inositol, N1-methyl-2-pyridone-5-carboxamide, O-sulfo-L-tyrosine, 2'deoxyuridine, pyrraline, N-delta-acetylornithine, phenyl sulfuric acid, phenylacetylglycine, anserine, homostachydrine, serine, N1-methyl-4-pyridone-3-carboxamide, methyl glycopyranoside (alpha+beta), 3-carboxy-1-methylpyridin-1-ium, hypotaurine, 1,5-anhydroglucitol (1,5-AG), 1-oleoyl-2-linoleoyl-GPC (18:1/18:2), methionine, glutamine, malic acid, pantothenic acid, 5,6-dihydrouridine, ceramide (d18:1/17:0 d17:1/18.0) N6-methyllysine, allantoin, N2-acetyllysine, N-acetylglutamine, stearoylcarnitine (C18), arachidoylcarnitine (C20), arabitol, xylitol, 1-methylhistamine, xanthosine, xanthine, 1-ribosyl-imidazoleacetic acid, 5-methyl-2'-deoxycytidine, sphingomyelin (d18:0/20:0, d16:0/22:0), 1-methyl-4-imidazoleacetic acid, inosine 5'-monophosphoric acid (IMP), 1,2-distearoyl-GPC (18:0/18:0), 3-methylcytidine, pipecolate, N-stearoyl-sphingadienine (d18:2/18:0), homoserine, carnosine, 1-palmitoyl-GPI (16:0), 1-stearoyl-GPI (18:0), N6-succinyladenosine, 2'-deoxycytidine, stearoyl-docosahexaenoyl-glycerol (18:0/22:6), trigonelline (N'-methylnicotinate), hydroxyasparagine, gamma-glutamylglutamic acid, 2-palmitoylglycerol (16:0), ceramide (d18:1/17:0, d17:1/18:0), thiamin (Vitamin B1), N6-methyllysine, N6,N6-dimethyllysine, 3-hydroxy-3-methylglutaric acid, campesterol, allantoin, stachydrine, N2-acetyllysine, phenyllactic acid (PLA), gamma-glutamyltryptophan, N-palmitoyl-sphingosine (d18:1/16:0), O-sulfo-L-tyrosine, indolelactic acid, gamma-glutamylglutamine, N-acetylglucosamine 6-phosphoric acid, 1-oleoyl-GPS (18:1), 3-hydroxypalmitoylcarnitine, myo-inositol, behenoyl sphingomyelin (d18:1/22:0), maltotetraose, maltotriose, N-acetylglucosamine/N-acetylgalactosamine, N1-methyladenosine, uracil, 1-oleoyl-GPI (18:1), sphingomyelin (d18:1/17:0, d17:1/18:0, d19:1/16:0), 3-ureidopropionic acid, 5-oxoproline, gamma-glutamyltyrosine, 1-(1-enyl-stearoyl)-GPE (P-18:0), cytidine 2',3'-cyclic monophosphoric acid, 2'-deoxyguanosine 5'-monophosphoric acid (dGMP), thymidine, N6,N6,N6-trimethyllysine, 1-palmitoyl-GPC (16:0), 1-(1-enyl-palmitoyl)-GPE (P-16:0), N-stearoyl-sphinganine (d18:0/18:0), N-arachidoyl-sphingosine (d18:1/20:0), 3'-dephosphocoenzyme A, 5-hydroxylysine, arabonic acid/xylonic acid, 1-palmitoyl-2-docosahexaenoyl-GPC (16:0/22:6), glutamine, 1-(1-enyl-palmitoyl)-2-palmitoyl-GPC (P-16:0/16:0), N-behenoyl-sphingadienine (d18:2/22:0), xylulose 5-phosphoric acid, 1-oleoyl-GPC (18:1), 1-stearoyl-GPE (18:0), glycerol 3-phosphoric acid, N-stearoyl-sphingosine (d18:1/18:0), 7-methylguanine, N2,N2-dimethylguanosine, N-acetylglutamine, methionine, pro-hydroxy-pro, dihydroxyacetone phosphoric acid (DHAP), 1-stearoyl-2-docosahexaenoyl-GPC (18:0/22:6), sphingomyelin (d18:1/20:0, d16:1/22:0), uric acid, adenylosuccinic acid, cystathionine, spermine, mannitol/sorbitol, 2-hydroxyadipic acid, N-palmitoyl-sphinganine (d18:0/16:0), sphingomyelin (d18:0/18:0, d19:0/17:0), sphingomyelin (d18:1/24:1, d18:2/24:0), alpha-hydroxyisovaleric acid, citrulline, ribulonic acid/xylulonic acid, succinylcarnitine (C4-DC), ceramide (d16:1/24:1, d18:1/22:1), hypoxanthine, 5,6-dihydrouridine, gamma-aminobutyric acid (GABA), oleoyl ethanolamide, choline, 1-palmitoyl-GPE (16:0), palmitoyl-linoleoyl-glycerol (16:0/18:2), ceramide (d18:2/24:1, d18:1/24:2), cholesterol, 2'-O-methylcytidine, nicotinamide riboside, pantothenic acid, pyridoxal, N-acetylaspartic acid (NAA), C-glycosyltryptophan, methionine sulfoxide, spermidine, 1-palmitoyl-2-oleoyl-GPG (16:0/18:1), lignoceroyl sphingomyelin (d18:1/24:0), desmosterol, N1-methylinosine, cytidine, N-acetyl-aspartyl-glutamic acid (NAAG), sedoheptulose, galactonic acid, cytidine 5'-monophospho-N-acetylneuraminic acid, glycerophosphoinositol, uridine, salicylic acid, N-acetylglutamic acid, gamma-glutamyl-epsilon-lysine, glycerophosphoserine, 1-stearoyl-2-oleoyl-GPE (18:0/18:1), beta-alanine, 5-methylcytidine, methylphosphoric acid, imidazole lactic acid, sedoheptulose-7-phosphoric acid, 1-palmitoyl-2-stearoyl-GPE (16:0/18:0), guanosine 5'-diphosphoric acid (GDP), 3-ureidoisobutyric acid, tryptophan, isoleucine, methyl succinic acid, S-adenosylmethionine (SAM), taurine, gamma-glutamylthreonine, arabitol/xylitol, erythronic acid, fumaric acid, stearoylcarnitine (C18), deoxycarnitine, cytidine 5'-diphosphocholine, 1-stearoyl-2-arachidonoyl-GPC (18:0/20:4), 1-stearoyl-2-arachidonoyl-GPI (18:0/20:4), glycerophosphoglycerol, N6-carbamoylthreonyladenosine, flavin adenine dinucleotide (FAD), 2-oxoarginine, lactic acid, gulonic acid, phenylalanine, 3-(4-hydroxyphenyl)lactic acid, 2-hydroxyglutaric acid, palmitoleoyl ethanolamide, 1-palmitoyl-2-stearoyl-GPC (16:0/18:0), 1-stearoyl-2-oleoyl-GPC (18:0/18:1), palmitoyl-oleoyl-glycerol (16:0/18:1), betaine, N-acetylneuraminic acid, malic acid, phosphoethanolamine, 1-myristoyl-2-arachidonoyl-GPC (14:0/20:4), beta-citrylglutamic acid, 1-methylhistidine, leucine, ethylmalonic acid, prolylglycine, stearoyl-arachidonoyl-glycerol (18:0/20:4), orotidine, 5-(galactosylhydroxy)-L-lysine, N-acetylglucosaminylasparagine, eicosenoylcarnitine (C20:1), cytidine-5'-diphosphoethanolamine, glycosyl-N-stearoyl-sphingosine (d18:1/18:0), palmitoyl dihydrosphingomyelin (d18:0/16:0), sphingosine, inosine, guanosine 5'-monophosphoric acid (5'-GMP), dimethylglycine, N-acetylalanine, aspartic acid, creatine, ribitol, 2-methylcitric acid/homocitric acid, arachidoylcarnitine (C20), S-methylglutathione, 1-palmitoyl-2-arachidonoyl-GPC (16:0/20:4n6), stearoyl sphingomyelin (d18:1/18:0), nicotinamide, N-formylmethionine, UDP-N-acetylglucosamine/galactosamine, glucoronic acid, 1,2-dipalmitoyl-GPE (16:0/16:0), pseudouridine, alanine, glutamic acid, 1-myristoyl-2-palmitoyl-GPC (14:0/16:0), 1,2-dipalmitoyl-GPC (16:0/16:0), 1-palmitoyl-2-oleoyl-GPC (16:0/18:1), sphingomyelin (d18:1/22:1, d18:2/22:0, d16:1/24:1), glycerophosphoethanolamine, 1-palmitoyl-2-palmitoleoyl-GPC (16:0/16:1), UDP-glucuronic acid, and 1-methylnicotinamide, or a salt thereof, or a combination thereof; and/or one or more bacterial species found in a maternal microbiome.

In certain embodiments, the present invention provides methods comprising administering to a female subject a composition comprising: a compound selected from trimethylamine-N-oxide (TMAO), N,N,N-trimethyl-5-aminovaleric acid (TMAV), imidazole propionic acid (IP), 3-indoxyl sulfuric acid (3-IS), hippuric acid (HIP), perfluorooctanesulfonic acid (PFOS), 3-sulfo-L-alanine, alpha-ketoglutaramic acid, 4-hydroxyglutamic acid, extoine, stachydrine, biotin, pyroglutamine, chiro-inositol, N1-methyl-2-pyridone-5-carboxamide, O-sulfo-L-tyrosine, 2'deoxyuridine, pyrraline, N-delta-acetylornithine, phenyl sulfuric acid, phenylacetylglycine, anserine, homostachydrine, serine, N1-methyl-4-pyridone-3-carboxamide, methyl glycopyranoside (alpha+beta), 3-carboxy-1-methylpyridin-1-ium, hypotaurine, 1,5-anhydroglucitol (1,5-AG), 1-oleoyl-2-linoleoyl-GPC (18:1/18:2), methionine, glutamine, malic acid, pantothenic acid, 5,6-dihydrouridine, ceramide (d18:1/17:0 d17:1/18.0) N6-methyllysine, allantoin, N2-acetyllysine, N-acetylglutamine, stearoylcarnitine (C18), arachidoylcarnitine (C20), arabitol, xylitol, 1-methylhistamine, xanthosine, xanthine, 1-ribosyl-imidazoleacetic acid, 5-methyl-2'-deoxycytidine, sphingomyelin (d18:0/20:0, d16:0/22:0), 1-methyl-4-imidazoleacetic acid, inosine 5'-monophosphoric acid (IMP), 1,2-distearoyl-GPC (18:0/18:0), 3-methylcytidine, pipecolate, N-stearoyl-sphingadienine (d18:2/18:0), homoserine, carnosine, 1-palmitoyl-GPI (16:0), 1-stearoyl-GPI (18:0), N6-succinyladenosine, 2'-deoxycytidine, stearoyl-docosahexaenoyl-glycerol (18:0/22:6), trigonelline (N'-methylnicotinate), hydroxyasparagine, gamma-glutamylglutamic acid, 2-palmitoylglycerol (16:0), ceramide (d18:1/17:0, d17:1/18:0), thiamin (Vitamin B1), N6-methyllysine, N6,N6-dimethyllysine, 3-hydroxy-3-methylglutaric acid, campesterol, allantoin, stachydrine, N2-acetyllysine, phenyllactic acid (PLA), gamma-glutamyltryptophan, N-palmitoyl-sphingosine (d18:1/16:0), O-sulfo-L-tyrosine, indolelactic acid, gamma-glutamylglutamine, N-acetylglucosamine 6-phosphoric acid, 1-oleoyl-GPS (18:1), 3-hydroxypalmitoylcarnitine, myo-inositol, behenoyl sphingomyelin (d18:1/22:0), maltotetraose, maltotriose, N-acetylglucosamine/N-acetylgalactosamine, N1-methyladenosine, uracil, 1-oleoyl-GPI (18:1), sphingomyelin (d18:1/17:0, d17:1/18:0, d19:1/16:0), 3-ureidopropionic acid, 5-oxoproline, gamma-glutamyltyrosine, 1-(1-enyl-stearoyl)-GPE (P-18:0), cytidine 2',3'-cyclic monophosphoric acid, 2'-deoxyguanosine 5'-monophosphoric acid (dGMP), thymidine, N6,N6,N6-trimethyllysine, 1-palmitoyl-GPC (16:0), 1-(1-enyl-palmitoyl)-GPE (P-16:0), N-stearoyl-sphinganine (d18:0/18:0), N-arachidoyl-sphingosine (d18:1/20:0), 3'-dephosphocoenzyme A, 5-hydroxylysine, arabonic acid/xylonic acid, 1-palmitoyl-2-docosahexaenoyl-GPC (16:0/22:6), glutamine, 1-(1-enyl-palmitoyl)-2-palmitoyl-GPC (P-16:0/16:0), N-behenoyl-sphingadienine (d18:2/22:0), xylulose 5-phosphoric acid, 1-oleoyl-GPC (18:1), 1-stearoyl-GPE (18:0), glycerol 3-phosphoric acid, N-stearoyl-sphingosine (d18:1/18:0), 7-methylguanine, N2,N2-dimethylguanosine, N-acetylglutamine, methionine, pro-hydroxy-pro, dihydroxyacetone phosphoric acid (DHAP), 1-stearoyl-2-docosahexaenoyl-GPC (18:0/22:6), sphingomyelin (d18:1/20:0, d16:1/22:0), uric acid, adenylosuccinic acid, cystathionine, spermine, mannitol/sorbitol, 2-hydroxyadipic acid, N-palmitoyl-sphinganine (d18:0/16:0), sphingomyelin (d18:0/18:0, d19:0/17:0), sphingomyelin (d18:1/24:1, d18:2/24:0), alpha-hydroxyisovaleric acid, citrulline, ribulonic acid/xylulonic acid, succinylcarnitine (C4-DC), ceramide (d16:1/24:1, d18:1/22:1), hypoxanthine, 5,6-dihydrouridine, gamma-aminobutyric acid (GABA), oleoyl ethanolamide, choline, 1-palmitoyl-GPE (16:0), palmitoyl-linoleoyl-glycerol (16:0/18:2), ceramide (d18:2/24:1, d18:1/24:2), cholesterol, 2'-O-methylcytidine, nicotinamide riboside, pantothenic acid, pyridoxal, N-acetylaspartic acid (NAA), C-glycosyltryptophan, methionine sulfoxide, spermidine, 1-palmitoyl-2-oleoyl-GPG (16:0/18:1), lignoceroyl sphingomyelin (d18:1/24:0), desmosterol, N1-methylinosine, cytidine, N-acetyl-aspartyl-glutamic acid (NAAG), sedoheptulose, galactonic acid, cytidine 5'-monophospho-N-acetylneuraminic acid, glycerophosphoinositol, uridine, salicylic acid, N-acetylglutamic acid, gamma-glutamyl-epsilon-lysine, glycerophosphoserine, 1-stearoyl-2-oleoyl-GPE (18:0/18:1), beta-alanine, 5-methylcytidine, methylphosphoric acid, imidazole lactic acid, sedoheptulose-7-phosphoric acid, 1-palmitoyl-2-stearoyl-GPE (16:0/18:0), guanosine 5'-diphosphoric acid (GDP), 3-ureidoisobutyric acid, tryptophan, isoleucine, methyl succinic acid, S-adenosylmethionine (SAM), taurine, gamma-glutamylthreonine, arabitol/xylitol, erythronic acid, fumaric acid, stearoylcarnitine (C18), deoxycarnitine, cytidine 5'-diphosphocholine, 1-stearoyl-2-arachidonoyl-GPC (18:0/20:4), 1-stearoyl-2-arachidonoyl-GPI (18:0/20:4), glycerophosphoglycerol, N6-carbamoylthreonyladenosine, flavin adenine dinucleotide (FAD), 2-oxoarginine, lactic acid, gulonic acid, phenylalanine, 3-(4-hydroxyphenyl)lactic acid, 2-hydroxyglutaric acid, palmitoleoyl ethanolamide, 1-palmitoyl-2-stearoyl-GPC (16:0/18:0), 1-stearoyl-2-oleoyl-GPC (18:0/18:1), palmitoyl-oleoyl-glycerol (16:0/18:1), betaine, N-acetylneuraminic acid, malic acid, phosphoethanolamine, 1-myristoyl-2-arachidonoyl-GPC (14:0/20:4), beta-citrylglutamic acid, 1-methylhistidine, leucine, ethylmalonic acid, prolylglycine, stearoyl-arachidonoyl-glycerol (18:0/20:4), orotidine, 5-(galactosylhydroxy)-L-lysine, N-acetylglucosaminylasparagine, eicosenoylcarnitine (C20:1), cytidine-5'-diphosphoethanolamine, glycosyl-N-stearoyl-sphingosine (d18:1/18:0), palmitoyl dihydrosphingomyelin (d18:0/16:0), sphingosine, inosine, guanosine 5'-monophosphoric acid (5'-GMP), dimethylglycine, N-acetylalanine, aspartic acid, creatine, ribitol, 2-methylcitric acid/homocitric acid, arachidoylcarnitine (C20), S-methylglutathione, 1-palmitoyl-2-arachidonoyl-GPC (16:0/20:4n6), stearoyl sphingomyelin (d18:1/18:0), nicotinamide, N-formylmethionine, UDP-N-acetylglucosamine/galactosamine, glucoronic acid, 1,2-dipalmitoyl-GPE (16:0/16:0), pseudouridine, alanine, glutamic acid, 1-myristoyl-2-palmitoyl-GPC (14:0/16:0), 1,2-dipalmitoyl-GPC (16:0/16:0), 1-palmitoyl-2-oleoyl-GPC (16:0/18:1), sphingomyelin (d18:1/22:1, d18:2/22:0, d16:1/24:1), glycerophosphoethanolamine, 1-palmitoyl-2-palmitoleoyl-GPC (16:0/16:1), UDP-glucuronic acid, and 1-methylnicotinamide, or a salt thereof, or a combination thereof; and/or one or more bacterial species found in a maternal microbiome; wherein the female subject is a fertile, ovulating female subject or a female subject seeking to implant an embryo.

Also disclosed herein are methods of inhibiting development of a disease or disorder in a fetus.

In certain embodiments, the present invention provides methods comprising administering to a maternal subject gestating the fetus, a composition comprising: a compound selected from trimethylamine-N-oxide (TMAO), N,N,N-trimethyl-5-aminovaleric acid (TMAV), imidazole propionic acid (IP), 3-indoxyl sulfuric acid (3-IS), hippuric acid (HIP), perfluorooctanesulfonic acid (PFOS), 3-sulfo-L-alanine, alpha-ketoglutaramic acid, 4-hydroxyglutamic acid, extoine, stachydrine, biotin, pyroglutamine, chiro-inositol, N1-methyl-2-pyridone-5-carboxamide, O-sulfo-L-tyrosine, 2'deoxyuridine, pyrraline, N-delta-acetylornithine, phenyl sulfuric acid, phenylacetylglycine, anserine, homostachydrine, serine, N1-methyl-4-pyridone-3-carboxamide, methyl glycopyranoside (alpha+beta), 3-carboxy-1-methylpyridin-1-ium, hypotaurine, 1,5-anhydroglucitol (1,5-AG), 1-oleoyl-2-linoleoyl-GPC (18:1/18:2), methionine, glutamine, malic acid, pantothenic acid, 5,6-dihydrouridine, ceramide (d18:1/17:0 d17:1/18.0) N6-methyllysine, allantoin, N2-acetyllysine, N-acetylglutamine, stearoylcarnitine (C18), arachidoylcarnitine (C20), arabitol, xylitol, 1-methylhistamine, xanthosine, xanthine, 1-ribosyl-imidazoleacetic acid, 5-methyl-2'-deoxycytidine, sphingomyelin (d18:0/20:0, d16:0/22:0), 1-methyl-4-imidazoleacetic acid, inosine 5'-monophosphoric acid (IMP), 1,2-distearoyl-GPC (18:0/18:0), 3-methylcytidine, pipecolate, N-stearoyl-sphingadienine (d18:2/18:0), homoserine, carnosine, 1-palmitoyl-GPI (16:0), 1-stearoyl-GPI (18:0), N6-succinyladenosine, 2'-deoxycytidine, stearoyl-docosahexaenoyl-glycerol (18:0/22:6), trigonelline (N'-methylnicotinate), hydroxyasparagine, gamma-glutamylglutamic acid, 2-palmitoylglycerol (16:0), ceramide (d18:1/17:0, d17:1/18:0), thiamin (Vitamin B1), N6-methyllysine, N6,N6-dimethyllysine, 3-hydroxy-3-methylglutaric acid, campesterol, allantoin, stachydrine, N2-acetyllysine, phenyllactic acid (PLA), gamma-glutamyltryptophan, N-palmitoyl-sphingosine (d18:1/16:0), O-sulfo-L-tyrosine, indolelactic acid, gamma-glutamylglutamine, N-acetylglucosamine 6-phosphoric acid, 1-oleoyl-GPS (18:1), 3-hydroxypalmitoylcarnitine, myo-inositol, behenoyl sphingomyelin (d18:1/22:0), maltotetraose, maltotriose, N-acetylglucosamine/N-acetylgalactosamine, N1-methyladenosine, uracil, 1-oleoyl-GPI (18:1), sphingomyelin (d18:1/17:0, d17:1/18:0, d19:1/16:0), 3-ureidopropionic acid, 5-oxoproline, gamma-glutamyltyrosine, 1-(1-enyl-stearoyl)-GPE (P-18:0), cytidine 2',3'-cyclic monophosphoric acid, 2'-deoxyguanosine 5'-monophosphoric acid (dGMP), thymidine, N6,N6,N6-trimethyllysine, 1-palmitoyl-GPC (16:0), 1-(1-enyl-palmitoyl)-GPE (P-16:0), N-stearoyl-sphinganine (d18:0/18:0), N-arachidoyl-sphingosine (d18:1/20:0), 3'-dephosphocoenzyme A, 5-hydroxylysine, arabonic acid/xylonic acid, 1-palmitoyl-2-docosahexaenoyl-GPC (16:0/22:6), glutamine, 1-(1-enyl-palmitoyl)-2-palmitoyl-GPC (P-16:0/16:0), N-behenoyl-sphingadienine (d18:2/22:0), xylulose 5-phosphoric acid, 1-oleoyl-GPC (18:1), 1-stearoyl-GPE (18:0), glycerol 3-phosphoric acid, N-stearoyl-sphingosine (d18:1/18:0), 7-methylguanine, N2,N2-dimethylguanosine, N-acetylglutamine, methionine, pro-hydroxy-pro, dihydroxyacetone phosphoric acid (DHAP), 1-stearoyl-2-docosahexaenoyl-GPC (18:0/22:6), sphingomyelin (d18:1/20:0, d16:1/22:0), uric acid, adenylosuccinic acid, cystathionine, spermine, mannitol/sorbitol, 2-hydroxyadipic acid, N-palmitoyl-sphinganine (d18:0/16:0), sphingomyelin (d18:0/18:0, d19:0/17:0), sphingomyelin (d18:1/24:1, d18:2/24:0), alpha-hydroxyisovaleric acid, citrulline, ribulonic acid/xylulonic acid, succinylcarnitine (C4-DC), ceramide (d16:1/24:1, d18:1/22:1), hypoxanthine, 5,6-dihydrouridine, gamma-aminobutyric acid (GABA), oleoyl ethanolamide, choline, 1-palmitoyl-GPE (16:0), palmitoyl-linoleoyl-glycerol (16:0/18:2), ceramide (d18:2/24:1, d18:1/24:2), cholesterol, 2'-O-methylcytidine, nicotinamide riboside, pantothenic acid, pyridoxal, N-acetylaspartic acid (NAA), C-glycosyltryptophan, methionine sulfoxide, spermidine, 1-palmitoyl-2-oleoyl-GPG (16:0/18:1), lignoceroyl sphingomyelin (d18:1/24:0), desmosterol, N1-methylinosine, cytidine, N-acetyl-aspartyl-glutamic acid (NAAG), sedoheptulose, galactonic acid, cytidine 5'-monophospho-N-acetylneuraminic acid, glycerophosphoinositol, uridine, salicylic acid, N-acetylglutamic acid, gamma-glutamyl-epsilon-lysine, glycerophosphoserine, 1-stearoyl-2-oleoyl-GPE (18:0/18:1), beta-alanine, 5-methylcytidine, methylphosphoric acid, imidazole lactic acid, sedoheptulose-7-phosphoric acid, 1-palmitoyl-2-stearoyl-GPE (16:0/18:0), guanosine 5'-diphosphoric acid (GDP), 3-ureidoisobutyric acid, tryptophan, isoleucine, methyl succinic acid, S-adenosylmethionine (SAM), taurine, gamma-glutamylthreonine, arabitol/xylitol, erythronic acid, fumaric acid, stearoylcarnitine (C18), deoxycarnitine, cytidine 5'-diphosphocholine, 1-stearoyl-2-arachidonoyl-GPC (18:0/20:4), 1-stearoyl-2-arachidonoyl-GPI (18:0/20:4), glycerophosphoglycerol, N6-carbamoylthreonyladenosine, flavin adenine dinucleotide (FAD), 2-oxoarginine, lactic acid, gulonic acid, phenylalanine, 3-(4-hydroxyphenyl)lactic acid, 2-hydroxyglutaric acid, palmitoleoyl ethanolamide, 1-palmitoyl-2-stearoyl-GPC (16:0/18:0), 1-stearoyl-2-oleoyl-GPC (18:0/18:1), palmitoyl-oleoyl-glycerol (16:0/18:1), betaine, N-acetylneuraminic acid, malic acid, phosphoethanolamine, 1-myristoyl-2-arachidonoyl-GPC (14:0/20:4), beta-citrylglutamic acid, 1-methylhistidine, leucine, ethylmalonic acid, prolylglycine, stearoyl-arachidonoyl-glycerol (18:0/20:4), orotidine, 5-(galactosylhydroxy)-L-lysine, N-acetylglucosaminylasparagine, eicosenoylcarnitine (C20:1), cytidine-5'-diphosphoethanolamine, glycosyl-N-stearoyl-sphingosine (d18:1/18:0), palmitoyl dihydrosphingomyelin (d18:0/16:0), sphingosine, inosine, guanosine 5'-monophosphoric acid (5'-GMP), dimethylglycine, N-acetylalanine, aspartic acid, creatine, ribitol, 2-methylcitric acid/homocitric acid, arachidoylcarnitine (C20), S-methylglutathione, 1-palmitoyl-2-arachidonoyl-GPC (16:0/20:4n6), stearoyl sphingomyelin (d18:1/18:0), nicotinamide, N-formylmethionine, UDP-N-acetylglucosamine/galactosamine, glucoronic acid, 1,2-dipalmitoyl-GPE (16:0/16:0), pseudouridine, alanine, glutamic acid, 1-myristoyl-2-palmitoyl-GPC (14:0/16:0), 1,2-dipalmitoyl-GPC (16:0/16:0), 1-palmitoyl-2-oleoyl-GPC (16:0/18:1), sphingomyelin (d18:1/22:1, d18:2/22:0, d16:1/24:1), glycerophosphoethanolamine, 1-palmitoyl-2-palmitoleoyl-GPC (16:0/16:1), UDP-glucuronic acid, and 1-methylnicotinamide, or a salt thereof, or a combination thereof; and/or one or more bacterial species found in a maternal microbiome.

In certain embodiments, the present invention provides methods comprising administering to a female subject a composition comprising: a compound selected from trimethylamine-N-oxide (TMAO), N,N,N-trimethyl-5-aminovaleric acid (TMAV), imidazole propionic acid (IP), 3-indoxyl sulfuric acid (3-IS), hippuric acid (HIP), perfluorooctanesulfonic acid (PFOS), 3-sulfo-L-alanine, alpha-ketoglutaramic acid, 4-hydroxyglutamic acid, extoine, stachydrine, biotin, pyroglutamine, chiro-inositol, N1-methyl-2-pyridone-5-carboxamide, O-sulfo-L-tyrosine, 2'deoxyuridine, pyrraline, N-delta-acetylornithine, phenyl sulfuric acid, phenylacetylglycine, anserine, homostachydrine, serine, N1-methyl-4-pyridone-3-carboxamide, methyl glycopyranoside (alpha+beta), 3-carboxy-1-methylpyridin-1-ium, hypotaurine, 1,5-anhydroglucitol (1,5-AG), 1-oleoyl-2-linoleoyl-GPC (18:1/18:2), methionine, glutamine, malic acid, pantothenic acid, 5,6-dihydrouridine, ceramide (d18:1/17:0 d17:1/18.0) N6-methyllysine, allantoin, N2-acetyllysine, N-acetylglutamine, stearoylcarnitine (C18), arachidoylcarnitine (C20), arabitol, xylitol, 1-methylhistamine, xanthosine, xanthine, 1-ribosyl-imidazoleacetic acid, 5-methyl-2'-deoxycytidine, sphingomyelin (d18:0/20:0, d16:0/22:0), 1-methyl-4-imidazoleacetic acid, inosine 5'-monophosphoric acid (IMP), 1,2-distearoyl-GPC (18:0/18:0), 3-methylcytidine, pipecolate, N-stearoyl-sphingadienine (d18:2/18:0), homoserine, carnosine, 1-palmitoyl-GPI (16:0), 1-stearoyl-GPI (18:0), N6-succinyladenosine, 2'-deoxycytidine, stearoyl-docosahexaenoyl-glycerol (18:0/22:6), trigonelline (N'-methylnicotinate), hydroxyasparagine, gamma-glutamylglutamic acid, 2-palmitoylglycerol (16:0), ceramide (d18:1/17:0, d17:1/18:0), thiamin (Vitamin B1), N6-methyllysine, N6,N6-dimethyllysine, 3-hydroxy-3-methylglutaric acid, campesterol, allantoin, stachydrine, N2-acetyllysine, phenyllactic acid (PLA), gamma-glutamyltryptophan, N-palmitoyl-sphingosine (d18:1/16:0), O-sulfo-L-tyrosine, indolelactic acid, gamma-glutamylglutamine, N-acetylglucosamine 6-phosphoric acid, 1-oleoyl-GPS (18:1), 3-hydroxypalmitoylcarnitine, myo-inositol, behenoyl sphingomyelin (d18:1/22:0), maltotetraose, maltotriose, N-acetylglucosamine/N-acetylgalactosamine, N1-methyladenosine, uracil, 1-oleoyl-GPI (18:1), sphingomyelin (d18:1/17:0, d17:1/18:0, d19:1/16:0), 3-ureidopropionic acid, 5-oxoproline, gamma-glutamyltyrosine, 1-(1-enyl-stearoyl)-GPE (P-18:0), cytidine 2',3'-cyclic monophosphoric acid, 2'-deoxyguanosine 5'-monophosphoric acid (dGMP), thymidine, N6,N6,N6-trimethyllysine, 1-palmitoyl-GPC (16:0), 1-(1-enyl-palmitoyl)-GPE (P-16:0), N-stearoyl-sphinganine (d18:0/18:0), N-arachidoyl-sphingosine (d18:1/20:0), 3'-dephosphocoenzyme A, 5-hydroxylysine, arabonic acid/xylonic acid, 1-palmitoyl-2-docosahexaenoyl-GPC (16:0/22:6), glutamine, 1-(1-enyl-palmitoyl)-2-palmitoyl-GPC (P-16:0/16:0), N-behenoyl-sphingadienine (d18:2/22:0), xylulose 5-phosphoric acid, 1-oleoyl-GPC (18:1), 1-stearoyl-GPE (18:0), glycerol 3-phosphoric acid, N-stearoyl-sphingosine (d18:1/18:0), 7-methylguanine, N2,N2-dimethylguanosine, N-acetylglutamine, methionine, pro-hydroxy-pro, dihydroxyacetone phosphoric acid (DHAP), 1-stearoyl-2-docosahexaenoyl-GPC (18:0/22:6), sphingomyelin (d18:1/20:0, d16:1/22:0), uric acid, adenylosuccinic acid, cystathionine, spermine, mannitol/sorbitol, 2-hydroxyadipic acid, N-palmitoyl-sphinganine (d18:0/16:0), sphingomyelin (d18:0/18:0, d19:0/17:0), sphingomyelin (d18:1/24:1, d18:2/24:0), alpha-hydroxyisovaleric acid, citrulline, ribulonic acid/xylulonic acid, succinylcarnitine (C4-DC), ceramide (d16:1/24:1, d18:1/22:1), hypoxanthine, 5,6-dihydrouridine, gamma-aminobutyric acid (GABA), oleoyl ethanolamide, choline, 1-palmitoyl-GPE (16:0), palmitoyl-linoleoyl-glycerol (16:0/18:2), ceramide (d18:2/24:1, d18:1/24:2), cholesterol, 2'-O-methylcytidine, nicotinamide riboside, pantothenic acid, pyridoxal, N-acetylaspartic acid (NAA), C-glycosyltryptophan, methionine sulfoxide, spermidine, 1-palmitoyl-2-oleoyl-GPG (16:0/18:1), lignoceroyl sphingomyelin (d18:1/24:0), desmosterol, N1-methylinosine, cytidine, N-acetyl-aspartyl-glutamic acid (NAAG), sedoheptulose, galactonic acid, cytidine 5'-monophospho-N-acetylneuraminic acid, glycerophosphoinositol, uridine, salicylic acid, N-acetylglutamic acid, gamma-glutamyl-epsilon-lysine, glycerophosphoserine, 1-stearoyl-2-oleoyl-GPE (18:0/18:1), beta-alanine, 5-methylcytidine, methylphosphoric acid, imidazole lactic acid, sedoheptulose-7-phosphoric acid, 1-palmitoyl-2-stearoyl-GPE (16:0/18:0), guanosine 5'-diphosphoric acid (GDP), 3-ureidoisobutyric acid, tryptophan, isoleucine, methyl succinic acid, S-adenosylmethionine (SAM), taurine, gamma-glutamylthreonine, arabitol/xylitol, erythronic acid, fumaric acid, stearoylcarnitine (C18), deoxycarnitine, cytidine 5'-diphosphocholine, 1-stearoyl-2-arachidonoyl-GPC (18:0/20:4), 1-stearoyl-2-arachidonoyl-GPI (18:0/20:4), glycerophosphoglycerol, N6-carbamoylthreonyladenosine, flavin adenine dinucleotide (FAD), 2-oxoarginine, lactic acid, gulonic acid, phenylalanine, 3-(4-hydroxyphenyl)lactic acid, 2-hydroxyglutaric acid, palmitoleoyl ethanolamide, 1-palmitoyl-2-stearoyl-GPC (16:0/18:0), 1-stearoyl-2-oleoyl-GPC (18:0/18:1), palmitoyl-oleoyl-glycerol (16:0/18:1), betaine, N-acetylneuraminic acid, malic acid, phosphoethanolamine, 1-myristoyl-2-arachidonoyl-GPC (14:0/20:4), beta-citrylglutamic acid, 1-methylhistidine, leucine, ethylmalonic acid, prolylglycine, stearoyl-arachidonoyl-glycerol (18:0/20:4), orotidine, 5-(galactosylhydroxy)-L-lysine, N-acetylglucosaminylasparagine, eicosenoylcarnitine (C20:1), cytidine-5'-diphosphoethanolamine, glycosyl-N-stearoyl-sphingosine (d18:1/18:0), palmitoyl dihydrosphingomyelin (d18:0/16:0), sphingosine, inosine, guanosine 5'-monophosphoric acid (5'-GMP), dimethylglycine, N-acetylalanine, aspartic acid, creatine, ribitol, 2-methylcitric acid/homocitric acid, arachidoylcarnitine (C20), S-methylglutathione, 1-palmitoyl-2-arachidonoyl-GPC (16:0/20:4n6), stearoyl sphingomyelin (d18:1/18:0), nicotinamide, N-formylmethionine, UDP-N-acetylglucosamine/galactosamine, glucoronic acid, 1,2-dipalmitoyl-GPE (16:0/16:0), pseudouridine, alanine, glutamic acid, 1-myristoyl-2-palmitoyl-GPC (14:0/16:0), 1,2-dipalmitoyl-GPC (16:0/16:0), 1-palmitoyl-2-oleoyl-GPC (16:0/18:1), sphingomyelin (d18:1/22:1, d18:2/22:0, d16:1/24:1), glycerophosphoethanolamine, 1-palmitoyl-2-palmitoleoyl-GPC (16:0/16:1), UDP-glucuronic acid, and 1-methylnicotinamide, or a salt thereof, or a combination thereof; and/or one or more bacterial species found in a maternal microbiome; wherein the female subject is a fertile, ovulating female subject or a female subject seeking to implant an embryo.

Such pharmaceutical preparations may be for use in treating or preventing a condition or disease as described herein.

BRIEF DESCRIPTION OF THE FIGURES

FIGS. 1A-1M: Depletion of the maternal microbiota during early gestation alters fetal brain gene expression and impairs fetal thalamocortical axonogenesis. 1A, Heatmap of differentially expressed genes in embryonic brains of E14.5 offspring from conventionally colonized (specific pathogen-free, SPF) and antibiotic-treated (ABX) dams (Wald Test, p<0.05, n=offspring from 3 dams). 1B, Representative immunofluorescence images of Netrin-G1a (magenta in the original image) and L1 (cyan in the original image) staining in embryonic brain sections (rostra' to caudal) from E14.5 offspring of SPF, ABX and germ-free (GF) dams. Scale bar=500 μm. 1C, Average Netrin-G1a fluorescence intensity per matched area of region of interest (ROI) ("yellow-in-the-original-image" dotted lines) across 800 μm of rostral to caudal embryonic brain sections of E14.5 offspring from SPF, ABX, and GF dams. (Two-way ANOVA with Tukey's, n=offspring from 5 SPF, 7 ABX, 4 GF dams). 1D, Average L1 fluorescence normalized to control SPF ROI ("yellow-in-the-original-image" dotted lines) area across 800 μm of rostral to caudal embryonic brain sections of E14.5 offspring from SPF, ABX, and GF dams (Two-way ANOVA with Tukey's, n=offspring from 5 SPF, 7 ABX, 4 GF dams). 1E, Representative 3-D rendering of Netrin-G1a staining (purple in the original image) in cleared whole embryonic brains of E14.5 offspring from SPF, ABX, and GF dams. Th=thalamus. Scale bar=100 μm. 1F, Volume of Netrin-G1a axons from cleared whole embryonic brains of E14.5 offspring of SPF, ABX, and GF dams. (Two-way ANOVA with Tukey's (SPF vs ABX); Mann-Whitney test (SPF vs GF), n=offspring from 5 dams per group). 1G, Length of Netrin-G1a axons in cleared whole embryonic brains from E14.5 offspring of SPF, ABX, and GF dams. (Two-way ANOVA with Tukey's, n=offspring from 5 dams per group). 1H, Distance from rostral tip of Netrin-G1a staining to the cortex in cleared whole embryonic brains from E14.5 offspring of SPF, ABX, and GF dams. (Two-way ANOVA with Tukey's (SPF vs ABX); Mann-Whitney test (SPF vs GF), n=offspring from 5 dams per group). 1I, Average circumference of the Netrin-G1 a axonal bundle at the internal capsule (IC) in whole embryonic brains from E14.5 offspring of SPF, ABX, and GF dams. (Two-way ANOVA with Tukey's (SPF vs ABX); Mann-Whitney test (SPF vs GF), n=offspring from 5 dams per group). 1J, Schematic of E14.5 thalamic (Th), striatal (St) and hypothalamic (Hy) explant co-culture for axon outgrowth assay. The bar (gray colored in the original image; to the left of Th) indicates site of Th axon quantification, proximal to St. 1K, Representative TUJ1 fluorescence images of axon outgrowth from i) SPF Th explant proximal to SPF St explant (top left), ii) ABX Th explant proximal to ABX St (top right), iii) SPF Th explant proximal to ABX St explant (bottom left), iv) ABX Th explant proximal to SPF St explant (bottom right). Scale bar=250 μm. 1L, Number of axons per 200 μm of Th perimeter proximal to St explant, normalized to measurements from Th monoculture. (Two-way ANOVA with Tukey's, n=offspring from 14 SPF+SPF, 20 ABX+ABX, 10 SPF+ABX, 10 ABX+SPF dams). 1M, Length of Th axons proximal to St explant, normalized to measurements from Th monoculture. (Two-way ANOVA with Tukey's, n=offspring from 14 SPF+SPF, 20 ABX+ABX, 10 SPF+ABX, 10 ABX+SPF dams). Data are presented as mean±SEM, *p<0.05, p<0.01, *p<0.001, ****p<0.0001, n.s.=not statistically significant.

FIGS. 4A-4E: L1 thalamocortical axons in embryonic brains of E14.5 offspring from gnotobiotic dams. 4A and 4B, Representative immunofluorescence images of Netrin-G1a (magenta in the original image) and L1 (cyan in the original image) in rostral to caudal embryonic brain sections from E14.5 offspring of SPF, ABX, GF and Sp-colonized dams. Scale bar=500 μm. 4C, Average L1 fluorescence intensity normalized to matched area of region of interest ("yellow-in-the-original-image" dotted lines) across 800 μm of rostral to caudal sections from embryonic brain sections of E14.5 offspring from SPF, ABX, GF and Sp-colonized dams. (Two-way ANOVA with Tukey's, n=offspring from 5 SPF, 7 ABX, 4 GF, 5 Sp dams). 4D, Average area of L1-positive staining across 800 μm of rostral to caudal sections from embryonic brain sections of E14.5 offspring from SPF, ABX, GF and Sp-colonized dams. (Two-way ANOVA with Tukey's, n=offspring from 4 SPF, 5 ABX, 3 GF, 5 Sp dams). 4E, L1 mean fluorescence intensity per L1-positive area across 800 μm of rostral to caudal sections from embryonic brain sections of E14.5 offspring from SPF, ABX, GF and Sp-colonized dams. (Two-way ANOVA with Tukey's, n=offspring from 4 SPF, 4 ABX, 4 GF, 4 Sp dams). Data are presented as mean±SEM, *p<0.05, p<0.01, **p<0.0001, n. s.=not statistically significant.

FIGS. 5A-5L: Number and length of axons from thalamic explant monocultures and co-cultures with striatal and hypothalamic explants. 5A, Diagram of E14.5 thalamic (Th) explant monoculture for the axon outgrowth assay. Representative immunofluorescence image of axon outgrowth from 48-hour monoculture of thalamic explants from E14.5 offspring of SPF, ABX and Sp-colonized dams. Scale bar=250 μm. 5B, Number of axons in monoculture of Th explants from E14.5 offspring of SPF, ABX and Sp-colonized dams (One-way ANOVA with Tukey's, n=offspring from 26 SPF, 20 ABX, 10 Sp dams). 5C, Length of axons in SPF, ABX, and Sp Th explant monoculture (One-way ANOVA with Tukey's, n=offspring from 20 dams). 5D, Schematic of E14.5 Th, striatal (St) and hypothalamic (Hy) explant co-culture in axon outgrowth assay. The bar (gray colored in the original image; to the right of Th) indicates site of Th axon quantification, proximal to Hy. Representative fluorescence images of axon outgrowth from i) SPF Th explant proximal to SPF Hy explant (top left), ii) ABX Th explant proximal to ABX Hy explant (top right), iii) SPF Th explant proximal to ABX Hy explant (bottom left), iv) ABX Th explant proximal to SPF Hy explant (bottom right). Scale bar=250 μm. 5E, Number of axons per 200 μm of Th perimeter proximal to Hy explant, normalized to measurements from corresponding Th monoculture. (One-way ANOVA with Tukey's, n=offspring from 14 SPF+SPF, 20 ABX+ABX, 9 SPF+ABX, 10 ABX+SPF dams). 5F, Length of Th axons proximal to Hy explant, normalized to measurements from corresponding Th monoculture. (One-way ANOVA with Tukey's, n=offspring from 14 SPF+SPF, 18 ABX+ABX, 9 SPF+ABX, 10 ABX+SPF dams). 5G, Schematic of E14.5 Th, St and Hy explant co-culture for axon outgrowth assay. The bar (gray colored in the original image; to the left of Th) indicates site of Th axon quantification, proximal to St. Representative fluorescence images of axon outgrowth from a i) SPF Th explant proximal to SPF St explant (top left), ii) ABX Th explant proximal to ABX St explant (top right), iii) Sp Th explant proximal to Sp St explant (bottom left), iv) Sp Th explant proximal to ABX St explant (bottom right). Scale bar=250 μm. 5H, Number of axons per 200 μm of Th perimeter proximal to St explant, normalized to a measurement from corresponding Th monoculture. (One-way ANOVA with Tukey's, n=offspring from 14 SPF+SPF, 20 ABX+ABX, 14 Sp+Sp, 6 Sp+ABX dams). 5I, Length of Th axons proximal to ST explant, normalized to measurements from corresponding Th monoculture. (One-way ANOVA with Tukey's, n=offspring from 14 SPF+SPF, 18 ABX+ABX, 14 Sp+Sp, 6 Sp+ABX dams). 5J, Schematic of E14.5 Th, St and Hy explant co-culture in axon outgrowth assay. The bar (gray colored in the original image; to the right of Th) indicates site of Th axon quantification, proximal to Hy. Representative fluorescence images of axon outgrowth from a i) SPF Th explant proximal to an SPF Hy explant (top left), ii) ABX Th explant proximal to an ABX Hy explant (top right), iii) Sp Th explant proximal to a Sp Hy explant (bottom left), iv) Sp Th explant proximal to an ABX Hy explant (bottom right). Scale bar=250 μm. Red (in the original image) arrows highlight sparse short axons. 5K, Number of axons per 200 μm of Th perimeter proximal to Hy explant, normalized to a measurement from Th corresponding monoculture. (One-way ANOVA with Tukey's, n=offspring from 14 SPF+SPF, 18 ABX+ABX, 14 Sp+Sp, 6 Sp+ABX dams). 5L, Length of Th axons proximal to Hy explant, normalized to measurements from corresponding Th monoculture. (One-way ANOVA with Tukey's, n=offspring from 14 SPF+SPF, 18 ABX+ABX, 14 Sp+Sp, 6 Sp+ABX dams). Data are presented as mean±SEM. *p<0.05, p<0.01, *p<0.001, ****p<0.0001, n. s.=not statistically significant.

FIGS. 9A-9F: Fetal brain gene expression in offspring of dams colonized with a consortium of spore-forming bacteria (Sp). 9A, Principal coordinate analysis of 16S rDNA sequencing data of feces from SPF compared to Sp-colonized dams at E14.5 (n=4 dams per group) 9B, Taxonomic diversity of the fecal microbiota of SPF and Sp-colonized dams (n=4 dams per group). 9C, Heatmap of genes that were similarly differentially expressed in embryonic brains from E14.5 offspring of SPF and SP dams compared to ABX dams (p<0.05; Wald test, n=offspring from 3 dams per group). Data shown for SPF and ABX are as displayed in FIGS. 1A-1M. Red font (in the original image) indicates axonogenesis-related genes tested by qRT-PCR. 9D, qRT-PCR for PRR12 expression in embryonic brains from E14.5 offspring of SPF, ABX, and Sp-colonized dams (One-way ANOVA with Tukey's; n=offspring from 11 SPF, 15 ABX, 8 Sp dams). 9E, qRT-PCR for NRCAM, NRP2, PLXNA3, and SEMA3F expression in embryonic brains from E14.5 offspring of SPF, ABX, and Sp-colonized dams (Two-way ANOVA with Tukey's; n=offspring from 10 SPF, 10 ABX, 8 Sp dams). 9F, qRT-PCR for expression of axonogenesis-related genes NTN1, SLIT1, DCC, UNC5A, UNC5B, UNC5C, ROBO1, ROBO2 in embryonic brains from E14.5 offspring of SPF, ABX, and Sp-colonized dams (Two-way ANOVA with Tukey's; n=offspring from 11 SPF, 16 ABX, 8 Sp dams). Data are presented as mean±SEM. *p<0.05, p<0.01, *p<0.001, ****p<0.0001, n. s.=not statistically significant.

FIGS. 12A-12I: The maternal microbiota modulates fetal brain metabolites during pregnancy. 12A, Unsupervised hierarchical clustering of 753 maternal serum metabolites, classified by metabolite super pathway (n=6 dams per group). 12B, Principal component analysis of 753 metabolites detected in maternal serum metabolomes from SPF, ABX, GF, and Sp-colonized dams on E14.5 (n=6 dams per group) 12C, Principal component analysis of 567 metabolites detected in fetal brain metabolomes from E14.5 offspring of SPF, ABX, GF, and Sp-colonized dams (n=offspring from 6 dams per group). 12D, Volcano plot of significantly regulated metabolites in SPF vs ABX (left) and SPF v GF (right). Orange dots (in the original image) indicate log 2fold>0.5. Red dots (in the original image) indicate p-value<0.05. Green dots (in the original image) indicate metabolites that are log 2fold>0.5 and p-value<0.05 (ANOVA with contrasts, n=offspring from 6 dams per group). 12E, Volcano plot of significantly regulated metabolites in Sp vs ABX (left) and Sp v GF (right). Orange dots (in the original image) indicate log 2fold>0.5. Red dots (in the original image) indicate p-value<0.05. Green dots (in the original image) indicate metabolites that are log 2fold>0.5 and p-value<0.05 (ANOVA with contrasts, n=offspring from 6 dams per group). 12F, Amino acid, lipid and xenobiotic metabolites significantly dysregulated in fetal brains of E14.5 offspring from ABX-treated dams compared to SPF controls (p<0.05; One-Way ANOVA, n=offspring from 6 dams per group). 12G, Amino acid, lipid and xenobiotic metabolites significantly dysregulated in fetal brains of E14.5 offspring from ABX-treated dams compared to Sp controls (p<0.05; One-Way ANOVA, n=offspring from 6 dams per group). 12H, Random Forest classification of top 30 metabolites in fetal brain that discriminate between maternal colonization with SPF and Sp microbiota compared to ABX and GF. Red highlight (in the original image) indicates select metabolites with >2-fold decrease in ABX and GF compared to SPF and Sp (n=offspring from 6 dams per group). 12I, Select metabolites significantly decreased in fetal brains from E14.5 embryos of ABX and GF dams versus SPF and Sp dams. (One-way ANOVA with Tukey's, n=offspring from 6 dams per group). Data are presented as mean±SEM. p<0.01, *p<0.001, ****p<0.0001.

FIGS. 14A-14I: The maternal microbiota modulates metabolites that promote fetal thalamocortical axonogenesis and adult sensory behavior. 14A, Schematic of axon outgrowth assay with individual metabolite supplementation. 14B, Representative fluorescence images of axon outgrowth from ABX thalamic explants proximal to an ABX striatal explant (top left), and supplemented with i) vehicle (top left), ii) Trimethylamine N-oxide (TMAO, 1 nM) iii) 5-aminovalerate (5-AV, 1 nM), iv) imidazole propionate (IP, 1 nM), v) 3-indoxyl-sulfate (3-IS, 1 nM) or vi) Hippurate (HIP, 1 nM). Scale bar=250 μm. 14C, Number of axons per 200 μm of thalamic perimeter proximal to striatal explant (One-way ANOVA with Tukey's, n=offspring from 14 SPF+SPF, 13 ABX+ABX, 7 TMAO, 7 5-AV, 7 IP, 7 3-IS, 8 HIP dams). 14D, Representative immunofluorescence images of Netrin-G1a (magenta in the original image) and L1 (cyan in the original image) staining in embryonic brain sections (rostral to caudal) from E14.5 offspring of ABX dams treated with vehicle or 4-microbial metabolites (4-MM: TMAO, 5-AV, IP, and HIP). Scale bar=500 μm. 14E, Average Netrin-G1a fluorescence intensity per matched area of region of interest (ROI) ("yellow-in-the-original-image" dotted lines) across 800 μm of rostral to caudal embryonic brain sections of E14.5 offspring from ABX dams treated with vehicle or 4-MM. (Two-way ANOVA with Tukey's, n=offspring from 8 dams per group). 14F, Average L1 fluorescence intensity of L1 per matched area of ROI ("yellow-in-the-original-image" dotted lines) across 800 μm of rostral to caudal embryonic brain sections of E14.5 offspring from ABX dams treated with vehicle or 4-MM. (Two-way ANOVA with Tukey's, n=offspring from 8 dams per group). 14G, Experimental timeline for ABX+Veh and ABX+4-MM groups. 14H, Force filament to induce 50% paw withdrawal in adult offspring of SPF, ABX, ABX+Veh, and ABX+4-MM dams (One-way ANOVA with Tukey's, n=offspring from 5 SPF, 7 ABX, 6 ABX+Veh, 7 ABX+4-MM dams). 14I, Left: Latency to contact the adhesive tape in adult offspring of SPF, ABX, ABX+Veh and ABX+4-MM dams (One-way ANOVA with Tukey's, n=offspring from 6 SPF, 6 ABX, 5 ABX+Veh, 5 ABX+4-MM dams). Middle: Latency to remove the adhesive tape after first contact in offspring of SPF, ABX, ABX+Veh and ABX+4-MM dams (One-way ANOVA with Tukey's, n=offspring from 6 SPF, 6 ABX, 5 ABX+Veh, 5 ABX+4-MM dams). Right: Pairwise comparison of latency to contact and latency to remove in offspring of SPF, ABX, ABX+Veh and ABX+4-MM dams (Two-way ANOVA with Sidak's, n=offspring from 6 SPF, 6 ABX, 5 ABX+Veh, 5 ABX+4-MM dams). Data shown for SPF and ABX as reference controls are as presented in FIGS. 1A-1M. 6A-6G, and 10A-10M. Data are presented as mean±SEM. *p<0.05, p<0.01, *p<0.001, ****p<0.0001, n. s.=not statistically significant.

DETAILED DESCRIPTION

Figure 1B:
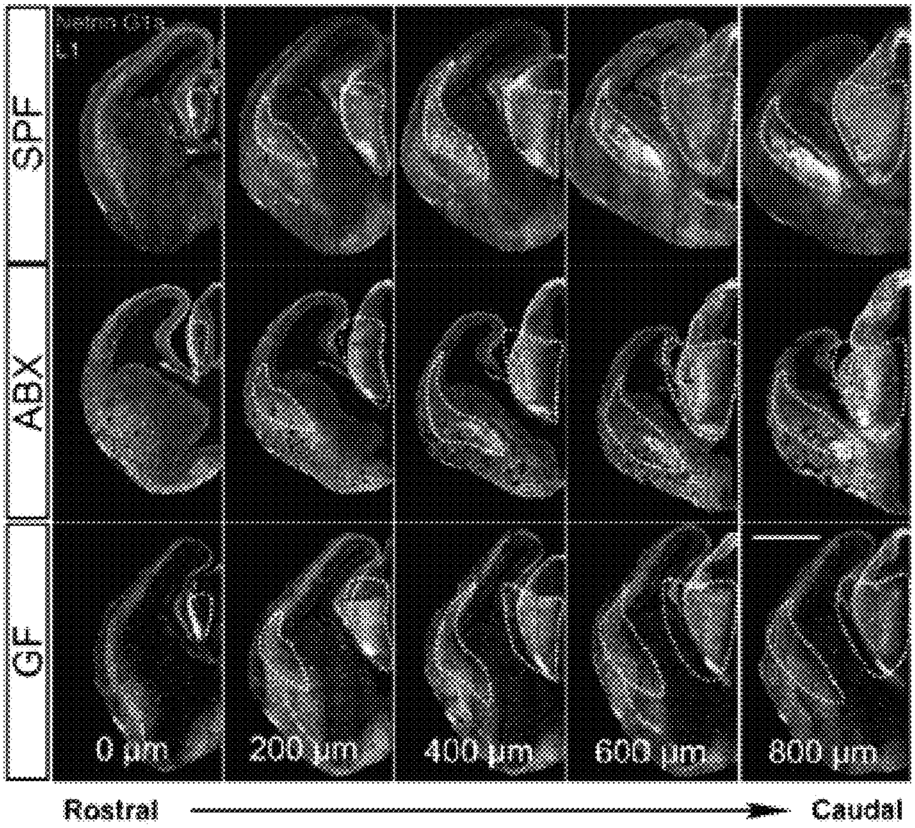
Figure 1F:
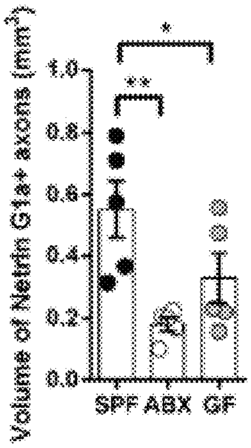
Figure 1G:
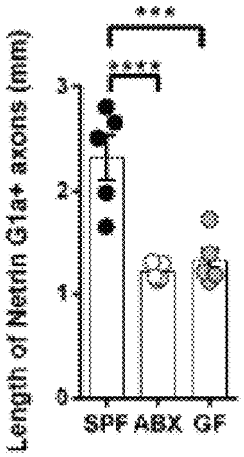
Figure 1H:
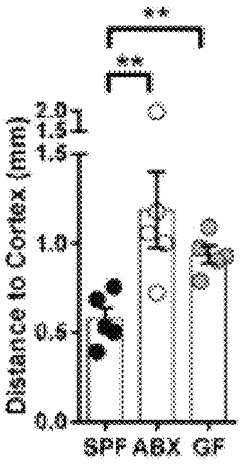
Figure 1I:
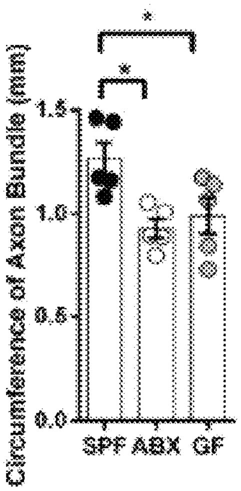
Figure 1J:
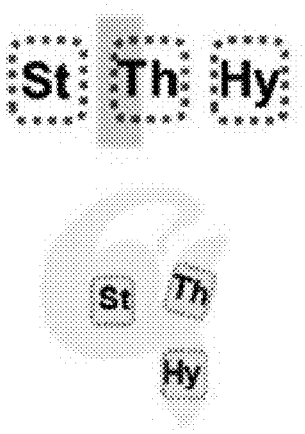
Figure 1K:
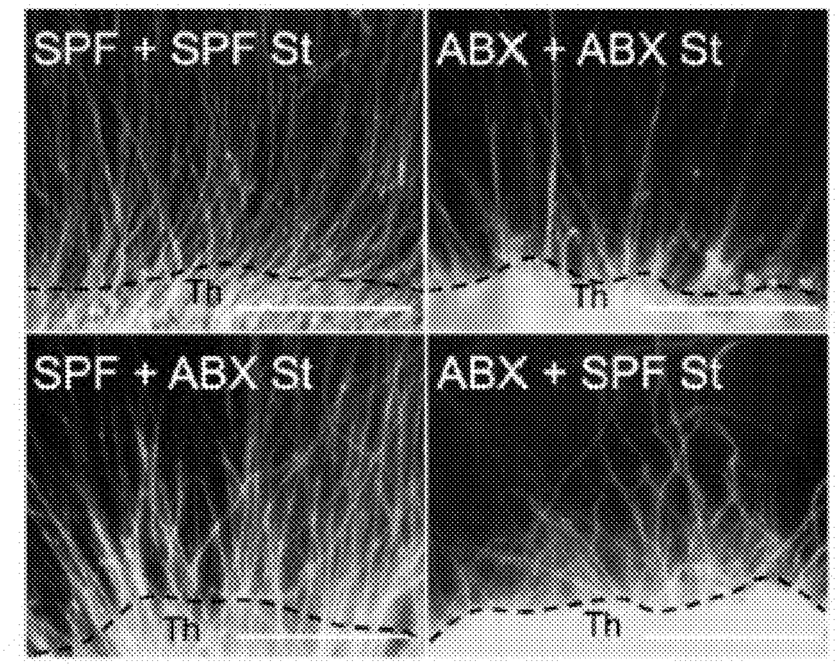
Figure 1L:
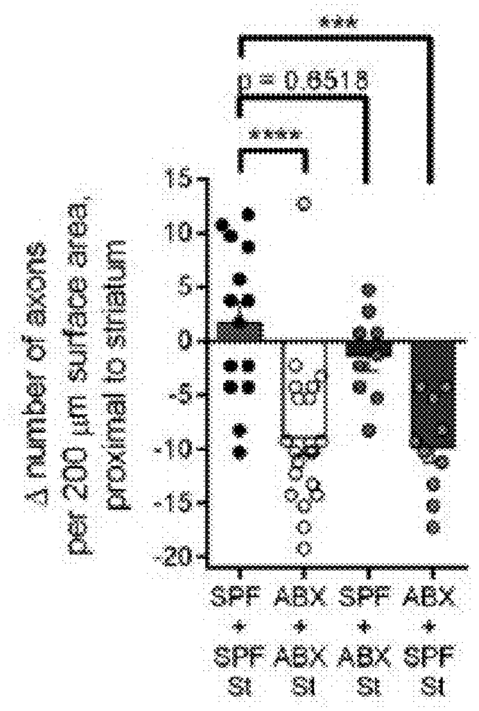
Figure 1M:
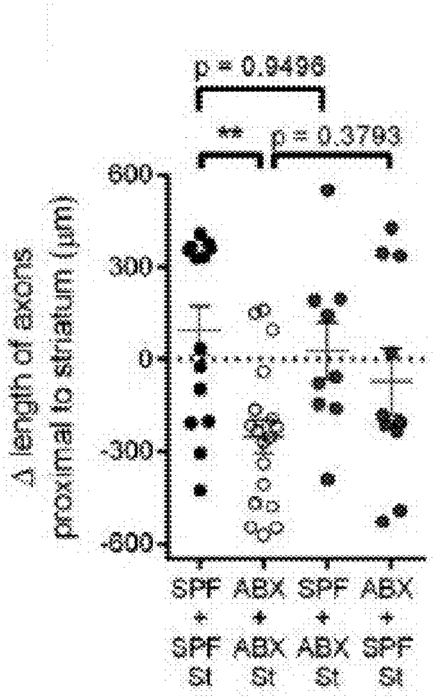

In some embodiments, the methods of the present disclosure are directed to promoting healthy neural development in an unborn baby, for example by administering to a subject (e.g., a maternal subject gestating the unborn baby, a female subject who plans to, expects to, or suspects of being pregnant) a composition, a bacterial composition, or both as disclosed herein.

In some embodiments, the methods of the present disclosure are directed to methods of conditioning a female subject for fostering healthy neural development in offspring, for example by administering to the subject a composition, a bacterial composition, or both as disclosed herein.

A composition that can be administered in these methods may comprise trimethylamine N-oxide (TMAO), 5-aminovalerate (5-AV), imidazole propionate (IP), hippurate (HIP), or a combination thereof (e.g., 5-AV and IP; 5-AV, IP, and TMAO; all 4 (4-MM)).

A bacterial composition that can be administered in these methods may comprise bacteria of the order Clostridiales. These bacteria can be of any of the following families: Lachnospiraceae, Ruminococcaceae, Clostridiaceae, or a combination thereof. In some embodiments, these bacteria are of any of the following genuses: *Clostridium*, Dehalobacterium, *Ruminococcus, Coprococcus, Dorea, Oscillospira*, or a combination thereof. In certain embodiments, these bacteria are spore-forming bacteria.

Healthy neural development can include healthy thalamocortical axon growth, healthy netrin-G1a+thalamocortical axogenesis, healthy tactile sensory development, or a combination thereof.

The disclosed compositions can be administered at various times. For example, they can be administered at least once (e.g., once during the full period, twice during the full period, once a day) during a period that runs from the first day of an expected-but-missed menstruation to a day that is two months after said first day. An alternative timing can be a period that runs from the second day of the expected-but-missed menstruation to a day that is 37 days after said second day (e.g., which for humans corresponds approximately to the mouse period from E7.5 to E14.5, which in units of days post conception (dpc) can be from 17 dpc to 52 dpc, at least in some subjects). Such timings can be useful to female subjects who prefer not to or cannot get tested for pregnancy though a professional facility. The administration time can also be at least once during a two-month period that ends with the day of an expected conception for the female subject. Such a timing can be useful for a subject who is planning pregnancy. The timing is, in some embodiments, at least once within the first trimester, second trimester, third trimester, or a combination thereof. More specific periods include the period that runs from the start of the third week after conception to the end of the eighth week after conception, and the period that runs from the $17^{th}$ dpc to the $52^{nd}$ dpc.

The disclosed methods can also be used to reduce adverse effects of antibiotic treatment on an unborn baby in a pregnant subject. For example, administering to the pregnant subject a composition that comprises trimethylamine N-oxide (TMAO), 5-aminovalerate (5-AV), imidazole propionate (IP), hippurate (HIP), or a combination thereof can promote healthy neural development, at least in comparison to a lack of such administration, in the unborn baby.

In certain embodiments, the methods of the present disclosure are directed to methods for selecting a female subject for conditioning to foster healthy neural development in offspring. These methods include determining that a compound has a level in a serum sample from the female subject that is at most 10%, 20%, 30%, 40%, 50%, 60%, or 70% of its level in a control serum sample representative of a healthy female subject, that bacteria of the order Clostridiales have a total level in a fecal sample from the female subject that is at most 0.5%, 1%, 2%, 3%, 4%, 5%, 6%, 7%, 8%, 9%, 10%, 12%, 14%, 16%, 18%, or 20% of their total level in a control fecal sample representative of a healthy female subject, or both, and selecting the female subject for conditioning to foster healthy neural development in offspring. In some embodiments, these criteria can be relaxed. For example, even if a subject has levels (of the compound, of the bacteria) that are similar to those of a healthy control, the subject may still be selected for treatment (e.g., with the bacterial compositions, which can be part of the normal gastrointestinal microbiome of a human) as a prophylactic measure.

In various embodiments, offspring can include babies carried by a surrogate mother, in which the baby need not be the biological offspring of the gestating female.

In these methods of selecting a female subject, the compound can be 2-(4-hydroxyphenyl)propionate; 3-(3-hydroxyphenyl)propionate sulfate; 3-indoxyl sulfate; 3-phenylpropionate (hydrocinnamate); 7-ketodeoxycholate; alpha-ketoglutaramate; alpha-muricholate; beta-muricholate; biotin; deoxycholate; hippurate; imidazole propionate; indolepropionate; N,N,N-trimethyl-5-aminovalerate; p-cresol sulfate; phenylpropionylglycine; pyrraline; stachydrine; taurodeoxycholate; taurohyodeoxycholic acid; trimethylamine N-oxide; ursodeoxycholate; or a combination thereof. Alternatively, the compound can be 3-indoxyl sulfate; biotin; hippurate; imidazole propionate; N,N,N-trimethyl-5-aminovalerate; pyrraline; stachydrine; trimethylamine N-oxide; or a combination thereof. The bacteria, in some of these embodiments, includes bacteria of the genus *Clostridium*, genus Dehalobacterium, genus *Ruminococcus*, genus *Coprococcus*, genus *Dorea*, genus *Oscillospira*, or a combination thereof. Once a female subject is selected, she can be treated by administering to her a composition, bacterial composition, or both as provided herein.

In certain embodiments, the methods of the present disclosure are directed to promoting healthy neural development in a fetus, such as by administering to a maternal subject gestating the fetus (or to a female subject) a composition as described herein. Preferably, the method results in the fetus exhibiting a lesser degree of impaired neural development relative to a fetus gestated by similar a maternal subject (e.g., a maternal subject having a similar or identical maternal microbiome) not receiving the composition. Preferably, the method results in an increase in one or more of fetal brain gene expression, fetal axonogenesis (e.g., fetal thalamocortical axonogenesis), fetal axon development, and adult tactile sensory behavior relative to a fetus gestated by similar a maternal subject (e.g., a maternal subject having a similar or identical maternal microbiome) not receiving the composition.

In additional embodiments of any of the aspects disclosed herein, the conjugate base forms or the conjugate acid forms of the disclosed compounds can be used, either instead of or together with their conjugate form. For example, in certain embodiments, hippuric acid can be used instead of or in addition to hippurate, imidazolepropionic acid can be used instead of or in addition to imidazole propionate, and 5-aminovaleric acid can be used instead of or in addition to 5-aminovalerate.

In certain embodiments, the methods of the present disclosure are directed to inhibiting development of a disease or disorder in a fetus, e.g., by administering to a maternal subject gestating the fetus (or to a female subject) a composition as described herein. Preferably, the method results in the fetus exhibiting a lesser degree of development of the disease or disorder (e.g., a metabolic disorder, a cardiovascular disorder, a cerebrovascular disorder, stroke, Alzheimer's disease, schizophrenia, depression, or autism) during the fetal period and throughout the lifetime of the eventual child, adolescent, and adult, relative to a fetus gestated by a similar maternal subject (e.g., a maternal subject having a similar or identical maternal microbiome) not receiving the composition.

In certain embodiments, the methods further comprise administering the composition to the maternal subject or a female subject prior to gestation. In certain embodiments, the female subject is a fertile, ovulating female subject. In certain embodiments, the female subject is a female subject seeking to implant an embryo.

In certain embodiments, the composition comprises a compound selected from trimethylamine-N-oxide (TMAO), N,N,N-trimethyl-5-aminovaleric acid (TMAV), imidazole propionic acid (IP), 3-indoxyl sulfuric acid (3-IS), hippuric acid (HIP), perfluorooctanesulfonic acid (PFOS), 3-sulfo-L-alanine, alpha-ketoglutaramic acid, 4-hydroxyglutamic acid, extoine, stachydrine, biotin, pyroglutamine, chiro-inositol, N1-methyl-2-pyridone-5-carboxamide, O-sulfo-L-tyrosine, 2'deoxyuridine, pyrraline, N-delta-acetylornithine, phenyl sulfuric acid, phenylacetylglycine, anserine, homostachydrine, serine, N1-methyl-4-pyridone-3-carboxamide, methyl glycopyranoside (alpha+beta), 3-carboxy-1-methylpyridin-1-ium, hypotaurine, 1,5-anhydroglucitol (1,5-AG), 1-oleoyl-2-linoleoyl-GPC (18:1/18:2), methionine, glutamine, malic acid, pantothenic acid, 5,6-dihydrouridine, ceramide (d18:1/17:0 d17:1/18.0) N6-methyllysine, allantoin, N2-acetyllysine, N-acetylglutamine, stearoylcarnitine (C18), arachidoylcarnitine (C20), arabitol, xylitol, 1-methylhistamine, xanthosine, xanthine, 1-ribosyl-imidazoleacetic acid, 5-methyl-2'-deoxycytidine, sphingomyelin (d18:0/20:0, d16:0/22:0), 1-methyl-4-imidazoleacetic acid, inosine 5'-monophosphoric acid (IMP), 1,2-distearoyl-GPC (18:0/18:0), 3-methylcytidine, pipecolate, N-stearoyl-sphingadienine (d18:2/18:0), homoserine, carnosine, 1-palmitoyl-GPI (16:0), 1-stearoyl-GPI (18:0), N6-succinyladenosine, 2'-deoxycytidine, stearoyl-docosahexaenoyl-glycerol (18:0/22:6), trigonelline (N'-methylnicotinate), hydroxyasparagine, gamma-glutamylglutamic acid, 2-palmitoylglycerol (16:0), ceramide (d18:1/17:0, d17:1/18:0), thiamin (Vitamin B1), N6-methyllysine, N6,N6-dimethyllysine, 3-hydroxy-3-methylglutaric acid, campesterol, allantoin, stachydrine, N2-acetyllysine, phenyllactic acid (PLA), gamma-glutamyltryptophan, N-palmitoyl-sphingosine (d18:1/16:0), O-sulfo-L-tyrosine, indolelactic acid, gamma-glutamylglutamine, N-acetylglucosamine 6-phosphoric acid, 1-oleoyl-GPS (18:1), 3-hydroxypalmitoylcarnitine, myo-inositol, behenoyl sphingomyelin (d18:1/22:0), maltotetraose, maltotriose, N-acetylglucosamine/N-acetylgalactosamine, N1-methyladenosine, uracil, 1-oleoyl-GPI (18:1), sphingomyelin (d18:1/17:0, d17:1/18:0, d19:1/16:0), 3-ureidopropionic acid, 5-oxoproline, gamma-glutamyltyrosine, 1-(1-enyl-stearoyl)-GPE (P-18:0), cytidine 2',3'-cyclic monophosphoric acid, 2'-deoxyguanosine 5'-monophosphoric acid (dGMP), thymidine, N6,N6,N6-trimethyllysine, 1-palmitoyl-GPC (16:0), 1-(1-enyl-palmitoyl)-GPE (P-16:0), N-stearoyl-sphinganine (d18:0/18:0), N-arachidoyl-sphingosine (d18:1/20:0), 3'-dephosphocoenzyme A, 5-hydroxylysine, arabonic acid/xylonic acid, 1-palmitoyl-2-docosahexaenoyl-GPC (16:0/22:6), glutamine, 1-(1-enyl-palmitoyl)-2-palmitoyl-GPC (P-16:0/16:0), N-behenoyl-sphingadienine (d18:2/22:0), xylulose 5-phosphoric acid, 1-oleoyl-GPC (18:1), 1-stearoyl-GPE (18:0), glycerol 3-phosphoric acid, N-stearoyl-sphingosine (d18:1/18:0), 7-methylguanine, N2,N2-dimethylguanosine, N-acetylglutamine, methionine, pro-hydroxy-pro, dihydroxyacetone phosphoric acid (DHAP), 1-stearoyl-2-docosahexaenoyl-GPC (18:0/22:6), sphingomyelin (d18:1/20:0, d16:1/22:0), uric acid, adenylosuccinic acid, cystathionine, spermine, mannitol/sorbitol, 2-hydroxyadipic acid, N-palmitoyl-sphinganine (d18:0/16:0), sphingomyelin (d18:0/18:0, d19:0/17:0), sphingomyelin (d18:1/24:1, d18:2/24:0), alpha-hydroxyisovaleric acid, citrulline, ribulonic acid/xylulonic acid, succinylcarnitine (C4-DC), ceramide (d16:1/24:1, d18:1/22:1), hypoxanthine, 5,6-dihydrouridine, gamma-aminobutyric acid (GABA), oleoyl ethanolamide, choline, 1-palmitoyl-GPE (16:0), palmitoyl-linoleoyl-glycerol (16:0/18:2), ceramide (d18:2/24:1, d18:1/24:2), cholesterol, 2'-O-methylcytidine, nicotinamide riboside, pantothenic acid, pyridoxal, N-acetylaspartic acid (NAA), C-glycosyltryptophan, methionine sulfoxide, spermidine, 1-palmitoyl-2-oleoyl-GPG (16:0/18:1), lignoceroyl sphingomyelin (d18:1/24:0), desmosterol, N1-methylinosine, cytidine, N-acetyl-aspartyl-glutamic acid (NAAG), sedoheptulose, galactonic acid, cytidine 5'-monophospho-N-acetylneuraminic acid, glycerophosphoinositol, uridine, salicylic acid, N-acetylglutamic acid, gamma-glutamyl-epsilon-lysine, glycerophosphoserine, 1-stearoyl-2-oleoyl-GPE (18:0/18:1), beta-alanine, 5-methylcytidine, methylphosphoric acid, imidazole lactic acid, sedoheptulose-7-phosphoric acid, 1-palmitoyl-2-stearoyl-GPE (16:0/18:0), guanosine 5'-diphosphoric acid (GDP), 3-ureidoisobutyric acid, tryptophan, isoleucine, methyl succinic acid, S-adenosylmethionine (SAM), taurine, gamma-glutamylthreonine, arabitol/xylitol, erythronic acid, fumaric acid, stearoylcarnitine (C18), deoxycarnitine, cytidine 5'-diphosphocholine, 1-stearoyl-2-arachidonoyl-GPC (18:0/20:4), 1-stearoyl-2-arachidonoyl-GPI (18:0/20:4), glycerophosphoglycerol, N6-carbamoylthreonyladenosine, flavin adenine dinucleotide (FAD), 2-oxoarginine, lactic acid, gulonic acid, phenylalanine, 3-(4-hydroxyphenyl)lactic acid, 2-hydroxyglutaric acid, palmitoleoyl ethanolamide, 1-palmitoyl-2-stearoyl-GPC (16:0/18:0), 1-stearoyl-2-oleoyl-GPC (18:0/18:1), palmitoyl-oleoyl-glycerol (16:0/18:1), betaine, N-acetylneuraminic acid, malic acid, phosphoethanolamine, 1-myristoyl-2-arachidonoyl-GPC (14:0/20:4), beta-citrylglutamic acid, 1-methylhistidine, leucine, ethylmalonic acid, prolylglycine, stearoyl-arachidonoyl-glycerol (18:0/20:4), orotidine, 5-(galactosylhydroxy)-L-lysine, N-acetylglucosaminylasparagine, eicosenoylcarnitine (C20:1), cytidine-5'-diphosphoethanolamine, glycosyl-N-stearoyl-sphingosine (d18:1/18:0), palmitoyl dihydrosphingomyelin (d18:0/16:0), sphingosine, inosine, guanosine 5'-monophosphoric acid (5'-GMP), dimethylglycine, N-acetylalanine, aspartic acid, creatine, ribitol, 2-methylcitric acid/homocitric acid, arachidoylcarnitine (C20), S-methylglutathione, 1-palmitoyl-2-arachidonoyl-GPC (16:0/20:4n6), stearoyl sphingomyelin (d18:1/18:0), nicotinamide, N-formylmethionine, UDP-N-acetylglucosamine/galactosamine, glucoronic acid, 1,2-dipalmitoyl-GPE (16:0/16:0), pseudouridine, alanine, glutamic acid, 1-myristoyl-2-palmitoyl-GPC (14:0/16:0), 1,2-dipalmitoyl-GPC (16:0/16:0), 1-palmitoyl-2-oleoyl-GPC (16:0/18:1), sphingomyelin (d18:1/22:1, d18:2/22:0, d16:1/24:1), glycerophosphoethanolamine, 1-palmitoyl-2-palmitoleoyl-GPC (16:0/16:1), UDP-glucuronic acid, and 1-methylnicotinamide, or a salt thereof, or a combination thereof.

In certain embodiments, the composition comprises a compound selected from trimethylamine-N-oxide (TMAO), N,N,N-trimethyl-5-aminovaleric acid (TMAV), imidazole propionic acid (IP), 3-indoxyl sulfuric acid (3-IS), hippuric acid (HIP), perfluorooctanesulfonic acid (PFOS), 3-sulfo-L-alanine, alpha-ketoglutaramic acid, 4-hydroxyglutamic acid, extoine, stachydrine, biotin, pyroglutamine, chiro-inositol, N1-methyl-2-pyridone-5-carboxamide, O-sulfo-L-tyrosine, 2'deoxyuridine, pyrraline, N-delta-acetylornithine, phenylsulfuric acid, phenylacetylglycine, anserine, homostachydrine, serine, N1-methyl-4-pyridone-3-carboxamide, methyl glycopyranoside (alpha+beta), 3-carboxy-1-methylpyridin-1-ium, hypotaurine, 1,5-anhydroglucitol (1,5-AG), 1-oleoyl-2-linoleoyl-GPC (18:1/18:2), methionine, glutamine, malic acid, pantothenic acid, 5,6-dihydrouridine, ceramide (d18:1/17:0 d17:1/18.0) N6-methyllysine, allantoin, N2-acetyllysine, N-acetylglutamine, stearoylcarnitine (C18), arachidoylcarnitine (C20), arabitol, and xylitol, or a salt thereof, or a combination thereof. In certain embodiments, the composition comprises a compound selected from 3-sulfo-L-alanine, TMAV, IP, TMAO, 3-IS, phenylsulfuric acid, stachydrine, hippuric acid, homostachydrine, pyrraline, alpha-ketoglutaramic acid, O-sulfo-L-tyrosine, methionine, 3-carboxy-1-methylpyridin-1-ium, biotin, glutamine, malic acid, pantothenic acid, pyroglutamine, anserine, 5,6-dihydrouridine, phenylacetylglycine, ceramide (d18:1/17:0 d17:1/18.0), N6-methyllysine, allantoin, N2-acetyllysine, N-acetylglutamine, stearoylcarnitine (C18), arachidoylcarnitine (C20), arabitol, and xylitol, or a salt thereof, or a combination thereof. In certain embodiments, the composition comprises a compound selected from methionine, glutamine, malic acid, pantothenic acid, 5,6-dihydrouridine, ceramide (d18:1/17:0 d17:1/18.0), N6-methyllysine, allantoin, N2-acetyllysine, N-acetylglutamine, stearoylcarnitine (C18), arachidoylcarnitine (C20), arabitol, and xylitol, or a salt thereof, or a combination thereof. In certain embodiments, the composition comprises a compound selected from TMAO, TMAV, HIP, IP, and 3-IS, or a salt thereof, or a combination thereof. In certain embodiments, the composition comprises a compound selected from TMAO, TMAV, and HIP, or a salt thereof, or a combination thereof. In certain embodiments, the composition comprises a compound selected from TMAO, TMAV, IP, and 3-IS, or a salt thereof, or a combination thereof. In certain embodiments, the composition comprises a compound selected from TMAO, TMAV, IP, and HIP, or a salt thereof, or a combination thereof. In certain embodiments, the composition comprises a compound selected from TMAV or TMAO, or a salt thereof, or a combination thereof. In certain embodiments, the composition comprises the compound TMAO or a salt thereof.

In some embodiments, the present invention is drawn to a composition comprising at least one bacterial species or bacterial strain (e.g., a probiotic bacterial strain) capable of promoting healthy neural development in a fetus and/or inhibiting development of a disease or disorder in a subject, optionally wherein the at least one bacterial species or bacterial strain is alive and capable of proliferation. Such bacteria (e.g., probiotic bacteria) inhibit one or more adverse effects of maternal microbiota depletion (e.g., in ABX subjects) on neural development, e.g., fetal brain gene expression, thalamocortical axon outgrowth, and offspring sensory behavior. In some embodiments, such bacteria restore expression of one or more genes relevant to axon guidance. In certain embodiments, the at least one bacterial species or bacterial strain is a bacterial species found in a maternal microbiome. In some embodiments, the one or more bacterial species is a spore-forming bacterial species.

In certain embodiments, the one or more bacteria in the composition are spore-forming bacteria. In certain embodiments, the one or more spore-forming bacteria are selected from order Clostridiales (e.g., family Lachnospiraceae, family Clostridiaceae, family Ruminococcaceae, family Dehalobacteriaceae), order Turicibacterales (e.g., family Turicibacteraceae), order Anaeroplasmatales (e.g., family Anaeroplasmataceae), order Erysipelotrichales (e.g., family Erysipelotrichaceae), and order RF39, or a combination thereof. In certain embodiments, the one or more spore-forming bacteria are selected from order Clostridiales.

In certain embodiments, the one or more bacteria in the composition are selected from order Lactobacillales (e.g., genus *Enterococcus*), order Clostridiales (e.g., family Clostridiaceae, family Peptostreptococcaceae, family Lachnospiraceae), order Turicibacterales (e.g., genus *Turicibacter*), order Erysipelotrichales (e.g., genus *Eubacterium*), order Enterobacteriales, order Bacteroidales (e.g., genus *Bacteroides*), or a combination thereof. In certain embodiments, the one or more bacteria are selected from order Bacteroidales (e.g., genus *Bacteroides*).

In certain embodiments, the one or more bacteria in the composition are selected from phylum Firmicutes, phylum Tenericutes, phylum Bacteroidetes, or a combination thereof. In certain embodiments, the one or more bacteria in the composition from phylum Firmicutes comprises one or more bacteria selected from class Clostridia, class Bacilli (e.g., order Lactobacillales, order Turicibacterales), class Erysipelotrichi, and class Gammaproteobacteria. In certain embodiments, the one or more bacteria in the composition from phylum Bacteroidetes comprises one or more bacteria selected from genus *Bacteroides* (e.g., *B. thetraiotaomicron, B. uniformis, B. vulgatus, B. ovatus, B. fragilus*). In certain embodiments, the one or more bacteria in the composition from phylum Tenericutes comprises one or more bacteria selected from class Mollicutes (e.g., order Anaeroplasmatales, order RF39).

Definitions

"Impaired neural development," as used herein, refers to abnormalities in brain function and behavior, in offspring. Examples of impaired neural development include, but are not limited to, impairments in fetal brain gene expression, fetal axonogenesis (such as fetal thalamocortical axonogenesis), and/or adult tactile sensory behavior (e.g., tactile hyposensitivity in sensorimotor behavioral tasks). Examples of "healthy neural development," as used herein, include, but are not limited to, healthy development in fetal brain gene expression, fetal axonogenesis, fetal axon development, and/or adult tactile sensory behavior.

"Microbiome," as used herein, refers to the microorganisms in a given environment, such as the body or a part of the body. The "maternal microbiome," as used herein, refers to the microorganisms in a maternal subject (i.e., a pregnant or gestating subject), particularly in the gut of the maternal subject. The gut microbiome modulates the bioavailability of hundreds of biochemicals in the circulating blood. During pregnancy, the maternal gut environment supplies nutrients and growth factors, from the maternal diet and other nutritional intake, to nurture offspring growth.

A "depleted" maternal microbiome is characterized by a reduced level of one or more microbial species (e.g., one or more bacterial species), such as 95%, 90%, 85%, 80%, 75%, 70%, 65%, 60%, 55%, 50%, 45%, 40%, 35%, 30%, 25%, 20%, 15%, 10%, 5%, 4%, 3%, 2%, 1%, 0.5%, or 0.1% of the level relative to a maternal subject without a depleted maternal microbiome.

"Germ-free" (GF) subjects, as used herein, are subjects with no microorganisms living in or on them. "Antibiotic-treated" (ABX) subjects, as used herein, are subjects treated with one or more antibiotic compounds, many representative examples of which are known in the art.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); and/or mammals, including commercially relevant mammals such as cattle, pigs, horses, sheep, goats, cats, and/or dogs. Preferred subjects are humans.

An "ovulating" female subject, as used herein, refers to a female subject having a regular cycle of menses, e.g., a female between menarche and menopause that is not employing hormonal birth control that inhibits ovulation. A "fertile" female subject, as used herein, refers to an ovulating female subject able to conceive offspring.

As used herein, a therapeutic that "prevents" a disorder or condition refers to a compound or composition that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the subject of one or more of the disclosed compositions. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic (i.e., it is intended to diminish, ameliorate, or stabilize the existing unwanted condition or side effects thereof).

The term "prodrug" is intended to encompass compounds which, under physiologic conditions, are converted into therapeutically active agents. A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) and esters or amides of phosphates and phosphonic acids are preferred prodrugs of the present invention.

As used herein, the term "about" is defined as being close to as understood by one of ordinary skill in the art. In one non-limiting embodiment, the term "about" is defined to be within 10%, preferably within 5%, more preferably within 1%, and most preferably within 0.5%.

As used herein, "stably stored" or "storage-stable" refer to a composition in which cells are able to withstand storage for extended periods of time (e.g., at least one month, or two, three, four, six, or twelve months or more) with a less than 95%, 90%, 80%, 70%, 60%, 50%, 40%, 30%, 20%, 15%, 10%, 5%, or 1% decrease in cell viability.

As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

Bacterial Compositions

In certain aspects, provided herein are bacterial compositions that include bacteria of the order Clostridiales. In some embodiments, the bacteria of the order Clostridiales include bacteria of the family Lachnospiraceae, family Ruminococcaceae, family Clostridiaceae, or a combination thereof. In certain embodiments, the bacteria of the order Clostridiales include bacteria of the genus *Clostridium*, genus Dehalobacterium, genus *Ruminococcus*, genus *Coprococcus*, genus *Dorea*, genus *Oscillospira*, or a combination thereof. The bacteria of the order Clostridiales can be spore-forming bacteria. In some embodiments, the bacteria are selected from those presented in Table 2.

In certain aspects, provided herein are bacterial compositions comprising one or more bacteria and optionally a compound selected from trimethylamine-N-oxide (TMAO), N,N,N-trimethyl-5-aminovaleric acid (TMAV), imidazole propionic acid (IP), 3-indoxyl sulfuric acid (3-IS), hippuric acid (HIP), perfluorooctanesulfonic acid (PFOS), 3-sulfo-L-alanine, alpha-ketoglutaramic acid, 4-hydroxyglutamic acid, extoine, stachydrine, biotin, pyroglutamine, chiro-inositol, N1-methyl-2-pyridone-5-carboxamide, O-sulfo-L-tyrosine, 2'deoxyuridine, pyrraline, N-delta-acetylornithine, phenylsulfuric acid, phenylacetylglycine, anserine, homostachydrine, serine, N1-methyl-4-pyridone-3-carboxamide, methyl glycopyranoside (alpha+beta), 3-carboxy-1-methylpyridin-1-ium, hypotaurine, 1,5-anhydroglucitol (1,5-AG), 1-oleoyl-2-linoleoyl-GPC (18:1/18:2), methionine, glutamine, malic acid, pantothenic acid, 5,6-dihydrouridine, ceramide (d18:1/17:0 d17:1/18.0) N6-methyllysine, allantoin, N2-acetyllysine, N-acetylglutamine, stearoylcarnitine (C18), arachidoylcarnitine (C20), arabitol, xylitol, 1-methylhistamine, xanthosine, xanthine, 1-ribosyl-imidazoleacetic acid, 5-methyl-2'-deoxycytidine, sphingomyelin (d18:0/20:0, d16:0/22:0), 1-methyl-4-imidazoleacetic acid, inosine 5'-monophosphoric acid (IMP), 1,2-distearoyl-GPC (18:0/18:0), 3-methylcytidine, pipecolate, N-stearoyl-sphingadienine (d18:2/18:0), homoserine, carnosine, 1-palmitoyl-GPI (16:0), 1-stearoyl-GPI (18:0), N6-succinyladenosine, 2'-deoxycytidine, stearoyl-docosahexaenoyl-glycerol (18:0/22:6), trigonelline (N'-methylnicotinate), hydroxyasparagine, gamma-glutamylglutamic acid, 2-palmitoylglycerol (16:0), ceramide (d18:1/17:0, d17:1/18:0), thiamin (Vitamin B1), N6-methyllysine, N6,N6-dimethyllysine, 3-hydroxy-3-methylglutaric acid, campesterol, allantoin, stachydrine, N2-acetyllysine, phenyllactic acid (PLA), gamma-glutamyltryptophan, N-palmitoyl-sphingosine (d18:1/16:0), O-sulfo-L-tyrosine, indolelactic acid, gamma-glutamylglutamine, N-acetylglucosamine 6-phosphoric acid, 1-oleoyl-GPS (18:1), 3-hydroxypalmitoylcarnitine, myo-inositol, behenoyl sphingomyelin (d18:1/22:0), maltotetraose, maltotriose, N-acetylglucosamine/N-acetylgalactosamine, N1-methyladenosine, uracil, 1-oleoyl-GPI (18:1), sphingomyelin (d18:1/17:0, d17:1/18:0, d19:1/16:0), 3-ureidopropionic acid, 5-oxoproline, gamma-glutamyltyrosine, 1-(1-enyl-stearoyl)-GPE (P-18:0), cytidine 2',3'-cyclic monophosphoric acid, 2'-deoxyguanosine 5'-monophosphoric acid (dGMP), thymidine, N6,N6,N6-trimethyllysine, 1-palmitoyl-GPC (16:0), 1-(1-enyl-palmitoyl)-GPE (P-16:0), N-stearoyl-sphinganine (d18:0/18:0), N-arachidoyl-sphingosine (d18:1/20:0), 3'-dephosphocoenzyme A, 5-hydroxylysine, arabonic acid/xylonic acid, 1-palmitoyl-2-docosahexaenoyl-GPC (16:0/22:6), glutamine, 1-(1-enyl-palmitoyl)-2-palmitoyl-GPC (P-16:0/16:0), N-behenoyl-sphingadienine (d18:2/22:0), xylulose 5-phosphoric acid, 1-oleoyl-GPC (18:1), 1-stearoyl-GPE (18:0), glycerol 3-phosphoric acid, N-stearoyl-sphingosine (d18:1/18:0), 7-methylguanine, N2,N2-dimethylguanosine, N-acetylglutamine, methionine, pro-hydroxy-pro, dihydroxyacetone phosphoric acid (DHAP), 1-stearoyl-2-docosahexaenoyl-GPC (18:0/22:6), sphingomyelin (d18:1/20:0, d16:1/22:0), uric acid, adenylosuccinic acid, cystathionine, spermine, mannitol/sorbitol, 2-hydroxyadipic acid, N-palmitoyl-sphinganine (d18:0/16:0), sphingomyelin (d18:0/18:0, d19:0/17:0), sphingomyelin (d18:1/24:1, d18:2/24:0), alpha-hydroxyisovaleric acid, citrulline, ribulonic acid/xylulonic acid, succinylcarnitine (C4-DC), ceramide (d16:1/24:1, d18:1/22:1), hypoxanthine, 5,6-dihydrouridine, gamma-aminobutyric acid (GABA), oleoyl ethanolamide, choline, 1-palmitoyl-GPE (16:0), palmitoyl-linoleoyl-glycerol (16:0/18:2), ceramide (d18:2/24:1, d18:1/24:2), cholesterol, 2'-O-methylcytidine, nicotinamide riboside, pantothenic acid, pyridoxal, N-acetylaspartic acid (NAA), C-glycosyltryptophan, methionine sulfoxide, spermidine, 1-palmitoyl-2-oleoyl-GPG (16:0/18:1), lignoceroyl sphingomyelin (d18:1/24:0), desmosterol, N1-methylinosine, cytidine, N-acetyl-aspartyl-glutamic acid (NAAG), sedoheptulose, galactonic acid, cytidine 5'-monophospho-N-acetylneuraminic acid, glycerophosphoinositol, uridine, salicylic acid, N-acetylglutamic acid, gamma-glutamyl-epsilon-lysine, glycerophosphoserine, 1-stearoyl-2-oleoyl-GPE (18:0/18:1), beta-alanine, 5-methylcytidine, methylphosphoric acid, imidazole lactic acid, sedoheptulose-7-phosphoric acid, 1-palmitoyl-2-stearoyl-GPE (16:0/18:0), guanosine 5'-diphosphoric acid (GDP), 3-ureidoisobutyric acid, tryptophan, isoleucine, methyl succinic acid, S-adenosylmethionine (SAM), taurine, gamma-glutamylthreonine, arabitol/xylitol, erythronic acid, fumaric acid, stearoylcarnitine (C18), deoxycarnitine, cytidine 5'-diphosphocholine, 1-stearoyl-2-arachidonoyl-GPC (18:0/20:4), 1-stearoyl-2-arachidonoyl-GPI (18:0/20:4), glycerophosphoglycerol, N6-carbamoylthreonyladenosine, flavin adenine dinucleotide (FAD), 2-oxoarginine, lactic acid, gulonic acid, phenylalanine, 3-(4-hydroxyphenyl)lactic acid, 2-hydroxyglutaric acid, palmitoleoyl ethanolamide, 1-palmitoyl-2-stearoyl-GPC (16:0/18:0), 1-stearoyl-2-oleoyl-GPC (18:0/18:1), palmitoyl-oleoyl-glycerol (16:0/18:1), betaine, N-acetylneuraminic acid, malic acid, phosphoethanolamine, 1-myristoyl-2-arachidonoyl-GPC (14:0/20:4), beta-citrylglutamic acid, 1-methylhistidine, leucine, ethylmalonic acid, prolylglycine, stearoyl-arachidonoyl-glycerol (18:0/20:4), orotidine, 5-(galactosylhydroxy)-L-lysine, N-acetylglucosaminylasparagine, eicosenoylcarnitine (C20:1), cytidine-5'-diphosphoethanolamine, glycosyl-N-stearoyl-sphingosine (d18:1/18:0), palmitoyl dihydrosphingomyelin (d18:0/16:0), sphingosine, inosine, guanosine 5'-monophosphoric acid (5'-GMP), dimethylglycine, N-acetylalanine, aspartic acid, creatine, ribitol, 2-methylcitric acid/homocitric acid, arachidoylcarnitine (C20), S-methylglutathione, 1-palmitoyl-2-arachidonoyl-GPC (16:0/20:4n6), stearoyl sphingomyelin (d18:1/18:0), nicotinamide, N-formylmethionine, UDP-N-acetylglucosamine/galactosamine, glucoronic acid, 1,2-dipalmitoyl-GPE (16:0/16:0), pseudouridine, alanine, glutamic acid, 1-myristoyl-2-palmitoyl-GPC (14:0/16:0), 1,2-dipalmitoyl-GPC (16:0/16:0), 1-palmitoyl-2-oleoyl-GPC (16:0/18:1), sphingomyelin (d18:1/22:1, d18:2/22:0, d16:1/24:1), glycerophosphoethanolamine, 1-palmitoyl-2-palmitoleoyl-GPC (16:0/16:1), UDP-glucuronic acid, and 1-methylnicotinamide, or a salt thereof, or a combination thereof.

In certain aspects, provided herein are bacterial compositions comprising one or more bacteria and optionally a compound selected from trimethylamine-N-oxide (TMAO), N,N,N-trimethyl-5-aminovaleric acid (TMAV), imidazole propionic acid (IP), 3-indoxyl sulfuric acid (3-IS), hippuric acid (HIP), perfluorooctanesulfonic acid (PFOS), 3-sulfo-L-alanine, alpha-ketoglutaramic acid, 4-hydroxyglutamic acid, extoine, stachydrine, biotin, pyroglutamine, chiro-inositol, N1-methyl-2-pyridone-5-carboxamide, O-sulfo-L-tyrosine, 2'deoxyuridine, pyrraline, N-delta-acetylornithine, phenylsulfuric acid, phenylacetylglycine, anserine, homostachydrine, serine, N1-methyl-4-pyridone-3-carboxamide, methyl glycopyranoside (alpha+beta), 3-carboxy-1-methylpyridin-1-ium, hypotaurine, 1,5-anhydroglucitol (1,5-AG), 1-oleoyl-2-linoleoyl-GPC (18:1/18:2), methionine, glutamine, malic acid, pantothenic acid, 5,6-dihydrouridine, ceramide (d18:1/17:0 d17:1/18.0) N6-methyllysine, allantoin, N2-acetyllysine, N-acetylglutamine, stearoylcarnitine (C18), arachidoylcarnitine (C20), arabitol, and xylitol, or a salt thereof, or a combination thereof. In certain aspects, provided herein are bacterial compositions comprising one or more bacteria and optionally a compound selected from 3-sulfo-L-alanine, TMAV, IP, TMAO, 3-IS, phenylsulfuric acid, stachydrine, hippuric acid, homostachydrine, pyrraline, alpha-ketoglutaramic acid, O-sulfo-L-tyrosine, methionine, 3-carboxy-1-methylpyridin-1-ium, biotin, glutamine, malic acid, pantothenic acid, pyroglutamine, anserine, 5,6-dihydrouridine, phenylacetylglycine, ceramide (d18:1/17:0 d17:1/18.0), N6-methyllysine, allantoin, N2-acetyllysine, N-acetylglutamine, stearoylcarnitine (C18), arachidoylcarnitine (C20), arabitol, and xylitol, or a salt thereof, or a combination thereof. In certain embodiments, provided herein are bacterial compositions comprising one or more bacteria and optionally a compound selected from methionine, glutamine, malic acid, pantothenic acid, 5,6-dihydrouridine, ceramide (d18:1/17:0 d17:1/18.0), N6-methyllysine, allantoin, N2-acetyllysine, N-acetylglutamine, stearoylcarnitine (C18), arachidoylcarnitine (C20), arabitol, and xylitol, or a salt thereof, or a combination thereof. In certain embodiments, provided herein are bacterial compositions comprising one or more bacteria and optionally a compound selected from TMAO, TMAV, HIP, IP, and 3-IS, or a salt thereof, or a combination thereof. In certain embodiments, provided herein are bacterial compositions comprising one or more bacteria and optionally a compound selected from TMAO, TMAV, and HIP, or a salt thereof, or a combination thereof. In certain embodiments, provided herein are bacterial compositions comprising one or more bacteria and optionally a compound selected from TMAO, TMAV, IP, and 3-IS, or a salt thereof, or a combination thereof. In certain embodiments, provided herein are bacterial compositions comprising one or more bacteria and optionally a compound selected from TMAO, TMAV, IP, and HIP, or a salt thereof, or a combination thereof. In certain embodiments, provided herein are bacterial compositions comprising one or more bacteria and optionally a compound selected from TMAV or TMAO, or a salt thereof, or a combination thereof. In certain embodiments, provided herein are bacterial compositions comprising one or more bacteria and optionally TMAO or a salt thereof. In certain embodiments, the one or more bacteria in the composition are spore-forming bacteria.

Preferably the bacterium is of a bacterial species found in the maternal microbiome (e.g., the maternal gut microbiome), including, but not limited to, a bacterial species selected from spore-forming bacteria (such as order Clostridiales (e.g., family Lachnospiraceae, family Clostridiaceae, family Ruminococcaceae, family Dehalobacteriaceae), order Turicibacterales (e.g., family Turicibacteraceae), order Anaeroplasmatales (e.g., family Anaeroplasmataceae), order Erysipelotrichales (e.g., family Erysipelotrichaceae), and order RF39), order Lactobacillales (e.g., genus *Enterococcus*), order Clostridiales (e.g., family Clostridiaceae, family Peptostreptococcaceae, family Lachnospiraceae), order Turicibacterales (e.g., genus *Turicibacter*), order Erysipelotrichales (e.g., genus *Eubacterium*), order Enterobacteriales, order Bacteroidales (e.g., genus *Bacteroides*), phylum Firmicutes (e.g., class Clostridia, class Bacilli (e.g., order Lactobacillales, order Turicibacterales), class Erysipelotrichi, and class Gammaproteobacteria), phylum Bacteroidetes (e.g., genus *Bacteroides* (such as *B. thetraiotaomicron, B. uniformis, B. vulgatus, B. ovatus, B. fragilus*)), phylum Tenericutes (e.g., class Mollicutes (e.g., order Anaeroplasmatales, order RF39)), or a combination thereof. In some embodiments, the bacterial formulation comprises a bacterium and/or a combination of bacteria described herein and a pharmaceutically acceptable carrier.

In certain embodiments, at least 50%, 55%, 60%, 65%, 70%, 75%, 80%, 85%, 90%, 91%, 92%, 93%, 94%, 95%, 96%, 97%, 98% or 99% of the bacteria in the bacterial composition are spore-forming bacteria selected from order Clostridiales (e.g., family Lachnospiraceae, family Clostridiaceae, family Ruminococcaceae, family Dehalobacteriaceae), order Turicibacterales (e.g., family Turicibacteraceae), order Anaeroplasmatales (e.g., family Anaeroplasmataceae), order Erysipelotrichales (e.g., family Erysipelotrichaceae), and order RF39, or a combination thereof, such as order Clostridiales. In certain embodiments, at least 50%, 55%, 60%, 65%, 70%, 75%, 80%, 85%, 90%, 91%, 92%, 93%, 94%, 95%, 96%, 97%, 98% or 99% of the bacteria in the bacterial composition are selected from order Lactobacillales (e.g., genus *Enterococcus*), order Clostridiales (e.g., family Clostridiaceae, family Peptostreptococcaceae, family Lachnospiraceae), order Turicibacterales (e.g., genus *Turicibacter*), order Erysipelotrichales (e.g., genus *Eubacterium*), order Enterobacteriales, and order Bacteroidales (e.g., genus *Bacteroides*), or a combination thereof. In certain embodiments, at least 50%, 55%, 60%, 65%, 70%, 75%, 80%, 85%, 90%, 91%, 92%, 93%, 94%, 95%, 96%, 97%, 98% or 99% of the bacteria in the bacterial composition are selected from phylum Firmicutes, phylum Tenericutes, phylum Bacteroidetes, or a combination thereof.

In certain embodiments, substantially all of the bacteria in the bacterial composition are spore-forming bacteria selected from order Clostridiales (e.g., family Lachnospiraceae, family Clostridiaceae, family Ruminococcaceae, family Dehalobacteriaceae), order Turicibacterales (e.g., family Turicibacteraceae), order Anaeroplasmatales (e.g., family Anaeroplasmataceae), order Erysipelotrichales (e.g., family Erysipelotrichaceae), and order RF39, or a combination thereof, such as order Clostridiales. In certain embodiments, substantially all of the bacteria in the bacterial composition are selected from order Lactobacillales (e.g., genus *Enterococcus*), order Clostridiales (e.g., family Clostridiaceae, family Peptostreptococcaceae, family Lachnospiraceae), order Turicibacterales (e.g., genus *Turicibacter*), order Erysipelotrichales (e.g., genus *Eubacterium*), order Enterobacteriales, and order Bacteroidales (e.g., genus *Bacteroides*), or a combination thereof. In certain embodiments, substantially all of the bacteria in the bacterial composition are phylum Firmicutes, phylum Tenericutes, or phylum Bacteroidetes, or a combination thereof.

In certain embodiments, the bacterial composition comprises at least $1\times10^3$ colony forming units (CFUs), $1\times10^4$ colony forming units (CFUs), $1\times10^5$ colony forming units (CFUs), $5\times10^5$ colony forming units (CFUs), $1\times10^6$ colony forming units (CFUs), $2\times10^6$ colony forming units (CFUs), $3\times10^6$ colony forming units (CFUs), $4\times10^6$ colony forming units (CFUs), $5\times10^6$ colony forming units (CFUs), $6\times10^6$ colony forming units (CFUs), $7\times10^6$ colony forming units (CFUs), $8\times10^6$ colony forming units (CFUs), $9\times10^6$ colony forming units (CFUs), $1\times10^7$ colony forming units (CFUs), $2\times10^7$ colony forming units (CFUs), $3\times10^7$ colony forming units (CFUs), $4\times10^7$ colony forming units (CFUs), $5\times10^7$ colony forming units (CFUs), $6\times10^7$ colony forming units (CFUs), $7\times10^7$ colony forming units (CFUs), $8\times10^7$ colony forming units (CFUs), $9\times10^7$ colony forming units (CFUs), $1\times10^8$ colony forming units (CFUs), $2\times10^8$ colony forming units (CFUs), $3\times10^8$ colony forming units (CFUs), $4\times10^8$ colony forming units (CFUs), $5\times10^8$ colony forming units (CFUs), $6\times10^8$ colony forming units (CFUs), $7\times10^8$ colony forming units (CFUs), $8\times10^8$ colony forming units (CFUs), $9\times10^8$ colony forming units (CFUs), $1\times10^9$ colony forming units (CFUs), $5\times10^9$ colony forming units (CFUs), $1\times10^{10}$ colony forming units (CFUs) $5\times10^{10}$ colony forming units (CFUs), $1\times10^{11}$ colony forming units (CFUs) $5\times10^{11}$ colony forming units (CFUs), $1\times10^{12}$ colony forming units (CFUs) $5\times10^{12}$ colony forming units (CFUs), $1\times10^{13}$ colony forming units (CFUs) spore-forming bacteria selected from order Clostridiales (e.g., family Lachnospiraceae, family Clostridiaceae, family Ruminococcaceae, family Dehalobacteriaceae), order Turicibacterales (e.g., family Turicibacteraceae), order Anaeroplasmatales (e.g., family Anaeroplasmataceae), order Erysipelotrichales (e.g., family Erysipelotrichaceae), and order RF39, or a combination thereof, such as order Clostridiales.

In certain embodiments, the bacterial composition comprises at least $1\times10^3$ colony forming units (CFUs), $1\times10^4$ colony forming units (CFUs), $1\times10^5$ colony forming units (CFUs), $5\times10^5$ colony forming units (CFUs), $1\times10^6$ colony forming units (CFUs), $2\times10^6$ colony forming units (CFUs), $3\times10^6$ colony forming units (CFUs), $4\times10^6$ colony forming units (CFUs), $5\times10^6$ colony forming units (CFUs), $6\times10^6$ colony forming units (CFUs), $7\times10^6$ colony forming units (CFUs), $8\times10^6$ colony forming units (CFUs), $9\times10^6$ colony forming units (CFUs), $1\times10^7$ colony forming units (CFUs), $2\times10^7$ colony forming units (CFUs), $3\times10^7$ colony forming units (CFUs), $4\times10^7$ colony forming units (CFUs), $5\times10^7$ colony forming units (CFUs), $6\times10^7$ colony forming units (CFUs), $7\times10^7$ colony forming units (CFUs), $8\times10^7$ colony forming units (CFUs), $9\times10^7$ colony forming units (CFUs), $1\times10^8$ colony forming units (CFUs), $2\times10^8$ colony forming units (CFUs), $3\times10^8$ colony forming units (CFUs), $4\times10^8$ colony forming units (CFUs), $5\times10^8$ colony forming units (CFUs), $6\times10^8$ colony forming units (CFUs), $7\times10^8$ colony forming units (CFUs), $8\times10^8$ colony forming units (CFUs), $9\times10^8$ colony forming units (CFUs), $1\times10^9$ colony forming units (CFUs), $5\times10^9$ colony forming units (CFUs), $1\times10^{10}$ colony forming units (CFUs) $5\times10^{10}$ colony forming units (CFUs), $1\times10^{11}$ colony forming units (CFUs) $5\times10^{11}$ colony forming units (CFUs), $1\times10^{12}$ colony forming units (CFUs) $5\times10^{12}$ colony forming units (CFUs), $1\times10^{13}$ colony forming units (CFUs) of bacteria selected from order Lactobacillales (e.g., genus *Enterococcus*), order Clostridiales (e.g., family Clostridiaceae, family Peptostreptococcaceae, family Lachnospiraceae), order Turicibacterales (e.g., genus *Turicibacter*), order Erysipelotrichales (e.g., genus *Eubacterium*), order Enterobacteriales, and order Bacteroidales (e.g., genus *Bacteroides*), or a combination thereof.

In certain embodiments, the bacterial composition comprises at least $1\times10^3$ colony forming units (CFUs), $1\times10^4$ colony forming units (CFUs), $1\times10^5$ colony forming units (CFUs), $5\times10^5$ colony forming units (CFUs), $1\times10^6$ colony forming units (CFUs), $2\times10^6$ colony forming units (CFUs), $3\times10^6$ colony forming units (CFUs), $4\times10^6$ colony forming units (CFUs), $5\times10^6$ colony forming units (CFUs), $6\times10^6$ colony forming units (CFUs), $7\times10^6$ colony forming units (CFUs), $8\times10^6$ colony forming units (CFUs), $9\times10^6$ colony forming units (CFUs), $1\times10^4$ colony forming units (CFUs), $2\times10^7$ colony forming units (CFUs), $3\times10^7$ colony forming units (CFUs), $4\times10^7$ colony forming units (CFUs), $5\times10^7$ colony forming units (CFUs), $6\times10^7$ colony forming units (CFUs), $7\times10^7$ colony forming units (CFUs), $8\times10^7$ colony forming units (CFUs), $9\times10^7$ colony forming units (CFUs), $1\times10^8$ colony forming units (CFUs), $2\times10^8$ colony forming units (CFUs), $3\times10^8$ colony forming units (CFUs), $4\times10^8$ colony forming units (CFUs), $5\times10^8$ colony forming units (CFUs), $6\times10^8$ colony forming units (CFUs), $7\times10^8$ colony forming units (CFUs), $8\times10^8$ colony forming units (CFUs), $9\times10^8$ colony forming units (CFUs), $1\times10^9$ colony forming units (CFUs), $5\times10^9$ colony forming units (CFUs), $1\times10^{10}$ colony forming units (CFUs) $5\times10^{10}$ colony forming units (CFUs), $1\times10^{11}$ colony forming units (CFUs) $5\times10^{11}$ colony forming units (CFUs), $1\times10^{12}$ colony forming units (CFUs) $5\times10^{12}$ colony forming units (CFUs), $1\times10^{13}$ colony forming units (CFUs) of phylum Firmicutes, phylum Tenericutes, or phylum Bacteroidetes, or a combination thereof.

The selected dosage level will depend upon a variety of factors including the subject's diet, the route of administration, the time of administration, the residence time of the particular microorganism being employed, the duration of the treatment, other drugs, compounds and/or materials used in combination with the particular composition employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the bacteria employed in the pharmaceutical composition at levels lower than that required in order to achieve the desired therapeutic effect and gradually increase the dosage until the desired effect is achieved.

In some embodiments, probiotic formulations containing a bacteria selected from spore-forming bacteria (order Clostridiales (e.g., family Lachnospiraceae, family Clostridiaceae, family Ruminococcaceae, family Dehalobacteriaceae), order Turicibacterales (e.g., family Turicibacteraceae), order Anaeroplasmatales (e.g., family Anaeroplasmataceae), order Erysipelotrichales (e.g., family Erysipelotrichaceae), order RF39), order Lactobacillales (e.g., genus *Enterococcus*), order Clostridiales (e.g., family Clostridiaceae, family Peptostreptococcaceae, family Lachnospiraceae), order Turicibacterales (e.g., genus *Turicibacter*), order Erysipelotrichales (e.g., genus *Eubacterium*), order Enterobacteriales, order Bacteroidales (e.g., genus *Bacteroides*), phylum Firmicutes (e.g., class Clostridia, class Bacilli (e.g., order Lactobacillales, order Turicibacterales), class Erysipelotrichi, and class Gammaproteobacteria), phylum Bacteroidetes (e.g., genus *Bacteroides* (such as *B. thetraiotaomicron, B. uniformis, B. vulgatus, B. ovatus, B. fragilus*)), and phylum Tenericutes (e.g., class Mollicutes (e.g., order Anaeroplasmatales, order RF39)), or a combination thereof are provided as encapsulated, enteric coated, or powder forms, with doses ranging up to $10^{11}$ cfu (e.g., up to $10^{10}$ cfu). In some embodiments, the composition comprises $5\times10^{11}$ cfu of a bacteria selected from spore-forming bacteria (order Clostridiales (e.g., family Lachnospiraceae, family Clostridiaceae, family Ruminococcaceae, family Dehalobacteriaceae), order Turicibacterales (e.g., family Turicibacteraceae), order Anaeroplasmatales (e.g., family Anaeroplasmataceae), order Erysipelotrichales (e.g., family Erysipelotrichaceae), order RF39), order Lactobacillales (e.g., genus *Enterococcus*), order Clostridiales (e.g., family Clostridiaceae, family Peptostreptococcaceae, family Lachnospiraceae), order Turicibacterales (e.g., genus *Turicibacter*), order Erysipelotrichales (e.g., genus *Eubacterium*), order Enterobacteriales, order Bacteroidales (e.g., genus *Bacteroides*), phylum Firmicutes (e.g., class Clostridia, class Bacilli (e.g., order Lactobacillales, order Turicibacterales), class Erysipelotrichi, and class Gammaproteobacteria), phylum Bacteroidetes (e.g., genus *Bacteroides* (such as *B. thetraiotaomicron, B. uniformis, B. vulgatus, B. ovatus, B. fragilus*)), and phylum Tenericutes (e.g., class Mollicutes (e.g., order Anaeroplasmatales, order RF39)), or a combination thereof, and 10% (w/w) corn starch in a capsule. In some embodiments, the capsule is enteric coated, e.g., for duodenal release at pH 5.5. In some embodiments, the composition comprises a powder of freeze-dried a bacteria selected from spore-forming bacteria (order Clostridiales (e.g., family Lachnospiraceae, family Clostridiaceae, family Ruminococcaceae, family Dehalobacteriaceae), order Turicibacterales (e.g., family Turicibacteraceae), order Anaeroplasmatales (e.g., family Anaeroplasmataceae), order Erysipelotrichales (e.g., family Erysipelotrichaceae), order RF39), order Lactobacillales (e.g., genus *Enterococcus*), order Clostridiales (e.g., family Clostridiaceae, family Peptostreptococcaceae, family Lachnospiraceae), order Turicibacterales (e.g., genus *Turicibacter*), order Erysipelotrichales (e.g., genus *Eubacterium*), order Enterobacteriales, order Bacteroidales (e.g., genus *Bacteroides*), phylum Firmicutes (e.g., class Clostridia, class Bacilli (e.g., order Lactobacillales, order Turicibacterales), class Erysipelotrichi, and class Gammaproteobacteria), phylum Bacteroidetes (e.g., genus *Bacteroides* (such as *B. thetraiotaomicron, B. uniformis, B. vulgatus, B. ovatus, B. fragilus*)), and phylum Tenericutes (e.g., class Mollicutes (e.g., order Anaeroplasmatales, order RF39)), or a combination thereof, which is deemed to have "Qualified Presumption of Safety" (QPS) status. In some embodiments, the composition is storage-stable at frozen or refrigerated temperature.

Methods for producing microbial compositions may include three main processing steps. The steps are: organism banking, organism production, and preservation. In certain embodiments, a sample that contains an abundance of a bacteria selected from spore-forming bacteria (order Clostridiales (e.g., family Lachnospiraceae, family Clostridiaceae, family Ruminococcaceae, family Dehalobacteriaceae), order Turicibacterales (e.g., family Turicibacteraceae), order Anaeroplasmatales (e.g., family Anaeroplasmataceae), order Erysipelotrichales (e.g., family Erysipelotrichaceae), order RF39), order Lactobacillales (e.g., genus *Enterococcus*), order Clostridiales (e.g., family Clostridiaceae, family Peptostreptococcaceae, family Lachnospiraceae), order Turicibacterales (e.g., genus *Turicibacter*), order Erysipelotrichales (e.g., genus *Eubacterium*), order Enterobacteriales, order Bacteroidales (e.g., genus *Bacteroides*), phylum Firmicutes (e.g., class Clostridia, class Bacilli (e.g., order Lactobacillales, order Turicibacterales), class Erysipelotrichi, and class Gammaproteobacteria), phylum Bacteroidetes (e.g., genus *Bacteroides* (such as *B. thetraiotaomicron, B. uniformis, B. vulgatus, B. ovatus, B. fragilus*)), phylum Tenericutes (e.g., class Mollicutes (e.g., order Anaeroplasmatales, order RF39)), or a combination thereof, may be cultured by avoiding an isolation step.

For banking, a bacteria selected from spore-forming bacteria (order Clostridiales (e.g., family Lachnospiraceae, family Clostridiaceae, family Ruminococcaceae, family Dehalobacteriaceae), order Turicibacterales (e.g., family Turicibacteraceae), order Anaeroplasmatales (e.g., family Anaeroplasmataceae), order Erysipelotrichales (e.g., family Erysipelotrichaceae), order RF39), order Lactobacillales (e.g., genus *Enterococcus*), order Clostridiales (e.g., family Clostridiaceae, family Peptostreptococcaceae, family Lachnospiraceae), order Turicibacterales (e.g., genus *Turicibacter*), order Erysipelotrichales (e.g., genus *Eubacterium*), order Enterobacteriales, order Bacteroidales (e.g., genus *Bacteroides*), phylum Firmicutes (e.g., class Clostridia, class Bacilli (e.g., order Lactobacillales, order Turicibacterales), class Erysipelotrichi, and class Gammaproteobacteria), phylum Bacteroidetes (e.g., genus *Bacteroides* (such as *B. thetraiotaomicron, B. uniformis, B. vulgatus, B. ovatus, B. fragilus*)), and phylum Tenericutes (e.g., class Mollicutes (e.g., order Anaeroplasmatales, order RF39)), or a combination thereof, included in the microbial composition may be (1) isolated directly from a specimen or taken from a banked stock, (2) optionally cultured on a nutrient agar or broth that supports growth to generate viable biomass, and (3) the biomass optionally preserved in multiple aliquots in long-term storage.

In embodiments using a culturing step, the agar or broth may contain nutrients that provide essential elements and specific factors that enable growth. An example would be a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 mg/L hemin chloride, 2 mg/L calcium chloride, 1 mg/L menadione. Another example would be a medium composed of 10 g/L beef extract, 10 g/L peptone, 5 g/L sodium chloride, 5 g/L dextrose, 3 g/L yeast extract, 3 g/L sodium acetate, 1 g/L soluble starch, and 0.5 g/L L-cysteine HCl, at pH 6.8. A variety of microbiological media and variations are well known in the art (e.g., R. M. Atlas, Handbook of Microbiological Media (2010) CRC Press). Culture media can be added to the culture at the start, may be added during the culture, or may be intermittently/continuously flowed through the culture. The strains in the bacterial composition may be cultivated alone, as a subset of the microbial composition, or as an entire collection comprising the microbial composition. As an example, a first strain may be cultivated together with a second strain in a mixed continuous culture, at a dilution rate lower than the maximum growth rate of either cell to prevent the culture from washing out of the cultivation.

The inoculated culture is incubated under favorable conditions for a time sufficient to build biomass. For microbial compositions for human use this is often at 37° C. temperature, pH, and other parameter with values similar to the normal human niche. The environment may be actively controlled, passively controlled (e.g., via buffers), or allowed to drift. For example, for anaerobic bacterial compositions, an anoxic/reducing environment may be employed. This can be accomplished by addition of reducing agents such as cysteine to the broth, and/or stripping it of oxygen. As an example, a culture of a bacterial composition may be grown at 37° C., pH 7, in the medium above, pre-reduced with 1 g/L cysteine-HCl.

When the culture has generated sufficient biomass, it may be preserved for banking. The organisms may be placed into a chemical milieu that protects from freezing (adding 'cryoprotectants'), drying ('lyoprotectants'), and/or osmotic shock ('osmoprotectants'), dispensing into multiple (optionally identical) containers to create a uniform bank, and then treating the culture for preservation. Containers are generally impermeable and have closures that assure isolation from the environment. Cryopreservation treatment is accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term microbial composition storage stability at temperatures elevated above cryogenic conditions. Microbial composition banking may be done by culturing and preserving the strains individually, or by mixing the strains together to create a combined bank. As an example of cryopreservation, a microbial composition culture may be harvested by centrifugation to pellet the cells from the culture medium, the supernatant decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Microbial production may be conducted using similar culture steps to banking, including medium composition and culture conditions described above. It may be conducted at larger scales of operation, especially for clinical development or commercial production. At larger scales, there may be several subcultivations of the microbial composition prior to the final cultivation. At the end of cultivation, the culture is harvested to enable further formulation into a dosage form for administration. This can involve concentration, removal of undesirable medium components, and/or introduction into a chemical milieu that preserves the microbial composition and renders it acceptable for administration via the chosen route. For example, a microbial composition may be cultivated to a concentration of $10^{10}$ CFU/mL, then concentrated 20-fold by tangential flow microfiltration; the spent medium may be exchanged by diafiltering with a preservative medium consisting of 2% gelatin, 100 mM trehalose, and 10 mM sodium phosphate buffer. The suspension can then be freeze-dried to a powder and titrated.

After drying, the powder may be blended to an appropriate potency, and mixed with other cultures and/or a filler such as microcrystalline cellulose for consistency and ease of handling, and the bacterial composition formulated as provided herein.

In certain aspects, provided are bacterial compositions for administration in subjects. In some embodiments, the bacterial compositions are combined with additional active and/or inactive materials in order to produce a final product, which may be in single dosage unit or in a multi-dose format.

In some embodiments, the composition comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

In some embodiments, the composition comprises at least one lipid. As used herein, a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In some embodiments the composition comprises at least one modified lipid, for example a lipid that has been modified by cooking.

In some embodiments, the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In some embodiments, the composition comprises at least one supplemental vitamin. The at least one vitamin can be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

In some embodiments, the composition comprises an excipient. Non-limiting examples of suitable excipients include a buffering agent, a preservative, a stabilizer, a binder, a compaction agent, a lubricant, a dispersion enhancer, a disintegration agent, a flavoring agent, a sweetener, and a coloring agent.

In some embodiments, the excipient is a buffering agent. Non-limiting examples of suitable buffering agents include sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In some embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, and combinations thereof.

In some embodiments, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments, the composition comprises a dispersion enhancer as an excipient. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments, the compositions of the present invention are combined with a carrier (e.g., a pharmaceutically acceptable carrier) which is physiologically compatible with the gastrointestinal tissue of the subject(s) to which it is administered. Carriers can be comprised of solid-based, dry materials for formulation into tablet, capsule or powdered form; or the carrier can be comprised of liquid or gel-based materials for formulations into liquid or gel forms. The specific type of carrier, as well as the final formulation depends, in part, upon the selected route(s) of administration. The therapeutic composition of the present invention may also include a variety of carriers and/or binders. In some embodiments, the carrier is micro-crystalline cellulose (MCC) added in an amount sufficient to complete the one gram dosage total weight. Carriers can be solid-based dry materials for formulations in tablet, capsule or powdered form, and can be liquid or gel-based materials for formulations in liquid or gel forms, which forms depend, in part, upon the routes of administration. Typical carriers for dry formulations include, but are not limited to: trehalose, malto-dextrin, rice flour, microcrystalline cellulose (MCC) magnesium sterate, inositol, FOS, GOS, dextrose, sucrose, and like carriers. Suitable liquid or gel-based carriers include but are not limited to: water and physiological salt solutions; urea; alcohols and derivatives (e.g., methanol, ethanol, propanol, butanol); glycols (e.g., ethylene glycol, propylene glycol, and the like). Preferably, water-based carriers possess a neutral pH value (i.e., pH 7.0). Other carriers or agents for administering the compositions described herein are known in the art, e.g., in U.S. Pat. No. 6,461,607.

In some embodiments, the composition comprises a disintegrant as an excipient. In some embodiments the disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. In some embodiments the disintegrant is an effervescent disintegrant. Non-limiting examples of suitable effervescent disintegrants include sodium bicarbonate in combination with citric acid, and sodium bicarbonate in combination with tartaric acid.

In some embodiments, the bacterial formulation comprises an enteric coating or micro encapsulation. In certain embodiments, the enteric coating or micro encapsulation improves targeting to a desired region of the gastrointestinal tract. For example, in certain embodiments, the bacterial composition comprises an enteric coating and/or microcapsules that dissolves at a pH associated with a particular region of the gastrointestinal tract. In some embodiments, the enteric coating and/or microcapsules dissolve at a pH of about 5.5-6.2 to release in the duodenum, at a pH value of about 7.2-7.5 to release in the ileum, and/or at a pH value of about 5.6-6.2 to release in the colon. Exemplary enteric coatings and microcapsules are described, for example, in U.S. Pat. Pub. No. 2016/0022592, which is hereby incorporated by reference in its entirety.

In some embodiments, the composition is a food product (e.g., a food or beverage) such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Specific examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, and Chinese soups; soups; dairy products such as milk, dairy beverages, ice creams, cheeses, and yogurts; fermented products such as fermented soybean pastes, yogurts, fermented beverages, and pickles; bean products; various confectionery products, including biscuits, cookies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies. The composition may be a fermented food product, such as, but not limited to, a fermented milk product. Non-limiting examples of fermented food products include kombucha, sauerkraut, pickles, miso, tempeh, natto, kimchi, raw cheese, and yogurt. The composition may also be a food additive, such as, but not limited to, an acidulent (e.g., vinegar). Food additives can be divided into several groups based on their effects. Non-limiting examples of food additives include acidulents (e.g., vinegar, citric acid, tartaric acid, malic acid, fumaric acid, and lactic acid), acidity regulators, anticaking agents, antifoaming agents, foaming agents, antioxidants (e.g., vitamin C), bulking agents (e.g., starch), food coloring, fortifying agents, color retention agents, emulsifiers, flavors and flavor enhancers (e.g., monosodium glutamate), flour treatment agents, glazing agents, humectants, tracer gas, preservatives, stabilizers, sweeteners, and thickeners.

In certain embodiments, the bacteria disclosed herein are administered in conjunction with a prebiotic to the subject. Prebiotics are carbohydrates which are generally indigestible by a host animal and are selectively fermented or metabolized by bacteria. Prebiotics may be short-chain carbohydrates (e.g., oligosaccharides) and/or simple sugars (e.g., mono- and di-saccharides) and/or mucins (heavily glycosylated proteins) that alter the composition or metabolism of a microbiome in the host. The short chain carbohydrates are also referred to as oligosaccharides, and usually contain from 2 or 3 and up to 8, 9, 10, 15 or more sugar moieties. When prebiotics are introduced to a host, the prebiotics affect the bacteria within the host and do not directly affect the host. In certain aspects, a prebiotic composition can selectively stimulate the growth and/or activity of one of a limited number of bacteria in a host. Prebiotics include oligosaccharides such as fructooligosaccharides (FOS) (including inulin), galactooligosaccharides (GOS), trans-galactooligosaccharides, xylooligosaccharides (XOS), chitooligosaccharides (COS), soy oligosaccharides (e.g., stachyose and raffinose) gentiooligosaccharides, isomaltooligosaccharides, mannooligosaccharides, maltooligosaccharides and mannanoligosaccharides. Oligosaccharides are not necessarily single components, and can be mixtures containing oligosaccharides with different degrees of oligomerization, sometimes including the parent disaccharide and the monomeric sugars. Various types of oligosaccharides are found as natural components in many common foods, including fruits, vegetables, milk, and honey. Specific examples of oligosaccharides are lactulose, lactosucrose, palatinose, glycosyl sucrose, guar gum, gum Arabic, tagalose, amylose, amylopectin, pectin, xylan, and cyclodextrins. Prebiotics may also be purified or chemically or enzymatically synthesized.

Pharmaceutical Compositions

The compositions and methods of the present invention may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase “pharmaceutically acceptable” is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

“Pharmaceutically acceptable salt” is used herein to refer to an acid addition salt or a basic addition salt which is suitable for or compatible with the treatment of patients.

The term “pharmaceutically acceptable acid addition salt” as used herein means any non-toxic organic or inorganic salt of the disclosed compounds. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, bitartaric, citric, ascorbic, maleic, benzoic, phenylacetic, cinnamic, salicylic, and sulfosalicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds disclosed herein are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds disclosed herein for laboratory use, or for subsequent conversion to a pharmaceutically acceptable acid addition salt.

The term "pharmaceutically acceptable basic addition salt" as used herein means any non-toxic organic or inorganic base addition salt of any acid compounds disclosed herein. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, intraocular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, about 0.1 to about 99.5% (more preferably, about 0.5 to about 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

In certain embodiments, compounds of the invention may be used alone or conjointly administered with another type of therapeutic agent.

In certain embodiments, conjoint administration of compounds of the invention with one or more additional therapeutic agent(s) provides improved efficacy relative to each individual administration of the compound of the invention or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

EXAMPLES

Example 1: The Maternal Microbiome Modulates Fetal Neurodevelopment and Offspring Sensory Behaviour Summary "Dysbiosis" of the maternal gut microbiome, in response to environmental challenges such as infection, altered diet and stress during pregnancy, has been increasingly associated with abnormalities in offspring brain function and behavior. However, whether the maternal gut microbiome regulates neurodevelopment in the absence of environmental challenge remains unclear. In addition, whether the maternal microbiome exerts such influences during critical periods of embryonic brain development is poorly understood. Here we investigate how depletion, and selective colonization, of the maternal gut microbiota influences fetal neurodevelopment. Embryos from antibiotic-treated and germ-free dams exhibit widespread transcriptomic alterations in the fetal brain relative to conventionally-colonized controls, with reduced expression of several genes involved in axonogenesis. In addition, embryos from microbiome-depleted mothers exhibit deficient thalamocortical axons and impaired thalamic axon outgrowth in response to cell-extrinsic guidance cues and growth factors. Consistent with the importance of fetal thalamocortical axonogenesis for shaping sensory processing neural circuits, restricted depletion of the maternal microbiome from pre-conception through mid-gestation yields offspring that exhibit tactile hyposensitivity in sensorimotor behavioral tasks. Gnotobiotic colonization of antibiotic-treated dams with a limited consortium of bacteria indigenous to the gut microbiome prevents abnormalities in fetal brain gene expression, fetal thalamocortical axonogenesis and adult tactile sensory behavior associated with maternal microbiome depletion. Metabolomic profiling reveals that the maternal microbiome regulates levels of numerous small molecules in the maternal serum as well as the brains of fetal offspring. Select microbiome-dependent metabolites—trimethylamine N-oxide, 5-aminovalerate, imidazole propionate, and hippurate—sufficiently promote axon outgrowth from fetal thalamic explants. Moreover, maternal supplementation with the metabolites during early gestation abrogates deficiencies in fetal thalamocortical axons and prevents abnormalities in tactile sensory behavior in offspring from microbiome-depleted dams. Altogether, these findings reveal that the maternal gut microbiome promotes fetal thalamocortical axonogenesis and offspring sensory behavior, likely by direct signaling of microbially modulated metabolites to neurons in the developing brain.

Results and Discussion

The intestinal microbiome is an important modulator of brain function and behavior[1]. However, whether the maternal gut microbiome impacts the brain development during prenatal critical periods is poorly understood. Various model organisms reared devoid of microbial colonization (germ-free, GF) or depleted of the gut microbiome (antibiotic-treated, ABX) exhibit altered neurophysiology and behavior compared to conventionally-colonized (specific pathogen-free, SPF) controls[2-4]. Interestingly, only a subset of phenotypes can be corrected by postnatal restoration of the microbiome[5-8], suggesting a role for the early life microbiome in regulating developmental processes that impact brain function and behavior in adulthood. Indeed, in animal models, the gut microbiome is required for mediating adverse effects of maternal challenges, such as immune activation[9,10], high fat diet[6] and psychosocial stress[11,12], on neurobehavioral abnormalities in adult offspring. It remains unclear, however, whether such microbial influences on neurodevelopment originate antenatally, via disrupted function of the maternal microbiome, and/or postnatally, via vertically transmitted alterations in the neonatal microbiome[13-15]. Moreover, while existing studies report that the maternal gut microbiome can modulate host responses to acute dietary-, stress- or inflammation-related insults, whether it impacts offspring development in the absence of environmental challenges requires investigation. Herein, we examine roles for the maternal gut microbiome during homeostasis in regulating early embryonic brain development and later-life behavior of the offspring.

Figure 2A:
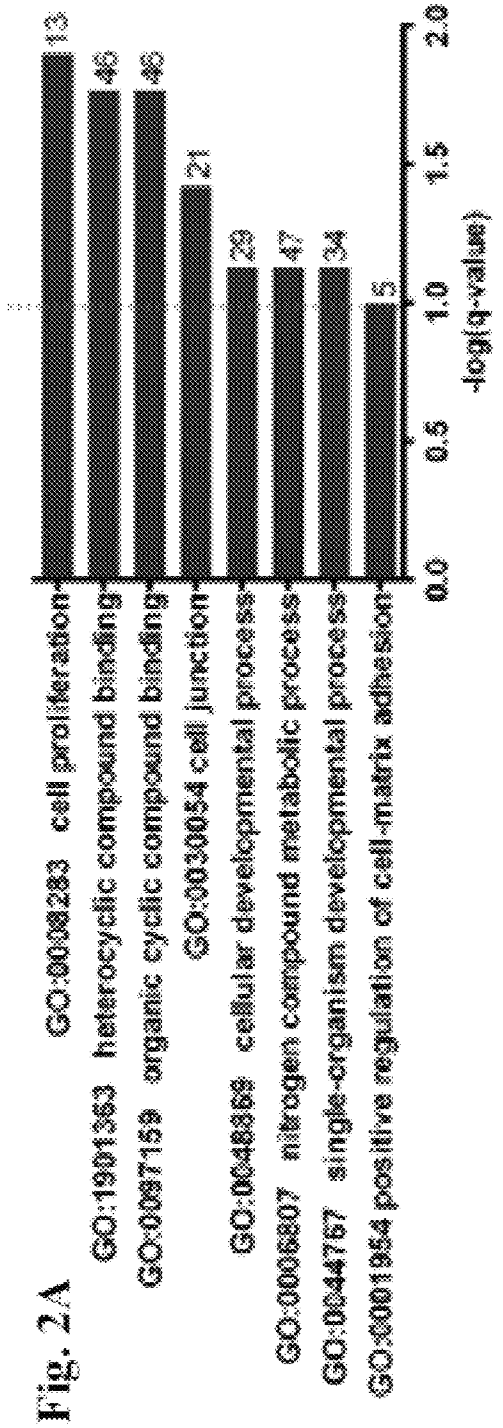
FIGS. 2A-2D: Network analysis and qPCR validation of fetal brain RNAseq data. 2A, DAVID gene ontology analysis of differentially expressed genes from whole embryonic brains from E14.5 offspring of SPF compared to those from ABX dams (Fisher exact, q<0.05, n=offspring from 3 dams per group). 2B, Quantitative RT-PCR for NTNG1 and LRRC4C expression in whole embryonic brains from E14.5 offspring of SPF, ABX or GF dams (Two-way ANOVA with Tukey's, n=offspring from 9 SPF, 15 ABX, 10 Sp dams). 2C, STRING protein interaction network of genes downregulated in whole embryonic brains from E14.5 offspring of ABX dams compared to those from SPF dams (q<0.05, n=offspring from 3 dams). 2D, STRING protein interaction networks of genes upregulated in whole embryonic brains from E14.5 offspring of ABX dams compared to those from SPF dams (q<0.05, n=offspring from 3 dams). Data are presented as mean±SEM. *p<0.05, n.s.=not statistically significant.
Figure 2B:
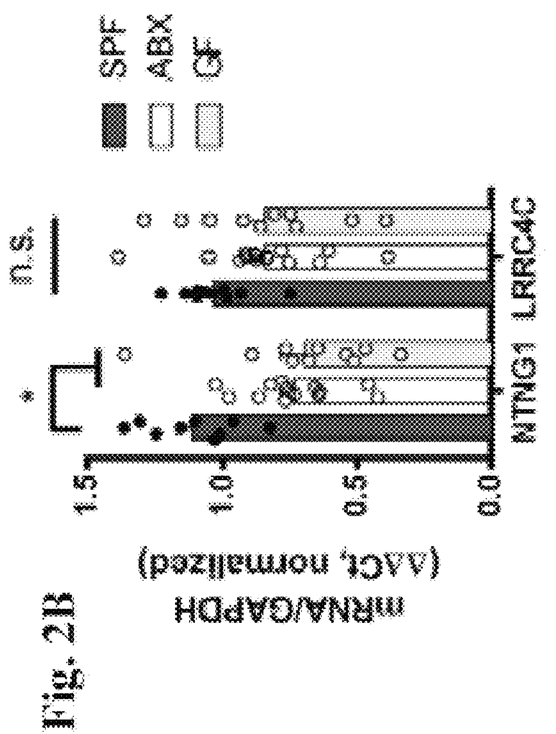
Figures 1, 2C:
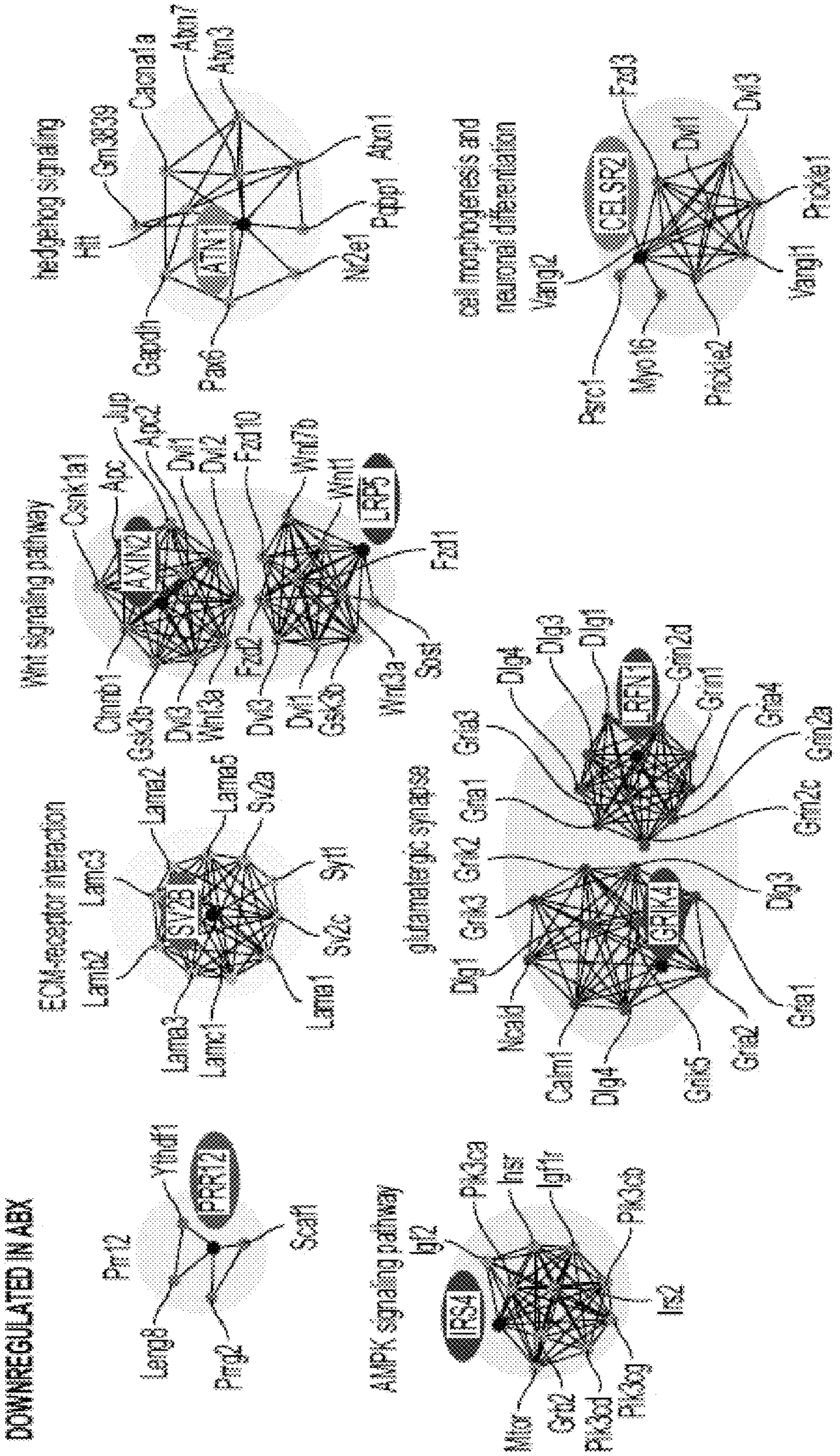
Figures 2, 2C:
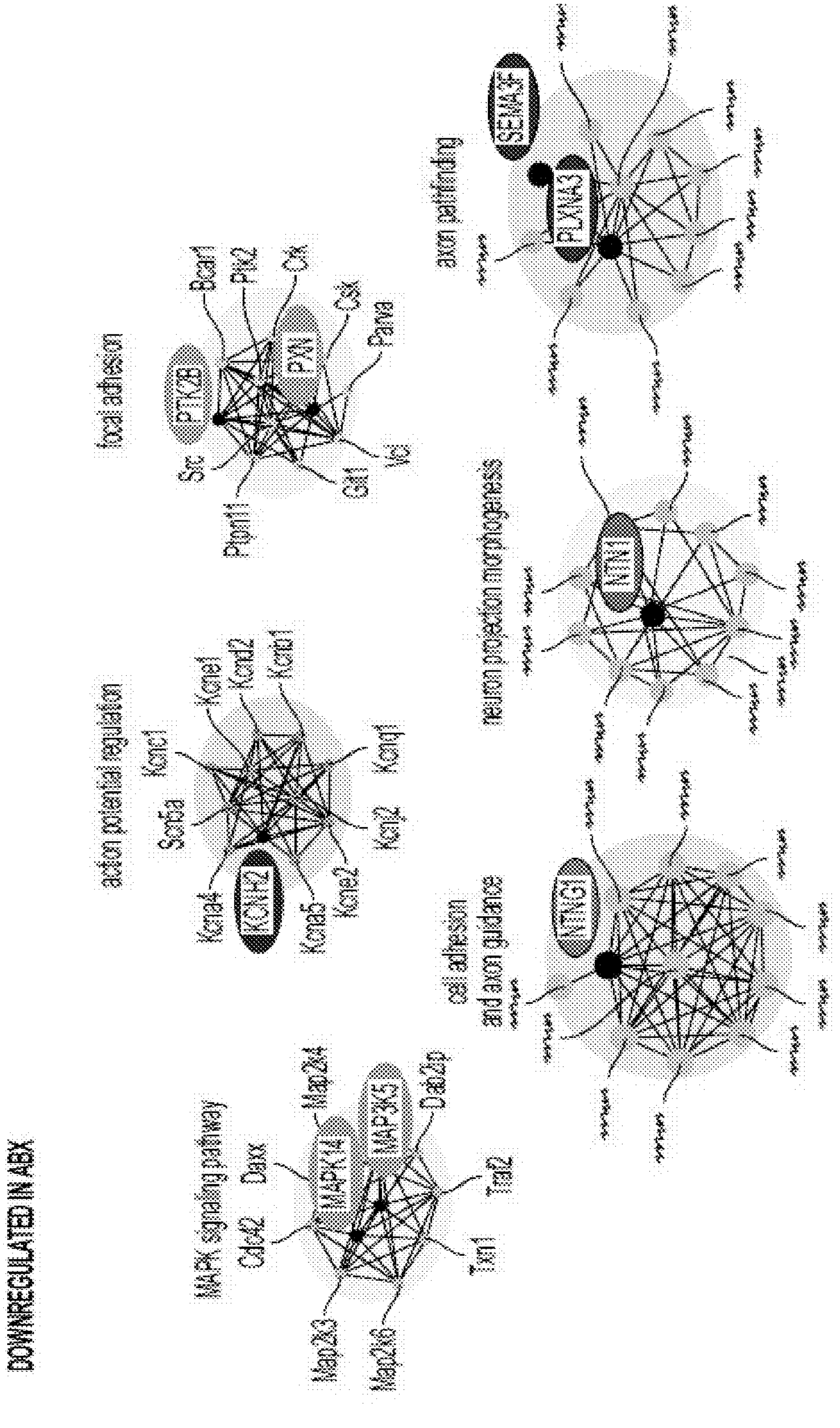
Figures 1, 2D:
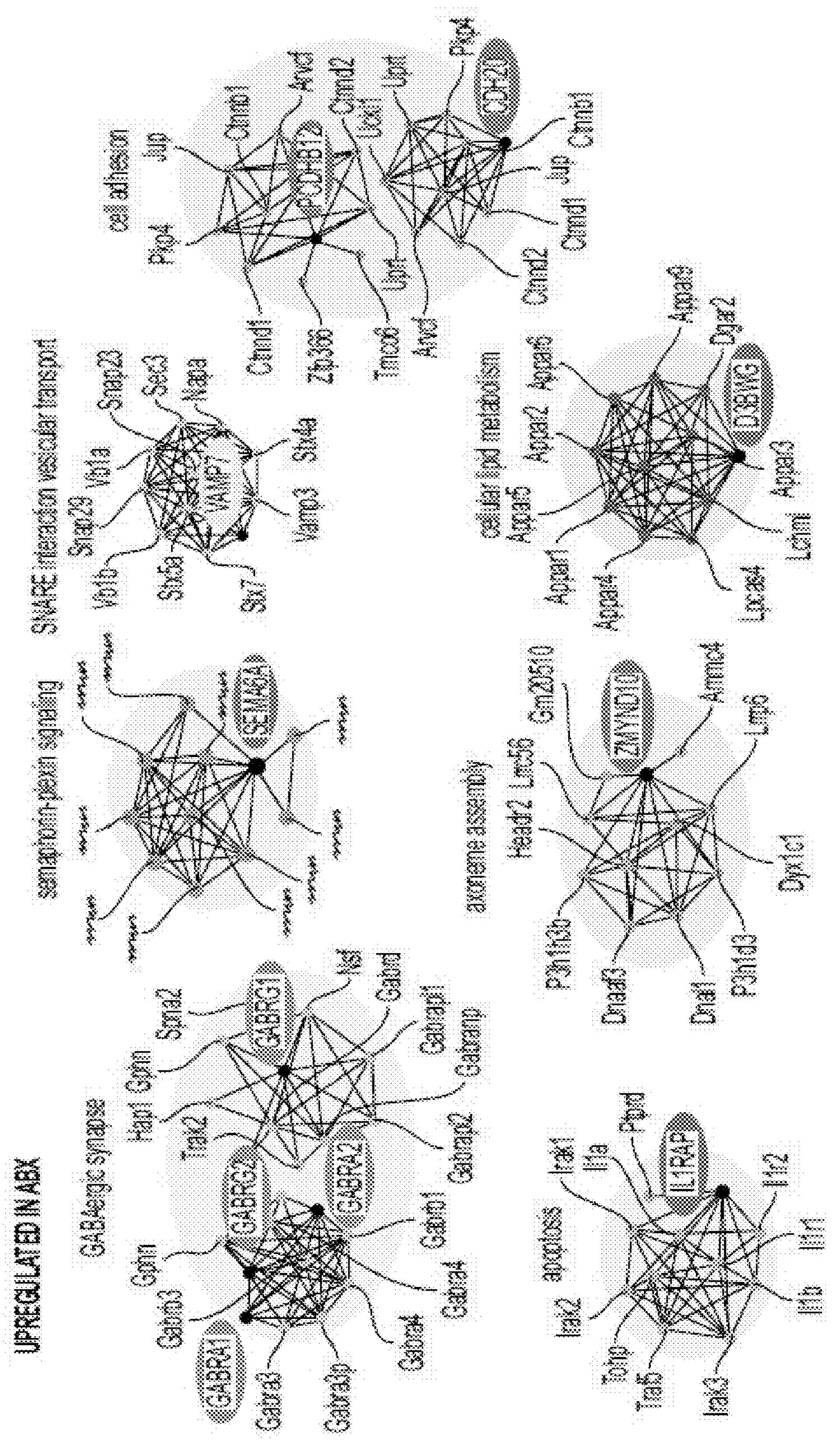
Figures 2, 2D:
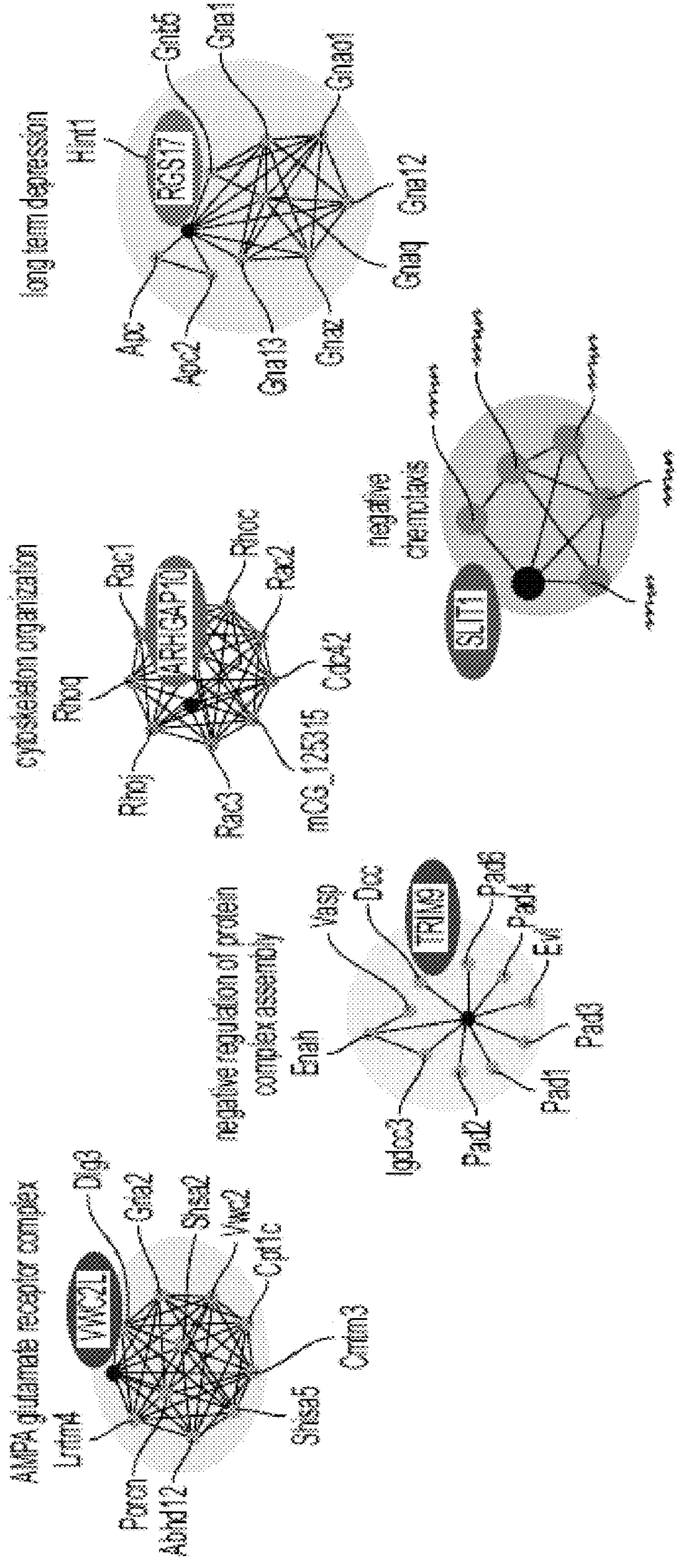
Figure 3A:
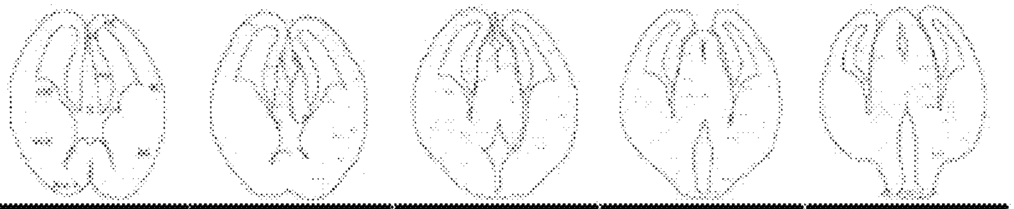
FIGS. 3A-3I: Netrin-G1a thalamocortical axons in embryonic brains of E14.5 offspring from gnotobiotic dams. 3A, Reference diagrams of E14.5 coronal embryonic brain sections. 3B, Immunofluorescence images of Netrin-G1a in four independent embryonic brain sections from E14.5 offspring of SPF dams. 200 μm intervals. Scale bar: 500 μm. 3C, Immunofluorescence image of Netrin-G1a in four independent embryonic brain sections from E14.5 offspring of ABX dams. 200 μm intervals. Scale bar: 500 μm. 3D, Immunofluorescence image of Netrin-G1a in four independent embryonic brain sections from E14.5 offspring of GF dams. 200 μm intervals. Scale bar: 500 μm. 3E, Immunofluorescence image of Netrin-G1a in four independent embryonic brain sections from E14.5 offspring of dams colonized with Sp bacteria. 200 μm intervals. Scale bar: 500 μm. 3F, Average Netrin-G1 a fluorescence intensity per matched area of region of interest (ROI) ("yellow-in-the-original-image" dotted lines) in 800 μm of rostral to caudal embryonic brain sections of E14.5 offspring from SPF, ABX, GF and Sp-colonized dams. (Two-way ANOVA with Tukey's, n=offspring from 5 SPF, 7 ABX, 4 GF, 5 Sp dams). 3G, Total Netrin-G1a fluorescence intensity across 800 μm of rostral to caudal sections of E14.5 embryonic brains from SPF, ABX, GF, and Sp-colonized dams. (Two-way ANOVA with Tukey's, n=offspring from 5 SPF, 7 ABX, 4 GF, 5 Sp dams). 3H, Average area of Netrin-G1a-positive staining across 800 μm of rostral to caudal embryonic brain sections of E14.5 offspring from SPF, ABX, GF and Sp-colonized dams. (Two-way ANOVA with Tukey's, n=offspring from 5 SPF, 7 ABX, 4 GF, 5 Sp dams). 3I, Average DAPI fluorescence intensity normalized to per matched ROI ("yellow-in-the-original-image" dotted lines) in 800 μm of rostral to caudal embryonic brain sections of E14.5 offspring from SPF, ABX, GF and Sp-colonized dams. (Two-way ANOVA with Tukey's, n=offspring from 5 SPF, 7 ABX, 4 GF, 5 Sp dams). Data are presented as mean±SEM. *p<0.05, p<0.01, *p<0.001, ****p<0.0001, n.s.=not statistically significant.
Figure 3B:
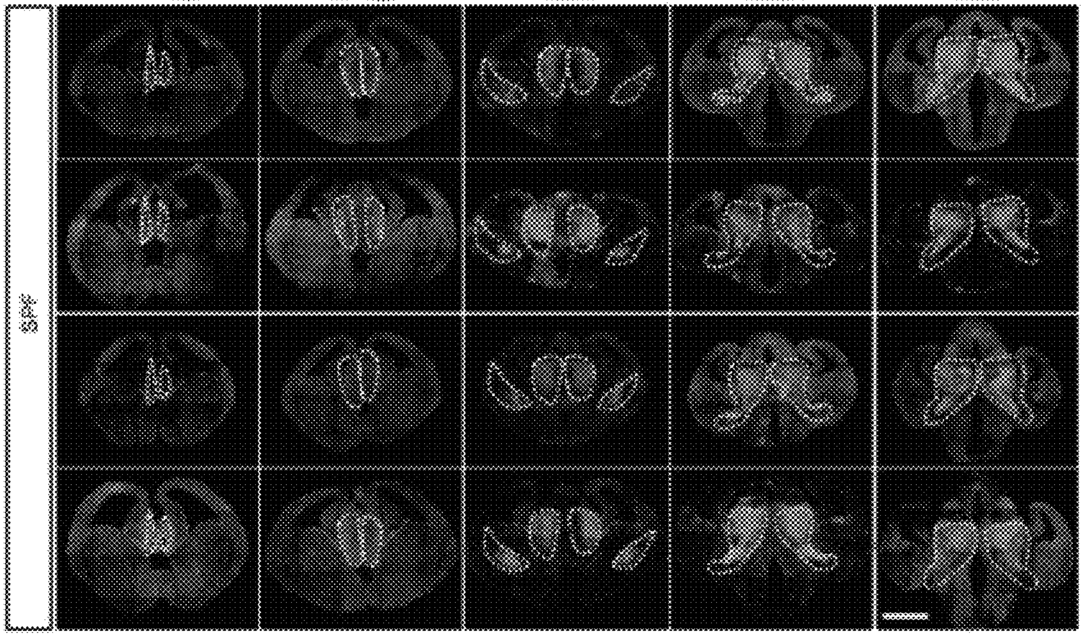
Figure 3C:
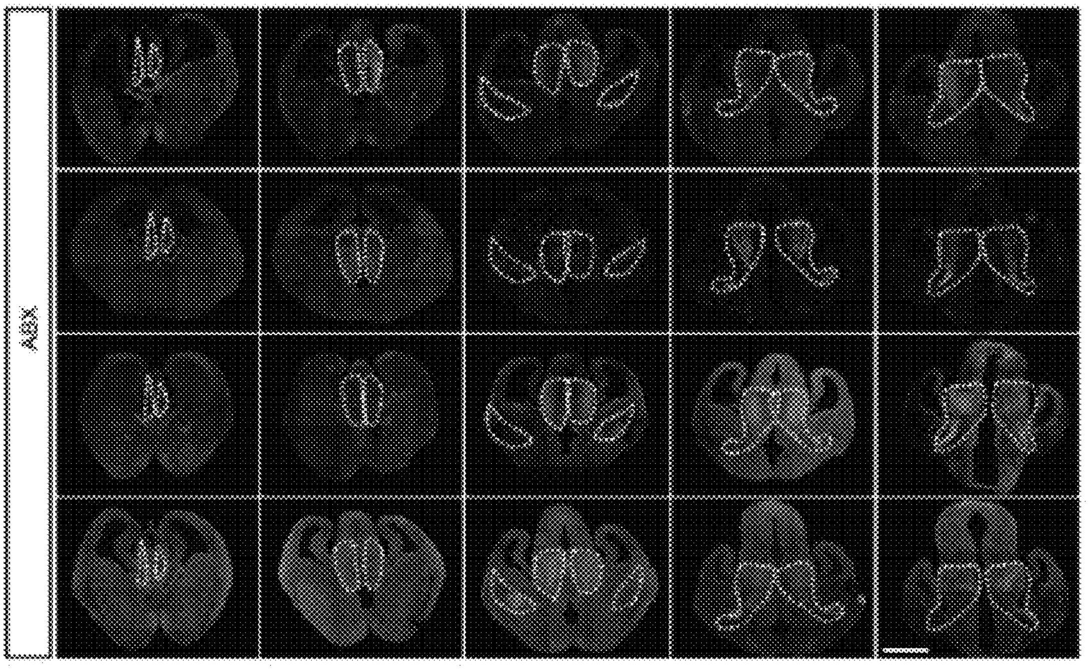
Figure 3D:
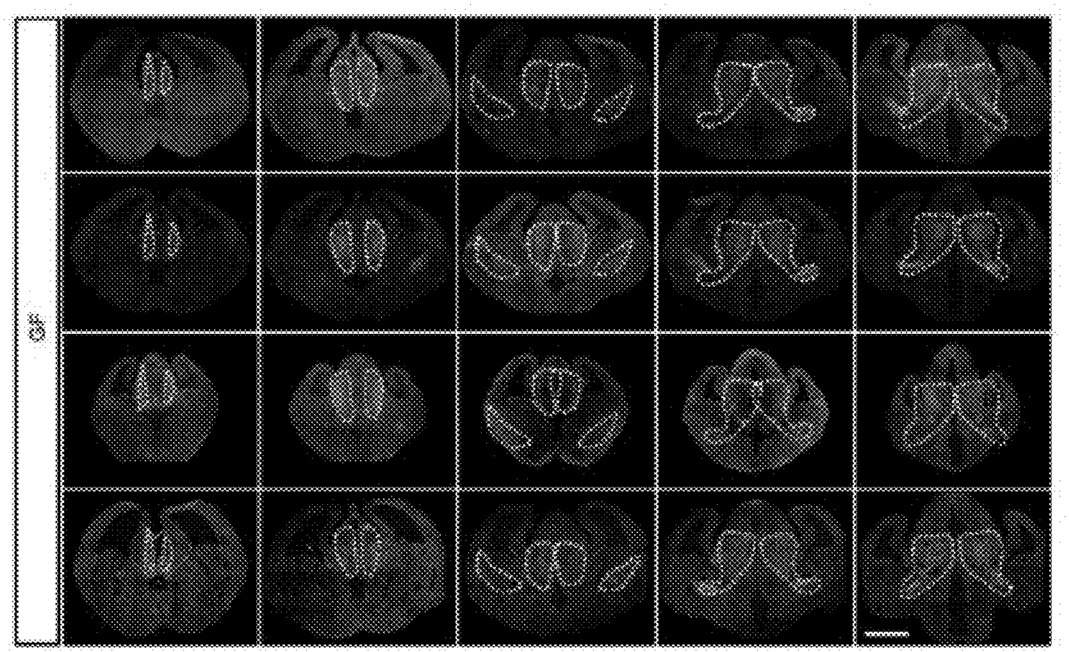
Figure 3E:
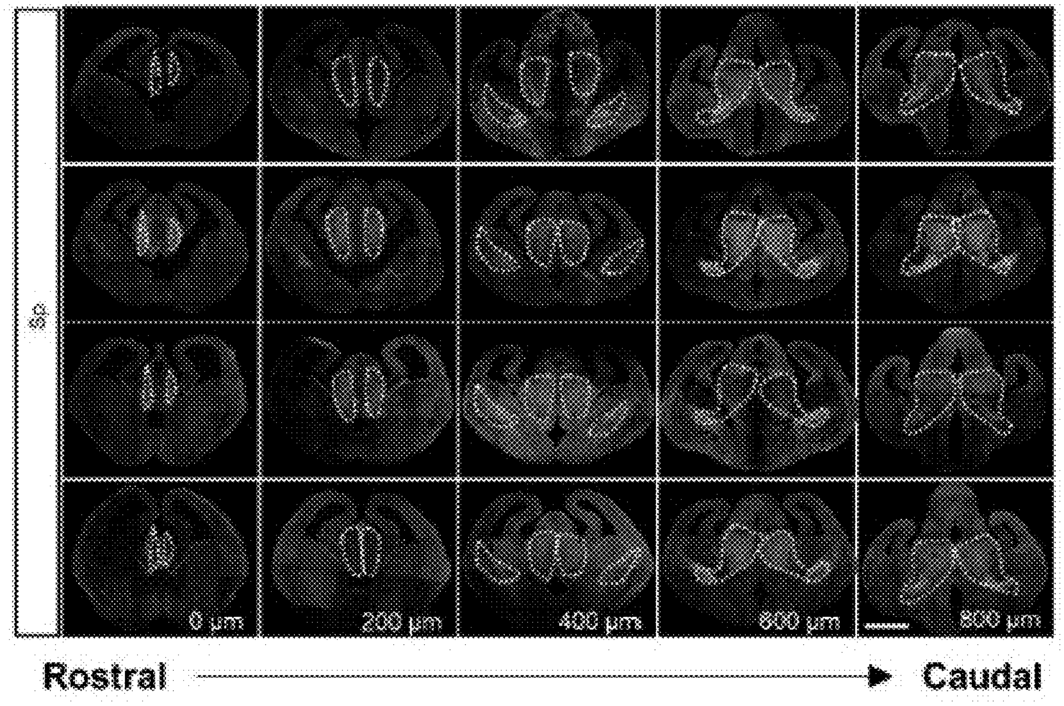
Figure 3F:
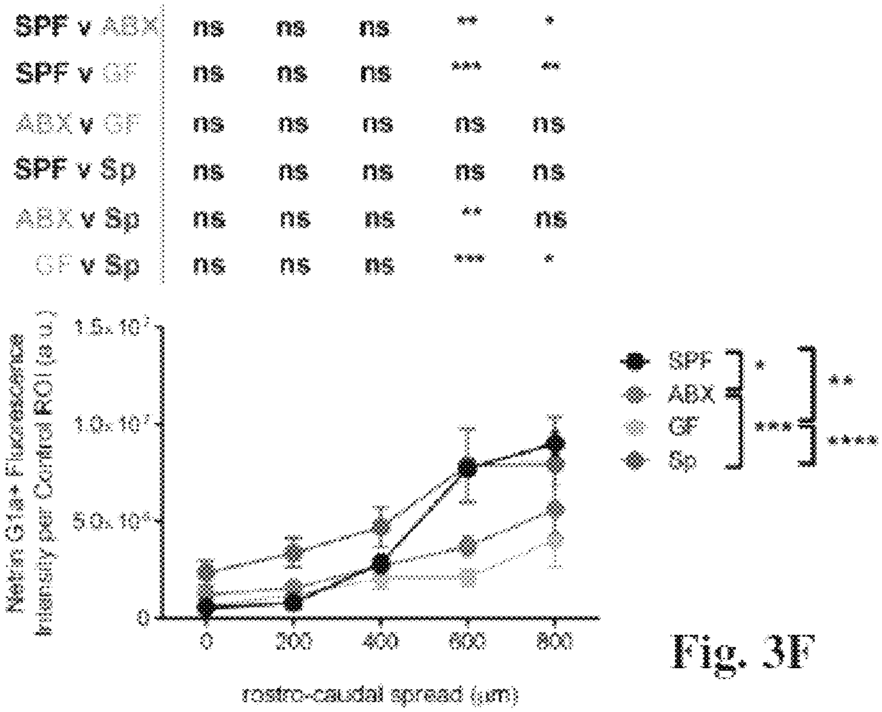
Figure 3G:
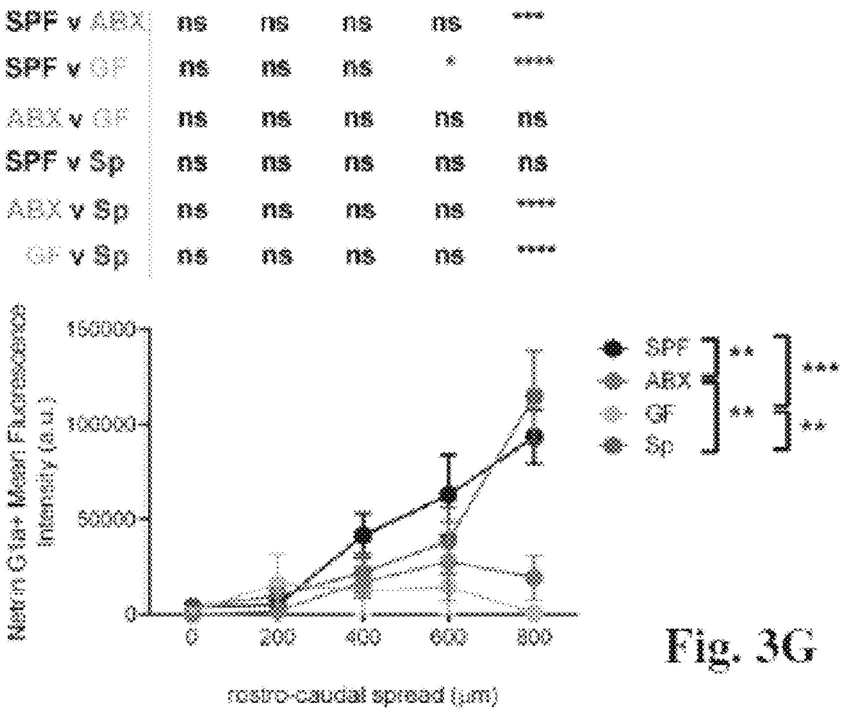
Figure 3H:
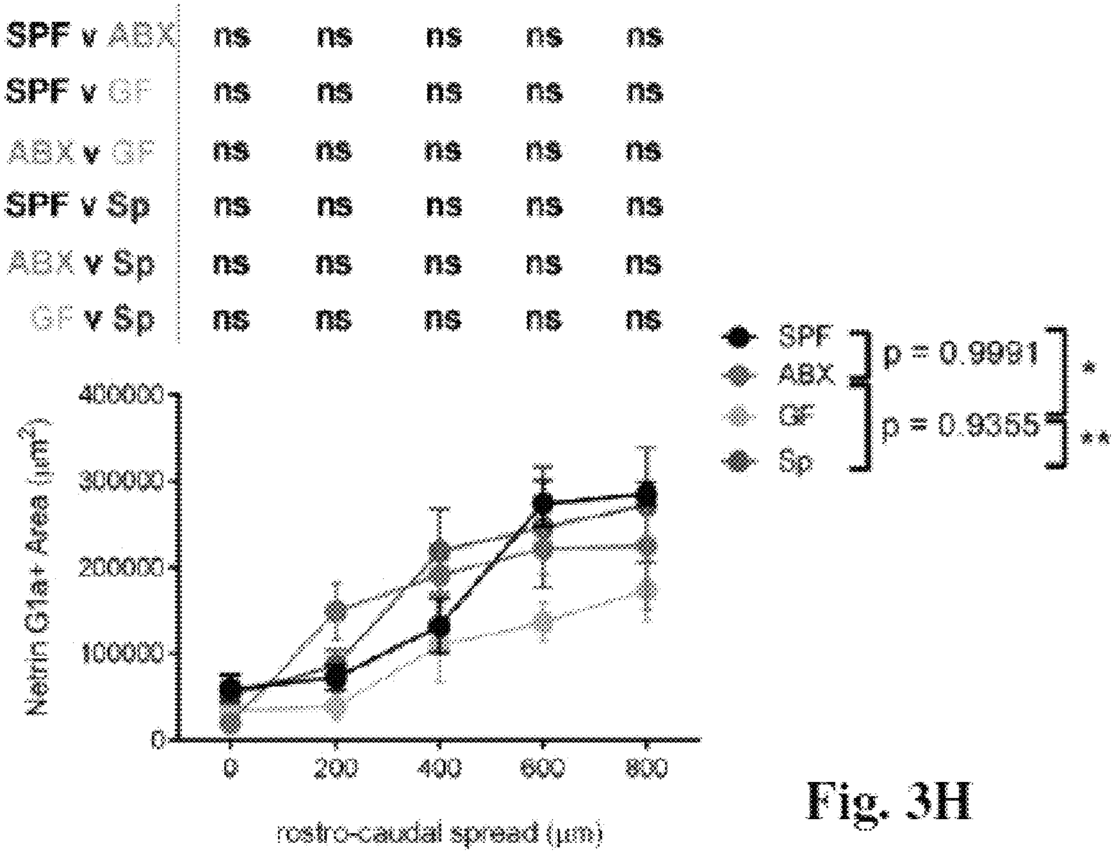
Figure 3I:
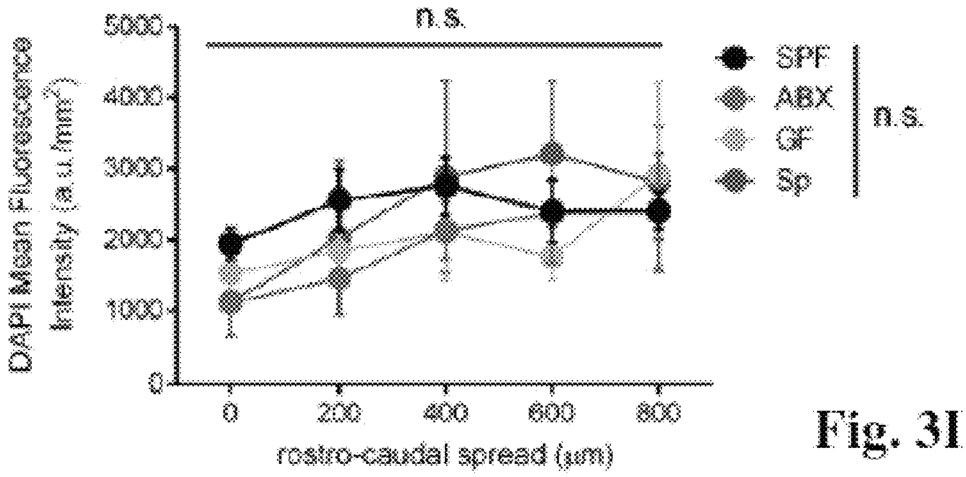
Figure 4A:
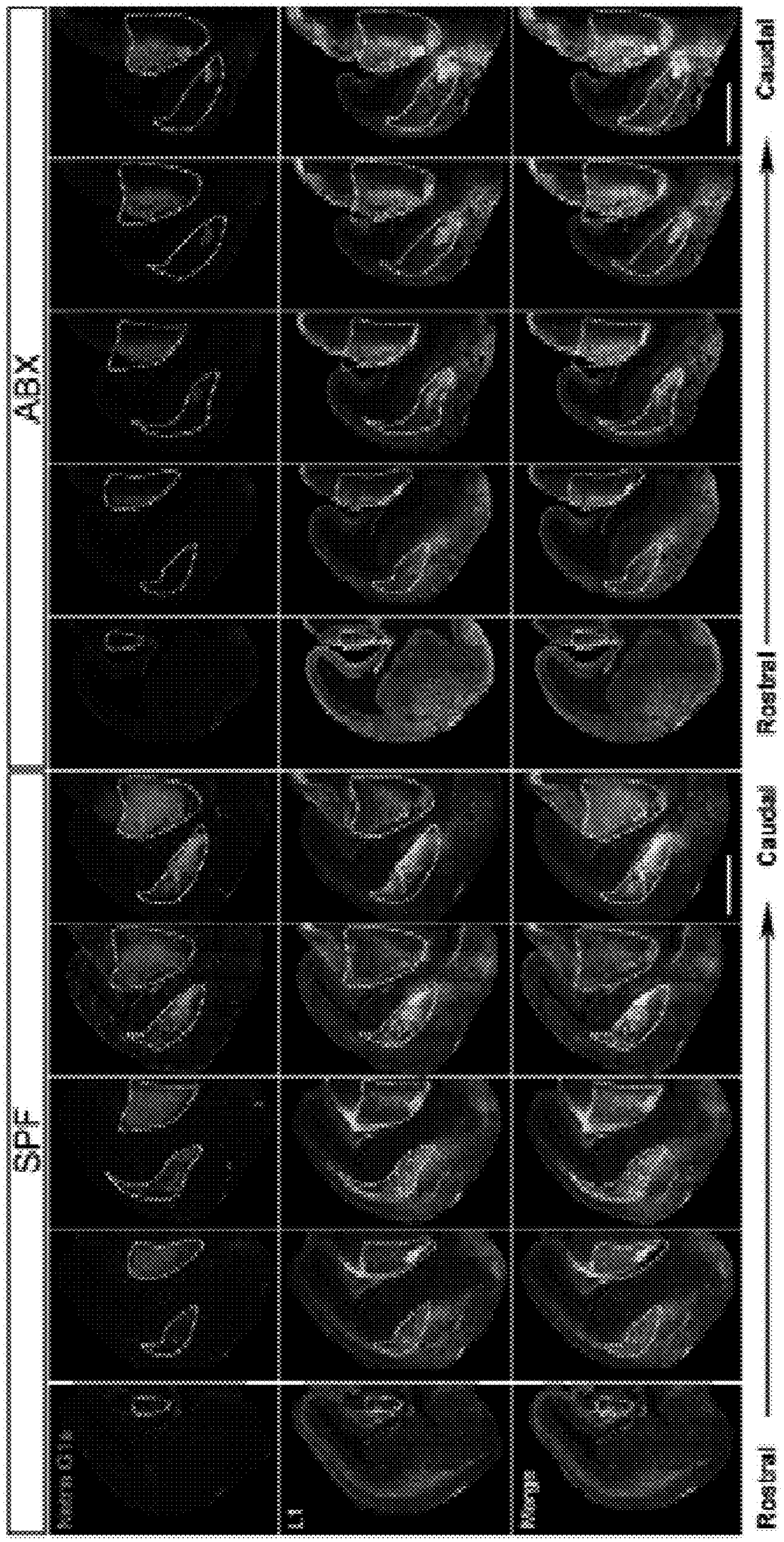
Figure 4B:
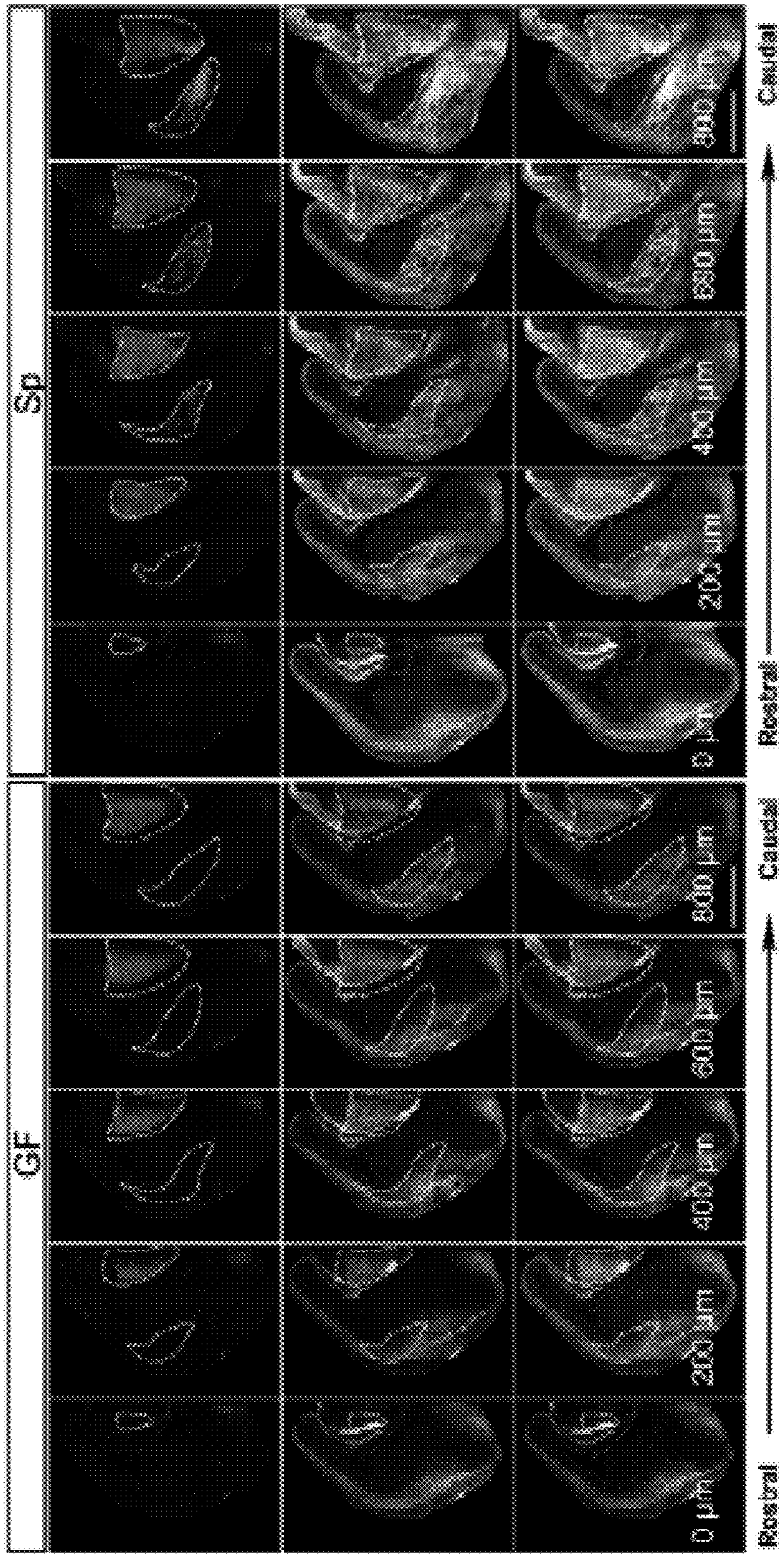

To determine whether the maternal microbiome influences fetal neurodevelopment, we first examined fetal brains from offspring of murine dams that were reared SPF, GF, or treated with broad-spectrum ABX to deplete the maternal gut microbiome from pre-conception through midgestation [embryonic day (E)14.5]. Transcriptomic profiling revealed that depletion of the maternal microbiome altered the expression of 333 genes in fetal brains of E14.5 embryos, including many involved in axonogenesis (FIG. 1A, Table 1). Gene ontology analysis indicated that these genes were relevant for cell proliferation, cell junction, cell-matrix adhesion and cellular developmental processes (FIG. 2A). The 160 downregulated genes mapped to protein interaction networks that included those relevant to axon guidance, Wnt signaling, cell morphogenesis, neuronal differentiation and glutamatergic synapse (FIG. 2C), whereas the 173 upregulated genes mapped to networks that included those relevant to apoptosis, long-term depression, cell adhesion and GABAergic synapse (FIG. 2D). Validation by qPCR revealed consistent downregulation of Netrin-G1 a (NTNG1), a glycosylphosphatidylinositol-tethered protein highly expressed by developing thalamocortical axons[16], in fetal brains from offspring of both ABX and GF dams (FIG. 2B). Consistent with observed reductions in NTNG1 transcript (FIG. 1A, FIG. 2C), fetal brain sections from E14.5 offspring of both ABX and GF dams exhibited reduced Netrin-G1a+immunoreactivity localized to thalamocortical neurons (FIGS. 1B-1C, FIGS. 3A-3I). In addition, evaluation of three-dimensional representations of Netrin-G1a+ thalamocortical axons in cleared whole embryonic brains revealed decreased axonal volume and length in E14.5 offspring from microbiome-depleted dams, with corresponding increases in distances from the leading axon to the cortex and reduced circumference of the axonal bundle at the internal capsule (FIGS. 1E-1I). Notably, fetal brains from ABX offspring displayed decreased L1+ axonal immunoreactivity compared to SPF control, but no significant differences in neuronal DAPI levels in the thalamus (FIG. 1D, FIGS. 31 and 4A-4E). This suggests that the reductions in Netrin-G1a expression reflect decreases in thalamocortical axonal projections, rather than diminished receptor expression on existing axons or the absence of thalamic neurons themselves.

These findings align with recent studies reporting reductions in adult axonal markers in the cortex and myenteric plexus in response to microbiota depletion[17-20] (Example 3). Overall, results from these experiments suggest that the maternal microbiome is required to support fetal thalamocortical axonogenesis in the developing offspring.

Figures 5A, 5B, 5C, 5D, 5E, 5F:
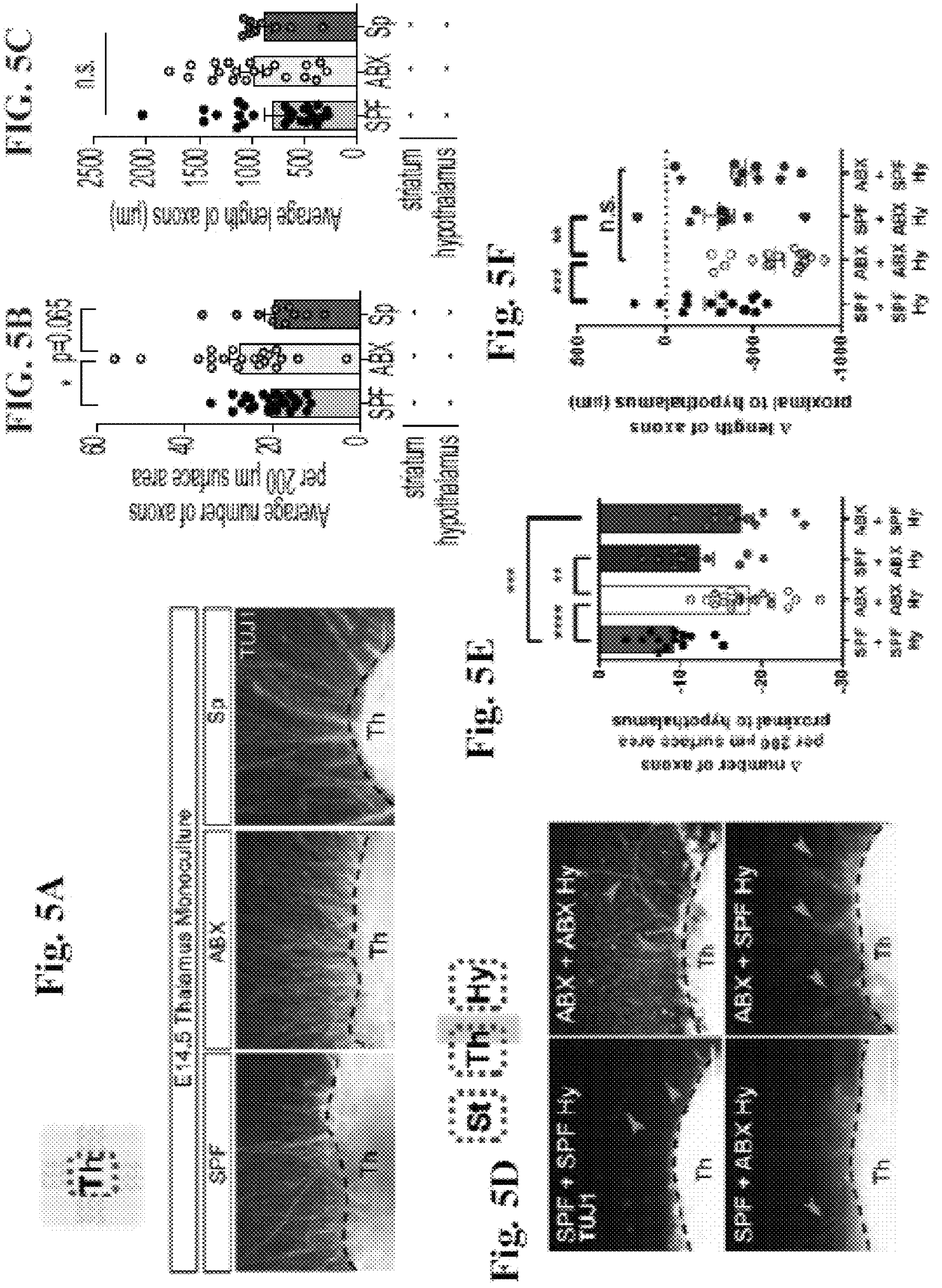

Axonogenesis involves cell intrinsic and extrinsic factors that work in concert to direct axon polarity, elongation and pathfinding. To gain insight into whether the reductions in Netrin-G1a+thalamocortical axons seen in response to maternal microbiome depletion were due to impaired axon formation, deficient axon guidance, or both, we cultured E14.5 thalamic explants, either alone or in the presence of endogenous cues from striatal and hypothalamic explants[21,22]. Monoculture of E14.5 thalamic explants from offspring of either SPF or ABX dams resulted in substantial axon outgrowth (FIGS. 5A-5C), suggesting that the reductions in Netrin-Ole axons seen in embryos of microbiome-depleted dams are not due to an intrinsic inability of the thalamus to form or elongate axons. Indeed, thalamic neurons from embryos of ABX dams generated increased numbers of axons when grown in cell culture matrices containing growth factors, with no significant difference in axon length, as compared to SPF controls (FIGS. 5A-5C); this suggests enhanced capacity for axon formation, but not elongation, in fetal thalamic neurons from ABX dams that are grown in rich media. However, in response to co-culture with fetal striatal and hypothalamic explants from ABX dams, fetal thalamic neurons from embryos of ABX dams exhibited impaired axon outgrowth, with decreased number and length of axons as compared to co-cultured control explants from SPF mothers (FIGS. 1J-1M, white vs. black). These abnormalities in cue-mediated axonal outgrowth were observed for thalamic axons proximal to the striatal explant (FIGS. 1J-1M, white vs. black), which produces growth promoting and attractive guidance cues[23,24], as well as axons proximal to the hypothalamic explant (FIGS. 5D-5F, white vs. black), which produces growth-inhibiting and repulsive guidance cues[25,26]. Taken together, these results indicate that fetal thalamic neurons from E14.5 offspring of ABX dams display deficient axon outgrowth in response to cell-extrinsic tissue-derived factors.

To gain further insight into whether depletion of the maternal microbiome alters tissue-derived cues to impair axon outgrowth, fetal thalamic explants from E14.5 embryos of SPF or ABX dams were co-cultured with striatal and hypothalamic explants from the contrasting experimental group. When thalamic explants from E14.5 embryos of SPF dams were co-cultured with fetal striatal and hypothalamic explants from offspring of ABX dams, there were no significant differences in the number or length of axons from SPF thalamic neurons proximal to the ABX striatal (FIGS. 1J-1M; purple in the original image vs. black) or hypothalamic explants (FIGS. 5D-5F; purple in the original image vs. black). This suggests that tissue-derived factors from ABX dams sufficiently support axon outgrowth from SPF thalamic neurons. In contrast, when thalamic explants from E14.5 embryos of ABX dams were co-cultured with fetal striatal and hypothalamic explants from offspring of SPF dams, fetal thalamic neurons from ABX offspring exhibited deficiencies in axon outgrowth, at levels similar to those seen in response to co-culture with ABX tissues (FIGS. 1J-1M, FIGS. 5D-5F; teal in the original image vs. white). This suggests that endogenous soluble factors from SPF explants are not sufficient to correct impairments in axon outgrowth of ABX thalamic neurons, and that ABX thalamic neurons display incorrect responses to factors from SPF tissues. Such impairments in axon outgrowth in response to tissue-derived cues could be attributed to erroneously repulsive responses to attractive guidance cues[27,28], hyperresponsiveness to repulsive cues[29] and/or cue-induced disruptions in responses to neurotrophic factors present in the culture media[30]. Overall, these findings indicate that tissue-derived cues are necessary but not sufficient for mediating maternal microbiota-dependent reductions in thalamic axonogenesis and further suggest that depletion of the maternal microbiome impairs responses of embryonic thalamocortical neurons to axonogenic cues.

Figure 6A:
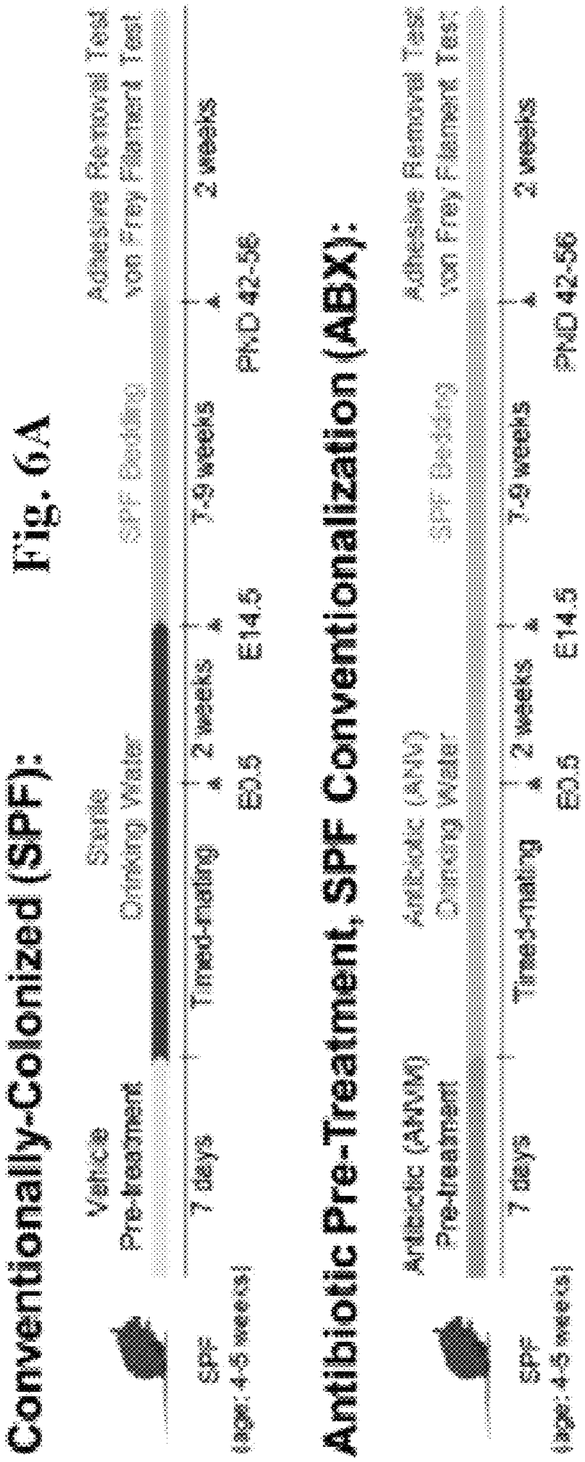
FIGS. 6A-6G: Depletion of the maternal microbiota during early gestation yields adult offspring with deficient tactile sensory behavior. 6A, Experimental timeline of vehicle or ABX treatment at 1 week prior to timed mating, conventionalization with SPF bedding on E14.5, and offspring behavioral testing at 6-8 weeks. 6B, The von Frey filament test applies filaments with increasing force (0.4, 0.6, 1, 1.4, 2, 4 grams) to the hindpaw to identify the threshold mechanical force needed to elicit a sensorimotor response. 6C, Force filament required to induce 50% paw withdrawal in adult offspring of SPF and ABX dams (One-way ANOVA with Tukey's, n=offspring from 5 SPF and 7 ABX dams). 6D, Adhesive removal test for sensorimotor behavioral measures sensitivity to detect and dexterity to remove an adhesive tape placed on the mouse forepaw. 6E, Forepaw sensitivity, as measured as the latency to contact the adhesive tape, in adult offspring of SPF and ABX dams (One-way ANOVA with Tukey's, n=offspring from 6 dams per group). 6F, Forepaw motor dexterity, as measured as the latency to remove the adhesive tape after first contact, in adult offspring of SPF and ABX dams (One-way ANOVA with Tukey's, n=offspring from 6 dams per group). 6G, Data for latency to contact and latency to remove the forepaw adhesive in individual mice. (Two-way ANOVA with Sidak's, n=offspring from 6 dams per group). Data are presented as mean±SEM. Data shown for SPF and ABX are as displayed in FIGS. 10A-10M, 12A-12I, 14A-14I, 7A-7F, and 17A-17F. Statistics reflect analysis together with experimental groups: Sp. p<0.01, *p<0.001.
Figure 6B:
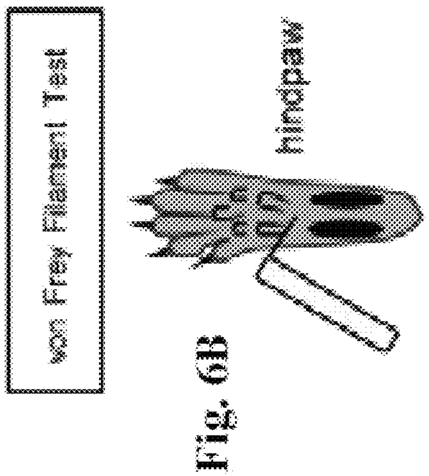
Figure 6C:
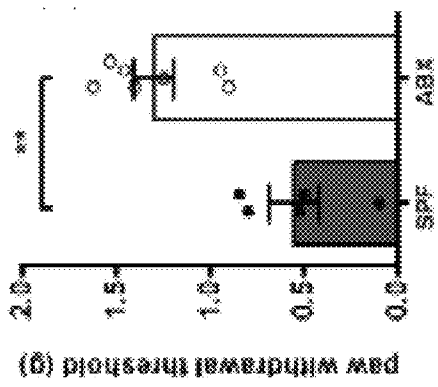
Figure 6D:
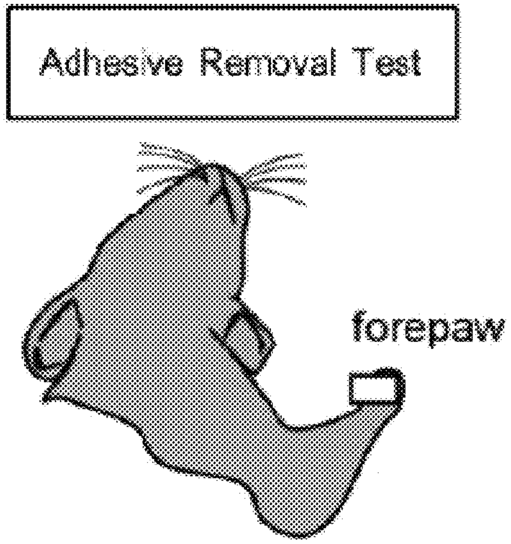
Figure 6E:
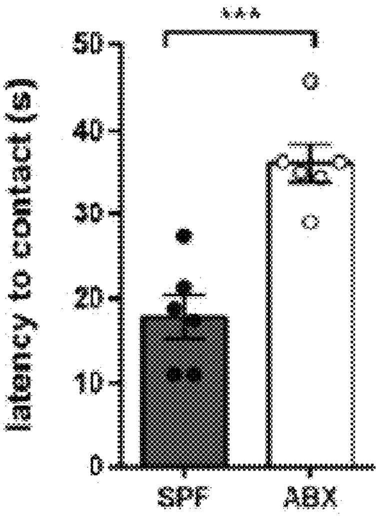
Figure 6F:
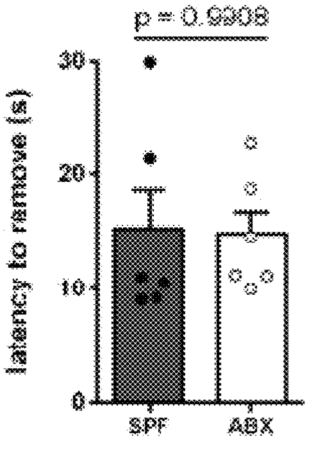
Figure 6G:
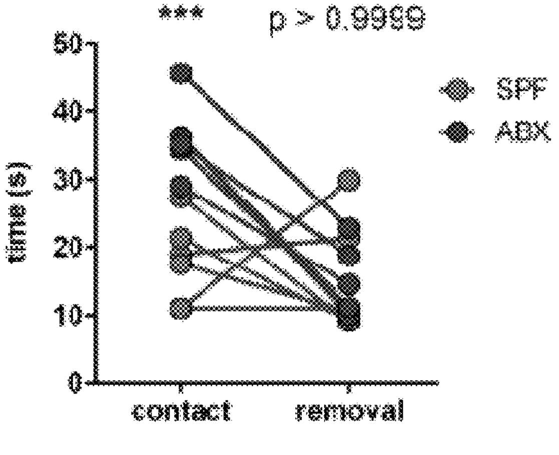
Figure 7A:
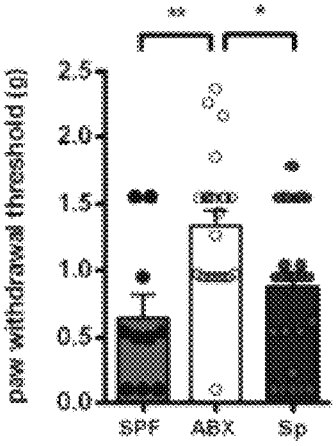
FIGS. 7A-7F: Absence of sex differences in behavioral performance of offspring from gnotobiotic dams. 7A, Force filament required to induce 50% paw withdrawal in adult offspring of SPF, ABX, and Sp dams (One-way ANOVA with Tukey's, n=10 SPF, 23 ABX, 25 Sp offspring). 7B, Latency to contact the adhesive tape, in adult offspring of SPF, ABX, Sp dams (One-way ANOVA with Tukey's, n=25 SPF, 19 ABX, 39 Sp offspring). 7C, Latency to remove the adhesive tape after first contact in adult offspring of SPF, ABX, and Sp dams (One-way ANOVA with Tukey's, n=25 SPF, 19 ABX, 39 Sp offspring). 7D, Force filament required to induce 50% paw withdrawal in male and female adult offspring of SPF, ABX, and Sp dams. Male and female comparisons per litter (left) or individual offspring (right) (Two-way ANOVA with Tukey's, n=10 male, 10 female SPF; 7 male, 16 female ABX; 13 male, 12 female Sp offspring). 7E, Latency to contact the adhesive tape in male and female adult offspring of SPF, ABX, Sp dams. Male and female comparisons per litter (left) or individual offspring (right) (Two-way ANOVA with Tukey's, 15 male, 10 female SPF; 4 male, 15 female ABX; 21 male, 18 female Sp offspring). 7F, Latency to remove the adhesive tape after first contact in male and female adult offspring of SPF, ABX, and Sp dams. Male and female comparisons per litter (left) or individual offspring (right) (Two-way ANOVA with Tukey's, n=15 male, 10 female SPF; 4 male, 15 female ABX; 20 male, 18 female Sp offspring). Data are presented as mean±SEM. *p<0.05, p<0.01, *p<0.001, n.s=not statistically significant.
Figure 7B:
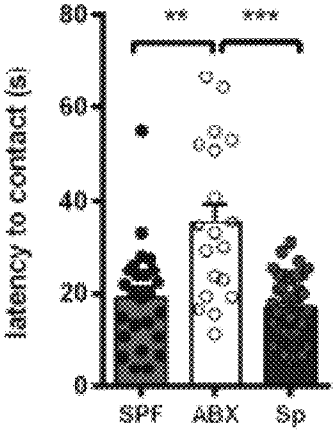
Figure 7C:
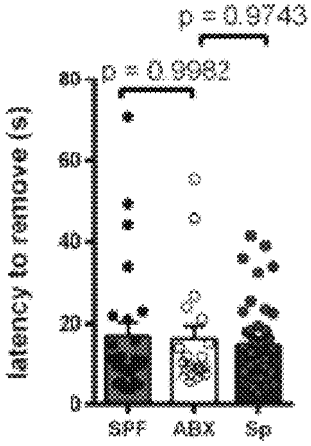
Figure 7D:
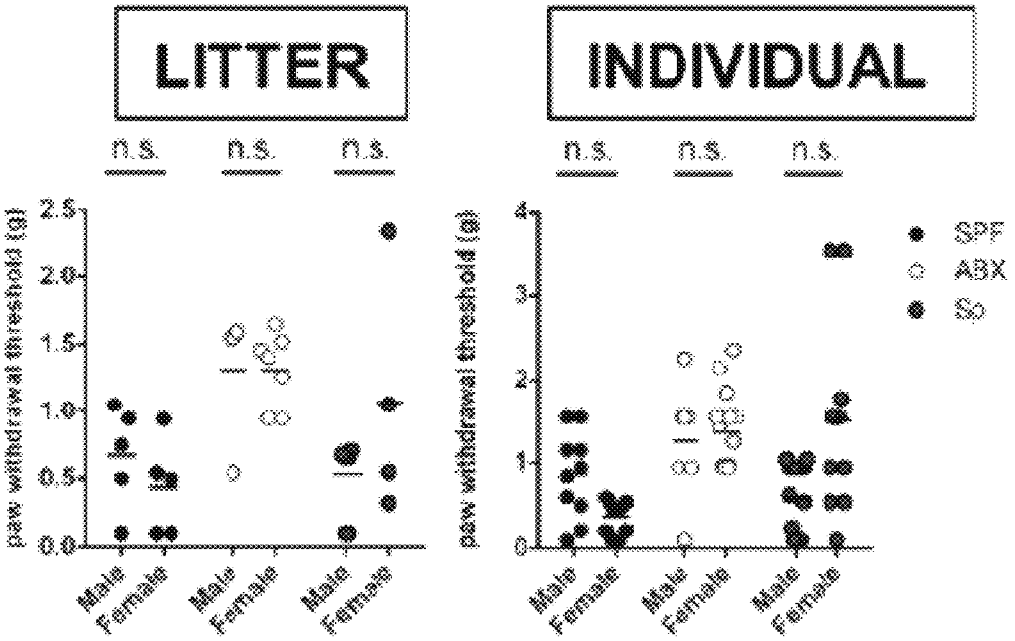
Figure 7E:
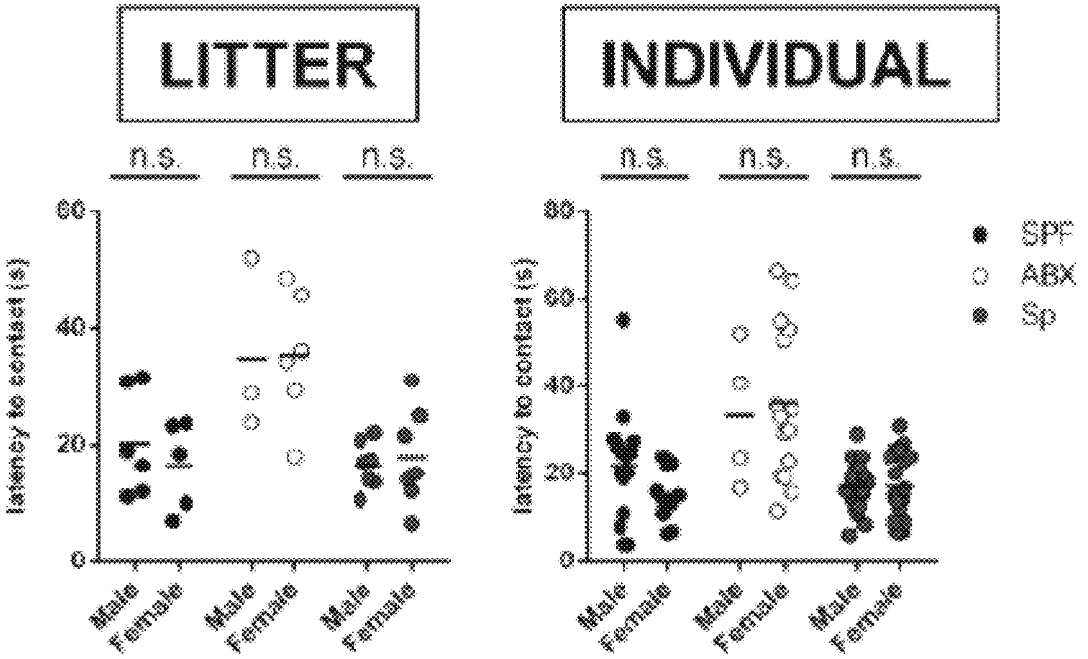
Figure 7F:
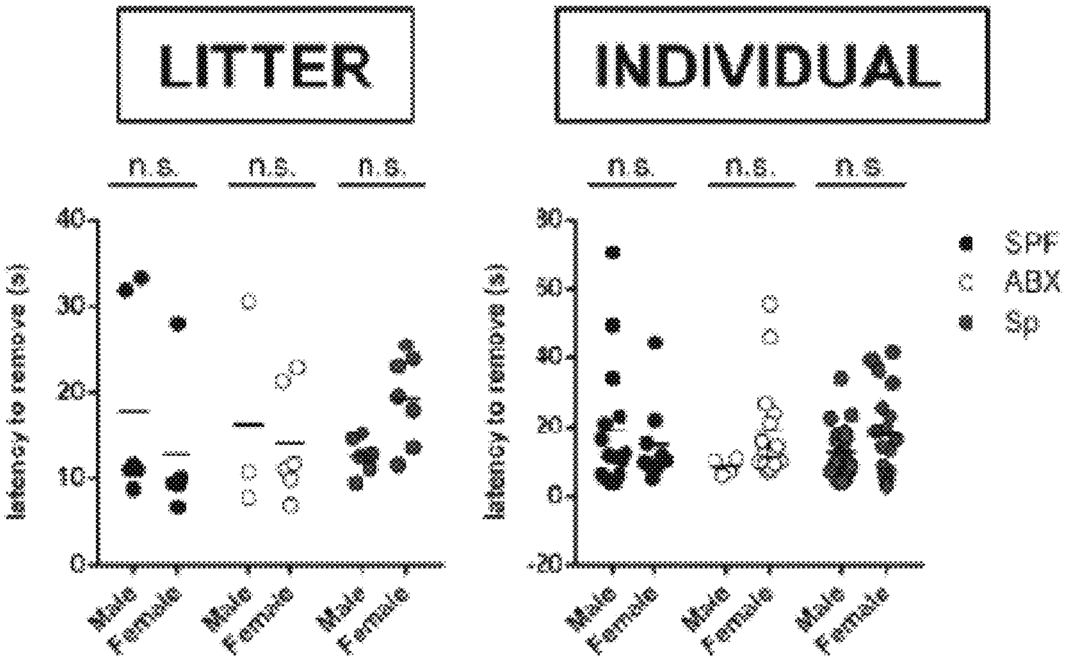
Figure 8C:
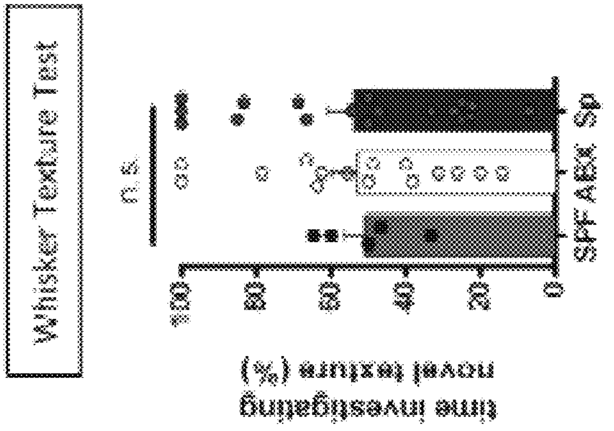
FIGS. 8A-8F: Thermal, visual, motor and acoustic sensory behaviors in adult offspring of gnotobiotic dams. 8A, Latency to withdraw in response to a hot plate in adult offspring of SPF, ABX, and Sp-colonized dams (One-way ANOVA with Tukey's; n=9 SPF, 19 ABX, 25 Sp offspring). 8B, Visual depth discrimination determined by a response towards the "safe" or "cliff" zone in the visual cliff test in adult offspring of SPF, ABX, and Sp-colonized dams (One-way ANOVA with Tukey's; n=9 SPF, 19 ABX, 25 Sp offspring). 8C, Percentage of time spent investigating novel texture in whisker texture test in adult offspring of SPF, ABX, and Sp-colonized dams (One-way ANOVA with Tukey's; n=5 SPF, 15 ABX, 18 Sp offspring). 8D, Time spent on the rotarod in adult offspring of SPF, ABX, and Sp-colonized dams (One-way ANOVA with Tukey's; n=45 SPF, 20 ABX, 55 Sp offspring). 8E, Habituation in response to three trials of 120 db acoustic tone in adult offspring of SPF, ABX, and Sp-colonized mice (Two-way ANOVA with Tukey's; n=45 SPF, 15 ABX, 54 Sp offspring). 8F, Inhibitory effect of 70, 75, and 80 db prepulse on startle response to a 120 db acoustic tone in adult offspring of SPF, ABX, and Sp-colonized mice (Two-way ANOVA with Tukey's; n=45 SPF, 15 ABX, 54 Sp offspring). Data are presented as mean±SEM. *p<0.05, **p<0.01, n. s=not statistically significant.
Figure 8B:
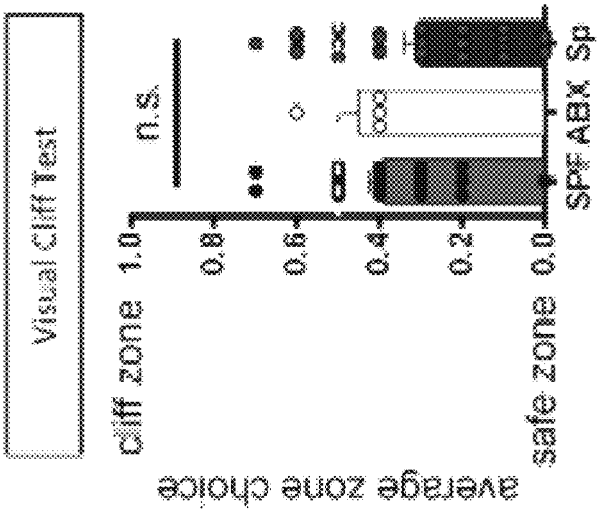
Figure 8A:
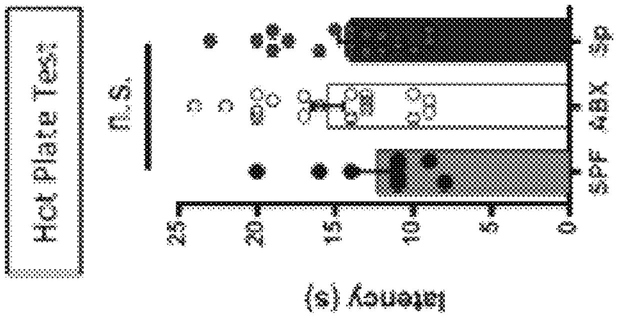
Figure 8D:
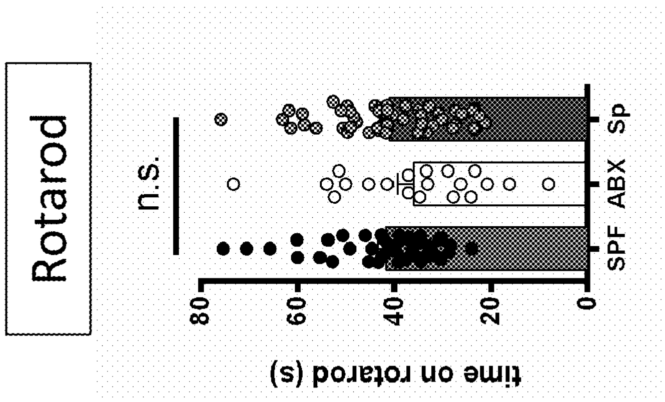
Figure 8E:
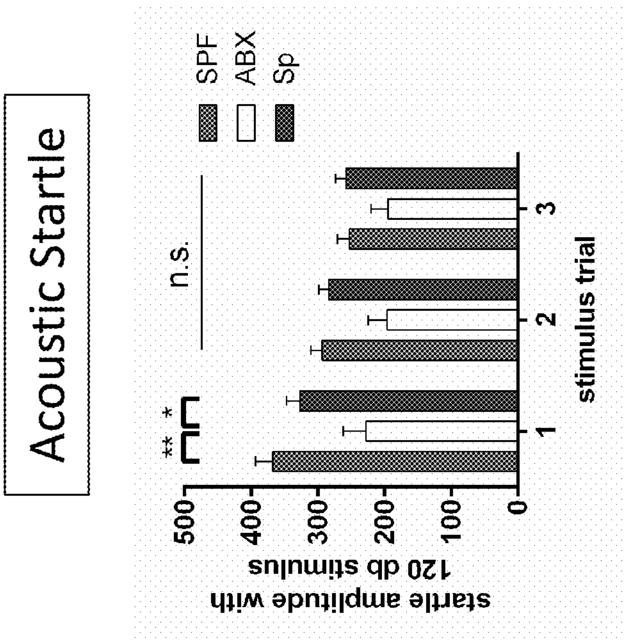
Figure 8F:
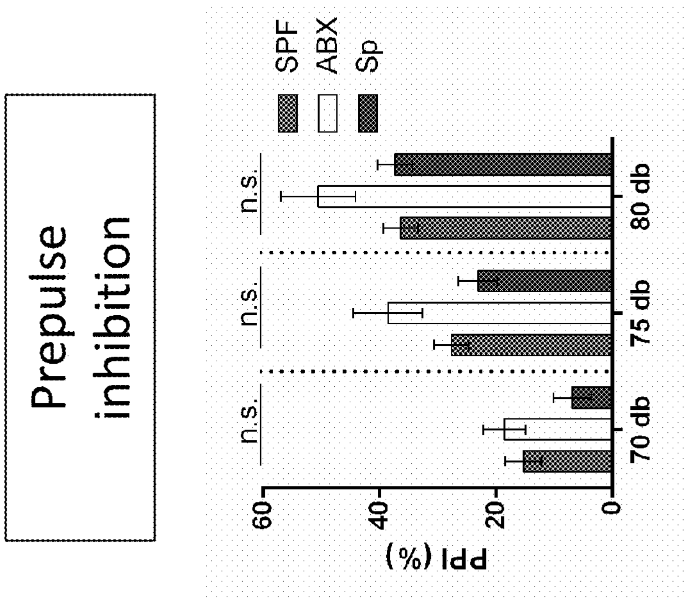

From prenatal through early postnatal development, thalamocortical axons are guided to the somatosensory cortex, where they form dense synaptic contacts with layer 4 neurons to mediate sensory processing[31-34]. To gain insight into whether microbiome-induced alterations in fetal thalamocortical axonogenesis confer lasting influences on offspring behavior, SPF dams were treated with ABX or vehicle from pre-conception through E14.5, and then colonized with a conventional SPF microbiome for the remainder of gestation through offspring postnatal development (FIG. 6A). Conventionalized offspring of ABX- or vehicle-treated dams were tested in a battery of sensory behavioral tasks (FIGS. 6A-6G, FIGS. 7A-7F and 8A-8F). In the von Frey filament test for hindpaw sensorimotor function[35,36], adult offspring of ABX dams required significantly increased force thresholds for paw withdrawal in response to hindpaw stimulation compared to control offspring from SPF dams (FIGS. 6B-6C), suggesting impaired tactile sensation. Consistent with this, in the adhesive removal test for forepaw sensorimotor function[37], adult offspring of ABX dams exhibited significantly increased latency to detect and contact the forepaw stimulus compared to control offspring from SPF dams (FIGS. 6D-6E). There was no difference in the time taken to remove the adhesive after first contact (FIG. 6F), suggesting that ABX offspring exhibit deficient initial paw tactile sensation, but no disruption in motor response (FIG. 6G). Statistically significant effects of the maternal microbiome on offspring tactile sensory behavior were observed when data were averaged by litter to represent individual dams as biological replicates (FIGS. 6A-6G), as well as when data from individual offspring were analyzed (FIGS. 7A-7C). There was no statistically significant difference in behavioral performance between male and female mice in these tasks (FIGS. 7D-7F). In addition, abnormalities in sensory behavior appeared to be limited to paw tactile responses, as there were no differences in behavioral performance between ABX and control SPF offspring in the hot plate test for thermosensory behavior[38], the visual cliff test for visual sensory behavior[39], the whisker-dependent texture discrimination test for vibrissae sensory perception[40], the rotarod test for motor coordination[41] and the prepulse inhibition task for acoustic startle response and sensorimotor gating[42] (FIG. 8A-8F). Altogether, these results demonstrate that depletion of the maternal gut microbiome during early to mid-gestation impairs fetal thalamocortical axonogenesis and yields adult offspring with disrupted neurobehavioral responses to forepaw and hindpaw tactile stimuli.

Figure 11A:
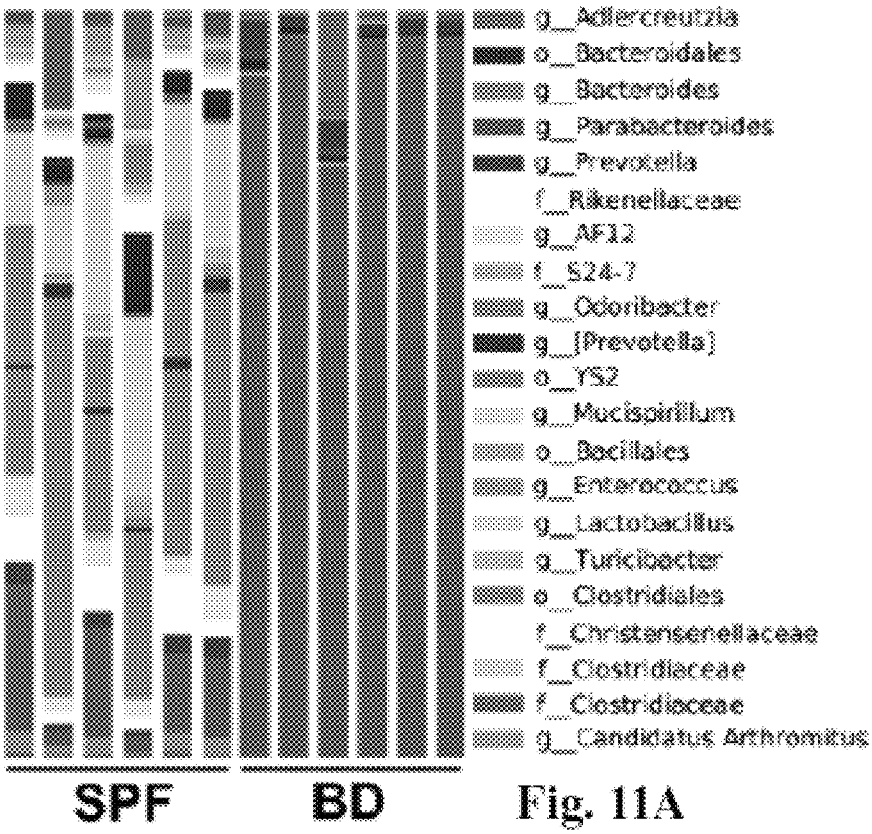
FIGS. 11A-11D: Fetal Netrin-G1a thalamocortical axons offspring of dams colonized with a consortium of *Bacteroides* species (BD). 11A, Taxonomic diversity of the fecal microbiota of SPF and BD colonized dams (n=6 dams). 11B, Representative immunofluorescence images of Netrin-G1a (magenta in the original image) and L1 (cyan in the original image) staining in embryonic brain sections (rostra' to caudal) from E14.5 offspring of BD-colonized dams. Scale bar=500 μm. 11C, Average Netrin-G1a fluorescence intensity per matched area of region of interest (ROI) ("yellow-in-the-original-image" dotted lines) across 800 μm of rostral to caudal embryonic brain sections of E14.5 offspring from SPF, ABX, and BD-colonized dams. (Two-way ANOVA with Tukey's, n=offspring from 5 SPF, 7 ABX, 4 BD dams). 11D, Average L1 fluorescence intensity per matched area of ROI ("yellow-in-the-original-image" dotted lines) across 800 μm of rostral to caudal embryonic brain sections of E14.5 offspring from SPF, ABX and BD-colonized dams. (Two-way ANOVA with Tukey's, n=offspring from 5 SPF, 7 ABX, 4 BD dams). Data are presented as mean±SEM. Data shown for SPF and ABX are as displayed in FIGS. 1A-1M, 10A-10M, 2A-2D, 3A-I. *p<0.05, p<0.01, **p<0.0001, n. s.=not statistically significant.
Figure 11B:
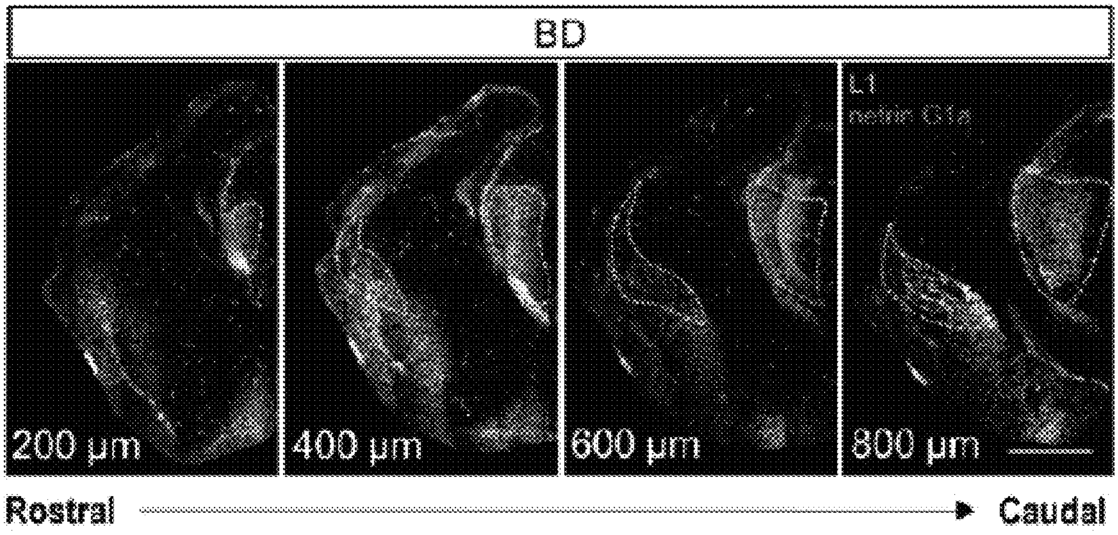
Figure 11C:
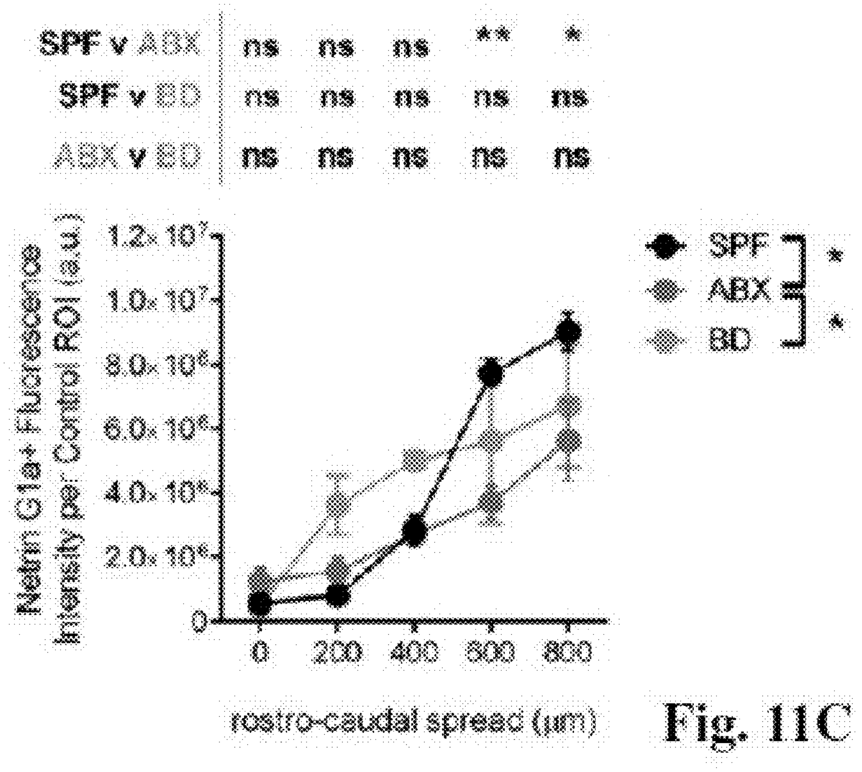
Figure 11D:
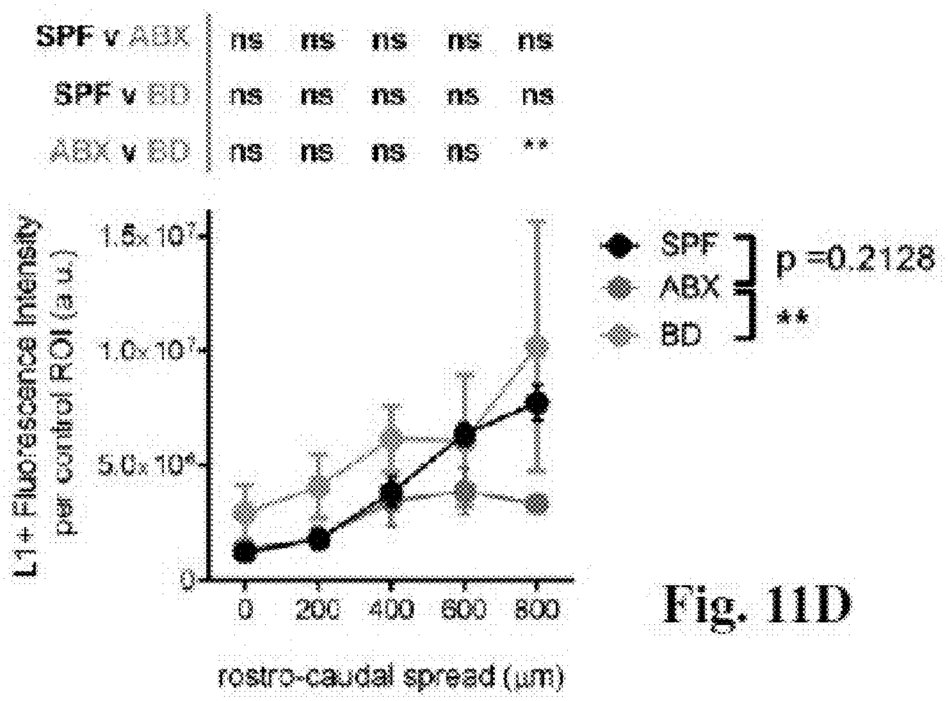

The gut microbiome is comprised of several hundred different bacterial taxa, many of which exhibit specialized functions and differential interactions with host physiology"[43-46]. To determine whether the effects of the maternal microbiome on offspring neurodevelopment and behavior are mediated by particular bacterial taxa, we colonized ABX-treated dams during preconception with a consortium of bacteria representing one of the two dominant phyla of the gut microbiota—Firmicutes and Bacteroidetes (FIGS. 9A-10B and 11A, Tables 2 and 3). Colonization of ABX-treated dams with Clostridia-dominant spore-forming bacteria (Sp) of the phylum Firmicutes abrogated many adverse effects of maternal microbiota depletion on fetal brain gene expression and thalamocortical axon outgrowth (FIGS. 10A-10M). E14.5 fetal brains from embryos of Sp-colonized dams exhibited transcriptomic profiles that clustered closely with samples derived from SPF controls, with restored expression of many genes relevant to axon guidance (FIG. 10A; FIGS. 9C-9F, Table 1). Notably, reductions in NTNG1 expression and Netrin-G1a+thalamocortical axons observed in response to maternal microbiome depletion were prevented by maternal colonization with Sp bacteria (FIGS. 10B-10J, FIGS. 3A-3I and 4A-4E, FIGS. 9C-9F). In contrast, colonizing ABX-treated dams with a consortium of *Bacteroides* (BD), containing *B. thetaiotaomicron, B. uniformis, B. vulgatus, B. ovatus* and *B. fragilis* (FIG. 11A), conferred only a modest increase in Netrin-G1a+thalamocortical axons in fetal brains from E14.5 offspring, which exhibited statistical significance by group, but not across individual rostral to caudal sections compared to ABX controls (FIGS. 11B-11D). Fetal thalamic explants from E14.5 embryos of Sp-colonized dams also exhibited significantly increased axon outgrowth compared to controls from ABX-treated dams (FIGS. 5G-5L). Deficiencies in paw tactile sensory behavior in the adhesive removal and von Frey filament tests seen in adult offspring of ABX-treated dams were also prevented by maternal colonization with Sp bacteria (FIGS. 10K-10M), with no differences in performance between males and females and in other sensory behavioral tasks (FIGS. 7A-7F and 8A-8F). Overall, these findings suggest that limited bacterial taxa, including Sp bacteria in particular, are sufficient to prevent the adverse effects of maternal microbiota depletion on fetal thalamocortical axonogenesis and offspring sensory behavior.

Figure 12A:
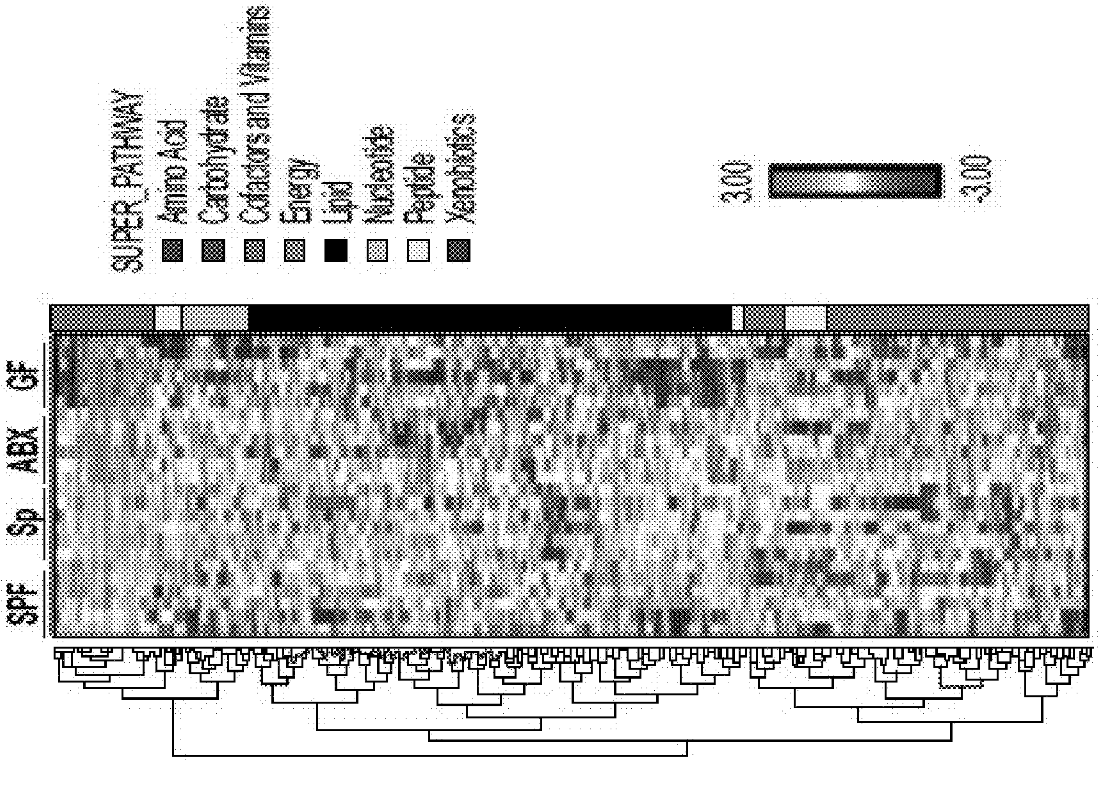
Figure 12B:
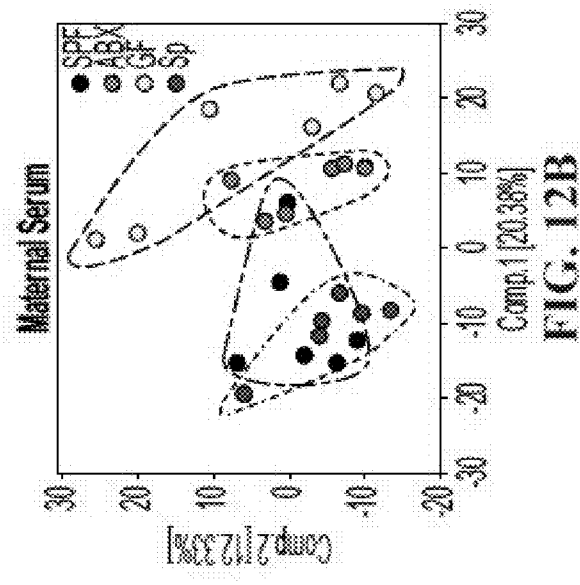
Figure 13A:
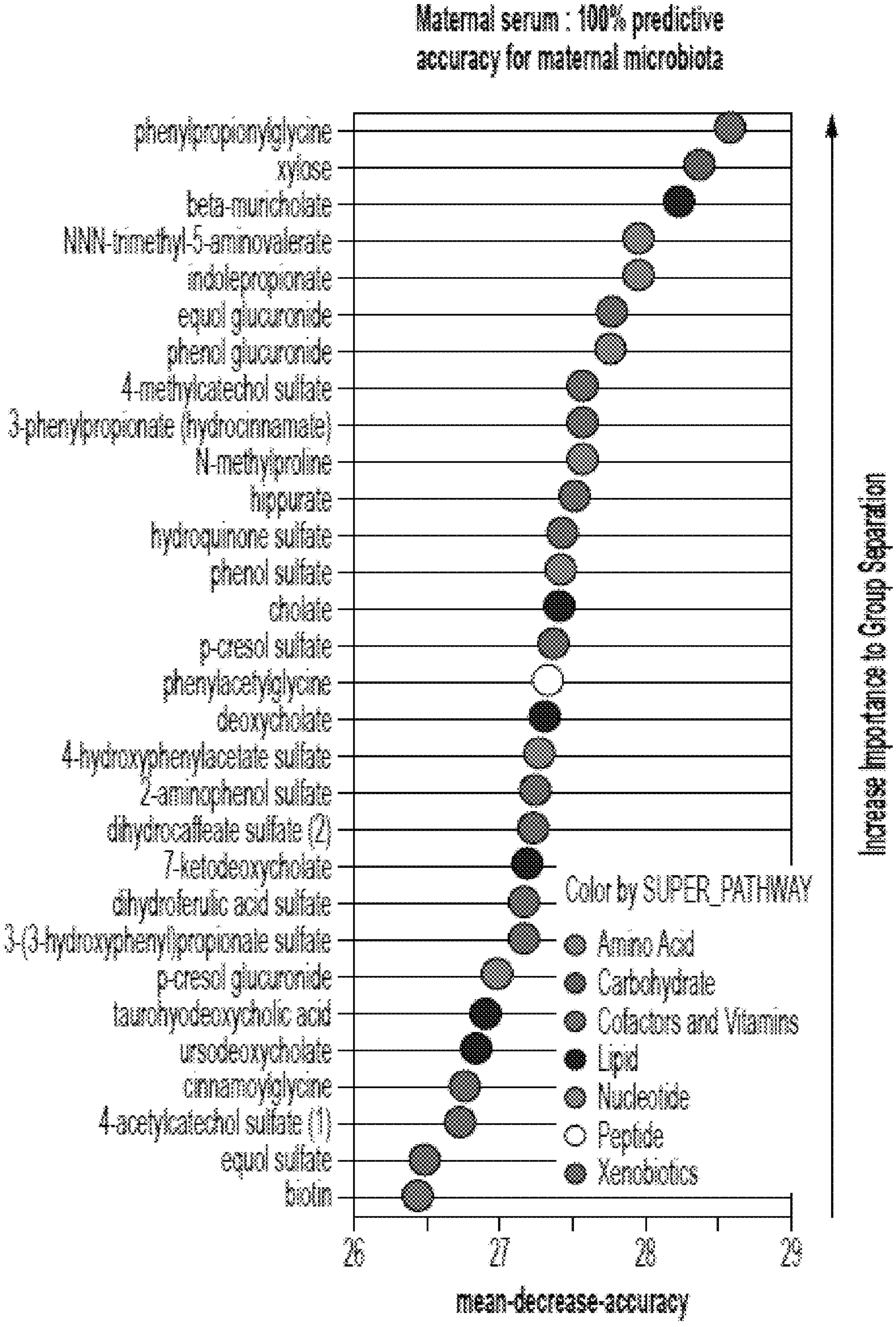
FIGS. 13A-13C: The maternal microbiota modulates maternal serum metabolites during pregnancy. 13A, Random Forest classification of top 30 metabolites in maternal serum that discriminate between maternal colonization with SPF and Sp compared to ABX and GF. Red font (in the original image) indicates metabolites similarly regulated in both maternal serum and fetal brain from SPF and Sp compared to ABX and GF conditions (n=6 dams per group). 13B, Relative concentrations of N, N, N-trimethyl-5-aminovalerate, trimethylamine N-oxide, imidazole propionate, hippurate, and 3-indoxyl-sulfate in maternal sera of SPF, ABX, GF, and Sp dams (One-way ANOVA with Tukey's; n=6 dams per group). 13C, Amino acid, lipid and xenobiotic metabolites significantly dysregulated in fetal brains of E14.5 offspring from GF dams compared to SPF controls (left) and GF dams compared to Sp dams (right) (p<0.05; One-way ANOVA, n=offspring from 6 dams per group). Data are presented as mean±SEM. *p<0.05, p<0.01, *p<0.001, ****p<0.0001, n. s.=not statistically significant.

The gut microbiome modulates the bioavailability of hundreds of biochemicals in the circulating blood[8,47-49]. During pregnancy, the maternal intrauterine environment supplies nutrients and growth factors to nurture offspring growth, which is particularly important for the rapidly developing fetal brain[50,51]. The blood brain barrier begins forming at E16.5 and continues developing during the first three weeks of postnatal life[52,53], rendering the developing fetal brain permeable to circulating metabolites. Based on our finding that the maternal microbiota is important for regulating fetal neurodevelopment, we hypothesized that the maternal microbiome regulates maternal circulating metabolites and thereby conditions metabolite profiles in the fetus. To investigate this, we performed tandem liquid chromatography mass spectrometry to globally profile biochemicals in maternal sera and fetal brain lysates from SPF, ABX, GF and Sp-colonized dams on E14.5 of gestation. A total of 753 metabolites were identified in maternal sera and 567 in fetal brain lysates, spanning amino acid, carbohydrate, co-factor and vitamin, energy, lipid, nucleotide, peptide and xenobiotic biochemical super pathways (Tables 4 and 5). Supervised hierarchical clustering of samples based on differential levels of maternal blood metabolites led to co-clustering of samples derived from SPF and Sp dams compared to GF and ABX dams (FIG. 12A). Metabolomic profiles in maternal blood from ABX and GF mice clustered closely by principal component analysis (PCA), whereas those from SPF and Sp-colonized dams formed a separate co-cluster (FIG. 12B). This suggests that Sp bacteria recapitulate many of the effects of the SPF microbiota on maternal blood biochemical profiles, and further aligns with the phenotypic similarities between offspring of ABX and GF dams versus SPF and Sp dams in fetal axonogenesis and adult sensory behavior. Random Forests analysis identified 30 maternal blood metabolites that discriminate maternal microbiota status with 100% predictive accuracy (FIG. 13A). Overall, these data reveal widespread effects of the maternal microbiome on circulating serum biochemicals during pregnancy.

Figure 12C:
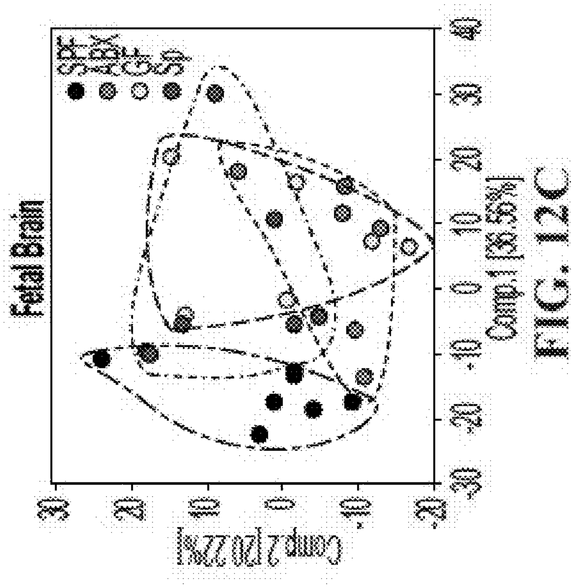
Figures 12F, 12G:
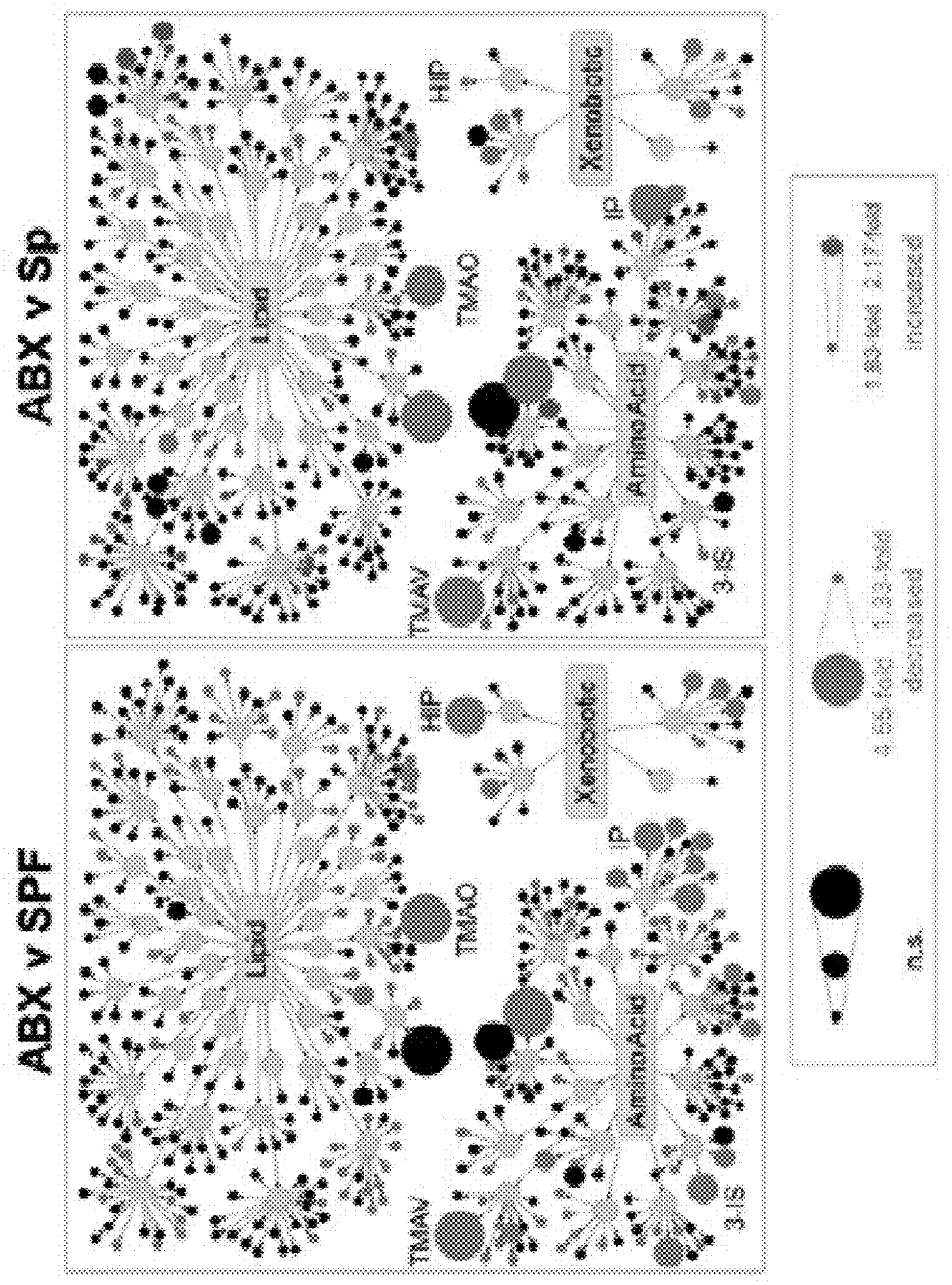
Figure 12H:
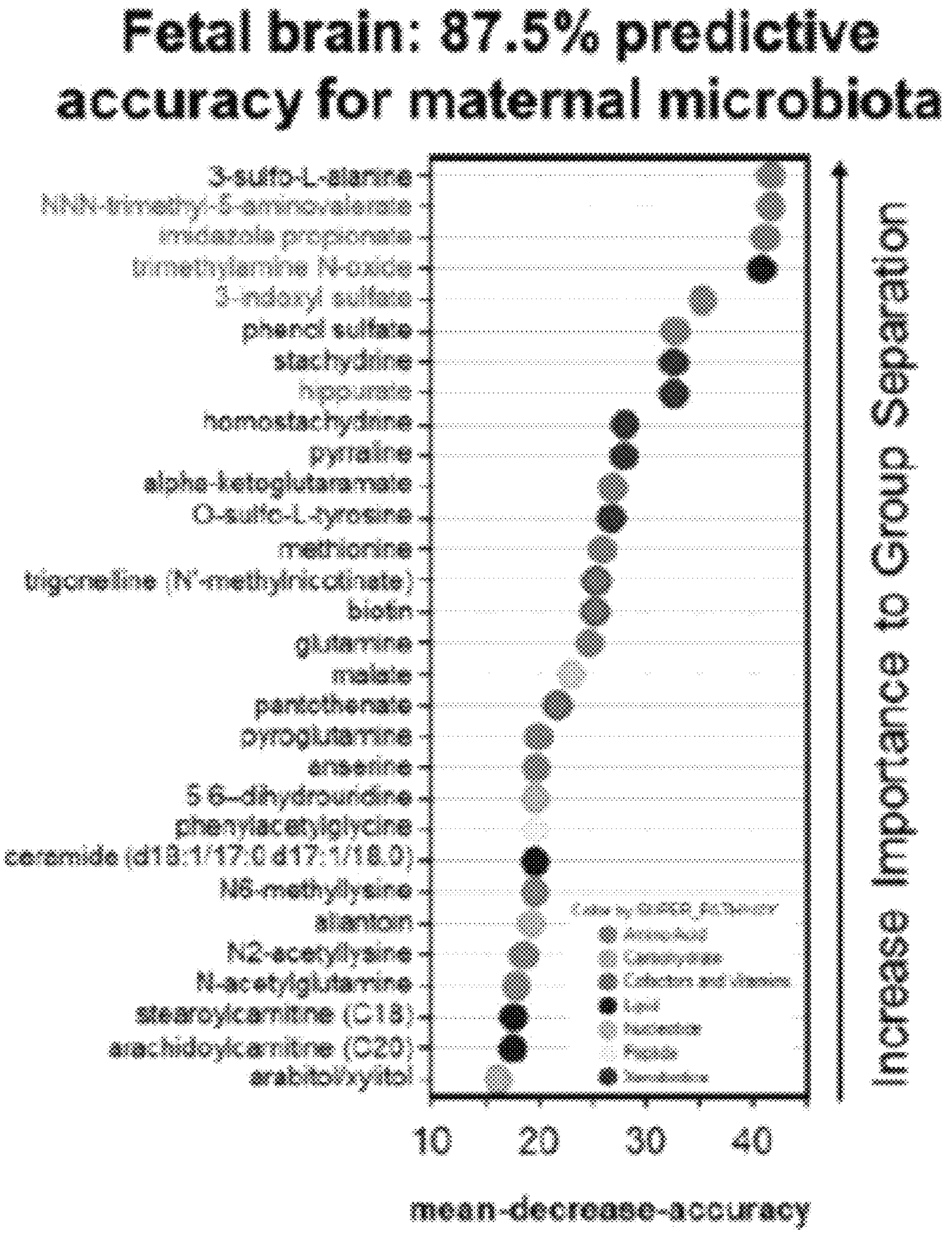
Figure 13B:
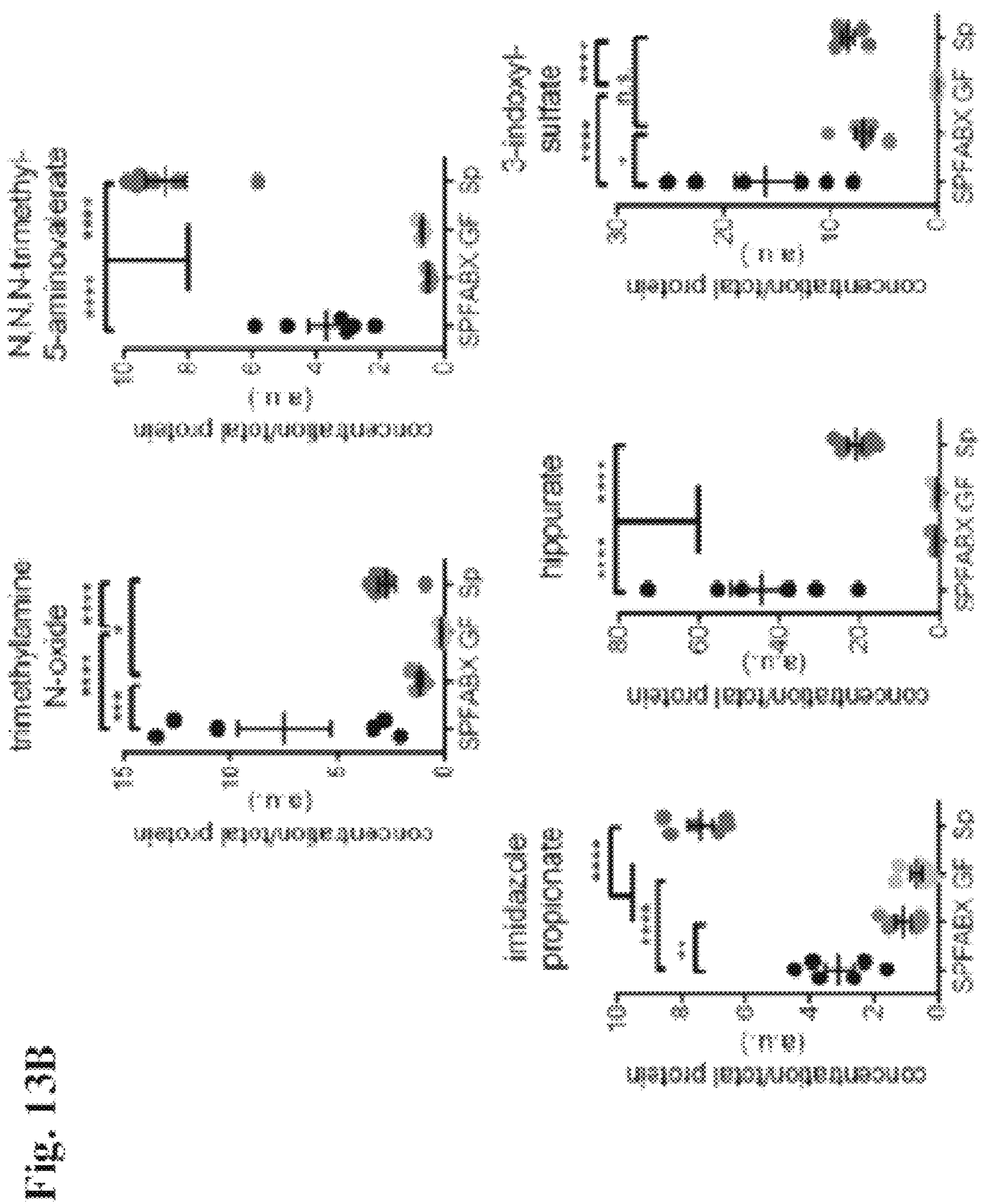
Figure 13C:
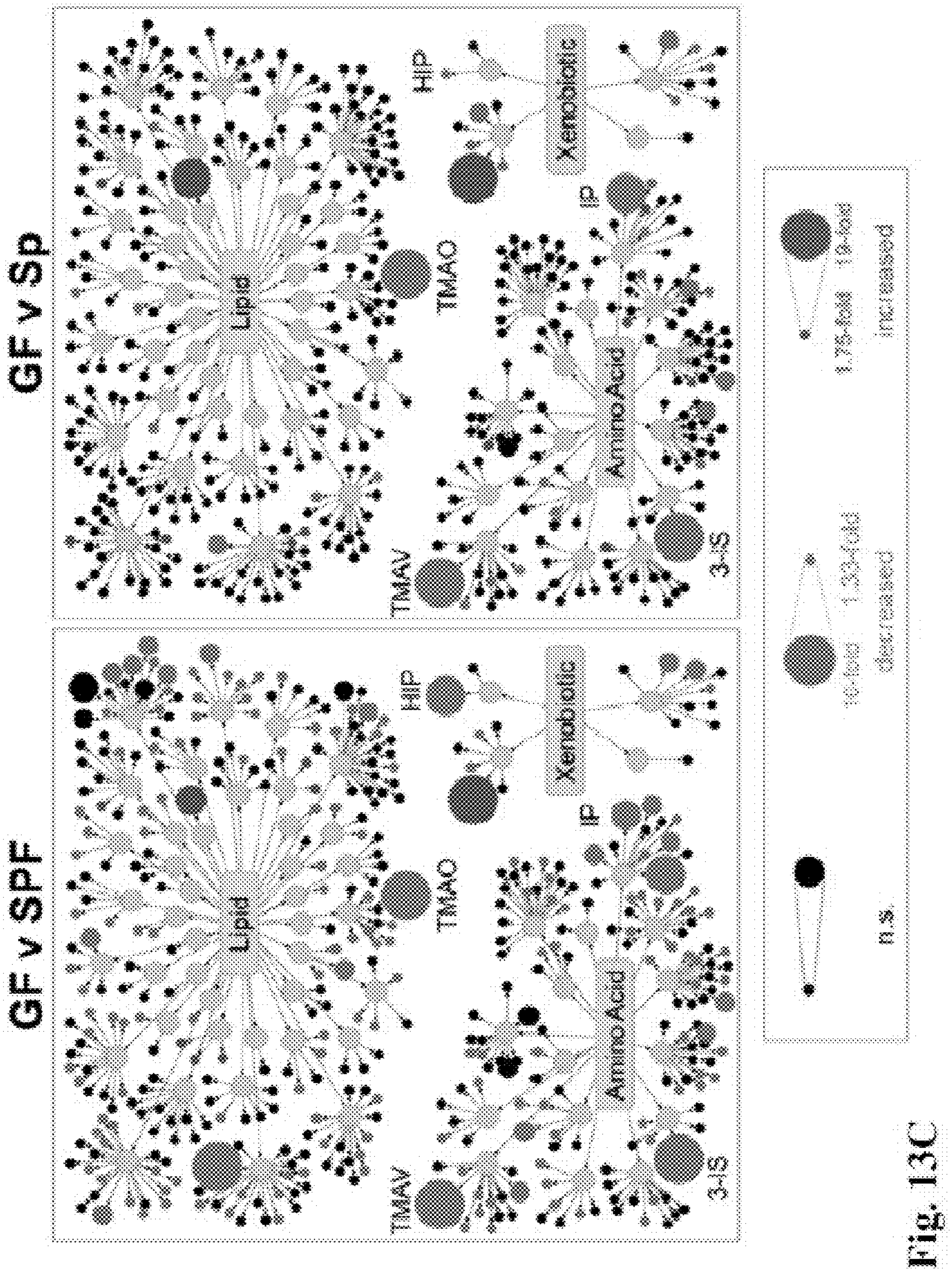

Interestingly, metabolomic profiles from fetal brain lysates of SPF dams clustered away from profiles from fetal brain lysates of Sp-colonized, ABX, and GF dams (FIG. 12C), suggesting that there are global alterations in fetal brain metabolomic profiles from E14.5 fetal brains of offspring from gnotobiotic mothers. 165 fetal brain metabolites were commonly downregulated in embryos from ABX and GF dams, relative to SPF controls (FIG. 12D, Table 4). 27 fetal brain metabolites were commonly downregulated in embryos from ABX and GF dams, relative to Sp controls (FIG. 12E, Table 4). Pathway analysis revealed alterations in several amino acid, lipid, and xenobiotic metabolites in fetal brain lysates from ABX and GF dams compared to SPF and Sp dams (FIGS. 12F-12G, FIG. 13C). Random Forests analysis identified the top 30 fetal brain metabolites that were predictive with 87.5% accuracy of maternal SPF and Sp versus ABX and GF microbiota status (FIG. 12H). 22 metabolites were similarly and significantly decreased in fetal brain lysates from ABX and GF dams relative to both SPF and Sp dams (Table 5). Of these 22 fetal brain metabolites, 8 were similarly differentially regulated in maternal sera from ABX and GF dams compared to SPF and Sp controls (Table 5), suggesting that the maternal microbiome modulates the bioavailability of these metabolites in maternal blood with direct effects on the bioavailability of the same metabolites in fetal brain. Overall, these findings reveal that the maternal microbiome modulates biochemical profiles and select metabolites in the fetal brains of developing offspring.

Figure 12I:
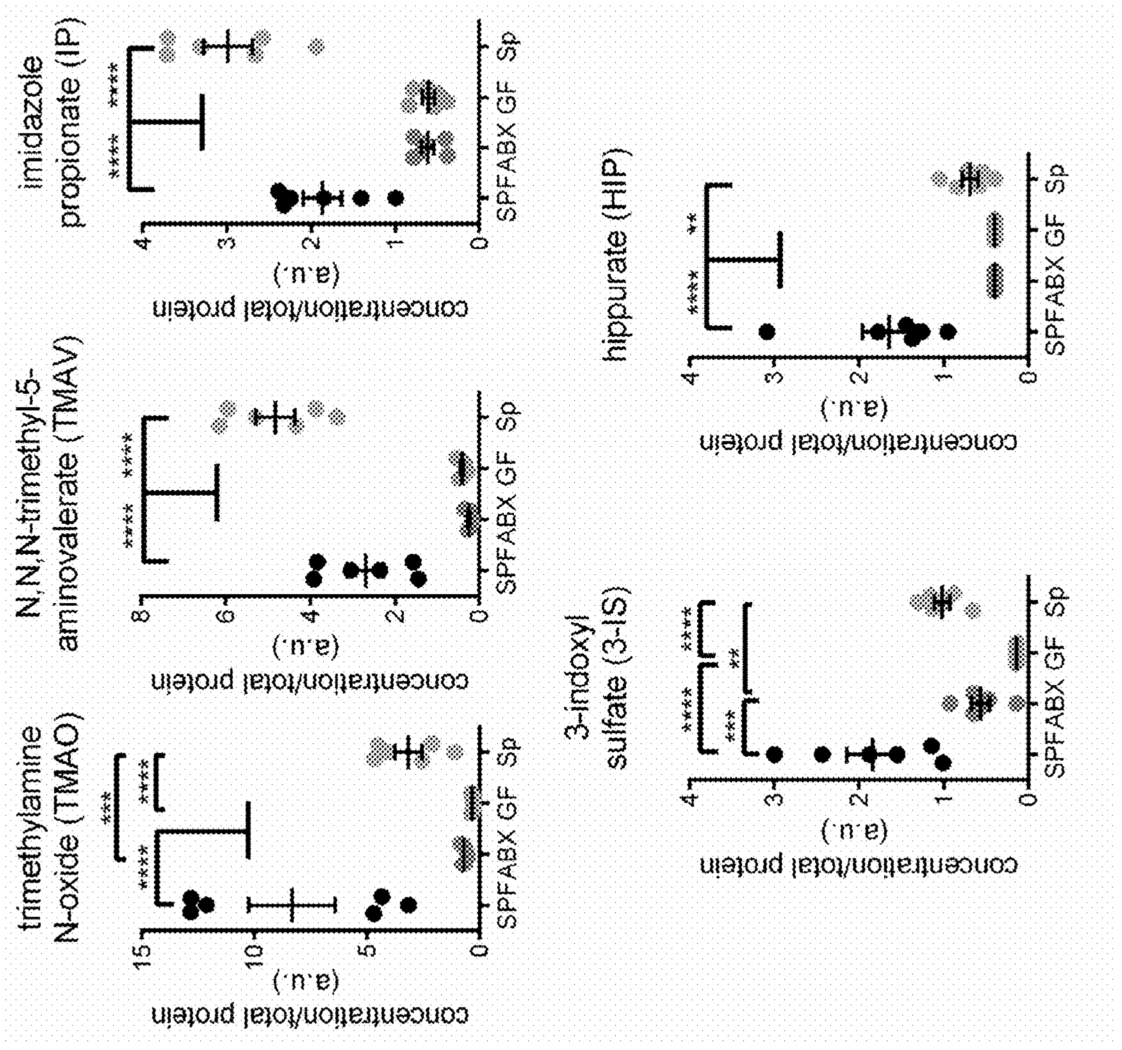
Figure 14A:
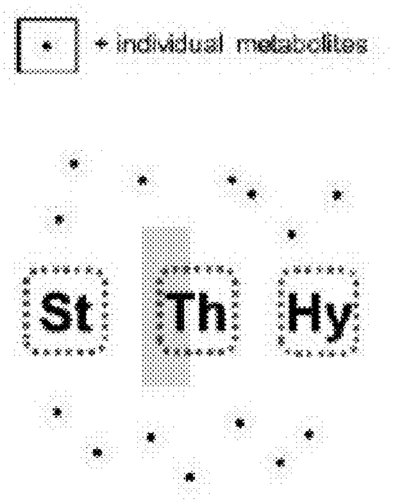
Figure 14B:
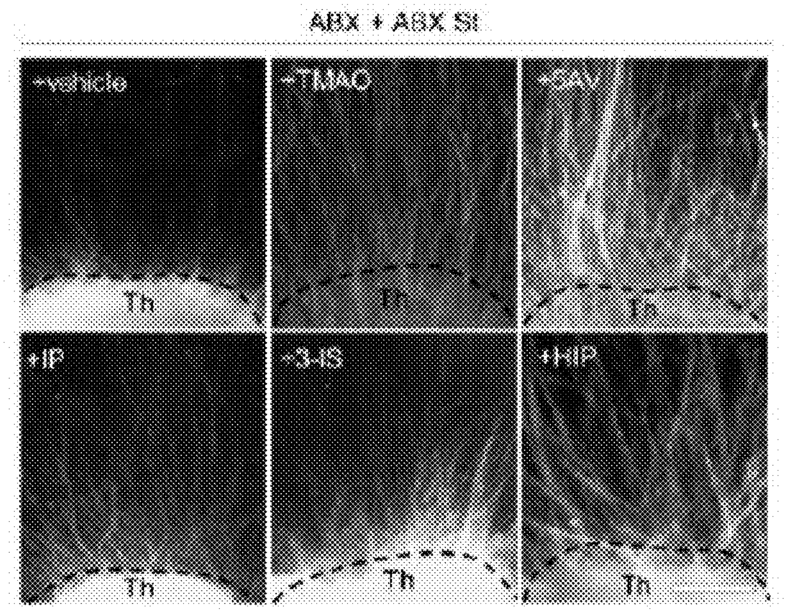
Figure 14C:
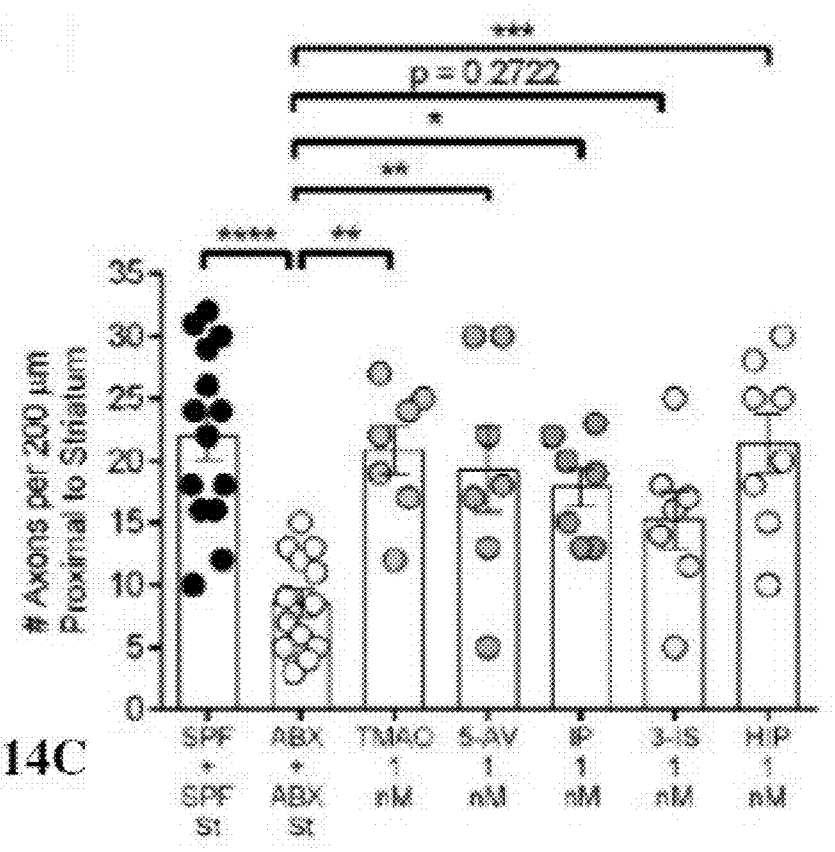
Figure 14D:
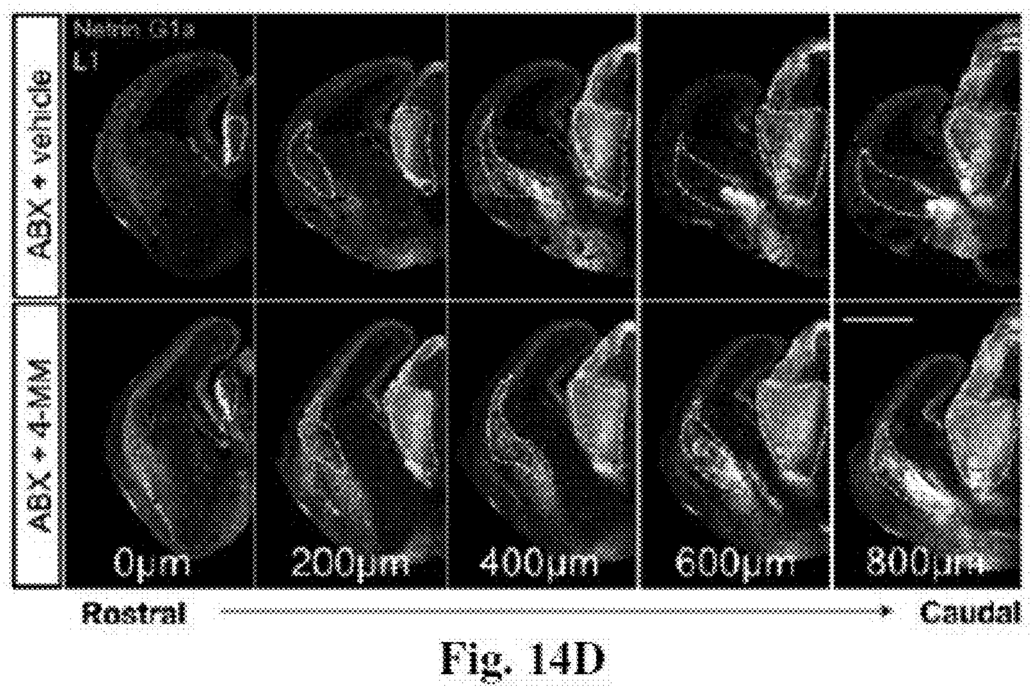
Figure 14E:
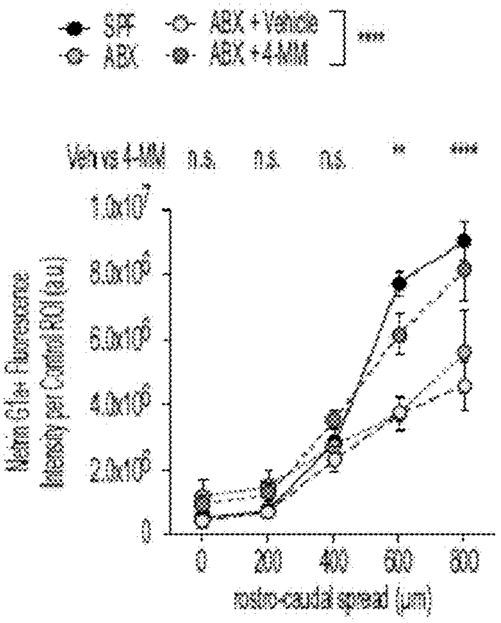
Figure 14F:
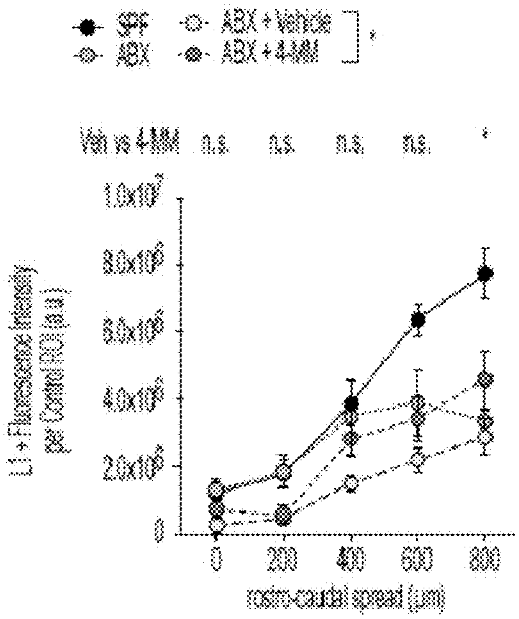
Figure 15A:
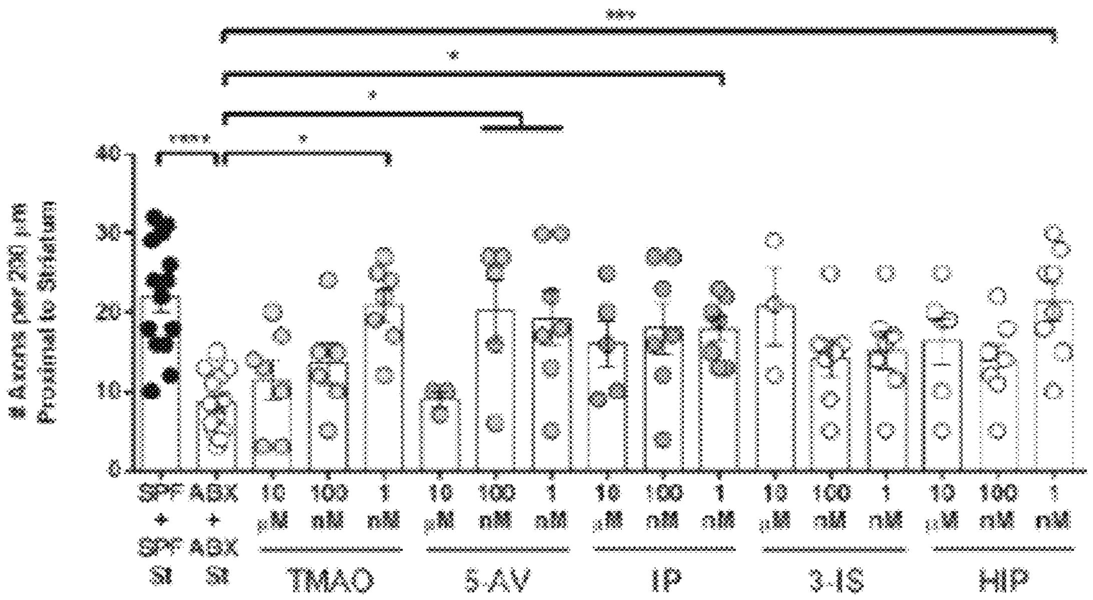
FIGS. 15A-15D: Dose effects of microbiome-dependent metabolites on thalamocortical axon outgrowth. 15A, Number of axons per 200 μm of thalamic perimeter proximal to striatal explant from i) SPF thalamic explant proximal to an SPF striatal explant ("SPF+SPF St", left), as positive control ii) ABX thalamic explant proximal to an ABX striatal explant ("ABX+ABX St"), as negative control, and iii) ABX+ABX St, supplemented with 1 nM, 100 nM, 10 uM of metabolites: trimethylamine N-oxide (TMAO), 5-aminovalerate (5-AV), imidazole propionate (IP), 3-indoxylsulfate (3-IS) or Hippurate (HIP). (One-way ANOVA with Tukey's, n=offspring from 14 SPF+SPF; 13 ABX+ABX; 7, 6, 7 TMAO; 3, 5, 7 5-AV; 5, 7, 7 IP; 3, 7, 7 3-IS; 6, 7, 8 HIP dams). 15B, Length of axons per 200 μm of thalamic perimeter proximal to striatal explant from i) SPF+SPF St as positive control ii) ABX+ABX St, as negative control, and iii) ABX+ABX St, supplemented with 1 nM, 100 nM, 10 1.1M of metabolites: TMAO, 5-AV, IP, 3-IS or HIP. (One-way ANOVA with Tukey's, n=offspring from 14 SPF+SPF; 12 ABX+ABX; 7, 6, 6 TMAO; 3, 5, 6 5-AV; 5, 7, 6 IP; 3, 7, 4 3-IS; 6, 7, 7 HIP dams). 15C, Number of axons per 200 μm of thalamic perimeter proximal to hypothalamic explant (Hy) from i) SPF+SPF Hy, as positive control ii) ABX+ABX Hy as negative control, and iii) ABX+ABX Hy, supplemented with 1 nM, 100 nM, 10 uM of metabolites: TMAO, 5-AV, IP, 3-IS or HIP. (One-way ANOVA with Tukey's, n=offspring from 14 SPF+SPF; 10 ABX+ABX; 6, 6, 7 TMAO; 3, 5, 7 5-AV; 3, 6, 7 IP; 3, 7, 5 3-IS; 5, 7, 8 HIP dams). 15D, Length of axons per 200 μm of thalamic perimeter proximal to hypothalamic explant from i) SPF+SPF Hy as positive control ii) ABX+ABX Hy as negative control, and iii) ABX+ABX Hy, supplemented with 1 nM, 100 nM, 10 uM of metabolites: TMAO, 5-AV, IP, 3-IS or HIP. (One-way ANOVA with Tukey's, n=offspring from 14 SPF+SPF; 9 ABX+ABX; 6, 6, 6 TMAO; 3, 5, 6 5-AV; 3, 7, 6 IP; 3, 7, 4 3-IS; 5, 7, 7 HIP dams). Data are presented as mean±SEM. *p<0.05. p<0.01, *p<0.001, ****p<0.0001, n. s.=not statistically significant.
Figure 15B:
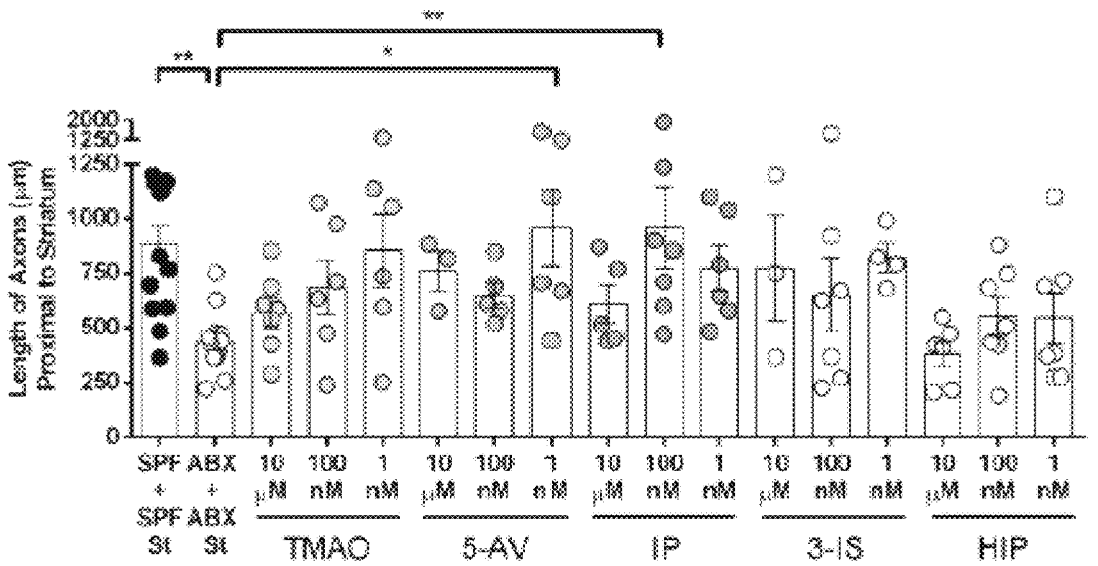
Figure 15C:
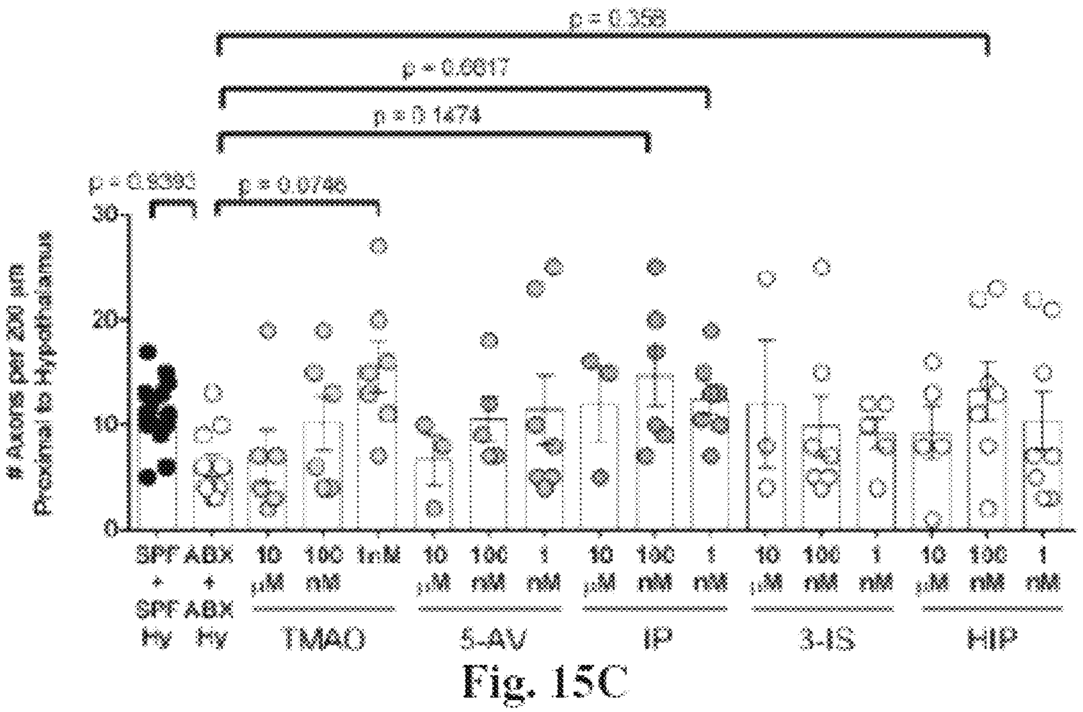
Figure 15D:
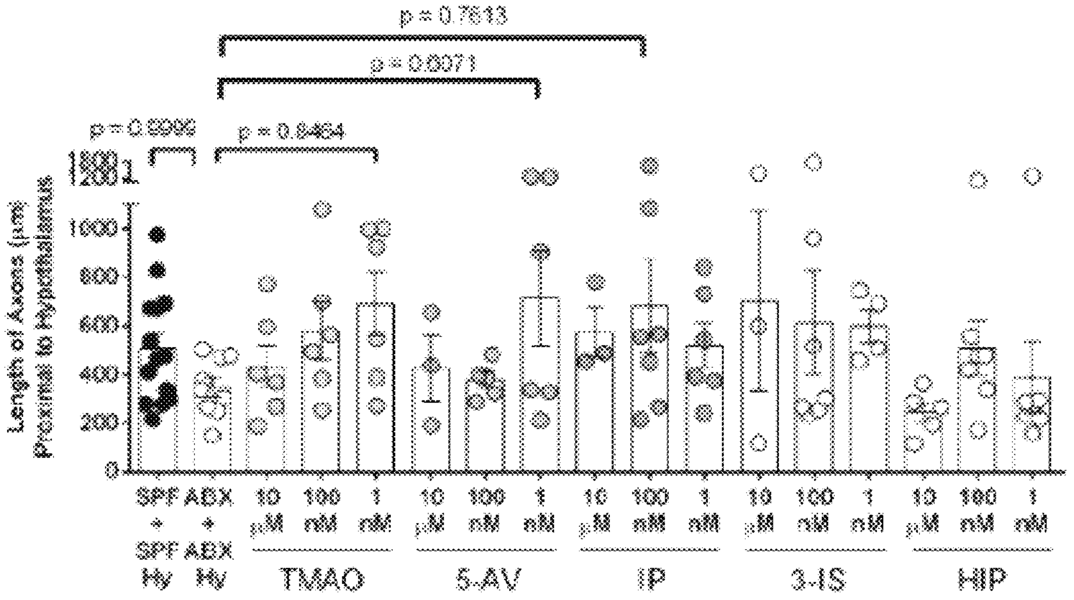
Figure 16A:
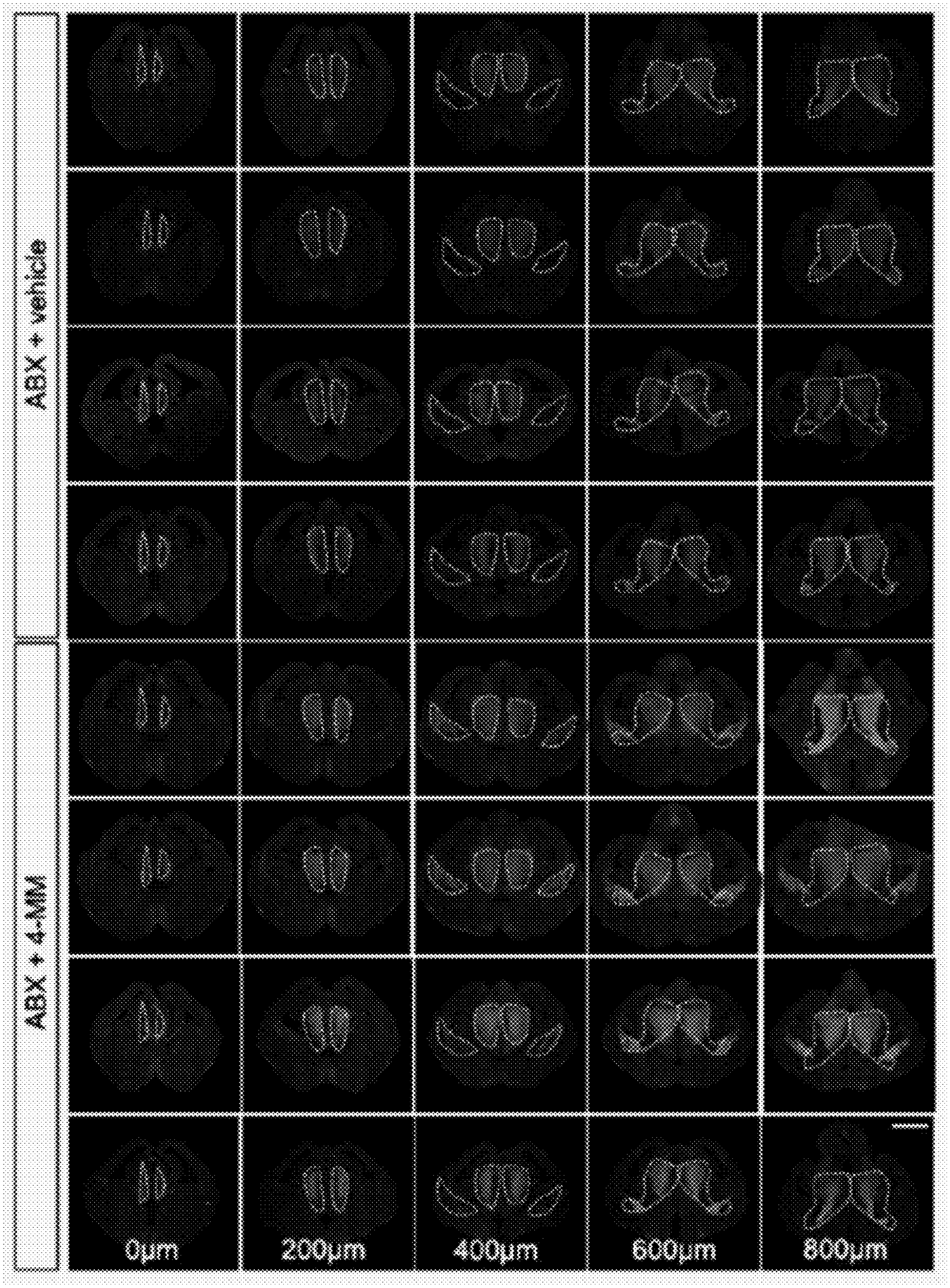
FIGS. 16A-16D: Netrin-G1a thalamocortical axons in embryonic brains of E14.5 offspring from metabolite supplementation dams. 16A, Immunofluorescence images of Netrin-G1a in four independent embryonic brain sections from E14.5 offspring of ABX+vehicle and ABX+4-MM dams at 200 μm intervals. Scale bar: 500 μm. 16B, Total Netrin-G1a fluorescence intensity across 800 μm of rostral to caudal sections of E14.5 embryonic brains from ABX+vehicle and ABX+4-MM dams. (Two-way ANOVA with Tukey's, n=offspring from 8 dams per group). 16C, Average area of Netrin-G1a-positive staining across 800 μm of rostral to caudal embryonic brain sections of E14.5 offspring from ABX+vehicle and ABX+4-MM dams. (Two-way ANOVA with Tukey's, n=offspring from 8 dams per group). 16D, Average DAPI fluorescence intensity normalized to per matched area of region of interest ("yellow-in-the-original-image" dotted lines) in 800 μm of rostral to caudal embryonic brain sections of E14.5 offspring from ABX+vehicle and ABX+4-MM dams. (Two-way ANOVA with Tukey's, n=offspring from 8 dams per group). Data are presented as mean±SEM. *p<0.05, p<0.01, *p<0.001, ****p<0.0001, n. s.=not statistically significant.
Figure 16B:
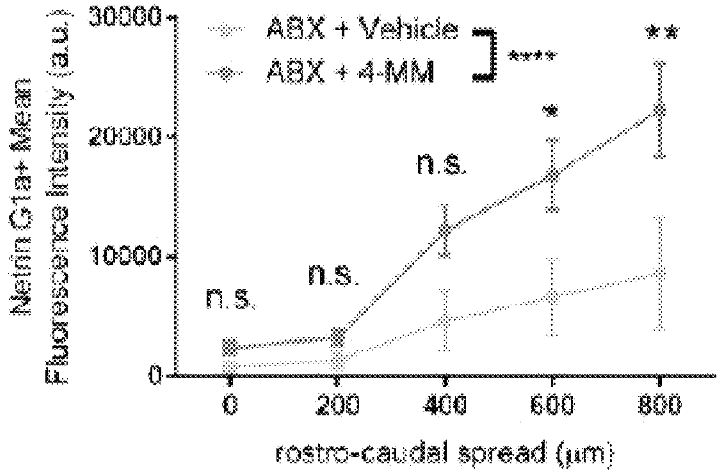
Figure 16C:
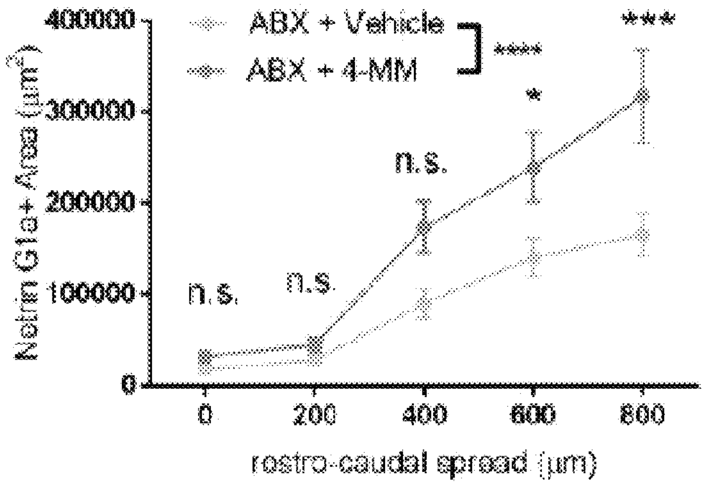
Figure 16D:
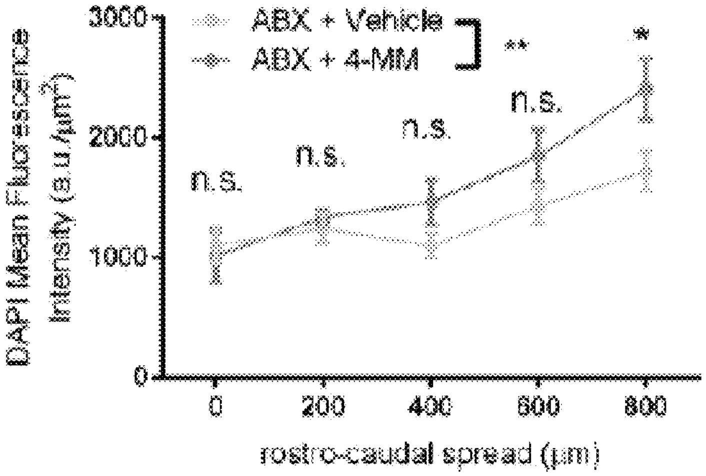
Figures 17A, 17B, 17C, 17D:
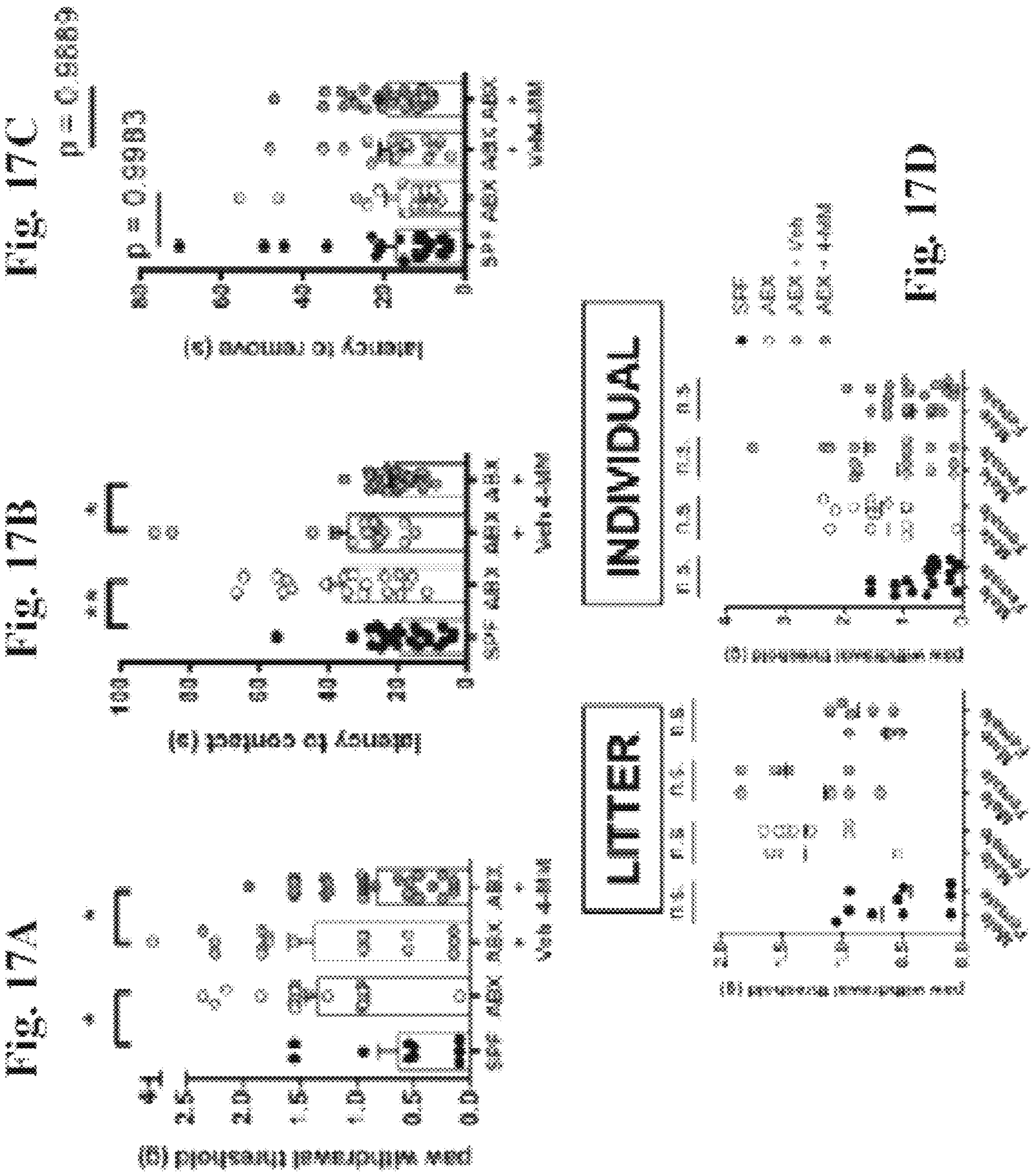
FIGS. 17A-17F: Absence of sex differences in behavioral performance of offspring from metabolite-treated dams. 17A, Force filament required to induce 50% paw withdrawal in adult offspring of SPF, ABX, ABX+Veh, ABX+4-MM dams (One-way ANOVA with Tukey's, n=10 SPF, 23 ABX, 19 ABX+Veh, 29 ABX+4-MM offspring). 17B, Latency to contact the adhesive tape, in adult offspring of SPF, ABX, ABX+Veh, ABX+4-MM dams (One-way ANOVA with Tukey's, n=25 SPF, 19 ABX, 19 ABX+Veh, 29 ABX+4-MM offspring). 17C, Latency to remove the adhesive tape after first contact in adult offspring of SPF, ABX, and Sp dams (One-way ANOVA with Tukey's, n=25 SPF, 19 ABX, 19 ABX+Veh, 29 ABX+4-MM offspring). 17D, Force filament to induce 50% paw withdrawal in male and female adult offspring of SPF, ABX, ABX+Veh, and ABX+4-MM dams. Male and female comparisons per litter (left) or individual offspring (right). (Two-way ANOVA with Tukey's, n=10 male, 10 female SPF; 7 male, 16 female ABX; 9 male, 10 female ABX+Veh; 13 male, 16 female ABX+4-MM dams). 17E, Latency to contact the adhesive tape, in male and female adult offspring of SPF, ABX, ABX+Veh, ABX+4-MM dams. Male and female comparisons per litter (left) or individual offspring (right). (Two-way ANOVA with Tukey's, n=15 male, 10 female SPF; 4 male, 15 female ABX; 6 male, 11 female ABX+Veh; 11 male, 16 female ABX+4-MM dams). 17F, Latency to remove the adhesive tape after first contact in male and female adult offspring of SPF, ABX, and Sp dams. Male and female comparisons per litter (left) or individual offspring (right). (Two-way ANOVA with Tukey's, n=15 male, 10 female SPF; 4 male, 15 female ABX; 6 male, 11 female ABX+Veh; 11 male, 16 female ABX+4-MM dams). Data are presented as mean±SEM. n. s=not statistically significant.
Figure 17E:
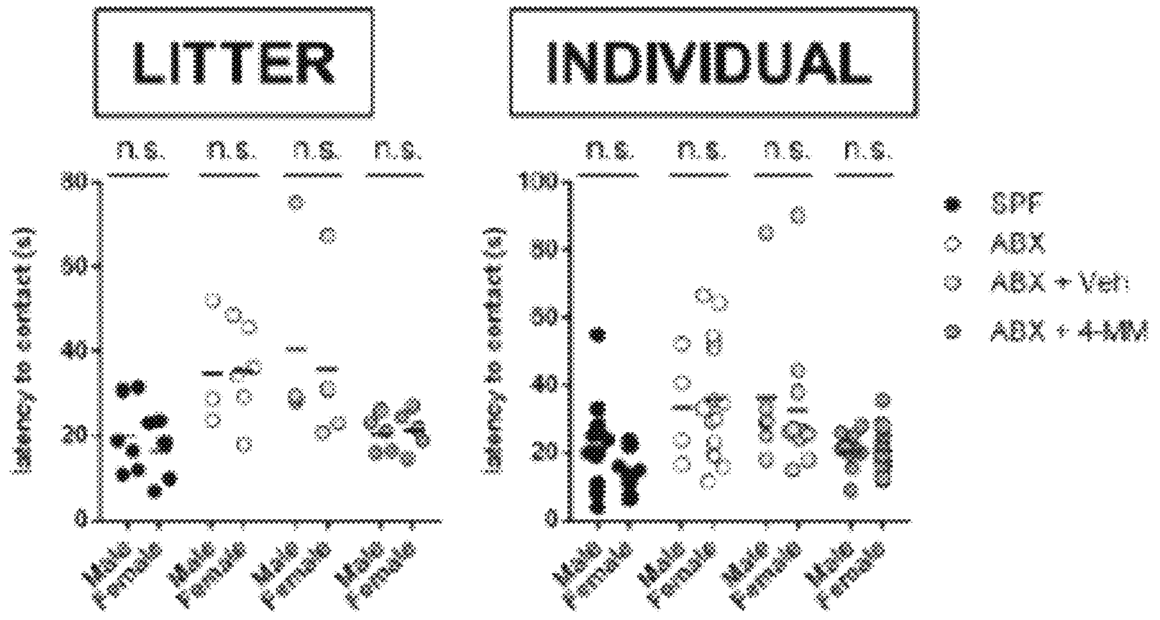
Figure 17F:
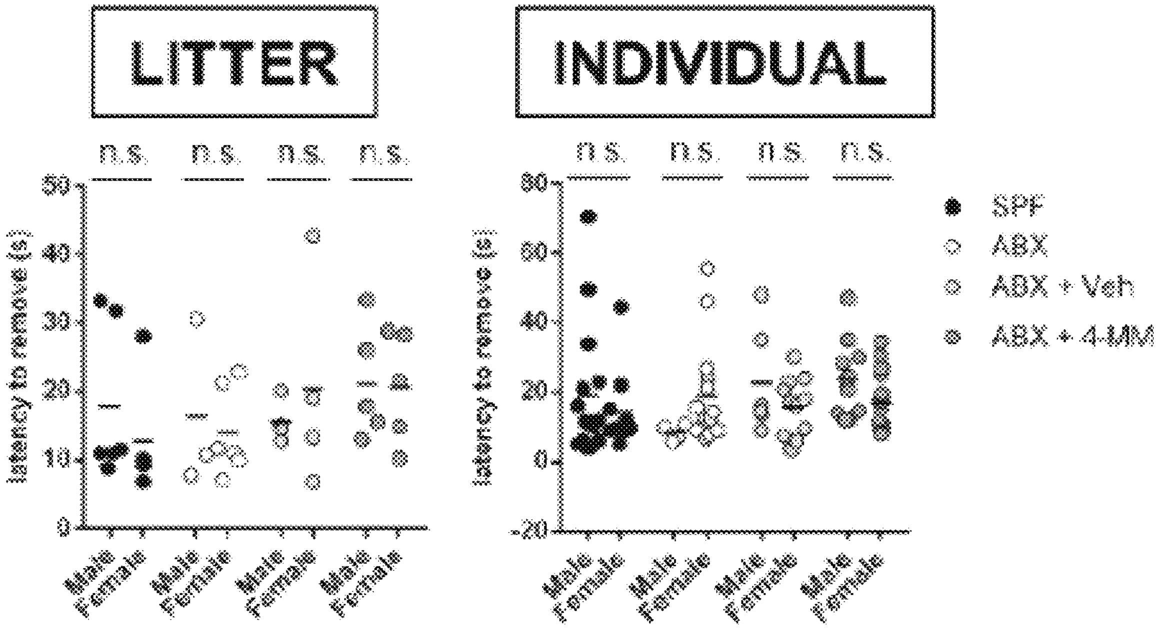
Figure 18:
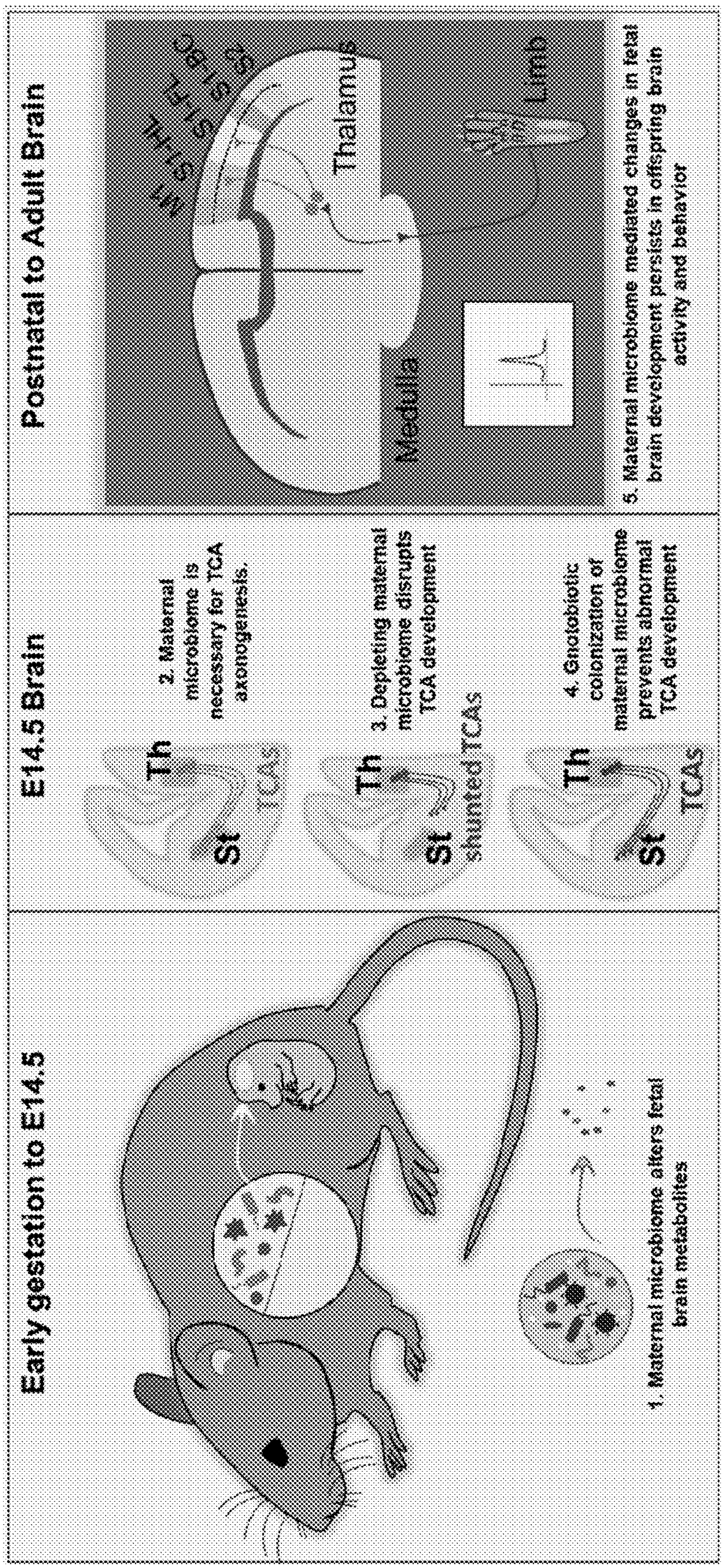
FIG. 18: A schematic depicting that the maternal microbiome mediates brain development and behaviours.

To further determine whether particular microbiota-dependent metabolites in the fetal brain mediate the ability of the maternal microbiome to promote fetal thalamocortical axonogenesis, thalamic explants from E14.5 embryos of ABX-treated dams were exposed to physiologically-relevant levels of select fetal brain biochemicals, and axon outgrowth was evaluated ex vivo. The metabolites trimethylamine-N-oxide (TMAO), N, N, N-trimethyl-5-aminovalerate (TMAV), imidazole propionate (IP), 3-indoxyl sulfate (3-IS) and hippurate (HIP) were selected based on their>2-fold reduction in both maternal blood and fetal brain lysates from ABX and GF dams, relative to SPF controls, and their restoration to SPF levels by maternal colonization with Sp bacteria (FIG. 12I, FIG. 13B). In addition, each metabolite is known to be regulated in adult stool, blood and/or prefrontal cortex by the gut microbiome[8,47,54,55]. Fetal thalamic explants harvested from E14.5 embryos of ABX dams exhibited impaired axonogenesis in response to co-culture with ABX striatal and hypothalamic explants, as previously described (FIGS. 1J-1M, FIG. 5A-5L, white vs. black). Notably, exposure to physiologically-relevant concentrations of TMAO, 5-AV, IP or HIP, but not 3-IS, significantly increased axon number to levels seen in fetal brain explants from embryos of SPF dams (FIGS. 14A-14C, FIG. 15A). 5-AV and IP also significantly increased axon length, whereas TMAO and 3-IS induced modest, but not statistically significant, increases in axon length, while HIP had no effect (FIG. 15B). No statistically significant changes were found in number and length of ABX thalamic axons proximal to hypothalamus in response to TMAO, 5-AV, IP, 3-IS, or HIP (FIGS. 15C-15D). To further test whether maternal metabolite supplementation impacts fetal neurodevelopment in vivo, ABX-treated dams were injected intraperitoneally with a cocktail of TMAO, 5-AV, IP, and HIP metabolites (4-MM) or vehicle from E7-14 of gestation, the developmental time frame during which thalamocortical axonogenesis occurs[56,57] Metabolite dosages were calculated based on maternal serum metabolomic data and physiological concentrations reported in literature to reflect daily levels needed to achieve those observed in SPF dams (see Methods section). Notably, maternal supplementation with 4-MM prevented the reductions in Netrin-G1 thalamocortical axons seen with maternal microbiome depletion (FIGS. 14D-14F, FIG. 16A-16D). Consistent with results from the axon outgrowth assay, these findings suggest that select microbial metabolites, including 4-MM, are important for promoting fetal thalamocortical axonogenesis. Furthermore, adult offspring of ABX dams that were supplemented with 4 MM exhibited improvements in tactile sensory behavior in the von Frey filament and adhesive removal tasks, relative to vehicle-treated ABX controls, which were statistically significant when analyzed by dam (FIGS. 14G-141) as well as by individual offspring (FIGS. 17A-17C). There were no significant differences observed between male and female mice in these behavioral tasks (FIGS. 17D-17F). Altogether, results from this study reveal that the maternal microbiome promotes fetal thalamocortical axonogenesis and postnatal tactile sensory behavior, likely via microbiome-dependent biochemicals, such as TMAO, 5-AV, IP, and HIP, in the fetal brain.

The gut microbiome modulates numerous bioactive molecules in the intestine, serum and various extraintestinal organs[54,58,59]. Findings from this work reveal that during pregnancy, the maternal gut microbiome regulates metabolites, not only in the maternal compartment, but also in the fetus itself, including the embryonic brain. Select fetal brain metabolites that are regulated by the maternal gut microbiome induce axon outgrowth from thalamic explants and promote fetal thalamocortical axonogenesis and adult tactile sensory behavior in offspring of microbiome-depleted dams. While the molecular mechanisms underlying the effects of select microbial metabolites on neurons remain unclear, some metabolites, such as TMAO, TMAV and HIP, have been associated with neurological conditions and factors related to neurite outgrowth[60-65] (Example 3). In addition, findings from this study parallel recent evidence that malnutrition-induced alterations in the maternal microbiome were associated with reduced white matter in the brains of adolescent and adult offspring and that inflammation-induced alterations in the maternal gut microbiome disrupted somatosensory cortical architecture in adult offspring[20,66-69.] Furthermore, a recent study of microbiomes in malnourished children reported that children with severe acute malnutrition exhibited dysregulation of several proteins associated with axonogenesis, including semaphorins, neurotrophins, netrin, slit and ephrin, which were ameliorated by treatment with microbiota-directed diets"[70]. Results presented herein support an important role for the maternal microbiome in promoting offspring neurodevelopment, and further suggest that interactions between the microbiome and nervous system begin prenatally through influences of the maternal gut microbiome on fetal brain metabolomic profiles and gene expression. Altogether, findings from this study identify early to mid-gestation as a critical period during which the maternal microbiome promotes fetal neurodevelopment to support developmental processes underlying adult tactile sensory behavior.

Example 2: Methods Used for Example 1

Mice

C57Bl/6J mice were purchased from Jackson Laboratories, reared as SPF or rederived as GF, and bred in flexible film isolators at the UCLA Center for Health Sciences barrier facility. Animals were maintained on a 12-h light-dark schedule in a temperature-controlled environment with autoclaved "breeder" chow (Lab Diets 5K52) and standard chow (Lab Diet 5010) and autoclaved water provided ad libitum.

Sample Size Determination 6-8 week-old mice were randomly assigned to experimental groups, which included age- and sex-matched cohorts of males and females for timed matings. Given that maternal microbiome status is the primary experimental variable across experiments, biological sample sizes reflect independent dams. Experiments evaluating fetal outcomes include at least 2 randomly selected embryos per dam, where data from offspring from a single dam were averaged to represent the dam as the biological "n". For behavioral assays, all offspring were behaviorally tested and data from offspring from the same dam were averaged to represent the dam as the biological "n". These data are presented in FIGS. 1A-1M, 6A-6G, 10A-10M, 12A-121, and 14A-141, whereas behavioral data per individual offspring are presented in the other figures. All experiments were performed in accordance with the NIH Guide for the Care and Use of Laboratory Animals using protocols approved by the Institutional Animal Care and Use Committee at UCLA.

Antibiotic Treatment and Conventionalization 4-5 week old SPF mice were gavaged twice daily (08:00 and 17:00) for 1 week with a cocktail of neomycin (100 mg/kg), metronidazole (100 mg/kg), and vancomycin (50 mg/kg), according to methods previously described to mimic GF status[71]. Ampicillin (1 mg/ml) was provided ad libitum in drinking water. Breeders were then paired and time-mated, where up to 2 additional weeks were required to conception. Gestational day 0.5 was determined by observation of copulation plug. Dams were then separated and maintained on ABX drinking water until E14.5 to preclude the daily stress of oral gavage in pregnant dams (1 mg/ml ampicillin, 1 mg/ml neomycin, and 0.5 mg/ml vancomycin; metronidazole was excluded due to its confounding bitter taste). Fecal samples from ABX-treated dams were collected and plated anaerobically on Schaedler's broth and tryptic soy agar to confirm bacterial clearance. For behavioral assays, pregnant dams were conventionalized at E14.5 with SPF bedding that was gathered from a male and female C57Bl/6J cage[72]. Pregnant dams were maintained in SPF bedding for the remainder of gestation, and offspring were reared with SPF bedding, added weekly, until behavioral testing. Conventionalization was validated by fecal 16S rDNA sequencing, as described in the "16S rDNA sequencing" section below.

Gnotobiotic Colonization

Figure 9A:
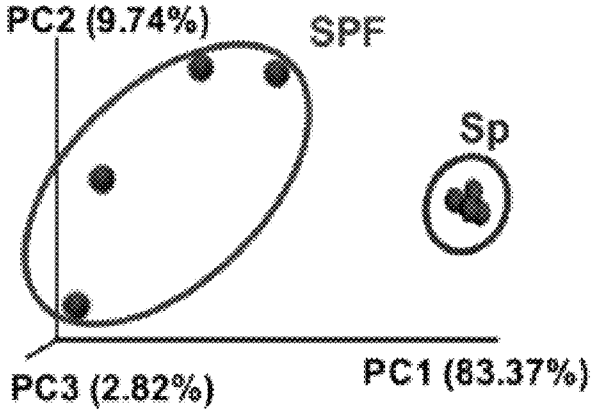
Figure 9B:
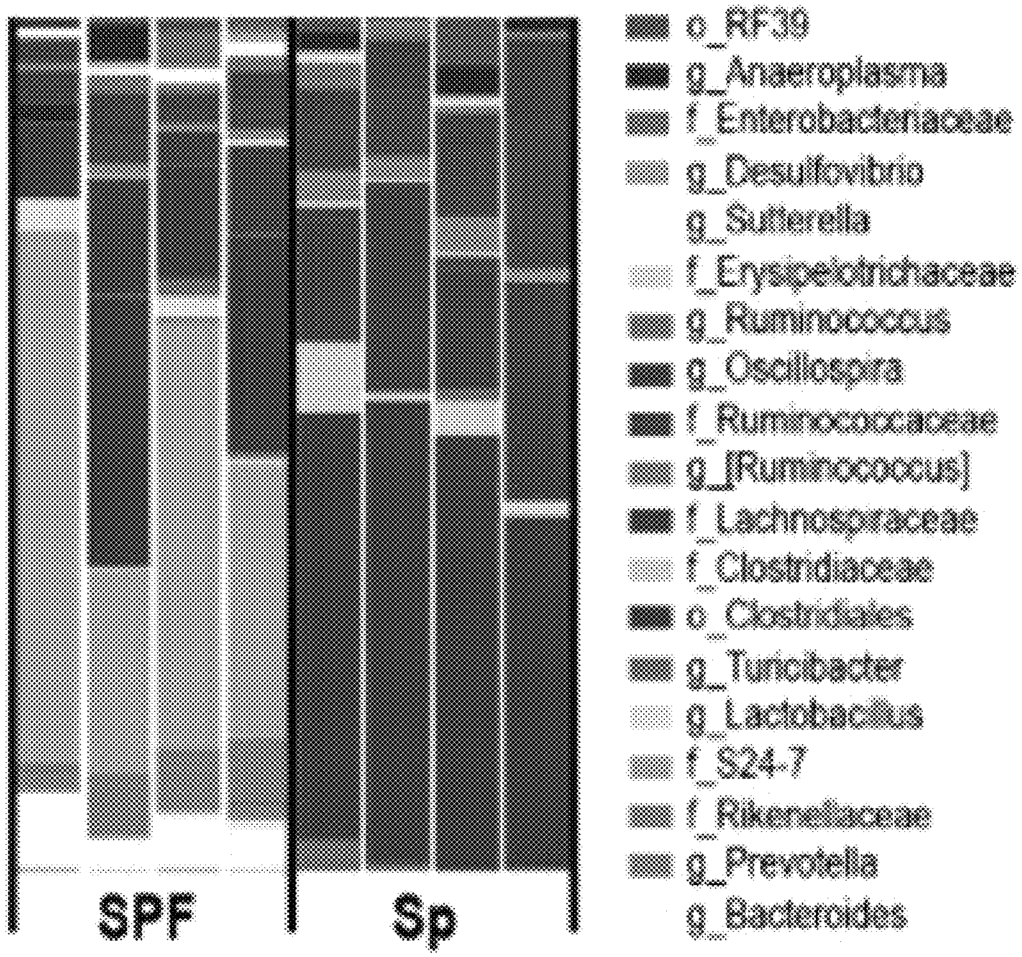
Figure 9E:
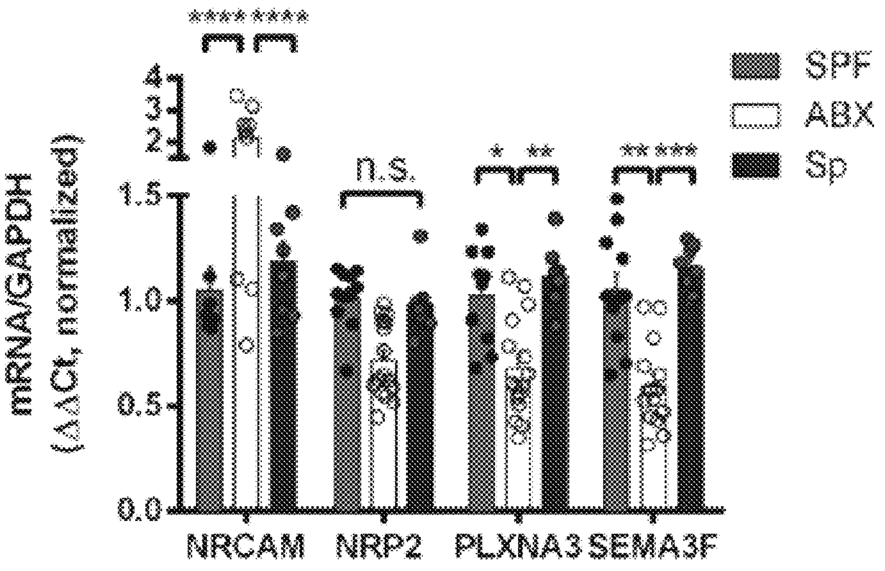
Figure 9F:
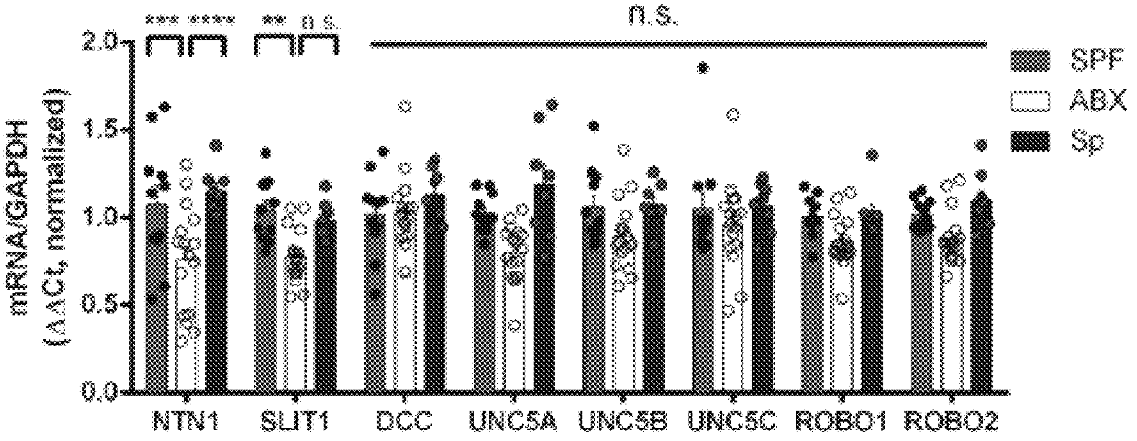
Figure 10A:
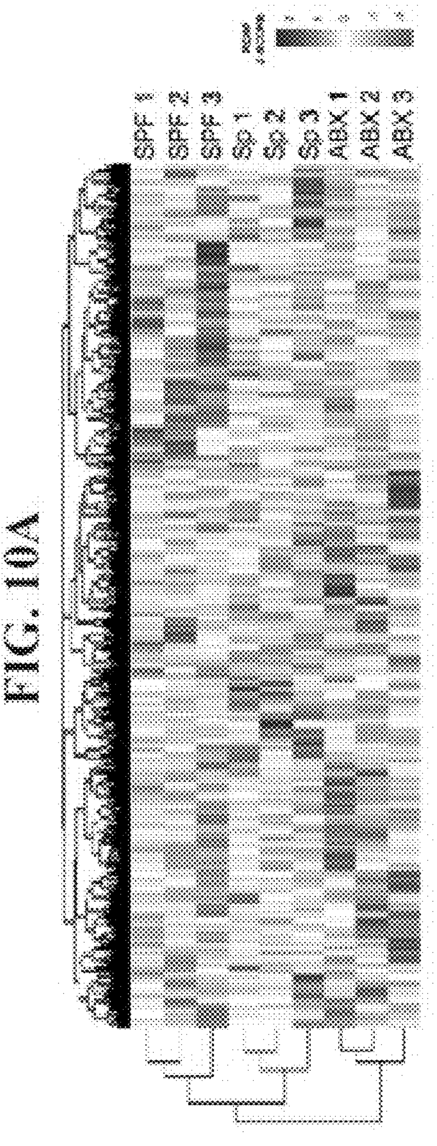
FIGS. 10A-10M: Gnotobiotic colonization of the maternal microbiota during early gestation prevents neurodevelopmental and behavioral abnormalities induced by maternal microbiota depletion. 10A, Heatmap of differentially expressed genes (p<0.05) in embryonic brains from E14.5 offspring of SPF, ABX, and Sp-colonized dams (Wald test, n=offspring from 3 dams). 10B, Expression of NTNG1 and LRRC4C as measured by quantitative RT-PCR in embryonic brains of E14.5 offspring from SPF, ABX, and Sp-colonized dams (Two-way ANOVA with Tukey's, n=offspring from 9 SPF, 15 ABX, 8 Sp dams). 10C, Representative immunofluorescence images of Netrin-G1a (magenta in the original image) and L1 (cyan in the original image) staining in embryonic brain sections (rostral to caudal) from E14.5 offspring from different dams. Scale bar=500 μm. 10D, Average Netrin-G1a fluorescence intensity per matched area of region of interest (ROI) ("yellow-in-the-original-image" dotted lines) across 800 μm of rostral to caudal embryonic brain sections of E14.5 offspring from SPF, ABX, and Sp-colonized dams. (Two-way ANOVA with Tukey's, n=offspring from 5 SPF, 7 ABX, 5 Sp dams). 10E, Average L1 fluorescence intensity of L1 per matched area of ROI ("yellow-in-the-original-image" dotted lines) across 800 μm of rostral to caudal embryonic brain sections of E14.5 offspring from SPF, ABX, and Sp-colonized dams (Two-way ANOVA with Tukey's, n=offspring from 5 SPF, 7 ABX, 5 Sp dams). 10F, Representative 3-D rendering of Netrin-G1a staining (green in the original image) in cleared whole embryonic brains from E14.5 offspring of Sp dams. Scale bar=100 μm. 10G, Volume of Netrin-G1a axons in cleared whole embryonic brains from E14.5 offspring of SPF, ABX, and Sp-colonized dams. (One-way ANOVA with Tukey's; n=offspring from 5 dams per group). 10H, Length of Netrin-G1a axons in cleared whole embryonic brains from E14.5 offspring of SPF, ABX, and GF dams. (One-way ANOVA with Tukey's; n=offspring from 5 dams per group). 10I, Distance from distal tip of Netrin-G1a staining to the cortex in whole embryonic brains from E14.5 offspring of SPF, ABX, and Sp-colonized dams. (One-way ANOVA with Tukey's; n=offspring from 5 dams per group). 10J, Average circumference of the Netrin-G1a axonal bundle at the internal capsule (IC) in whole embryonic brains from E14.5 offspring of SPF, ABX, and Sp-colonized dams. (One-way ANOVA with Tukey's; n=offspring from 5 dams per group). 10K, Experimental timeline of ABX treatment and Sp colonization prior to breeding, conventionalization with SPF microbiota on E14.5, and offspring behavioral testing at 6-8 weeks. 10L, Force filament required to induce 50% paw withdrawal in adult offspring of SPF, ABX and Sp-colonized dams (One-way ANOVA with Tukey's, n=offspring from 5 SPF, 7 ABX, 7 Sp dams). 10M, left: Forepaw sensitivity, as measured as the latency to contact the adhesive tape, in adult offspring of SPF, ABX and Sp-colonized dams (One-way ANOVA with Tukey's, n=offspring from 6 SPF, 6 ABX, 7 Sp dams). right: Forepaw motor dexterity, as measured as the latency to remove the adhesive tape after first contact, in adult offspring of SPF, ABX and Sp-colonized dams (One-way ANOVA with Tukey's, n=offspring from 6 SPF, 6 ABX, 7 Sp dams). Data are presented as mean±SEM. Data shown for SPF and ABX are as displayed in FIGS. 1A-1M, 6A-6G, 14A-14I, 3A-3I, 4A-4D, 5A-5L, and 7A-7F. *p<0.05, p<0.01, *p<0.001, ****p<0.0001, n. s.=not statistically significant.
Figure 10B:
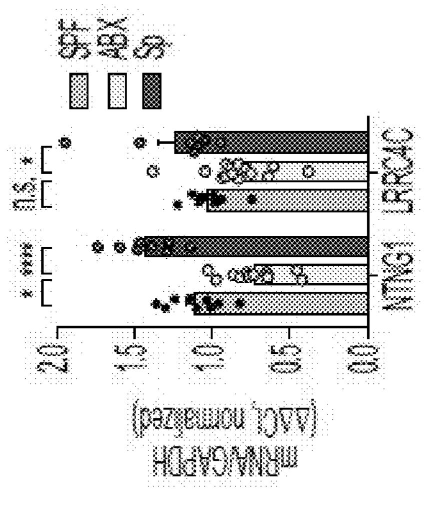
Figure 10C:
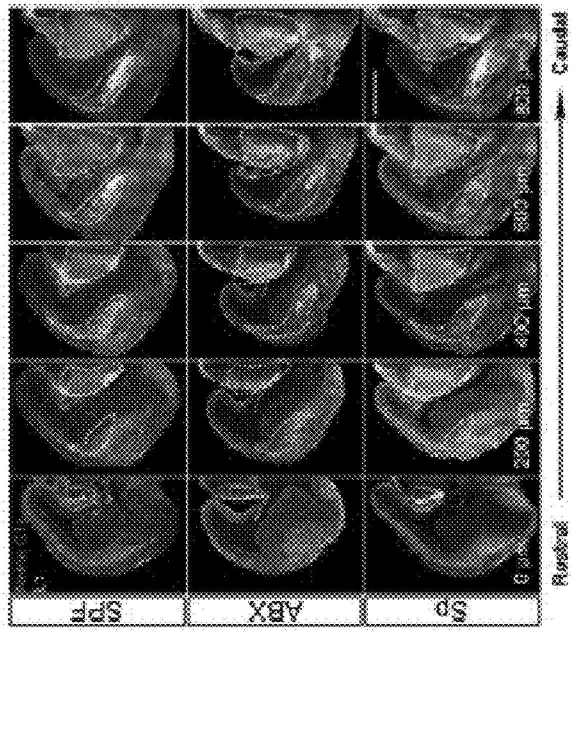
Figure 10D:
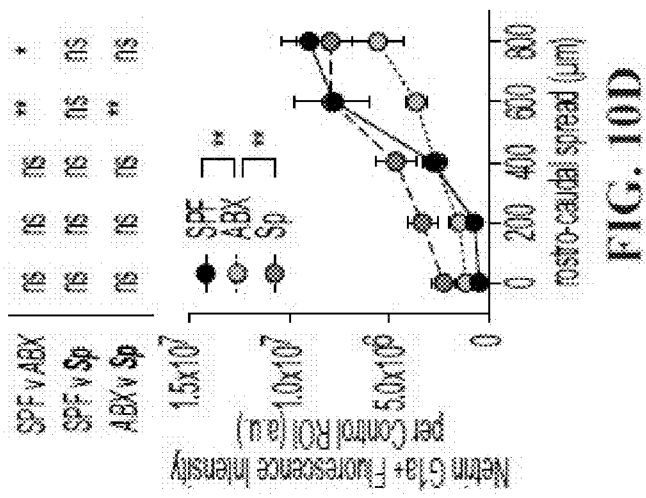
Figure 10E:
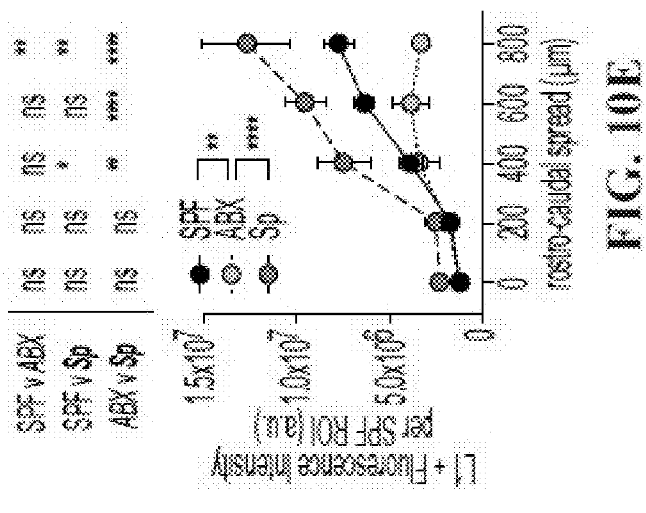
Figures 10F, 10G, 10H, 10I, 10J, 10K, 10L, 10M:
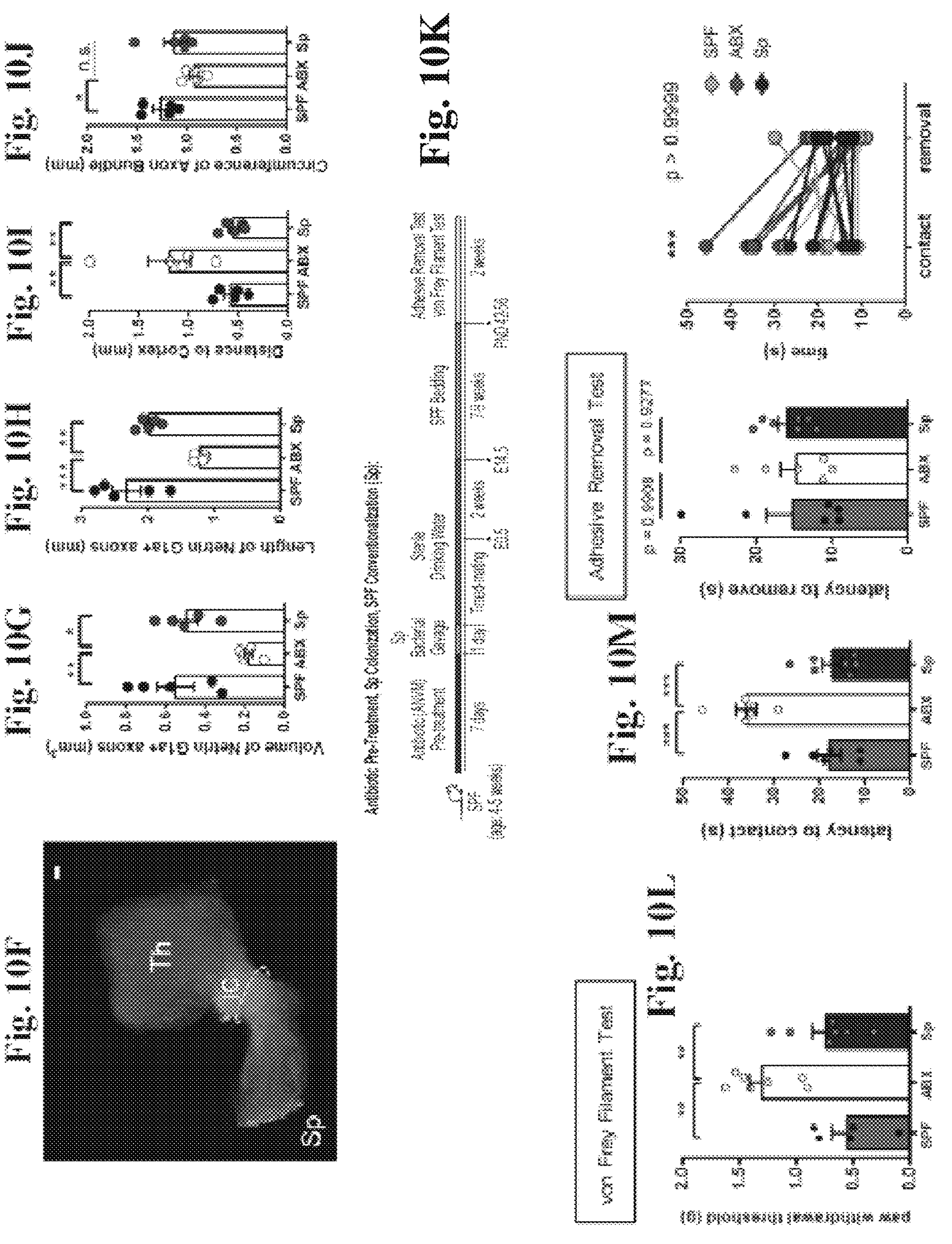

Mice were treated with ABX as described in the "antibiotic treatment" section above, then given sterile water and orally gavaged 1 day later with Sp or BD bacteria. Sp-colonized mice were generated as previously described'. Briefly, fecal pellets from C57Bl/6J SPF mice were freshly suspended in a 10× volume of pre-reduced PBS in an anaerobic chamber. Chloroform was added to 3% (vol/vol), the sample was shaken vigorously and incubated at 37° C. for 1 hr. Chloroform was removed by percolation with $CO_2$ from a compressed cylinder. 200 ul of the resultant suspension was orally gavaged into adult GF C57Bl/6J "founder" mice housed in designated gnotobiotic isolators. Fecal samples were collected from the Sp mice at >2 weeks after gavage and suspended at 50 mg/ml in pre-reduced PBS. 200 ul of the suspension was orally gavaged to ABX-treated experimental mice. For the *Bacteroides* (BD) consortium, *B. thetaiotaomicron* (ATCC 29148), *B. vulgatus* (ATCC 8482) and *B. uniformis* (ATCC 8492), *B. ovatus* (ATCC 8483) and *B. fragilis* (NCTC 9343) were grown in Brain Heart Infusion media (BD Biosciences) supplemented with 5 μg/ml hemin (Frontier Scientific) and 0.5 μg/ml vitamin K1 (Sigma Aldrich) under anaerobic conditions. A 200 μl suspension of 1:1:1:1:1 OD of each strain was orally gavaged into ABX-treated mice. Colonization status was validated by 16S rDNA sequencing of fecal samples collected on E14.5 (FIGS. 9B and 11A). For BD, total relative abundance of *Bacteroides* was 95.24%, and individual species distributions were determined by qPCR as *B. thetaiotaomicron:* 9.38%, *B. vulgatus:* 18.75% and *B. uniformis:* 15.63%, *B. ovatus:* 46.88% and *B. fragilis:* 9.38%.

Fetal Brain RNA Sequencing

Dams were sacrificed on E14.5 by cervical dislocation to preclude confounding effects of $CO_2$ on maternal and fetal physiology. Embryonic brains were microdissected from SPF, ABX, and Sp colonized mice and placed in Trizol (Invitrogen). RNA was extracted using the RNAeasy Mini kit with on-column genomic DNA-digest (Qiagen), and cDNA synthesis was performed using the qScript cDNA synthesis kit (Quantabio). RNA quality of RIN>8.0 was confirmed using the 4200 Tapestation system (Agilent). RNA was prepared using the TruSeq RNA Library Prep kit and 2×69 bp paired-end sequencing was performed using the Illumina HiSeq 4000 platform by the UCLA Neuroscience Genomics Core. FastQC v0.11.8 and HiSAT2 2.1.0[74,75] were used for quality filtering and mapping. Reads were aligned to UCSC Genome Browser assembly ID: mm10. Differential expression analysis was conducted using DESeq2 1.24.0[76]. Heatmaps were generated using the pheatmap package for R. GO term enrichment analysis of differentially expressed genes with q<0.05 was conducted using DAVID v6.8[77].

Quantitative RT-PCR

Dams were sacrificed on E14.5 by cervical dislocation to preclude confounding effects of $CO_2$ on maternal and fetal physiology. Embryonic brains were microdissected on E14.5 and sonicated in Trizol for RNA isolation using the RNAeasy Mini kit with on-column genomic DNA-digest (Qiagen). cDNA synthesis was performed using the qScript cDNA synthesis kit (Quantabio). qRT-PCR was performed on a QuantStudio 5 thermocycler (ThermoFisher Scientific) using SYBR green master mix with Rox passive reference dye and validated primer sets obtained from Primerbank (Harvard).

Axon Outgrowth Assay

Dams were sacrificed on E14.5 by cervical dislocation to preclude confounding effects of $CO_2$ on maternal and fetal physiology. Thalamic, striatal, and hypothalamic explants were isolated from E14.5 embryonic brains and transferred to ice-cold HBSS (Invitrogen). Explants were sliced to ~500 μm and placed on a thin layer of 50 μl BD Matrigel (Beckton Dickinson) on a 15 mm coverslip. Each coverslip contained a thalamic explant at the center and a striatal and hypothalamic explant on each side, at 1 mm equidistant from the thalamic explant. Explants were incubated in warmed neurobasal complete media containing 1× neurobasal medium (Thermofisher Scientific), 1× GlutaMax (Thermofisher Scientific), and 2% B-27 (Thermofisher Scientific) for 48 hrs at 37° C., and fed with fresh media every 24 hrs. After 48 hrs, media was gently aspirated and replaced with 4% PFA for 1 hr and processed for immunofluorescence staining with 1:500 (3 tubulin III anti-mouse antibody (EMD Millipore MAB1637). Axons were imaged using a Leica DMi8 epifluorescence microscope and quantified using Fiji software[78]. Axon numbers were quantified per 200 μm of thalamus at a distance of 200 μm from the thalamus. Length of axons was quantified by averaging length of the 10 longest axons proximal to striatum or hypothalamus. Data for number and length of axons in the explant co-culture system was normalized by subtraction of data from monoculture of thalamic explants from the corresponding experimental group.

Metabolite Supplementation

Thalamic, striatal, and hypothalamic explants from ABX-treated dams were harvested and cultured as described in the "axon outgrowth assay" section above. For metabolite treatment, BD Matrigel was supplemented with 10 1.1M, 100 nM, or 1 nM of trimethylamine-N-oxide (TMAO), 5-aminovalerate (5-AV), imidazole propionate (IP), 3-indoxylsulfate (3-IS), or hippurate (llip)[48,79-81]. 5-aminovalerate is a precursor to N,N,N-trimethyl-5-aminovalerate (TMAV), which is not commercially available, and both are implicated in carnitine metabolism[82,83]. Metabolite concentrations were determined as physiologically relevant, based on reported concentrations detected in blood and/or cerebrum from the mouse multiple tissue metabolomic database (MMIvIDB), human metabolome database (HMDB) and existing literature[48,79-81]. Axons were stained, imaged and analyzed as described in the "axon outgrowth assay" section above.

In Vivo Metabolite Supplementation

To test the effects of TMAO, 5-AV, IP, and HIP on fetal axonogenesis and behavior, physiological concentrations of metabolites were administered intraperitoneally as a single dose per each day in order to limit stress to pregnant dams. Controls were injected with vehicle. Metabolite concentrations were calculated based on physiological levels reported in mouse blood[48,79-81], total blood volume of pregnant mouse dams (approximately 58.5 ml/kg[84]), and relative reductions observed in maternal sera of ABX dams compared SPF dams (Table 5). The metabolite mixture (4-MM): 121 ug (TMAO), 9 ug (5-AV), 92 ug (IP), and 2 ug (HIP) in 200 ul of 0.1 M PBS was injected intraperitoneally into E7.5 ABX dams once a day for 7 days. To assess fetal thalamocortical axon levels, dams treated with 4-MM or vehicle were sacrificed on E14.5, and fetal brains were harvested and processed as described in the "immunofluorescence staining" and "modified CLARITY" sections below. To test for behavioral effects, E14.5 pregnant dams were taken off antibiotic water (ANV) on E14.5, transferred into cages with sterile water, and conventionalized as described in the "conventionalization" section above. Adult offspring (P42-P56) were tested in the von Frey filament test and adhesive removal test as described in the "behavioral assay" section below.

Immunofluorescence Staining

E14.5 embryos were fixed in 4% paraformaldehyde for 24 hrs at 4° C., cryoprotected in 30% sucrose 24 hrs at 4° C. and sectioned at 10 μm using a Leica CM1950 cryostat. Sections were blocked with 10% donkey serum for 1 hr. Primary antibodies were diluted in 3% donkey serum and incubated for 15-18 hrs at 4° C. with Netrin-G1a anti-goat antibody (1:100, R&D Systems, AF1166) or Neural Cell Adhesion Molecule L1 anti-rat antibody (1:500, EMD Millipore, MAB5272). Sections were then incubated for 2 hrs at room temperature in their corresponding donkey anti-goat and anti-rat secondary antibodies conjugated to Alexa Fluor 568 or 488 (1:1000, Thermofisher Scientific). Images were acquired using the Zeiss Axio Examiner LSM 780 confocal microscope. Rostral to caudal sections were adjusted in Fiji: process>noise>despeckle, to remove non-specific staining. Fluorescence intensity of stains was quantified in Fiji based on a set region of interest drawn to encompass Netrin-G1a staining observed in SPF samples.

Tissue Clearing and Imaging

E14.5 embryos were collected and fixed in 4% paraformaldehyde for 48 hours at 4° C. Tissue was rendered transparent using methods for CLARITY-based clearing[85] with the following modifications. Tissues were incubated in a hydrogel solution containing 4% paraformaldehyde, 4% acrylamide (Bio-Rad), 0.05% bis-acrylamide (Bio-Rad), 0.25% VA-044 (A4P4B0.05) for 3 days at 4° C. Prior to hydrogel polymerization, the solution was exchanged with new solution lacking bis-acrylamide and paraformaldehyde (A4PO4) and polymerized at 37° C. for 3 hrs. Samples were passively cleared in 8% SDS for 2 weeks at 42° C., and then incubated with primary antibodies (Netrin-G1 a anti-goat (1:100, R&D Systems, AF1166) and L1 anti-rat (1:500, EMD Millipore, MAB5272)) for 1 week at 25° C. Samples were washed and then incubated in secondary antibodies (1:1000, Thermofisher Scientific) for 5 days at 25° C. Samples were equilibrated for 15-18 hrs in a histodenz-based refractive index matching solution (RI 1.47; Sigma Aldrich, D2158) and imaged on a Zeiss LSM 780 with 488 or 561 nm illumination using a 5× objective with 3 um z-slices. Images were adjusted for brightness and contrast post hoc using Arivis Vision4D v3.0. 3D reconstructions were optically z-sliced for quantification of stain volume, length of axons, circumference of internal capsule and distance of rostral axon tip to cortical surface. Positively stained areas of interest were segmented and visualized using CTAn and CTVol software packages (Bruker Corporation), respectively.

Behavioral Assays

For behavioral assays, investigators were blinded to experimental groups. For each behavioral test, cages were brought to the testing room at least 30 minutes before testing to enable acclimation and reduce stress. Equipment and testing chambers were thoroughly cleaned with Accel disinfectant (Unimed) before and after each trial.

Adhesive Removal Test

The adhesive removal test was performed according to methods adapted from Bouet et al. 2009[37]. Briefly, mice were acclimated to the testing cage for 5 min A small adhesive tape (0.3 cm×0.4 cm) was gently applied to both forepaws, and mice were returned to the testing cage. Mice were observed for contact time, as defined as the latency to which the mouse reacts to the presence of the adhesive tape, and for removal time, as defined as the latency to which the mouse removes both pieces of tape completely. Contact time and removal time were manually recorded using a standard lab multi-timer by experimenters blinded to the mouse experimental group.

Von Frey Filament Test

The von Frey filament test was performed according to methods adapted from Dixon et al., 1980[86]. Briefly, mice were placed on a wide gauge, wire mesh surface in a testing chamber and acclimated for 10 minutes daily for two consecutive days prior to testing day. On the testing day, mice were placed in the testing chamber, acclimated for 10 minutes, and von Frey filaments were applied from the underside of the mesh to the plantar surface of the hindpaw. The process is repeated with increasing gauges (0.4, 0.6, 1, 1.4, 2, 4, 6 grams of force) of von Frey filaments until stimulation elicits a hindpaw withdrawal, wherein the mouse responds by flicking its paw away from the stimulus. Upon paw withdrawal, the next weaker stimulus is defined as threshold. Responses of up-down paw stimulation were manually recorded and analyzed according to the Chaplan Method of 50% paw withdrawal threshold[36].

Prepulse Inhibition Test

The prepulse inhibition test was performed to measure sensorimotor gating[87]. Mice were placed in a restraint tube mounted on a startle measuring platform (San Diego Instruments) and acclimated to the testing chamber for 10 minutes. White noise is presented in the recording chamber for 5 minutes, followed by 6 startle presentations and a pseudo-randomized prepulse inhibition phase, which consisted of either no startle, 120 db startle stimulus only, or 70 db prepulse with startle, 75 db prepulse with startle, or 80 db prepulse with startle. Acoustic startle was recorded with a pliezo-electric sensory, and the percent prepulse inhibition was defined as: [((the startle stimulus only−prepulse with startle)/startle stimulus only)*100].

Hot Plate Test

To test for somatic pain response[1], mice were acclimated to a clear plastic cylinder for 30 s, then placed on an advanced hot plate (VWR) that was heated to 52° C. The latency to show nociceptive response as indicated by a paw lick, paw flick, vocalization, or a jump was recorded, and mouse was immediately returned to the home cage.

Novel Whisker Texture Test

The whisker texture test was performed according to methods adapted from Wu et al., 2013[2]. Mice were habituated in 50 cm×50 cm white plexiglass testing chamber for 10 minutes for 2 consecutive days. On testing day, mice were first subjected to a learning phase in which they were placed in the testing chamber for 5 minutes with two objects of identical texture (aluminum oxide sand paper, 80 grit). Mice were then returned to home cage for 5 minutes. In the test phase, mice were placed back into chamber with two objects, one with the original texture (80 grit) and one with new texture (220 grit). The trials were recorded with an overhead video camera and Ethovision software (Noldus) was used to analyze number of times and duration spent investigating the novel and familiar textures.

Visual Cliff Avoidance Test

To assess depth perception and visual impairment[3], mice were placed in a 42.5 cm×60 cm clear plexiglass testing chamber on top of a 3 ft×4 ft rectangular table. One third of the chamber hung over the edge of the table to create a visual effect of a cliff drop-off at a height of 3 ft. Mice were placed in the middle of the chamber 10 times. Mice were given 5 minutes to either exit off the platform towards the table or toward the cliff side of the chamber. Each choice was recorded and averaged by an experimenter blinded to mouse experimental group.

Rotarod Test

To test for motor coordination and balance[4], mice were placed in one of 4 compartments in a rotarod apparatus (Rotamex, Columbus Instruments) consisting of a cylinder that rotates speeds accelerating from 5 rpm to 60 rpm in 300 seconds. On the first day, mice acclimated to the apparatus with no rotation for 2 minutes. On the testing day, mice were returned to the apparatus and rotation was initiated. Latency to fall and final speed achieved by the accelerating rod before falling was detected by an infrared sensor and recorded. Mice were tested three times and scores were averaged.

16S rDNA Sequencing

Bacterial genomic DNA was extracted from mouse fecal samples using the MoBio PowerSoil Kit. The library was generated according to methods adapted from Caporaso et al. 2011[88]. The V4 regions of the 16S rRNA gene were PCR amplified using individually barcoded universal primers and 30 ng of the extracted genomic DNA. The PCR reaction was set up in triplicate, and the PCR product was purified using the Qiaquick PCR purification kit (Qiagen). 250 ng of purified PCR product from each sample were pooled and sequenced by Laragen, Inc. using the Illumina MiSeq platform and 2×250 bp reagent kit for paired-end sequencing. Operational taxonomic units (OTUs) were chosen by open reference OTU picking based on 97% sequence similarity to the Greengenes 13_5 database. Taxonomy assignment and rarefaction were performed using QIIME1.8.0[89].

Metabolomics

At E14.5 maternal serum was collected by cardiac puncture, separated using SST vacutainer tubes (Beckton Dickinson) and frozen at −80° C. Embryonic brains were collected and immediately snap frozen in liquid nitrogen. Each fetal brain sample consisted of 5 embryonic brains pooled from the same litter. Samples were prepared using the automated MicroLab STAR system (Hamilton Company) and analyzed on GC/MS, LC/MS and LC/MS/MS platforms by Metabolon, Inc. Protein fractions were removed by serial extractions with organic aqueous solvents, concentrated using a TurboVap system (Zymark) and vacuum dried. For LC/MS and LC-MS/MS, samples were reconstituted in acidic or basic LC-compatible solvents containing >11 injection standards and run on a Waters ACQUITY UPLC and Thermo-Finnigan LTQ mass spectrometer, with a linear ion-trap frontend and a Fourier transform ion cyclotron resonance mass spectrometer back-end. For GC/MS, samples were derivatized under dried nitrogen using bistrimethyl-silyl-trifluoroacetamide and analyzed on a Thermo-Finnigan Trace DSQ fast-scanning single-quadrupole mass spectrometer using electron impact ionization. Chemical entities were identified by comparison to metabolomic library entries of purified standards. Following log transformation and imputation with minimum observed values for each compound, data were analyzed using one-way ANOVA to test for group effects. P and q-values were calculated based on two-way ANOVA contrasts. Principal components analysis was used to visualize variance distributions. Supervised Random Forest analysis was conducted to identify metabolomics prediction accuracies. Volcano plots were generated using R, with differentially regulated metabolites at $q<0.05$.

Statistical Methods

Statistical analysis was performed using Prism software (GraphPad). Data were assessed for normal distribution and plotted in the figures as mean±SEM. For each figure, n=the number of independent maternal biological replicates. For assessments involving fetal brains, each maternal biological sample reflects an average of 2-5 embryo "technical" replicates. For behavioral assessments, all offspring were tested. Data for littermates from the same dam were averaged and presented in the FIGS. 1A-1M, 6A-6G, 10A-10M, 12A-12I, and 14A-14I with n=independent maternal dams; individual data for each offspring are provided in the other figures. No samples or animals were excluded from the analyses. Differences among >2 groups with only one variable were assessed using one-way ANOVA with Tukey's post hoc test. Taxonomic comparisons from 16S rDNA sequencing analysis were analyzed by Kruskal-Wallis test with Tukey's post hoc test. Two-way ANOVA with Tukey's post-hoc test was used for >2 groups with two variables. Significant differences emerging from the above tests are indicated in the figures by $^{*}p<0.05$, $^{}p<0.01$, $^{*}p<0.001$, $^{****}p<0.0001$. Notable non-significant differences are indicated in the figures by "n.s.".

Example 3: Additional Discussion Regarding Example 1

Gut Microbiota Modulation of Axons and Myelination

Results from this study reveal that the maternal microbiome promotes fetal thalamocortical axonogenesis. We observe deficiencies in L1 and Netrin-G1a expression in E14.5 brains of ABX dams (FIGS. 1B-1D). Consistent with a previous report, we observe only modest changes in L1 expression in E14.5 brains of fetuses from GF dams relative to SPF controls[90] (FIGS. 1B-1D), pointing to potential compensatory effects of GF rearing as compared to acute microbiome depletion. Our finding extends several previous reports that the gut microbiota modulates axon structure and axonal myelination in adult animals. Adolescent (4 weeks) and adult (12 weeks) GF mice display reduced white matter structure in the corpus callosum, anterior commissure and internal capsule[20], which is a defining anatomical structure for thalamocortical axon projections (FIGS. 1E-1I). Consistent with this, brains of GF mice also exhibit reduced expression of neuronal (NeuN), axonal (neurofilament-L), and myelination (MBP) markers relative to control mice colonized with a healthy human microbiota[19]. In a recent ultrastructural study, microbiota depleted mice exhibited reduced axon diameter and increased myelination in the brain'. Finally, children aged 6-36 months with healthy microbiome exhibit increased expression of central nervous system development proteins compared to children with severe acute malnutrition microbiomes. These proteins are associated with axonogenesis, including semaphorins (SEMA3A, SEMA5A, SEMA6A, SEMA6B), neurotrophins (NTRK2, NTRK3), netrin (UNC5D), slit (SLITRK5) and ephrin (EFNA5), which were ameliorated by treatment with microbiota-directed diets". Microbiome-dependent alterations in axons may extend beyond the brain itself, as adult GF and ABX-treated mice exhibited reduced axonal innervations of the colonic epithelium[17] and ABX treatment of a mouse model of multiple sclerosis increased axon numbers in the spinal cord[92]. Altogether, we propose that the maternal gut microbiome during pregnancy plays an important role in regulating fetal thalamocortical axonogenesis, Potential Mechanisms of Microbially Modulated Metabolites Results from this study indicate that the maternal microbiome modulates numerous biochemicals in the fetal brain, and that select metabolites—TMAO, 5-AV, IP, and HIP—promote fetal thalamocortical axonogenesis and offspring tactile sensory behavior. While microbiome-dependent regulation of TMAO, 5-AV, IP and HIP has been reported across metabolomic datasets for adult mouse and human blood, urine, and/or intestine[48,54,93,94], little is known regarding the functional roles for each metabolite on host physiology.

Dysregulation of TMAO, produced through a two-step enzymatic process performed by gut microbes and the liver, has been implicated in metabolic, cardiovascular, cerebrovascular, stroke and Alzheimer's disease[62,64,95] Although a cognate receptor for TMAO has not been described, TMAO is reported to modulate glucocorticoid receptors and the Gi3y subunit of GPCRs, to promote protein stability and folding as an organic osmolyte, and to regulate the phosphorylation of insulin-like growth factor 2 (IGF2)[96-99]. Such effects on IGF2 have been reported to increase sympathetic neurite outgrowth[100], which could be relevant to the observed axonogenic effects of TMAO on thalamocortical neurons.

TMAV is metabolized from dietary glycine and is associated with glucose metabolism and diets rich in whole grain[82,94,101]. Increases in TMAV have been associated with type 1 diabetes with microalbuminuria and metformin-treated type 2 diabetes[102,103], but the relation of TMAV to axon or brain development has not been previously reported. 5-AV, a precursor for TMAV, is microbially produced from L-lysine. L-lysine monooxygenase (DavB) and 5-aminovaleramide amidohydrolase (DavA) are key enzymes in the 5-AV pathway, whereby DavB catalyzes the oxidation of L-lysine to produce 5-aminovaleramide; DavA then converts 5-aminovaleramide into 5-AV[104,105]. 5-AV has been shown to negatively regulate baclofen, a GABAB receptor agonist, to suppress naloxone-stimulated luteinizing hormone-releasing hormone[106]. Further, 5-AV has been associated with reductions in the inhibitory effect of baclofen on norepinephrine release from noradrenergic terminals[106]. Separately, application of 5-AV onto rat hippocampal slices reduced pyramidal cell GABAB-mediated ICE inhibitory postsynaptic potential (IPSP)[107]. Though the exact mechanism by which 5-AV alters axon outgrowth is unclear, one hypothesis is that the influences of 5-AV on GABAB receptors, which are key regulators of synaptic release and axonal trafficking[108,109], can impact cortical neuronal migration and axon/dendrite morphological maturation by modulating cAMP signaling[110,111].

IP is a product of direct microbial, but not murine, metabolism[47]. IP is a microbial metabolite derived from histidine and has been reported to impair insulin signaling through mTORC1[48]. IP is associated with nonalcoholic fatty liver disease and is a potential inducer of steatosis and hepatic inflammation[112,113]. In another study, IP was found in urine of IBS patients 112,113. There have been no previous reports of IP regulation of axon development, however, activation of mTOR has been shown to increase axonal growth capacity[114] and promote axon regeneration after injury or disease[115,116].

HIP, synthesized through glycine conjugation with benzoate in the liver, is a metabolite of folic acid, which affects neural tube formation and brain development[65]. Decreased excretion of HIP has been described in patients with schizophrenia, depression, stroke, autism, and gastrointestinal disorder, and in animal models of acute and chronic stress[117-119]. While HIP has not been previously implicated in axon development, the HIP precursor, benzoate, has been shown to have anti-inflammatory properties and to reduce microglial and astroglial inflammatory responses in the experimental autoimmune encephalomyelitis (EAE) model of multiple sclerosis[120].

Overall, a few previous reports have associated altered microbiome-related metabolites with altered neurodevelopment and adverse neurological outcomes. However, extensive further research is needed to uncover functional roles for microbially-modulated metabolites on host health and disease, and to identify the molecular and cellular mechanisms underlying the axonogenic effects of TMAO, 5-AV, IP and HIP on thalamic neurons.

Example 4: References for Examples 1-3

1 Vuong, H. E., Yano, J. M., Fung, T. C. & Hsiao, E. Y. The Microbiome and Host Behavior. *Annu Rev Neurosci* 40, 21-49, doi:10.1146/annurev-neuro-072116-031347 (2017).

2 Clarke, G. et al. The microbiome-gut-brain axis during early life regulates the hippocampal serotonergic system in a sex-dependent manner. *Molecular psychiatry* 18, 666-673, doi:10.1038/mp.2012.77 (2013).

3 Phelps, D. et al. Microbial colonization is required for normal neurobehavioral development in zebrafish. *Sci Rep* 7, 11244, doi:10.1038/s41598-017-10517-5 (2017).

4 Sharon, G. et al. Commensal bacteria play a role in mating preference of *Drosophila melanogaster. Proceedings of the National Academy of Sciences of the United States of America* 107, 20051-20056, doi:10.1073/pnas.1009906107 (2010).

5 Bravo, J. A. et al. Ingestion of *Lactobacillus* strain regulates emotional behavior and central GABA receptor expression in a mouse via the vagus nerve. *Proceedings of the National Academy of Sciences of the United States of America* 108, 16050-16055, doi:10.1073/pnas.1102999108 (2011).

6 Buffington, S. A. et al. Microbial Reconstitution Reverses Maternal Diet-Induced Social and Synaptic Deficits in Offspring. *Cell* 165, 1762-1775, doi:10.1016/j.cell.2016.06.001 (2016).

7 Hsiao, E. Y. et al. Microbiota modulate behavioral and physiological abnormalities associated with neurodevelopmental disorders. *Cell* 155, 1451-1463, doi:10.1016/j.cell.2013.11.024 (2013).

8 Olson, C. A. et al. The Gut Microbiota Mediates the Anti-Seizure Effects of the Ketogenic Diet. *Cell* 174, 497, doi:10.1016/j.cell.2018.06.051 (2018).

9 Kim, S. et al. Maternal gut bacteria promote neurodevelopmental abnormalities in mouse offspring. *Nature* 549, 528-532, doi:10.1038/nature23910 (2017).

10 Shin Yim, Y. et al. Reversing behavioural abnormalities in mice exposed to maternal inflammation. *Nature* 549, 482-487, doi:10.1038/nature23909 (2017).

11 De Palma, G. et al. Microbiota and host determinants of behavioural phenotype in maternally separated mice. *Nature communications* 6, 7735, doi:10.1038/ncomms8735 (2015).

12 Jasarevic, E. et al. The maternal vaginal microbiome partially mediates the effects of prenatal stress on offspring gut and hypothalamus. *Nat Neurosci* 21, 1061-1071, doi:10.1038/s41593-018-0182-5 (2018).

13 Backhed, F. et al. Dynamics and Stabilization of the Human Gut Microbiome during the First Year of Life. *Cell Host Microbe* 17, 690-703, doi:10.1016/j.chom.2015.04.004 (2015).

14 Ferretti, P. et al. Mother-to-Infant Microbial Transmission from Different Body Sites Shapes the Developing Infant Gut Microbiome. *Cell Host Microbe* 24, 133-145 e135, doi:10.1016/j.chom.2018.06.005 (2018).

15 Mueller, N. T., Bakacs, E., Combellick, J., Grigoryan, Z. & Dominguez-Bello, M. G. The infant microbiome development: mom matters. *Trends Mol Med* 21, 109-117, doi:10.1016/j.molmed.2014.12.002 (2015).
16 Nakashiba, T. et al. Netrin-G1: a novel glycosyl phosphatidylinositol-linked mammalian netrin that is functionally divergent from classical netrins. *I Neurosci* 20, 6540-6550 (2000).
17 De Vadder, F. et al. Gut microbiota regulates maturation of the adult enteric nervous system via enteric serotonin networks. *Proc Natl Acad Sci USA* 115, 6458-6463, doi:10.1073/pnas.1720017115 (2018).
18 Gacias, M. et al. Microbiota-driven transcriptional changes in prefrontal cortex override genetic differences in social behavior. *eLife* 5, doi:10.7554/eLife.13442 (2016).
19 Lu, J. et al. Effects of Intestinal Microbiota on Brain Development in Humanized Gnotobiotic Mice. *Scientific reports* 8, 5443, doi:10.1038/s41598-018-23692-w (2018).
20 Lu, J. et al. Microbiota influence the development of the brain and behaviors in C57BL/6J mice. *PLoS One* 13, e0201829, doi:10.1371/journal.pone.0201829 (2018).
21 Rennie, S., Lotto, R. B. & Price, D. J. Growth-promoting interactions between the murine neocortex and thalamus in organotypic co-cultures. *Neuroscience* 61, 547-564 (1994).
22 Yamada, A. et al. Role of pre- and postsynaptic activity in thalamocortical axon branching. *Proc Nall Acad Sci USA* 107, 7562-7567, doi:10.1073/pnas.0900613107 (2010).
23 Braisted, J. E. et al. Netrin-1 promotes thalamic axon growth and is required for proper development of the thalamocortical projection. *J Neurosci* 20, 5792-5801 (2000).
24 Mitsogiannis, M. D., Little, G. E. & Mitchell, K. J. Semaphorin-Plexin signaling influences early ventral telencephalic development and thalamocortical axon guidance. *Neural Dev* 12, 6, doi:10.1186/s13064-017-0083-4 (2017).
25 Braisted, J. E., Ringstedt, T. & O'Leary, D. D. Slits are chemorepellents endogenous to hypothalamus and steer thalamocortical axons into ventral telencephalon. *Cereb Cortex* 19 Suppl 1, i144-151, doi:10.1093/cercor/bhp035 (2009).
26 Braisted, J. E., Tuttle, R. & O'Leary D, D. Thalamocortical axons are influenced by chemorepellent and chemoattractant activities localized to decision points along their path. *Dev Biol* 208, 430-440, doi:10.1006/dbio.1999.9216 (1999).
27 Song, H. et al. Conversion of neuronal growth cone responses from repulsion to attraction by cyclic nucleotides. *Science* 281, 1515-1518, doi:10.1126/science.281.5382.1515 (1998).
28 Song, H. J., Ming, G. L. & Poo, M. M. cAMP-induced switching in turning direction of nerve growth cones. *Nature* 388, 275-279, doi:10.1038/40864 (1997).
29 Stevens, A. & Jacobs, J. R. Integrins regulate responsiveness to slit repellent signals. *J Neurosci* 22, 4448-4455, doi:20026413 (2002).
30 Dontchev, V. D. & Letourneau, P. C. Nerve growth factor and semaphorin 3A signaling pathways interact in regulating sensory neuronal growth cone motility. *J Neurosci* 22, 6659-6669, doi:20026638 (2002).
31 Enriquez-Barreto, L., Palaz7etti, C., Brennaman, L. H., Maness, P. F. & Fairen, A. Neural cell adhesion molecule, NCAM, regulates thalamocortical axon pathfinding and the organization of the cortical somatosensory representation in mouse. *Front Mol Neurosci* 5, 76, doi:10.3389/fnmo1.2012.00076 (2012).
32 Leingartner, A. et al. Cortical area size dictates performance at modality-specific behaviors. *Proc Nall Acad Sci USA* 104, 4153-4158, doi:10.1073/pnas.0611723104 (2007).
33 Li, C. X., Chappell, T. D., Ramshur, J. T. & Waters, R. S. Forelimb amputation-induced reorganization in the ventral posterior lateral nucleus (VPL) provides a substrate for large-scale cortical reorganization in rat forepaw barrel subfield (FBS). *Brain Res* 1583, 89-108, doi:10.1016/j.brainres.2014.07.022 (2014).
34 Petersen, C. C. The functional organization of the barrel cortex. *Neuron* 56, 339-355, doi:10.1016/j.neuron.2007.09.017 (2007).
35 Xiong, W. et al. Enhancing excitatory activity of somatosensory cortex alleviates neuropathic pain through regulating homeostatic plasticity. *Sci Rep* 7, 12743, doi:10.1038/s41598-017-12972-6 (2017).
36 Chaplan, S. R., Bach, F. W., Pogrel, J. W., Chung, J. M. & Yaksh, T. L. Quantitative assessment of tactile allodynia in the rat paw. *J Neurosci Methods* 53, 55-63 (1994).
37 Bouet, V. et al. The adhesive removal test: a sensitive method to assess sensorimotor deficits in mice. *Nat Protoc* 4, 1560-1564, doi:10.1038/nprot.2009.125 (2009).
38 Eddy, N. B. & Leimbach, D. Synthetic analgesics. II. Dithienylbutenyl- and dithienylbutylamines. 1 *Pharmacol Exp Ther* 107, 385-393 (1953).
39 Fox, M. W. The visual cliff test for the study of visual depth perception in the mouse. *Anim Behav* 13, 232-233 (1965).
40 Wu, H. P., Ioffe, J. C., Iverson, M. M., Boon, J. M. & Dyck, R. H. Novel, whisker-dependent texture discrimination task for mice. *Behav Brain Res* 237, 238-242, doi:10.1016/j.bbr.2012.09.044 (2013).
41 Deacon, R. M. Measuring motor coordination in mice. *J Vis Exp*, e2609, doi:10.3791/2609 (2013).
42 Valsamis, B. & Schmid, S. Habituation and prepulse inhibition of acoustic startle in rodents. *J Vis Exp*, e3446, doi:10.3791/3446 (2011).
43 Turnbaugh, P. J. et al. A core gut microbiome in obese and lean twins. *Nature* 457, 480-484, doi:10.1038/nature07540 (2009).
44 Belkaid, Y. & Hand, T. W. Role of the microbiota in immunity and inflammation. *Cell* 157, 121141, doi:10.1016/j.cell.2014.03.011 (2014).
45 Labus, J. S. et al. Differences in gut microbial composition correlate with regional brain volumes in irritable bowel syndrome. *Microbiome* 5, 49, doi:10.1186/s40168-017-0260-z (2017).
46 Schretter, C. E. et al. A gut microbial factor modulates locomotor behaviour in *Drosophila*. *Nature* 563, 402-406, doi:10.1038/s41586-018-0634-9 (2018).
47 Fujisaka, S. et al. Diet, Genetics, and the Gut Microbiome Drive Dynamic Changes in Plasma Metabolites. *Cell Rep* 22, 3072-3086, doi:10.1016/j.celrep.2018.02.060 (2018).
48 Koh, A. et al. Microbially Produced Imidsyole Propionate Impairs Insulin Signaling through mTORC1. *Cell* 175, 947-961 e917, doi:10.1016/j.cell.2018.09.055 (2018).
49 Schugar, R. C. et al. The TMAO-Producing Enzyme Flavin-Containing Monooxygenase 3 Regulates Obesity and the Beiging of White Adipose Tissue. *Cell Rep* 19, 2451-2461, doi:10.1016/j.celrep.2017.05.077 (2017).
50 Buss, C., Entringer, S. & Wadhwa, P. D. Fetal programming of brain development: intrauterine stress and susceptibility to psychopathology. *Sci Signal* 5, pt 7, doi:10.1126/scisignal.2003406 (2012).

51 Monk, C., Georgieff, M. K. & Osterholm, E. A. Research review: maternal prenatal distress and poor nutrition—mutually influencing risk factors affecting infant neurocognitive development. *J Child Psychol Psychiatry* 54, 115-130, doi:10.1111/jcpp.12000 (2013).

52 Braniste, V. et al. The gut microbiota influences blood-brain barrier permeability in mice. *Sci Transl Med* 6, 263ra158, doi:10.1126/scitranslmed.3009759 (2014).

53 Saunders, N. R., Liddelow, S. A. & Dziegielewska, K. M. Barrier mechanisms in the developing brain. *Front Pharmacol* 3, 46, doi:10.3389/fphar.2012.00046 (2012).

54 Wikoff, W. R. et al. Metabolomics analysis reveals large effects of gut microflora on mammalian blood metabolites. *Proc Natl Acad Sci USA* 106, 3698-3703, doi:10.1073/pnas.0812874106 (2009).

55 Matsumoto, M. et al. Cerebral low-molecular metabolites influenced by intestinal microbiota: a pilot study. *Frontiers in systems neuroscience* 7, 9, doi:10.3389/fnsys.2013.00009 (2013).

56 Anton-Bolanos, N. et al. Prenatal activity from thalamic neurons governs the emergence of functional cortical maps in mice. *Science* 364, 987-990, doi:10.1126/science.aav7617 (2019).

57 Molnar, Z., Garel, S., Lopez-Bendito, G., Maness, P. & Price, D. J. Mechanisms controlling the guidance of thalamocortical axons through the embryonic forebrain. *Eur .1 Neurosci* 35, 15731585, doi:10.1111/j.1460-9568.2012.08119.x (2012).

58 Vernocchi, P., Del Chierico, F. & Putignani, L. Gut Microbiota Profiling: Metabolomics Based Approach to Unravel Compounds Affecting Human Health. *Front Microbiol* 7, 1144, doi:10.3389/fmicb.2016.01144 (2016).

59 Holmes, E., Li, J. V., Athanasiou, T., Ashrafian, H. & Nicholson, J. K. Understanding the role of gut microbiome-host metabolic signal disruption in health and disease. *Trends Microbiol* 19, 349359, doi:10.1016/j.tim.2011.05.006 (2011).

60 Barrea, L. et al. Trimethylamine-N-oxide (TMAO) as Novel Potential Biomarker of Early Predictors of Metabolic Syndrome. *Nutrients* 10, doi:10.3390/nu10121971 (2018).

61 Cai, H. L. et al. Metabolomic analysis of biochemical changes in the plasma and urine of first-episode neuroleptic-naive schizophrenia patients after treatment with risperidone. .1 *Proteome Res* 11, 4338-4350, doi:10.1021/pr300459d (2012).

62 Haghikia, A. et al. Gut Microbiota-Dependent Trimethylamine N-Oxide Predicts Risk of Cardiovascular Events in Patients With Stroke and Is Related to Proinflammatory Monocytes. *Arterioscler Thromb Vasc Biol* 38, 2225-2235, doi:10.1161/ATVBAHA.118.311023 (2018).

63 Li, D. et al. Trimethylamine-N-oxide promotes brain aging and cognitive impairment in mice. *Aging Cell, e*12768, doi:10.111$^{1}/_{a}$ce1.12768 (2018).

64 Vogt, N. M. et al. The gut microbiota-derived metabolite trimethylamine N-oxide is elevated in Alzheimer's disease. *Alzheimers Res Ther* 10, 124, doi:10.1186/s13195-018-0451-2 (2018).

65 Webb, R. E., Shah, E. & Stokstad, E. L. Effect of folic acid and vitamin B-12 on excretion of hippuric acid and formiminoglutamic acid. *Proc Soc Exp Biol Med* 121, 19-24, doi:10.3181/00379727-121-30685 (1966).

66 Ong, I. M. et al. Gut microbiome populations are associated with structure-specific changes in white matter architecture. *Transl Psychiatry* 8, 6, doi:10.1038/s41398-017-0022-5 (2018).

67 Indrio, F. et al. Epigenetic Matters: The Link between Early Nutrition, Microbiome, and Longterm Health Development. *Front Pediatr* 5, 178, doi:10.3389/fped.2017.00178 (2017).

68 Keunen, K., van Elburg, R. M., van Bel, F. & Benders, M. J. Impact of nutrition on brain development and its neuroprotective implications following preterm birth. *Pediatr Res* 77, 148155, doi:10.1038/pr.2014.171 (2015).

69 Ou, X., Thakali, K. M., Shankar, K., Andres, A. & Badger, T. M. Maternal adiposity negatively influences infant brain white matter development. *Obesity (Silver Spring)* 23, 1047-1054, doi:10.1002/oby.21055 (2015).

70 Gehrig, J. L. et al. Effects of microbiota-directed foods in gnotobiotic animals and undernourished children. *Science* 365, doi:10.1126/science.aau4732 (2019).

71 Reikvam, D. H. et al. Depletion of murine intestinal microbiota: effects on gut mucosa and epithelial gene expression. *PLoS One* 6, e17996, doi:10.1371/journal-.pone.0017996 (2011).

72 McVey Neufeld, K. A., Perez-Burgos, A., Mao, Y. K., Bienenstock, J. & Kunze, W. A. The gut microbiome restores intrinsic and extrinsic nerve function in germ-free mice accompanied by changes in calbindin. *Neurogastroenterol Motil* 27, 627-636, doi:10.1111/nmo.12534 (2015).

73 Yano, J. M. et al. Indigenous bacteria from the gut microbiota regulate host serotonin biosynthesis. *Cell* 161, 264-276, doi:10.1016/j.cell.2015.02.047 (2015).

74 Kim, D., Langmead, B. & Salzberg, S. L. HISAT: a fast spliced aligner with low memory requirements. *Nat Methods* 12, 357-360, doi:10.1038/nmeth.3317 (2015).

75 Pertea, M., Kim, D., Pertea, G. M., Leek, J. T. & Salzberg, S. L. Transcript-level expression analysis of RNA-seq experiments with HISAT, StringTie and Ballgown. *Nat Protoc* 11, 16501667, doi:10.1038/nprot.2016.095 (2016).

76 Love, M. I., Huber, W. & Anders, S. Moderated estimation of fold change and dispersion for RNA-seq data with DESeq2. *Genome Biol* 15, 550, doi:10.1186/s13059-014-0550-8 (2014).

77 Huang da, W., Sherman, B. T. & Lempicki, R. A. Systematic and integrative analysis of large gene lists using DAVID bioinformatics resources. *Nat Protoc* 4, 44-57, doi:10.1038/nprot.2008.211 (2009).

78 Schindelin, J. et al. Fiji: an open-source platform for biological-image analysis. *Nat Methods* 9, 676-682, doi:10.1038/nmeth.2019 (2012).

79 Mishima, E. et al. Evaluation of the impact of gut microbiota on uremic solute accumulation by a CE-TOFMS-based metabolomics approach. *Kidney Int* 92, 634-645, doi:10.1016/j.kint.2017.02.011 (2017).

80 Soga, T. et al. Differential metabolomics reveals ophthalmic acid as an oxidative stress biomarker indicating hepatic glutathione consumption. *I Biol Chem* 281 , 16768-16776, doi:10.1074/jbc.M601876200 (2006).

81 Soga, T. et al. Quantitative metabolome analysis using capillary electrophoresis mass spectrometry. 0.1 *Proteome Res* 2, 488-494 (2003).

82 Karkkainen, O. et al. Whole grain intake associated molecule 5-aminovaleric acid betaine decreases beta-oxidation of fatty acids in mouse cardiomyocytes. *Sci Rep* 8 , 13036, doi:10.1038/s41598-018-31484-5 (2018).

83 Fothergill, J. C. & Guest, J. R. Catabolism of L-lysine by *Pseudomonas aeruginosa. J Gen Microbiol* 99, 139-155, doi:10.1099/00221287-99-1-139 (1977).
84 Diehl, K. H. et al. A good practice guide to the administration of substances and removal of blood, including routes and volumes. .1¯ *Appl Toxicol* 21, 15-23 (2001).
85 Chung, K. et al. Structural and molecular interrogation of intact biological systems. *Nature* 497, 332-337, doi: 10.1038/nature12107 (2013).
86 Deuis, J. R., Dvorakova, L. S. & Vetter, I. Methods Used to Evaluate Pain Behaviors in Rodents. *Front Mol Neurosci* 10, 284, doi:10.3389/fnmo1.2017.00284 (2017).
87 Perry, W., Minassian, A., Lopez, B., Maron, L. & Lincoln, A. Sensorimotor gating deficits in adults with autism. *Biol Psychiatry* 61, 482-486, doi:10.1016/j.biopsych.2005.09.025 (2007).
88 Caporaso, J. G. et al. Global patterns of 16S rRNA diversity at a depth of millions of sequences per sample. *Proceedings of the National Academy of Sciences of the United States of America* 108 Suppl 1, 4516-4522, doi: 10.1073/pnas.1000080107 (2011).
89 Caporaso, J. G. et al. QI1ME allows analysis of high-throughput community sequencing data. *Nature methods* 7, 335-336, doi:10.1038/nmeth.f.303 (2010).
90 Thion, M. S. et al. Microbiome Influences Prenatal and Adult Microglia in a Sex-Specific Manner. *Cell* 172, 500-516 e516, doi:10.1016/j.cell.2017.11.042 (2018).
91 Radulescu, C. I. et al. Manipulation of microbiota reveals altered callosal myelination and white matter plasticity in a model of Huntington disease. *Neurobiol Dis* 127, 65-75, doi:10.1016/j.nbd.2019.02.011 (2019).
92 Mestre, L. et al. Manipulation of Gut Microbiota Influences Immune Responses, Axon Preservation, and Motor Disability in a Model of Progressive Multiple Sclerosis. *Front Immunol* 10, 1374, doi:10.3389/fimmu.2019.01374 (2019).
93 Zhu, W. et al. Gut Microbial Metabolite TMAO Enhances Platelet Hyperreactivity and Thrombosis Risk. *Cell* 165, 111-124, doi:10.1016/j.cell.2016.02.011 (2016).
94 Koistinen, V. M. et al. Contribution of gut microbiota to metabolism of dietary glycine betaine in mice and in vitro colonic fermentation. *Microbiome* 7, 103, doi:10.1186/s40168-019-0718-2 (2019).
95 Janeiro, M. H., Ramirez, M. J., Milagro, F. I., Martinez, J. A. & Solas, M. Implication of Trimethylamine N-Oxide (TMAO) in Disease: Potential Biomarker or New Therapeutic Target. *Nutrients* 10, doi:10.3390/nu10101398 (2018).
96 Kumar, R., Lee, J. C., Bolen, D. W. & Thompson, E. B. The conformation of the glucocorticoid receptor afl/taul domain induced by osmolyte binds co-regulatory proteins. *I—Biol Chem* 276, 18146-18152, doi:10.1074/jbc.M100825200 (2001).
97 Schugar, R. C., Willard, B., Wang, Z. & Brown, J. M. Postprandial gut microbiota-driven choline metabolism links dietary cues to adipose tissue dysfunction. *Adipocyte* 7, 49-56, doi:10.1080/21623945.2017.1398295 (2018).
98 Seldin, M. M. et al. Trimethylamine N-Oxide Promotes Vascular Inflammation Through Signaling of Mitogen-Activated Protein Kinase and Nuclear Factor-kappaB. *J Am Heart Assoc* 5, doi:10.1161/JAHA.115.002767 (2016).
99 Zou, Q., Bennion, B. J., Daggett, V. & Murphy, K. P. The molecular mechanism of stabilization of proteins by TMAO and its ability to counteract the effects of urea. *J Am Chem Soc* 124, 11921202, doi:10.1021/ja004206b (2002).
100 Jeong, E. Y. et al. Enhancement of IGF-2-induced neurite outgrowth by IGF-binding protein-2 and osteoglycin in SH-SYSY human neuroblastoma cells. *Neurosci Lett* 548, 249-254, doi:10.1016/j.neulet.2013.05.038 (2013).
101 Karkkainen, O. et al. Diets rich in whole grains increase betainized compounds associated with glucose metabolism. *Am .1¯ Clin Nutr* 108, 971-979, doi:10.1093/ajcn-inqy169 (2018).
102 Adam, J. et al. Metformin Effect on Nontargeted Metabolite Profiles in Patients With Type 2 Diabetes and in Multiple Murine Tissues. *Diabetes* 65, 3776-3785, doi:10.2337/db16-0512 (2016).
103 Haukka, J. K. et al. Metabolomic Profile Predicts Development of Microalbuminuria in Individuals with Type 1 Diabetes. *Sci Rep* 8, 13853, doi:10.1038/s41598-018-32085-y (2018).
104 Revelles, O., Espinosa-Urgel, M., Fuhrer, T., Sauer, U. & Ramos, J. L. Multiple and interconnected pathways for L-lysine catabolism in *Pseudomonas putida* KT2440. *J Bacteriol* 187, 7500-7510, doi:10.1128/JB.187.21.7500-7510.2005 (2005).
105 Revelles, 0., Espinosa-Urgel, M., Molin, S. & Ramos, J. L. The davDT operon of *Pseudomonas putida*, involved in lysine catabolism, is induced in response to the pathway intermediate delta-aminovaleric acid. *J Bacteriol* 186, 3439-3446, doi:10.1128/JB.186.11.3439-3446.2004 (2004).
106 Masotto, C., Wisniewski, G. & Negro-Vilar, A. Different gamma-aminobutyric acid receptor subtypes are involved in the regulation of opiate-dependent and independent luteinizing hormone-releasing hormone secretion. *Endocrinology* 125, 548-553, doi:10.1210/endo-125-1-548 (1989).
107 Domann, R., Dorn, T. & Witte, 0. W. Afterpotentials following penicillin-induced paroxysmal depolarizations in rat hippocampal CA1 pyramidal cells in vitro. *Pflugers Arch* 417, 469-478 (1991).
108 Dinamarca, M. C. et al. Complex formation of APP with GABAB receptors links axonal trafficking to amyloidogenic processing. *Nat Commun* 10, 1331, doi:10.1038/s41467-019-09164-3 (2019).
109 Biermann, B. et al. The Sushi domains of GABAB receptors function as axonal targeting signals. .1 *Neurosci* 30, 1385-1394, doi:10.1523/JNEUROSCI.3172-09.2010 (2010).
110 Bony, G. et al. Non-hyperpolarizing GABAB receptor activation regulates neuronal migration and neurite growth and specification by cAMP/LKB1. *Nat Commun* 4 , 1800, doi:10.1038/ncomms2820 (2013).
111 Priest, C. A. & Puche, A. C. GABAB receptor expression and function in olfactory receptor neuron axon growth. .1 *Neurobiol* 60, 154-165, doi:10.1002/neu.20011 (2004).
112 Knudsen, C., Neyrinck, A. M., Lanthier, N. & Delzenne, N. M. Microbiota and nonalcoholic fatty liver disease: promising prospects for clinical interventions? *Curr Opin* Clin *Nutr Metab* Care, doi:10.1097/MC0.0000000000000584 (2019).
113 Yamamoto, M., Pinto-Sanchez, M. I., Bercik, P. & Britz-McKibbin, P. Metabolomics reveals elevated urinary excretion of collagen degradation and epithelial cell turnover products in irritable bowel syndrome patients. Metabolomics 15, 82, doi:10.1007/s11306-019-1543-0 (2019).
114 Abe, N., Borson, S. H., Gambello, M. J., Wang, F. & Cavalli, V. Mammalian target of rapamycin (mTOR)

activation increases axonal growth capacity of injured peripheral nerves. *I Biol Chem* 285, 28034-28043, doi: 10.1074/jbc.M110.125336 (2010).

115 Zhang, J., Yang, D., Huang, H., Sun, Y. & Hu, Y. Coordination of Necessary and Permissive Signals by PTEN Inhibition for CNS Axon Regeneration. *Front Neurosci* 12, 558, doi:10.3389/fnins.2018.00558 (2018).

116 Terenzio, M. et al. Locally translated mTOR controls axonal local translation in nerve injury. *Science* 359, 1416-1421, doi:10.1126/science.aan1053 (2018).

117 Lees, H. J., Swann, J. R., Wilson, I. D., Nicholson, J. K. & Holmes, E. Hippurate: the natural history of a mammalian-microbial cometabolite. .1 *Proteome Res* 12, 1527-1546, doi:10.1021/pr300900b (2013).

118 Jung, J. Y. et al. 1H-NMR-based metabolomics study of cerebral infarction. *Stroke* 42, 12821288, doi:10.1161/STROKEAHA.110.598789 (2011).

119 Pallister, T. et al. Hippurate as a metabolomic marker of gut microbiome diversity: Modulation by diet and relationship to metabolic syndrome. *Sci Rep* 7, 13670, doi: 10.1038/s41598-017-13722-4 (2017).

120 Mangalam, A. et al. Profile of Circulatory Metabolites in a Relapsing-remitting Animal Model of Multiple Sclerosis using Global Metabolomics. *J Clin Cell Immunol* 4, doi:10.4172/2155-9899.1000150 (2013).

Example 5: Table 1 for Examples 1-3, Provided as Parts Tables 1A and 1B

Tables 1A and 1B (collectively "Table 1") relate to genes differentially regulated in fetal brains from E14.5 offspring of SPF, ABX or Sp dams [log 2(fold change), $p<0.05$].

TABLE 1A

| gene | SPF1 | SPF2 | SPF3 | ABX1 | ABX2 | ABχ3 |
|---|---|---|---|---|---|---|
| 1700017B05Rik | −0.013691 | −0.002052 | 0.015593 | 0.025156 | 0.058023 | 0.028209 |
| 1810055G02Rik | −0.061343 | 0.014947 | 0.044343 | 0.197809 | 0.145103 | 0.091112 |
| 2610015P09Rik | −0.011342 | 0.011362 | −0.000109 | −0.021900 | −0.004519 | −0.017002 |
| 2610020C07Rik | −0.014458 | −0.001735 | 0.016030 | 0.050565 | 0.046883 | 0.061797 |
| 2700046A07Rik | −0.009163 | −0.004508 | 0.013571 | 0.023998 | 0.044703 | 0.049588 |
| 2810408I11Rik | 0.007824 | −0.005805 | −0.002053 | −0.010604 | −0.013178 | −0.013934 |
| 2810468N07Rik | −0.004334 | 0.002402 | 0.001923 | −0.008982 | 0.002462 | 0.016393 |
| 3830406C13Rik | −0.001768 | 0.000824 | 0.000942 | 0.044060 | 0.044487 | 0.034581 |
| 4930447A16Rik | −0.013183 | 0.001102 | 0.011971 | −0.018683 | −0.030010 | −0.023630 |
| 4930511A08Rik | 0.000961 | −0.001008 | 0.000046 | 0.023827 | 0.024982 | 0.028427 |
| 4933439C10Rik | 0.005944 | −0.005483 | −0.000484 | −0.035563 | −0.021005 | −0.034008 |
| 5930403L14Rik | −0.007801 | −0.012516 | 0.020101 | 0.009663 | 0.040193 | 0.038374 |
| 6330415G19Rik | 0.023579 | −0.023759 | −0.000208 | −0.029023 | −0.023986 | −0.032611 |
| 6330549D23Rik | −0.002816 | 0.008622 | −0.005846 | −0.000361 | −0.003263 | 0.008310 |
| 6430573F11Rik | −0.002783 | 0.003907 | −0.001133 | 0.030136 | 0.035753 | 0.047103 |
| 6530402F18Rik | −0.009169 | −0.019152 | 0.027893 | 0.016504 | 0.006367 | 0.035088 |
| 9130019P16Rik | 0.008037 | −0.003473 | −0.004598 | 0.041812 | −0.004955 | 0.026020 |
| 9430065F17Rik | 0.006487 | −0.004295 | −0.002215 | 0.040504 | 0.034990 | 0.043795 |
| A330069E16Rik | 0.021457 | 0.000467 | −0.022255 | −0.039767 | −0.021666 | −0.028666 |
| A930003O13Rik | 0.008534 | −0.004075 | −0.004498 | 0.031827 | 0.020610 | 0.015188 |
| Acad9 | 0.014002 | −0.004695 | −0.009413 | 0.011991 | −0.017004 | 0.017679 |
| Acsbg1 | −0.001349 | 0.011006 | −0.009733 | 0.035657 | 0.019684 | 0.025965 |
| Acsf2 | −0.014025 | 0.009749 | 0.004169 | 0.045994 | 0.027336 | 0.014967 |
| Adamts8 | −0.005227 | −0.004093 | 0.009275 | 0.038792 | 0.005886 | 0.003352 |
| Agap3 | −0.004007 | 0.002240 | 0.001759 | 0.006894 | 0.015122 | 0.019847 |
| Airn | −0.014368 | 0.024494 | −0.010444 | 0.060721 | 0.016651 | −0.007511 |
| Ak7 | 0.006079 | −0.015814 | 0.009604 | 0.026037 | 0.027584 | 0.033285 |
| Aldoc | −0.008723 | 0.003713 | 0.004970 | 0.050519 | 0.042087 | 0.025349 |
| Alpl | −0.026255 | 0.032967 | −0.007348 | 0.063191 | −0.003241 | 0.009526 |
| Ankrd11 | −0.007986 | −0.002796 | 0.010717 | 0.009465 | 0.021113 | 0.019980 |
| Ankrd6 | 0.010002 | −0.008794 | −0.001270 | 0.009612 | 0.021290 | 0.033858 |
| Ap1s1 | −0.005761 | 0.004385 | 0.001357 | 0.011485 | −0.023600 | −0.026905 |
| Ap3s1 | 0.026425 | −0.021761 | −0.005080 | −0.016582 | −0.033174 | −0.032931 |
| Arhgap10 | −0.010300 | −0.001443 | 0.011658 | 0.036992 | 0.026512 | 0.048041 |
| Arid1a | −0.006357 | −0.013669 | 0.019811 | 0.013765 | 0.017112 | 0.037745 |
| Arl6ip1 | −0.005105 | 0.005298 | −0.000212 | 0.019671 | 0.028489 | 0.009925 |
| Armt1 | −0.005414 | 0.000823 | 0.004573 | −0.018029 | −0.007078 | −0.012271 |
| Arrb2 | 0.000805 | 0.000221 | −0.001027 | 0.010841 | 0.029075 | 0.035742 |
| Arsa | −0.013241 | 0.014601 | −0.001495 | 0.020089 | 0.002528 | 0.001705 |
| Arxes2 | 0.034379 | −0.017030 | −0.017974 | −0.019434 | −0.002059 | 0.000409 |
| Ate1 | 0.008769 | −0.008560 | −0.000260 | −0.023434 | −0.021123 | −0.017943 |
| Atg4d | −0.016432 | 0.023325 | −0.007194 | 0.022272 | 0.004867 | 0.009955 |
| Atn1 | −0.013192 | 0.027587 | −0.014796 | 0.035722 | 0.022566 | −0.011805 |
| Atp5h | 0.001910 | −0.002401 | 0.000488 | −0.020770 | −0.010187 | −0.019857 |
| Atp6ap2 | 0.011443 | −0.007599 | −0.003915 | −0.028920 | −0.020698 | −0.019311 |
| Atp6v1b2 | 0.000791 | −0.002553 | 0.001759 | −0.018028 | −0.020296 | −0.018980 |
| Atp8b1 | −0.000387 | 0.000071 | 0.000316 | 0.034696 | 0.036054 | 0.005977 |
| Atpafl | −0.000147 | 0.005012 | −0.004881 | 0.035659 | 0.031654 | 0.018562 |
| Atxn2 | 0.011466 | −0.021734 | 0.010024 | 0.024880 | 0.027287 | 0.055831 |
| Aven | −0.006599 | 0.003708 | 0.002868 | 0.028375 | 0.039584 | 0.014862 |
| AW209491 | 0.000205 | 0.007619 | −0.007866 | 0.037580 | 0.045194 | 0.032102 |
| AW549877 | 0.026798 | −0.010848 | −0.016333 | −0.027213 | −0.008327 | −0.012785 |
| Axin2 | 0.005063 | −0.011303 | 0.006174 | 0.019507 | 0.039106 | 0.049395 |
| B230307C23Rik | 0.023502 | −0.013659 | −0.010136 | 0.018593 | 0.011025 | −0.002458 |
| B3galt2 | 0.025716 | −0.015715 | −0.010354 | −0.025490 | −0.024071 | −0.028417 |
| B4galt4 | 0.000734 | 0.000744 | −0.001479 | −0.018939 | −0.004451 | −0.045745 |

TABLE 1A-continued

| gene | SPF1 | SPF2 | SPF3 | ABX1 | ABX2 | ABχ3 |
|---|---|---|---|---|---|---|
| Bahcc1 | −0.009021 | 0.017805 | −0.008950 | 0.033934 | 0.040962 | 0.048132 |
| Baiap2l1 | −0.006255 | −0.005406 | 0.011591 | 0.026503 | 0.020592 | 0.032249 |
| BC020402 | 0.009038 | −0.011837 | 0.002720 | −0.027330 | −0.042233 | −0.023153 |
| BC024139 | −0.016769 | 0.039915 | −0.023999 | 0.037852 | 0.027411 | 0.046107 |
| Blzf1 | 0.005958 | −0.019611 | 0.013445 | 0.028175 | 0.040626 | 0.041971 |
| Bola1 | −0.018362 | 0.007986 | 0.010201 | 0.003714 | 0.008970 | 0.049348 |
| Brd4 | 0.003335 | −0.021785 | 0.018168 | 0.037761 | 0.012085 | 0.025806 |
| Brox | 0.012174 | 0.003414 | −0.015729 | −0.026016 | −0.010931 | −0.034093 |
| C1galt1c1 | −0.000854 | 0.001332 | −0.000478 | 0.016391 | −0.015485 | −0.002103 |
| C1ql3 | −0.004347 | −0.002109 | 0.006433 | −0.017748 | 0.007530 | 0.002770 |
| C330006A16Rik | −0.015080 | 0.023234 | −0.008445 | 0.044709 | 0.012585 | 0.016892 |
| C77080 | −0.004162 | 0.003333 | 0.000819 | 0.013053 | −0.006343 | 0.031779 |
| C77370 | 0.027254 | −0.013995 | −0.013650 | −0.025613 | −0.017690 | −0.037493 |
| Cadm2 | 0.040193 | 0.002283 | −0.043698 | −0.030855 | −0.021279 | −0.064849 |
| Camk1d | 0.000337 | −0.012317 | 0.011879 | −0.015921 | −0.043106 | −0.038512 |
| Camk2d | 0.004607 | 0.030487 | −0.035868 | −0.010691 | −0.031988 | −0.053633 |
| Capn3 | 0.027683 | 0.018873 | −0.047729 | 0.014403 | 0.043743 | 0.075704 |
| Capns2 | 0.004877 | −0.004142 | −0.000750 | 0.038492 | −0.000046 | 0.026689 |
| Card9 | −0.003258 | 0.007833 | −0.004607 | −0.003916 | 0.014272 | 0.011576 |
| Carns1 | −0.004446 | 0.017186 | −0.012907 | 0.006516 | 0.026279 | 0.010374 |
| Cartpt | −0.002567 | 0.007039 | −0.004499 | 0.004503 | −0.008416 | 0.003896 |
| Casp9 | −0.014370 | 0.008107 | 0.006156 | 0.015928 | −0.005713 | 0.015670 |
| Casz1 | −0.022234 | 0.021494 | 0.000409 | 0.060426 | 0.024529 | 0.027321 |
| Cc2d1a | −0.257968 | 0.083484 | 0.142951 | 0.335001 | 0.272811 | 0.208523 |
| Ccbl2 | 0.003477 | 0.003221 | −0.006721 | −0.026898 | −0.037175 | −0.014036 |
| Ccdc102a | −0.031371 | 0.017031 | 0.013834 | 0.035437 | 0.051464 | 0.014786 |
| Ccdc137 | 0.008489 | −0.005540 | −0.002988 | −0.038536 | −0.019412 | −0.029305 |
| Ccdc162 | 0.002568 | −0.006305 | 0.003717 | 0.007030 | 0.018654 | 0.026689 |
| Ccdc18 | −0.000572 | −0.008631 | 0.009148 | −0.007838 | 0.006226 | −0.032179 |
| Ccdc71l | 0.005088 | 0.000476 | −0.005584 | 0.022939 | 0.031096 | 0.004786 |
| Ccdc88b | −0.011836 | 0.001540 | 0.010211 | 0.017762 | 0.017957 | −0.001311 |
| Ccne1 | 0.002665 | −0.012001 | 0.009254 | 0.039234 | 0.020589 | 0.039957 |
| Cd34 | −0.003419 | 0.006727 | −0.003332 | −0.036170 | −0.016832 | −0.025070 |
| Cdc14b | 0.009504 | −0.006412 | −0.003141 | 0.006548 | 0.013176 | 0.040384 |
| Cdca2 | −0.266534 | 0.070071 | 0.162103 | 0.411964 | 0.319834 | 0.252383 |
| Cdh20 | 0.008465 | 0.002678 | −0.011214 | 0.020026 | 0.032882 | 0.042300 |
| Cdh24 | −0.017059 | −0.005905 | 0.022672 | 0.031148 | 0.016972 | 0.044253 |
| Cdk6 | −0.003797 | 0.001883 | 0.001906 | 0.007143 | 0.007508 | 0.019817 |
| Cdr1 | −0.016600 | 0.003017 | 0.013422 | 0.058517 | 0.040913 | 0.022276 |
| Celsr2 | −0.025725 | 0.030497 | −0.005334 | 0.043664 | 0.062178 | 0.014182 |
| Cenpb | −0.017236 | 0.007523 | 0.009559 | 0.014506 | 0.021959 | 0.032934 |
| Cep250 | −0.013055 | −0.005236 | 0.018109 | 0.019258 | 0.021353 | 0.019959 |
| Cep85l | −0.003983 | 0.012911 | −0.009019 | 0.015615 | 0.028534 | 0.053004 |
| Cerk | −0.010242 | 0.009021 | 0.001156 | 0.002380 | 0.010758 | 0.014197 |
| Chml | 0.009298 | −0.001418 | −0.007932 | 0.031669 | 0.035364 | 0.044170 |
| Cit | −0.018667 | −0.016421 | 0.034460 | 0.021447 | 0.019356 | 0.055051 |
| Cklf | −0.008200 | −0.009877 | 0.017908 | −0.014710 | 0.010322 | −0.015076 |
| Cks1b | −0.001601 | 0.016342 | −0.014911 | 0.001054 | 0.005292 | 0.003786 |
| Clic3 | −0.005059 | −0.002885 | 0.007911 | 0.011067 | 0.008871 | 0.015261 |
| Clic6 | 0.002859 | 0.021987 | −0.025237 | −0.047145 | −0.018982 | −0.052512 |
| Clmn | −0.009099 | −0.005537 | 0.014523 | 0.082723 | −0.002874 | 0.014205 |
| Clock | 0.014457 | −0.002232 | −0.012353 | −0.014854 | −0.008199 | −0.024915 |
| Cmc1 | −0.018338 | −0.000061 | 0.018168 | 0.004406 | 0.049142 | 0.051443 |
| Cntnap5b | −0.016586 | 0.008286 | 0.008158 | 0.003131 | 0.008968 | 0.008780 |
| Coch | −0.001445 | 0.018071 | −0.016839 | 0.026409 | 0.030949 | 0.038882 |
| Col7a1 | −0.002193 | −0.002355 | 0.004537 | 0.017110 | 0.018107 | 0.023445 |
| Commd9 | −0.002758 | 0.007875 | −0.005150 | −0.021648 | −0.023572 | −0.003816 |
| Cplx2 | 0.017446 | −0.017357 | −0.000299 | 0.021516 | 0.008766 | 0.016710 |
| Cpped1 | 0.032194 | −0.005421 | −0.027405 | −0.057051 | −0.027413 | −0.015832 |
| Cramp1l | −0.004812 | −0.012143 | 0.016798 | 0.019807 | 0.017316 | 0.035009 |
| Creb3l1 | 0.000881 | −0.009094 | 0.008160 | 0.022693 | 0.024629 | 0.027213 |
| Creb5 | 0.006540 | −0.017713 | 0.011008 | 0.000149 | 0.012897 | 0.039606 |
| Crebrf | 0.009161 | −0.011623 | 0.002384 | −0.023723 | −0.019569 | −0.023265 |
| Cryab | −0.002842 | 0.002140 | 0.000697 | 0.021712 | 0.031529 | 0.028885 |
| Cryzl1 | −0.009324 | −0.008925 | 0.018077 | 0.023165 | 0.022803 | 0.057894 |
| Ctrl | −0.017782 | 0.017056 | 0.000515 | −0.012540 | −0.013972 | −0.007952 |
| Ctsa | −0.021223 | 0.017967 | 0.002985 | 0.029892 | 0.040181 | 0.008847 |
| Ctss | 0.004135 | 0.008322 | −0.012541 | 0.023067 | 0.037548 | 0.010570 |
| Cuedc1 | 0.004721 | 0.008828 | −0.013648 | 0.023554 | 0.031999 | 0.025011 |
| Cyb561 | −0.025178 | 0.009752 | 0.015095 | −0.008772 | −0.042851 | −0.036849 |
| Cyb5a | 0.008189 | 0.004498 | −0.012774 | 0.039605 | 0.030557 | 0.008247 |
| Cycs | −0.008731 | 0.004820 | 0.003872 | 0.019464 | 0.029763 | 0.038929 |
| Cyp27b1 | −0.009895 | 0.016250 | −0.006495 | 0.005391 | 0.032703 | 0.031313 |
| D030068K23Rik | 0.014014 | −0.006894 | −0.007222 | 0.014070 | 0.008443 | 0.025314 |
| D11Wsu47e | 0.016323 | −0.014643 | −0.001848 | 0.026474 | 0.015762 | 0.009628 |
| Dbx2 | −0.009244 | 0.022217 | −0.013236 | −0.000435 | 0.030839 | 0.016024 |
| Ddx25 | −0.020833 | 0.014566 | 0.006031 | 0.044811 | 0.051798 | 0.024080 |
| Ddx27 | −0.002956 | 0.005537 | −0.002596 | 0.030404 | 0.034883 | 0.032498 |

TABLE 1A-continued

| gene | SPF1 | SPF2 | SPF3 | ABX1 | ABX2 | ABχ3 |
|---|---|---|---|---|---|---|
| Deb1 | −0.001152 | −0.011867 | 0.012911 | −0.019768 | −0.032047 | −0.030629 |
| Dennd1c | 0.000212 | −0.002196 | 0.001981 | 0.006279 | −0.004790 | 0.005813 |
| Dennd2a | −0.014606 | 0.001585 | 0.012888 | 0.018377 | 0.020808 | 0.029888 |
| Dimt1 | 0.013622 | −0.006121 | −0.007598 | −0.020443 | −0.019826 | −0.010126 |
| Dio3os | −0.012568 | −0.002213 | 0.014650 | −0.033654 | −0.031932 | −0.025854 |
| Dlx5 | −0.014187 | 0.002352 | 0.011716 | 0.024353 | 0.034172 | 0.027894 |
| Dmd | 0.001628 | 0.005958 | −0.007619 | 0.031223 | 0.015562 | 0.012080 |
| Dnaaf2 | −0.001262 | −0.013143 | 0.014274 | 0.023126 | 0.038542 | 0.027179 |
| Dnah8 | −0.008404 | 0.023940 | −0.015847 | −0.016825 | −0.037441 | −0.047572 |
| Dnase1 | −0.008909 | −0.006020 | 0.014812 | 0.041121 | 0.026113 | 0.026609 |
| Dok2 | −0.013260 | 0.004552 | 0.008614 | 0.037157 | 0.033690 | 0.013780 |
| Dpp10 | 0.019643 | −0.002160 | −0.017727 | −0.029691 | −0.032823 | −0.036993 |
| Dpy19l3 | 0.009264 | −0.018870 | 0.009422 | −0.049102 | −0.026817 | −0.012825 |
| E130012A19Rik | −0.000807 | 0.000399 | 0.000407 | 0.005042 | 0.029057 | 0.041743 |
| E130307A14Rik | 0.007925 | −0.013096 | 0.005081 | 0.009247 | 0.006031 | 0.007514 |
| E2f8 | 0.004428 | −0.003275 | −0.001165 | 0.005423 | 0.044469 | 0.036104 |
| Ece1 | −0.009918 | −0.009007 | 0.018741 | 0.049753 | 0.025776 | 0.016607 |
| Efhb | −0.024910 | 0.013484 | 0.011106 | 0.000963 | 0.007163 | 0.031476 |
| Elk4 | 0.002294 | 0.009720 | −0.012100 | 0.032681 | 0.027819 | 0.031420 |
| Emp2 | 0.017869 | −0.025995 | 0.007762 | 0.051533 | 0.021452 | 0.042750 |
| En2 | −0.000753 | −0.006176 | 0.006898 | 0.019659 | 0.023398 | 0.034555 |
| Epas1 | −0.024938 | 0.022076 | 0.002475 | 0.021593 | 0.030437 | 0.036091 |
| Ephb2 | −0.015079 | −0.004089 | 0.018958 | 0.009054 | 0.022220 | 0.034428 |
| Epor | −0.019207 | −0.003296 | 0.022200 | 0.036909 | 0.025510 | 0.048726 |
| Erbb2 | −0.018271 | 0.015545 | 0.002525 | 0.044054 | 0.015948 | 0.011309 |
| Esd | −0.004985 | 0.002110 | 0.002862 | −0.025372 | −0.028868 | −0.009583 |
| Exo5 | 0.007018 | −0.010454 | 0.003377 | −0.034123 | −0.001907 | −0.009558 |
| Exph5 | 0.004080 | 0.006158 | −0.010294 | 0.062642 | 0.020350 | 0.009826 |
| F11r | −0.016389 | 0.009750 | 0.006498 | 0.046693 | 0.031773 | 0.016056 |
| F8 | 0.007068 | 0.005149 | −0.012296 | −0.011191 | −0.040813 | −0.050165 |
| Fah | 0.009051 | −0.004302 | −0.004792 | −0.012398 | −0.032889 | −0.038826 |
| Fam122b | −0.008536 | 0.009272 | −0.000791 | 0.014354 | −0.016323 | −0.015643 |
| Fam126a | 0.008034 | −0.006720 | −0.001353 | −0.008075 | −0.012619 | 0.000457 |
| Fam160b2 | −0.008582 | 0.008630 | −0.000100 | 0.022511 | −0.003434 | 0.006279 |
| Fam199x | 0.023852 | 0.003553 | −0.027875 | −0.004559 | −0.010494 | −0.045552 |
| Fam19a1 | −0.030689 | 0.011926 | 0.018274 | 0.041559 | 0.028945 | 0.054458 |
| Fam207a | −0.006397 | 0.005546 | 0.000825 | −0.021166 | −0.014093 | 0.000665 |
| Fam208a | −0.020957 | −0.007026 | 0.027550 | 0.040359 | 0.027260 | 0.034140 |
| Fam20a | 0.002328 | 0.002379 | −0.004718 | 0.005715 | 0.021642 | 0.020349 |
| Fam43b | −0.010221 | −0.010278 | 0.020284 | 0.027201 | 0.025763 | 0.044832 |
| Fam76b | −0.000292 | 0.011086 | −0.010878 | 0.019934 | −0.016597 | 0.014410 |
| Fgf1 | −0.010076 | 0.026548 | −0.016851 | −0.030351 | −0.016212 | −0.028811 |
| Fkbp1b | −0.004434 | 0.005703 | −0.001288 | 0.119524 | 0.006504 | 0.007270 |
| Fndc3c1 | −0.000850 | −0.005531 | 0.006357 | 0.012678 | −0.002435 | −0.001269 |
| Fndc5 | 0.013699 | 0.007673 | −0.021619 | 0.045342 | 0.013837 | −0.003374 |
| Foxn2 | 0.040966 | −0.015444 | −0.026432 | −0.001597 | −0.018413 | −0.006774 |
| Frem3 | 0.006236 | −0.004570 | −0.001688 | 0.002182 | 0.012172 | 0.042928 |
| Fuk | −0.007673 | −0.001861 | 0.009481 | 0.018893 | 0.028899 | 0.028713 |
| Fut9 | 0.037894 | −0.018821 | −0.019834 | −0.034702 | −0.014858 | −0.029450 |
| Gabra2 | −0.012137 | 0.020750 | −0.008840 | 0.038159 | 0.027390 | 0.032088 |
| Gabra4 | 0.027922 | −0.033223 | 0.004643 | −0.031251 | −0.057597 | −0.027506 |
| Gabrg1 | −0.022641 | −0.006214 | 0.028384 | 0.016926 | 0.030820 | 0.053906 |
| Gabrg2 | −0.006649 | −0.000634 | 0.007249 | 0.017533 | 0.031502 | 0.029195 |
| Gale | −0.007989 | 0.014799 | −0.006925 | −0.009497 | 0.017537 | 0.006901 |
| Galntl6 | 0.003718 | −0.000059 | −0.003669 | 0.034606 | 0.010471 | 0.015599 |
| Gas2l1 | −0.006452 | 0.003168 | 0.003262 | 0.021277 | 0.030483 | −0.008577 |
| Gcc1 | 0.007802 | −0.013064 | 0.005172 | 0.023867 | 0.030108 | 0.025183 |
| Gcnt1 | −0.023484 | 0.001719 | 0.021414 | −0.021974 | −0.031170 | −0.041239 |
| Gemin4 | −0.016717 | 0.005171 | 0.011395 | 0.036510 | 0.027933 | 0.024970 |
| Glg1 | 0.008494 | −0.010990 | 0.002427 | 0.037385 | 0.000554 | 0.010301 |
| Gli1 | −0.005896 | −0.002743 | 0.008599 | 0.023753 | 0.017393 | 0.054424 |
| Glis3 | −0.013147 | 0.039712 | −0.027435 | 0.016750 | 0.017155 | 0.018998 |
| Glra2 | −0.016243 | −0.007444 | 0.023386 | 0.051520 | 0.006376 | 0.004759 |
| Gm11346 | 0.000188 | 0.008639 | −0.008881 | 0.032643 | 0.007474 | −0.002293 |
| Gm11974 | −0.011616 | −0.005927 | 0.017378 | 0.025509 | 0.020509 | −0.015357 |
| Gm14164 | −0.011594 | 0.012996 | −0.001507 | 0.022174 | 0.023665 | 0.019001 |
| Gm15880 | 0.005391 | 0.010988 | −0.016525 | −0.027724 | −0.027951 | −0.030568 |
| Gm16740 | 0.001744 | −0.005880 | 0.004117 | 0.015317 | 0.012325 | 0.021215 |
| Gm17750 | −0.030053 | 0.011486 | 0.018096 | 0.061282 | 0.042948 | 0.016125 |
| Gm17769 | −0.002742 | −0.004903 | 0.007614 | 0.014283 | 0.019365 | 0.019778 |
| Gm20324 | −0.003894 | 0.000389 | 0.003495 | 0.031336 | 0.024251 | 0.037550 |
| Gm6981 | 0.003595 | −0.003087 | −0.000515 | 0.009235 | 0.021544 | 0.013821 |
| Gm7173 | 0.023755 | −0.003202 | −0.020903 | −0.034955 | −0.032778 | −0.024608 |
| Gpatch1 | 0.009433 | −0.006669 | −0.002813 | 0.276563 | −0.004951 | 0.271455 |
| Gpm6a | 0.029635 | −0.017120 | −0.012981 | −0.021001 | −0.014083 | −0.030517 |
| Gpr137 | −0.003506 | 0.016493 | −0.013146 | 0.028135 | 0.054863 | 0.017631 |
| Gps2 | −0.004506 | 0.003335 | 0.001160 | 0.009569 | 0.006660 | 0.012407 |
| Grhl3 | −0.026228 | 0.013782 | 0.012092 | 0.018489 | 0.036071 | 0.048555 |

TABLE 1A-continued

| gene | SPF1 | SPF2 | SPF3 | ABX1 | ABX2 | ABχ3 |
|---|---|---|---|---|---|---|
| Gria1 | 0.022711 | −0.017778 | −0.005231 | −0.027065 | −0.034088 | −0.027728 |
| Grik4 | −0.007499 | 0.015619 | −0.008249 | 0.018959 | 0.011380 | 0.004104 |
| Grin1 | −0.002179 | 0.013335 | −0.011264 | 0.006259 | 0.074773 | 0.024808 |
| Gsr | −0.000673 | −0.000140 | 0.000813 | 0.004357 | 0.034764 | 0.025348 |
| Gsta4 | −0.018132 | 0.007389 | 0.010572 | 0.027919 | 0.025005 | 0.033530 |
| Gstm6 | −0.005456 | −0.001919 | 0.007345 | 0.028025 | 0.030047 | 0.023084 |
| Gtf3c3 | 0.011578 | −0.002246 | −0.009411 | 0.018668 | 0.009081 | −0.005064 |
| Gucy1b3 | 0.016377 | 0.008318 | −0.025028 | −0.028804 | −0.016967 | −0.031624 |
| Hcn4 | −0.018446 | 0.011088 | 0.007180 | 0.017274 | 0.017466 | 0.051995 |
| Hdgf | −0.000720 | −0.009349 | 0.010004 | 0.028164 | 0.023238 | 0.010883 |
| Hebp2 | −0.011866 | −0.004097 | 0.015822 | −0.022133 | −0.011312 | −0.029528 |
| Heca | 0.017557 | −0.001909 | −0.015842 | 0.038117 | 0.021492 | 0.009732 |
| Hist1h2bg | 0.000117 | −0.005956 | 0.005815 | 0.002649 | 0.006984 | 0.043465 |
| Hist1h4b | −0.017282 | −0.004497 | 0.021508 | 0.024550 | 0.021334 | 0.042603 |
| Hist2h3b | −0.013489 | −0.005956 | 0.019241 | 0.031055 | 0.060190 | 0.007006 |
| Hmgb1 | 0.024149 | −0.018646 | −0.005838 | −0.013967 | 0.003214 | −0.000944 |
| Hnrnph2 | 0.010933 | −0.003525 | −0.007472 | −0.007997 | −0.006749 | −0.016987 |
| Hpca | −0.002052 | 0.019062 | −0.017241 | −0.027830 | −0.022917 | −0.051506 |
| Hs6st2 | 0.021908 | −0.003338 | −0.018863 | −0.032517 | −0.017529 | −0.029308 |
| Hsd3b6 | 0.004440 | −0.006236 | 0.001774 | 0.010785 | 0.013232 | 0.015326 |
| Htr2c | 0.000032 | 0.001532 | −0.001566 | 0.027368 | 0.047326 | 0.034566 |
| ICa1 | 0.004933 | 0.008384 | −0.013412 | −0.030380 | −0.018243 | −0.049227 |
| Il1rap | 0.003743 | −0.001886 | −0.001865 | 0.028159 | 0.025304 | 0.029632 |
| Inpp5f | 0.017837 | −0.001651 | −0.016390 | −0.016983 | −0.021727 | −0.019904 |
| Iqcb1 | 0.019984 | −0.001183 | −0.019065 | −0.034960 | −0.009793 | −0.004832 |
| Irs1 | −0.002404 | −0.004789 | 0.007164 | 0.017327 | 0.010217 | 0.023965 |
| Irs4 | 0.003252 | 0.021427 | −0.025059 | 0.048015 | 0.049916 | 0.028053 |
| Irx2 | −0.011814 | 0.010835 | 0.000889 | 0.034875 | 0.024138 | 0.018274 |
| Ism1 | −0.002012 | 0.003227 | −0.001221 | 0.028359 | 0.017715 | 0.024066 |
| Itga1 | 0.006588 | −0.019118 | 0.012336 | −0.029112 | −0.004857 | −0.025854 |
| Jak2 | 0.022039 | −0.010863 | −0.011432 | −0.014345 | −0.017060 | −0.030606 |
| Kank2 | −0.031797 | 0.030973 | 0.000141 | 0.054543 | 0.033444 | 0.018352 |
| Kcnd1 | 0.003423 | −0.002401 | −0.001028 | 0.005455 | 0.014243 | 0.036797 |
| Kcnh2 | −0.015605 | 0.000170 | 0.015270 | 0.030850 | 0.028812 | 0.043416 |
| Kctd5 | −0.018456 | −0.005896 | 0.024021 | 0.026000 | 0.026669 | 0.037530 |
| Kdm1b | 0.023451 | −0.025446 | 0.001580 | −0.037429 | −0.014961 | −0.033708 |
| Khk | −0.000828 | 0.000802 | 0.000026 | 0.023286 | 0.028787 | 0.028469 |
| Kif27 | −0.007329 | −0.000466 | 0.007756 | 0.030706 | 0.017263 | 0.010164 |
| Kiss1r | −0.014366 | 0.005794 | 0.008464 | 0.017392 | 0.014083 | 0.026831 |
| Kitl | 0.043310 | −0.028800 | −0.015535 | −0.015555 | −0.035147 | −0.038968 |
| Kmt2d | 0.022014 | −0.037309 | 0.014575 | −0.011650 | −0.013011 | 0.031589 |
| Knstrn | −0.003808 | −0.012292 | 0.015954 | −0.030941 | −0.016816 | −0.020409 |
| Kri1 | −0.009467 | 0.000410 | 0.008997 | 0.042767 | 0.024702 | 0.004916 |
| Lama5 | −0.012741 | −0.000298 | 0.012925 | 0.042904 | 0.024527 | 0.022320 |
| Lamtor5 | 0.023062 | −0.010714 | −0.012627 | −0.029369 | −0.015333 | −0.018669 |
| Lars2 | −0.009459 | 0.000777 | 0.008625 | 0.035127 | 0.015773 | 0.014660 |
| Lbh | −0.009505 | 0.005817 | 0.003640 | 0.007157 | 0.008740 | 0.022590 |
| Lingo1 | 0.002140 | 0.011866 | −0.014125 | 0.009461 | 0.017063 | 0.017708 |
| Lipt2 | 0.010499 | 0.009588 | −0.020299 | −0.018888 | −0.028080 | −0.035831 |
| Lmx1b | −0.017149 | 0.032330 | −0.015732 | −0.020461 | −0.023881 | −0.036729 |
| LOC100862268 | 0.009827 | −0.002010 | −0.007874 | −0.044395 | −0.032873 | −0.014472 |
| Loxl2 | −0.016265 | 0.043373 | −0.028131 | 0.085802 | 0.036707 | 0.017138 |
| Lpcat1 | −0.006534 | 0.003221 | 0.003291 | 0.001024 | 0.010501 | 0.002687 |
| Lppr4 | −0.005162 | 0.004518 | 0.000627 | 0.041989 | 0.029693 | 0.018026 |
| Lrfn1 | −0.009936 | 0.020630 | −0.010918 | 0.052619 | 0.028086 | −0.014969 |
| Lrp1b | 0.026165 | −0.004242 | −0.022340 | 0.021101 | 0.023812 | 0.003189 |
| Lrp5 | −0.018291 | 0.007110 | 0.011006 | 0.043552 | 0.054254 | −0.003701 |
| Lrrl | −0.021191 | 0.002217 | 0.018696 | 0.020177 | 0.020899 | 0.022818 |
| Lrrc29 | 0.005285 | −0.011797 | 0.006439 | 0.041038 | −0.007727 | 0.003862 |
| Lsm12 | 0.000810 | −0.005931 | 0.005100 | −0.005960 | 0.027091 | 0.003818 |
| Magel2 | −0.003451 | −0.002270 | 0.005704 | 0.028603 | 0.011827 | 0.017125 |
| Map1a | −0.020664 | 0.001537 | 0.018856 | 0.021269 | 0.028047 | 0.035120 |
| Map3k14 | −0.032854 | 0.006272 | 0.025962 | −0.012985 | 0.026582 | −0.001720 |
| Map3k19 | −0.008404 | −0.004815 | 0.013126 | 0.057283 | 0.020289 | 0.022257 |
| Map3k5 | −0.081534 | 0.147625 | −0.078253 | 0.053402 | 0.108373 | −0.079263 |
| Map7d1 | −0.018393 | 0.004044 | 0.014156 | 0.023904 | 0.022336 | 0.016662 |
| Mapk8 | 0.017699 | −0.014199 | −0.003683 | −0.016678 | −0.025807 | −0.023579 |
| Mapkapk2 | −0.019839 | 0.009033 | 0.010602 | 0.028023 | 0.016046 | 0.036993 |
| Maz | −0.016298 | −0.001251 | 0.017351 | 0.015865 | 0.024987 | 0.027710 |
| Mcc | −0.014304 | 0.000542 | 0.013627 | 0.067357 | 0.007270 | 0.021967 |
| Mcfd2 | 0.000426 | 0.009580 | −0.010072 | −0.002821 | −0.020723 | −0.020233 |
| Mdc1 | −0.030340 | 0.001336 | 0.028405 | 0.048642 | 0.041175 | 0.034226 |
| Med10 | 0.009287 | −0.008403 | −0.000939 | −0.022674 | −0.021754 | −0.024607 |
| Mier2 | −0.008238 | 0.008359 | −0.000169 | 0.012308 | 0.019737 | 0.053714 |
| Mier3 | 0.020612 | −0.000336 | −0.020570 | −0.013814 | −0.019443 | −0.029076 |
| Mir3081 | 0.000351 | −0.009182 | 0.008775 | 0.010811 | 0.005576 | 0.035663 |
| Mir411 | 0.006437 | 0.003800 | −0.010294 | 0.019085 | 0.013746 | 0.025397 |
| Mir6236 | −0.013751 | 0.005090 | 0.008561 | 0.076410 | 0.032753 | −0.000536 |

TABLE 1A-continued

| gene | SPF1 | SPF2 | SPF3 | ABX1 | ABX2 | ABχ3 |
|---|---|---|---|---|---|---|
| Mir6353 | 0.003664 | −0.002011 | −0.001660 | −0.005129 | 0.046421 | 0.037742 |
| Mllt6 | 0.011340 | −0.008914 | −0.002500 | 0.005730 | 0.020099 | 0.026116 |
| Mpeg1 | −0.024779 | 0.038005 | −0.014010 | 0.011250 | 0.034966 | 0.025008 |
| Mpnd | 0.010233 | 0.007810 | −0.018215 | −0.013031 | −0.032260 | −0.013999 |
| Mrpl22 | 0.009821 | −0.002185 | −0.007692 | −0.004029 | −0.016490 | −0.021003 |
| Mrps18b | −0.002930 | −0.007410 | 0.010281 | −0.016610 | −0.029240 | −0.028656 |
| Mrps33 | 0.012591 | −0.011405 | −0.001286 | −0.019534 | −0.015692 | −0.002915 |
| Mtcl1 | −0.017168 | 0.013297 | 0.003703 | 0.020775 | 0.022441 | 0.021541 |
| Mttp | 0.002595 | 0.003111 | −0.005723 | −0.017351 | −0.019059 | −0.046066 |
| Mtx3 | 0.013996 | −0.007548 | −0.006551 | −0.010210 | −0.011360 | −0.014171 |
| Mum1 | 0.007587 | 0.006498 | −0.014189 | 0.009866 | −0.003450 | −0.009214 |
| Mvk | −0.000333 | −0.003340 | 0.003664 | −0.001120 | 0.008702 | 0.005543 |
| Myh14 | −0.008945 | 0.002133 | 0.006766 | 0.082437 | 0.007931 | 0.003062 |
| Myo5b | −0.004927 | 0.011230 | −0.006369 | 0.048034 | 0.001301 | −0.006029 |
| Myo6 | −0.007993 | 0.003364 | 0.004596 | 0.021841 | −0.007853 | −0.022369 |
| Mzf1 | −0.017218 | 0.001290 | 0.015739 | −0.018263 | −0.023176 | −0.011228 |
| Nans | 0.000711 | 0.001281 | −0.001995 | −0.034288 | 0.001118 | −0.018664 |
| Nap1l5 | 0.006232 | −0.008835 | 0.002560 | −0.033905 | −0.043003 | −0.046929 |
| Ncmap | −0.003776 | 0.015359 | −0.011718 | 0.025284 | 0.005807 | 0.024104 |
| Ncor2 | −0.015291 | 0.028574 | −0.013713 | −0.024608 | −0.030869 | −0.007514 |
| Ndufs4 | 0.011829 | −0.009173 | −0.002736 | −0.031533 | −0.020066 | −0.015932 |
| Necab1 | 0.008373 | −0.000349 | −0.008070 | −0.031710 | −0.029761 | −0.041638 |
| Nek11 | −0.002918 | −0.011713 | 0.014507 | −0.007641 | −0.025728 | −0.009841 |
| Nexn | 0.028425 | −0.004457 | −0.024463 | −0.018251 | −0.010557 | −0.010331 |
| Nfs1 | −0.002135 | −0.006732 | 0.008823 | −0.034498 | −0.025832 | −0.026292 |
| Nipa2 | 0.013274 | −0.015719 | 0.002297 | −0.039300 | −0.012938 | −0.031812 |
| Nipal2 | −0.014130 | 0.005121 | 0.008903 | −0.020718 | −0.034423 | −0.030661 |
| Nmd3 | 0.017927 | −0.005239 | −0.012867 | −0.020403 | −0.024094 | −0.037752 |
| Nol4 | 0.016709 | −0.018429 | 0.001505 | −0.041465 | −0.012868 | −0.014388 |
| Notch3 | −0.040705 | 0.008761 | 0.031013 | 0.028291 | 0.041644 | 0.044335 |
| Nptxr | −0.003279 | 0.006671 | −0.003415 | 0.031615 | 0.017866 | 0.024378 |
| Npy1r | 0.001244 | 0.011105 | −0.012445 | 0.037032 | 0.018236 | −0.030671 |
| Nr5a2 | 0.009878 | 0.005378 | −0.015382 | −0.004256 | −0.006021 | 0.002077 |
| Nrcam | 0.012295 | −0.006825 | −0.005549 | 0.009287 | 0.011469 | 0.003472 |
| Nsun6 | 0.020092 | −0.009873 | −0.010431 | −0.030156 | −0.021543 | −0.029621 |
| Ntn1 | 0.005978 | −0.001328 | −0.004671 | −0.028408 | −0.019801 | −0.035034 |
| Ntng1 | 0.021517 | 0.009888 | −0.031951 | −0.029923 | −0.039840 | −0.032436 |
| Nudt11 | −0.004422 | −0.014007 | 0.018239 | 0.007596 | −0.004717 | −0.003711 |
| Nup214 | 0.017379 | 0.013747 | −0.031641 | −0.041918 | −0.047491 | −0.043206 |
| Oxsm | 0.004297 | −0.011414 | 0.007048 | 0.001348 | 0.024905 | 0.025040 |
| Pcdh20 | 0.023639 | −0.001203 | −0.022811 | −0.026525 | −0.038849 | −0.038645 |
| Pcdh7 | 0.003534 | 0.011239 | −0.014898 | −0.010953 | −0.019754 | −0.035595 |
| Pcdha11 | −0.022670 | 0.006607 | 0.015785 | −0.010027 | −0.044659 | −0.044411 |
| Pcdha7-g | −0.010005 | −0.006479 | 0.016342 | −0.034866 | −0.006901 | −0.025434 |
| Pcdhb12 | −0.012498 | 0.006894 | 0.005523 | −0.027142 | −0.044063 | −0.026985 |
| Pcdhb20 | 0.018064 | 0.000261 | −0.018557 | −0.025144 | −0.023118 | −0.031505 |
| Pcdhb22 | −0.011889 | 0.008329 | 0.003484 | −0.035698 | −0.027813 | −0.037372 |
| Pcdhgb5 | −0.003894 | −0.009070 | 0.012872 | −0.039541 | −0.035397 | −0.050953 |
| Pde4d | −0.006608 | 0.012885 | −0.006364 | −0.044989 | −0.031616 | −0.035750 |
| Pdia4 | −0.006346 | 0.001444 | 0.004878 | 0.033812 | 0.031569 | 0.002745 |
| Pdss2 | 0.004271 | 0.007096 | −0.011436 | 0.029407 | 0.016528 | 0.035478 |
| Pex11b | 0.001524 | −0.000007 | −0.001519 | −0.035175 | −0.028986 | −0.013867 |
| Pgbd1 | 0.004859 | 0.000938 | −0.005818 | −0.022896 | 0.001550 | −0.011179 |
| Phf5a | 0.001928 | −0.016349 | 0.014257 | −0.031943 | −0.026539 | 0.000463 |
| Phyhip | 0.008792 | 0.006281 | −0.015192 | −0.017888 | −0.036329 | −0.038415 |
| Pip4k2a | 0.010530 | −0.002978 | −0.007615 | −0.013783 | −0.020200 | −0.030017 |
| Pisd-ps3 | −0.045314 | 0.010817 | 0.033364 | −0.003239 | −0.038375 | −0.055206 |
| Plagl2 | 0.006606 | 0.005413 | −0.012095 | −0.017949 | −0.019388 | −0.048270 |
| Plcd | −0.007514 | 0.019600 | −0.012291 | 0.031706 | −0.000887 | 0.018776 |
| Pld2 | 0.008658 | 0.005440 | −0.014205 | −0.037315 | −0.041158 | −0.016724 |
| Plek | 0.023422 | 0.012021 | −0.036133 | −0.020604 | −0.009310 | −0.016587 |
| Plekhn1 | −0.018748 | −0.000333 | 0.018836 | 0.010464 | 0.045068 | 0.034149 |
| Plp2 | 0.003632 | 0.000865 | −0.004509 | −0.039208 | −0.068040 | −0.034770 |
| Plxna3 | 0.010246 | 0.003164 | −0.013512 | −0.020572 | −0.022906 | −0.029430 |
| Pmaip1 | −0.015985 | 0.012651 | 0.003187 | −0.033896 | −0.040987 | −0.031887 |
| Poli | −0.008654 | −0.003660 | 0.012231 | −0.004677 | −0.054700 | −0.033878 |
| Polr3c | 0.001293 | −0.004817 | 0.003512 | −0.008154 | −0.017295 | 0.011259 |
| Polr3gl | −0.016605 | −0.000946 | 0.017351 | 0.011359 | 0.014296 | 0.008375 |
| Polrmt | −0.008069 | 0.010393 | −0.002386 | 0.032318 | 0.002574 | 0.025351 |
| Pou2f2 | 0.007522 | −0.004407 | −0.003144 | 0.027385 | 0.023020 | 0.044023 |
| Pou6f2 | 0.016915 | −0.003890 | −0.013190 | −0.038737 | −0.031669 | −0.004319 |
| Ppap2b | 0.003073 | −0.006233 | 0.003140 | −0.027927 | −0.031911 | −0.038361 |
| Ppp1r3fos | 0.025256 | 0.005432 | −0.031256 | 0.011713 | −0.016233 | 0.018778 |
| Prr12 | 0.019562 | 0.007179 | −0.027145 | −0.038234 | −0.023189 | −0.032791 |
| Prr36 | 0.010415 | −0.017502 | 0.006927 | 0.013732 | −0.000494 | 0.039650 |
| Prrc2a | −0.022121 | −0.014583 | 0.036009 | 0.017364 | 0.031456 | 0.041011 |
| Prrg1 | 0.024562 | −0.009391 | −0.015495 | −0.030528 | −0.066212 | −0.030298 |
| Psg16 | 0.010298 | −0.002768 | −0.007589 | −0.030109 | −0.021847 | −0.067258 |

TABLE 1A-continued

| gene | SPF1 | SPF2 | SPF3 | ABX1 | ABX2 | ABχ3 |
|---|---|---|---|---|---|---|
| Pstpip2 | −0.014425 | 0.015278 | −0.001007 | −0.018167 | −0.028999 | −0.029915 |
| Ptch2 | −0.010309 | 0.007732 | 0.002517 | 0.032688 | 0.030106 | 0.024728 |
| Ptk2b | −0.022265 | 0.013349 | 0.008657 | −0.055288 | −0.024587 | −0.035177 |
| Ptprf | −0.024287 | 0.002195 | 0.021723 | 0.020469 | 0.022752 | 0.024853 |
| Pus7 | −0.016915 | 0.000304 | 0.016418 | −0.018272 | −0.034009 | −0.034447 |
| Pxn | 0.011143 | −0.006321 | −0.004887 | −0.018441 | 0.002311 | 0.002613 |
| Rapgef1 | −0.006112 | −0.015870 | 0.021718 | 0.022698 | 0.017193 | 0.035272 |
| Rcan2 | −0.016526 | 0.020618 | −0.004340 | −0.023357 | −0.041106 | −0.021282 |
| Reps2 | 0.022723 | −0.007819 | −0.015185 | −0.039149 | −0.031480 | −0.041976 |
| Rgs17 | 0.012416 | −0.005070 | −0.007428 | −0.028242 | −0.043635 | −0.022940 |
| Rhof | 0.005288 | −0.012451 | 0.007082 | −0.030062 | −0.034903 | −0.025996 |
| Ric8b | 0.015228 | −0.007809 | −0.007541 | −0.014912 | −0.034270 | −0.020248 |
| Rilpl1 | 0.002712 | 0.003608 | −0.006341 | −0.005501 | −0.007587 | −0.009483 |
| Rin3 | −0.014830 | 0.004207 | 0.010502 | 0.016494 | 0.034052 | 0.035408 |
| Rint1 | 0.010160 | −0.003744 | −0.006471 | −0.038676 | −0.050862 | −0.006302 |
| Rn45s | 0.012530 | 0.006240 | −0.018962 | −0.034615 | −0.051512 | −0.018833 |
| Rnf126 | −0.028653 | 0.014928 | 0.013304 | 0.013297 | 0.022822 | 0.023288 |
| Rnpep | −0.007857 | −0.000687 | 0.008498 | 0.034274 | 0.014885 | 0.027546 |
| Rnpepl1 | −0.019349 | −0.001627 | 0.020697 | 0.040673 | 0.015002 | 0.031729 |
| Rpl19 | −0.009816 | 0.005865 | 0.003901 | −0.003314 | −0.026377 | −0.009122 |
| Rpl23a | −0.007372 | −0.011625 | 0.018808 | −0.010686 | 0.007123 | 0.001361 |
| Rpl3 | −0.007286 | 0.015932 | −0.008780 | −0.002991 | −0.023046 | −0.018411 |
| Rpn2 | −0.012772 | 0.012127 | 0.000538 | 0.040068 | 0.020043 | 0.007737 |
| Rps12 | −0.006454 | 0.012701 | −0.006331 | −0.000015 | −0.018088 | −0.004917 |
| Rps2 | −0.003782 | −0.002971 | 0.006730 | −0.003623 | −0.009712 | 0.008957 |
| Rwdd2b | 0.010165 | −0.003971 | −0.006249 | −0.010412 | −0.037133 | −0.065397 |
| Rxfp3 | −0.012760 | 0.021961 | −0.009457 | 0.036721 | 0.013645 | 0.025178 |
| Ryr2 | 0.009468 | 0.012583 | −0.022309 | −0.038208 | −0.022667 | −0.030954 |
| S100a11 | 0.002840 | 0.013107 | −0.016099 | −0.006264 | 0.004612 | −0.019450 |
| Sall2 | −0.011825 | 0.002894 | 0.008853 | 0.016678 | 0.017757 | 0.025393 |
| Sarnp | 0.019599 | −0.029818 | 0.009746 | −0.014753 | 0.004823 | −0.021101 |
| Sash3 | 0.000140 | −0.019687 | 0.019285 | 0.000651 | −0.035287 | −0.030888 |
| Scaf1 | −0.024879 | 0.010482 | 0.014076 | 0.024125 | 0.031139 | 0.036283 |
| Scd4 | 0.000404 | −0.001321 | 0.000916 | 0.039579 | 0.005706 | 0.029497 |
| Scn1a | 0.029830 | −0.000974 | −0.029465 | −0.030302 | −0.026805 | −0.066524 |
| Scrib | −0.019934 | 0.010178 | 0.009551 | 0.014896 | 0.026881 | 0.030888 |
| Scrt1 | 0.001305 | 0.010579 | −0.011973 | −0.022429 | −0.024621 | −0.024599 |
| Scube1 | −0.025287 | 0.029126 | −0.004362 | −0.031709 | −0.034672 | −0.038635 |
| Scx | −0.012935 | 0.024398 | −0.011776 | −0.013270 | −0.029412 | −0.027498 |
| Sdha | 0.004352 | 0.005067 | −0.009465 | −0.002049 | −0.011239 | −0.007797 |
| Sema3f | 0.001632 | −0.004266 | 0.002624 | −0.025954 | −0.024357 | −0.019785 |
| Sema6a | 0.012876 | 0.024367 | −0.038004 | −0.060562 | −0.022630 | −0.065122 |
| Senp7 | 0.019679 | −0.011813 | −0.008072 | −0.018142 | −0.014763 | −0.039642 |
| Sfxn4 | 0.007113 | −0.000770 | −0.006375 | −0.030690 | −0.025937 | −0.022274 |
| Sgk3 | −0.002299 | −0.019698 | 0.021697 | −0.057281 | −0.023063 | −0.044107 |
| Sh3bgrl2 | −0.003420 | 0.013913 | −0.010603 | −0.017819 | −0.026839 | −0.025606 |
| Sh3bp4 | −0.008671 | −0.002980 | 0.011576 | 0.033888 | 0.030763 | 0.018081 |
| Shisa9 | 0.008869 | 0.008787 | −0.017819 | −0.039235 | −0.030927 | −0.023212 |
| Shmt2 | −0.011753 | −0.026609 | 0.037577 | 0.039428 | 0.032039 | 0.030435 |
| Sigmar1 | 0.004379 | −0.003622 | −0.000769 | 0.022653 | 0.023540 | 0.038625 |
| Slc10a3 | 0.004188 | −0.008621 | 0.004395 | 0.038554 | 0.020932 | 0.031304 |
| Slc15a4 | 0.011103 | −0.003419 | −0.007752 | −0.037626 | −0.019966 | −0.058918 |
| Slc17a5 | 0.019953 | −0.017586 | −0.002615 | −0.035722 | −0.024544 | −0.025056 |
| Slc1a5 | −0.013425 | 0.006442 | 0.006890 | −0.035908 | −0.038050 | −0.017909 |
| Slc22a12 | −0.014598 | 0.006600 | 0.007887 | 0.001005 | −0.016955 | −0.002747 |
| Slc24a3 | −0.006701 | −0.011528 | 0.018054 | −0.043770 | −0.022563 | −0.030934 |
| Slc25a1 | −0.017147 | 0.009831 | 0.007163 | 0.014053 | 0.032417 | 0.020103 |
| Slc29a4 | 0.016903 | −0.016003 | −0.001088 | 0.033645 | 0.017912 | 0.032389 |
| Slc35f3 | −0.015911 | 0.019353 | −0.003664 | 0.001338 | −0.023620 | −0.000806 |
| Slc36a4 | 0.019354 | 0.014566 | −0.034534 | −0.035845 | −0.010997 | −0.050029 |
| Slc37a2 | −0.010758 | −0.007981 | 0.018557 | 0.020876 | 0.027231 | 0.031998 |
| Slc52a2 | −0.013902 | 0.025494 | −0.011934 | 0.013856 | 0.011449 | 0.033675 |
| Slc6a8 | −0.003339 | −0.001963 | 0.005286 | 0.018356 | 0.030737 | 0.018864 |
| Slco2b1 | −0.010552 | 0.011054 | −0.000583 | 0.043834 | 0.048050 | 0.014267 |
| Slitrk4 | 0.007124 | 0.014255 | −0.021628 | −0.022324 | −0.033070 | −0.034216 |
| Smarca5-ps | 0.005849 | 0.009971 | −0.015954 | −0.037944 | −0.027329 | −0.024792 |
| Smim20 | −0.022286 | 0.005181 | 0.016826 | −0.028832 | −0.042365 | −0.016469 |
| Smim3 | −0.010199 | 0.006428 | 0.003716 | 0.052992 | 0.021058 | 0.012297 |
| Smim8 | −0.019799 | 0.019320 | 0.000213 | −0.007489 | −0.007999 | −0.011845 |
| Smpdl3a | −0.026893 | −0.013970 | 0.039987 | −0.024862 | −0.022771 | −0.024425 |
| Snhg1 | −0.003079 | −0.011730 | 0.014683 | −0.029954 | −0.015735 | 0.001372 |
| Snora15 | 0.000551 | −0.013847 | 0.013169 | −0.038679 | −0.026570 | −0.037862 |
| Snora23 | 0.021673 | −0.001825 | −0.020153 | −0.012766 | −0.021076 | −0.025328 |
| Snord91a | 0.002435 | −0.005583 | 0.003132 | 0.011095 | 0.044474 | 0.020983 |
| Socs6 | −0.000791 | 0.026411 | −0.026097 | −0.027661 | −0.030910 | −0.019523 |
| Sox13 | 0.000539 | 0.005293 | −0.005853 | 0.025914 | 0.029097 | 0.030091 |
| Sox4 | −0.001663 | −0.004362 | 0.006005 | 0.000642 | 0.006085 | 0.007327 |
| Spry3 | 0.010023 | 0.013463 | −0.023778 | 0.000726 | 0.016737 | −0.000700 |

TABLE 1A-continued

| gene | SPF1 | SPF2 | SPF3 | ABX1 | ABX2 | ABχ3 |
|---|---|---|---|---|---|---|
| Spsb1 | −0.000132 | 0.013928 | −0.013930 | −0.021138 | −0.020941 | −0.005620 |
| Sqrdl | −0.004965 | 0.003341 | 0.001611 | −0.017190 | −0.027351 | −0.028406 |
| Srbd1 | 0.000813 | −0.000241 | −0.000572 | −0.020799 | 0.011609 | −0.020928 |
| Src | −0.021455 | 0.005947 | 0.015256 | 0.017420 | 0.028482 | 0.024690 |
| Srcap | 0.002458 | −0.015759 | 0.013153 | 0.014770 | 0.014343 | 0.026788 |
| Srp54b | 0.001813 | 0.008845 | −0.010726 | −0.024740 | −0.020908 | −0.005128 |
| St3gal3 | −0.001947 | 0.013125 | −0.011283 | 0.023552 | 0.019318 | 0.034874 |
| St8sia6 | 0.043534 | −0.024469 | −0.020073 | −0.043456 | −0.041574 | −0.026120 |
| Stard5 | −0.005244 | −0.006021 | 0.011199 | −0.018216 | −0.025443 | −0.034054 |
| Stxbp3-ps | 0.011052 | 0.009172 | −0.020440 | −0.037943 | −0.013422 | −0.040494 |
| Supt6 | 0.003228 | −0.005452 | 0.002208 | 0.014245 | 0.014766 | 0.024974 |
| Sv2b | 0.038616 | −0.001189 | −0.038457 | −0.042965 | −0.049963 | −0.040797 |
| Svopl | −0.015065 | 0.015237 | −0.000331 | −0.006704 | 0.002560 | −0.012317 |
| Synpo2 | −0.023778 | 0.012197 | 0.011290 | 0.027852 | 0.057355 | 0.010588 |
| Syt17 | 0.013027 | −0.003593 | −0.009529 | −0.036883 | −0.014745 | −0.025348 |
| Syt3 | −0.008239 | 0.009751 | −0.001570 | −0.020546 | −0.036464 | −0.028218 |
| Syvn1 | −0.019328 | 0.009312 | 0.009824 | 0.011102 | 0.037692 | 0.039538 |
| Tacc1 | −0.000906 | 0.005976 | −0.005092 | −0.021800 | 0.021032 | −0.026515 |
| Tada1 | 0.001590 | −0.003640 | 0.002043 | −0.034684 | −0.008010 | −0.027514 |
| Taf1a | 0.017011 | −0.005710 | −0.011459 | −0.020314 | −0.009568 | −0.020910 |
| Taf4a | 0.031887 | 0.009970 | −0.042877 | −0.033405 | −0.042192 | −0.044984 |
| Taok2 | 0.004774 | 0.000322 | −0.005113 | 0.017756 | 0.021997 | 0.014852 |
| Tas1r1 | 0.001524 | −0.001561 | 0.000035 | −0.015380 | −0.008555 | −0.003584 |
| Tatdn1 | −0.025233 | 0.020336 | 0.004527 | −0.031775 | −0.030837 | −0.031760 |
| Tbc1d10a | −0.008675 | 0.001772 | 0.006860 | 0.022187 | −0.001686 | 0.006209 |
| Tbc1d4 | −0.009719 | 0.003963 | 0.005707 | −0.019637 | 0.001366 | −0.005345 |
| Tbc1d9 | −0.004999 | 0.005437 | −0.000457 | −0.001518 | 0.017596 | 0.007560 |
| Tbx2 | −0.029950 | 0.019117 | 0.010360 | 0.081200 | 0.023088 | 0.017227 |
| Tcf3 | −0.030448 | −0.003033 | 0.032783 | 0.022485 | 0.023775 | 0.043199 |
| Tenm1 | 0.010046 | 0.015652 | −0.026052 | −0.023777 | −0.035682 | −0.030103 |
| Tfcp2l1 | 0.020540 | −0.001251 | −0.019568 | −0.036448 | −0.034980 | −0.037405 |
| Them4 | 0.002209 | 0.014996 | −0.017390 | −0.025831 | −0.014387 | −0.016045 |
| Thoc7 | 0.016809 | −0.017870 | 0.000852 | −0.036856 | −0.027174 | −0.034740 |
| Thsd4 | 0.006019 | 0.005836 | −0.011929 | −0.047726 | −0.046408 | −0.006245 |
| Tigar | −0.002701 | 0.011342 | −0.008714 | 0.017069 | 0.037864 | 0.033421 |
| Timm9 | −0.005605 | 0.013310 | −0.007798 | −0.004740 | −0.000800 | 0.012257 |
| Tm4sf1 | 0.028563 | −0.006535 | −0.022502 | −0.015783 | −0.005930 | −0.017539 |
| Tmc7 | −0.006083 | 0.004833 | 0.001228 | −0.011373 | 0.004561 | −0.031664 |
| Tmem170b | −0.000658 | −0.004610 | 0.005251 | −0.001248 | 0.008376 | −0.007683 |
| Tmem180 | −0.003636 | −0.001435 | 0.005057 | −0.042603 | −0.028332 | −0.022672 |
| Tmem185b | 0.011836 | −0.014195 | 0.002240 | −0.001541 | −0.004751 | −0.012033 |
| Tmem203 | −0.012320 | 0.001317 | 0.010908 | −0.022027 | −0.025258 | −0.015142 |
| Tmem29 | 0.005702 | −0.007076 | 0.001345 | −0.014522 | −0.030633 | −0.053734 |
| Tmem81 | −0.021138 | −0.000753 | 0.021574 | −0.020405 | −0.030635 | −0.031197 |
| Tmem8b | −0.017438 | 0.006082 | 0.011195 | 0.026036 | 0.020533 | 0.009567 |
| Tmem9 | 0.009546 | −0.004700 | −0.004894 | −0.028288 | −0.032638 | −0.018057 |
| Tmppe | −0.016695 | −0.004086 | 0.020531 | 0.021167 | 0.022400 | 0.031954 |
| Tnfrsf19 | 0.006787 | −0.010305 | 0.003462 | 0.008369 | 0.027508 | 0.031933 |
| Tomm5 | 0.000929 | 0.012976 | −0.014031 | −0.017698 | −0.038827 | −0.037850 |
| Tpcn1 | −0.011163 | 0.008714 | 0.002378 | 0.009310 | 0.040114 | 0.049309 |
| Trim13 | 0.019233 | −0.004542 | −0.014903 | −0.029189 | −0.013496 | −0.030691 |
| Trim9 | 0.007306 | −0.006910 | −0.000431 | −0.006094 | −0.006103 | −0.001308 |
| Tshz3 | 0.002918 | 0.015158 | −0.018274 | −0.048314 | −0.012300 | −0.039350 |
| Tspan13 | 0.007890 | −0.000036 | −0.007897 | −0.006777 | −0.009938 | −0.012938 |
| Ttc39aos1 | −0.003346 | 0.009217 | −0.005917 | −0.023948 | −0.012736 | −0.006059 |
| Tuft1 | 0.001296 | 0.001697 | −0.002998 | 0.003914 | −0.008725 | 0.001321 |
| Txnrd3 | 0.003943 | −0.004030 | 0.000075 | −0.040823 | −0.029196 | −0.022389 |
| Ubap2 | 0.007254 | −0.021887 | 0.014378 | 0.011429 | 0.026834 | 0.034243 |
| Ubb | 0.005381 | −0.007630 | 0.002217 | −0.023365 | −0.020315 | −0.010179 |
| Ube2j2 | 0.008102 | −0.008789 | 0.000637 | 0.010031 | −0.007326 | −0.011033 |
| Ube2r2 | −0.003064 | −0.004666 | 0.007698 | 0.021720 | 0.012959 | 0.021269 |
| Uck2 | 0.001256 | −0.007776 | 0.006484 | 0.023998 | 0.030929 | 0.022775 |
| Utp11l | 0.003668 | 0.007234 | −0.010967 | −0.016373 | −0.014688 | −0.019780 |
| Vac14 | 0.009450 | −0.014758 | 0.005192 | 0.004690 | 0.010709 | 0.039612 |
| Vamp7 | −0.007581 | 0.009221 | −0.001691 | −0.048348 | −0.037779 | −0.013205 |
| Vangl2 | −0.008416 | −0.013115 | 0.021290 | 0.016466 | 0.019586 | 0.050076 |
| Vasp | −0.026147 | 0.013322 | 0.012474 | 0.032668 | 0.028802 | 0.036944 |
| Vcpip1 | 0.021563 | −0.002627 | −0.019228 | −0.021589 | −0.015551 | −0.022061 |
| Vwa8 | −0.001728 | 0.008831 | −0.007148 | 0.028282 | 0.021707 | 0.021273 |
| Vwc2l | −0.009752 | 0.011764 | −0.002095 | −0.027229 | −0.022005 | −0.026290 |
| Wfs1 | 0.017082 | 0.008069 | −0.025499 | −0.028008 | −0.024851 | −0.042632 |
| Xlr3a | −0.000673 | 0.002167 | −0.001497 | −0.029158 | −0.021372 | −0.030573 |
| Xylt1 | 0.007624 | 0.025160 | −0.033409 | −0.031928 | −0.042862 | −0.034861 |
| Yipf2 | 0.016655 | −0.004826 | −0.011983 | 0.011403 | −0.006338 | 0.034880 |
| Zbtb45 | 0.018195 | −0.004690 | −0.013692 | −0.036749 | −0.026237 | −0.029094 |
| Zbtb46 | 0.023025 | 0.001658 | −0.025086 | −0.023924 | −0.033067 | −0.041451 |
| Zc3h10 | 0.011316 | −0.015060 | 0.003617 | −0.008523 | −0.023412 | −0.002397 |
| Zc3h12b | 0.008060 | 0.015084 | −0.023435 | −0.029989 | −0.037946 | −0.030011 |

TABLE 1A-continued

| gene | SPF1 | SPF2 | SPF3 | ABX1 | ABX2 | ABχ3 |
|---|---|---|---|---|---|---|
| Zc3h18 | −0.014044 | −0.004449 | 0.018301 | 0.014335 | 0.028638 | 0.029885 |
| Zeb2os | 0.011561 | −0.004064 | −0.007569 | −0.040244 | −0.029679 | −0.027164 |
| Zfhx3 | 0.016317 | −0.003908 | −0.012561 | −0.031074 | −0.014626 | −0.011462 |
| Zfp212 | −0.004695 | −0.000668 | 0.005345 | −0.005263 | 0.004276 | 0.009323 |
| Zfp330 | 0.006770 | −0.006066 | −0.000733 | −0.018707 | −0.020203 | −0.030827 |
| Zfp35 | 0.020093 | 0.002335 | −0.022749 | −0.038052 | −0.015884 | −0.041656 |
| Zfp362 | 0.002379 | −0.011557 | 0.009102 | 0.035827 | 0.021264 | 0.019315 |
| Zfp36l1 | 0.010031 | −0.020700 | 0.010448 | 0.035114 | 0.041138 | 0.016446 |
| Zfp628 | 0.018878 | −0.012513 | −0.006558 | 0.005431 | −0.020178 | 0.001984 |
| Zfp651 | −0.007410 | 0.010234 | −0.002882 | 0.023355 | 0.014911 | 0.014142 |
| Zfp710 | 0.000379 | −0.013536 | 0.013035 | 0.017175 | 0.033010 | 0.025302 |
| Zfp809 | −0.013000 | 0.011480 | 0.001416 | 0.003336 | −0.001140 | −0.008168 |
| Zfp839 | −0.002056 | 0.000260 | 0.001793 | 0.006397 | 0.014099 | 0.007840 |
| Zfp85 | 0.014042 | 0.018837 | −0.033456 | −0.021231 | −0.046299 | −0.031123 |
| Zfp850 | 0.010219 | −0.008903 | −0.001380 | 0.006155 | −0.004383 | −0.006469 |
| Zfpm1 | −0.021619 | −0.001184 | 0.022465 | 0.000153 | 0.020359 | −0.023700 |
| Zic5 | −0.011661 | 0.014379 | −0.002840 | −0.037437 | −0.021909 | −0.049901 |
| Zmynd10 | −0.015754 | −0.000094 | 0.015677 | −0.025473 | −0.032960 | −0.029013 |
| Zscan12 | 0.004344 | −0.016879 | 0.012376 | −0.016942 | −0.015238 | −0.011926 |
| Zscan2 | −0.004701 | 0.013244 | −0.008638 | 0.014394 | 0.032285 | 0.032744 |
| Zswim8 | −0.017699 | 0.000092 | 0.017393 | 0.015412 | 0.021578 | 0.035259 |

TABLE 1B

| gene | SP1 | SP2 | SP3 | SPF v ABX p-value | Sp v ABX p-value |
|---|---|---|---|---|---|
| 1700017B05Rik | 0.018638 | −0.004432 | 0.049365 | 0.020742 | 0.346030 |
| 1810055G02Rik | 0.031917 | 0.020735 | −0.014757 | 0.003495 | 0.971940 |
| 2610015P09Rik | 0.018861 | −0.000999 | 0.032038 | 0.296571 | 0.025047 |
| 2610020C07Rik | 0.035140 | 0.036800 | −0.012333 | 0.992996 | 0.011782 |
| 2700046A07Rik | −0.001661 | −0.007484 | −0.002094 | 0.013359 | 0.116251 |
| 2810408I11Rik | 0.004373 | 0.009511 | 0.020696 | 0.295913 | 0.044638 |
| 2810468N07Rik | 0.014534 | 0.026114 | 0.051083 | 0.383007 | 0.015117 |
| 3830406C13Rik | 0.020414 | 0.064631 | 0.034712 | 0.927670 | 0.005845 |
| 4930447A16Rik | −0.028895 | −0.028465 | −0.018808 | 0.049218 | 0.914526 |
| 4930511A08Rik | 0.011405 | 0.005374 | 0.003392 | 0.781974 | 0.036947 |
| 4933439C10Rik | −0.007199 | −0.023143 | −0.006832 | 0.021055 | 0.166271 |
| 5930403L14Rik | 0.037099 | 0.001931 | −0.005865 | 0.047893 | 0.233449 |
| 6330415G19Rik | −0.011281 | −0.015162 | −0.007935 | 0.027276 | 0.187974 |
| 6330549D23Rik | −0.018105 | −0.024910 | −0.055949 | 0.002299 | 0.030601 |
| 6430573F11Rik | 0.031887 | 0.018290 | 0.038128 | 0.014222 | 0.629827 |
| 6530402F18Rik | 0.006070 | −0.017917 | −0.021293 | 0.209688 | 0.043199 |
| 9130019P16Rik | −0.002109 | −0.019938 | −0.001767 | 0.136514 | 0.041045 |
| 9430065F17Rik | 0.011807 | 0.018180 | 0.003938 | 0.008398 | 0.095445 |
| A330069E16Rik | −0.031137 | −0.015269 | −0.018878 | 0.023845 | 0.535954 |
| A930003O13Rik | −0.003694 | −0.002218 | −0.000522 | 0.063207 | 0.040377 |
| Acad9 | −0.020673 | −0.013996 | −0.036059 | 0.964761 | 0.003238 |
| Acsbg1 | −0.009494 | −0.002390 | −0.024497 | 0.195912 | 0.032880 |
| Acsf2 | 0.007830 | 0.021217 | 0.002728 | 0.715813 | 0.026933 |
| Adamts8 | −0.005202 | −0.008857 | −0.014714 | 0.008054 | 0.365332 |
| Agap3 | 0.003172 | −0.004897 | −0.009828 | 0.036757 | 0.180482 |
| Airn | −0.032133 | 0.008081 | −0.013357 | 0.212826 | 0.044750 |
| Ak7 | 0.030155 | 0.012369 | 0.058683 | 0.113220 | 0.045880 |
| Aldoc | 0.019091 | 0.005108 | −0.009872 | 0.167400 | 0.036699 |
| Alpl | −0.018661 | −0.005526 | −0.019086 | 0.819387 | 0.014538 |
| Ankrd11 | 0.007595 | 0.014692 | 0.002831 | 0.897735 | 0.004728 |
| Ankrd6 | 0.018971 | 0.010460 | 0.002472 | 0.187595 | 0.028505 |
| Ap1s1 | 0.011447 | 0.022753 | 0.017971 | 0.041310 | 0.298544 |
| Ap3s1 | −0.015266 | 0.013899 | 0.004645 | 0.039435 | 0.292725 |
| Arhgap10 | 0.018213 | 0.023605 | −0.012254 | 0.329280 | 0.020090 |
| Arid1a | 0.014766 | 0.016211 | −0.004863 | 0.039376 | 0.036938 |
| Arl6ip1 | −0.014357 | −0.012329 | −0.038201 | 0.466523 | 0.016309 |
| Armt1 | 0.007545 | 0.015379 | 0.022269 | 0.032507 | 0.176439 |
| Arrb2 | 0.007874 | 0.024731 | 0.023994 | 0.020977 | 0.008638 |
| Arsa | −0.028240 | −0.004958 | −0.037616 | 0.334779 | 0.034061 |
| Arxes2 | 0.022150 | 0.034058 | 0.015139 | 0.028753 | 0.562367 |
| Ate1 | −0.016000 | −0.011618 | −0.026385 | 0.590575 | 0.028250 |
| Atg4d | −0.022400 | −0.003575 | −0.023475 | 0.581787 | 0.042946 |
| Atn1 | −0.039266 | −0.019820 | −0.026779 | 0.028445 | 0.762889 |
| Atp5h | 0.006702 | −0.002794 | 0.005798 | 0.414676 | 0.041331 |
| Atp6ap2 | 0.001933 | −0.018617 | 0.000114 | 0.001091 | 0.018647 |
| Atp6v1b2 | −0.008792 | −0.012530 | −0.025810 | 0.069472 | 0.029589 |
| Atp8b1 | 0.003365 | 0.013959 | 0.000712 | 0.034991 | 0.104766 |
| Atpaf1 | 0.010982 | 0.016225 | 0.009383 | 0.026162 | 0.675041 |
| Atxn2 | 0.021957 | 0.020479 | 0.019710 | 0.036812 | 0.110005 |

TABLE 1B-continued

| gene | SP1 | SP2 | SP3 | SPF v ABX p-value | Sp v ABX p-value |
|---|---|---|---|---|---|
| Aven | 0.004074 | 0.016877 | 0.016698 | 0.028744 | 0.212447 |
| AW209491 | 0.003241 | 0.022375 | 0.015654 | 0.010607 | 0.424536 |
| AW549877 | −0.000175 | 0.002798 | 0.031642 | 0.036804 | 0.255979 |
| Axin2 | 0.010689 | −0.004838 | 0.018189 | 0.015686 | 0.104696 |
| B230307C23Rik | −0.012088 | −0.017021 | −0.034730 | 0.559672 | 0.037047 |
| B3galt2 | −0.037332 | −0.008679 | −0.009353 | 0.048749 | 0.560575 |
| B4galt4 | 0.007768 | 0.027834 | −0.007646 | 0.129087 | 0.029637 |
| Bahcc1 | 0.025570 | 0.013260 | 0.018734 | 0.025823 | 0.744577 |
| Baiap2l1 | 0.026465 | 0.023471 | 0.030968 | 0.048076 | 0.251265 |
| BC020402 | −0.014143 | −0.034449 | −0.031436 | 0.004676 | 0.127490 |
| BC024139 | 0.037316 | −0.009068 | 0.019397 | 0.223102 | 0.008794 |
| Blzf1 | 0.021608 | 0.035501 | 0.048987 | 0.043345 | 0.020862 |
| Bola1 | −0.000238 | −0.023571 | −0.011696 | 0.165591 | 0.030429 |
| Brd4 | 0.017478 | −0.001701 | −0.003086 | 0.044653 | 0.090765 |
| Brox | −0.012965 | −0.006479 | −0.024291 | 0.027580 | 0.408589 |
| C1galt1c1 | −0.037322 | −0.035471 | −0.025821 | 0.111284 | 0.007125 |
| C1ql3 | 0.037193 | 0.027143 | 0.014681 | 0.872241 | 0.031389 |
| C330006A16Rik | 0.002048 | −0.021937 | −0.000064 | 0.107636 | 0.037658 |
| C77080 | −0.012379 | −0.018685 | −0.022032 | 0.330408 | 0.023274 |
| C77370 | −0.008607 | −0.018310 | −0.050701 | 0.031353 | 0.879897 |
| Cadm2 | −0.031666 | 0.007890 | −0.057798 | 0.028136 | 0.492641 |
| Camk1d | 0.002103 | −0.021799 | −0.059723 | 0.042962 | 0.630926 |
| Camk2d | −0.008343 | −0.012511 | −0.036507 | 0.039911 | 0.438039 |
| Capn3 | 0.051819 | 0.028995 | 0.059326 | 0.997838 | 0.020373 |
| Capns2 | −0.003440 | −0.012476 | −0.000049 | 0.088467 | 0.033376 |
| Card9 | −0.023401 | −0.012078 | −0.017604 | 0.546193 | 0.034352 |
| Carns1 | 0.024050 | 0.039077 | 0.042899 | 0.081707 | 0.011544 |
| Cartpt | −0.035145 | −0.028518 | −0.033365 | 0.073177 | 0.029756 |
| Casp9 | −0.017788 | −0.036192 | −0.004406 | 0.539597 | 0.046217 |
| Casz1 | 0.002292 | 0.032986 | 0.017368 | 0.020482 | 0.212097 |
| Cc2d1a | 0.097035 | 0.099738 | −0.034594 | 0.011647 | 0.502015 |
| Ccbl2 | −0.006229 | 0.000580 | 0.001696 | 0.043134 | 0.054697 |
| Ccdc102a | 0.010610 | 0.025094 | 0.025529 | 0.042402 | 0.398813 |
| Ccdc137 | −0.039338 | −0.025673 | 0.003822 | 0.041148 | 0.509689 |
| Ccdc162 | −0.013561 | −0.001696 | −0.010546 | 0.144079 | 0.027583 |
| Ccdc18 | −0.006137 | 0.022216 | 0.056094 | 0.510450 | 0.026744 |
| Ccdc71l | −0.009176 | −0.006485 | 0.005317 | 0.093585 | 0.049559 |
| Ccdc88b | −0.016783 | −0.013084 | −0.010888 | 0.364219 | 0.042417 |
| Ccne1 | 0.006161 | 0.025424 | 0.051622 | 0.024593 | 0.743732 |
| Cd34 | −0.026160 | −0.009905 | 0.005988 | 0.041522 | 0.203911 |
| Cdc14b | −0.001812 | −0.022454 | −0.006940 | 0.142560 | 0.028082 |
| Cdca2 | 0.104941 | 0.080389 | −0.102077 | 0.028613 | 0.652675 |
| Cdh20 | 0.021184 | 0.006032 | 0.069896 | 0.006466 | 0.491841 |
| Cdh24 | 0.042088 | 0.015338 | 0.007160 | 0.030229 | 0.528470 |
| Cdk6 | 0.210440 | 0.004094 | 0.026616 | 0.023904 | 0.917203 |
| Cdr1 | 0.035166 | 0.051098 | 0.010499 | 0.020388 | 0.027370 |
| Celsr2 | −0.014931 | 0.014921 | −0.028445 | 0.009650 | 0.344513 |
| Cenpb | 0.015016 | 0.020412 | 0.012149 | 0.021735 | 0.450704 |
| Cep250 | 0.018036 | 0.018775 | 0.014792 | 0.048492 | 0.764264 |
| Cep85l | −0.007781 | 0.011068 | −0.013573 | 0.005658 | 0.466966 |
| Cerk | −0.010458 | −0.022563 | −0.016745 | 0.411210 | 0.019926 |
| Chml | −0.004348 | 0.005401 | 0.025792 | 0.423096 | 0.004320 |
| Cit | 0.035513 | 0.019627 | 0.016589 | 0.043276 | 0.571517 |
| Cklf | 0.017535 | 0.024583 | 0.025101 | 0.651082 | 0.045471 |
| Cks1b | −0.029856 | −0.029412 | −0.022161 | 0.931788 | 0.010456 |
| Clic3 | 0.022312 | 0.032462 | 0.057672 | 0.028433 | 0.575114 |
| Clic6 | 0.008745 | −0.058586 | −0.067127 | 0.040161 | 0.867916 |
| Clmn | −0.034623 | −0.003282 | 0.017750 | 0.072765 | 0.036426 |
| Clock | −0.007399 | 0.001717 | 0.022307 | 0.142595 | 0.048130 |
| Cmc1 | −0.002725 | 0.000092 | 0.007827 | 0.037876 | 0.867438 |
| Cntnap5b | 0.028115 | 0.034920 | 0.036105 | 0.049453 | 0.478204 |
| Coch | 0.022825 | 0.028824 | 0.025967 | 0.023138 | 0.653057 |
| Col7a1 | −0.030405 | −0.004274 | −0.008851 | 0.603427 | 0.012553 |
| Commd9 | 0.017122 | 0.012919 | 0.011169 | 0.193251 | 0.017034 |
| Cplx2 | −0.008452 | 0.003553 | −0.020655 | 0.181157 | 0.035215 |
| Cpped1 | −0.022119 | −0.007738 | −0.015496 | 0.041069 | 0.287429 |
| Cramp1l | 0.011951 | 0.015843 | −0.008129 | 0.036474 | 0.128318 |
| Creb3l1 | 0.026893 | 0.012759 | 0.059775 | 0.002724 | 0.056047 |
| Creb5 | −0.011651 | −0.018401 | −0.014097 | 0.214237 | 0.021926 |
| Crebrf | −0.014195 | −0.015965 | −0.014085 | 0.026364 | 0.460324 |
| Cryab | 0.002648 | 0.045479 | −0.004698 | 0.045840 | 0.373904 |
| Cryzl1 | 0.022225 | 0.025653 | 0.001220 | 0.012692 | 0.815966 |
| Ctrl | 0.022104 | 0.018738 | 0.001256 | 0.360539 | 0.047253 |
| Ctsa | 0.002983 | 0.003214 | 0.014448 | 0.046033 | 0.128335 |
| Ctss | −0.017689 | −0.003842 | 0.008522 | 0.093315 | 0.045646 |
| Cuedc1 | −0.000589 | 0.026350 | −0.007672 | 0.041105 | 0.117277 |
| Cyb561 | −0.006971 | −0.019293 | −0.021704 | 0.048446 | 0.375684 |
| Cyb5a | −0.000247 | 0.012845 | 0.022998 | 0.036503 | 0.249784 |

TABLE 1B-continued

| gene | SP1 | SP2 | SP3 | SPF v ABX p-value | Sp v ABX p-value |
|---|---|---|---|---|---|
| Cycs | 0.025624 | 0.038795 | 0.042975 | 0.207770 | 0.005689 |
| Cyp27b1 | −0.012760 | 0.008048 | −0.020800 | 0.099154 | 0.022989 |
| D030068K23Rik | 0.023832 | 0.056173 | 0.026594 | 0.031285 | 0.793041 |
| D11Wsu47e | −0.025550 | −0.012995 | −0.005751 | 0.198305 | 0.015147 |
| Dbx2 | −0.014612 | −0.011878 | −0.008449 | 0.271487 | 0.049120 |
| Ddx25 | 0.011662 | 0.018683 | 0.006078 | 0.016479 | 0.516485 |
| Ddx27 | 0.015589 | 0.003057 | 0.016676 | 0.478136 | 0.003401 |
| Deb1 | −0.014179 | −0.023216 | −0.043748 | 0.049450 | 0.947544 |
| Dennd1c | 0.039914 | 0.021151 | 0.018293 | 0.526756 | 0.012549 |
| Dennd2a | 0.015498 | 0.018643 | 0.017465 | 0.035084 | 0.580602 |
| Dimt1 | 0.023691 | −0.003179 | 0.011145 | 0.194220 | 0.033471 |
| Dio3os | −0.024838 | −0.034409 | −0.003964 | 0.021019 | 0.463275 |
| Dlx5 | 0.008132 | 0.013721 | 0.015256 | 0.169939 | 0.010225 |
| Dmd | −0.013903 | −0.025774 | −0.006702 | 0.048507 | 0.714606 |
| Dnaaf2 | 0.036197 | 0.008713 | 0.025264 | 0.031924 | 0.673984 |
| Dnah8 | −0.016055 | 0.001490 | −0.037444 | 0.024992 | 0.264581 |
| Dnase1 | 0.023842 | 0.009648 | 0.013157 | 0.197763 | 0.010572 |
| Dok2 | 0.003324 | 0.008689 | 0.025085 | 0.034923 | 0.239246 |
| Dpp10 | −0.015441 | −0.007954 | −0.079981 | 0.046930 | 0.923224 |
| Dpy19l3 | −0.008278 | −0.002545 | −0.039768 | 0.035831 | 0.361002 |
| E130012A19Rik | 0.031515 | 0.049468 | 0.017424 | 0.038801 | 0.968489 |
| E130307A14Rik | −0.038934 | 0.001919 | −0.024048 | 0.583594 | 0.043410 |
| E2f8 | 0.026167 | 0.034633 | 0.008660 | 0.009712 | 0.917045 |
| Ece1 | 0.015416 | 0.011281 | 0.018303 | 0.017200 | 0.212793 |
| Efhb | −0.017393 | −0.024828 | −0.031038 | 0.003463 | 0.316554 |
| Elk4 | 0.001924 | 0.005306 | 0.002035 | 0.102711 | 0.004677 |
| Emp2 | 0.013323 | 0.008407 | 0.019759 | 0.015086 | 0.313877 |
| En2 | 0.010765 | 0.007161 | 0.022204 | 0.028315 | 0.970905 |
| Epas1 | 0.008288 | 0.028333 | 0.013615 | 0.046416 | 0.376189 |
| Ephb2 | 0.007012 | 0.015649 | 0.016260 | 0.035094 | 0.363879 |
| Epor | 0.027620 | −0.013964 | −0.026050 | 0.012732 | 0.049408 |
| Erbb2 | −0.019501 | −0.005355 | −0.006818 | 0.105376 | 0.016819 |
| Esd | 0.016940 | −0.012689 | 0.012556 | 0.073803 | 0.020485 |
| Exo5 | 0.003297 | 0.017595 | 0.019780 | 0.275763 | 0.036255 |
| Exph5 | 0.001529 | 0.014966 | 0.011504 | 0.022686 | 0.107954 |
| F11r | 0.004515 | 0.013337 | −0.003539 | 0.025888 | 0.057087 |
| F8 | −0.053619 | −0.014388 | −0.017645 | 0.033635 | 0.718812 |
| Fah | −0.001477 | −0.013936 | −0.017790 | 0.034176 | 0.192238 |
| Fam122b | 0.014118 | 0.034620 | 0.022356 | 0.680812 | 0.038356 |
| Fam126a | 0.015455 | 0.001616 | 0.017247 | 0.468843 | 0.048096 |
| Fam160b2 | −0.020819 | −0.023256 | −0.026721 | 0.359031 | 0.007140 |
| Fam199x | −0.005638 | 0.010653 | 0.025052 | 0.173394 | 0.048549 |
| Fam19a1 | 0.021594 | 0.023319 | 0.054835 | 0.004305 | 0.504384 |
| Fam207a | 0.033239 | 0.023405 | −0.002020 | 0.393933 | 0.023381 |
| Fam208a | 0.014999 | 0.021287 | −0.019797 | 0.060989 | 0.011493 |
| Fam20a | −0.017786 | −0.002093 | −0.008460 | 0.195143 | 0.036055 |
| Fam43b | 0.036932 | 0.021262 | −0.013308 | 0.012179 | 0.563795 |
| Fam76b | 0.038818 | 0.043033 | 0.034589 | 0.729838 | 0.010527 |
| Fgf1 | −0.018777 | −0.018809 | −0.024725 | 0.046123 | 0.735814 |
| Fkbp1b | 0.018456 | 0.123274 | 0.042743 | 0.163818 | 0.012659 |
| Fndc3c1 | −0.025908 | −0.035647 | −0.017845 | 0.039584 | 0.900612 |
| Fndc5 | −0.011716 | 0.002985 | −0.030904 | 0.239289 | 0.043973 |
| Foxn2 | 0.015202 | 0.030201 | 0.026947 | 0.481911 | 0.038159 |
| Frem3 | −0.004221 | −0.009371 | −0.010530 | 0.136985 | 0.034447 |
| Fuk | 0.017014 | 0.031916 | 0.014904 | 0.046977 | 0.738661 |
| Fut9 | −0.006006 | −0.008610 | −0.002278 | 0.035590 | 0.131621 |
| Gabra2 | −0.010751 | 0.015139 | −0.020382 | 0.024792 | 0.032847 |
| Gabra4 | −0.008958 | −0.007002 | −0.049786 | 0.023421 | 0.316284 |
| Gabrg1 | 0.034790 | 0.025006 | 0.006969 | 0.056384 | 0.026992 |
| Gabrg2 | 0.016472 | 0.031945 | 0.004880 | 0.009039 | 0.020003 |
| Gale | −0.031557 | −0.026603 | −0.014513 | 0.717324 | 0.031829 |
| Galntl6 | 0.041419 | 0.018695 | 0.036613 | 0.049727 | 0.932152 |
| Gas2l1 | 0.022574 | 0.048417 | 0.037917 | 0.011182 | 0.096764 |
| Gcc1 | 0.015686 | 0.013415 | 0.044273 | 0.014638 | 0.069673 |
| Gcnt1 | −0.031554 | −0.005250 | 0.017868 | 0.005124 | 0.030855 |
| Gemin4 | 0.012289 | 0.005809 | 0.029216 | 0.036616 | 0.088258 |
| Glg1 | −0.010511 | −0.017862 | −0.025994 | 0.021195 | 0.284436 |
| Gli1 | 0.047563 | 0.006019 | 0.009137 | 0.027881 | 0.024868 |
| Glis3 | −0.005923 | −0.028775 | −0.013641 | 0.333521 | 0.004438 |
| Glra2 | −0.016204 | −0.020663 | −0.015720 | 0.351010 | 0.043765 |
| Gm11346 | −0.019898 | −0.002056 | −0.027717 | 0.022763 | 0.920717 |
| Gm11974 | −0.014786 | −0.027986 | −0.018898 | 0.353110 | 0.031054 |
| Gm14164 | 0.019515 | 0.032459 | 0.060170 | 0.045991 | 0.482338 |
| Gm15880 | −0.029035 | −0.014696 | −0.005096 | 0.463778 | 0.026944 |
| Gm16740 | 0.012690 | 0.014370 | 0.067154 | 0.022138 | 0.447401 |
| Gm17750 | −0.006194 | 0.027237 | 0.018766 | 0.027149 | 0.330994 |
| Gm17769 | 0.004824 | −0.004512 | −0.001662 | 0.354129 | 0.047460 |
| Gm20324 | −0.005273 | 0.017530 | 0.007365 | 0.023321 | 0.964918 |

TABLE 1B-continued

| gene | SP1 | SP2 | SP3 | SPF v ABX p-value | Sp v ABX p-value |
|---|---|---|---|---|---|
| Gm6981 | −0.000080 | −0.015038 | −0.014025 | 0.029086 | 0.677523 |
| Gm7173 | 0.008156 | −0.014436 | −0.014937 | 0.019471 | 0.976726 |
| Gpatch1 | 0.431739 | −0.003996 | 0.280313 | 0.219813 | 0.041289 |
| Gpm6a | −0.002108 | −0.004307 | −0.014204 | 0.027061 | 0.087990 |
| Gpr137 | 0.017024 | 0.017506 | 0.002054 | 0.048779 | 0.008619 |
| Gps2 | 0.028868 | 0.029826 | 0.017192 | 0.033398 | 0.175325 |
| Grhl3 | 0.009362 | −0.004203 | 0.020328 | 0.016927 | 0.122013 |
| Gria1 | −0.013471 | −0.008409 | −0.069541 | 0.948533 | 0.016241 |
| Grik4 | 0.026827 | 0.054345 | 0.052835 | 0.922786 | 0.011260 |
| Grin1 | 0.010083 | 0.012392 | 0.080391 | 0.038090 | 0.915147 |
| Gsr | −0.010725 | −0.003364 | −0.014168 | 0.005286 | 0.015590 |
| Gsta4 | 0.012697 | 0.017652 | 0.043070 | 0.023978 | 0.803534 |
| Gstm6 | 0.002286 | 0.011797 | 0.033479 | 0.580243 | 0.031027 |
| Gtf3c3 | 0.090914 | 0.003015 | 0.013426 | 0.011348 | 0.286818 |
| Gucy1b3 | −0.004266 | 0.009719 | −0.006044 | 0.036949 | 0.406598 |
| Hcn4 | 0.019155 | 0.016333 | −0.010748 | 0.007430 | 0.013347 |
| Hdgf | 0.008440 | 0.017392 | 0.027469 | 0.048896 | 0.058432 |
| Hebp2 | 0.008291 | 0.016743 | −0.009318 | 0.049848 | 0.160435 |
| Heca | 0.001433 | −0.001576 | −0.006025 | 0.031399 | 0.759350 |
| Hist1h2bg | −0.019083 | −0.027260 | −0.008214 | 0.110010 | 0.046006 |
| Hist1h4b | 0.015243 | 0.001834 | 0.041077 | 0.066468 | 0.041696 |
| Hist2h3b | −0.004677 | −0.003625 | 0.032882 | 0.020184 | 0.907305 |
| Hmgb1 | 0.052492 | −0.014904 | 0.043829 | 0.035175 | 0.488319 |
| Hnrnph2 | −0.004077 | 0.003290 | 0.038536 | 0.034967 | 0.116214 |
| Hpca | −0.020165 | −0.015338 | −0.073335 | 0.770022 | 0.032902 |
| Hs6st2 | −0.028857 | −0.013711 | −0.032853 | 0.371762 | 0.043064 |
| Hsd3b6 | 0.002284 | −0.036960 | −0.041971 | 0.049202 | 0.961327 |
| Htr2c | 0.003401 | 0.010898 | 0.046356 | 0.032362 | 0.919583 |
| ICa1 | −0.001715 | −0.012359 | −0.047567 | 0.020965 | 0.637254 |
| Il1rap | 0.025303 | 0.038021 | 0.015543 | 0.004016 | 0.909725 |
| Inpp5f | −0.015269 | −0.007679 | −0.025605 | 0.031420 | 0.393950 |
| Iqcb1 | 0.016659 | 0.007740 | 0.012789 | 0.007165 | 0.008668 |
| Irs1 | 0.011937 | 0.005462 | 0.005573 | 0.037654 | 0.717298 |
| Irs4 | 0.011919 | 0.020235 | −0.026328 | 0.217456 | 0.035111 |
| Irx2 | 0.025774 | 0.000577 | 0.017257 | 0.039486 | 0.253553 |
| Ism1 | −0.006999 | 0.005236 | 0.002375 | 0.027306 | 0.005707 |
| Itga1 | −0.010312 | 0.021954 | 0.021167 | 0.046973 | 0.404084 |
| Jak2 | −0.011425 | −0.010001 | −0.012302 | 0.049424 | 0.049844 |
| Kank2 | 0.028024 | 0.031366 | 0.025058 | 0.164542 | 0.031171 |
| Kcnd1 | 0.000315 | −0.014348 | −0.013143 | 0.046624 | 0.385936 |
| Kcnh2 | 0.018974 | 0.015479 | 0.028023 | 0.036855 | 0.634312 |
| Kctd5 | 0.028005 | 0.009671 | 0.001124 | 0.134992 | 0.026917 |
| Kdm1b | −0.008466 | −0.004597 | 0.003408 | 0.014526 | 0.123053 |
| Khk | 0.027590 | 0.009110 | 0.005840 | 0.816021 | 0.022254 |
| Kif27 | −0.023430 | −0.000880 | −0.004603 | 0.024864 | 0.054733 |
| Kiss1r | −0.003762 | −0.024762 | −0.000403 | 0.024309 | 0.304737 |
| Kitl | −0.005738 | −0.011038 | −0.023262 | 0.157655 | 0.032926 |
| Kmt2d | 0.096876 | 0.065628 | 0.005145 | 0.162448 | 0.034969 |
| Knstrn | −0.020536 | 0.005269 | 0.041495 | 0.037241 | 0.295019 |
| Kri1 | −0.006259 | −0.007213 | −0.004070 | 0.008644 | 0.181103 |
| Lama5 | 0.011523 | 0.008852 | −0.001478 | 0.123793 | 0.025420 |
| Lamtor5 | 0.001776 | 0.005946 | 0.012516 | 0.015375 | 0.027874 |
| Lars2 | −0.007470 | −0.015614 | −0.005249 | 0.027652 | 0.282781 |
| Lbh | −0.011895 | −0.007872 | −0.009642 | 0.023526 | 0.073483 |
| Lingo1 | −0.000110 | −0.012315 | −0.051318 | 0.108854 | 0.040087 |
| Lipt2 | −0.006800 | −0.009957 | 0.015414 | 0.014612 | 0.013521 |
| Lmx1b | −0.000908 | −0.010401 | 0.002150 | 0.188943 | 0.020214 |
| LOC100862268 | −0.016624 | −0.012309 | −0.017358 | 0.325547 | 0.018428 |
| Loxl2 | −0.019644 | 0.063617 | 0.043249 | 0.043888 | 0.047965 |
| Lpcat1 | −0.010591 | −0.030695 | −0.012863 | 0.046482 | 0.084511 |
| Lppr4 | 0.011425 | 0.009866 | 0.011001 | 0.046268 | 0.472235 |
| Lrfn1 | −0.010303 | −0.016641 | −0.025801 | 0.668287 | 0.043557 |
| Lrp1b | −0.009740 | −0.013339 | −0.058090 | 0.004669 | 0.342096 |
| Lrp5 | 0.010065 | −0.012394 | −0.016613 | 0.027559 | 0.016373 |
| Lrrl | −0.006631 | −0.005001 | −0.007123 | 0.012557 | 0.157604 |
| Lrrc29 | −0.011883 | −0.032442 | −0.014291 | 0.006046 | 0.586725 |
| Lsm12 | −0.016523 | −0.014899 | −0.023510 | 0.045080 | 0.000860 |
| Magel2 | −0.004009 | −0.017388 | −0.010299 | 0.381163 | 0.027234 |
| Map1a | 0.033386 | 0.033376 | −0.012497 | 0.746662 | 0.008371 |
| Map3k14 | −0.023962 | −0.029427 | −0.042339 | 0.017543 | 0.746454 |
| Map3k19 | −0.000946 | 0.018588 | −0.009143 | 0.039981 | 0.515667 |
| Map3k5 | −0.080160 | −0.077027 | −0.080044 | 0.024002 | 0.039304 |
| Map7d1 | 0.018792 | 0.008053 | 0.007415 | 0.783532 | 0.011803 |
| Mapk8 | −0.004944 | −0.011569 | −0.014343 | 0.049502 | 0.018504 |
| Mapkapk2 | 0.012316 | 0.007317 | 0.019279 | 0.042055 | 0.348361 |
| Maz | 0.014000 | 0.006374 | 0.015134 | 0.017093 | 0.213478 |
| Mcc | 0.023116 | 0.027314 | 0.010548 | 0.020662 | 0.218258 |
| Mcfd2 | 0.009132 | 0.018027 | 0.003504 | 0.020501 | 0.251379 |

TABLE 1B-continued

| gene | SP1 | SP2 | SP3 | SPF v ABX p-value | Sp v ABX p-value |
|---|---|---|---|---|---|
| Mdc1 | 0.038584 | −0.004562 | 0.011400 | 0.032824 | 0.393925 |
| Med10 | 0.008634 | −0.009239 | 0.015578 | 0.238786 | 0.049517 |
| Mier2 | 0.005842 | 0.008916 | 0.014886 | 0.003054 | 0.188440 |
| Mier3 | −0.016152 | 0.019792 | 0.016457 | 0.063984 | 0.022814 |
| Mir3081 | −0.015702 | 0.000201 | −0.014117 | 0.014512 | 0.060784 |
| Mir411 | −0.020688 | −0.001140 | −0.009810 | 0.099324 | 0.031397 |
| Mir6236 | 0.012516 | −0.003319 | 0.013316 | 0.181492 | 0.034979 |
| Mir6353 | 0.006485 | 0.004458 | 0.005059 | 0.024869 | 0.945670 |
| Mllt6 | 0.035633 | 0.030711 | 0.029398 | 0.015416 | 0.013526 |
| Mpeg1 | −0.008183 | 0.002809 | −0.022620 | 0.041339 | 0.100833 |
| Mpnd | −0.041822 | −0.042997 | −0.045820 | 0.012077 | 0.148882 |
| Mrpl22 | 0.020230 | −0.003243 | 0.022213 | 0.183606 | 0.048035 |
| Mrps18b | 0.016544 | 0.007835 | 0.026162 | 0.016675 | 0.064731 |
| Mrps33 | 0.018575 | 0.010301 | 0.020973 | 0.302529 | 0.044620 |
| Mtcl1 | 0.024644 | 0.005838 | 0.009012 | 0.662584 | 0.026472 |
| Mttp | −0.012786 | −0.016086 | −0.000475 | 0.339442 | 0.028464 |
| Mtx3 | 0.000892 | 0.015037 | 0.011776 | 0.047104 | 0.445012 |
| Mum1 | −0.037530 | −0.033799 | −0.040715 | 0.048264 | 0.199749 |
| Mvk | −0.024913 | −0.025223 | −0.010270 | 0.252348 | 0.047026 |
| Myh14 | 0.006294 | 0.004921 | 0.021386 | 0.020653 | 0.598630 |
| Myo5b | −0.021851 | −0.007909 | −0.015674 | 0.713086 | 0.044993 |
| Myo6 | −0.030094 | −0.019024 | −0.032756 | 0.042033 | 0.167508 |
| Mzf1 | −0.029430 | −0.030792 | −0.038825 | 0.314615 | 0.043194 |
| Nans | 0.006464 | 0.005343 | 0.015659 | 0.871903 | 0.041878 |
| Nap1l5 | −0.019423 | −0.014022 | −0.020209 | 0.985883 | 0.013392 |
| Ncmap | −0.005604 | −0.010358 | −0.007121 | 0.176687 | 0.035744 |
| Ncor2 | −0.029185 | −0.031420 | −0.051929 | 0.031998 | 0.782385 |
| Ndufs4 | −0.021712 | −0.017029 | −0.015262 | 0.168259 | 0.046741 |
| Necab1 | −0.003495 | −0.010480 | −0.001512 | 0.015047 | 0.041328 |
| Nek11 | 0.035591 | 0.003662 | −0.003164 | 0.040074 | 0.698646 |
| Nexn | −0.001135 | 0.015271 | 0.041953 | 0.012171 | 0.556460 |
| Nfs1 | −0.010039 | −0.014407 | −0.021444 | 0.286667 | 0.047529 |
| Nipa2 | −0.022149 | −0.006146 | 0.003086 | 0.368505 | 0.039745 |
| Nipal2 | −0.014866 | −0.011007 | −0.020556 | 0.022815 | 0.280505 |
| Nmd3 | −0.002417 | −0.014549 | −0.011316 | 0.042559 | 0.157364 |
| Nol4 | −0.011938 | −0.007492 | −0.016707 | 0.022873 | 0.291237 |
| Notch3 | 0.024110 | 0.012356 | 0.058559 | 0.028682 | 0.153752 |
| Nptxr | 0.009444 | −0.001270 | −0.037407 | 0.049716 | 0.380070 |
| Npy1r | −0.005141 | −0.031118 | −0.040788 | 0.025919 | 0.738308 |
| Nr5a2 | 0.018370 | −0.004263 | 0.063872 | 0.129014 | 0.036957 |
| Nrcam | −0.027789 | −0.036241 | 0.005793 | 0.568245 | 0.040336 |
| Nsun6 | −0.024628 | −0.024481 | −0.007071 | 0.845330 | 0.044071 |
| Ntn1 | −0.000454 | 0.004978 | −0.022781 | 0.039911 | 0.523536 |
| Ntng1 | −0.020643 | −0.009866 | −0.072752 | 0.018614 | 0.014514 |
| Nudt11 | −0.034167 | −0.042052 | −0.043198 | 0.005847 | 0.110883 |
| Nup214 | −0.016064 | −0.010920 | −0.017894 | 0.227635 | 0.015183 |
| Oxsm | 0.000108 | −0.027689 | −0.024744 | 0.043659 | 0.656196 |
| Pcdh20 | −0.046386 | 0.011414 | −0.051713 | 0.030321 | 0.296739 |
| Pcdh7 | −0.009136 | −0.003067 | −0.021611 | 0.029445 | 0.358402 |
| Pcdha11 | −0.016520 | −0.006303 | −0.033986 | 0.717416 | 0.015041 |
| Pcdha7-g | 0.015709 | 0.021023 | 0.019379 | 0.000916 | 0.055733 |
| Pcdhb12 | −0.022938 | −0.027371 | −0.035569 | 0.084061 | 0.046426 |
| Pcdhb20 | 0.015139 | 0.023659 | −0.028714 | 0.022486 | 0.393469 |
| Pcdhb22 | −0.026040 | 0.003917 | −0.043745 | 0.006210 | 0.731849 |
| Pcdhgb5 | −0.006142 | −0.031473 | −0.043141 | 0.029102 | 0.811529 |
| Pde4d | −0.016159 | −0.022694 | −0.035925 | 0.043676 | 0.872993 |
| Pdia4 | 0.014149 | 0.006092 | 0.041729 | 0.042968 | 0.065241 |
| Pdss2 | −0.005670 | 0.010365 | 0.003197 | 0.048344 | 0.738162 |
| Pex11b | −0.011763 | −0.031600 | −0.021690 | 0.389610 | 0.012478 |
| Pgbd1 | 0.005909 | 0.027700 | 0.045936 | 0.190243 | 0.037125 |
| Phf5a | 0.013185 | −0.012260 | 0.030815 | 0.015158 | 0.015097 |
| Phyhip | −0.027370 | −0.056446 | −0.017696 | 0.096354 | 0.042792 |
| Pip4k2a | −0.005582 | 0.001053 | 0.018494 | 0.155510 | 0.018271 |
| Pisd-ps3 | 0.015974 | 0.014262 | 0.041224 | 0.008284 | 0.084244 |
| Plagl2 | −0.024060 | −0.038497 | −0.053664 | 0.289714 | 0.044201 |
| Plcd | −0.026596 | 0.007100 | −0.023762 | 0.372860 | 0.013936 |
| Pld2 | −0.001880 | −0.010518 | 0.005762 | 0.302955 | 0.044939 |
| Plek | 0.014273 | 0.035281 | 0.001704 | 0.042558 | 0.134711 |
| Plekhn1 | 0.001478 | 0.015303 | 0.008011 | 0.003210 | 0.261697 |
| Plp2 | −0.042152 | −0.007583 | −0.062007 | 0.026038 | 0.658918 |
| Plxna3 | −0.012183 | −0.025374 | −0.010284 | 0.043487 | 0.564727 |
| Pmaip1 | −0.033413 | −0.021818 | −0.033117 | 0.002717 | 0.521253 |
| Poli | −0.027254 | −0.016261 | −0.021448 | 0.430680 | 0.033796 |
| Polr3c | 0.032982 | 0.024394 | 0.034560 | 0.118620 | 0.016826 |
| Polr3gl | −0.026299 | −0.019661 | −0.007798 | 0.015321 | 0.342353 |
| Polrmt | −0.008579 | −0.003345 | −0.019847 | 0.088073 | 0.013188 |
| Pou2f2 | 0.023079 | 0.011029 | 0.023008 | 0.073404 | 0.016659 |
| Pou6f2 | −0.019664 | −0.023395 | −0.044026 | 0.778235 | 0.038026 |

TABLE 1B-continued

| gene | SP1 | SP2 | SP3 | SPF v ABX p-value | Sp v ABX p-value |
|---|---|---|---|---|---|
| Ppap2b | −0.013443 | −0.018915 | −0.041617 | 0.000165 | 0.023058 |
| Ppp1r3fos | −0.022930 | −0.034195 | −0.022321 | 0.177841 | 0.036070 |
| Prr12 | 0.000408 | 0.006244 | −0.014256 | 0.038289 | 0.218137 |
| Prr36 | −0.001649 | −0.016707 | −0.011756 | 0.425295 | 0.020097 |
| Prrc2a | 0.028833 | 0.018199 | −0.008305 | 0.010493 | 0.492499 |
| Prrg1 | −0.029342 | −0.025494 | −0.039247 | 0.033721 | 0.673008 |
| Psg16 | −0.034634 | −0.027356 | −0.043255 | 0.026303 | 0.465575 |
| Pstpip2 | −0.023110 | −0.016239 | −0.022393 | 0.117648 | 0.014116 |
| Ptch2 | 0.019629 | 0.021218 | 0.017524 | 0.043590 | 0.500718 |
| Ptk2b | −0.033335 | −0.046415 | −0.020438 | 0.024813 | 0.295167 |
| Ptprf | 0.027177 | 0.012659 | 0.005862 | 0.056717 | 0.017803 |
| Pus7 | −0.012930 | −0.010325 | −0.022733 | 0.040313 | 0.162859 |
| Pxn | 0.008070 | 0.027649 | 0.044857 | 0.034487 | 0.376161 |
| Rapgef1 | 0.026076 | 0.008201 | −0.010935 | 0.016439 | 0.161608 |
| Rcan2 | −0.006063 | −0.002870 | −0.042517 | 0.008899 | 0.489697 |
| Reps2 | −0.002231 | 0.005908 | −0.055310 | 0.038873 | 0.146985 |
| Rgs17 | −0.018515 | −0.027431 | −0.040410 | 0.034399 | 0.393311 |
| Rhof | 0.014475 | −0.008579 | −0.036521 | 0.544761 | 0.031812 |
| Ric8b | −0.022708 | −0.009367 | −0.008797 | 0.047973 | 0.057975 |
| Rilpl1 | 0.018131 | 0.014790 | 0.026362 | 0.029016 | 0.268459 |
| Rin3 | 0.018495 | 0.001943 | −0.017445 | 0.000006 | 0.000009 |
| Rint1 | 0.000529 | −0.020646 | −0.026900 | 0.178331 | 0.038604 |
| Rn45s | −0.024654 | −0.026216 | −0.056303 | 0.023593 | 0.309697 |
| Rnf126 | −0.013695 | −0.010554 | −0.002962 | 0.040727 | 0.066057 |
| Rnpep | 0.018020 | 0.009638 | 0.014513 | 0.347253 | 0.022571 |
| Rnpepl1 | 0.014489 | 0.006981 | −0.012017 | 0.792351 | 0.024831 |
| Rpl19 | 0.051816 | 0.002780 | −0.007315 | 0.133847 | 0.036330 |
| Rpl23a | 0.020451 | 0.039462 | 0.034281 | 0.029363 | 0.197851 |
| Rpl3 | 0.007858 | −0.009074 | 0.018929 | 0.422576 | 0.046796 |
| Rpn2 | 0.004384 | 0.007587 | 0.016861 | 0.954155 | 0.011491 |
| Rps12 | 0.004672 | 0.011981 | 0.018951 | 0.021748 | 0.521966 |
| Rps2 | −0.002592 | 0.061200 | 0.044995 | 0.078156 | 0.017869 |
| Rwdd2b | −0.025276 | −0.036682 | −0.018135 | 0.049240 | 0.612527 |
| Rxfp3 | 0.003426 | −0.016492 | −0.010865 | 0.609581 | 0.042259 |
| Ryr2 | 0.006002 | −0.014505 | −0.067860 | 0.036844 | 0.235109 |
| S100a11 | 0.011627 | 0.020455 | 0.031766 | 0.463287 | 0.029505 |
| Sall2 | 0.001304 | 0.005391 | 0.019090 | 0.126702 | 0.016347 |
| Sarnp | 0.024587 | 0.022710 | 0.020918 | 0.015203 | 0.317385 |
| Sash3 | −0.038351 | −0.033062 | −0.032397 | 0.048925 | 0.223167 |
| Scaf1 | 0.010574 | 0.029857 | 0.014365 | 0.017131 | 0.535487 |
| Scd4 | 0.010427 | 0.007816 | 0.010159 | 0.022813 | 0.340116 |
| Scn1a | −0.024593 | −0.017361 | −0.047242 | 0.012351 | 0.015618 |
| Scrib | 0.019390 | 0.013519 | 0.010277 | 0.006038 | 0.169800 |
| Scrt1 | 0.009206 | −0.010709 | 0.048185 | 0.018440 | 0.057750 |
| Scube1 | −0.031373 | −0.015979 | −0.039461 | 0.402390 | 0.049442 |
| Scx | −0.021443 | −0.024279 | −0.055883 | 0.001297 | 0.018102 |
| Sdha | 0.003565 | 0.013838 | 0.012220 | 0.030519 | 0.813458 |
| Sema3f | −0.010080 | −0.025308 | −0.044520 | 0.047955 | 0.410188 |
| Sema6a | −0.036419 | −0.053792 | −0.062240 | 0.014880 | 0.000975 |
| Senp7 | −0.023767 | −0.022385 | −0.017452 | 0.025477 | 0.982830 |
| Sfxn4 | −0.026274 | −0.015870 | −0.004334 | 0.030785 | 0.122576 |
| Sgk3 | −0.010629 | −0.028230 | −0.043582 | 0.038094 | 0.818412 |
| Sh3bgrl2 | −0.030125 | −0.014748 | −0.065309 | 0.043309 | 0.381214 |
| Sh3bp4 | −0.002200 | 0.015595 | 0.010299 | 0.028955 | 0.614611 |
| Shisa9 | 0.004435 | −0.013156 | −0.006440 | 0.032249 | 0.231346 |
| Shmt2 | 0.016896 | 0.008504 | 0.033869 | 0.018573 | 0.009103 |
| Sigmar1 | 0.018354 | 0.032954 | 0.014076 | 0.008505 | 0.283162 |
| Slc10a3 | −0.006094 | 0.037101 | 0.007231 | 0.012541 | 0.622515 |
| Slc15a4 | −0.028915 | −0.003453 | 0.003059 | 0.033385 | 0.012740 |
| Slc17a5 | −0.005964 | −0.009700 | −0.021747 | 0.160643 | 0.002824 |
| Slc1a5 | 0.006838 | −0.018641 | 0.025391 | 0.067103 | 0.023492 |
| Slc22a12 | −0.035056 | −0.017173 | −0.044232 | 0.033994 | 0.998381 |
| Slc24a3 | −0.029199 | −0.031243 | −0.034836 | 0.034300 | 0.121706 |
| Slc25a1 | 0.002239 | 0.000769 | −0.018320 | 0.618569 | 0.041550 |
| Slc29a4 | 0.035100 | 0.035407 | 0.012864 | 0.064916 | 0.031130 |
| Slc35f3 | −0.021162 | −0.038196 | −0.038610 | 0.210300 | 0.038326 |
| Slc36a4 | −0.032364 | −0.036189 | −0.038922 | 0.045337 | 0.647478 |
| Slc37a2 | 0.013064 | −0.013841 | −0.012535 | 0.024325 | 0.261275 |
| Slc52a2 | 0.006082 | −0.021065 | −0.021000 | 0.026544 | 0.305108 |
| Slc6a8 | 0.013178 | 0.029358 | 0.009919 | 0.034750 | 0.641018 |
| Slco2b1 | 0.033816 | 0.028829 | −0.011804 | 0.046977 | 0.556896 |
| Slitrk4 | −0.026302 | −0.011678 | −0.009704 | 0.030259 | 0.242694 |
| Smarca5-ps | −0.046446 | −0.010108 | −0.014790 | 0.521651 | 0.034725 |
| Smim20 | −0.008697 | −0.033753 | −0.019639 | 0.001939 | 0.043682 |
| Smim3 | 0.007351 | 0.013678 | 0.019040 | 0.321499 | 0.027693 |
| Smim8 | −0.004283 | 0.032803 | 0.039115 | 0.410445 | 0.032207 |
| Smpdl3a | −0.023696 | −0.021220 | −0.050329 | 0.148628 | 0.023830 |
| Snhg1 | 0.001395 | 0.007754 | 0.041992 | 0.040737 | 0.401207 |

TABLE 1B-continued

| gene | SP1 | SP2 | SP3 | SPF v ABX p-value | Sp v ABX p-value |
|---|---|---|---|---|---|
| Snora15 | −0.022127 | −0.023847 | −0.015141 | 0.226943 | 0.011575 |
| Snora23 | 0.000930 | 0.005307 | 0.029130 | 0.027766 | 0.697849 |
| Snord91a | 0.014503 | 0.027195 | 0.003526 | 0.473271 | 0.042213 |
| Socs6 | −0.007457 | −0.009155 | 0.033285 | 0.736071 | 0.031995 |
| Sox13 | 0.022255 | 0.009403 | 0.037126 | 0.105570 | 0.003372 |
| Sox4 | −0.011833 | −0.007360 | −0.006515 | 0.039293 | 0.175793 |
| Spry3 | −0.044153 | −0.012015 | −0.023512 | 0.465213 | 0.044173 |
| Spsb1 | −0.034845 | −0.021166 | −0.039115 | 0.045003 | 0.271950 |
| Sqrdl | −0.016003 | −0.003938 | −0.005364 | 0.043374 | 0.256555 |
| Srbd1 | −0.001835 | 0.018203 | 0.030946 | 0.952371 | 0.012168 |
| Src | 0.025614 | 0.011662 | −0.005819 | 0.071406 | 0.034419 |
| Srcap | 0.013889 | 0.010037 | 0.001168 | 0.033057 | 0.137941 |
| Srp54b | 0.003898 | 0.033965 | 0.021679 | 0.924223 | 0.030002 |
| St3gal3 | 0.014004 | 0.000853 | −0.030394 | 0.009096 | 0.281437 |
| St8sia6 | −0.029909 | −0.014567 | −0.036468 | 0.046459 | 0.906104 |
| Stard5 | −0.012664 | −0.021311 | −0.039125 | 0.024665 | 0.079743 |
| Stxbp3-ps | −0.041555 | −0.034946 | −0.010246 | 0.001381 | 0.502383 |
| Supt6 | 0.005264 | 0.005502 | 0.001141 | 0.681687 | 0.027374 |
| Sv2b | −0.027744 | 0.019267 | −0.038717 | 0.047655 | 0.525657 |
| Svopl | 0.007425 | 0.033150 | 0.037057 | 0.045666 | 0.443553 |
| Synpo2 | 0.018899 | 0.009129 | 0.038190 | 0.047874 | 0.241506 |
| Syt17 | −0.016357 | −0.011964 | −0.018973 | 0.042350 | 0.423596 |
| Syt3 | −0.003711 | 0.003187 | −0.036472 | 0.007208 | 0.195332 |
| Syvn1 | 0.038976 | 0.013094 | 0.000391 | 0.047307 | 0.115132 |
| Tacc1 | −0.031168 | −0.026673 | −0.028568 | 0.826929 | 0.012318 |
| Tada1 | 0.007209 | −0.009175 | −0.013250 | 0.003895 | 0.037537 |
| Taf1a | 0.001648 | 0.006096 | 0.011809 | 0.022153 | 0.233880 |
| Taf4a | −0.025033 | −0.020285 | −0.046823 | 0.005478 | 0.017439 |
| Taok2 | 0.013017 | 0.006513 | 0.006553 | 0.015141 | 0.109765 |
| Tas1r1 | −0.030587 | −0.031952 | −0.033793 | 0.517938 | 0.026129 |
| Tatdn1 | −0.027544 | −0.017623 | −0.027386 | 0.215561 | 0.009350 |
| Tbc1d10a | −0.032363 | −0.010165 | −0.021231 | 0.421191 | 0.032140 |
| Tbc1d4 | 0.025394 | 0.060200 | 0.001359 | 0.021283 | 0.067948 |
| Tbc1d9 | −0.000923 | −0.010408 | −0.030709 | 0.027054 | 0.039845 |
| Tbx2 | −0.009147 | 0.027857 | −0.009265 | 0.041785 | 0.641620 |
| Tcf3 | 0.015857 | 0.017926 | 0.036660 | 0.024555 | 0.700512 |
| Tenm1 | −0.012318 | −0.013079 | −0.051320 | 0.008946 | 0.644578 |
| Tfcp2l1 | −0.023127 | −0.010180 | −0.078130 | 0.160185 | 0.021888 |
| Them4 | 0.016759 | 0.003096 | 0.018030 | 0.131877 | 0.004031 |
| Thoc7 | −0.009868 | −0.045513 | −0.047251 | 0.011767 | 0.084348 |
| Thsd4 | −0.027370 | −0.025840 | −0.055998 | 0.028647 | 0.316746 |
| Tigar | 0.022699 | −0.001033 | 0.025361 | 0.883286 | 0.044757 |
| Timm9 | −0.011365 | −0.019122 | −0.053909 | 0.005228 | 0.626517 |
| Tm4sf1 | 0.008194 | 0.021260 | 0.043833 | 0.387656 | 0.030942 |
| Tmc7 | 0.039193 | 0.002364 | 0.011948 | 0.007576 | 0.141423 |
| Tmem170b | 0.029747 | 0.047088 | 0.010735 | 0.024699 | 0.531595 |
| Tmem180 | −0.003963 | −0.038750 | −0.026556 | 0.034971 | 0.013434 |
| Tmem185b | −0.017185 | −0.036561 | −0.043515 | 0.117839 | 0.047499 |
| Tmem203 | −0.009165 | 0.019021 | 0.007152 | 0.017875 | 0.111372 |
| Tmem29 | −0.024870 | 0.006120 | −0.014121 | 0.005064 | 0.035425 |
| Tmem81 | −0.011352 | −0.013953 | 0.000315 | 0.176745 | 0.048772 |
| Tmem8b | 0.012024 | −0.012465 | −0.026381 | 0.037704 | 0.842948 |
| Tmem9 | −0.031405 | −0.009650 | −0.030312 | 0.077764 | 0.027167 |
| Tmppe | −0.004292 | 0.003297 | −0.016387 | 0.033296 | 0.741548 |
| Tnfrsf19 | 0.013263 | 0.011495 | 0.032847 | 0.010138 | 0.745693 |
| Tomm5 | −0.030245 | −0.028115 | −0.017621 | 0.025877 | 0.534480 |
| Tpcn1 | 0.030030 | 0.042158 | −0.001416 | 0.055730 | 0.035567 |
| Trim13 | 0.010992 | −0.000632 | −0.001788 | 0.019807 | 0.860509 |
| Trim9 | 0.016622 | 0.044166 | 0.015041 | 0.022648 | 0.393678 |
| Tshz3 | −0.006809 | −0.017449 | −0.038020 | 0.251620 | 0.020916 |
| Tspan13 | 0.015132 | 0.003456 | 0.011988 | 0.490731 | 0.028235 |
| Ttc39aos1 | 0.012827 | 0.009621 | 0.024336 | 0.013988 | 0.394096 |
| Tuft1 | −0.028904 | −0.018103 | −0.038787 | 0.022311 | 0.801384 |
| Txnrd3 | 0.017104 | −0.003527 | −0.020654 | 0.044973 | 0.471432 |
| Ubap2 | 0.010416 | 0.014737 | 0.022548 | 0.131212 | 0.024075 |
| Ubb | 0.027814 | −0.001839 | −0.001780 | 0.003985 | 0.001519 |
| Ube2j2 | −0.035874 | −0.031261 | −0.035263 | 0.042438 | 0.731477 |
| Ube2r2 | 0.014788 | 0.011837 | 0.019800 | 0.016326 | 0.296872 |
| Uck2 | 0.003620 | 0.015707 | 0.024337 | 0.177775 | 0.023297 |
| Utp11l | 0.006537 | 0.021734 | 0.008165 | 0.159251 | 0.046604 |
| Vac14 | 0.005399 | −0.009972 | −0.019644 | 0.338518 | 0.010671 |
| Vamp7 | −0.020817 | −0.038301 | −0.028122 | 0.032586 | 0.196035 |
| Vangl2 | 0.027570 | 0.011155 | −0.004344 | 0.014601 | 0.180576 |
| Vasp | 0.022478 | 0.009889 | 0.013098 | 0.060357 | 0.027992 |
| Vcpip1 | −0.000370 | 0.002315 | 0.011009 | 0.064182 | 0.044061 |
| Vwa8 | 0.016948 | −0.021590 | −0.004131 | 0.010375 | 0.793385 |
| Vwc2l | −0.003988 | −0.004835 | −0.011561 | 0.006493 | 0.055444 |
| Wfs1 | −0.017658 | 0.003797 | −0.027011 | 0.036360 | 0.126604 |

TABLE 1B-continued

| gene | SP1 | SP2 | SP3 | SPF v ABX p-value | Sp v ABX p-value |
|---|---|---|---|---|---|
| Xlr3a | −0.001045 | 0.007115 | −0.029520 | 0.041290 | 0.002879 |
| Xylt1 | −0.001563 | −0.034582 | −0.036647 | 0.343656 | 0.043102 |
| Yipf2 | −0.008423 | −0.021047 | −0.016476 | 0.011844 | 0.321436 |
| Zbtb45 | −0.009410 | −0.032308 | −0.026251 | 0.854544 | 0.033262 |
| Zbtb46 | −0.020206 | −0.010232 | −0.043049 | 0.014133 | 0.275086 |
| Zc3h10 | 0.022429 | 0.016654 | 0.023124 | 0.011035 | 0.054442 |
| Zc3h12b | −0.017373 | −0.022318 | −0.048962 | 0.041581 | 0.514408 |
| Zc3h18 | 0.010884 | 0.005419 | 0.032800 | 0.136289 | 0.006597 |
| Zeb2os | −0.016041 | 0.000340 | −0.017544 | 0.001761 | 0.130684 |
| Zfhx3 | 0.007403 | 0.013639 | 0.012865 | 0.551818 | 0.046705 |
| Zfp212 | −0.030576 | −0.008674 | −0.030651 | 0.815397 | 0.038840 |
| Zfp330 | −0.038913 | −0.038766 | −0.026564 | 0.011652 | 0.035811 |
| Zfp35 | 0.005323 | 0.035270 | −0.028103 | 0.807564 | 0.016913 |
| Zfp362 | 0.010752 | 0.000498 | 0.009570 | 0.033042 | 0.123477 |
| Zfp36l1 | −0.004408 | 0.005355 | 0.048543 | 0.039471 | 0.379769 |
| Zfp628 | 0.075411 | 0.012088 | 0.002199 | 0.011149 | 0.177113 |
| Zfp651 | −0.000945 | −0.008611 | −0.019467 | 0.147411 | 0.023751 |
| Zfp710 | −0.000914 | 0.022121 | 0.031224 | 0.038968 | 0.540622 |
| Zfp809 | −0.027268 | −0.025658 | −0.034189 | 0.952685 | 0.028810 |
| Zfp839 | −0.023959 | −0.009542 | −0.016994 | 0.466468 | 0.040120 |
| Zfp85 | −0.022880 | −0.021387 | 0.018662 | 0.042518 | 0.131547 |
| Zfp850 | 0.023734 | 0.022703 | 0.027762 | 0.886796 | 0.028716 |
| Zfpm1 | −0.036579 | −0.024816 | −0.040454 | 0.003382 | 0.120900 |
| Zic5 | −0.009495 | −0.010065 | −0.046133 | 0.832814 | 0.025530 |
| Zmynd10 | −0.034549 | −0.026550 | −0.023509 | 0.014819 | 0.028386 |
| Zscan12 | −0.001104 | 0.005937 | 0.033403 | 0.262373 | 0.036247 |
| Zscan2 | 0.017638 | 0.030782 | 0.035367 | 0.040146 | 0.929530 |
| Zswim8 | 0.015606 | 0.024358 | −0.011696 | 0.041154 | 0.222639 |

Example 6: Table 2 for Examples 1-3, Provided as Parts Tables 2A and 2B

Tables 2A and 2B (collectively “Table 2”) relate 16S rDNA sequencing of SPF vs. Sp fecal microbiota. The “No” in the tables 2A and 2B is used to connect the two tables to each other (e.g., to relate the taxonomic unit of Table 2A to the values in Table 2B, which do not fit into a single table here due to space constraints), and need not correspond to the “No” used in Tables 3A and 3B.

TABLE 2A

| #OTU ID | No |
|---|---|
| Unassigned; Other; Other; Other; Other; Other | 1 |
| k__Bacteria; p__Actinobacteria; c__Actinobacteria; o__Bifidobacteriales; f__Bifidobacteriaceae; g__*Bifidobacterium* | 2 |
| k__Bacteria; p__Actinobacteria; c__Coriobacteriia; o__Coriobacteriales; f__Coriobacteriaceae; g | 3 |
| k__Bacteria; p__Actinobacteria; c__Coriobacteriia; o__Coriobacteriales; f__Coriobacteriaceae; g__*Adlercreutzia* | 4 |
| k__Bacteria; p__Bacteroidetes; c__Bacteroidia; o__Bacteroidales; f__; g | 5 |
| k__Bacteria; p__Bacteroidetes; c__Bacteroidia; o__Bacteroidales; f__Bacteroidaceae; g__*Bacteroides* | 6 |
| k__Bacteria; p__Bacteroidetes; c__Bacteroidia; o__Bacteroidales; f__Porphyromonadaceae; g__*Parabacteroides* | 7 |
| k__Bacteria; p__Bacteroidetes; c__Bacteroidia; o__Bacteroidales; f__Prevotellaceae; g__*Prevotella* | 8 |
| k__Bacteria; p__Bacteroidetes; c__Bacteroidia; o__Bacteroidales; f__Rikenellaceae; g__ | 9 |
| k__Bacteria; p__Bacteroidetes; c__Bacteroidia; o__Bacteroidales; f__S24-7; g__ | 10 |
| k__Bacteria; p__Bacteroidetes; c__Bacteroidia; o__Bacteroidales; f__[Odoribacteraceae]; g__*Odoribacter* | 11 |
| k__Bacteria; p__Cyanobacteria; c__4C0d-2; o__MLE1-12; f__; g__ | 12 |
| k__Bacteria; p__Cyanobacteria; c__4C0d-2; o__YS2; f__; g__ | 13 |
| k__Bacteria; p__Cyanobacteria; c__Chloroplast; o__Streptophyta; f__; g__ | 14 |
| k__Bacteria; p__Firmicutes; c__Bacilli; Other; Other; Other | 15 |
| k__Bacteria; p__Firmicutes; c__Bacilli; o__Bacillales; Other; Other | 16 |
| k__Bacteria; p__Firmicutes; c__Bacilli; o__Bacillales; f__Bacillaceae; g__*Bacillus* | 17 |
| k__Bacteria; p__Firmicutes; c__Bacilli; o__Bacillales; f__Staphylococcaceae; g__*Staphylococcus* | 18 |
| k__Bacteria; p__Firmicutes; c__Bacilli; o__Lactobacillales; f__Enterococcaceae; g__*Enterococcus* | 19 |
| k__Bacteria; p__Firmicutes; c__Bacilli; o__Lactobacillales; f__Lactobacillaceae; g__*Lactobacillus* | 20 |
| k__Bacteria; p__Firmicutes; c__Bacilli; o__Lactobacillales; f__Streptococcaceae; g__*Lactococcus* | 21 |
| k__Bacteria; p__Firmicutes; c__Bacilli; o__Lactobacillales; f__Streptococcaceae; g__*Streptococcus* | 22 |

TABLE 2A-continued

| #OTU ID | No |
|---|---|
| k__Bacteria; p__Firmicutes; c__Bacilli; o__Turicibacterales; f__Turicibacteraceae; g__*Turicibacter* | 23 |
| k__Bacteria; p__Firmicutes; c__Clostridia; o__Clostridiales; Other; Other | 24 |
| k__Bacteria; p__Firmicutes; c__Clostridia; o__Clostridiales; f__; g__ | 25 |
| k__Bacteria; p__Firmicutes; c__Clostridia; o__Clostridiales; f__Clostridiaceae; Other | 26 |
| k__Bacteria; p__Firmicutes; c__Clostridia; o__Clostridiales; f__Clostridiaceae; g__ | 27 |
| k__Bacteria; p__Firmicutes; c__Clostridia; o__Clostridiales; f__Clostridiaceae; g__*Candidatus Arthromitus* | 28 |
| k__Bacteria; p__Firmicutes; c__Clostridia; o__Clostridiales; f__Clostridiaceae; g__*Clostridium* | 29 |
| k__Bacteria; p__Firmicutes; c__Clostridia; o__Clostridiales; f__Dehalobacteriaceae; g__*Dehalobacterium* | 30 |
| k__Bacteria; p__Firmicutes; c__Clostridia; o__Clostridiales; f__Lachnospiraceae; Other | 31 |
| k__Bacteria; p__Firmicutes; c__Clostridia; o__Clostridiales; f__Lachnospiraceae; g__ | 32 |
| k__Bacteria; p__Firmicutes; c__Clostridia; o__Clostridiales; f__Lachnospiraceae; g__*Blautia* | 33 |
| k__Bacteria; p__Firmicutes; c__Clostridia; o__Clostridiales; f__Lachnospiraceae; g__*Coprococcus* | 34 |
| k__Bacteria; p__Firmicutes; c__Clostridia; o__Clostridiales; f__Lachnospiraceae; g__*Dorea* | 35 |
| k__Bacteria; p__Firmicutes; c__Clostridia; o__Clostridiales; f__Lachnospiraceae; g__*Roseburia* | 36 |
| k__Bacteria; p__Firmicutes; c__Clostridia; o__Clostridiales; f__Lachnospiraceae; g__[*Ruminococcus*] | 37 |
| k__Bacteria; p__Firmicutes; c__Clostridia; o__Clostridiales; f__Peptostreptococcaceae; g__ | 38 |
| k__Bacteria; p__Firmicutes; c__Clostridia; o__Clostridiales; f__Ruminococcaceae; Other | 39 |
| k__Bacteria; p__Firmicutes; c__Clostridia; o__Clostridiales; f__Ruminococcaceae; g__ | 40 |
| k__Bacteria; p__Firmicutes; c__Clostridia; o__Clostridiales; f__Ruminococcaceae; g__*Oscillospira* | 41 |
| k__Bacteria; p__Firmicutes; c__Clostridia; o__Clostridiales; f__Ruminococcaceae; g__*Ruminococcus* | 42 |
| k__Bacteria; p__Firmicutes; c__Clostridia; o__Clostridiales; f__[Mogibacteriaceae]; g__ | 43 |
| k__Bacteria; p__Firmicutes; c__Erysipelotrichi; o__Erysipelotrichales; f__Erysipelotrichaceae; g__ | 44 |
| k__Bacteria; p__Firmicutes; c__Erysipelotrichi; o__Erysipelotrichales; f__Erysipelotrichaceae; g__*Allobaculum* | 45 |
| k__Bacteria; p__Proteobacteria; c__Alphaproteobacteria; o__; f__; g__ | 46 |
| k__Bacteria; p__Proteobacteria; c__Betaproteobacteria; o__Burkholderiales; f__Alcaligenaceae; g__*Sutterella* | 47 |
| k__Bacteria; p__Proteobacteria; c__Deltaproteobacteria; o__Desulfovibrionales; f__Desulfovibrionaceae; g__ | 48 |
| k__Bacteria; p__Proteobacteria; c__Deltaproteobacteria; o__Desulfovibrionales; f__Desulfovibrionaceae; g__*Bilophila* | 49 |
| k__Bacteria; p__Proteobacteria; c__Deltaproteobacteria; o__Desulfovibrionales; f__Desulfovibrionaceae; g__*Desulfovibrio* | 50 |
| k__Bacteria; p__Proteobacteria; c__Gammaproteobacteria; o__Enterobacteriales; f__Enterobacteriaceae; Other | 51 |
| k__Bacteria; p__Proteobacteria; c__Gammaproteobacteria; o__Enterobacteriales; f__Enterobacteriaceae; g__ | 52 |
| k__Bacteria; p__Proteobacteria; c__Gammaproteobacteria; o__Enterobacteriales; f__Enterobacteriaceae; g__*Morganella* | 53 |
| k__Bacteria; p__Proteobacteria; c__Gammaproteobacteria; o__Enterobacteriales; f__Enterobacteriaceae; g__*Proteus* | 54 |
| k__Bacteria; p__Proteobacteria; c__Gammaproteobacteria; o__Pseudomonadales; f__Moraxellaceae; g__ | 55 |
| k__Bacteria; p__Proteobacteria; c__Gammaproteobacteria; o__Pseudomonadales; f__Moraxellaceae; g__*Acinetobacter* | 56 |
| k__Bacteria; p__Tenericutes; c__Mollicutes; o__Anaeroplasmatales; f__Anaeroplasmataceae; g__*Anaeroplasma* | 57 |
| k__Bacteria; p__Tenericutes; c__Mollicutes; o__RF39; f__; g__ | 58 |
| k__Bacteria; p__Verrucomicrobia; c__Verrucomicrobiae; o__Verrucomicrobiales; f__Verrucomicrobiaceae; g__*Akkermansia* | 59 |

TABLE 2B

| No | SPF | SPF | SPF | SPF | Sp | Sp | Sp | Sp |
|---|---|---|---|---|---|---|---|---|
| 1 | 0.000053 | 0.000035 | 0.000000 | 0.000000 | 0.000000 | 0.000000 | 0.000000 | 0.000000 |
| 2 | 0.000000 | 0.000000 | 0.000000 | 0.000000 | 0.000000 | 0.000000 | 0.000000 | 0.000000 |
| 3 | 0.000088 | 0.000000 | 0.000000 | 0.000000 | 0.000000 | 0.000000 | 0.000000 | 0.000000 |

TABLE 2B-continued

| No | SPF | SPF | SPF | SPF | Sp | Sp | Sp | Sp |
|---|---|---|---|---|---|---|---|---|
| 4 | 0.001069 | 0.001073 | 0.000369 | 0.000643 | 0.000000 | 0.000000 | 0.000000 | 0.000000 |
| 5 | 0.002174 | 0.000969 | 0.002277 | 0.001608 | 0.000000 | 0.000000 | 0.000000 | 0.000000 |
| 6 | 0.087961 | 0.035185 | 0.062068 | 0.049326 | 0.000018 | 0.000014 | 0.000020 | 0.000000 |
| 7 | 0.002016 | 0.002388 | 0.006137 | 0.009789 | 0.000129 | 0.000086 | 0.000059 | 0.000000 |
| 8 | 0.027451 | 0.008757 | 0.024723 | 0.017608 | 0.000000 | 0.000000 | 0.000000 | 0.000000 |
| 9 | 0.006083 | 0.065299 | 0.047169 | 0.077124 | 0.000000 | 0.000043 | 0.000000 | 0.000000 |
| 10 | 0.620863 | 0.237054 | 0.501377 | 0.319813 | 0.000331 | 0.000229 | 0.000357 | 0.000195 |
| 11 | 0.000000 | 0.000000 | 0.000000 | 0.000000 | 0.000000 | 0.000000 | 0.000000 | 0.000000 |
| 12 | 0.000000 | 0.000000 | 0.000000 | 0.000000 | 0.000000 | 0.000000 | 0.000000 | 0.000000 |
| 13 | 0.001683 | 0.001160 | 0.003990 | 0.000784 | 0.000000 | 0.000000 | 0.000000 | 0.000000 |
| 14 | 0.000000 | 0.000000 | 0.000217 | 0.000000 | 0.000000 | 0.000000 | 0.000000 | 0.000000 |
| 15 | 0.000000 | 0.000000 | 0.000087 | 0.000040 | 0.000000 | 0.000000 | 0.000020 | 0.000000 |
| 16 | 0.000000 | 0.000000 | 0.000000 | 0.000000 | 0.000000 | 0.000000 | 0.000000 | 0.000000 |
| 17 | 0.000000 | 0.000000 | 0.000000 | 0.000000 | 0.000000 | 0.000000 | 0.000000 | 0.000000 |
| 18 | 0.000000 | 0.000000 | 0.000000 | 0.000000 | 0.000000 | 0.000000 | 0.000000 | 0.000000 |
| 19 | 0.000035 | 0.000017 | 0.000000 | 0.000000 | 0.000000 | 0.000000 | 0.000000 | 0.000000 |
| 20 | 0.038231 | 0.004586 | 0.025243 | 0.006854 | 0.000202 | 0.000243 | 0.000258 | 0.000180 |
| 21 | 0.000000 | 0.000000 | 0.000000 | 0.000000 | 0.000000 | 0.000000 | 0.000000 | 0.000015 |
| 22 | 0.000000 | 0.000000 | 0.000000 | 0.000000 | 0.000000 | 0.000000 | 0.000000 | 0.000000 |
| 23 | 0.001350 | 0.000485 | 0.020776 | 0.008281 | 0.035306 | 0.007929 | 0.000119 | 0.002869 |
| 24 | 0.000000 | 0.000000 | 0.000043 | 0.000000 | 0.000644 | 0.000057 | 0.000000 | 0.000015 |
| 25 | 0.085945 | 0.313621 | 0.132398 | 0.249824 | 0.499917 | 0.542613 | 0.509793 | 0.411759 |
| 26 | 0.000000 | 0.000000 | 0.000000 | 0.000000 | 0.000754 | 0.000072 | 0.000991 | 0.000075 |
| 27 | 0.001017 | 0.000588 | 0.000542 | 0.000462 | 0.081099 | 0.009517 | 0.039468 | 0.018443 |
| 28 | 0.024120 | 0.001021 | 0.001453 | 0.000784 | 0.000000 | 0.000000 | 0.000000 | 0.000000 |
| 29 | 0.000000 | 0.000000 | 0.000000 | 0.000000 | 0.000975 | 0.000014 | 0.000218 | 0.000165 |
| 30 | 0.000561 | 0.001315 | 0.000976 | 0.002633 | 0.000846 | 0.000572 | 0.000000 | 0.000000 |
| 31 | 0.000245 | 0.001004 | 0.000087 | 0.000221 | 0.001490 | 0.000887 | 0.013163 | 0.000315 |
| 32 | 0.038143 | 0.134285 | 0.036802 | 0.103013 | 0.143194 | 0.232651 | 0.139694 | 0.244785 |
| 33 | 0.000000 | 0.000017 | 0.000000 | 0.000020 | 0.000000 | 0.000043 | 0.000000 | 0.000030 |
| 34 | 0.001613 | 0.004431 | 0.001496 | 0.001869 | 0.013339 | 0.012923 | 0.016057 | 0.013517 |
| 35 | 0.000684 | 0.001713 | 0.002299 | 0.005829 | 0.005041 | 0.001288 | 0.003251 | 0.001877 |
| 36 | 0.000000 | 0.000017 | 0.000000 | 0.000000 | 0.000000 | 0.000000 | 0.000000 | 0.000000 |
| 37 | 0.004645 | 0.012098 | 0.006636 | 0.013447 | 0.038526 | 0.026434 | 0.042124 | 0.007284 |
| 38 | 0.000018 | 0.000000 | 0.000000 | 0.000020 | 0.000000 | 0.000043 | 0.000000 | 0.000015 |
| 39 | 0.000070 | 0.001142 | 0.000087 | 0.000382 | 0.000110 | 0.001331 | 0.001388 | 0.003935 |
| 40 | 0.008116 | 0.040325 | 0.019887 | 0.029768 | 0.059831 | 0.073648 | 0.083733 | 0.179830 |
| 41 | 0.020281 | 0.044219 | 0.015614 | 0.037024 | 0.035545 | 0.063358 | 0.036990 | 0.090396 |
| 42 | 0.001630 | 0.018051 | 0.008176 | 0.016080 | 0.029088 | 0.017990 | 0.007929 | 0.006233 |
| 43 | 0.000000 | 0.000294 | 0.000000 | 0.000181 | 0.000000 | 0.000000 | 0.000000 | 0.000000 |
| 44 | 0.000824 | 0.000675 | 0.000586 | 0.001990 | 0.014774 | 0.002218 | 0.012449 | 0.001517 |
| 45 | 0.000088 | 0.000744 | 0.003405 | 0.001508 | 0.000000 | 0.000014 | 0.000000 | 0.000000 |
| 46 | 0.000000 | 0.000000 | 0.000000 | 0.000000 | 0.000000 | 0.000000 | 0.000000 | 0.000000 |
| 47 | 0.009886 | 0.006352 | 0.015506 | 0.013467 | 0.000000 | 0.000000 | 0.000059 | 0.000000 |
| 48 | 0.000105 | 0.000952 | 0.000195 | 0.001246 | 0.000000 | 0.000000 | 0.000000 | 0.000000 |
| 49 | 0.000298 | 0.005175 | 0.000130 | 0.001367 | 0.000000 | 0.000000 | 0.000000 | 0.000000 |
| 50 | 0.001087 | 0.004050 | 0.001345 | 0.011658 | 0.000000 | 0.000000 | 0.000000 | 0.000000 |
| 51 | 0.000035 | 0.000017 | 0.000260 | 0.000040 | 0.000055 | 0.000043 | 0.000000 | 0.000030 |
| 52 | 0.000876 | 0.000121 | 0.043374 | 0.008884 | 0.000129 | 0.000186 | 0.000198 | 0.000240 |
| 53 | 0.000000 | 0.000000 | 0.000000 | 0.000000 | 0.000000 | 0.000000 | 0.000000 | 0.000000 |
| 54 | 0.000053 | 0.000052 | 0.000065 | 0.000020 | 0.000018 | 0.000072 | 0.000040 | 0.000015 |
| 55 | 0.000000 | 0.000000 | 0.000000 | 0.000000 | 0.000000 | 0.000000 | 0.000000 | 0.000000 |
| 56 | 0.000000 | 0.000000 | 0.000000 | 0.000000 | 0.000000 | 0.000000 | 0.000000 | 0.000000 |
| 57 | 0.008169 | 0.043008 | 0.003231 | 0.000985 | 0.024212 | 0.000000 | 0.034552 | 0.016235 |
| 58 | 0.002384 | 0.007667 | 0.009889 | 0.005186 | 0.014406 | 0.005424 | 0.057031 | 0.000015 |
| 59 | 0.000053 | 0.000035 | 0.001084 | 0.000221 | 0.000018 | 0.000057 | 0.000040 | 0.000015 |

Example 7: Table 3 for Examples 1-3, Provided as Parts Tables 3A and 3B

Tables 3A and 3B (collectively "Table 3") relate to fecal 16S rDNA sequencing from BD colonized dams. The "No" in the tables 3A and 3B is used to connect the two tables to each other (e.g., to relate the taxonomic unit of Table 3A to the values in Table 3B, which do not fit into a single table here due to space constraints), and need not correspond to the "No" used in Tables 2A and 2B.

TABLE 3A

| Taxonomy | No |
|---|---|
| Unassigned; Other; Other; Other; Other; Other | 1 |
| k__Bacteria; p__Actinobacteria; c__Coriobacteriia; o__Coriobacteriales; f__Coriobacteriaceae; g__*Adlercreutzia* | 2 |
| k__Bacteria; p__Bacteroidetes; c__Bacteroidia; o__Bacteroidales; f__; g__ | 3 |
| k__Bacteria; p__Bacteroidetes; c__Bacteroidia; o__Bacteroidales; f__Bacteroidaceae; g__*Bacteroides* | 4 |
| k__Bacteria; p__Bacteroidetes; c__Bacteroidia; o__Bacteroidales; f__Porphyromonadaceae; g__*Parabacteroides* | 5 |

TABLE 3A-continued

| Taxonomy | No |
|---|---|
| k__Bacteria; p__Bacteroidetes; c__Bacteroidia; o__Bacteroidales; f__Prevotellaceae; g__*Prevotella* | 6 |
| k__Bacteria; p__Bacteroidetes; c__Bacteroidia; o__Bacteroidales; f__Rikenellaceae; g__ | 7 |
| k__Bacteria; p__Bacteroidetes; c__Bacteroidia; o__Bacteroidales; f__Rikenellaceae; g__AF12 | 8 |
| k__Bacteria; p__Bacteroidetes; c__Bacteroidia; o__Bacteroidales; f__S24-7; g__ | 9 |
| k__Bacteria; p__Bacteroidetes; c__Bacteroidia; o__Bacteroidales; f__[Odoribacteraceae]; g__*Odoribacter* | 10 |
| k__Bacteria; p__Bacteroidetes; c__Bacteroidia; o__Bacteroidales; f__[Paraprevotellaceae]; g__[*Prevotella*] | 11 |
| k__Bacteria; p__Cyanobacteria; c__4C0d-2; o__YS2; f__; g__ | 12 |
| k__Bacteria; p__Deferribacteres; c__Deferribacteres; o__Deferribacterales; f__Deferribacteraceae; g__*Mucispirillum* | 13 |
| k__Bacteria; p__Firmicutes; c__Bacilli; o__Bacillales; Other; Other | 14 |
| k__Bacteria; p__Firmicutes; c__Bacilli; o__Lactobacillales; f__Enterococcaceae; g__*Enterococcus* | 15 |
| k__Bacteria; p__Firmicutes; c__Bacilli; o__Lactobacillales; f__Lactobacillaceae; g__*Lactobacillus* | 16 |
| k__Bacteria; p__Firmicutes; c__Bacilli; o__Turicibacterales; f__Turicibacteraceae; g__*Turicibacter* | 17 |
| k__Bacteria; p__Firmicutes; c__Clostridia; o__Clostridiales; Other; Other | 18 |
| k__Bacteria; p__Firmicutes; c__Clostridia; o__Clostridiales; f__; g__ | 19 |
| k__Bacteria; p__Firmicutes; c__Clostridia; o__Clostridiales; f__Christensenellaceae; g__ | 20 |
| k__Bacteria; p__Firmicutes; c__Clostridia; o__Clostridiales; f__Clostridiaceae; Other | 21 |
| k__Bacteria; p__Firmicutes; c__Clostridia; o__Clostridiales; f__Clostridiaceae; g__ | 22 |
| k__Bacteria; p__Firmicutes; c__Clostridia; o__Clostridiales; f__Clostridiaceae; g__*Candidatus Arthromitus* | 23 |
| k__Bacteria; p__Firmicutes; c__Clostridia; o__Clostridiales; f__Clostridiaceae; g__*Clostridium* | 24 |
| k__Bacteria; p__Firmicutes; c__Clostridia; o__Clostridiales; f__Dehalobacteriaceae; g__*Dehalobacterium* | 25 |
| k__Bacteria; p__Firmicutes; c__Clostridia; o__Clostridiales; f__Lachnospiraceae; Other | 26 |
| k__Bacteria; p__Firmicutes; c__Clostridia; o__Clostridiales; f__Lachnospiraceae; g__ | 27 |
| k__Bacteria; p__Firmicutes; c__Clostridia; o__Clostridiales; f__Lachnospiraceae; g__*Blautia* | 28 |
| k__Bacteria; p__Firmicutes; c__Clostridia; o__Clostridiales; f__Lachnospiraceae; g__*Coprococcus* | 29 |
| k__Bacteria; p__Firmicutes; c__Clostridia; o__Clostridiales; f__Lachnospiraceae; g__*Dorea* | 30 |
| k__Bacteria; p__Firmicutes; c__Clostridia; o__Clostridiales; f__Lachnospiraceae; g__[*Ruminococcus*] | 31 |
| k__Bacteria; p__Firmicutes; c__Clostridia; o__Clostridiales; f__Peptococcaceae; g__ | 32 |
| k__Bacteria; p__Firmicutes; c__Clostridia; o__Clostridiales; f__Peptostreptococcaceae; Other | 33 |
| k__Bacteria; p__Firmicutes; c__Clostridia; o__Clostridiales; f__Peptostreptococcaceae; g__ | 34 |
| k__Bacteria; p__Firmicutes; c__Clostridia; o__Clostridiales; f__Ruminococcaceae; g__ | 35 |
| k__Bacteria; p__Firmicutes; c__Clostridia; o__Clostridiales; f__Ruminococcaceae; g__*Oscillospira* | 36 |
| k__Bacteria; p__Firmicutes; c__Clostridia; o__Clostridiales; f__Ruminococcaceae; g__*Ruminococcus* | 37 |
| k__Bacteria; p__Firmicutes; c__Clostridia; o__Clostridiales; f__[Mogibacteriaceae]; g__ | 38 |
| k__Bacteria; p__Firmicutes; c__Erysipelotrichi; o__Erysipelotrichales; f__Erysipelotrichaceae; g__ | 39 |
| k__Bacteria; p__Firmicutes; c__Erysipelotrichi; o__Erysipelotrichales; f__Erysipelotrichaceae; g__*Allobaculum* | 40 |
| k__Bacteria; p__Firmicutes; c__Erysipelotrichi; o__Erysipelotrichales; f__Erysipelotrichaceae; g__*Coprobacillus* | 41 |
| k__Bacteria; p__Firmicutes; c__Erysipelotrichi; o__Erysipelotrichales; f__Erysipelotrichaceae; g__[*Eubacterium*] | 42 |
| k__Bacteria; p__Proteobacteria; c__Alphaproteobacteria; o__; f__; g__ | 43 |
| k__Bacteria; p__Proteobacteria; c__Alphaproteobacteria; o__RF32; f__; g__ | 44 |
| k__Bacteria; p__Proteobacteria; c__Betaproteobacteria; o__Burkholderiales; f__Alcaligenaceae; g__*Sutterella* | 45 |
| k__Bacteria; p__Proteobacteria; c__Deltaproteobacteria; o__Desulfovibrionales; f__Desulfovibrionaceae; g__ | 46 |
| k__Bacteria; p__Proteobacteria; c__Deltaproteobacteria; o__Desulfovibrionales; f__Desulfovibrionaceae; g__*Bilophila* | 47 |
| k__Bacteria; p__Proteobacteria; c__Deltaproteobacteria; o__Desulfovibrionales; f__Desulfovibrionaceae; g__*Desulfovibrio* | 48 |
| k__Bacteria; p__Proteobacteria; c__Epsilonproteobacteria; o__Campylobacterales; f__Helicobacteraceae; Other | 49 |

TABLE 3A-continued

| Taxonomy | No |
|---|---|
| k__Bacteria; p__Proteobacteria; c__Epsilonproteobacteria; o__Campylobacterales; f__Helicobacteraceae; g__*Flexispira* | 50 |
| k__Bacteria; p__Proteobacteria; c__Epsilonproteobacteria; o__Campylobacterales; f__Helicobacteraceae; g__*Helicobacter* | 51 |
| k__Bacteria; p__Proteobacteria; c__Gammaproteobacteria; o__Enterobacteriales; f__Enterobacteriaceae; g__ | 52 |
| k__Bacteria; p__Tenericutes; c__Mollicutes; o__Anaeroplasmatales; f__Anaeroplasmataceae; g__*Anaeroplasma* | 53 |
| k__Bacteria; p__Tenericutes; c__Mollicutes; o__RF39; f__; g__ | 54 |
| k__Bacteria; p__Verrucomicrobia; c__Verrucomicrobiae; o__Verrucomicrobiales; f__Verrucomicrobiaceae; g__*Akkermansia* | 55 |

TABLE 3B

| No | BD1 | BD2 | BD3 | BD4 | BD5 |
|---|---|---|---|---|---|
| 1 | 0.000041 | 0.000115 | 0.000110 | 0.000125 | 0.000145 |
| 2 | 0.000000 | 0.000000 | 0.000000 | 0.000000 | 0.000000 |
| 3 | 0.000000 | 0.000000 | 0.000000 | 0.000000 | 0.000000 |
| 4 | 0.913785 | 0.965081 | 0.959434 | 0.961139 | 0.962127 |
| 5 | 0.000000 | 0.000000 | 0.000024 | 0.000010 | 0.000026 |
| 6 | 0.000027 | 0.000012 | 0.000000 | 0.000000 | 0.000000 |
| 7 | 0.000014 | 0.000023 | 0.000024 | 0.000010 | 0.000043 |
| 8 | 0.000000 | 0.000000 | 0.000000 | 0.000000 | 0.000000 |
| 9 | 0.000027 | 0.000058 | 0.000110 | 0.000042 | 0.000120 |
| 10 | 0.000000 | 0.000000 | 0.000012 | 0.000000 | 0.000000 |
| 11 | 0.000082 | 0.000023 | 0.000049 | 0.000031 | 0.000009 |
| 12 | 0.000000 | 0.000000 | 0.000000 | 0.000000 | 0.000000 |
| 13 | 0.000000 | 0.000012 | 0.000000 | 0.000010 | 0.000009 |
| 14 | 0.000014 | 0.000058 | 0.000000 | 0.001190 | 0.000026 |
| 15 | 0.000219 | 0.000230 | 0.000085 | 0.000177 | 0.000060 |
| 16 | 0.000027 | 0.000035 | 0.000049 | 0.000000 | 0.000009 |
| 17 | 0.000260 | 0.000219 | 0.000329 | 0.000282 | 0.000273 |
| 18 | 0.001532 | 0.000622 | 0.000268 | 0.000480 | 0.000316 |
| 19 | 0.000315 | 0.000219 | 0.000097 | 0.000136 | 0.000111 |
| 20 | 0.000000 | 0.000000 | 0.000000 | 0.000000 | 0.000000 |
| 21 | 0.001177 | 0.000426 | 0.000134 | 0.000334 | 0.000333 |
| 22 | 0.000219 | 0.000092 | 0.000061 | 0.000084 | 0.000077 |
| 23 | 0.000000 | 0.000000 | 0.000000 | 0.000000 | 0.000000 |
| 24 | 0.000000 | 0.000000 | 0.000000 | 0.000000 | 0.000000 |
| 25 | 0.000014 | 0.000000 | 0.000000 | 0.000000 | 0.000000 |
| 26 | 0.000575 | 0.000703 | 0.000000 | 0.000731 | 0.000265 |
| 27 | 0.000698 | 0.000346 | 0.000304 | 0.000198 | 0.000171 |
| 28 | 0.016841 | 0.008710 | 0.007124 | 0.005543 | 0.006968 |
| 29 | 0.005062 | 0.002431 | 0.000146 | 0.002025 | 0.000837 |
| 30 | 0.000014 | 0.000000 | 0.000000 | 0.000000 | 0.000000 |
| 31 | 0.000000 | 0.000012 | 0.000012 | 0.000000 | 0.000009 |
| 32 | 0.000000 | 0.000000 | 0.000000 | 0.000000 | 0.000000 |
| 33 | 0.000465 | 0.000184 | 0.000256 | 0.000261 | 0.000239 |
| 34 | 0.046952 | 0.013779 | 0.013907 | 0.016732 | 0.015354 |
| 35 | 0.000014 | 0.000012 | 0.000000 | 0.000021 | 0.000009 |

TABLE 3B-continued

| No | BD1 | BD2 | BD3 | BD4 | BD5 |
|---|---|---|---|---|---|
| 36 | 0.000014 | 0.000012 | 0.000000 | 0.000010 | 0.000017 |
| 37 | 0.000000 | 0.000000 | 0.000000 | 0.000000 | 0.000000 |
| 38 | 0.000000 | 0.000000 | 0.000000 | 0.000000 | 0.000000 |
| 39 | 0.000000 | 0.000012 | 0.000000 | 0.000000 | 0.000000 |
| 40 | 0.000055 | 0.000012 | 0.000049 | 0.000000 | 0.000026 |
| 41 | 0.000000 | 0.000000 | 0.000000 | 0.000000 | 0.000000 |
| 42 | 0.002709 | 0.001682 | 0.003629 | 0.001054 | 0.000666 |
| 43 | 0.000000 | 0.000000 | 0.000000 | 0.000000 | 0.000000 |
| 44 | 0.000000 | 0.000000 | 0.000000 | 0.000000 | 0.000000 |
| 45 | 0.000000 | 0.000000 | 0.000012 | 0.000000 | 0.000000 |
| 46 | 0.000000 | 0.000012 | 0.000000 | 0.000000 | 0.000017 |
| 47 | 0.000000 | 0.000000 | 0.000000 | 0.000000 | 0.000000 |
| 48 | 0.000000 | 0.000000 | 0.000000 | 0.000000 | 0.000000 |
| 49 | 0.000000 | 0.000000 | 0.000000 | 0.000000 | 0.000000 |
| 50 | 0.000027 | 0.000000 | 0.000024 | 0.000042 | 0.000009 |
| 51 | 0.000014 | 0.000000 | 0.000000 | 0.000010 | 0.000017 |
| 52 | 0.008797 | 0.004862 | 0.013749 | 0.009280 | 0.011716 |
| 53 | 0.000000 | 0.000000 | 0.000000 | 0.000010 | 0.000000 |
| 54 | 0.000000 | 0.000000 | 0.000000 | 0.000000 | 0.000000 |
| 55 | 0.000014 | 0.000012 | 0.000000 | 0.000031 | 0.000000 |

Example 8: Table 4 for Examples 1-3, Provided as Parts Tables 4A Through 4E

Tables 4A through 4E (collectively "Table 4") relate to metabolites in E14.5 SPF, ABX, GF, and Sp fetal brains. The cells can be classified from the given data based on $p<0.05$ or $0.05<p<0.10$, as well as based on the mean values being significantly higher or not for each comparison. PSO stands for pathway sort order. Table 4C provides "fold of change," in which columns 2 through 7 are the ANOVA contrasts, and the "GE" is group effect for one-way ANOVA. The ANOVA contrasts are further provided in Tables 4D and 4E.

TABLE 4A

| PSO | Super Pathway | Sub Pathway | Biochemical Name |
|---|---|---|---|
| 1 | Amino_Acid | Glycine, Serine and Threonine Metabolism | glycine |
| 2 | | | N-acetylglycine |
| 5 | | | dimethylglycine |
| 6 | | | betaine |
| 9 | | | serine |
| 10 | | | N-acetylserine |
| 14 | | | 3-phosphoserine |
| 16 | | | threonine |
| 17 | | | N-acetylthreonine |
| 18 | | | allo-threonine |
| 21 | | | homoserine |
| 28 | | Alanine and Aspartate Metabolism | alanine |
| 30 | | | N-acetylalanine |
| 34 | | | aspartate |
| 35 | | | N-acetylaspartate (NAA) |
| 38 | | | asparagine |
| 39 | | | N-acetylasparagine |
| 40 | | | hydroxyasparagine** |

TABLE 4A-continued

| PSO | Super Pathway | Sub Pathway | Biochemical Name |
|---|---|---|---|
| 41 | | Glutamate Metabolism | glutamate |
| 42 | | | glutamine |
| 43 | | | alpha-ketoglutaramate* |
| 44 | | | N-acetylglutamate |
| 45 | | | N-acetylglutamine |
| 47 | | | 4-hydroxyglutamate |
| 50 | | | glutamate, gamma-methyl ester |
| 51 | | | pyroglutamine* |
| 52 | | | N-acetyl-aspartyl-glutamate (NAAG) |
| 53 | | | beta-citrylglutamate |
| 54 | | | gamma-aminobutyrate (GABA) |
| 55 | | | carboxyethyl-GABA |
| 56 | | | N-methyl-GABA |
| 59 | | | S-1-pyrroline-5-carboxylate |
| 65 | | Histidine Metabolism | histidine |
| 66 | | | 1-methylhistidine |
| 67 | | | 3-methylhistidine |
| 68 | | | N-acetylhistidine |
| 74 | | | imidazole propionate |
| 75 | | | formiminoglutamate |
| 76 | | | imidazole lactate |
| 77 | | | carnosine |
| 80 | | | anserine |
| 82 | | | 1-methylhistamine |
| 83 | | | 1-methyl-4-imidazoleacetate |
| 84 | | | 1-ribosyl-imidazoleacetate* |
| 92 | | Lysine Metabolism | lysine |
| 93 | | | N2-acetyllysine |
| 99 | | | N6-methyllysine |
| 100 | | | N6,N6-dimethyllysine |
| 101 | | | N6,N6,N6-trimethyllysine |
| 102 | | | 5-hydroxylysine |
| 103 | | | 5-(galactosylhydroxy)-L-lysine |
| 105 | | | 2-aminoadipate |
| 107 | | | 2-oxoadipate |
| 113 | | | pipecolate |
| 114 | | | 6-oxopiperidine-2-carboxylate |
| 117 | | | 5-aminovalerate |
| 119 | | | N,N,N-trimethyl-5-aminovalerate |
| 120 | | Phenylalanine | phenylalanine |
| 121 | | Metabolism | N-acetylphenylalanine |
| 122 | | | 1-carboxyethylphenylalanine |
| 126 | | | phenyllactate (PLA) |
| 137 | | Tyrosine Metabolism | tyrosine |
| 138 | | | N-acetyltyrosine |
| 150 | | | 3-(4-hydroxyphenyl)lactate |
| 154 | | | phenol sulfate |
| 180 | | | o-Tyrosine |
| 181 | | | O-methyltyrosine |
| 191 | | | N-formylphenylalanine |
| 210 | | Tryptophan Metabolism | tryptophan |
| 217 | | | C-glycosyltryptophan |
| 221 | | | kynurenine |
| 227 | | | N-formylanthranilic acid |
| 241 | | | indolelactate |
| 254 | | | 3-indoxyl sulfate |
| 261 | | Leucine, Isoleucine and | leucine |
| 263 | | Valine Metabolism | 1-carboxyethylleucine |
| 265 | | | 4-methyl-2-oxopentanoate |
| 273 | | | isovalerylcarnitine (C5) |
| 280 | | | beta-hydroxyisovalerate |
| 296 | | | isoleucine |
| 299 | | | 1-carboxyethylisoleucine |
| 300 | | | 3-methyl-2-oxovalerate |
| 301 | | | alpha-hydroxyisovalerate |
| 303 | | | 2-methylbutyrylcarnitine (C5) |
| 306 | | | tiglylcarnitine (C5:1-DC) |
| 311 | | | ethylmalonate |
| 312 | | | methylsuccinate |
| 318 | | | valine |
| 321 | | | 1-carboxyethylvaline |
| 323 | | | 3-methyl-2-oxobutyrate |
| 326 | | | isobutyrylcarnitine (C4) |
| 328 | | | 3-hydroxyisobutyrate |
| 332 | | Methionine, Cysteine, | methionine |
| 333 | | SAM and Taurine | N-acetylmethionine |
| 334 | | Metabolism | N-formylmethionine |
| 337 | | | methionine sulfoxide |

TABLE 4A-continued

| PSO | Super Pathway | Sub Pathway | Biochemical Name |
|---|---|---|---|
| 342 | | | S-adenosylmethionine (SAM) |
| 343 | | | S-adenosylhomocysteine (SAH) |
| 349 | | | cystathionine |
| 351 | | | cysteine |
| 353 | | | S-methylcysteine |
| 362 | | | cysteine sulfinic acid |
| 363 | | | hypotaurine |
| 364 | | | taurine |
| 365 | | | N-acetyltaurine |
| 367 | | | taurocyamine |
| 369 | | | 3-sulfo-L-alanine |
| 371 | | Urea cycle; Arginine and Proline Metabolism | arginine |
| 372 | | | argininosuccinate |
| 373 | | | urea |
| 375 | | | ornithine |
| 379 | | | 2-oxoarginine* |
| 380 | | | citrulline |
| 381 | | | homoarginine |
| 382 | | | homocitrulline |
| 383 | | | proline |
| 386 | | | dimethylarginine (SDMA + ADMA) |
| 387 | | | N-acetylarginine |
| 392 | | | N-delta-acetylornithine |
| 397 | | | trans-4-hydroxyproline |
| 399 | | | pro-hydroxy-pro |
| 405 | | | argininate* |
| 410 | | Creatine Metabolism | guanidinoacetate |
| 411 | | | creatine |
| 412 | | | creatinine |
| 418 | | Polyamine Metabolism | putrescine |
| 421 | | | spermidine |
| 426 | | | spermine |
| 429 | | | 5-methylthioadenosine (MTA) |
| 430 | | | N-acetylputrescine |
| 436 | | | (N(1) + N(8))-acetylspermidine |
| 438 | | Guanidino and Acetamido Metabolism | 1-methylguanidine |
| 439 | | | 4-guanidinobutanoate |
| 442 | | Glutathione Metabolism | glutathione, reduced (GSH) |
| 443 | | | glutathione, oxidized (GSSG) |
| 445 | | | cysteine-glutathione disulfide |
| 446 | | | S-methylglutathione |
| 447 | | | S-lactoylglutathione |
| 451 | | | 5-oxoproline |
| 454 | | | 2-hydroxybutyrate/2-hydroxyisobutyrate |
| 456 | | | ophthalmate |
| 459 | | | 4-hydroxy-nonenal-glutathione |
| 460 | | | 3'-dephospho-CoA-glutathione* |
| 461 | | | CoA-glutathione* |
| 465 | Peptide | Gamma-glutamyl Amino Acid | gamma-glutamylalanine |
| 467 | | | gamma-glutamylglutamate |
| 468 | | | gamma-glutamylglutamine |
| 469 | | | gamma-glutamylglycine |
| 471 | | | gamma-glutamylisoleucine* |
| 472 | | | gamma-glutamylleucine |
| 473 | | | gamma-glutamyl-alpha-lysine |
| 474 | | | gamma-glutamyl-epsilon-lysine |
| 475 | | | gamma-glutamylmethionine |
| 476 | | | gamma-glutamylphenylalanine |
| 477 | | | gamma-glutamylthreonine |
| 478 | | | gamma-glutamyltryptophan |
| 479 | | | gamma-glutamyltyrosine |
| 480 | | | gamma-glutamylvaline |
| 756 | | Dipeptide | prolylglycine |
| 929 | | Acetylated Peptides | phenylacetylglycine |
| 955 | Carbohydrate | Glycolysis, Gluconeogenesis, and Pyruvate Metabolism | 1,5-anhydroglucitol (1,5-AG) |
| 958 | | | glucose |
| 959 | | | glucose 6-phosphate |
| 965 | | | fructose 1,6-diphosphate/ glucose 1,6-diphosphate/ myo-inositol diphosphates |
| 967 | | | dihydroxyacetone phosphate (DHAP) |
| 972 | | | 3-phosphoglycerate |
| 973 | | | phosphoenolpyruvate (PEP) |
| 974 | | | pyruvate |
| 975 | | | lactate |
| 978 | | | glycerate |

TABLE 4A-continued

| PSO | Super Pathway | Sub Pathway | Biochemical Name |
|---|---|---|---|
| 981 | | Pentose Phosphate | 6-phosphogluconate |
| 982 | | Pathway | ribulose 5-phosphate |
| 983 | | | ribose 5-phosphate |
| 984 | | | ribose 1-phosphate |
| 986 | | | sedoheptulose-7-phosphate |
| 993 | | Pentose Metabolism | ribose |
| 994 | | | ribitol |
| 995 | | | ribonate |
| 997 | | | xylulose 5-phosphate |
| 1018 | | | arabitol/xylitol |
| 1020 | | | arabonate/xylonate |
| 1023 | | | sedoheptulose |
| 1024 | | | ribulonate/xylulonate* |
| 1028 | | Glycogen Metabolism | maltotetraose |
| 1030 | | | maltotriose |
| 1033 | | | maltose |
| 1073 | | Fructose, Mannose and | fructose |
| 1078 | | Galactose Metabolism | mannitol/sorbitol |
| 1079 | | | mannose |
| 1080 | | | mannose-6-phosphate |
| 1090 | | | galactose 1-phosphate |
| 1099 | | | galactonate |
| 1104 | | Nucleotide Sugar | UDP-glucose |
| 1108 | | | UDP-galactose |
| 1109 | | | UDP-glucuronate |
| 1111 | | | guanosine 5'-diphospho-fucose |
| 1115 | | | UDP-N-acetylglucosamine/galactosamine |
| 1116 | | | cytidine 5'-monophospho-N-acetylneuraminic acid |
| 1123 | | Aminosugar Metabolism | glucosamine-6-phosphate |
| 1127 | | | glucuronate |
| 1131 | | | N-acetylglucosamine 6-phosphate |
| 1132 | | | N-acetyl-glucosamine 1-phosphate |
| 1138 | | | N-acetylneuraminate |
| 1149 | | | N-acetylglucosaminylasparagine |
| 1150 | | | erythronate* |
| 1152 | | | N-acetylglucosamine/ N-acetylgalactosamine |
| 1157 | Energy | TCA Cycle | citrate |
| 1163 | | | alpha-ketoglutarate |
| 1165 | | | succinylcarnitine (C4-DC) |
| 1166 | | | succinate |
| 1167 | | | fumarate |
| 1169 | | | malate |
| 1179 | | | 2-methylcitrate/homocitrate |
| 1181 | | Oxidative | acetylphosphate |
| 1183 | | Phosphorylation | phosphate |
| 1201 | Lipid | Medium Chain Fatty Acid | caproate (6:0) |
| 1203 | | | caprylate (8:0) |
| 1204 | | | pelargonate (9:0) |
| 1205 | | | caprate (10:0) |
| 1217 | | Long Chain Fatty Acid | palmitate (16:0) |
| 1218 | | | palmitoleate (16:1n7) |
| 1223 | | | stearate (18:0) |
| 1225 | | | oleate/vaccenate (18:1) |
| 1236 | | | arachidate (20:0) |
| 1239 | | | eicosenoate (20:1) |
| 1244 | | | erucate (22:1n9) |
| 1247 | | | nervonate (24:1n9)* |
| 1253 | | Polyunsaturated Fatty | hexadecadienoate (16:2n6) |
| 1258 | | Acid (n3 and n6) | eicosapentaenoate (EPA; 20:5n3) |
| 1259 | | | docosapentaenoate (n3 DPA; 22:5n3) |
| 1260 | | | docosahexaenoate (DHA; 22:6n3) |
| 1264 | | | nisinate (24:6n3) |
| 1265 | | | linoleate (18:2n6) |
| 1267 | | | linolenate [alpha or gamma; (18:3n3 or 6)] |
| 1269 | | | dihomo-linolenate (20:3n3 or n6) |
| 1270 | | | arachidonate (20:4n6) |
| 1271 | | | adrenate (22:4n6) |
| 1272 | | | docosapentaenoate (n6 DPA; 22:5n6) |
| 1273 | | | docosadienoate (22:2n6) |
| 1274 | | | dihomo-linoleate (20:2n6) |
| 1276 | | | mead acid (20:3n9) |
| 1277 | | | docosatrienoate (22:3n6)* |
| 1351 | | Fatty Acid, | glutarate (C5-DC) |
| 1355 | | Dicarboxylate | 2-hydroxyglutarate |
| 1359 | | | 2-hydroxyadipate |

TABLE 4A-continued

| PSO | Super Pathway | Sub Pathway | Biochemical Name |
|---|---|---|---|
| 1360 | | | 3-hydroxyadipate* |
| 1363 | | | maleate |
| 1372 | | | sebacate (C10-DC) |
| 1430 | | Fatty Acid, Amino | 2-aminoheptanoate |
| 1446 | | Fatty Acid Metabolism | butyrylcarnitine (C4) |
| 1449 | | (also BCAA Metabolism) | propionylcarnitine (C3) |
| 1452 | | | methylmalonate (MMA) |
| 1480 | | Fatty Acid | acetylcarnitine (C2) |
| 1482 | | Metabolism(Acyl | 3-hydroxybutyrylcarnitine (1) |
| 1483 | | Carnitine) | 3-hydroxybutyrylcarnitine (2) |
| 1485 | | | hexanoylcarnitine (C6) |
| 1487 | | | 3-hydroxyhexanoylcarnitine (1) |
| 1488 | | | octanoylcarnitine (C8) |
| 1495 | | | laurylcarnitine (C12) |
| 1496 | | | myristoylcarnitine (C14) |
| 1498 | | | palmitoylcarnitine (C16) |
| 1499 | | | palmitoleoylcarnitine (C16:1)* |
| 1500 | | | stearoylcarnitine (C18) |
| 1501 | | | linoleoylcarnitine (C18:2)* |
| 1503 | | | 3-hydroxyoleoylcarnitine |
| 1504 | | | oleoylcarnitine (C18:1) |
| 1506 | | | myristoleoylcarnitine (C14:1)* |
| 1517 | | | arachidoylcarnitine (C20)* |
| 1518 | | | arachidonoylcarnitine (C20:4) |
| 1519 | | | adrenoylcarnitine (C22:4)* |
| 1521 | | | meadoylcarnitine (C20:3n9)* |
| 1522 | | | dihomo-linolenoylcarnitine (C20:3n3 or 6)* |
| 1523 | | | dihomo-linoleoylcarnitine (C20:2)* |
| 1524 | | | eicosenoylcarnitine (C20:1)* |
| 1527 | | | docosatrienoylcarnitine (C22:3)* |
| 1528 | | | docosapentaenoylcarnitine (C22:5n3)* |
| 1529 | | | docosahexaenoylcarnitine (C22:6)* |
| 1536 | | | pentadecanoylcarnitine (C15)* |
| 1537 | | | docosapentaenoylcarnitine (C22:5n6)* |
| 1539 | | | 3-hydroxypalmitoylcarnitine |
| 1541 | | Carnitine Metabolism | deoxycarnitine |
| 1542 | | | carnitine |
| 1547 | | Ketone Bodies | 3-hydroxybutyrate (BHBA) |
| 1565 | | Fatty Acid, Monohydroxy | 2-hydroxyheptanoate* |
| 1567 | | | 2-hydroxydecanoate |
| 1582 | | | 3-hydroxydecanoate |
| 1711 | | Eicosanoid | 12-HHTrE |
| 1718 | | Endocannabinoid | oleoyl ethanolamide |
| 1721 | | | palmitoyl ethanolamide |
| 1731 | | | N-stearoyltaurine |
| 1732 | | | N-palmitoyltaurine |
| 1744 | | | palmitoleoyl ethanolamide* |
| 1753 | | Inositol Metabolism | myo-inositol |
| 1754 | | | chiro-inositol |
| 1782 | | Phospholipid Metabolism | choline |
| 1783 | | | choline phosphate |
| 1784 | | | cytidine 5'-diphosphocholine |
| 1786 | | | glycerophosphorylcholine (GPC) |
| 1788 | | | phosphoethanolamine |
| 1789 | | | cytidine-5'-diphosphoethanolamine |
| 1790 | | | glycerophosphoethanolamine |
| 1791 | | | glycerophosphoserine* |
| 1792 | | | glycerophosphoinositol* |
| 1793 | | | trimethylamine N-oxide |
| 1811 | | Phosphatidylcholine | 1-myristoyl-2-palmitoyl-GPC (14:0/16:0) |
| 1815 | | (PC) | 1-myristoyl-2-arachidonoyl-GPC (14:0/20:4)* |
| 1827 | | | 1,2-dipalmitoyl-GPC (16:0/16:0) |
| 1828 | | | 1-palmitoyl-2-palmitoleoyl-GPC (16:0/16:1)* |
| 1829 | | | 1-palmitoyl-2-stearoyl-GPC (16:0/18:0) |
| 1831 | | | 1-palmitoyl-2-oleoyl-GPC (16:0/18:1) |
| 1834 | | | 1-palmitoyl-2-linoleoyl-GPC (16:0/18:2) |
| 1837 | | | 1-palmitoyl-2-gamma-linolenoyl-GPC (16:0/18:3n6)* |
| 1841 | | | 1-palmitoyl-2-dihomo-linolenoyl-GPC (16:0/20:3n3 or 6)* |
| 1845 | | | 1-palmitoyl-2-arachidonoyl-GPC (16:0/20:4n6) |
| 1851 | | | 1-palmitoyl-2-docosahexaenoyl-GPC (16:0/22:6) |
| 1866 | | | 1,2-distearoyl-GPC (18:0/18:0) |
| 1867 | | | 1-stearoyl-2-oleoyl-GPC (18:0/18:1) |
| 1870 | | | 1-stearoyl-2-linoleoyl-GPC (18 :0/18:2)* |
| 1878 | | | 1-stearoyl-2-arachidonoyl-GPC (18:0/20:4) |
| 1884 | | | 1-stearoyl-2-docosahexaenoyl-GPC (18:0/22:6) |
| 1889 | | | 1,2-dioleoyl-GPC (18:1/18:1) |
| 1892 | | | 1-oleoyl-2-linoleoyl-GPC (18:1/18:2)* |
| 1902 | | | 1-oleoyl-2-docosahexaenoyl-GPC (18:1/22:6)* |

TABLE 4A-continued

| PSO | Super Pathway | Sub Pathway | Biochemical Name |
|---|---|---|---|
| 1903 | | | 1,2-dilinoleoyl-GPC (18:2/18:2) |
| 1907 | | | 1-linoleoyl-2-arachidonoyl-GPC (18:2/20:4n6)* |
| 1945 | | Phosphatidylethanolamine (PE) | 1,2-dipalmitoyl-GPE (16:0/16:0)* |
| 1948 | | | 1-palmitoyl-2-stearoyl-GPE (16:0/18:0)* |
| 1949 | | | 1-palmitoyl-2-oleoyl-GPE (16:0/18:1) |
| 1950 | | | 1-palmitoyl-2-linoleoyl-GPE (16:0/18:2) |
| 1953 | | | 1-palmitoyl-2-arachidonoyl-GPE (16:0/20:4)* |
| 1955 | | | 1-palmitoyl-2-docosahexaenoyl-GPE (16:0/22:6)* |
| 1962 | | | 1-stearoyl-2-oleoyl-GPE (18:0/18:1) |
| 1970 | | | 1-stearoyl-2-arachidonoyl-GPE (18:0/20:4) |
| 1974 | | | 1-stearoyl-2-docosahexaenoyl-GPE (18:0/22:6)* |
| 1975 | | | 1,2-dioleoyl-GPE (18:1/18:1) |
| 1976 | | | 1-oleoyl-2-linoleoyl-GPE (18:1/18:2)* |
| 1979 | | | 1-oleoyl-2-arachidonoyl-GPE (18:1/20:4)* |
| 1982 | | | 1-oleoyl-2-docosahexaenoyl-GPE (18:1/22:6)* |
| 1985 | | | 1-linoleoyl-2-arachidonoyl-GPE (18:2/20:4)* |
| 2016 | | Phosphatidylserine (PS) | 1-palmitoyl-2-oleoyl-GPS (16:0/18:1) |
| 2021 | | | 1-stearoyl-2-oleoyl-GPS (18:0/18:1) |
| 2024 | | | 1-stearoyl-2-arachidonoyl-GPS (18:0/20:4) |
| 2034 | | Phosphatidylglycerol (PG) | 1-palmitoyl-2-oleoyl-GPG (16:0/18:1) |
| 2052 | | Phosphatidylinositol (PI) | 1-palmitoyl-2-arachidonoyl-GPI (16:0/20:4)* |
| 2067 | | | 1-stearoyl-2-arachidonoyl-GPI (18:0/20:4) |
| 2072 | | | 1-oleoyl-2-arachidonoyl-GPI (18:1/20:4)* |
| 2105 | | Lysophospholipid | 1-palmitoyl-GPC (16:0) |
| 2106 | | | 2-palmitoyl-GPC (16:0)* |
| 2107 | | | 1-palmitoleoyl-GPC (16:1)* |
| 2113 | | | 1-stearoyl-GPC (18:0) |
| 2115 | | | 1-oleoyl-GPC (18:1) |
| 2118 | | | 1-linoleoyl-GPC (18:2) |
| 2136 | | | 1-arachidonoyl-GPC (20:4n6)* |
| 2157 | | | 1-palmitoyl-GPE (16:0) |
| 2164 | | | 1-stearoyl-GPE (18:0) |
| 2165 | | | 2-stearoyl-GPE (18:0)* |
| 2166 | | | 1-oleoyl-GPE (18:1) |
| 2168 | | | 1-linoleoyl-GPE (18:2)* |
| 2179 | | | 1-arachidonoyl-GPE (20:4n6)* |
| 2192 | | | 1-palmitoyl-GPS (16:0)* |
| 2193 | | | 1-stearoyl-GPS (18:0)* |
| 2194 | | | 1-oleoyl-GPS (18:1) |
| 2199 | | | 1-palmitoyl-GPG (16:0)* |
| 2203 | | | 1-oleoyl-GPG (18:1)* |
| 2206 | | | 1-palmitoyl-GPI (16:0) |
| 2209 | | | 1-stearoyl-GPI (18:0) |
| 2211 | | | 1-oleoyl-GPI (18:1)* |
| 2217 | | | 1-arachidonoyl-GPI (20:4)* |
| 2310 | | Plasmalogen | 1-(1-enyl-palmitoyl)-2-oleoyl-GPE (P-16:0/18:1)* |
| 2311 | | | 1-(1-enyl-palmitoyl)-2-linoleoyl-GPE (P-16:0/18:2)* |
| 2312 | | | 1-(1-enyl-palmitoyl)-2-palmitoyl-GPC (P-16:0/16:0)* |
| 2313 | | | 1-(1-enyl-palmitoyl)-2-palmitoleoyl-GPC (P-16:0/16:1)* |
| 2314 | | | 1-(1-enyl-palmitoyl)-2-arachidonoyl-GPE (P-16:0/20:4)* |
| 2318 | | | 1-(1-enyl-stearoyl)-2-oleoyl-GPE (P-18:0/18:1) |
| 2327 | | | 1-(1-enyl-stearoyl)-2-arachidonoyl-GPE (P-18:0/20:4)* |
| 2343 | | Lysoplasmalogen | 1-(1-enyl-palmitoyl)-GPE (P-16:0)* |
| 2345 | | | 1-(1-enyl-oleoyl)-GPE (P-18:1)* |
| 2347 | | | 1-(1-enyl-stearoyl)-GPE (P-18:0)* |
| 2348 | | | 1-(1-enyl-oleoyl)-2-oleoyl-GPE (P-18:1/18:1)* |
| 2350 | | Glycerolipid Metabolism | glycerol |
| 2351 | | | glycerol 3-phosphate |
| 2356 | | | glycerophosphoglycerol |
| 2357 | | Monoacylglycerol | 1-myristoylglycerol (14:0) |
| 2360 | | | 1-palmitoylglycerol (16:0) |
| 2361 | | | 1-palmitoleoylglycerol (16:1)* |
| 2364 | | | 1-oleoylglycerol (18:1) |
| 2371 | | | 1-arachidonylglycerol (20:4) |
| 2374 | | | 1-docosahexaenoylglycerol (22:6) |
| 2375 | | | 2-myristoylglycerol (14:0) |
| 2376 | | | 2-palmitoylglycerol (16:0) |
| 2379 | | | 2-oleoylglycerol (18:1) |
| 2381 | | | 2-arachidonoylglycerol (20:4) |
| 2383 | | | 2-docosahexaenoylglycerol (22:6)* |
| 2394 | | Diacylglycerol | diacylglycerol (14:0/18:1, 16:0/16:1) [2]* |
| 2395 | | | diacylglycerol (16:1/18:2 [2], 16:0/18:3 [1])* |
| 2407 | | | palmitoyl-palmitoyl-glycerol (16:0/16:0) [2]* |
| 2411 | | | palmitoyl-oleoyl-glycerol (16:0/18:1) [2]* |
| 2413 | | | palmitoyl-linoleoyl-glycerol (16:0/18:2) [2]* |
| 2416 | | | palmitoleoyl-oleoyl-glycerol (16:1/18:1) [2]* |
| 2418 | | | palmitoy1-dihomo-linolenoyl-glycerol (16:0/20:3n3 or 6) [2]* |

TABLE 4A-continued

| PSO | Super Pathway | Sub Pathway | Biochemical Name |
|---|---|---|---|
| 2419 | | | palmitoyl-arachidonoyl-glycerol (16:0/20:4) [1]* |
| 2420 | | | palmitoyl-arachidonoyl-glycerol (16:0/20:4) [2]* |
| 2422 | | | palmitoyl-docosahexaenoyl-glycerol (16:0/22:6) [1]* |
| 2423 | | | palmitoyl-docosahexaenoyl-glycerol (16:0/22:6) [2]* |
| 2426 | | | stearoyl-linoleoyl-glycerol (18:0/18:2) [2]* |
| 2429 | | | oleoyl-oleoyl-glycerol (18:1/18:1) [2]* |
| 2431 | | | oleoyl-linoleoyl-glycerol (18:1/18:2) [1] |
| 2432 | | | oleoyl-linoleoyl-glycerol (18:1/18:2) [2] |
| 2442 | | | stearoyl-arachidonoyl-glycerol (18:0/20:4) [1]* |
| 2443 | | | stearoyl-arachidonoyl-glycerol (18:0/20:4) [2]* |
| 2445 | | | oleoyl-arachidonoyl-glycerol (18:1/20:4) [2]* |
| 2448 | | | stearoyl-docosahexaenoyl-glycerol (18:0/22:6) [1]* |
| 2449 | | | stearoyl-docosahexaenoyl-glycerol (18:0/22:6) [2]* |
| 2474 | | Sphingolipid Synthesis | sphinganine |
| 2480 | | Dihydroceramides | N-palmitoyl-sphinganine (d18:0/16:0) |
| 2481 | | | N-stearoyl-sphinganine (d18:0/18:0)* |
| 2488 | | Ceramides | N-palmitoyl-sphingosine (d18:1/16:0) |
| 2491 | | | N-stearoyl-sphingosine (d18:1/18:0)* |
| 2493 | | | N-arachidoyl-sphingosine (d18:1/20:0)* |
| 2498 | | | N-stearoyl-sphingadienine (d18:2/18:0)* |
| 2499 | | | N-behenoyl-sphingadienine (d18:2/22:0)* |
| 2513 | | | ceramide (d18:1/14:0, d16:1/16:0)* |
| 2514 | | | ceramide (d18:1/17:0, d17:1/18:0)* |
| 2517 | | | ceramide (d16:1/24:1, d18:1/22:1)* |
| 2518 | | | ceramide (d18:2/24:1, d18:1/24:2)* |
| 2520 | | Hexosylceramides (HCER) | glycosyl-N-stearoyl-sphinganine (d18:0/18:0)* |
| 2522 | | | glycosyl-N-palmitoyl-sphingosine (d18:1/16:0) |
| 2523 | | | glycosyl-N-stearoyl-sphingosine (d18:1/18:0) |
| 2525 | | | glycosyl-N-behenoyl-sphingosine (d18:1/22:0)* |
| 2543 | | | glycosyl ceramide (d18:1/20:0, d16:1/22:0)* |
| 2547 | | | glycosyl ceramide (d18:2/24:1, d18:1/24:2)* |
| 2549 | | Lactosylceramides (LCER) | lactosyl-N-palmitoyl-sphingosine (d18:1/16:0) |
| 2561 | | Dihydrosphingomyelins | palmitoyl dihydrosphingomyelin (d18:0/16:0)* |
| 2563 | | | sphingomyelin (d18:0/18:0, d19:0/17:0)* |
| 2564 | | | sphingomyelin (d18:0/20:0, d16:0/22:0)* |
| 2565 | | Sphingomyelins | palmitoyl sphingomyelin (d18:1/16:0) |
| 2566 | | | hydroxypalmitoyl sphingomyelin (d18:1/16:0(OH))** |
| 2567 | | | stearoyl sphingomyelin (d18:1/18:0) |
| 2568 | | | behenoyl sphingomyelin (d18:1/22:0)* |
| 2569 | | | tricosanoyl sphingomyelin (d18:1/23:0)* |
| 2570 | | | lignoceroyl sphingomyelin (d18:1/24:0) |
| 2575 | | | sphingomyelin (d18:1/14:0, d16:1/16:0)* |
| 2577 | | | sphingomyelin (d17:1/16:0, d18:1/15:0, d16:1/17:0)* |
| 2579 | | | sphingomyelin (d18:2/16:0, d18:1/16:1)* |
| 2580 | | | sphingomyelin (d18:1/17:0, d17:1/18:0, d19:1/16:0) |
| 2581 | | | sphingomyelin (d18:1/18:1, d18:2/18:0) |
| 2583 | | | sphingomyelin (d18:1/20:0, d16:1/22:0)* |
| 2588 | | | sphingomyelin (d18:1/22:1, d18:2/22:0, d16:1/24:1)* |
| 2591 | | | sphingomyelin (d18:1/24:1, d18:2/24:0)* |
| 2592 | | | sphingomyelin (d18:2/24:1, d18:1/24:2)* |
| 2594 | | Sphingosines | sphingosine |
| 2610 | | Mevalonate Metabolism | 3-hydroxy-3-methylglutarate |
| 2624 | | Sterol | desmosterol |
| 2625 | | | cholesterol |
| 2649 | | | 4-cholesten-3-one |
| 2652 | | | campesterol |
| 2669 | | | 7-hydroxycholesterol (alpha or beta) |
| 3453 | Nucleotide | Purine Metabolism, (Hypo(Xanthine/Inosine containing | inosine 5'-monophosphate (IMP) |
| 3454 | | | inosine |
| 3455 | | | hypoxanthine |
| 3456 | | | xanthine |
| 3458 | | | xanthosine |
| 3461 | | | N1-methylinosine |
| 3462 | | | 2'-deoxyinosine |
| 3464 | | | urate |
| 3466 | | | allantoin |
| 3471 | | Purine Metbolism, Adenine containing | adenosine 5'-diphosphate (ADP) |
| 3472 | | | adenosine 5'-monophosphate (AMP) |
| 3473 | | | adenosine 3'-monophosphate (3'-AMP) |
| 3474 | | | adenosine 2'-monophosphate (2'-AMP) |
| 3478 | | | adenylosuccinate |
| 3479 | | | adenosine |
| 3480 | | | adenine |
| 3485 | | | N1-methyladenosine |
| 3495 | | | N6-carbamoylthreonyladenosine |
| 3498 | | | 2'-deoxyadenosine 5'-monophosphate |
| 3505 | | | N6-succinyladenosine |

TABLE 4A-continued

| PSO | Super Pathway | Sub Pathway | Biochemical Name |
|---|---|---|---|
| 3507 | | Purine Metabolism, | guanosine 5'-diphosphate (GDP) |
| 3508 | | Guanine containing | guanosine 5'-monophosphate (5'-GMP) |
| 3513 | | | guanosine |
| 3514 | | | guanine |
| 3516 | | | 7-methylguanine |
| 3522 | | | N2,N2-dimethylguanosine |
| 3528 | | | 2'-deoxyguanosine 5'-monophosphate (dGMP) |
| 3530 | | | 2'-deoxyguanosine |
| 3533 | | | N-carbamoylaspartate |
| 3534 | | Pyrimidine Metabolism, | dihydroorotate |
| 3535 | | Orotate containing | orotate |
| 3537 | | | orotidine |
| 3541 | | Pyrimidine Metabolism, | uridine 5'-diphosphate (UDP) |
| 3542 | | Uracil containing | uridine 5'-monophosphate (UMP) |
| 3547 | | | uridine |
| 3548 | | | uracil |
| 3549 | | | pseudouridine |
| 3550 | | | 5,6-dihydrouridine |
| 3552 | | | 5-methyluridine (ribothymidine) |
| 3563 | | | 2'-deoxyuridine |
| 3565 | | | 3-ureidoisobutyrate |
| 3566 | | | 3-ureidopropionate |
| 3567 | | | beta-alanine |
| 3568 | | | N-acetyl-beta-alanine |
| 3572 | | Pyrimidine Metabolism, | cytidine diphosphate |
| 3573 | | Cytidine containing | cytidine 5'-monophosphate (5'-CMP) |
| 3576 | | | cytidine 2',3'-cyclic monophosphate |
| 3577 | | | cytidine |
| 3578 | | | cytosine |
| 3579 | | | 3-methylcytidine |
| 3580 | | | 5-methylcytidine |
| 3585 | | | 2'-deoxycytidine 5'-monophosphate |
| 3587 | | | 2'-deoxycytidine |
| 3588 | | | 2'-O-methylcytidine |
| 3589 | | | 5-methyl-2'-deoxycytidine |
| 3598 | | Pyrimidine Metabolism, | thymidine |
| 3599 | | Thymine containing | thymine |
| 3602 | | | 3-aminoisobutyrate |
| 3603 | | Purine and Pyrimidine Metabolism | methylphosphate |
| 3607 | | Dinucleotide | (3'-5')-adenylyluridine |
| 3608 | | | (3'-5')-adenylyladenosine* |
| 3624 | Cofactors and | Nicotinate and | nicotinamide |
| 3627 | Vitamins | Nicotinamide Metabolism | nicotinamide riboside |
| 3628 | | | nicotinamide adenine dinucleotide (NAD+) |
| 3636 | | | 1-methylnicotinamide |
| 3641 | | | trigonelline (N'-methylnicotinate) |
| 3643 | | | N1-Methyl-2-pyridone-5-carboxamide |
| 3644 | | | N1-Methyl-4-pyridone-3-carboxamide |
| 3648 | | Riboflavin Metabolism | riboflavin (Vitamin B2) |
| 3649 | | | flavin adenine dinucleotide (FAD) |
| 3650 | | | flavin mononucleotide (FMN) |
| 3651 | | Pantothenate and CoA | pantothenate |
| 3653 | | Metabolism | phosphopantetheine |
| 3654 | | | 3'-dephosphocoenzyme A |
| 3656 | | | coenzyme A |
| 3658 | | | pantetheine |
| 3662 | | Ascorbate and Aldarate | ascorbate (Vitamin C) |
| 3663 | | Metabolism | dehydroascorbate |
| 3664 | | | threonate |
| 3667 | | | oxalate (ethanedioate) |
| 3668 | | | gulonate* |
| 3670 | | Tocopherol Metabolism | alpha-tocopherol |
| 3694 | | Biotin Metabolism | biotin |
| 3698 | | Folate Metabolism | 5-methyltetrahydrofolate (5MeTHF) |
| 3714 | | Hemoglobin and | heme |
| 3715 | | Porphyrin Metabolism | bilirubin (Z,Z) |
| 3718 | | | biliverdin |
| 3727 | | Thiamine Metabolism | thiamin (Vitamin B1) |
| 3728 | | | thiamin monophosphate |
| 3751 | | Vitamin B6 Metabolism | pyridoxamine |
| 3754 | | | pyridoxal |
| 3757 | Xenobiotics | Benzoate Metabolism | hippurate |
| 3771 | | | benzoate |
| 3978 | | Food Component/Plant | 3-formylindole |
| 4000 | | | gluconate |
| 4079 | | | ergothioneine |

TABLE 4A-continued

| PSO | Super Pathway | Sub Pathway | Biochemical Name |
|---|---|---|---|
| 4108 | | | homostachydrine* |
| 4131 | | | mannonate* |
| 4144 | | | N-glycolylneuraminate |
| 4221 | | | stachydrine |
| 4246 | | | methyl glucopyranoside (alpha + beta) |
| 4274 | | | pyrraline |
| 4363 | | Bacterial/Fungal | tartronate (hydroxymalonate) |
| 4756 | | Drug - Topical Agents | salicylate |
| 4832 | | Chemical | sulfate* |
| 4835 | | | O-sulfo-L-tyrosine |
| 4899 | | | ectoine |
| 4926 | | | phenol red |
| 4930 | | | perfluorooctanesulfonate (PFOS) |
| 4971 | | | thioproline |

TABLE 4B

| PSO | Platform | Comp ID | KEGG | HMDB | PUBCHEM |
|---|---|---|---|---|---|
| 1 | LC/MS pos early | 58 | C00037 | HMDB00123 | 750 |
| 2 | LC/MS pos early | 27710 | | HMDB00532 | 10972 |
| 5 | LC/MS pos early | 5086 | C01026 | HMDB00092 | 673 |
| 6 | LC/MS pos early | 3141 | C00719 | HMDB00043 | 247 |
| 9 | LC/MS pos early | 1648 | C00065 | HMDB00187 | 5951 |
| 10 | LC/MS polar | 37076 | | HMDB02931 | 65249 |
| 14 | LC/MS pos early | 543 | C01005 | HMDB00272 | 68841 |
| 16 | LC/MS pos early | 1284 | C00188 | HMDB00167 | 6288 |
| 17 | LC/MS neg | 33939 | | HMDB62557 | 152204 |
| 18 | LC/MS polar | 15142 | C05519 | HMDB04041 | 99289 |
| 21 | LC/MS polar | 18351 | C00263 | HMDB00719 | 12647 |
| 28 | LC/MS pos early | 1126 | C00041 | HMDB00161 | 5950 |
| 30 | LC/MS polar | 1585 | C02847 | HMDB00766 | 88064 |
| 34 | LC/MS pos early | 443 | C00049 | HMDB00191 | 5960 |
| 35 | LC/MS polar | 22185 | C01042 | HMDB00812 | 65065 |
| 38 | LC/MS pos early | 512 | C00152 | HMDB00168 | 6267 |
| 39 | LC/MS polar | 33942 | | HMDB06028 | 99715 |
| 40 | LC/MS pos early | 62060 | C03124 | HMDB32332 | 97663 |
| 41 | LC/MS pos early | 57 | C00025 | HMDB00148 | 611 |
| 42 | LC/MS pos early | 53 | C00064 | HMDB00641 | 5961 |
| 43 | LC/MS polar | 62101 | | | |
| 44 | LC/MS polar | 15720 | C00624 | HMDB01138 | 70914 |
| 45 | LC/MS pos early | 33943 | C02716 | HMDB06029 | 182230 |
| 47 | LC/MS pos early | 40499 | C03079 | HMDB01344 | 439902 |
| 50 | LC/MS pos early | 33487 | | HMDB61715 | 68662 |
| 51 | LC/MS pos early | 46225 | | | 134508 |
| 52 | LC/MS pos early | 35665 | C12270 | HMDB01067 | 5255 |
| 53 | LC/MS neg | 54923 | C20775 | | 7E+07 |
| 54 | LC/MS pos early | 1416 | C00334 | HMDB00112 | 119 |
| 55 | LC/MS pos early | 40007 | | HMDB02201 | 2572 |
| 56 | LC/MS pos early | 39577 | C15987 | | 70703 |
| 59 | LC/MS pos early | 42370 | C04322 | HMDB01301 | 1196 |
| 65 | LC/MS pos early | 59 | C00135 | HMDB00177 | 6274 |
| 66 | LC/MS pos early | 30460 | C01152 | HMDB00001 | 92105 |
| 67 | LC/MS pos early | 15677 | C01152 | HMDB00479 | 64969 |
| 68 | LC/MS pos early | 33946 | C02997 | HMDB32055 | 75619 |
| 74 | LC/MS pos early | 40730 | | HMDB02271 | 70630 |
| 75 | LC/MS pos early | 43493 | C00439 | HMDB00854 | 439233 |
| 76 | LC/MS pos early | 15716 | C05568 | HMDB02320 | 440129 |
| 77 | LC/MS pos early | 1768 | C00386 | HMDB00033 | 439224 |
| 80 | LC/MS pos early | 15747 | C01262 | HMDB00194 | 112072 |
| 82 | LC/MS pos early | 43831 | C05127 | HMDB00898 | 3614 |
| 83 | LC/MS pos early | 32350 | C05828 | HMDB02820 | 75810 |
| 84 | LC/MS pos early | 61868 | C05131 | HMDB02331 | 5E+06 |
| 92 | LC/MS pos early | 1301 | C00047 | HMDB00182 | 5962 |
| 93 | LC/MS polar | 36751 | C12989 | HMDB00446 | 92907 |
| 99 | LC/MS pos early | 62860 | C02728 | HMDB02038 | 164795 |
| 100 | LC/MS pos early | 62862 | C05545 | HMDB13287 | 193344 |
| 101 | LC/MS pos early | 1498 | C03793 | HMDB01325 | 440120 |
| 102 | LC/MS pos early | 15685 | C16741 | HMDB00450 | 1029 |
| 103 | LC/MS pos early | 43582 | | | |
| 105 | LC/MS neg | 6146 | C00956 | HMDB00510 | 469 |
| 107 | LC/MS polar | 38347 | C00322 | HMDB00225 | 71 |
| 113 | LC/MS pos early | 1444 | C00408 | HMDB00070 | 849 |
| 114 | LC/MS polar | 43231 | | HMDB61705 | 3E+06 |
| 117 | LC/MS pos early | 18319 | C00431 | HMDB03355 | 138 |

TABLE 4B-continued

| PSO | Platform | Comp ID | KEGG | HMDB | PUBCHEM |
|---|---|---|---|---|---|
| 119 | LC/MS pos early | 57687 | | | |
| 120 | LC/MS pos early | 64 | C00079 | HMDB00159 | 6140 |
| 121 | LC/MS neg | 33950 | C03519 | HMDB00512 | 74839 |
| 122 | LC/MS neg | 62566 | | | |
| 126 | LC/MS polar | 22130 | C05607 | HMDB00779 | 3848 |
| 137 | LC/MS neg | 1299 | C00082 | HMDB00158 | 6057 |
| 138 | LC/MS neg | 32390 | | HMDB00866 | 68310 |
| 150 | LC/MS neg | 32197 | C03672 | HMDB00755 | 9378 |
| 154 | LC/MS neg | 32553 | C02180 | HMDB60015 | 74426 |
| 180 | LC/MS pos early | 43392 | | HMDB06050 | 91482 |
| 181 | LC/MS pos early | 37451 | | HMDB14903 | 76957 |
| 191 | LC/MS neg | 48433 | | | 759256 |
| 210 | LC/MS pos early | 54 | C00078 | HMDB00929 | 6305 |
| 217 | LC/MS pos early | 48782 | | | 1E+07 |
| 221 | LC/MS pos early | 15140 | C00328 | HMDB00684 | 161166 |
| 227 | LC/MS polar | 43549 | C05653 | HMDB04089 | 101399 |
| 241 | LC/MS neg | 18349 | C02043 | HMDB00671 | 92904 |
| 254 | LC/MS neg | 27672 | | HMDB00682 | 10258 |
| 261 | LC/MS pos early | 60 | C00123 | HMDB00687 | 6106 |
| 263 | LC/MS neg | 62559 | | | |
| 265 | LC/MS neg | 22116 | C00233 | HMDB00695 | 70 |
| 273 | LC/MS pos early | 34407 | | HMDB00688 | 6E+06 |
| 280 | LC/MS polar | 12129 | | HMDB00754 | 69362 |
| 296 | LC/MS pos early | 1125 | C00407 | HMDB00172 | 6306 |
| 299 | LC/MS neg | 62558 | | | |
| 300 | LC/MS neg | 15676 | C00671 | HMDB03736 | 47 |
| 301 | LC/MS polar | 46537 | | HMDB00407 | 99823 |
| 303 | LC/MS pos early | 45095 | | HMDB00378 | 6E+06 |
| 306 | LC/MS pos early | 35428 | | HMDB02366 | 2E+07 |
| 311 | LC/MS polar | 15765 | | HMDB00622 | 11756 |
| 312 | LC/MS polar | 15745 | | HMDB01844 | 10349 |
| 318 | LC/MS pos early | 1649 | C00183 | HMDB00883 | 6287 |
| 321 | LC/MS neg | 62562 | | | |
| 323 | LC/MS polar | 44526 | C00141 | HMDB00019 | 49 |
| 326 | LC/MS pos early | 33441 | | HMDB00736 | 168379 |
| 328 | LC/MS polar | 1549 | C06001 | HMDB00336 | 87 |
| 332 | LC/MS pos early | 1302 | C00073 | HMDB00696 | 6137 |
| 333 | LC/MS neg | 1589 | C02712 | HMDB11745 | 448580 |
| 334 | LC/MS neg | 2829 | C03145 | HMDB01015 | 439750 |
| 337 | LC/MS pos early | 18374 | C02989 | HMDB02005 | 158980 |
| 342 | LC/MS pos early | 15915 | C00019 | HMDB01185 | 34756 |
| 343 | LC/MS neg | 42382 | C00021 | HMDB00939 | 439155 |
| 349 | LC/MS pos early | 15705 | C02291 | HMDB00099 | 439258 |
| 351 | LC/MS pos early | 1868 | C00097 | HMDB00574 | 5862 |
| 353 | LC/MS pos early | 39592 | | HMDB02108 | 24417 |
| 362 | LC/MS pos early | 37443 | C00606 | HMDB00996 | 109 |
| 363 | LC/MS pos early | 590 | C00519 | HMDB00965 | 107812 |
| 364 | LC/MS neg | 2125 | C00245 | HMDB00251 | 1123 |
| 365 | LC/MS neg | 48187 | | | 159864 |
| 367 | LC/MS neg | 35117 | C01959 | HMDB03584 | 68340 |
| 369 | LC/MS polar | 47089 | C00506 | HMDB02757 | 72886 |
| 371 | LC/MS pos early | 1638 | C00062 | HMDB00517 | 232 |
| 372 | LC/MS pos early | 15497 | C03406 | HMDB00052 | 828 |
| 373 | LC/MS pos early | 1670 | C00086 | HMDB00294 | 1176 |
| 375 | LC/MS pos early | 1493 | C00077 | HMDB03374 | 6262 |
| 379 | LC/MS pos early | 55072 | C03771 | HMDB04225 | 558 |
| 380 | LC/MS pos early | 2132 | C00327 | HMDB00904 | 9750 |
| 381 | LC/MS pos early | 22137 | C01924 | HMDB00670 | 9085 |
| 382 | LC/MS polar | 22138 | C02427 | HMDB00679 | 65072 |
| 383 | LC/MS neg | 1898 | C00148 | HMDB00162 | 145742 |
| 386 | LC/MS pos early | 36808 | C03626 | HMDB01539 | 123831 |
| 387 | LC/MS pos early | 33953 | C02562 | HMDB04620 | 67427 |
| 392 | LC/MS neg | 43249 | | | 1E+07 |
| 397 | LC/MS pos early | 32306 | C01157 | HMDB00725 | 5810 |
| 399 | LC/MS pos early | 35127 | | HMDB06695 | 1E+07 |
| 405 | LC/MS pos early | 57461 | | HMDB03148 | 160437 |
| 410 | LC/MS pos early | 43802 | C00581 | HMDB00128 | 763 |
| 411 | LC/MS pos early | 27718 | C00300 | HMDB00064 | 586 |
| 412 | LC/MS pos early | 513 | C00791 | HMDB00562 | 588 |
| 418 | LC/MS pos early | 1408 | C00134 | HMDB01414 | 1045 |
| 421 | LC/MS pos early | 485 | C00315 | HMDB01257 | 1102 |
| 426 | LC/MS pos early | 603 | C00750 | HMDB01256 | 1103 |
| 429 | LC/MS pos early | 1419 | C00170 | HMDB01173 | 439176 |
| 430 | LC/MS pos early | 37496 | C02714 | HMDB02064 | 122356 |
| 436 | LC/MS pos early | 57814 | | | |
| 438 | LC/MS pos early | 48114 | C02294 | HMDB01522 | 10111 |
| 439 | LC/MS pos early | 15681 | C01035 | HMDB03464 | 500 |
| 442 | LC/MS pos early | 2127 | C00051 | HMDB00125 | 124886 |

TABLE 4B-continued

| PSO | Platform | Comp ID | KEGG | HMDB | PUBCHEM |
|---|---|---|---|---|---|
| 443 | LC/MS pos early | 27727 | C00127 | HMDB03337 | 65359 |
| 445 | LC/MS pos early | 35159 | | HMDB00656 | 4E+06 |
| 446 | LC/MS pos early | 33944 | C11347 | | 4E+06 |
| 447 | LC/MS pos early | 15731 | C03451 | HMDB01066 | 440018 |
| 451 | LC/MS neg | 1494 | C01879 | HMDB00267 | 7405 |
| 454 | LC/MS polar | 52281 | | | |
| 456 | LC/MS pos early | 34592 | | HMDB05765 | 7E+06 |
| 459 | LC/MS neg | 48487 | | | |
| 460 | LC/MS neg | 62807 | | | |
| 461 | LC/MS neg | 62804 | C00920 | | 1E+07 |
| 465 | LC/MS pos early | 37063 | | HMDB29142 | 440103 |
| 467 | LC/MS pos early | 36738 | C05282 | HMDB11737 | 92865 |
| 468 | LC/MS pos early | 2730 | C05283 | HMDB11738 | 150914 |
| 469 | LC/MS pos early | 33949 | | HMDB11667 | 165527 |
| 471 | LC/MS pos early | 34456 | | HMDB11170 | 1E+07 |
| 472 | LC/MS neg | 18369 | | HMDB11171 | 151023 |
| 473 | LC/MS pos early | 55015 | | | 65254 |
| 474 | LC/MS pos early | 33934 | | HMDB03869 | 7E+06 |
| 475 | LC/MS pos early | 44872 | | HMDB29155 | 7E+06 |
| 476 | LC/MS neg | 33422 | | HMDB00594 | 111299 |
| 477 | LC/MS pos early | 33364 | | HMDB29159 | 8E+07 |
| 478 | LC/MS pos early | 33947 | | HMDB29160 | 4E+06 |
| 479 | LC/MS pos early | 2734 | | HMDB11741 | 94340 |
| 480 | LC/MS pos early | 43829 | | HMDB11172 | 7E+06 |
| 756 | LC/MS pos early | 40703 | | HMDB11178 | 6E+06 |
| 929 | LC/MS neg | 33945 | C05598 | HMDB00821 | 68144 |
| 955 | LC/MS neg | 20675 | C07326 | HMDB02712 | 64960 |
| 958 | LC/MS polar | 20488 | C00031 | HMDB00122 | 79025 |
| 959 | LC/MS polar | 31260 | C00668 | HMDB01401 | 5958 |
| 965 | LC/MS neg | 46896 | C00354 | | |
| 967 | LC/MS neg | 15522 | C00111 | HMDB01473 | 668 |
| 972 | LC/MS neg | 1414 | C00597 | HMDB00807 | 724 |
| 973 | LC/MS neg | 597 | C00074 | HMDB00263 | 1005 |
| 974 | LC/MS polar | 22250 | C00022 | HMDB00243 | 1060 |
| 975 | LC/MS polar | 527 | C00186 | HMDB00190 | 612 |
| 978 | LC/MS polar | 1572 | C00258 | HMDB00139 | 752 |
| 981 | LC/MS neg | 15442 | C00345 | HMDB01316 | 91493 |
| 982 | LC/MS polar | 1474 | C00199 | HMDB00618 | 439184 |
| 983 | LC/MS polar | 561 | C00117 | HMDB01548 | |
| 984 | LC/MS polar | 1763 | C00620 | HMDB01489 | 439236 |
| 986 | LC/MS pos early | 35649 | C05382 | HMDB01068 | 616 |
| 993 | LC/MS polar | 1471 | C00121 | HMDB00283 | 5779 |
| 994 | LC/MS polar | 15772 | C00474 | HMDB00508 | 6912 |
| 995 | LC/MS polar | 27731 | C01685 | HMDB00867 | 5E+06 |
| 997 | LC/MS polar | 37285 | C00231 | HMDB00868 | 439190 |
| 1018 | LC/MS polar | 48885 | C01904 | | 6912 |
| 1020 | LC/MS polar | 48255 | | | |
| 1023 | LC/MS polar | 53237 | | HMDB03219 | 5E+06 |
| 1024 | LC/MS polar | 61858 | | | |
| 1028 | LC/MS neg | 15910 | C02052 | HMDB01296 | 446495 |
| 1030 | LC/MS neg | 44688 | C01835 | HMDB01262 | 439586 |
| 1033 | LC/MS polar | 15586 | C00208 | HMDB00163 | 1E+07 |
| 1073 | LC/MS polar | 577 | C00095 | HMDB00660 | 5984 |
| 1078 | LC/MS polar | 46142 | C00794 | HMDB00247 | 5780 |
| 1079 | LC/MS polar | 584 | C00159 | HMDB00169 | 18950 |
| 1080 | LC/MS polar | 1469 | C00275 | HMDB01078 | 439198 |
| 1090 | LC/MS polar | 15706 | C00446 | HMDB00645 | 123912 |
| 1099 | LC/MS polar | 27719 | C00880 | HMDB00565 | 128869 |
| 1104 | LC/MS polar | 32344 | C00029 | HMDB00286 | 8629 |
| 1108 | LC/MS polar | 15860 | C00052 | HMDB00302 | 18068 |
| 1109 | LC/MS neg | 2763 | C00167 | HMDB00935 | 17473 |
| 1111 | LC/MS polar | 15903 | | | |
| 1115 | LC/MS neg | 46148 | | | |
| 1116 | LC/MS polar | 36831 | C00128 | HMDB01176 | 448209 |
| 1123 | LC/MS polar | 580 | C00352 | HMDB01254 | 439217 |
| 1127 | LC/MS polar | 15443 | C00191 | HMDB00127 | 444791 |
| 1131 | LC/MS polar | 15107 | C00357 | HMDB02817 | 439219 |
| 1132 | LC/MS polar | 15741 | C04256 | HMDB01367 | 440364 |
| 1138 | LC/MS pos early | 32377 | C00270 | HMDB00230 | 439197 |
| 1149 | LC/MS pos early | 48149 | C04540 | HMDB00489 | 123826 |
| 1150 | LC/MS polar | 42420 | | HMDB00613 | 3E+06 |
| 1152 | LC/MS pos early | 46539 | | HMDB00215 | 24139 |
| 1157 | LC/MS neg | 1564 | C00158 | HMDB00094 | 311 |
| 1163 | LC/MS polar | 528 | C00026 | HMDB00208 | 51 |
| 1165 | LC/MS pos early | 37058 | | HMDB61717 | 7E+07 |
| 1166 | LC/MS polar | 1437 | C00042 | HMDB00254 | 1110 |
| 1167 | LC/MS polar | 1643 | C00122 | HMDB00134 | 444972 |
| 1169 | LC/MS neg | 1303 | C00149 | HMDB00156 | 525 |

TABLE 4B-continued

| PSO | Platform | Comp ID | KEGG | HMDB | PUBCHEM |
|---|---|---|---|---|---|
| 1179 | LC/MS neg | 52282 | | | |
| 1181 | LC/MS polar | 15488 | C00227 | HMDB01494 | 186 |
| 1183 | LC/MS neg | 42109 | C00009 | HMDB01429 | 1061 |
| 1201 | LC/MS neg | 32489 | C01585 | HMDB00535 | 8892 |
| 1203 | LC/MS neg | 32492 | C06423 | HMDB00482 | 379 |
| 1204 | LC/MS neg | 12035 | C01601 | HMDB00847 | 8158 |
| 1205 | LC/MS neg | 1642 | C01571 | HMDB00511 | 2969 |
| 1217 | LC/MS neg | 1336 | C00249 | HMDB00220 | 985 |
| 1218 | LC/MS neg | 33447 | C08362 | HMDB03229 | 445638 |
| 1223 | LC/MS neg | 1358 | C01530 | HMDB00827 | 5281 |
| 1225 | LC/MS neg | 52285 | | | |
| 1236 | LC/MS neg | 1118 | C06425 | HMDB02212 | 10467 |
| 1239 | LC/MS neg | 33587 | C16526 | HMDB02231 | 5E+06 |
| 1244 | LC/MS neg | 1552 | C08316 | HMDB02068 | 5E+06 |
| 1247 | LC/MS neg | 52674 | C08323 | HMDB02368 | 5E+06 |
| 1253 | LC/MS neg | 57652 | | HMDB00477 | |
| 1258 | LC/MS neg | 18467 | C06428 | HMDB01999 | 446284 |
| 1259 | LC/MS neg | 32504 | C16513 | HMDB06528 | 6E+06 |
| 1260 | LC/MS neg | 44675 | C06429 | HMDB02183 | 445580 |
| 1264 | LC/MS neg | 57810 | | HMDB02007 | 1E+07 |
| 1265 | LC/MS neg | 1105 | C01595 | HMDB00673 | 5E+06 |
| 1267 | LC/MS neg | 34035 | C06426 | HMDB03073 | 5E+06 |
| 1269 | LC/MS neg | 35718 | C03242 | HMDB02925 | 5E+06 |
| 1270 | LC/MS neg | 1110 | C00219 | HMDB01043 | 444899 |
| 1271 | LC/MS neg | 32980 | C16527 | HMDB02226 | 5E+06 |
| 1272 | LC/MS neg | 37478 | C16513 | HMDB01976 | 6E+06 |
| 1273 | LC/MS neg | 32415 | C16533 | HMDB61714 | 5E+06 |
| 1274 | LC/MS neg | 17805 | C16525 | HMDB05060 | 6E+06 |
| 1276 | LC/MS neg | 35174 | | HMDB10378 | 5E+06 |
| 1277 | LC/MS neg | 57467 | | | |
| 1351 | LC/MS polar | 396 | C00489 | HMDB00661 | 743 |
| 1355 | LC/MS polar | 37253 | C02630 | HMDB00606 | 43 |
| 1359 | LC/MS polar | 31934 | C02360 | HMDB00321 | 193530 |
| 1360 | LC/MS polar | 62069 | | HMDB00345 | 151913 |
| 1363 | LC/MS polar | 20676 | C01384 | HMDB00176 | 444266 |
| 1372 | LC/MS polar | 32398 | C08277 | HMDB00792 | 5192 |
| 1430 | LC/MS pos early | 43761 | | | 227939 |
| 1446 | LC/MS pos early | 32412 | C02862 | HMDB02013 | 439829 |
| 1449 | LC/MS pos early | 32452 | C03017 | HMDB00824 | 107738 |
| 1452 | LC/MS polar | 1496 | C02170 | HMDB00202 | 487 |
| 1480 | LC/MS pos early | 32198 | C02571 | HMDB00201 | 1 |
| 1482 | LC/MS pos early | 43264 | | HMDB13127 | 5E+07 |
| 1483 | LC/MS pos early | 52984 | | HMDB13127 | |
| 1485 | LC/MS pos late | 32328 | | HMDB00705 | 6E+06 |
| 1487 | LC/MS pos early | 62557 | | | |
| 1488 | LC/MS pos late | 33936 | C02838 | HMDB00791 | 123701 |
| 1495 | LC/MS pos late | 34534 | | HMDB02250 | 1E+07 |
| 1496 | LC/MS pos late | 33952 | | HMDB05066 | 6E+06 |
| 1498 | LC/MS pos late | 44681 | C02990 | HMDB00222 | 461 |
| 1499 | LC/MS pos late | 53223 | | | 7E+07 |
| 1500 | LC/MS pos late | 34409 | | HMDB00848 | 6E+06 |
| 1501 | LC/MS pos late | 46223 | | HMDB06469 | 6E+06 |
| 1503 | LC/MS pos late | 61840 | | | |
| 1504 | LC/MS pos late | 35160 | | HMDB05065 | 6E+06 |
| 1506 | LC/MS pos late | 48182 | | | 9E+07 |
| 1517 | LC/MS pos late | 57513 | | HMDB06460 | |
| 1518 | LC/MS pos late | 57518 | | | |
| 1519 | LC/MS pos late | 57528 | | | |
| 1521 | LC/MS pos late | 62436 | | | |
| 1522 | LC/MS pos late | 57521 | | | |
| 1523 | LC/MS pos late | 57520 | | | |
| 1524 | LC/MS pos late | 57519 | | | |
| 1527 | LC/MS pos late | 57527 | | | |
| 1528 | LC/MS pos late | 57529 | | | |
| 1529 | LC/MS pos late | 57523 | | | |
| 1536 | LC/MS pos late | 57522 | | | |
| 1537 | LC/MS pos late | 57530 | | | |
| 1539 | LC/MS pos late | 61839 | | | |
| 1541 | LC/MS pos early | 36747 | C01181 | HMDB01161 | 134 |
| 1542 | LC/MS pos early | 15500 | C00318 | HMDB00062 | 10917 |
| 1547 | LC/MS polar | 542 | C01089 | HMDB00357 | 441 |
| 1565 | LC/MS polar | 61827 | | | 3E+06 |
| 1567 | LC/MS neg | 42489 | | | 21488 |
| 1582 | LC/MS neg | 22053 | | HMDB02203 | 26612 |
| 1711 | LC/MS neg | 57393 | C20388 | HMDB12535 | 5E+06 |
| 1718 | LC/MS pos late | 38102 | | HMDB02088 | 5E+06 |
| 1721 | LC/MS pos late | 38165 | C16512 | HMDB02100 | 4671 |
| 1731 | LC/MS neg | 39730 | | | 168274 |

TABLE 4B-continued

| PSO | Platform | Comp ID | KEGG | HMDB | PUBCHEM |
|---|---|---|---|---|---|
| 1732 | LC/MS neg | 39835 | | | |
| 1744 | LC/MS pos late | 57541 | | HMDB13648 | 1E+07 |
| 1753 | LC/MS polar | 1124 | C00137 | HMDB00211 | 892 |
| 1754 | LC/MS polar | 37112 | C19891 | HMDB34220 | |
| 1782 | LC/MS pos early | 15506 | C00114 | HMDB00097 | 305 |
| 1783 | LC/MS pos early | 34396 | C00588 | HMDB01565 | 1014 |
| 1784 | LC/MS polar | 34418 | C00307 | HMDB01413 | 13804 |
| 1786 | LC/MS pos early | 15990 | C00670 | HMDB00086 | 71920 |
| 1788 | LC/MS pos early | 1600 | C00346 | HMDB00224 | 1015 |
| 1789 | LC/MS neg | 34410 | C00570 | HMDB01564 | 123727 |
| 1790 | LC/MS pos early | 37455 | C01233 | HMDB00114 | 123874 |
| 1791 | LC/MS pos early | 57404 | | | 3E+06 |
| 1792 | LC/MS pos early | 52307 | | | 167572 |
| 1793 | LC/MS pos early | 40406 | C01104 | HMDB00925 | 1145 |
| 1811 | LC/MS pos late | 19258 | | HMDB07869 | 129657 |
| 1815 | LC/MS pos late | 53195 | | HMDB07883 | |
| 1827 | LC/MS pos late | 19130 | | HMDB00564 | 452110 |
| 1828 | LC/MS pos late | 52470 | | HMDB07969 | |
| 1829 | LC/MS pos late | 52616 | | HMDB07970 | |
| 1831 | LC/MS pos late | 52461 | | HMDB07972 | 6E+06 |
| 1834 | LC/MS pos late | 42446 | | HMDB07973 | 5E+06 |
| 1837 | LC/MS pos late | 54812 | | HMDB07974 | |
| 1841 | LC/MS pos late | 52454 | | | |
| 1845 | LC/MS pos late | 52462 | | HMDB07982 | 1E+07 |
| 1851 | LC/MS pos late | 52610 | | HMDB07991 | 6E+06 |
| 1866 | LC/MS pos late | 19132 | | HMDB08036 | 94190 |
| 1867 | LC/MS pos late | 52438 | | HMDB08038 | |
| 1870 | LC/MS pos late | 52452 | | HMDB08039 | |
| 1878 | LC/MS pos late | 42450 | | HMDB08048 | 2E+07 |
| 1884 | LC/MS pos late | 52611 | | HMDB08057 | |
| 1889 | LC/MS pos late | 52457 | | | 1E+07 |
| 1892 | LC/MS pos late | 52453 | | | |
| 1902 | LC/MS pos late | 52697 | | HMDB08123 | |
| 1903 | LC/MS pos late | 52603 | | HMDB08138 | 5E+06 |
| 1907 | LC/MS pos late | 52710 | | HMDB08147 | |
| 1945 | LC/MS pos late | 57341 | | HMDB08923 | 445468 |
| 1948 | LC/MS pos late | 57388 | | HMDB08925 | 5E+06 |
| 1949 | LC/MS pos late | 19263 | | HMDB05320 | 5E+06 |
| 1950 | LC/MS pos late | 42449 | | HMDB05322 | 1E+07 |
| 1953 | LC/MS pos late | 52464 | | HMDB05323 | 1E+07 |
| 1955 | LC/MS pos late | 52465 | | HMDB05324 | 1E+07 |
| 1962 | LC/MS pos late | 42448 | | HMDB08993 | |
| 1970 | LC/MS pos late | 52447 | | HMDB09003 | 5E+06 |
| 1974 | LC/MS pos late | 52466 | | HMDB05334 | 1E+07 |
| 1975 | LC/MS pos late | 52609 | | | 1E+07 |
| 1976 | LC/MS pos late | 52687 | | HMDB05349 | 1E+07 |
| 1979 | LC/MS pos late | 55041 | | HMDB09069 | |
| 1982 | LC/MS pos late | 53209 | | | |
| 1985 | LC/MS pos late | 53189 | | HMDB09102 | |
| 2016 | LC/MS pos late | 19261 | C13880 | HMDB12357 | 5E+06 |
| 2021 | LC/MS pos late | 19265 | | HMDB10163 | 1E+07 |
| 2024 | LC/MS pos late | 52235 | | HMDB12383 | |
| 2034 | LC/MS pos late | 52448 | | | 5E+06 |
| 2052 | LC/MS pos late | 52467 | | HMDB09789 | |
| 2067 | LC/MS pos late | 52449 | | HMDB09815 | |
| 2072 | LC/MS pos late | 54994 | | HMDB09844 | |
| 2105 | LC/MS pos late | 33955 | | HMDB10382 | 86554 |
| 2106 | LC/MS pos late | 35253 | | HMDB61702 | 2E+07 |
| 2107 | LC/MS pos late | 33230 | | HMDB10383 | 2E+07 |
| 2113 | LC/MS pos late | 33961 | | HMDB10384 | 497299 |
| 2115 | LC/MS pos late | 48258 | | HMDB02815 | 2E+07 |
| 2118 | LC/MS pos late | 34419 | C04100 | HMDB10386 | 1E+07 |
| 2136 | LC/MS neg | 34061 | C05208 | HMDB10395 | |
| 2157 | LC/MS pos late | 35631 | | HMDB11503 | 1E+07 |
| 2164 | LC/MS pos late | 42398 | | HMDB11130 | 1E+07 |
| 2165 | LC/MS neg | 41220 | | HMDB11129 | |
| 2166 | LC/MS pos late | 35628 | | HMDB11506 | 1E+07 |
| 2168 | LC/MS pos late | 36600 | | HMDB11507 | 5E+07 |
| 2179 | LC/MS neg | 35186 | | HMDB11517 | 4E+07 |
| 2192 | LC/MS neg | 46130 | | | 1E+07 |
| 2193 | LC/MS neg | 45966 | | | 1E+07 |
| 2194 | LC/MS neg | 19260 | | HMDB61694 | 1E+07 |
| 2199 | LC/MS neg | 45970 | | | 3E+06 |
| 2203 | LC/MS neg | 45968 | | | |
| 2206 | LC/MS neg | 35305 | | HMDB61695 | |
| 2209 | LC/MS neg | 19324 | | HMDB61696 | |
| 2211 | LC/MS neg | 36602 | | | |
| 2217 | LC/MS neg | 34214 | | HMDB61690 | |

TABLE 4B-continued

| PSO | Platform | Comp ID | KEGG | HMDB | PUBCHEM |
|---|---|---|---|---|---|
| 2310 | LC/MS pos late | 52477 | | HMDB11342 | |
| 2311 | LC/MS pos late | 52677 | | HMDB11343 | |
| 2312 | LC/MS pos late | 52716 | | HMDB11206 | 1E+07 |
| 2313 | LC/MS pos late | 52713 | | HMDB11207 | |
| 2314 | LC/MS pos late | 52673 | | HMDB11352 | |
| 2318 | LC/MS pos late | 52614 | | HMDB11375 | |
| 2327 | LC/MS pos late | 52475 | | HMDB05779 | 1E+07 |
| 2343 | LC/MS pos late | 39270 | | | |
| 2345 | LC/MS pos late | 44621 | | | |
| 2347 | LC/MS pos late | 39271 | | | |
| 2348 | LC/MS pos late | 54691 | | HMDB11441 | |
| 2350 | LC/MS neg | 15122 | C00116 | HMDB00131 | 753 |
| 2351 | LC/MS pos early | 43847 | C00093 | HMDB00126 | 754 |
| 2356 | LC/MS polar | 48857 | C03274 | | 439964 |
| 2357 | LC/MS neg | 35625 | C01885 | HMDB11561 | 79050 |
| 2360 | LC/MS neg | 21127 | | HMDB31074 | 14900 |
| 2361 | LC/MS neg | 52431 | | HMDB11565 | |
| 2364 | LC/MS neg | 21184 | | HMDB11567 | 5E+06 |
| 2371 | LC/MS neg | 34397 | C13857 | HMDB11549 | 5E+06 |
| 2374 | LC/MS neg | 35153 | | HMDB11587 | |
| 2375 | LC/MS neg | 34383 | | HMDB11530 | 137938 |
| 2376 | LC/MS neg | 33419 | | HMDB11533 | 123409 |
| 2379 | LC/MS neg | 21232 | | HMDB11537 | 5E+06 |
| 2381 | LC/MS neg | 19266 | C13856 | HMDB04666 | 5E+06 |
| 2383 | LC/MS neg | 48675 | | HMDB11557 | |
| 2394 | LC/MS pos late | 54954 | | | |
| 2395 | LC/MS pos late | 54966 | | | |
| 2407 | LC/MS pos late | 54990 | | HMDB07098 | |
| 2411 | LC/MS pos late | 54942 | C13861 | HMDB07102 | |
| 2413 | LC/MS pos late | 52634 | | HMDB07103 | |
| 2416 | LC/MS pos late | 52631 | | | |
| 2418 | LC/MS pos late | 54941 | | | |
| 2419 | LC/MS pos late | 54957 | | HMDB07112 | |
| 2420 | LC/MS pos late | 54958 | | HMDB07112 | |
| 2422 | LC/MS pos late | 57373 | | HMDB07121 | |
| 2423 | LC/MS pos late | 57374 | | HMDB07121 | |
| 2426 | LC/MS pos late | 54947 | | | |
| 2429 | LC/MS pos late | 54946 | | HMDB07218 | |
| 2431 | LC/MS pos late | 46798 | | HMDB07219 | |
| 2432 | LC/MS pos late | 46799 | | HMDB07219 | |
| 2442 | LC/MS pos late | 57450 | | | |
| 2443 | LC/MS pos late | 57449 | | | |
| 2445 | LC/MS pos late | 54961 | | HMDB07228 | |
| 2448 | LC/MS pos late | 57387 | | | |
| 2449 | LC/MS pos late | 57368 | | | |
| 2474 | LC/MS pos late | 17769 | C00836 | HMDB00269 | 3126 |
| 2480 | LC/MS pos late | 52604 | | HMDB11760 | 5E+06 |
| 2481 | LC/MS pos late | 1759 | | | 5E+06 |
| 2488 | LC/MS pos late | 44877 | | HMDB04949 | 5E+06 |
| 2491 | LC/MS pos late | 54979 | | HMDB04950 | 5E+06 |
| 2493 | LC/MS pos late | 57424 | | HMDB04951 | 5E+06 |
| 2498 | LC/MS pos late | 57417 | | | |
| 2499 | LC/MS pos late | 57372 | | | |
| 2513 | LC/MS pos late | 57432 | | | |
| 2514 | LC/MS pos late | 57434 | | | |
| 2517 | LC/MS pos late | 57437 | | | |
| 2518 | LC/MS pos late | 57443 | | | |
| 2520 | LC/MS pos late | 57418 | | | 6E+06 |
| 2522 | LC/MS pos late | 53013 | | | |
| 2523 | LC/MS pos late | 52234 | | | |
| 2525 | LC/MS pos late | 57371 | | | |
| 2543 | LC/MS pos late | 57595 | | | |
| 2547 | LC/MS pos late | 57453 | | | |
| 2549 | LC/MS pos late | 53010 | | | |
| 2561 | LC/MS pos late | 52434 | | | 1E+07 |
| 2563 | LC/MS pos late | 57473 | | HMDB12087 | |
| 2564 | LC/MS pos late | 57476 | | | |
| 2565 | LC/MS pos late | 37506 | | | 1E+07 |
| 2566 | LC/MS pos late | 62851 | | | |
| 2567 | LC/MS pos late | 19503 | C00550 | HMDB01348 | 6E+06 |
| 2568 | LC/MS pos late | 48492 | | HMDB12103 | |
| 2569 | LC/MS pos late | 52436 | | HMDB12105 | |
| 2570 | LC/MS pos late | 57330 | | | |
| 2575 | LC/MS pos late | 42463 | | HMDB12097 | 1E+07 |
| 2577 | LC/MS pos late | 52433 | | | |
| 2579 | LC/MS pos late | 42459 | | | |
| 2580 | LC/MS pos late | 52615 | | | |
| 2581 | LC/MS pos late | 37529 | | HMDB12101 | 6E+06 |

TABLE 4B-continued

| PSO | Platform | Comp ID | KEGG | HMDB | PUBCHEM |
|---|---|---|---|---|---|
| 2583 | LC/MS pos late | 48490 | | HMDB12102 | |
| 2588 | LC/MS pos late | 48493 | | HMDB12104 | |
| 2591 | LC/MS pos late | 47153 | | HMDB12107 | |
| 2592 | LC/MS pos late | 52437 | | | |
| 2594 | LC/MS pos late | 17747 | C00319 | HMDB00252 | 5E+06 |
| 2610 | LC/MS polar | 531 | C03761 | HMDB00355 | 1662 |
| 2624 | LC/MS pos late | 6065 | C01802 | HMDB02719 | 439577 |
| 2625 | LC/MS pos late | 63 | C00187 | HMDB00067 | 1E+07 |
| 2649 | LC/MS pos late | 38125 | C00599 | HMDB00921 | 91477 |
| 2652 | LC/MS pos late | 33997 | C01789 | HMDB02869 | 173183 |
| 2669 | LC/MS pos late | 47890 | | HMDB06119 | 107722 |
| 3453 | LC/MS pos early | 2133 | C00130 | HMDB00175 | 8582 |
| 3454 | LC/MS neg | 1123 | C00294 | HMDB00195 | 6021 |
| 3455 | LC/MS pos early | 3127 | C00262 | HMDB00157 | 790 |
| 3456 | LC/MS pos early | 3147 | C00385 | HMDB00292 | 1188 |
| 3458 | LC/MS neg | 15136 | C01762 | HMDB00299 | 64959 |
| 3461 | LC/MS pos early | 48351 | | HMDB02721 | 65095 |
| 3462 | LC/MS neg | 15076 | C05512 | HMDB00071 | 65058 |
| 3464 | LC/MS neg | 1604 | C00366 | HMDB00289 | 1175 |
| 3466 | LC/MS pos early | 1107 | C02350 | HMDB00462 | 204 |
| 3471 | LC/MS neg | 3108 | C00008 | HMDB01341 | 6022 |
| 3472 | LC/MS pos early | 32342 | C00020 | HMDB00045 | 6083 |
| 3473 | LC/MS neg | 35142 | C01367 | HMDB03540 | 41211 |
| 3474 | LC/MS neg | 36815 | C00946 | HMDB11617 | 94136 |
| 3478 | LC/MS neg | 57838 | C03794 | HMDB00536 | 195 |
| 3479 | LC/MS pos early | 555 | C00212 | HMDB00050 | 60961 |
| 3480 | LC/MS pos early | 554 | C00147 | HMDB00034 | 190 |
| 3485 | LC/MS pos early | 15650 | C02494 | HMDB03331 | 27476 |
| 3495 | LC/MS neg | 35157 | | HMDB41623 | 161466 |
| 3498 | LC/MS neg | 46333 | C00360 | HMDB00905 | 12599 |
| 3505 | LC/MS pos early | 48130 | | HMDB00912 | 165243 |
| 3507 | LC/MS neg | 2848 | C00035 | HMDB01201 | 8977 |
| 3508 | LC/MS pos early | 2849 | C00144 | HMDB01397 | 6804 |
| 3513 | LC/MS pos early | 1573 | C00387 | HMDB00133 | 6802 |
| 3514 | LC/MS pos early | 32352 | C00242 | HMDB00132 | 764 |
| 3516 | LC/MS pos early | 35114 | C02242 | HMDB00897 | 11361 |
| 3522 | LC/MS pos early | 35137 | | HMDB04824 | 92919 |
| 3528 | LC/MS pos early | 35662 | C00362 | HMDB01044 | 65059 |
| 3530 | LC/MS neg | 1411 | C00330 | HMDB00085 | 187790 |
| 3533 | LC/MS polar | 1594 | C00438 | HMDB00828 | 93072 |
| 3534 | LC/MS polar | 601 | C00337 | HMDB03349 | 648 |
| 3535 | LC/MS polar | 1505 | C00295 | HMDB00226 | 967 |
| 3537 | LC/MS polar | 35172 | | HMDB00788 | 92751 |
| 3541 | LC/MS neg | 5345 | C00015 | HMDB00295 | 6031 |
| 3542 | LC/MS pos early | 2856 | C00105 | HMDB00288 | 6030 |
| 3547 | LC/MS neg | 606 | C00299 | HMDB00296 | 6029 |
| 3548 | LC/MS neg | 605 | C00106 | HMDB00300 | 1174 |
| 3549 | LC/MS neg | 33442 | C02067 | HMDB00767 | 15047 |
| 3550 | LC/MS neg | 61833 | | | 94312 |
| 3552 | LC/MS neg | 35136 | | HMDB00884 | 445408 |
| 3563 | LC/MS neg | 52602 | C00526 | HMDB00012 | 13712 |
| 3565 | LC/MS pos early | 57549 | C05100 | HMDB02031 | 160663 |
| 3566 | LC/MS pos early | 3155 | C02642 | HMDB00026 | 111 |
| 3567 | LC/MS pos early | 55 | C00099 | HMDB00056 | 239 |
| 3568 | LC/MS polar | 37432 | C01073 | | 76406 |
| 3572 | LC/MS neg | 2841 | C00112 | HMDB01546 | 6132 |
| 3573 | LC/MS pos early | 2372 | C00055 | HMDB00095 | 6131 |
| 3576 | LC/MS neg | 37465 | C02354 | HMDB11691 | 417654 |
| 3577 | LC/MS pos early | 514 | C00475 | HMDB00089 | 6175 |
| 3578 | LC/MS pos early | 573 | C00380 | HMDB00630 | 597 |
| 3579 | LC/MS pos early | 35132 | | | 159649 |
| 3580 | LC/MS pos early | 22119 | | HMDB00982 | 92918 |
| 3585 | LC/MS pos early | 533 | C00239 | HMDB01202 | 13945 |
| 3587 | LC/MS pos early | 15949 | C00881 | HMDB00014 | 13711 |
| 3588 | LC/MS pos early | 57554 | | | 150971 |
| 3589 | LC/MS pos early | 38159 | C03592 | HMDB02224 | 440055 |
| 3598 | LC/MS neg | 2183 | C00214 | HMDB00273 | 5789 |
| 3599 | LC/MS neg | 604 | C00178 | HMDB00262 | 1135 |
| 3602 | LC/MS pos early | 1566 | C05145 | HMDB03911 | 64956 |
| 3603 | LC/MS pos early | 37070 | | HMDB61711 | 13130 |
| 3607 | LC/MS neg | 52740 | | | 112074 |
| 3608 | LC/MS neg | 62396 | | | 94231 |
| 3624 | LC/MS pos early | 594 | C00153 | HMDB01406 | 936 |
| 3627 | LC/MS pos early | 33013 | C03150 | HMDB00855 | 439924 |
| 3628 | LC/MS neg | 5278 | C00003 | HMDB00902 | 5893 |
| 3636 | LC/MS pos early | 27665 | C02918 | HMDB00699 | 1E+07 |
| 3641 | LC/MS pos early | 32401 | C01004 | HMDB00875 | 5570 |
| 3643 | LC/MS neg | 40469 | C05842 | HMDB04193 | 69698 |

TABLE 4B-continued

| PSO | Platform | Comp ID | KEGG | HMDB | PUBCHEM |
|---|---|---|---|---|---|
| 3644 | LC/MS pos early | 57584 | C05843 | HMDB04194 | 440810 |
| 3648 | LC/MS neg | 1827 | C00255 | HMDB00244 | 493570 |
| 3649 | LC/MS neg | 2134 | C00016 | HMDB01248 | 643975 |
| 3650 | LC/MS neg | 15797 | C00061 | HMDB01520 | 710 |
| 3651 | LC/MS pos early | 1508 | C00864 | HMDB00210 | 6613 |
| 3653 | LC/MS neg | 15504 | C01134 | HMDB01416 | 987 |
| 3654 | LC/MS neg | 18289 | C00882 | HMDB01373 | 444485 |
| 3656 | LC/MS neg | 46322 | C00010 | HMDB01423 | 317 |
| 3658 | LC/MS polar | 57555 | C00831 | | 439322 |
| 3662 | LC/MS pos early | 32354 | C00072 | HMDB00044 | |
| 3663 | LC/MS polar | 1659 | C05422 | HMDB01264 | 835 |
| 3664 | LC/MS polar | 27738 | C01620 | HMDB00943 | 151152 |
| 3667 | LC/MS neg | 20694 | C00209 | HMDB02329 | 971 |
| 3668 | LC/MS polar | 46957 | C00257 | HMDB03290 | 1E+07 |
| 3670 | LC/MS pos late | 1561 | C02477 | HMDB01893 | 14985 |
| 3694 | LC/MS pos early | 568 | C00120 | HMDB00030 | 171548 |
| 3698 | LC/MS neg | 18330 | C00440 | HMDB01396 | 146 |
| 3714 | LC/MS pos late | 41754 | C00032 | HMDB03178 | 26945 |
| 3715 | LC/MS pos late | 43807 | C00486 | HMDB00054 | 5E+06 |
| 3718 | LC/MS pos late | 2137 | C00500 | HMDB01008 | 5E+06 |
| 3727 | LC/MS pos early | 5341 | C00378 | HMDB00235 | 1130 |
| 3728 | LC/MS neg | 15798 | C01081 | HMDB02666 | 3E+06 |
| 3751 | LC/MS pos early | 2150 | C00534 | HMDB01431 | 1052 |
| 3754 | LC/MS pos early | 1651 | C00250 | HMDB01545 | 1050 |
| 3757 | LC/MS neg | 15753 | C01586 | HMDB00714 | 464 |
| 3771 | LC/MS neg | 15778 | C00180 | HMDB01870 | 243 |
| 3978 | LC/MS pos early | 62863 | C08493 | HMDB29737 | 10256 |
| 4000 | LC/MS polar | 587 | C00257 | HMDB00625 | 10690 |
| 4079 | LC/MS pos early | 37459 | C05570 | HMDB03045 | 3E+06 |
| 4108 | LC/MS pos early | 33009 | C08283 | HMDB33433 | 441447 |
| 4131 | LC/MS polar | 62864 | | | 3E+06 |
| 4144 | LC/MS pos early | 37123 | C03410 | HMDB00833 | 123802 |
| 4221 | LC/MS pos early | 34384 | C10172 | HMDB04827 | 115244 |
| 4246 | LC/MS neg | 46144 | | | |
| 4274 | LC/MS pos early | 48428 | | HMDB33143 | 122228 |
| 4363 | LC/MS neg | 20693 | C02287 | HMDB35227 | 45 |
| 4756 | LC/MS polar | 1515 | C00805 | HMDB01895 | 338 |
| 4832 | LC/MS neg | 46960 | C00059 | HMDB01448 | 1118 |
| 4835 | LC/MS neg | 45413 | | | 514186 |
| 4899 | LC/MS pos early | 35651 | C06231 | | 126041 |
| 4926 | LC/MS neg | 36817 | C12600 | | 4766 |
| 4930 | LC/MS polar | 57564 | C18142 | HMDB59586 | 74483 |
| 4971 | LC/MS pos early | 53231 | | | 93176 |

TABLE 4C

| PSO | Sp/ SPF | ABX/ SPF | GF/ SPF | Sp/ ABX | GF/ ABX | GF/ Sp | GE |
|---|---|---|---|---|---|---|---|
| 1 | 0.83 | 0.82 | 0.94 | 1.01 | 1.15 | 1.14 | |
| 2 | 0.91 | 1.01 | 1.38 | 0.91 | 1.37 | 1.51 | |
| 5 | 0.76 | 0.69 | 0.83 | 1.10 | 1.20 | 1.09 | Y |
| 6 | 0.81 | 0.66 | 0.80 | 1.23 | 1.21 | 0.98 | Y |
| 9 | 0.85 | 1.07 | 1.04 | 0.79 | 0.97 | 1.23 | |
| 10 | 0.80 | 0.82 | 0.90 | 0.98 | 1.10 | 1.12 | Y |
| 14 | 0.80 | 1.01 | 1.53 | 0.79 | 1.51 | 1.91 | |
| 16 | 0.79 | 0.80 | 0.92 | 0.98 | 1.14 | 1.17 | |
| 17 | 0.90 | 0.84 | 1.01 | 1.07 | 1.19 | 1.12 | |
| 18 | 0.79 | 0.68 | 0.82 | 1.16 | 1.21 | 1.04 | |
| 21 | 0.39 | 0.29 | 0.52 | 1.32 | 1.78 | 1.35 | Y |
| 28 | 0.82 | 0.83 | 0.86 | 0.99 | 1.04 | 1.05 | y |
| 30 | 0.82 | 0.72 | 0.83 | 1.15 | 1.16 | 1.01 | Y |
| 34 | 0.82 | 0.81 | 0.83 | 1.01 | 1.03 | 1.01 | Y |
| 35 | 0.79 | 0.69 | 0.73 | 1.15 | 1.06 | 0.92 | Y |
| 38 | 0.95 | 0.95 | 0.96 | 1.00 | 1.01 | 1.01 | |
| 39 | 0.92 | 0.87 | 0.98 | 1.06 | 1.13 | 1.07 | |
| 40 | 0.69 | 0.55 | 0.56 | 1.27 | 1.03 | 0.81 | Y |
| 41 | 0.87 | 0.84 | 0.86 | 1.04 | 1.03 | 0.99 | Y |
| 42 | 0.86 | 0.70 | 0.67 | 1.23 | 0.96 | 0.78 | Y |
| 43 | 1.87 | 0.77 | 0.63 | 2.42 | 0.81 | 0.34 | Y |
| 44 | 0.77 | 0.76 | 0.75 | 1.02 | 1.00 | 0.98 | y |
| 45 | 0.83 | 0.70 | 0.69 | 1.18 | 0.97 | 0.83 | Y |
| 47 | 0.64 | 1.04 | 1.05 | 0.61 | 1.01 | 1.65 | Y |
| 50 | 0.82 | 0.71 | 0.84 | 1.16 | 1.19 | 1.02 | |
| 51 | 0.97 | 0.73 | 0.51 | 1.34 | 0.70 | 0.52 | Y |

TABLE 4C-continued

| PSO | Sp/ SPF | ABX/ SPF | GF/ SPF | Sp/ ABX | GF/ ABX | GF/ Sp | GE |
|---|---|---|---|---|---|---|---|
| 52 | 0.84 | 0.80 | 0.74 | 1.05 | 0.93 | 0.88 | Y |
| 53 | 0.88 | 0.85 | 0.81 | 1.04 | 0.95 | 0.92 | Y |
| 54 | 0.80 | 0.75 | 0.72 | 1.06 | 0.96 | 0.90 | Y |
| 55 | 0.83 | 0.88 | 0.60 | 0.94 | 0.68 | 0.72 | |
| 56 | 0.76 | 1.22 | 0.72 | 0.62 | 0.59 | 0.95 | |
| 59 | 0.81 | 1.70 | 0.63 | 0.47 | 0.37 | 0.78 | y |
| 65 | 0.96 | 1.14 | 0.96 | 0.85 | 0.85 | 1.00 | |
| 66 | 0.81 | 1.35 | 0.81 | 0.60 | 0.60 | 1.00 | Y |
| 67 | 0.73 | 1.01 | 0.70 | 0.72 | 0.70 | 0.96 | |
| 68 | 0.70 | 0.94 | 1.02 | 0.74 | 1.08 | 1.46 | y |
| 74 | 1.60 | 0.33 | 0.33 | 4.81 | 0.99 | 0.20 | Y |
| 75 | 1.22 | 1.80 | 1.53 | 0.68 | 0.85 | 1.26 | y |
| 76 | 0.90 | 0.81 | 0.76 | 1.11 | 0.94 | 0.84 | Y |
| 77 | 0.39 | 0.34 | 0.52 | 1.15 | 1.53 | 1.33 | Y |
| 80 | 0.82 | 0.40 | 0.42 | 2.04 | 1.04 | 0.51 | Y |
| 82 | 0.42 | 0.27 | 0.22 | 1.54 | 0.82 | 0.53 | y |
| 83 | 0.51 | 0.36 | 0.41 | 1.42 | 1.15 | 0.81 | y |
| 84 | 0.33 | 0.43 | 0.36 | 0.76 | 0.85 | 1.11 | Y |
| 92 | 0.89 | 0.90 | 0.94 | 0.98 | 1.04 | 1.06 | |
| 93 | 0.88 | 0.49 | 0.58 | 1.80 | 1.18 | 0.66 | Y |
| 99 | 0.86 | 0.64 | 0.57 | 1.35 | 0.89 | 0.66 | Y |
| 100 | 0.75 | 0.57 | 0.57 | 1.30 | 0.99 | 0.76 | Y |
| 101 | 0.73 | 0.61 | 0.65 | 1.19 | 1.06 | 0.90 | Y |
| 102 | 0.66 | 0.79 | 0.66 | 0.83 | 0.83 | 1.00 | Y |
| 103 | 0.82 | 0.77 | 0.82 | 1.07 | 1.06 | 0.99 | Y |
| 105 | 0.85 | 1.05 | 1.07 | 0.80 | 1.02 | 1.27 | |

TABLE 4C-continued

| PSO | Sp/ SPF | ABX/ SPF | GF/ SPF | Sp/ ABX | GF/ ABX | GF/ Sp | GE |
|---|---|---|---|---|---|---|---|
| 107 | 1.01 | 1.09 | 1.50 | 0.93 | 1.38 | 1.49 | |
| 113 | 0.75 | 0.57 | 0.47 | 1.32 | 0.83 | 0.63 | Y |
| 114 | 0.96 | 1.02 | 1.70 | 0.94 | 1.66 | 1.77 | |
| 117 | 0.98 | 0.85 | 0.60 | 1.16 | 0.71 | 0.62 | |
| 119 | 1.79 | 0.09 | 0.16 | 19.45 | 1.71 | 0.09 | Y |
| 120 | 0.90 | 0.82 | 0.79 | 1.10 | 0.96 | 0.88 | Y |
| 121 | 1.09 | 0.83 | 0.81 | 1.31 | 0.98 | 0.74 | |
| 122 | 0.95 | 0.79 | 0.82 | 1.19 | 1.03 | 0.87 | |
| 126 | 0.73 | 0.60 | 0.58 | 1.22 | 0.96 | 0.79 | y |
| 137 | 0.97 | 0.89 | 0.79 | 1.10 | 0.90 | 0.82 | y |
| 138 | 0.85 | 0.75 | 0.52 | 1.14 | 0.70 | 0.61 | Y |
| 150 | 1.01 | 0.81 | 0.79 | 1.24 | 0.97 | 0.78 | Y |
| 154 | 0.63 | 0.44 | 0.44 | 1.43 | 1.00 | 0.70 | Y |
| 180 | 0.91 | 0.95 | 1.00 | 0.96 | 1.04 | 1.09 | |
| 181 | 0.88 | 0.91 | 1.07 | 0.97 | 1.19 | 1.22 | |
| 191 | 0.98 | 0.40 | 0.77 | 2.41 | 1.90 | 0.79 | |
| 210 | 0.79 | 0.81 | 0.77 | 0.98 | 0.95 | 0.97 | Y |
| 217 | 0.78 | 0.71 | 0.73 | 1.11 | 1.03 | 0.93 | Y |
| 221 | 0.91 | 0.86 | 0.82 | 1.06 | 0.95 | 0.89 | |
| 227 | 0.85 | 0.34 | 0.88 | 2.49 | 2.60 | 1.04 | |
| 241 | 0.74 | 0.48 | 0.59 | 1.56 | 1.24 | 0.80 | |
| 254 | 0.56 | 0.31 | 0.08 | 1.79 | 0.25 | 0.14 | Y |
| 261 | 0.86 | 0.82 | 0.81 | 1.04 | 0.98 | 0.95 | y |
| 263 | 0.92 | 0.78 | 0.97 | 1.18 | 1.24 | 1.05 | |
| 265 | 1.33 | 1.28 | 1.26 | 1.04 | 0.98 | 0.95 | |
| 273 | 0.95 | 0.90 | 1.12 | 1.05 | 1.25 | 1.18 | |
| 280 | 0.72 | 0.89 | 0.80 | 0.81 | 0.90 | 1.11 | Y |
| 296 | 0.87 | 0.77 | 0.77 | 1.13 | 1.01 | 0.89 | Y |
| 299 | 1.15 | 0.75 | 0.66 | 1.54 | 0.89 | 0.58 | |
| 300 | 1.35 | 0.96 | 1.21 | 1.40 | 1.26 | 0.90 | |
| 301 | 0.64 | 0.83 | 0.71 | 0.77 | 0.85 | 1.10 | Y |
| 303 | 0.95 | 0.90 | 0.97 | 1.05 | 1.07 | 1.02 | |
| 306 | 0.87 | 0.83 | 0.87 | 1.04 | 1.05 | 1.01 | |
| 311 | 0.89 | 0.69 | 0.81 | 1.30 | 1.18 | 0.90 | Y |
| 312 | 0.72 | 0.67 | 0.77 | 1.08 | 1.15 | 1.06 | Y |
| 318 | 0.87 | 0.85 | 0.91 | 1.02 | 1.07 | 1.05 | |
| 321 | 0.95 | 0.69 | 0.88 | 1.37 | 1.27 | 0.92 | y |
| 323 | 1.23 | 1.13 | 1.21 | 1.09 | 1.07 | 0.98 | |
| 326 | 1.01 | 1.03 | 1.20 | 0.99 | 1.17 | 1.18 | |
| 328 | 0.80 | 0.76 | 1.02 | 1.06 | 1.34 | 1.27 | |
| 332 | 0.74 | 0.68 | 0.69 | 1.09 | 1.02 | 0.94 | Y |
| 333 | 1.03 | 0.69 | 0.89 | 1.49 | 1.28 | 0.86 | Y |
| 334 | 0.82 | 0.86 | 0.85 | 0.95 | 0.98 | 1.03 | y |
| 337 | 0.77 | 0.47 | 0.73 | 1.65 | 1.57 | 0.95 | Y |
| 342 | 0.87 | 0.79 | 0.77 | 1.09 | 0.97 | 0.89 | Y |
| 343 | 0.82 | 0.91 | 0.81 | 0.90 | 0.89 | 0.98 | |
| 349 | 0.70 | 0.53 | 0.70 | 1.31 | 1.31 | 1.00 | Y |
| 351 | 0.68 | 1.04 | 0.66 | 0.66 | 0.63 | 0.96 | y |
| 353 | 0.67 | 1.21 | 1.04 | 0.55 | 0.86 | 1.56 | |
| 362 | 0.80 | 0.86 | 0.98 | 0.92 | 1.14 | 1.23 | |
| 363 | 0.80 | 0.96 | 0.98 | 0.84 | 1.02 | 1.22 | Y |
| 364 | 0.84 | 0.80 | 0.77 | 1.05 | 0.97 | 0.92 | Y |
| 365 | 0.92 | 0.74 | 0.94 | 1.25 | 1.27 | 1.01 | |
| 367 | 0.64 | 0.71 | 0.54 | 0.89 | 0.75 | 0.84 | Y |
| 369 | 0.92 | 0.37 | 0.40 | 2.49 | 1.08 | 0.43 | Y |
| 371 | 0.88 | 0.88 | 0.93 | 1.00 | 1.06 | 1.06 | |
| 372 | 0.76 | 0.82 | 0.86 | 0.93 | 1.05 | 1.12 | |
| 373 | 0.98 | 0.79 | 0.87 | 1.25 | 1.11 | 0.89 | |
| 375 | 0.84 | 0.77 | 0.92 | 1.08 | 1.19 | 1.11 | |
| 379 | 0.82 | 0.80 | 0.78 | 1.02 | 0.97 | 0.95 | |
| 380 | 0.82 | 0.78 | 0.71 | 1.05 | 0.92 | 0.88 | |
| 381 | 0.90 | 0.86 | 0.77 | 1.06 | 0.90 | 0.85 | |
| 382 | 0.95 | 0.84 | 0.52 | 1.13 | 0.62 | 0.55 | Y |
| 383 | 0.82 | 0.87 | 0.93 | 0.94 | 1.06 | 1.13 | |
| 386 | 1.07 | 0.89 | 0.93 | 1.21 | 1.05 | 0.87 | |
| 387 | 0.84 | 0.86 | 0.80 | 0.98 | 0.93 | 0.96 | |
| 392 | 1.01 | 0.75 | 0.40 | 1.35 | 0.54 | 0.40 | Y |
| 397 | 0.86 | 0.93 | 0.91 | 0.92 | 0.97 | 1.06 | Y |
| 399 | 0.81 | 0.67 | 0.69 | 1.22 | 1.03 | 0.85 | Y |
| 405 | 0.68 | 0.70 | 0.65 | 0.97 | 0.93 | 0.96 | |
| 410 | 0.91 | 0.88 | 1.00 | 1.03 | 1.13 | 1.09 | |
| 411 | 0.88 | 0.82 | 0.83 | 1.07 | 1.01 | 0.94 | Y |
| 412 | 0.88 | 0.83 | 0.93 | 1.06 | 1.12 | 1.06 | |
| 418 | 0.91 | 0.99 | 0.93 | 0.93 | 0.94 | 1.01 | |
| 421 | 0.71 | 0.77 | 0.73 | 0.93 | 0.94 | 1.02 | y |
| 426 | 0.68 | 0.74 | 0.70 | 0.92 | 0.95 | 1.03 | |
| 429 | 0.92 | 0.79 | 0.84 | 1.16 | 1.06 | 0.92 | |

TABLE 4C-continued

| PSO | Sp/ SPF | ABX/ SPF | GF/ SPF | Sp/ ABX | GF/ ABX | GF/ Sp | GE |
|---|---|---|---|---|---|---|---|
| 430 | 1.16 | 0.94 | 1.10 | 1.23 | 1.17 | 0.95 | |
| 436 | 1.01 | 0.68 | 0.97 | 1.47 | 1.41 | 0.96 | Y |
| 438 | 0.72 | 0.72 | 0.72 | 1.00 | 1.00 | 1.00 | |
| 439 | 0.72 | 0.83 | 0.82 | 0.87 | 0.98 | 1.13 | y |
| 442 | 0.75 | 1.06 | 0.66 | 0.71 | 0.62 | 0.88 | |
| 443 | 0.84 | 0.87 | 0.83 | 0.96 | 0.95 | 0.99 | |
| 445 | 1.10 | 0.21 | 1.00 | 5.28 | 4.83 | 0.92 | |
| 446 | 0.77 | 0.82 | 0.84 | 0.94 | 1.03 | 1.10 | Y |
| 447 | 0.66 | 1.50 | 0.46 | 0.44 | 0.31 | 0.70 | Y |
| 451 | 0.74 | 0.65 | 0.63 | 1.13 | 0.97 | 0.86 | Y |
| 454 | 0.95 | 1.37 | 2.06 | 0.69 | 1.51 | 2.18 | |
| 456 | 0.56 | 0.72 | 0.92 | 0.77 | 1.29 | 1.66 | Y |
| 459 | 1.35 | 0.13 | 0.96 | 10.23 | 7.30 | 0.71 | Y |
| 460 | 0.94 | 0.89 | 0.72 | 1.06 | 0.82 | 0.77 | |
| 461 | 0.91 | 1.14 | 1.02 | 0.80 | 0.90 | 1.12 | |
| 465 | 0.48 | 0.81 | 0.63 | 0.59 | 0.78 | 1.32 | y |
| 467 | 0.60 | 0.77 | 0.56 | 0.78 | 0.73 | 0.94 | Y |
| 468 | 0.67 | 0.78 | 0.59 | 0.86 | 0.76 | 0.88 | Y |
| 469 | 0.53 | 0.79 | 0.66 | 0.67 | 0.84 | 1.25 | Y |
| 471 | 0.91 | 0.89 | 0.75 | 1.01 | 0.84 | 0.83 | |
| 472 | 0.86 | 0.81 | 0.84 | 1.07 | 1.04 | 0.97 | |
| 473 | 0.94 | 0.79 | 1.11 | 1.19 | 1.40 | 1.18 | |
| 474 | 0.78 | 0.66 | 0.75 | 1.18 | 1.14 | 0.97 | Y |
| 475 | 0.61 | 0.82 | 0.60 | 0.74 | 0.72 | 0.98 | y |
| 476 | 1.01 | 0.81 | 0.86 | 1.25 | 1.06 | 0.85 | |
| 477 | 0.74 | 0.74 | 0.77 | 1.00 | 1.04 | 1.04 | y |
| 478 | 0.57 | 0.73 | 0.58 | 0.77 | 0.80 | 1.03 | Y |
| 479 | 0.87 | 0.66 | 0.63 | 1.33 | 0.95 | 0.72 | y |
| 480 | 0.90 | 0.88 | 0.86 | 1.02 | 0.97 | 0.96 | |
| 756 | 0.90 | 0.74 | 0.81 | 1.21 | 1.09 | 0.90 | |
| 929 | 0.80 | 0.45 | 0.45 | 1.79 | 1.00 | 0.56 | Y |
| 955 | 0.53 | 0.80 | 2.04 | 0.66 | 2.54 | 3.85 | Y |
| 958 | 0.70 | 0.58 | 3.16 | 1.20 | 5.42 | 4.51 | Y |
| 959 | 0.77 | 0.55 | 0.74 | 1.41 | 1.34 | 0.95 | Y |
| 965 | 0.88 | 0.58 | 0.82 | 1.51 | 1.41 | 0.93 | Y |
| 967 | 0.74 | 0.70 | 0.69 | 1.07 | 0.99 | 0.93 | Y |
| 972 | 0.99 | 0.85 | 1.07 | 1.17 | 1.26 | 1.08 | |
| 973 | 0.99 | 0.87 | 1.14 | 1.15 | 1.32 | 1.15 | |
| 974 | 0.82 | 0.76 | 0.87 | 1.08 | 1.15 | 1.06 | y |
| 975 | 0.77 | 0.73 | 0.78 | 1.05 | 1.07 | 1.02 | Y |
| 978 | 1.10 | 0.61 | 1.14 | 1.81 | 1.87 | 1.03 | |
| 981 | 1.68 | 0.60 | 1.12 | 2.81 | 1.87 | 0.66 | Y |
| 982 | 0.80 | 0.47 | 0.79 | 1.69 | 1.66 | 0.99 | |
| 983 | 1.24 | 1.23 | 1.22 | 1.00 | 0.99 | 0.98 | |
| 984 | 1.13 | 1.12 | 1.12 | 1.01 | 1.00 | 0.99 | |
| 986 | 0.80 | 0.68 | 0.76 | 1.17 | 1.12 | 0.95 | Y |
| 993 | 0.73 | 0.94 | 0.87 | 0.78 | 0.93 | 1.19 | y |
| 994 | 0.72 | 0.67 | 0.83 | 1.07 | 1.23 | 1.15 | Y |
| 995 | 0.83 | 0.86 | 0.89 | 0.97 | 1.04 | 1.07 | |
| 997 | 0.74 | 0.72 | 0.68 | 1.03 | 0.94 | 0.91 | Y |
| 1018 | 0.87 | 0.61 | 0.77 | 1.42 | 1.25 | 0.88 | Y |
| 1020 | 0.71 | 0.59 | 0.66 | 1.20 | 1.12 | 0.93 | Y |
| 1023 | 0.79 | 0.66 | 0.74 | 1.20 | 1.12 | 0.93 | Y |
| 1024 | 0.68 | 0.79 | 0.71 | 0.85 | 0.89 | 1.04 | Y |
| 1028 | 0.72 | 0.58 | 0.61 | 1.24 | 1.04 | 0.84 | Y |
| 1030 | 0.69 | 0.53 | 0.61 | 1.30 | 1.14 | 0.88 | Y |
| 1033 | 0.67 | 0.52 | 0.69 | 1.28 | 1.31 | 1.02 | |
| 1073 | 0.88 | 0.64 | 1.06 | 1.38 | 1.66 | 1.20 | y |
| 1078 | 0.76 | 0.67 | 0.70 | 1.13 | 1.04 | 0.92 | Y |
| 1079 | 0.62 | 0.56 | 0.87 | 1.11 | 1.56 | 1.40 | Y |
| 1080 | 0.78 | 0.53 | 0.77 | 1.48 | 1.46 | 0.99 | Y |
| 1090 | 0.66 | 0.38 | 0.64 | 1.75 | 1.71 | 0.98 | y |
| 1099 | 0.77 | 0.74 | 0.74 | 1.03 | 0.99 | 0.96 | Y |
| 1104 | 0.87 | 0.80 | 0.87 | 1.09 | 1.09 | 1.00 | |
| 1108 | 0.79 | 0.72 | 0.86 | 1.10 | 1.20 | 1.09 | y |
| 1109 | 0.98 | 0.89 | 0.91 | 1.10 | 1.01 | 0.92 | y |
| 1111 | 0.59 | 0.39 | 0.62 | 1.53 | 1.61 | 1.05 | Y |
| 1115 | 0.89 | 0.81 | 0.85 | 1.10 | 1.05 | 0.96 | Y |
| 1116 | 0.73 | 0.68 | 0.74 | 1.07 | 1.09 | 1.02 | Y |
| 1123 | 0.84 | 0.50 | 0.78 | 1.68 | 1.55 | 0.92 | |
| 1127 | 0.86 | 0.83 | 0.85 | 1.04 | 1.03 | 0.99 | Y |
| 1131 | 0.53 | 0.53 | 0.59 | 1.00 | 1.13 | 1.12 | Y |
| 1132 | 0.82 | 1.10 | 0.80 | 0.74 | 0.73 | 0.98 | |
| 1138 | 0.87 | 0.84 | 0.80 | 1.03 | 0.95 | 0.93 | Y |
| 1149 | 0.82 | 0.80 | 0.82 | 1.03 | 1.03 | 0.99 | Y |
| 1150 | 0.76 | 0.74 | 0.77 | 1.02 | 1.04 | 1.01 | Y |
| 1152 | 0.72 | 0.70 | 0.61 | 1.02 | 0.87 | 0.86 | y |

TABLE 4C-continued

| PSO | Sp/ SPF | ABX/ SPF | GF/ SPF | Sp/ ABX | GF/ ABX | GF/ Sp | GE |
|---|---|---|---|---|---|---|---|
| 1157 | 1.03 | 0.94 | 1.10 | 1.10 | 1.18 | 1.07 | |
| 1163 | 1.16 | 1.11 | 1.35 | 1.04 | 1.21 | 1.16 | |
| 1165 | 0.65 | 0.75 | 0.71 | 0.87 | 0.94 | 1.09 | Y |
| 1166 | 1.03 | 1.11 | 1.37 | 0.93 | 1.23 | 1.33 | |
| 1167 | 0.78 | 0.78 | 0.77 | 1.01 | 0.99 | 0.98 | y |
| 1169 | 0.88 | 0.81 | 0.80 | 1.09 | 0.98 | 0.90 | Y |
| 1179 | 0.82 | 0.79 | 0.83 | 1.05 | 1.05 | 1.01 | Y |
| 1181 | 1.08 | 0.93 | 1.08 | 1.16 | 1.16 | 1.00 | |
| 1183 | 0.92 | 0.89 | 0.70 | 1.02 | 0.78 | 0.76 | Y |
| 1201 | 1.18 | 1.09 | 0.95 | 1.08 | 0.87 | 0.81 | |
| 1203 | 0.84 | 1.06 | 1.03 | 0.80 | 0.97 | 1.22 | |
| 1204 | 1.13 | 1.41 | 1.40 | 0.80 | 0.99 | 1.24 | |
| 1205 | 0.92 | 0.96 | 1.13 | 0.96 | 1.17 | 1.23 | |
| 1217 | 0.75 | 0.95 | 0.77 | 0.79 | 0.81 | 1.02 | |
| 1218 | 0.68 | 0.86 | 0.62 | 0.79 | 0.73 | 0.92 | Y |
| 1223 | 0.78 | 0.96 | 0.84 | 0.81 | 0.87 | 1.08 | |
| 1225 | 0.52 | 0.90 | 0.50 | 0.58 | 0.56 | 0.97 | Y |
| 1236 | 0.65 | 0.97 | 0.80 | 0.68 | 0.82 | 1.22 | |
| 1239 | 0.66 | 0.84 | 0.67 | 0.79 | 0.80 | 1.02 | |
| 1244 | 0.62 | 1.17 | 0.72 | 0.53 | 0.61 | 1.16 | |
| 1247 | 0.60 | 0.85 | 0.52 | 0.71 | 0.62 | 0.87 | y |
| 1253 | 0.76 | 0.86 | 0.82 | 0.88 | 0.96 | 1.09 | Y |
| 1258 | 0.60 | 0.99 | 0.54 | 0.61 | 0.55 | 0.89 | Y |
| 1259 | 0.47 | 0.98 | 0.42 | 0.49 | 0.43 | 0.89 | Y |
| 1260 | 0.43 | 0.77 | 0.37 | 0.56 | 0.48 | 0.87 | Y |
| 1264 | 0.38 | 1.03 | 0.32 | 0.37 | 0.31 | 0.83 | |
| 1265 | 0.49 | 0.89 | 0.54 | 0.55 | 0.61 | 1.11 | Y |
| 1267 | 0.76 | 0.91 | 0.71 | 0.83 | 0.78 | 0.94 | |
| 1269 | 0.41 | 0.88 | 0.44 | 0.46 | 0.49 | 1.07 | Y |
| 1270 | 0.45 | 0.77 | 0.42 | 0.58 | 0.54 | 0.93 | Y |
| 1271 | 0.61 | 0.87 | 0.57 | 0.71 | 0.65 | 0.93 | |
| 1272 | 0.51 | 0.78 | 0.49 | 0.66 | 0.63 | 0.96 | |
| 1273 | 0.52 | 0.83 | 0.65 | 0.63 | 0.79 | 1.25 | |
| 1274 | 0.51 | 0.88 | 0.53 | 0.58 | 0.60 | 1.04 | y |
| 1276 | 0.51 | 1.09 | 0.49 | 0.47 | 0.45 | 0.95 | |
| 1277 | 0.50 | 0.94 | 0.57 | 0.52 | 0.60 | 1.14 | |
| 1351 | 0.98 | 0.68 | 0.81 | 1.45 | 1.20 | 0.83 | y |
| 1355 | 0.79 | 0.77 | 0.79 | 1.02 | 1.03 | 1.01 | Y |
| 1359 | 0.74 | 0.72 | 0.70 | 1.03 | 0.98 | 0.95 | y |
| 1360 | 0.88 | 0.80 | 1.03 | 1.10 | 1.29 | 1.17 | |
| 1363 | 0.87 | 0.85 | 0.94 | 1.02 | 1.11 | 1.08 | |
| 1372 | 0.86 | 1.08 | 1.02 | 0.80 | 0.94 | 1.18 | |
| 1430 | 0.80 | 0.73 | 0.89 | 1.09 | 1.22 | 1.12 | |
| 1446 | 1.07 | 0.93 | 1.15 | 1.15 | 1.23 | 1.07 | y |
| 1449 | 0.91 | 0.84 | 0.96 | 1.08 | 1.14 | 1.05 | |
| 1452 | 0.97 | 0.69 | 0.89 | 1.39 | 1.29 | 0.92 | Y |
| 1480 | 0.94 | 0.81 | 0.99 | 1.16 | 1.22 | 1.05 | Y |
| 1482 | 0.79 | 0.82 | 1.14 | 0.96 | 1.39 | 1.44 | |
| 1483 | 0.80 | 0.86 | 0.90 | 0.92 | 1.04 | 1.13 | |
| 1485 | 1.26 | 0.98 | 1.50 | 1.29 | 1.53 | 1.19 | Y |
| 1487 | 0.95 | 0.86 | 0.91 | 1.10 | 1.06 | 0.97 | |
| 1488 | 1.45 | 0.91 | 1.74 | 1.60 | 1.92 | 1.20 | Y |
| 1495 | 1.37 | 0.82 | 1.77 | 1.68 | 2.17 | 1.29 | Y |
| 1496 | 1.24 | 0.81 | 1.19 | 1.52 | 1.46 | 0.96 | Y |
| 1498 | 1.03 | 0.70 | 0.91 | 1.48 | 1.30 | 0.88 | Y |
| 1499 | 1.25 | 0.77 | 1.34 | 1.62 | 1.74 | 1.07 | Y |
| 1500 | 0.90 | 0.69 | 0.77 | 1.31 | 1.13 | 0.86 | Y |
| 1501 | 1.22 | 0.76 | 1.66 | 1.60 | 2.17 | 1.36 | Y |
| 1503 | 0.73 | 0.89 | 0.59 | 0.82 | 0.66 | 0.81 | Y |
| 1504 | 1.07 | 0.71 | 1.14 | 1.50 | 1.60 | 1.06 | Y |
| 1506 | 1.50 | 0.83 | 1.90 | 1.81 | 2.29 | 1.27 | Y |
| 1517 | 1.03 | 0.75 | 0.83 | 1.36 | 1.10 | 0.80 | Y |
| 1518 | 0.92 | 0.76 | 0.96 | 1.21 | 1.27 | 1.05 | |
| 1519 | 0.86 | 0.68 | 0.93 | 1.26 | 1.36 | 1.08 | y |
| 1521 | 1.00 | 0.99 | 1.09 | 1.01 | 1.10 | 1.09 | |
| 1522 | 1.04 | 0.77 | 1.25 | 1.34 | 1.62 | 1.21 | Y |
| 1523 | 1.05 | 0.76 | 1.07 | 1.39 | 1.42 | 1.02 | Y |
| 1524 | 0.97 | 0.69 | 0.82 | 1.40 | 1.19 | 0.85 | Y |
| 1527 | 0.66 | 0.71 | 0.74 | 0.94 | 1.04 | 1.12 | |
| 1528 | 0.79 | 0.82 | 0.68 | 0.97 | 0.84 | 0.86 | |
| 1529 | 0.84 | 0.82 | 0.81 | 1.03 | 0.99 | 0.96 | |
| 1536 | 0.93 | 0.73 | 1.06 | 1.28 | 1.45 | 1.13 | |
| 1537 | 0.97 | 0.73 | 0.83 | 1.34 | 1.14 | 0.85 | |
| 1539 | 0.86 | 0.82 | 0.60 | 1.04 | 0.73 | 0.70 | Y |
| 1541 | 0.83 | 0.73 | 0.77 | 1.13 | 1.05 | 0.93 | y |
| 1542 | 0.95 | 0.90 | 0.95 | 1.06 | 1.05 | 0.99 | |
| 1547 | 0.82 | 1.05 | 3.32 | 0.79 | 3.16 | 4.03 | Y |

TABLE 4C-continued

| PSO | Sp/ SPF | ABX/ SPF | GF/ SPF | Sp/ ABX | GF/ ABX | GF/ Sp | GE |
|---|---|---|---|---|---|---|---|
| 1565 | 0.96 | 0.35 | 0.77 | 2.77 | 2.23 | 0.81 | |
| 1567 | 1.02 | 0.70 | 0.93 | 1.45 | 1.32 | 0.91 | |
| 1582 | 1.08 | 0.95 | 0.97 | 1.14 | 1.02 | 0.90 | |
| 1711 | 0.69 | 0.40 | 0.64 | 1.75 | 1.61 | 0.92 | |
| 1718 | 0.78 | 0.83 | 0.72 | 0.95 | 0.87 | 0.92 | Y |
| 1721 | 0.88 | 0.95 | 0.92 | 0.93 | 0.98 | 1.05 | |
| 1731 | 0.63 | 0.79 | 0.63 | 0.79 | 0.80 | 1.01 | |
| 1732 | 0.47 | 0.73 | 0.47 | 0.64 | 0.65 | 1.00 | y |
| 1744 | 0.79 | 0.84 | 0.79 | 0.94 | 0.94 | 1.00 | y |
| 1753 | 0.74 | 0.64 | 0.60 | 1.15 | 0.93 | 0.81 | Y |
| 1754 | 1.70 | 0.72 | 0.90 | 2.35 | 1.24 | 0.53 | Y |
| 1782 | 0.70 | 0.83 | 0.72 | 0.84 | 0.86 | 1.03 | Y |
| 1783 | 0.92 | 0.95 | 0.97 | 0.97 | 1.02 | 1.05 | |
| 1784 | 0.94 | 0.66 | 0.77 | 1.43 | 1.18 | 0.82 | Y |
| 1786 | 1.02 | 0.76 | 0.94 | 1.34 | 1.24 | 0.92 | Y |
| 1788 | 0.88 | 0.82 | 0.80 | 1.08 | 0.98 | 0.91 | Y |
| 1789 | 0.87 | 0.80 | 0.82 | 1.08 | 1.02 | 0.95 | Y |
| 1790 | 0.95 | 0.83 | 0.89 | 1.14 | 1.07 | 0.94 | Y |
| 1791 | 0.83 | 0.81 | 0.75 | 1.02 | 0.93 | 0.91 | y |
| 1792 | 0.84 | 0.87 | 0.74 | 0.96 | 0.84 | 0.88 | Y |
| 1793 | 0.38 | 0.08 | 0.04 | 4.61 | 0.48 | 0.10 | Y |
| 1811 | 0.93 | 0.88 | 0.86 | 1.07 | 0.99 | 0.93 | y |
| 1815 | 0.82 | 0.78 | 0.80 | 1.05 | 1.03 | 0.98 | y |
| 1827 | 0.91 | 0.86 | 0.88 | 1.05 | 1.02 | 0.97 | Y |
| 1828 | 0.95 | 0.93 | 0.90 | 1.03 | 0.97 | 0.95 | |
| 1829 | 0.87 | 0.73 | 0.79 | 1.18 | 1.07 | 0.91 | Y |
| 1831 | 0.91 | 0.87 | 0.88 | 1.05 | 1.01 | 0.96 | Y |
| 1834 | 0.91 | 0.99 | 0.99 | 0.92 | 1.00 | 1.09 | |
| 1837 | 0.83 | 0.93 | 0.96 | 0.89 | 1.04 | 1.16 | |
| 1841 | 0.82 | 0.97 | 0.93 | 0.84 | 0.96 | 1.14 | y |
| 1845 | 0.89 | 0.82 | 0.84 | 1.08 | 1.02 | 0.95 | Y |
| 1851 | 0.76 | 0.78 | 0.66 | 0.97 | 0.85 | 0.87 | Y |
| 1866 | 0.66 | 0.56 | 0.44 | 1.19 | 0.79 | 0.66 | Y |
| 1867 | 0.88 | 0.84 | 0.79 | 1.04 | 0.93 | 0.90 | Y |
| 1870 | 0.85 | 0.94 | 0.99 | 0.90 | 1.05 | 1.16 | |
| 1878 | 0.86 | 0.82 | 0.77 | 1.04 | 0.93 | 0.90 | Y |
| 1884 | 0.79 | 0.83 | 0.69 | 0.95 | 0.84 | 0.88 | Y |
| 1889 | 0.97 | 1.01 | 0.91 | 0.95 | 0.90 | 0.95 | |
| 1892 | 0.81 | 1.11 | 1.17 | 0.73 | 1.06 | 1.46 | Y |
| 1902 | 0.75 | 0.86 | 0.67 | 0.86 | 0.77 | 0.89 | Y |
| 1903 | 0.54 | 0.93 | 0.94 | 0.59 | 1.02 | 1.73 | Y |
| 1907 | 0.78 | 1.00 | 0.99 | 0.78 | 1.00 | 1.28 | |
| 1945 | 0.90 | 0.90 | 0.85 | 1.00 | 0.95 | 0.95 | y |
| 1948 | 0.86 | 0.78 | 0.76 | 1.10 | 0.98 | 0.89 | Y |
| 1949 | 0.88 | 0.91 | 0.82 | 0.97 | 0.90 | 0.94 | Y |
| 1950 | 0.89 | 1.10 | 0.99 | 0.81 | 0.90 | 1.12 | |
| 1953 | 0.83 | 0.92 | 0.86 | 0.91 | 0.93 | 1.03 | |
| 1955 | 0.85 | 0.94 | 0.74 | 0.90 | 0.79 | 0.88 | |
| 1962 | 0.84 | 0.85 | 0.75 | 0.99 | 0.89 | 0.89 | Y |
| 1970 | 0.85 | 0.90 | 0.81 | 0.95 | 0.90 | 0.94 | y |
| 1974 | 0.80 | 0.88 | 0.69 | 0.90 | 0.79 | 0.87 | Y |
| 1975 | 0.89 | 1.05 | 0.94 | 0.85 | 0.89 | 1.05 | |
| 1976 | 0.77 | 1.18 | 1.06 | 0.66 | 0.90 | 1.38 | |
| 1979 | 0.87 | 1.06 | 0.95 | 0.82 | 0.90 | 1.09 | |
| 1982 | 0.86 | 0.99 | 0.76 | 0.88 | 0.77 | 0.87 | |
| 1985 | 0.74 | 1.15 | 1.06 | 0.65 | 0.92 | 1.42 | |
| 2016 | 0.90 | 0.93 | 0.92 | 0.97 | 0.99 | 1.02 | |
| 2021 | 0.92 | 0.91 | 0.88 | 1.00 | 0.97 | 0.97 | |
| 2024 | 0.86 | 0.91 | 0.85 | 0.94 | 0.93 | 0.99 | |
| 2034 | 0.84 | 0.72 | 0.73 | 1.17 | 1.01 | 0.86 | Y |
| 2052 | 0.77 | 0.83 | 0.71 | 0.93 | 0.85 | 0.91 | Y |
| 2067 | 0.80 | 0.83 | 0.77 | 0.96 | 0.92 | 0.96 | Y |
| 2072 | 0.76 | 0.91 | 0.74 | 0.84 | 0.81 | 0.97 | y |
| 2105 | 0.83 | 0.56 | 0.65 | 1.49 | 1.16 | 0.78 | |
| 2106 | 0.91 | 0.61 | 0.76 | 1.50 | 1.25 | 0.83 | y |
| 2107 | 0.88 | 0.65 | 0.75 | 1.36 | 1.17 | 0.86 | |
| 2113 | 0.89 | 0.56 | 0.71 | 1.60 | 1.28 | 0.80 | |
| 2115 | 0.88 | 0.61 | 0.68 | 1.45 | 1.12 | 0.77 | |
| 2118 | 0.86 | 0.85 | 0.94 | 1.01 | 1.11 | 1.10 | |
| 2136 | 0.49 | 0.75 | 0.39 | 0.65 | 0.51 | 0.78 | |
| 2157 | 0.89 | 0.61 | 0.72 | 1.45 | 1.18 | 0.81 | |
| 2164 | 0.80 | 0.70 | 0.68 | 1.15 | 0.97 | 0.85 | Y |
| 2165 | 0.60 | 0.91 | 0.64 | 0.67 | 0.70 | 1.05 | |
| 2166 | 0.96 | 0.75 | 0.84 | 1.27 | 1.11 | 0.87 | |
| 2168 | 0.91 | 0.84 | 0.99 | 1.08 | 1.18 | 1.09 | |
| 2179 | 0.88 | 0.57 | 0.92 | 1.53 | 1.60 | 1.04 | |
| 2192 | 0.73 | 0.50 | 0.69 | 1.46 | 1.38 | 0.95 | |

TABLE 4C-continued

| PSO | Sp/ SPF | ABX/ SPF | GF/ SPF | Sp/ ABX | GF/ ABX | GF/ Sp | GE |
|---|---|---|---|---|---|---|---|
| 2193 | 0.81 | 0.38 | 0.71 | 2.12 | 1.87 | 0.88 | y |
| 2194 | 0.66 | 0.76 | 0.59 | 0.87 | 0.78 | 0.90 | |
| 2199 | 0.43 | 0.82 | 0.37 | 0.53 | 0.45 | 0.85 | y |
| 2203 | 0.60 | 0.98 | 0.64 | 0.61 | 0.65 | 1.07 | |
| 2206 | 0.61 | 0.59 | 0.52 | 1.04 | 0.87 | 0.84 | |
| 2209 | 0.60 | 0.63 | 0.53 | 0.96 | 0.85 | 0.88 | y |
| 2211 | 0.74 | 0.61 | 0.62 | 1.22 | 1.02 | 0.84 | |
| 2217 | 0.56 | 0.91 | 0.51 | 0.61 | 0.56 | 0.92 | y |
| 2310 | 0.88 | 1.04 | 0.90 | 0.85 | 0.86 | 1.02 | |
| 2311 | 0.84 | 1.23 | 1.01 | 0.69 | 0.83 | 1.20 | |
| 2312 | 0.77 | 0.73 | 0.67 | 1.05 | 0.91 | 0.87 | Y |
| 2313 | 0.87 | 0.81 | 0.75 | 1.08 | 0.93 | 0.86 | |
| 2314 | 0.82 | 0.99 | 0.88 | 0.83 | 0.89 | 1.07 | |
| 2318 | 0.84 | 1.01 | 0.81 | 0.84 | 0.81 | 0.97 | |
| 2327 | 0.80 | 0.92 | 0.82 | 0.87 | 0.89 | 1.03 | |
| 2343 | 0.77 | 0.73 | 0.65 | 1.05 | 0.90 | 0.85 | Y |
| 2345 | 0.79 | 0.91 | 0.70 | 0.87 | 0.77 | 0.88 | Y |
| 2347 | 0.76 | 0.75 | 0.63 | 1.01 | 0.84 | 0.83 | Y |
| 2348 | 0.89 | 1.16 | 0.97 | 0.77 | 0.84 | 1.09 | |
| 2350 | 0.84 | 0.85 | 0.85 | 0.99 | 1.00 | 1.01 | |
| 2351 | 0.64 | 0.79 | 0.68 | 0.81 | 0.86 | 1.06 | y |
| 2356 | 0.76 | 0.66 | 0.77 | 1.14 | 1.17 | 1.02 | Y |
| 2357 | 0.72 | 0.91 | 0.80 | 0.78 | 0.88 | 1.12 | |
| 2360 | 0.71 | 0.94 | 0.69 | 0.76 | 0.74 | 0.97 | |
| 2361 | 0.61 | 1.00 | 0.75 | 0.61 | 0.75 | 1.24 | |
| 2364 | 0.74 | 0.95 | 0.76 | 0.77 | 0.80 | 1.03 | |
| 2371 | 0.50 | 1.02 | 0.74 | 0.49 | 0.73 | 1.49 | |
| 2374 | 0.44 | 1.03 | 0.58 | 0.43 | 0.57 | 1.34 | |
| 2375 | 0.75 | 0.80 | 0.73 | 0.94 | 0.91 | 0.98 | |
| 2376 | 0.60 | 0.74 | 0.56 | 0.81 | 0.76 | 0.94 | |
| 2379 | 0.74 | 0.81 | 0.65 | 0.91 | 0.81 | 0.89 | |
| 2381 | 0.44 | 0.81 | 0.70 | 0.54 | 0.86 | 1.59 | |
| 2383 | 0.49 | 0.99 | 0.56 | 0.49 | 0.57 | 1.15 | |
| 2394 | 0.72 | 0.88 | 0.74 | 0.82 | 0.85 | 1.04 | y |
| 2395 | 0.58 | 0.95 | 0.86 | 0.61 | 0.90 | 1.47 | Y |
| 2407 | 0.81 | 0.81 | 0.90 | 1.01 | 1.11 | 1.10 | |
| 2411 | 0.81 | 0.83 | 0.79 | 0.98 | 0.96 | 0.97 | |
| 2413 | 0.63 | 0.84 | 0.72 | 0.75 | 0.86 | 1.15 | Y |
| 2416 | 1.03 | 1.30 | 1.16 | 0.79 | 0.90 | 1.13 | |
| 2418 | 0.65 | 0.94 | 0.88 | 0.69 | 0.93 | 1.36 | Y |
| 2419 | 0.78 | 1.04 | 0.76 | 0.75 | 0.73 | 0.97 | |
| 2420 | 0.78 | 0.84 | 0.76 | 0.93 | 0.91 | 0.97 | y |
| 2422 | 0.71 | 0.96 | 0.61 | 0.74 | 0.63 | 0.85 | Y |
| 2423 | 0.41 | 0.62 | 0.19 | 0.66 | 0.31 | 0.47 | Y |
| 2426 | 0.61 | 0.87 | 0.69 | 0.70 | 0.79 | 1.13 | Y |
| 2429 | 0.85 | 0.91 | 0.82 | 0.93 | 0.90 | 0.97 | |
| 2431 | 0.58 | 0.85 | 0.71 | 0.68 | 0.83 | 1.22 | |
| 2432 | 0.72 | 0.96 | 0.84 | 0.74 | 0.87 | 1.17 | Y |
| 2442 | 0.78 | 0.93 | 0.96 | 0.84 | 1.03 | 1.23 | |
| 2443 | 0.77 | 0.80 | 0.81 | 0.95 | 1.01 | 1.06 | y |
| 2445 | 0.77 | 0.89 | 0.78 | 0.86 | 0.88 | 1.02 | |
| 2448 | 0.95 | 0.92 | 0.61 | 1.03 | 0.66 | 0.64 | y |
| 2449 | 0.66 | 0.72 | 0.55 | 0.91 | 0.76 | 0.84 | Y |
| 2474 | 0.86 | 0.84 | 0.79 | 1.02 | 0.95 | 0.93 | |
| 2480 | 0.77 | 0.83 | 0.70 | 0.92 | 0.84 | 0.91 | Y |
| 2481 | 0.84 | 0.79 | 0.65 | 1.06 | 0.83 | 0.78 | Y |
| 2488 | 0.72 | 0.83 | 0.58 | 0.87 | 0.70 | 0.80 | Y |
| 2491 | 0.79 | 0.72 | 0.68 | 1.09 | 0.94 | 0.86 | Y |
| 2493 | 0.75 | 0.72 | 0.65 | 1.05 | 0.91 | 0.87 | Y |
| 2498 | 0.69 | 0.58 | 0.47 | 1.19 | 0.80 | 0.68 | Y |
| 2499 | 0.72 | 0.71 | 0.67 | 1.02 | 0.95 | 0.93 | Y |
| 2513 | 0.78 | 0.90 | 0.77 | 0.87 | 0.86 | 0.99 | Y |
| 2514 | 0.73 | 0.63 | 0.56 | 1.16 | 0.88 | 0.76 | Y |
| 2517 | 0.80 | 0.84 | 0.71 | 0.95 | 0.85 | 0.89 | Y |
| 2518 | 0.70 | 0.75 | 0.72 | 0.93 | 0.96 | 1.03 | Y |
| 2520 | 0.87 | 0.94 | 0.89 | 0.92 | 0.95 | 1.03 | |
| 2522 | 0.95 | 1.08 | 1.11 | 0.88 | 1.02 | 1.16 | |
| 2523 | 0.88 | 0.86 | 0.82 | 1.01 | 0.95 | 0.93 | |
| 2525 | 0.87 | 0.88 | 0.95 | 0.99 | 1.08 | 1.09 | |
| 2543 | 0.90 | 0.94 | 0.94 | 0.95 | 1.00 | 1.05 | |
| 2547 | 0.75 | 0.90 | 0.99 | 0.83 | 1.10 | 1.33 | |
| 2549 | 0.98 | 0.90 | 1.22 | 1.08 | 1.35 | 1.25 | |
| 2561 | 0.81 | 0.82 | 0.82 | 0.98 | 0.99 | 1.01 | y |
| 2563 | 0.84 | 0.67 | 0.70 | 1.24 | 1.03 | 0.83 | Y |
| 2564 | 0.55 | 0.40 | 0.39 | 1.38 | 0.98 | 0.71 | Y |
| 2565 | 0.98 | 0.93 | 0.99 | 1.05 | 1.06 | 1.01 | |
| 2566 | 0.86 | 0.84 | 0.88 | 1.03 | 1.05 | 1.02 | |

TABLE 4C-continued

| PSO | Sp/ SPF | ABX/ SPF | GF/ SPF | Sp/ ABX | GF/ ABX | GF/ Sp | GE |
|---|---|---|---|---|---|---|---|
| 2567 | 0.96 | 0.84 | 0.84 | 1.15 | 1.01 | 0.87 | y |
| 2568 | 0.80 | 0.64 | 0.60 | 1.25 | 0.95 | 0.76 | Y |
| 2569 | 0.67 | 0.53 | 0.71 | 1.26 | 1.33 | 1.06 | y |
| 2570 | 0.80 | 0.64 | 0.73 | 1.25 | 1.15 | 0.92 | Y |
| 2575 | 0.96 | 0.87 | 0.98 | 1.10 | 1.12 | 1.02 | |
| 2577 | 0.96 | 0.75 | 0.87 | 1.28 | 1.15 | 0.90 | |
| 2579 | 0.88 | 0.80 | 0.91 | 1.10 | 1.14 | 1.04 | |
| 2580 | 0.77 | 0.55 | 0.62 | 1.39 | 1.13 | 0.81 | Y |
| 2581 | 0.91 | 0.75 | 0.82 | 1.21 | 1.09 | 0.90 | |
| 2583 | 0.84 | 0.68 | 0.69 | 1.24 | 1.02 | 0.83 | Y |
| 2588 | 0.92 | 0.84 | 0.88 | 1.09 | 1.04 | 0.95 | |
| 2591 | 0.91 | 0.75 | 0.70 | 1.21 | 0.93 | 0.77 | Y |
| 2592 | 0.80 | 0.81 | 0.94 | 0.98 | 1.16 | 1.18 | Y |
| 2594 | 0.88 | 0.84 | 0.82 | 1.05 | 0.98 | 0.94 | |
| 2610 | 0.73 | 0.52 | 0.57 | 1.40 | 1.11 | 0.79 | Y |
| 2624 | 0.91 | 0.78 | 0.73 | 1.17 | 0.94 | 0.80 | Y |
| 2625 | 0.86 | 0.78 | 0.72 | 1.11 | 0.93 | 0.84 | Y |
| 2649 | 1.10 | 0.66 | 0.97 | 1.67 | 1.46 | 0.87 | Y |
| 2652 | 0.80 | 0.65 | 0.57 | 1.22 | 0.87 | 0.71 | Y |
| 2669 | 1.20 | 0.11 | 0.74 | 10.96 | 6.75 | 0.62 | |
| 3453 | 0.51 | 0.57 | 0.43 | 0.90 | 0.76 | 0.85 | Y |
| 3454 | 0.90 | 0.90 | 0.82 | 1.00 | 0.91 | 0.91 | Y |
| 3455 | 0.81 | 0.80 | 0.71 | 1.01 | 0.89 | 0.88 | y |
| 3456 | 0.56 | 0.45 | 0.31 | 1.24 | 0.69 | 0.56 | Y |
| 3458 | 0.38 | 0.67 | 0.28 | 0.57 | 0.42 | 0.74 | Y |
| 3461 | 0.83 | 0.69 | 0.73 | 1.20 | 1.05 | 0.88 | Y |
| 3462 | 0.94 | 0.91 | 0.79 | 1.03 | 0.87 | 0.84 | Y |
| 3464 | 0.84 | 0.46 | 0.69 | 1.81 | 1.49 | 0.83 | Y |
| 3466 | 0.72 | 0.60 | 0.57 | 1.19 | 0.95 | 0.80 | Y |
| 3471 | 1.03 | 0.77 | 1.07 | 1.35 | 1.40 | 1.04 | y |
| 3472 | 1.01 | 0.98 | 1.07 | 1.03 | 1.10 | 1.07 | |
| 3473 | 1.16 | 0.78 | 0.92 | 1.49 | 1.18 | 0.79 | y |
| 3474 | 1.15 | 0.83 | 1.05 | 1.40 | 1.27 | 0.91 | Y |
| 3478 | 0.73 | 0.75 | 0.69 | 0.97 | 0.91 | 0.94 | Y |
| 3479 | 0.85 | 0.86 | 1.06 | 0.98 | 1.23 | 1.25 | |
| 3480 | 0.89 | 1.01 | 0.98 | 0.88 | 0.97 | 1.10 | |
| 3485 | 0.70 | 0.61 | 0.61 | 1.16 | 1.00 | 0.87 | Y |
| 3495 | 0.87 | 0.78 | 0.77 | 1.12 | 0.99 | 0.88 | Y |
| 3498 | 1.05 | 1.18 | 1.17 | 0.89 | 1.00 | 1.12 | |
| 3505 | 0.65 | 0.73 | 0.53 | 0.89 | 0.72 | 0.81 | Y |
| 3507 | 0.83 | 0.73 | 0.76 | 1.13 | 1.04 | 0.92 | Y |
| 3508 | 0.83 | 0.90 | 0.82 | 0.92 | 0.91 | 0.98 | Y |
| 3513 | 0.83 | 1.05 | 0.89 | 0.79 | 0.84 | 1.07 | |
| 3514 | 0.73 | 1.07 | 0.82 | 0.69 | 0.76 | 1.11 | |
| 3516 | 0.74 | 0.69 | 0.68 | 1.07 | 0.98 | 0.91 | Y |
| 3522 | 0.76 | 0.58 | 0.68 | 1.32 | 1.17 | 0.89 | Y |
| 3528 | 0.84 | 0.74 | 0.64 | 1.15 | 0.87 | 0.76 | y |
| 3530 | 0.91 | 0.94 | 0.88 | 0.98 | 0.94 | 0.96 | |
| 3533 | 1.11 | 1.07 | 1.58 | 1.04 | 1.48 | 1.42 | Y |
| 3534 | 0.97 | 0.89 | 1.88 | 1.08 | 2.10 | 1.94 | Y |
| 3535 | 0.99 | 0.81 | 0.94 | 1.22 | 1.15 | 0.95 | |
| 3537 | 0.81 | 0.77 | 0.81 | 1.05 | 1.05 | 1.00 | y |
| 3541 | 0.58 | 0.81 | 0.55 | 0.72 | 0.68 | 0.95 | |
| 3542 | 0.97 | 0.99 | 1.11 | 0.98 | 1.12 | 1.14 | |
| 3547 | 0.82 | 0.86 | 0.74 | 0.95 | 0.86 | 0.90 | Y |
| 3548 | 0.68 | 0.82 | 0.61 | 0.82 | 0.74 | 0.90 | Y |
| 3549 | 0.97 | 0.80 | 0.85 | 1.21 | 1.06 | 0.88 | Y |
| 3550 | 0.91 | 0.73 | 0.71 | 1.26 | 0.98 | 0.78 | Y |
| 3552 | 1.14 | 0.91 | 0.73 | 1.25 | 0.80 | 0.64 | Y |
| 3563 | 1.07 | 0.78 | 0.86 | 1.37 | 1.11 | 0.81 | |
| 3565 | 0.74 | 0.63 | 0.76 | 1.18 | 1.20 | 1.02 | |
| 3566 | 0.79 | 0.64 | 0.62 | 1.23 | 0.98 | 0.79 | Y |
| 3567 | 0.83 | 0.74 | 0.75 | 1.13 | 1.02 | 0.90 | Y |
| 3568 | 0.84 | 0.79 | 1.03 | 1.06 | 1.31 | 1.23 | Y |
| 3572 | 0.58 | 0.81 | 0.65 | 0.72 | 0.81 | 1.12 | |
| 3573 | 0.90 | 0.98 | 1.06 | 0.92 | 1.09 | 1.18 | |
| 3576 | 0.64 | 0.65 | 0.63 | 0.99 | 0.97 | 0.98 | Y |
| 3577 | 0.77 | 0.84 | 0.73 | 0.92 | 0.87 | 0.95 | Y |
| 3578 | 0.86 | 0.90 | 1.01 | 0.96 | 1.12 | 1.17 | |
| 3579 | 0.54 | 0.50 | 0.45 | 1.07 | 0.90 | 0.84 | Y |
| 3580 | 0.82 | 0.72 | 0.75 | 1.14 | 1.04 | 0.92 | y |
| 3585 | 0.76 | 0.93 | 0.89 | 0.81 | 0.95 | 1.17 | |
| 3587 | 0.59 | 0.68 | 0.54 | 0.86 | 0.80 | 0.93 | Y |
| 3588 | 0.80 | 0.73 | 0.72 | 1.10 | 0.98 | 0.89 | Y |
| 3589 | 0.46 | 0.35 | 0.36 | 1.31 | 1.04 | 0.79 | Y |
| 3598 | 0.72 | 0.79 | 0.64 | 0.91 | 0.82 | 0.89 | Y |
| 3599 | 1.09 | 0.81 | 0.96 | 1.35 | 1.18 | 0.88 | |

TABLE 4C-continued

| PSO | Sp/ SPF | ABX/ SPF | GF/ SPF | Sp/ ABX | GF/ ABX | GF/ Sp | GE |
|---|---|---|---|---|---|---|---|
| 3602 | 0.68 | 0.91 | 0.80 | 0.74 | 0.87 | 1.18 | |
| 3603 | 0.67 | 0.74 | 0.75 | 0.91 | 1.02 | 1.12 | Y |
| 3607 | 0.49 | 1.11 | 0.44 | 0.44 | 0.40 | 0.90 | Y |
| 3608 | 0.56 | 1.00 | 0.61 | 0.56 | 0.61 | 1.08 | Y |
| 3624 | 0.84 | 0.85 | 0.84 | 0.99 | 0.99 | 1.00 | Y |
| 3627 | 0.88 | 0.70 | 0.72 | 1.26 | 1.03 | 0.82 | |
| 3628 | 0.85 | 0.85 | 0.88 | 1.00 | 1.04 | 1.04 | |
| 3636 | 1.58 | 1.35 | 1.41 | 1.17 | 1.04 | 0.89 | Y |
| 3641 | 0.90 | 0.58 | 0.55 | 1.55 | 0.95 | 0.61 | Y |
| 3643 | 1.59 | 1.08 | 0.93 | 1.48 | 0.86 | 0.58 | Y |
| 3644 | 1.65 | 1.04 | 0.97 | 1.58 | 0.94 | 0.59 | Y |
| 3648 | 0.89 | 0.95 | 0.88 | 0.94 | 0.92 | 0.98 | |
| 3649 | 0.87 | 0.77 | 0.77 | 1.13 | 1.00 | 0.88 | Y |
| 3650 | 0.77 | 0.85 | 0.71 | 0.91 | 0.83 | 0.92 | |
| 3651 | 0.98 | 0.80 | 0.72 | 1.22 | 0.90 | 0.74 | Y |
| 3653 | 0.65 | 0.97 | 0.69 | 0.68 | 0.71 | 1.05 | Y |
| 3654 | 0.84 | 0.82 | 0.65 | 1.03 | 0.79 | 0.77 | Y |
| 3656 | 0.81 | 0.94 | 0.84 | 0.87 | 0.89 | 1.03 | |
| 3658 | 0.65 | 0.78 | 0.57 | 0.84 | 0.74 | 0.88 | y |
| 3662 | 0.67 | 1.07 | 0.60 | 0.63 | 0.57 | 0.91 | |
| 3663 | 0.85 | 0.24 | 0.66 | 3.56 | 2.77 | 0.78 | |
| 3664 | 1.08 | 0.51 | 1.20 | 2.10 | 2.35 | 1.12 | y |
| 3667 | 1.03 | 0.61 | 0.99 | 1.68 | 1.62 | 0.96 | |
| 3668 | 0.80 | 0.74 | 0.78 | 1.07 | 1.05 | 0.98 | Y |
| 3670 | 0.61 | 1.31 | 0.90 | 0.46 | 0.69 | 1.49 | |
| 3694 | 0.81 | 0.37 | 0.44 | 2.17 | 1.17 | 0.54 | Y |
| 3698 | 1.12 | 0.92 | 0.80 | 1.22 | 0.87 | 0.71 | |
| 3714 | 0.42 | 0.89 | 0.41 | 0.47 | 0.46 | 0.97 | Y |
| 3715 | 0.53 | 0.78 | 0.66 | 0.68 | 0.84 | 1.25 | y |
| 3718 | 0.66 | 0.92 | 0.71 | 0.72 | 0.78 | 1.08 | |
| 3727 | 0.64 | 0.67 | 0.56 | 0.96 | 0.84 | 0.88 | Y |
| 3728 | 0.89 | 0.84 | 0.83 | 1.06 | 0.99 | 0.93 | |
| 3751 | 0.81 | 0.95 | 0.58 | 0.85 | 0.61 | 0.72 | Y |
| 3754 | 0.89 | 0.83 | 0.72 | 1.07 | 0.87 | 0.81 | Y |
| 3757 | 0.42 | 0.24 | 0.24 | 1.72 | 1.00 | 0.58 | Y |
| 3771 | 0.92 | 0.96 | 1.12 | 0.96 | 1.17 | 1.22 | |
| 3978 | 0.84 | 0.59 | 0.81 | 1.43 | 1.37 | 0.96 | |
| 4000 | 1.01 | 0.67 | 1.24 | 1.52 | 1.86 | 1.22 | y |
| 4079 | 0.98 | 1.19 | 0.79 | 0.83 | 0.66 | 0.80 | Y |
| 4108 | 0.72 | 0.38 | 0.46 | 1.91 | 1.24 | 0.65 | Y |
| 4131 | 0.88 | 0.94 | 1.00 | 0.93 | 1.07 | 1.14 | |
| 4144 | 0.95 | 0.75 | 0.84 | 1.26 | 1.12 | 0.88 | y |
| 4221 | 0.77 | 0.44 | 0.57 | 1.75 | 1.28 | 0.73 | Y |
| 4246 | 1.45 | 0.62 | 0.98 | 2.32 | 1.57 | 0.68 | Y |
| 4274 | 0.98 | 0.46 | 0.40 | 2.14 | 0.87 | 0.41 | Y |
| 4363 | 1.03 | 0.56 | 0.78 | 1.84 | 1.39 | 0.76 | |
| 4756 | 0.92 | 0.71 | 0.74 | 1.29 | 1.04 | 0.80 | |
| 4832 | 0.95 | 1.06 | 0.96 | 0.90 | 0.91 | 1.02 | |
| 4835 | 0.95 | 0.47 | 0.58 | 2.01 | 1.22 | 0.61 | Y |
| 4899 | 1.68 | 0.81 | 0.62 | 2.09 | 0.77 | 0.37 | Y |
| 4926 | 0.91 | 0.91 | 18.88 | 1.00 | 20.85 | 20.85 | Y |
| 4930 | 2.31 | 1.16 | 1.25 | 1.99 | 1.07 | 0.54 | Y |
| 4971 | 0.47 | 1.08 | 0.56 | 0.44 | 0.52 | 1.19 | |

TABLE 4D

| | Sp/SPF | | ABX/SPF | | GF/SPF | |
|---|---|---|---|---|---|---|
| PSO | p-value | q-value | p-value | q-value | p-value | q-value |
| 1 | 0.0548 | 0.0477 | 0.0416 | 0.0281 | 0.5657 | 0.2280 |
| 2 | 0.5443 | 0.2032 | 0.9539 | 0.2475 | 0.1960 | 0.1011 |
| 5 | 0.0091 | 0.0213 | 0.0012 | 0.0040 | 0.0690 | 0.0459 |
| 6 | 0.0331 | 0.0377 | 0.0003 | 0.0022 | 0.0297 | 0.0247 |
| 9 | 0.2191 | 0.1076 | 0.4977 | 0.1556 | 0.6786 | 0.2604 |
| 10 | 0.0084 | 0.0209 | 0.0133 | 0.0134 | 0.1705 | 0.0922 |
| 14 | 0.4825 | 0.1882 | 0.7326 | 0.2040 | 0.0829 | 0.0532 |
| 16 | 0.0387 | 0.0399 | 0.0549 | 0.0335 | 0.3766 | 0.1644 |
| 17 | 0.2213 | 0.1081 | 0.0664 | 0.0374 | 0.9339 | 0.3236 |
| 18 | 0.4364 | 0.1725 | 0.1559 | 0.0679 | 0.4767 | 0.1979 |
| 21 | 0.0088 | 0.0212 | 0.0011 | 0.0040 | 0.0114 | 0.0136 |
| 28 | 0.0245 | 0.0336 | 0.0321 | 0.0238 | 0.0642 | 0.0430 |
| 30 | 0.0167 | 0.0286 | 0.0003 | 0.0022 | 0.0277 | 0.0239 |
| 34 | 0.0155 | 0.0279 | 0.0118 | 0.0128 | 0.0201 | 0.0194 |

TABLE 4D-continued

| | Sp/SPF | | ABX/SPF | | GF/SPF | |
|---|---|---|---|---|---|---|
| PSO | p-value | q-value | p-value | q-value | p-value | q-value |
| 35 | 0.0443 | 0.0428 | 0.0034 | 0.0064 | 0.0098 | 0.0118 |
| 38 | 0.7219 | 0.2444 | 0.7369 | 0.2044 | 0.7925 | 0.2902 |
| 39 | 0.7490 | 0.2502 | 0.4928 | 0.1543 | 0.9183 | 0.3196 |
| 40 | 0.0816 | 0.0595 | 0.0044 | 0.0068 | 0.0056 | 0.0083 |
| 41 | 0.0264 | 0.0342 | 0.0075 | 0.0095 | 0.0229 | 0.0214 |
| 42 | 0.0903 | 0.0627 | 0.0010 | 0.0037 | 0.0003 | 0.0015 |
| 43 | 0.0006 | 0.0059 | 0.1065 | 0.0509 | 0.0061 | 0.0089 |
| 44 | 0.0287 | 0.0345 | 0.0218 | 0.0186 | 0.0291 | 0.0244 |
| 45 | 0.0628 | 0.0518 | 0.0020 | 0.0053 | 0.0009 | 0.0028 |
| 47 | 0.0001 | 0.0027 | 0.7104 | 0.2003 | 0.6574 | 0.2548 |
| 50 | 0.1912 | 0.0992 | 0.0265 | 0.0216 | 0.2104 | 0.1066 |
| 51 | 0.9870 | 0.3040 | 0.0347 | 0.0252 | 0.0001 | 0.0006 |
| 52 | 0.0932 | 0.0637 | 0.0362 | 0.0260 | 0.0068 | 0.0095 |
| 53 | 0.0239 | 0.0336 | 0.0056 | 0.0078 | 0.0007 | 0.0024 |
| 54 | 0.0188 | 0.0303 | 0.0044 | 0.0068 | 0.0013 | 0.0034 |
| 55 | 0.3565 | 0.1494 | 0.5096 | 0.1583 | 0.0636 | 0.0427 |
| 56 | 0.4956 | 0.1903 | 0.2803 | 0.1053 | 0.2762 | 0.1323 |
| 59 | 0.7848 | 0.2596 | 0.0683 | 0.0379 | 0.4103 | 0.1738 |
| 65 | 0.6905 | 0.2378 | 0.2604 | 0.0996 | 0.6012 | 0.2402 |
| 66 | 0.1604 | 0.0917 | 0.0568 | 0.0340 | 0.0824 | 0.0532 |
| 67 | 0.2818 | 0.1273 | 0.8419 | 0.2253 | 0.1039 | 0.0620 |
| 68 | 0.0272 | 0.0345 | 0.7633 | 0.2109 | 0.9673 | 0.3316 |
| 74 | 0.0121 | 0.0243 | 0.0000 | 0.0001 | 0.0000 | 0.0001 |
| 75 | 0.6028 | 0.2164 | 0.0170 | 0.0160 | 0.1938 | 0.1008 |
| 76 | 0.1781 | 0.0958 | 0.0119 | 0.0128 | 0.0017 | 0.0038 |
| 77 | 0.0140 | 0.0262 | 0.0074 | 0.0095 | 0.0179 | 0.0181 |
| 80 | 0.5221 | 0.1970 | 0.0042 | 0.0068 | 0.0025 | 0.0052 |
| 82 | 0.2101 | 0.1043 | 0.0282 | 0.0222 | 0.0321 | 0.0263 |
| 83 | 0.1343 | 0.0794 | 0.0130 | 0.0134 | 0.0286 | 0.0241 |
| 84 | 0.0083 | 0.0209 | 0.0441 | 0.0290 | 0.0181 | 0.0182 |
| 92 | 0.0650 | 0.0521 | 0.1027 | 0.0494 | 0.3484 | 0.1549 |
| 93 | 0.3313 | 0.1431 | 0.0010 | 0.0038 | 0.0049 | 0.0076 |
| 99 | 0.1851 | 0.0975 | 0.0010 | 0.0037 | 0.0001 | 0.0006 |
| 100 | 0.0973 | 0.0650 | 0.0029 | 0.0060 | 0.0025 | 0.0051 |
| 101 | 0.0311 | 0.0364 | 0.0022 | 0.0053 | 0.0064 | 0.0092 |
| 102 | 0.0016 | 0.0108 | 0.0450 | 0.0294 | 0.0020 | 0.0043 |
| 103 | 0.0304 | 0.0358 | 0.0048 | 0.0070 | 0.0259 | 0.0229 |
| 105 | 0.5712 | 0.2107 | 0.6866 | 0.1972 | 0.9818 | 0.3354 |
| 107 | 0.9162 | 0.2896 | 0.6989 | 0.1994 | 0.4234 | 0.1784 |
| 113 | 0.1014 | 0.0665 | 0.0036 | 0.0064 | 0.0001 | 0.0010 |
| 114 | 0.6511 | 0.2261 | 0.9454 | 0.2458 | 0.0955 | 0.0583 |
| 117 | 0.6489 | 0.2261 | 0.7412 | 0.2052 | 0.2420 | 0.1197 |
| 119 | 0.0019 | 0.0111 | 0.0000 | 0.0000 | 0.0000 | 0.0000 |
| 120 | 0.1662 | 0.0923 | 0.0256 | 0.0213 | 0.0087 | 0.0109 |
| 121 | 0.9196 | 0.2899 | 0.2821 | 0.1053 | 0.1915 | 0.1003 |
| 122 | 0.6361 | 0.2231 | 0.2334 | 0.0912 | 0.2963 | 0.1388 |
| 126 | 0.2086 | 0.1039 | 0.0302 | 0.0231 | 0.0242 | 0.0223 |
| 137 | 0.5909 | 0.2140 | 0.2049 | 0.0843 | 0.0185 | 0.0184 |
| 138 | 0.3525 | 0.1484 | 0.1922 | 0.0805 | 0.0027 | 0.0053 |
| 150 | 0.8465 | 0.2728 | 0.0460 | 0.0300 | 0.0199 | 0.0193 |
| 154 | 0.1993 | 0.1020 | 0.0115 | 0.0126 | 0.0115 | 0.0136 |
| 180 | 0.4578 | 0.1794 | 0.6131 | 0.1813 | 0.7601 | 0.2840 |
| 181 | 0.3765 | 0.1552 | 0.5436 | 0.1663 | 0.8418 | 0.3054 |
| 191 | 0.9835 | 0.3040 | 0.1710 | 0.0733 | 0.8645 | 0.3090 |
| 210 | 0.0070 | 0.0206 | 0.0132 | 0.0134 | 0.0034 | 0.0059 |
| 217 | 0.0075 | 0.0209 | 0.0005 | 0.0025 | 0.0012 | 0.0033 |
| 221 | 0.3849 | 0.1568 | 0.2091 | 0.0856 | 0.0576 | 0.0398 |
| 227 | 0.9087 | 0.2891 | 0.0715 | 0.0387 | 0.7673 | 0.2859 |
| 241 | 0.2545 | 0.1190 | 0.0215 | 0.0185 | 0.0593 | 0.0404 |
| 254 | 0.0326 | 0.0377 | 0.0000 | 0.0005 | 0.0000 | 0.0000 |
| 261 | 0.0657 | 0.0521 | 0.0277 | 0.0221 | 0.0178 | 0.0181 |
| 263 | 0.8071 | 0.2640 | 0.2960 | 0.1084 | 0.8947 | 0.3140 |
| 265 | 0.1993 | 0.1020 | 0.2448 | 0.0944 | 0.5508 | 0.2238 |
| 273 | 0.6969 | 0.2387 | 0.4676 | 0.1503 | 0.3594 | 0.1577 |
| 280 | 0.0017 | 0.0110 | 0.1725 | 0.0737 | 0.0246 | 0.0224 |
| 296 | 0.1239 | 0.0764 | 0.0076 | 0.0096 | 0.0102 | 0.0122 |
| 299 | 0.5620 | 0.2085 | 0.5203 | 0.1602 | 0.4476 | 0.1864 |
| 300 | 0.1808 | 0.0961 | 0.8696 | 0.2306 | 0.4480 | 0.1864 |
| 301 | 0.0001 | 0.0027 | 0.0530 | 0.0331 | 0.0015 | 0.0037 |
| 303 | 0.7050 | 0.2403 | 0.4495 | 0.1471 | 0.7707 | 0.2864 |
| 306 | 0.2561 | 0.1190 | 0.2443 | 0.0944 | 0.3871 | 0.1679 |
| 311 | 0.1138 | 0.0721 | 0.0000 | 0.0004 | 0.0056 | 0.0083 |
| 312 | 0.0053 | 0.0186 | 0.0013 | 0.0041 | 0.0261 | 0.0230 |
| 318 | 0.2549 | 0.1190 | 0.1778 | 0.0754 | 0.3973 | 0.1712 |
| 321 | 0.7147 | 0.2424 | 0.0173 | 0.0161 | 0.3452 | 0.1542 |
| 323 | 0.2006 | 0.1020 | 0.3965 | 0.1348 | 0.3583 | 0.1577 |

TABLE 4D-continued

| | Sp/SPF | | ABX/SPF | | GF/SPF | |
|---|---|---|---|---|---|---|
| PSO | p-value | q-value | p-value | q-value | p-value | q-value |
| 326 | 0.8307 | 0.2693 | 0.8387 | 0.2249 | 0.2531 | 0.1233 |
| 328 | 0.1707 | 0.0927 | 0.0695 | 0.0382 | 0.8619 | 0.3088 |
| 332 | 0.0001 | 0.0027 | 0.0000 | 0.0001 | 0.0000 | 0.0002 |
| 333 | 0.7058 | 0.2403 | 0.0006 | 0.0029 | 0.1961 | 0.1011 |
| 334 | 0.0211 | 0.0316 | 0.0908 | 0.0447 | 0.0492 | 0.0356 |
| 337 | 0.0590 | 0.0504 | 0.0000 | 0.0005 | 0.0536 | 0.0374 |
| 342 | 0.0399 | 0.0407 | 0.0021 | 0.0053 | 0.0008 | 0.0026 |
| 343 | 0.2256 | 0.1086 | 0.6827 | 0.1968 | 0.1918 | 0.1003 |
| 349 | 0.0381 | 0.0398 | 0.0012 | 0.0040 | 0.0270 | 0.0234 |
| 351 | 0.0860 | 0.0614 | 0.7037 | 0.1994 | 0.0583 | 0.0402 |
| 353 | 0.3788 | 0.1558 | 0.5034 | 0.1566 | 0.8886 | 0.3131 |
| 362 | 0.2909 | 0.1299 | 0.4077 | 0.1371 | 0.9112 | 0.3186 |
| 363 | 0.0071 | 0.0206 | 0.5988 | 0.1787 | 0.7948 | 0.2905 |
| 364 | 0.0104 | 0.0222 | 0.0019 | 0.0050 | 0.0005 | 0.0022 |
| 365 | 0.4673 | 0.1827 | 0.0249 | 0.0208 | 0.6053 | 0.2406 |
| 367 | 0.0296 | 0.0351 | 0.1076 | 0.0511 | 0.0040 | 0.0066 |
| 369 | 0.5338 | 0.2006 | 0.0000 | 0.0000 | 0.0000 | 0.0001 |
| 371 | 0.0869 | 0.0616 | 0.0806 | 0.0420 | 0.3378 | 0.1526 |
| 372 | 0.1303 | 0.0780 | 0.2841 | 0.1053 | 0.4466 | 0.1864 |
| 373 | 0.9750 | 0.3020 | 0.1934 | 0.0807 | 0.4323 | 0.1814 |
| 375 | 0.2567 | 0.1190 | 0.1054 | 0.0505 | 0.6188 | 0.2452 |
| 379 | 0.0693 | 0.0535 | 0.0548 | 0.0335 | 0.0373 | 0.0294 |
| 380 | 0.1268 | 0.0773 | 0.0793 | 0.0414 | 0.0176 | 0.0180 |
| 381 | 0.3829 | 0.1563 | 0.1361 | 0.0611 | 0.0191 | 0.0188 |
| 382 | 0.7542 | 0.2514 | 0.2125 | 0.0861 | 0.0000 | 0.0003 |
| 383 | 0.1610 | 0.0917 | 0.3459 | 0.1223 | 0.6412 | 0.2520 |
| 386 | 0.5064 | 0.1936 | 0.1941 | 0.0808 | 0.3594 | 0.1577 |
| 387 | 0.0810 | 0.0593 | 0.1523 | 0.0667 | 0.0508 | 0.0366 |
| 392 | 0.5783 | 0.2127 | 0.3183 | 0.1152 | 0.0002 | 0.0014 |
| 397 | 0.0039 | 0.0164 | 0.1396 | 0.0619 | 0.0523 | 0.0371 |
| 399 | 0.1296 | 0.0780 | 0.0046 | 0.0069 | 0.0082 | 0.0108 |
| 405 | 0.1108 | 0.0713 | 0.1095 | 0.0513 | 0.0484 | 0.0353 |
| 410 | 0.2713 | 0.1242 | 0.1277 | 0.0577 | 0.9608 | 0.3309 |
| 411 | 0.0330 | 0.0377 | 0.0028 | 0.0059 | 0.0039 | 0.0065 |
| 412 | 0.1453 | 0.0850 | 0.0390 | 0.0271 | 0.3557 | 0.1571 |
| 418 | 0.2303 | 0.1103 | 0.8272 | 0.2228 | 0.3077 | 0.1424 |
| 421 | 0.0230 | 0.0326 | 0.0705 | 0.0385 | 0.0402 | 0.0309 |
| 426 | 0.0270 | 0.0345 | 0.0755 | 0.0401 | 0.0473 | 0.0347 |
| 429 | 0.3171 | 0.1389 | 0.0397 | 0.0275 | 0.1222 | 0.0698 |
| 430 | 0.1178 | 0.0736 | 0.4832 | 0.1523 | 0.2921 | 0.1376 |
| 436 | 0.8713 | 0.2798 | 0.0040 | 0.0065 | 0.6503 | 0.2531 |
| 438 | 0.1247 | 0.0764 | 0.1218 | 0.0557 | 0.1437 | 0.0795 |
| 439 | 0.0073 | 0.0209 | 0.1116 | 0.0520 | 0.0862 | 0.0547 |
| 442 | 0.3193 | 0.1395 | 0.6039 | 0.1795 | 0.1953 | 0.1011 |
| 443 | 0.0373 | 0.0394 | 0.1022 | 0.0493 | 0.0326 | 0.0265 |
| 445 | 0.8455 | 0.2728 | 0.0907 | 0.0447 | 0.7607 | 0.2840 |
| 446 | 0.0053 | 0.0186 | 0.0323 | 0.0239 | 0.0711 | 0.0471 |
| 447 | 0.2880 | 0.1291 | 0.0659 | 0.0373 | 0.0518 | 0.0369 |
| 451 | 0.0141 | 0.0262 | 0.0016 | 0.0046 | 0.0007 | 0.0025 |
| 454 | 0.9387 | 0.2935 | 0.4996 | 0.1558 | 0.1163 | 0.0676 |
| 456 | 0.0039 | 0.0164 | 0.0880 | 0.0441 | 0.3507 | 0.1552 |
| 459 | 0.5363 | 0.2011 | 0.0261 | 0.0214 | 0.6215 | 0.2458 |
| 460 | 0.6506 | 0.2261 | 0.4757 | 0.1514 | 0.0551 | 0.0383 |
| 461 | 0.9395 | 0.2935 | 0.4258 | 0.1416 | 0.8906 | 0.3131 |
| 465 | 0.0159 | 0.0282 | 0.4488 | 0.1471 | 0.0853 | 0.0543 |
| 467 | 0.0016 | 0.0108 | 0.0623 | 0.0356 | 0.0005 | 0.0022 |
| 468 | 0.0084 | 0.0209 | 0.0848 | 0.0430 | 0.0012 | 0.0033 |
| 469 | 0.0037 | 0.0164 | 0.2144 | 0.0861 | 0.0361 | 0.0288 |
| 471 | 0.3007 | 0.1331 | 0.3236 | 0.1158 | 0.0192 | 0.0188 |
| 472 | 0.1667 | 0.0923 | 0.0533 | 0.0331 | 0.1041 | 0.0620 |
| 473 | 0.5885 | 0.2138 | 0.0817 | 0.0423 | 0.5027 | 0.2078 |
| 474 | 0.0174 | 0.0289 | 0.0004 | 0.0025 | 0.0123 | 0.0144 |
| 475 | 0.0411 | 0.0412 | 0.4510 | 0.1473 | 0.0372 | 0.0294 |
| 476 | 0.8311 | 0.2693 | 0.2204 | 0.0880 | 0.3746 | 0.1640 |
| 477 | 0.0375 | 0.0394 | 0.0332 | 0.0243 | 0.0585 | 0.0402 |
| 478 | 0.0015 | 0.0108 | 0.0764 | 0.0404 | 0.0030 | 0.0056 |
| 479 | 0.3103 | 0.1366 | 0.0275 | 0.0221 | 0.0150 | 0.0161 |
| 480 | 0.3659 | 0.1522 | 0.3202 | 0.1152 | 0.2309 | 0.1148 |
| 756 | 0.3654 | 0.1522 | 0.0271 | 0.0218 | 0.0923 | 0.0569 |
| 929 | 0.5433 | 0.2032 | 0.0079 | 0.0096 | 0.0079 | 0.0107 |
| 955 | 0.0098 | 0.0218 | 0.2877 | 0.1058 | 0.0012 | 0.0033 |
| 958 | 0.3663 | 0.1522 | 0.1561 | 0.0679 | 0.1130 | 0.0660 |
| 959 | 0.1689 | 0.0924 | 0.0053 | 0.0075 | 0.1106 | 0.0654 |
| 965 | 0.2470 | 0.1167 | 0.0022 | 0.0053 | 0.1838 | 0.0969 |
| 967 | 0.0286 | 0.0345 | 0.0079 | 0.0096 | 0.0032 | 0.0057 |
| 972 | 0.7869 | 0.2599 | 0.3870 | 0.1326 | 0.5267 | 0.2158 |

TABLE 4D-continued

| | Sp/SPF | | ABX/SPF | | GF/SPF | |
|---|---|---|---|---|---|---|
| PSO | p-value | q-value | p-value | q-value | p-value | q-value |
| 973 | 0.8061 | 0.2640 | 0.4549 | 0.1476 | 0.3339 | 0.1517 |
| 974 | 0.0447 | 0.0428 | 0.0129 | 0.0134 | 0.1791 | 0.0949 |
| 975 | 0.0005 | 0.0056 | 0.0001 | 0.0005 | 0.0010 | 0.0032 |
| 978 | 0.9885 | 0.3040 | 0.1867 | 0.0786 | 0.6942 | 0.2643 |
| 981 | 0.0542 | 0.0477 | 0.2267 | 0.0893 | 0.6479 | 0.2526 |
| 982 | 0.4432 | 0.1744 | 0.0189 | 0.0171 | 0.4315 | 0.1814 |
| 983 | 0.9472 | 0.2949 | 0.8998 | 0.2365 | 0.6677 | 0.2567 |
| 984 | 0.3448 | 0.1469 | 0.3587 | 0.1256 | 0.4059 | 0.1733 |
| 986 | 0.0624 | 0.0518 | 0.0033 | 0.0064 | 0.0320 | 0.0262 |
| 993 | 0.0148 | 0.0272 | 0.4881 | 0.1535 | 0.2286 | 0.1140 |
| 994 | 0.0012 | 0.0093 | 0.0003 | 0.0021 | 0.0457 | 0.0339 |
| 995 | 0.0638 | 0.0521 | 0.1599 | 0.0694 | 0.2922 | 0.1376 |
| 997 | 0.0215 | 0.0318 | 0.0158 | 0.0152 | 0.0053 | 0.0081 |
| 1018 | 0.0900 | 0.0627 | 0.0000 | 0.0001 | 0.0047 | 0.0075 |
| 1020 | 0.0287 | 0.0345 | 0.0035 | 0.0064 | 0.0170 | 0.0174 |
| 1023 | 0.0217 | 0.0319 | 0.0002 | 0.0018 | 0.0049 | 0.0076 |
| 1024 | 0.0027 | 0.0145 | 0.0472 | 0.0305 | 0.0085 | 0.0109 |
| 1028 | 0.1334 | 0.0791 | 0.0128 | 0.0134 | 0.0090 | 0.0111 |
| 1030 | 0.0753 | 0.0566 | 0.0030 | 0.0060 | 0.0086 | 0.0109 |
| 1033 | 0.1458 | 0.0850 | 0.0289 | 0.0222 | 0.1117 | 0.0658 |
| 1073 | 0.4055 | 0.1633 | 0.0188 | 0.0171 | 0.9752 | 0.3338 |
| 1078 | 0.0016 | 0.0108 | 0.0001 | 0.0005 | 0.0001 | 0.0011 |
| 1079 | 0.0262 | 0.0342 | 0.0095 | 0.0111 | 0.2445 | 0.1201 |
| 1080 | 0.2055 | 0.1030 | 0.0061 | 0.0083 | 0.1997 | 0.1020 |
| 1090 | 0.1167 | 0.0732 | 0.0096 | 0.0111 | 0.1746 | 0.0941 |
| 1099 | 0.0249 | 0.0338 | 0.0150 | 0.0149 | 0.0128 | 0.0148 |
| 1104 | 0.1581 | 0.0910 | 0.0287 | 0.0222 | 0.1761 | 0.0942 |
| 1108 | 0.0419 | 0.0418 | 0.0133 | 0.0134 | 0.1971 | 0.1012 |
| 1109 | 0.6916 | 0.2378 | 0.0258 | 0.0213 | 0.0405 | 0.0310 |
| 1111 | 0.0517 | 0.0465 | 0.0038 | 0.0065 | 0.1108 | 0.0654 |
| 1115 | 0.0624 | 0.0518 | 0.0026 | 0.0055 | 0.0142 | 0.0156 |
| 1116 | 0.0131 | 0.0257 | 0.0056 | 0.0078 | 0.0259 | 0.0229 |
| 1123 | 0.4137 | 0.1653 | 0.0221 | 0.0187 | 0.3392 | 0.1526 |
| 1127 | 0.0211 | 0.0316 | 0.0045 | 0.0069 | 0.0153 | 0.0163 |
| 1131 | 0.0093 | 0.0213 | 0.0160 | 0.0152 | 0.0518 | 0.0369 |
| 1132 | 0.1700 | 0.0926 | 0.6435 | 0.1878 | 0.0936 | 0.0576 |
| 1138 | 0.0251 | 0.0338 | 0.0104 | 0.0118 | 0.0017 | 0.0038 |
| 1149 | 0.0057 | 0.0192 | 0.0023 | 0.0053 | 0.0058 | 0.0086 |
| 1150 | 0.0137 | 0.0262 | 0.0079 | 0.0096 | 0.0192 | 0.0188 |
| 1152 | 0.0663 | 0.0522 | 0.0569 | 0.0340 | 0.0157 | 0.0167 |
| 1157 | 0.9363 | 0.2935 | 0.6088 | 0.1806 | 0.6641 | 0.2558 |
| 1163 | 0.3487 | 0.1475 | 0.4639 | 0.1495 | 0.1786 | 0.0949 |
| 1165 | 0.0005 | 0.0056 | 0.0114 | 0.0126 | 0.0042 | 0.0069 |
| 1166 | 0.7412 | 0.2482 | 0.4717 | 0.1513 | 0.1773 | 0.0946 |
| 1167 | 0.0315 | 0.0366 | 0.0193 | 0.0172 | 0.0247 | 0.0224 |
| 1169 | 0.0391 | 0.0401 | 0.0016 | 0.0046 | 0.0007 | 0.0024 |
| 1179 | 0.0346 | 0.0379 | 0.0080 | 0.0096 | 0.0489 | 0.0355 |
| 1181 | 0.5308 | 0.1999 | 0.4388 | 0.1446 | 0.5643 | 0.2280 |
| 1183 | 0.3341 | 0.1438 | 0.2221 | 0.0884 | 0.0003 | 0.0014 |
| 1201 | 0.6309 | 0.2222 | 0.7208 | 0.2018 | 0.8625 | 0.3088 |
| 1203 | 0.1969 | 0.1019 | 0.6710 | 0.1942 | 0.8455 | 0.3061 |
| 1204 | 0.5120 | 0.1952 | 0.1269 | 0.0577 | 0.1178 | 0.0681 |
| 1205 | 0.3455 | 0.1469 | 0.6358 | 0.1859 | 0.3340 | 0.1517 |
| 1217 | 0.0487 | 0.0447 | 0.5537 | 0.1687 | 0.0778 | 0.0511 |
| 1218 | 0.0081 | 0.0209 | 0.2226 | 0.0884 | 0.0021 | 0.0044 |
| 1223 | 0.0920 | 0.0633 | 0.5789 | 0.1745 | 0.2451 | 0.1201 |
| 1225 | 0.0182 | 0.0297 | 0.4807 | 0.1520 | 0.0185 | 0.0184 |
| 1236 | 0.0501 | 0.0455 | 0.6842 | 0.1969 | 0.3370 | 0.1526 |
| 1239 | 0.0940 | 0.0641 | 0.2318 | 0.0908 | 0.0870 | 0.0549 |
| 1244 | 0.1143 | 0.0722 | 0.9588 | 0.2475 | 0.3050 | 0.1415 |
| 1247 | 0.0625 | 0.0518 | 0.2825 | 0.1053 | 0.0204 | 0.0196 |
| 1253 | 0.0042 | 0.0169 | 0.1081 | 0.0511 | 0.0397 | 0.0307 |
| 1258 | 0.0044 | 0.0169 | 0.9563 | 0.2475 | 0.0011 | 0.0032 |
| 1259 | 0.0197 | 0.0311 | 0.7007 | 0.1994 | 0.0100 | 0.0121 |
| 1260 | 0.0178 | 0.0293 | 0.3749 | 0.1300 | 0.0074 | 0.0101 |
| 1264 | 0.1640 | 0.0923 | 0.7715 | 0.2128 | 0.0881 | 0.0552 |
| 1265 | 0.0063 | 0.0199 | 0.4549 | 0.1476 | 0.0232 | 0.0215 |
| 1267 | 0.1873 | 0.0980 | 0.7023 | 0.1994 | 0.0899 | 0.0560 |
| 1269 | 0.0071 | 0.0206 | 0.5167 | 0.1594 | 0.0168 | 0.0173 |
| 1270 | 0.0212 | 0.0317 | 0.4066 | 0.1371 | 0.0149 | 0.0161 |
| 1271 | 0.2503 | 0.1176 | 0.7887 | 0.2163 | 0.1964 | 0.1011 |
| 1272 | 0.0850 | 0.0610 | 0.4064 | 0.1371 | 0.0909 | 0.0564 |
| 1273 | 0.0286 | 0.0345 | 0.2812 | 0.1053 | 0.1121 | 0.0658 |
| 1274 | 0.0260 | 0.0342 | 0.4067 | 0.1371 | 0.0465 | 0.0343 |
| 1276 | 0.0764 | 0.0567 | 0.9658 | 0.2488 | 0.0825 | 0.0532 |
| 1277 | 0.0949 | 0.0642 | 0.5427 | 0.1663 | 0.1451 | 0.0800 |

TABLE 4D-continued

| | Sp/SPF | | ABX/SPF | | GF/SPF | |
|---|---|---|---|---|---|---|
| PSO | p-value | q-value | p-value | q-value | p-value | q-value |
| 1351 | 0.7712 | 0.2561 | 0.0131 | 0.0134 | 0.1758 | 0.0942 |
| 1355 | 0.0084 | 0.0209 | 0.0049 | 0.0071 | 0.0128 | 0.0148 |
| 1359 | 0.0699 | 0.0537 | 0.0477 | 0.0305 | 0.0236 | 0.0218 |
| 1360 | 0.3241 | 0.1413 | 0.2133 | 0.0861 | 0.9511 | 0.3284 |
| 1363 | 0.2205 | 0.1080 | 0.2480 | 0.0954 | 0.7531 | 0.2828 |
| 1372 | 0.1691 | 0.0924 | 0.6654 | 0.1930 | 0.8791 | 0.3125 |
| 1430 | 0.2336 | 0.1110 | 0.1155 | 0.0531 | 0.7501 | 0.2822 |
| 1446 | 0.3972 | 0.1611 | 0.3729 | 0.1296 | 0.1014 | 0.0608 |
| 1449 | 0.4257 | 0.1687 | 0.1443 | 0.0635 | 0.7732 | 0.2865 |
| 1452 | 0.6222 | 0.2205 | 0.0018 | 0.0050 | 0.2910 | 0.1376 |
| 1480 | 0.2975 | 0.1322 | 0.0096 | 0.0111 | 0.8213 | 0.2991 |
| 1482 | 0.1755 | 0.0947 | 0.2191 | 0.0877 | 0.9634 | 0.3309 |
| 1483 | 0.0839 | 0.0607 | 0.2273 | 0.0893 | 0.2445 | 0.1201 |
| 1485 | 0.0564 | 0.0487 | 0.9090 | 0.2379 | 0.0029 | 0.0055 |
| 1487 | 0.4882 | 0.1896 | 0.1128 | 0.0524 | 0.3045 | 0.1415 |
| 1488 | 0.0472 | 0.0435 | 0.9923 | 0.2543 | 0.0141 | 0.0156 |
| 1495 | 0.2233 | 0.1081 | 0.2683 | 0.1018 | 0.0081 | 0.0108 |
| 1496 | 0.1398 | 0.0823 | 0.0738 | 0.0393 | 0.1609 | 0.0875 |
| 1498 | 0.9880 | 0.3040 | 0.0047 | 0.0069 | 0.3986 | 0.1714 |
| 1499 | 0.1241 | 0.0764 | 0.0420 | 0.0281 | 0.0286 | 0.0241 |
| 1500 | 0.2032 | 0.1024 | 0.0006 | 0.0028 | 0.0143 | 0.0156 |
| 1501 | 0.2558 | 0.1190 | 0.0716 | 0.0387 | 0.0031 | 0.0056 |
| 1503 | 0.0172 | 0.0288 | 0.3248 | 0.1160 | 0.0003 | 0.0017 |
| 1504 | 0.8159 | 0.2659 | 0.0072 | 0.0094 | 0.3279 | 0.1496 |
| 1506 | 0.0715 | 0.0547 | 0.2859 | 0.1057 | 0.0022 | 0.0046 |
| 1517 | 0.7317 | 0.2468 | 0.0046 | 0.0069 | 0.0445 | 0.0332 |
| 1518 | 0.5518 | 0.2056 | 0.0733 | 0.0392 | 0.7864 | 0.2891 |
| 1519 | 0.3448 | 0.1469 | 0.0184 | 0.0170 | 0.5347 | 0.2182 |
| 1521 | 0.7746 | 0.2568 | 0.8307 | 0.2231 | 0.5747 | 0.2301 |
| 1522 | 0.9261 | 0.2915 | 0.0898 | 0.0447 | 0.1337 | 0.0750 |
| 1523 | 0.8055 | 0.2640 | 0.0315 | 0.0235 | 0.6361 | 0.2511 |
| 1524 | 0.6031 | 0.2164 | 0.0004 | 0.0022 | 0.0360 | 0.0288 |
| 1527 | 0.0665 | 0.0522 | 0.1610 | 0.0696 | 0.0940 | 0.0576 |
| 1528 | 0.2146 | 0.1060 | 0.2077 | 0.0853 | 0.0377 | 0.0295 |
| 1529 | 0.3545 | 0.1489 | 0.3191 | 0.1152 | 0.2719 | 0.1305 |
| 1536 | 0.6262 | 0.2210 | 0.1112 | 0.0519 | 0.6477 | 0.2526 |
| 1537 | 0.8225 | 0.2675 | 0.2419 | 0.0938 | 0.3417 | 0.1534 |
| 1539 | 0.2014 | 0.1021 | 0.0827 | 0.0426 | 0.0004 | 0.0018 |
| 1541 | 0.1004 | 0.0660 | 0.0157 | 0.0152 | 0.0395 | 0.0306 |
| 1542 | 0.3747 | 0.1548 | 0.0708 | 0.0385 | 0.3478 | 0.1549 |
| 1547 | 0.5716 | 0.2107 | 0.9753 | 0.2508 | 0.0327 | 0.0265 |
| 1565 | 0.9697 | 0.3014 | 0.1068 | 0.0509 | 0.7466 | 0.2814 |
| 1567 | 0.9168 | 0.2896 | 0.0633 | 0.0361 | 0.7791 | 0.2875 |
| 1582 | 0.6348 | 0.2231 | 0.9787 | 0.2513 | 0.9842 | 0.3356 |
| 1711 | 0.4223 | 0.1677 | 0.0600 | 0.0347 | 0.1683 | 0.0913 |
| 1718 | 0.0160 | 0.0282 | 0.0500 | 0.0315 | 0.0027 | 0.0053 |
| 1721 | 0.0170 | 0.0287 | 0.2792 | 0.1053 | 0.1217 | 0.0697 |
| 1731 | 0.1086 | 0.0705 | 0.1284 | 0.0578 | 0.1056 | 0.0627 |
| 1732 | 0.0286 | 0.0345 | 0.1384 | 0.0619 | 0.0282 | 0.0241 |
| 1744 | 0.0207 | 0.0316 | 0.0809 | 0.0420 | 0.0226 | 0.0213 |
| 1753 | 0.0277 | 0.0345 | 0.0025 | 0.0055 | 0.0006 | 0.0023 |
| 1754 | 0.0125 | 0.0248 | 0.3481 | 0.1228 | 0.9189 | 0.3196 |
| 1782 | 0.0003 | 0.0041 | 0.0289 | 0.0222 | 0.0007 | 0.0024 |
| 1783 | 0.1458 | 0.0850 | 0.3440 | 0.1219 | 0.5211 | 0.2144 |
| 1784 | 0.5126 | 0.1952 | 0.0039 | 0.0065 | 0.0645 | 0.0431 |
| 1786 | 0.7888 | 0.2600 | 0.0000 | 0.0002 | 0.1827 | 0.0966 |
| 1788 | 0.0463 | 0.0435 | 0.0035 | 0.0064 | 0.0017 | 0.0038 |
| 1789 | 0.0629 | 0.0518 | 0.0061 | 0.0083 | 0.0131 | 0.0150 |
| 1790 | 0.2736 | 0.1246 | 0.0007 | 0.0030 | 0.0164 | 0.0170 |
| 1791 | 0.0956 | 0.0642 | 0.0729 | 0.0392 | 0.0086 | 0.0109 |
| 1792 | 0.0243 | 0.0336 | 0.0732 | 0.0392 | 0.0004 | 0.0018 |
| 1793 | 0.0018 | 0.0110 | 0.0000 | 0.0000 | 0.0000 | 0.0000 |
| 1811 | 0.2022 | 0.1022 | 0.0224 | 0.0189 | 0.0136 | 0.0154 |
| 1815 | 0.0511 | 0.0462 | 0.0210 | 0.0183 | 0.0359 | 0.0288 |
| 1827 | 0.0410 | 0.0412 | 0.0038 | 0.0065 | 0.0095 | 0.0116 |
| 1828 | 0.2319 | 0.1105 | 0.0908 | 0.0447 | 0.0269 | 0.0234 |
| 1829 | 0.0521 | 0.0466 | 0.0003 | 0.0022 | 0.0030 | 0.0056 |
| 1831 | 0.0691 | 0.0535 | 0.0087 | 0.0104 | 0.0130 | 0.0150 |
| 1834 | 0.0912 | 0.0631 | 0.8257 | 0.2228 | 0.7553 | 0.2831 |
| 1837 | 0.0672 | 0.0525 | 0.4757 | 0.1514 | 0.6439 | 0.2521 |
| 1841 | 0.0114 | 0.0232 | 0.7067 | 0.1998 | 0.2837 | 0.1345 |
| 1845 | 0.0922 | 0.0633 | 0.0090 | 0.0106 | 0.0198 | 0.0193 |
| 1851 | 0.0139 | 0.0262 | 0.0306 | 0.0232 | 0.0006 | 0.0024 |
| 1866 | 0.0090 | 0.0213 | 0.0019 | 0.0050 | 0.0001 | 0.0008 |
| 1867 | 0.0499 | 0.0455 | 0.0160 | 0.0152 | 0.0014 | 0.0036 |
| 1870 | 0.0405 | 0.0411 | 0.4123 | 0.1381 | 0.8618 | 0.3088 |
| 1878 | 0.0375 | 0.0394 | 0.0120 | 0.0128 | 0.0013 | 0.0034 |
| 1884 | 0.0288 | 0.0345 | 0.0973 | 0.0471 | 0.0017 | 0.0038 |
| 1889 | 0.5884 | 0.2138 | 0.7778 | 0.2137 | 0.1166 | 0.0676 |
| 1892 | 0.0752 | 0.0566 | 0.3546 | 0.1245 | 0.2182 | 0.1094 |
| 1902 | 0.0538 | 0.0476 | 0.3969 | 0.1348 | 0.0084 | 0.0109 |
| 1903 | 0.0006 | 0.0059 | 0.6230 | 0.1829 | 0.5669 | 0.2280 |
| 1907 | 0.2068 | 0.1033 | 0.8675 | 0.2305 | 0.9916 | 0.3375 |
| 1945 | 0.0786 | 0.0581 | 0.0850 | 0.0430 | 0.0159 | 0.0168 |
| 1948 | 0.0559 | 0.0485 | 0.0044 | 0.0068 | 0.0022 | 0.0046 |
| 1949 | 0.0343 | 0.0378 | 0.1087 | 0.0511 | 0.0031 | 0.0056 |
| 1950 | 0.2685 | 0.1232 | 0.3529 | 0.1242 | 0.8509 | 0.3064 |
| 1953 | 0.0886 | 0.0623 | 0.4607 | 0.1488 | 0.1507 | 0.0824 |
| 1955 | 0.2317 | 0.1105 | 0.7745 | 0.2132 | 0.0378 | 0.0295 |
| 1962 | 0.0467 | 0.0435 | 0.0585 | 0.0344 | 0.0029 | 0.0055 |
| 1970 | 0.0617 | 0.0518 | 0.2124 | 0.0861 | 0.0138 | 0.0155 |
| 1974 | 0.0868 | 0.0616 | 0.4107 | 0.1378 | 0.0084 | 0.0109 |
| 1975 | 0.3281 | 0.1423 | 0.6139 | 0.1813 | 0.5231 | 0.2148 |
| 1976 | 0.1638 | 0.0923 | 0.3077 | 0.1118 | 0.8335 | 0.3030 |
| 1979 | 0.4077 | 0.1638 | 0.5491 | 0.1677 | 0.7717 | 0.2864 |
| 1982 | 0.4393 | 0.1733 | 0.8521 | 0.2272 | 0.1430 | 0.0793 |
| 1985 | 0.2107 | 0.1043 | 0.4184 | 0.1394 | 0.8870 | 0.3131 |
| 2016 | 0.2000 | 0.1020 | 0.3786 | 0.1307 | 0.2785 | 0.1328 |
| 2021 | 0.2644 | 0.1217 | 0.2679 | 0.1018 | 0.1227 | 0.0699 |
| 2024 | 0.1691 | 0.0924 | 0.4538 | 0.1476 | 0.1497 | 0.0821 |
| 2034 | 0.0629 | 0.0518 | 0.0021 | 0.0053 | 0.0027 | 0.0053 |
| 2052 | 0.0363 | 0.0394 | 0.1278 | 0.0577 | 0.0064 | 0.0092 |
| 2067 | 0.0224 | 0.0321 | 0.0593 | 0.0346 | 0.0082 | 0.0108 |
| 2072 | 0.0453 | 0.0429 | 0.5134 | 0.1588 | 0.0280 | 0.0240 |
| 2105 | 0.3666 | 0.1522 | 0.0287 | 0.0222 | 0.0529 | 0.0373 |
| 2106 | 0.5821 | 0.2132 | 0.0201 | 0.0177 | 0.1236 | 0.0702 |
| 2107 | 0.4095 | 0.1641 | 0.0375 | 0.0264 | 0.1132 | 0.0660 |
| 2113 | 0.5529 | 0.2056 | 0.0359 | 0.0259 | 0.1489 | 0.0819 |
| 2115 | 0.4946 | 0.1903 | 0.0558 | 0.0337 | 0.0822 | 0.0532 |
| 2118 | 0.1650 | 0.0923 | 0.2025 | 0.0838 | 0.5402 | 0.2200 |
| 2136 | 0.1751 | 0.0947 | 0.3200 | 0.1152 | 0.0845 | 0.0540 |
| 2157 | 0.4918 | 0.1901 | 0.0437 | 0.0290 | 0.1009 | 0.0607 |
| 2164 | 0.0747 | 0.0566 | 0.0102 | 0.0117 | 0.0034 | 0.0059 |
| 2165 | 0.1129 | 0.0719 | 0.3057 | 0.1116 | 0.1384 | 0.0772 |
| 2166 | 0.5884 | 0.2138 | 0.0952 | 0.0463 | 0.1986 | 0.1017 |
| 2168 | 0.4012 | 0.1623 | 0.2840 | 0.1053 | 0.8893 | 0.3131 |
| 2179 | 0.5866 | 0.2138 | 0.0575 | 0.0343 | 0.4381 | 0.1834 |
| 2192 | 0.2598 | 0.1201 | 0.0312 | 0.0235 | 0.2109 | 0.1066 |
| 2193 | 0.6240 | 0.2207 | 0.0152 | 0.0149 | 0.2129 | 0.1073 |
| 2194 | 0.1190 | 0.0741 | 0.0888 | 0.0443 | 0.0485 | 0.0353 |
| 2199 | 0.0448 | 0.0428 | 0.3891 | 0.1330 | 0.0138 | 0.0155 |
| 2203 | 0.1164 | 0.0732 | 0.6948 | 0.1988 | 0.2237 | 0.1119 |
| 2206 | 0.1325 | 0.0788 | 0.0645 | 0.0366 | 0.0254 | 0.0229 |
| 2209 | 0.0833 | 0.0605 | 0.0417 | 0.0281 | 0.0139 | 0.0155 |
| 2211 | 0.2750 | 0.1249 | 0.0560 | 0.0337 | 0.0920 | 0.0569 |
| 2217 | 0.0385 | 0.0399 | 0.6518 | 0.1894 | 0.0255 | 0.0229 |
| 2310 | 0.3826 | 0.1563 | 0.6344 | 0.1859 | 0.4011 | 0.1721 |
| 2311 | 0.4184 | 0.1665 | 0.2032 | 0.0839 | 0.9296 | 0.3227 |
| 2312 | 0.0036 | 0.0164 | 0.0008 | 0.0033 | 0.0001 | 0.0006 |
| 2313 | 0.4932 | 0.1902 | 0.2142 | 0.0861 | 0.0865 | 0.0547 |
| 2314 | 0.1989 | 0.1020 | 0.9039 | 0.2371 | 0.3942 | 0.1702 |
| 2318 | 0.2850 | 0.1284 | 0.8459 | 0.2260 | 0.1606 | 0.0875 |
| 2327 | 0.1595 | 0.0915 | 0.7144 | 0.2004 | 0.2137 | 0.1074 |
| 2343 | 0.0140 | 0.0262 | 0.0073 | 0.0094 | 0.0005 | 0.0022 |
| 2345 | 0.0547 | 0.0477 | 0.4353 | 0.1439 | 0.0075 | 0.0103 |
| 2347 | 0.0150 | 0.0273 | 0.0160 | 0.0152 | 0.0003 | 0.0014 |
| 2348 | 0.6456 | 0.2260 | 0.2830 | 0.1053 | 0.8884 | 0.3131 |
| 2350 | 0.1878 | 0.0980 | 0.2129 | 0.0861 | 0.2994 | 0.1399 |
| 2351 | 0.0004 | 0.0051 | 0.0402 | 0.0275 | 0.0017 | 0.0038 |
| 2356 | 0.0198 | 0.0311 | 0.0022 | 0.0053 | 0.0283 | 0.0241 |
| 2357 | 0.1659 | 0.0923 | 0.4181 | 0.1394 | 0.3269 | 0.1495 |
| 2360 | 0.2235 | 0.1081 | 0.4487 | 0.1471 | 0.2069 | 0.1051 |
| 2361 | 0.3381 | 0.1452 | 0.7991 | 0.2179 | 0.6023 | 0.2402 |
| 2364 | 0.1868 | 0.0980 | 0.5694 | 0.1720 | 0.3092 | 0.1428 |
| 2371 | 0.1001 | 0.0660 | 0.8120 | 0.2202 | 0.6437 | 0.2521 |
| 2374 | 0.0525 | 0.0467 | 0.7956 | 0.2177 | 0.2565 | 0.1241 |
| 2375 | 0.2803 | 0.1269 | 0.1729 | 0.0737 | 0.2444 | 0.1201 |
| 2376 | 0.1088 | 0.0705 | 0.1646 | 0.0710 | 0.0993 | 0.0601 |
| 2379 | 0.1843 | 0.0975 | 0.2257 | 0.0891 | 0.0827 | 0.0532 |
| 2381 | 0.0891 | 0.0624 | 0.2917 | 0.1070 | 0.6854 | 0.2625 |
| 2383 | 0.0643 | 0.0521 | 0.5668 | 0.1716 | 0.1260 | 0.0711 |
| 2394 | 0.0210 | 0.0316 | 0.3783 | 0.1307 | 0.0611 | 0.0415 |

TABLE 4D-continued

| | Sp/SPF | | ABX/SPF | | GF/SPF | |
|---|---|---|---|---|---|---|
| PSO | p-value | q-value | p-value | q-value | p-value | q-value |
| 2395 | 0.0038 | 0.0164 | 0.5901 | 0.1768 | 0.3208 | 0.1471 |
| 2407 | 0.0991 | 0.0657 | 0.0869 | 0.0437 | 0.3387 | 0.1526 |
| 2411 | 0.0649 | 0.0521 | 0.0837 | 0.0427 | 0.0371 | 0.0294 |
| 2413 | 0.0001 | 0.0027 | 0.0694 | 0.0382 | 0.0038 | 0.0064 |
| 2416 | 0.6176 | 0.2196 | 0.1180 | 0.0541 | 0.3773 | 0.1644 |
| 2418 | 0.0046 | 0.0169 | 0.6502 | 0.1894 | 0.3113 | 0.1434 |
| 2419 | 0.1624 | 0.0922 | 0.8803 | 0.2330 | 0.1207 | 0.0693 |
| 2420 | 0.0372 | 0.0394 | 0.1086 | 0.0511 | 0.0214 | 0.0204 |
| 2422 | 0.0598 | 0.0509 | 0.9172 | 0.2393 | 0.0083 | 0.0108 |
| 2423 | 0.0094 | 0.0213 | 0.2131 | 0.0861 | 0.0000 | 0.0004 |
| 2426 | 0.0005 | 0.0054 | 0.2399 | 0.0932 | 0.0087 | 0.0109 |
| 2429 | 0.2051 | 0.1030 | 0.4357 | 0.1439 | 0.1204 | 0.0693 |
| 2431 | 0.0469 | 0.0435 | 0.6202 | 0.1825 | 0.1842 | 0.0969 |
| 2432 | 0.0083 | 0.0209 | 0.7253 | 0.2027 | 0.1761 | 0.0942 |
| 2442 | 0.1478 | 0.0859 | 0.8064 | 0.2193 | 0.7849 | 0.2891 |
| 2443 | 0.0163 | 0.0285 | 0.0428 | 0.0285 | 0.0537 | 0.0374 |
| 2445 | 0.0450 | 0.0428 | 0.3723 | 0.1296 | 0.0526 | 0.0372 |
| 2448 | 0.5207 | 0.1970 | 0.5978 | 0.1787 | 0.0149 | 0.0161 |
| 2449 | 0.0055 | 0.0186 | 0.0219 | 0.0186 | 0.0002 | 0.0014 |
| 2474 | 0.1808 | 0.0961 | 0.1395 | 0.0619 | 0.0590 | 0.0404 |
| 2480 | 0.0045 | 0.0169 | 0.0332 | 0.0243 | 0.0005 | 0.0022 |
| 2481 | 0.0371 | 0.0394 | 0.0107 | 0.0120 | 0.0001 | 0.0008 |
| 2488 | 0.0029 | 0.0150 | 0.0703 | 0.0385 | 0.0000 | 0.0004 |
| 2491 | 0.0167 | 0.0286 | 0.0024 | 0.0055 | 0.0004 | 0.0020 |
| 2493 | 0.0060 | 0.0195 | 0.0026 | 0.0055 | 0.0002 | 0.0014 |
| 2498 | 0.0885 | 0.0623 | 0.0306 | 0.0232 | 0.0016 | 0.0038 |
| 2499 | 0.0104 | 0.0222 | 0.0130 | 0.0134 | 0.0044 | 0.0072 |
| 2513 | 0.0028 | 0.0145 | 0.1401 | 0.0619 | 0.0019 | 0.0042 |
| 2514 | 0.0106 | 0.0222 | 0.0012 | 0.0040 | 0.0001 | 0.0008 |
| 2517 | 0.0194 | 0.0310 | 0.0676 | 0.0378 | 0.0012 | 0.0034 |
| 2518 | 0.0003 | 0.0041 | 0.0025 | 0.0055 | 0.0008 | 0.0027 |
| 2520 | 0.1306 | 0.0780 | 0.4579 | 0.1482 | 0.2646 | 0.1277 |
| 2522 | 0.8132 | 0.2655 | 0.4760 | 0.1514 | 0.3804 | 0.1653 |
| 2523 | 0.1104 | 0.0713 | 0.0936 | 0.0457 | 0.0270 | 0.0234 |
| 2525 | 0.2281 | 0.1096 | 0.2717 | 0.1028 | 0.7022 | 0.2668 |
| 2543 | 0.3249 | 0.1413 | 0.5644 | 0.1712 | 0.5335 | 0.2182 |
| 2547 | 0.0437 | 0.0428 | 0.4813 | 0.1520 | 0.8825 | 0.3131 |
| 2549 | 0.7965 | 0.2620 | 0.4758 | 0.1514 | 0.2817 | 0.1339 |
| 2561 | 0.0273 | 0.0345 | 0.0440 | 0.0290 | 0.0412 | 0.0313 |
| 2563 | 0.1660 | 0.0923 | 0.0064 | 0.0086 | 0.0079 | 0.0107 |
| 2564 | 0.0206 | 0.0316 | 0.0029 | 0.0060 | 0.0013 | 0.0034 |
| 2565 | 0.7399 | 0.2482 | 0.1970 | 0.0818 | 0.8012 | 0.2923 |
| 2566 | 0.0719 | 0.0548 | 0.0466 | 0.0302 | 0.1348 | 0.0754 |
| 2567 | 0.6504 | 0.2261 | 0.0375 | 0.0264 | 0.0429 | 0.0321 |
| 2568 | 0.0958 | 0.0642 | 0.0030 | 0.0060 | 0.0009 | 0.0027 |
| 2569 | 0.0424 | 0.0418 | 0.0188 | 0.0171 | 0.1251 | 0.0708 |
| 2570 | 0.0657 | 0.0521 | 0.0014 | 0.0042 | 0.0126 | 0.0147 |
| 2575 | 0.5810 | 0.2132 | 0.2394 | 0.0932 | 0.7882 | 0.2892 |
| 2577 | 0.6112 | 0.2184 | 0.0852 | 0.0430 | 0.2963 | 0.1388 |
| 2579 | 0.1690 | 0.0924 | 0.0378 | 0.0264 | 0.3443 | 0.1542 |
| 2580 | 0.0682 | 0.0531 | 0.0007 | 0.0032 | 0.0045 | 0.0072 |
| 2581 | 0.5201 | 0.1970 | 0.0367 | 0.0262 | 0.1406 | 0.0782 |
| 2583 | 0.1795 | 0.0960 | 0.0045 | 0.0069 | 0.0048 | 0.0076 |
| 2588 | 0.2229 | 0.1081 | 0.0267 | 0.0217 | 0.0728 | 0.0481 |
| 2591 | 0.3315 | 0.1431 | 0.0211 | 0.0183 | 0.0040 | 0.0066 |
| 2592 | 0.0085 | 0.0209 | 0.0161 | 0.0152 | 0.4130 | 0.1744 |
| 2594 | 0.1249 | 0.0764 | 0.0578 | 0.0343 | 0.0357 | 0.0288 |
| 2610 | 0.0764 | 0.0567 | 0.0013 | 0.0040 | 0.0039 | 0.0065 |
| 2624 | 0.3112 | 0.1367 | 0.0280 | 0.0222 | 0.0088 | 0.0110 |
| 2625 | 0.1087 | 0.0705 | 0.0212 | 0.0183 | 0.0052 | 0.0080 |
| 2649 | 0.3812 | 0.1563 | 0.0407 | 0.0278 | 0.8738 | 0.3112 |
| 2652 | 0.2180 | 0.1073 | 0.0672 | 0.0377 | 0.0066 | 0.0093 |
| 2669 | 0.6185 | 0.2196 | 0.0772 | 0.0405 | 0.8669 | 0.3093 |
| 3453 | 0.0242 | 0.0336 | 0.0542 | 0.0334 | 0.0031 | 0.0056 |
| 3454 | 0.0444 | 0.0428 | 0.0494 | 0.0312 | 0.0012 | 0.0033 |
| 3455 | 0.0019 | 0.0111 | 0.0012 | 0.0040 | 0.0000 | 0.0002 |
| 3456 | 0.1786 | 0.0958 | 0.0475 | 0.0305 | 0.0014 | 0.0034 |
| 3458 | 0.0003 | 0.0041 | 0.0613 | 0.0352 | 0.0000 | 0.0002 |
| 3461 | 0.1908 | 0.0992 | 0.0125 | 0.0132 | 0.0263 | 0.0231 |
| 3462 | 0.3962 | 0.1610 | 0.2241 | 0.0887 | 0.0066 | 0.0093 |
| 3464 | 0.3465 | 0.1470 | 0.0005 | 0.0026 | 0.0306 | 0.0253 |
| 3466 | 0.0265 | 0.0342 | 0.0021 | 0.0053 | 0.0006 | 0.0022 |
| 3471 | 0.9736 | 0.3020 | 0.0529 | 0.0331 | 0.6629 | 0.2558 |
| 3472 | 0.9410 | 0.2935 | 0.8073 | 0.2193 | 0.3894 | 0.1685 |
| 3473 | 0.3425 | 0.1467 | 0.1141 | 0.0526 | 0.4976 | 0.2061 |
| 3474 | 0.1635 | 0.0923 | 0.0402 | 0.0275 | 0.6912 | 0.2636 |

TABLE 4D-continued

| | Sp/SPF | | ABX/SPF | | GF/SPF | |
|---|---|---|---|---|---|---|
| PSO | p-value | q-value | p-value | q-value | p-value | q-value |
| 3478 | 0.0289 | 0.0345 | 0.0589 | 0.0345 | 0.0095 | 0.0116 |
| 3479 | 0.1493 | 0.0865 | 0.1882 | 0.0790 | 0.5662 | 0.2280 |
| 3480 | 0.5984 | 0.2156 | 0.8916 | 0.2354 | 0.9427 | 0.3261 |
| 3485 | 0.0114 | 0.0232 | 0.0012 | 0.0040 | 0.0008 | 0.0027 |
| 3495 | 0.0979 | 0.0651 | 0.0041 | 0.0067 | 0.0034 | 0.0059 |
| 3498 | 0.5917 | 0.2140 | 0.1733 | 0.0737 | 0.2553 | 0.1240 |
| 3505 | 0.0114 | 0.0232 | 0.0556 | 0.0337 | 0.0013 | 0.0034 |
| 3507 | 0.0797 | 0.0586 | 0.0106 | 0.0120 | 0.0228 | 0.0214 |
| 3508 | 0.0021 | 0.0118 | 0.0537 | 0.0332 | 0.0009 | 0.0028 |
| 3513 | 0.2646 | 0.1217 | 0.6812 | 0.1968 | 0.3490 | 0.1549 |
| 3514 | 0.3741 | 0.1548 | 0.4891 | 0.1535 | 0.6556 | 0.2546 |
| 3516 | 0.0065 | 0.0199 | 0.0014 | 0.0042 | 0.0012 | 0.0033 |
| 3522 | 0.1280 | 0.0775 | 0.0035 | 0.0064 | 0.0298 | 0.0247 |
| 3528 | 0.2914 | 0.1299 | 0.0835 | 0.0427 | 0.0161 | 0.0169 |
| 3530 | 0.6132 | 0.2186 | 0.7112 | 0.2003 | 0.4071 | 0.1735 |
| 3533 | 0.2981 | 0.1322 | 0.4774 | 0.1515 | 0.0028 | 0.0055 |
| 3534 | 0.8764 | 0.2804 | 0.6160 | 0.1816 | 0.0061 | 0.0089 |
| 3535 | 0.9155 | 0.2896 | 0.0937 | 0.0457 | 0.6611 | 0.2557 |
| 3537 | 0.0338 | 0.0377 | 0.0151 | 0.0149 | 0.0419 | 0.0316 |
| 3541 | 0.1127 | 0.0719 | 0.6886 | 0.1974 | 0.0873 | 0.0549 |
| 3542 | 0.7662 | 0.2549 | 0.9583 | 0.2475 | 0.2509 | 0.1226 |
| 3547 | 0.0007 | 0.0065 | 0.0077 | 0.0096 | 0.0000 | 0.0002 |
| 3548 | 0.0010 | 0.0080 | 0.0613 | 0.0352 | 0.0001 | 0.0006 |
| 3549 | 0.7416 | 0.2482 | 0.0088 | 0.0105 | 0.0532 | 0.0374 |
| 3550 | 0.5658 | 0.2094 | 0.0190 | 0.0171 | 0.0142 | 0.0156 |
| 3552 | 0.4037 | 0.1629 | 0.4328 | 0.1436 | 0.0426 | 0.0320 |
| 3563 | 0.4968 | 0.1904 | 0.1138 | 0.0526 | 0.2681 | 0.1291 |
| 3565 | 0.1300 | 0.0780 | 0.0420 | 0.0281 | 0.0635 | 0.0427 |
| 3566 | 0.1118 | 0.0717 | 0.0036 | 0.0064 | 0.0015 | 0.0037 |
| 3567 | 0.0657 | 0.0521 | 0.0038 | 0.0065 | 0.0053 | 0.0080 |
| 3568 | 0.0569 | 0.0489 | 0.0192 | 0.0172 | 0.7120 | 0.2700 |
| 3572 | 0.0334 | 0.0377 | 0.5222 | 0.1604 | 0.0886 | 0.0554 |
| 3573 | 0.2473 | 0.1167 | 0.8240 | 0.2228 | 0.5571 | 0.2259 |
| 3576 | 0.0102 | 0.0222 | 0.0288 | 0.0222 | 0.0221 | 0.0210 |
| 3577 | 0.0001 | 0.0026 | 0.0033 | 0.0064 | 0.0000 | 0.0002 |
| 3578 | 0.2476 | 0.1167 | 0.3862 | 0.1326 | 0.9624 | 0.3309 |
| 3579 | 0.0043 | 0.0169 | 0.0034 | 0.0064 | 0.0011 | 0.0033 |
| 3580 | 0.0954 | 0.0642 | 0.0111 | 0.0123 | 0.0250 | 0.0227 |
| 3585 | 0.0252 | 0.0338 | 0.5135 | 0.1588 | 0.2787 | 0.1328 |
| 3587 | 0.0000 | 0.0001 | 0.0001 | 0.0007 | 0.0000 | 0.0000 |
| 3588 | 0.0078 | 0.0209 | 0.0005 | 0.0026 | 0.0003 | 0.0017 |
| 3589 | 0.0059 | 0.0193 | 0.0008 | 0.0033 | 0.0013 | 0.0034 |
| 3598 | 0.0039 | 0.0164 | 0.0367 | 0.0262 | 0.0003 | 0.0014 |
| 3599 | 0.6955 | 0.2387 | 0.2867 | 0.1057 | 0.7785 | 0.2875 |
| 3602 | 0.0654 | 0.0521 | 0.7969 | 0.2177 | 0.3002 | 0.1400 |
| 3603 | 0.0080 | 0.0209 | 0.0315 | 0.0235 | 0.0411 | 0.0313 |
| 3607 | 0.0470 | 0.0435 | 0.5630 | 0.1712 | 0.0297 | 0.0247 |
| 3608 | 0.0223 | 0.0321 | 0.8988 | 0.2365 | 0.0510 | 0.0366 |
| 3624 | 0.0054 | 0.0186 | 0.0067 | 0.0089 | 0.0055 | 0.0083 |
| 3627 | 0.6088 | 0.2180 | 0.0478 | 0.0305 | 0.0782 | 0.0511 |
| 3628 | 0.1849 | 0.0975 | 0.1812 | 0.0765 | 0.3182 | 0.1462 |
| 3636 | 0.0064 | 0.0199 | 0.0597 | 0.0347 | 0.0392 | 0.0305 |
| 3641 | 0.4532 | 0.1780 | 0.0025 | 0.0055 | 0.0005 | 0.0022 |
| 3643 | 0.0003 | 0.0041 | 0.3915 | 0.1336 | 0.5707 | 0.2290 |
| 3644 | 0.0040 | 0.0164 | 0.7307 | 0.2038 | 0.9146 | 0.3192 |
| 3648 | 0.0849 | 0.0610 | 0.3833 | 0.1320 | 0.0461 | 0.0341 |
| 3649 | 0.0424 | 0.0418 | 0.0007 | 0.0030 | 0.0005 | 0.0022 |
| 3650 | 0.2000 | 0.1020 | 0.3075 | 0.1118 | 0.0965 | 0.0587 |
| 3651 | 0.6854 | 0.2376 | 0.0044 | 0.0069 | 0.0002 | 0.0014 |
| 3653 | 0.0092 | 0.0213 | 0.8277 | 0.2228 | 0.0163 | 0.0170 |
| 3654 | 0.0761 | 0.0567 | 0.0481 | 0.0305 | 0.0002 | 0.0011 |
| 3656 | 0.3493 | 0.1475 | 0.7140 | 0.2004 | 0.4046 | 0.1732 |
| 3658 | 0.0368 | 0.0394 | 0.3339 | 0.1189 | 0.0258 | 0.0229 |
| 3662 | 0.9285 | 0.2917 | 0.3212 | 0.1153 | 0.8509 | 0.3064 |
| 3663 | 0.6881 | 0.2376 | 0.0771 | 0.0405 | 0.4082 | 0.1735 |
| 3664 | 0.8371 | 0.2708 | 0.0375 | 0.0264 | 0.6870 | 0.2626 |
| 3667 | 0.9126 | 0.2896 | 0.1669 | 0.0717 | 0.9067 | 0.3176 |
| 3668 | 0.0261 | 0.0342 | 0.0056 | 0.0078 | 0.0215 | 0.0204 |
| 3670 | 0.4144 | 0.1653 | 0.3356 | 0.1193 | 0.7271 | 0.2752 |
| 3694 | 0.4864 | 0.1893 | 0.0004 | 0.0025 | 0.0017 | 0.0038 |
| 3698 | 0.5218 | 0.1970 | 0.7344 | 0.2041 | 0.2026 | 0.1032 |
| 3714 | 0.0031 | 0.0157 | 0.6019 | 0.1792 | 0.0027 | 0.0053 |
| 3715 | 0.0103 | 0.0222 | 0.3680 | 0.1286 | 0.0731 | 0.0482 |
| 3718 | 0.2237 | 0.1081 | 0.9102 | 0.2379 | 0.5205 | 0.2144 |
| 3727 | 0.0000 | 0.0008 | 0.0001 | 0.0006 | 0.0000 | 0.0000 |
| 3728 | 0.3102 | 0.1366 | 0.1275 | 0.0577 | 0.1000 | 0.0603 |

TABLE 4D-continued

| PSO | Sp/SPF p-value | Sp/SPF q-value | ABX/SPF p-value | ABX/SPF q-value | GF/SPF p-value | GF/SPF q-value |
|---|---|---|---|---|---|---|
| 3751 | 0.1212 | 0.0752 | 0.7036 | 0.1994 | 0.0008 | 0.0027 |
| 3754 | 0.2859 | 0.1285 | 0.0837 | 0.0427 | 0.0032 | 0.0056 |
| 3757 | 0.0000 | 0.0008 | 0.0000 | 0.0000 | 0.0000 | 0.0000 |
| 3771 | 0.6871 | 0.2376 | 0.8631 | 0.2297 | 0.8469 | 0.3061 |
| 3978 | 0.5977 | 0.2156 | 0.1399 | 0.0619 | 0.7387 | 0.2790 |
| 4000 | 0.7347 | 0.2473 | 0.0932 | 0.0457 | 0.2557 | 0.1240 |
| 4079 | 0.8714 | 0.2798 | 0.1472 | 0.0646 | 0.0621 | 0.0420 |
| 4108 | 0.0336 | 0.0377 | 0.0000 | 0.0001 | 0.0000 | 0.0004 |
| 4131 | 0.7310 | 0.2468 | 0.9343 | 0.2433 | 0.6398 | 0.2520 |
| 4144 | 0.6993 | 0.2391 | 0.0197 | 0.0175 | 0.1272 | 0.0716 |
| 4221 | 0.0223 | 0.0321 | 0.0000 | 0.0000 | 0.0000 | 0.0003 |
| 4246 | 0.0340 | 0.0377 | 0.0068 | 0.0090 | 0.6059 | 0.2406 |
| 4274 | 0.8733 | 0.2799 | 0.0036 | 0.0064 | 0.0003 | 0.0016 |
| 4363 | 0.8887 | 0.2838 | 0.0681 | 0.0379 | 0.2316 | 0.1149 |
| 4756 | 0.4899 | 0.1898 | 0.0583 | 0.0344 | 0.0979 | 0.0594 |
| 4832 | 0.2738 | 0.1246 | 0.2556 | 0.0980 | 0.4107 | 0.1738 |
| 4835 | 0.7093 | 0.2411 | 0.0004 | 0.0025 | 0.0027 | 0.0053 |
| 4899 | 0.1277 | 0.0775 | 0.5813 | 0.1745 | 0.0416 | 0.0315 |
| 4926 | 0.8925 | 0.2845 | 0.8925 | 0.2354 | 0.0070 | 0.0097 |
| 4930 | 0.0000 | 0.0001 | 0.2618 | 0.0998 | 0.0828 | 0.0532 |
| 4971 | 0.1580 | 0.0910 | 0.5798 | 0.1745 | 0.1922 | 0.1003 |

TABLE 4E

| PSO | Sp/ABX p-value | Sp/ABX q-value | GF/ABX p-value | GF/ABX q-value | GF/Sp p-value | GF/Sp q-value |
|---|---|---|---|---|---|---|
| 1 | 0.8917 | 0.5563 | 0.1267 | 0.3091 | 0.1609 | 0.5562 |
| 2 | 0.5072 | 0.4333 | 0.2155 | 0.3855 | 0.0648 | 0.4168 |
| 5 | 0.3900 | 0.3727 | 0.0802 | 0.2676 | 0.3465 | 0.7016 |
| 6 | 0.0506 | 0.1713 | 0.0562 | 0.2376 | 0.9585 | 0.8691 |
| 9 | 0.0641 | 0.1838 | 0.7898 | 0.6001 | 0.1067 | 0.5131 |
| 10 | 0.8368 | 0.5346 | 0.2106 | 0.3803 | 0.1487 | 0.5562 |
| 14 | 0.3008 | 0.3317 | 0.1547 | 0.3609 | 0.0194 | 0.2317 |
| 16 | 0.8637 | 0.5475 | 0.2699 | 0.4251 | 0.2055 | 0.5984 |
| 17 | 0.5051 | 0.4333 | 0.0564 | 0.2376 | 0.1932 | 0.5864 |
| 18 | 0.5041 | 0.4333 | 0.4624 | 0.5230 | 0.9457 | 0.8691 |
| 21 | 0.3804 | 0.3666 | 0.3223 | 0.4661 | 0.9073 | 0.8681 |
| 28 | 0.8984 | 0.5563 | 0.7342 | 0.5835 | 0.6409 | 0.8251 |
| 30 | 0.1043 | 0.2278 | 0.0667 | 0.2508 | 0.8144 | 0.8519 |
| 34 | 0.9011 | 0.5563 | 0.8090 | 0.6041 | 0.9064 | 0.8681 |
| 35 | 0.2546 | 0.2999 | 0.6489 | 0.5695 | 0.4855 | 0.7453 |
| 38 | 0.9840 | 0.5782 | 0.9418 | 0.6284 | 0.9258 | 0.8691 |
| 39 | 0.7121 | 0.4942 | 0.4316 | 0.5036 | 0.6730 | 0.8315 |
| 40 | 0.1827 | 0.2616 | 0.9116 | 0.6254 | 0.2193 | 0.6064 |
| 41 | 0.5689 | 0.4508 | 0.6138 | 0.5695 | 0.9476 | 0.8691 |
| 42 | 0.0500 | 0.1713 | 0.5935 | 0.5688 | 0.0161 | 0.2066 |
| 43 | 0.0000 | 0.0007 | 0.1850 | 0.3746 | 0.0000 | 0.0001 |
| 44 | 0.8981 | 0.5563 | 0.8933 | 0.6233 | 0.9951 | 0.8795 |
| 45 | 0.1288 | 0.2311 | 0.7327 | 0.5835 | 0.0679 | 0.4298 |
| 47 | 0.0001 | 0.0019 | 0.9421 | 0.6284 | 0.0000 | 0.0026 |
| 50 | 0.3096 | 0.3368 | 0.2838 | 0.4431 | 0.9536 | 0.8691 |
| 51 | 0.0359 | 0.1496 | 0.0114 | 0.1024 | 0.0001 | 0.0026 |
| 52 | 0.6346 | 0.4691 | 0.4478 | 0.5190 | 0.2233 | 0.6097 |
| 53 | 0.5166 | 0.4340 | 0.3668 | 0.4776 | 0.1289 | 0.5309 |
| 54 | 0.5193 | 0.4340 | 0.6166 | 0.5695 | 0.2579 | 0.6316 |
| 55 | 0.7881 | 0.5248 | 0.2108 | 0.3803 | 0.3198 | 0.6817 |
| 56 | 0.0863 | 0.2155 | 0.0374 | 0.2039 | 0.6752 | 0.8321 |
| 59 | 0.0394 | 0.1566 | 0.0119 | 0.1042 | 0.5790 | 0.7830 |
| 65 | 0.1339 | 0.2311 | 0.1067 | 0.2848 | 0.9002 | 0.8681 |
| 66 | 0.0024 | 0.0325 | 0.0010 | 0.0306 | 0.7145 | 0.8380 |
| 67 | 0.2056 | 0.2747 | 0.0711 | 0.2551 | 0.5567 | 0.7770 |
| 68 | 0.0509 | 0.1713 | 0.7325 | 0.5835 | 0.0250 | 0.2775 |
| 74 | 0.0000 | 0.0000 | 0.9507 | 0.6291 | 0.0000 | 0.0000 |
| 75 | 0.0512 | 0.1713 | 0.2229 | 0.3875 | 0.4242 | 0.7283 |
| 76 | 0.1850 | 0.2618 | 0.3984 | 0.4995 | 0.0369 | 0.3243 |
| 77 | 0.7740 | 0.5212 | 0.6904 | 0.5790 | 0.9111 | 0.8681 |
| 80 | 0.0181 | 0.0987 | 0.8231 | 0.6041 | 0.0111 | 0.1537 |
| 82 | 0.2972 | 0.3287 | 0.9509 | 0.6291 | 0.3254 | 0.6900 |
| 83 | 0.2580 | 0.3016 | 0.7178 | 0.5835 | 0.4344 | 0.7283 |
| 84 | 0.4436 | 0.4017 | 0.6744 | 0.5775 | 0.7261 | 0.8380 |
| 92 | 0.8109 | 0.5274 | 0.4620 | 0.5230 | 0.3329 | 0.6976 |

TABLE 4E-continued

| PSO | Sp/ABX p-value | Sp/ABX q-value | GF/ABX p-value | GF/ABX q-value | GF/Sp p-value | GF/Sp q-value |
|---|---|---|---|---|---|---|
| 93 | 0.0100 | 0.0718 | 0.5070 | 0.5413 | 0.0423 | 0.3453 |
| 99 | 0.0217 | 0.1120 | 0.2581 | 0.4219 | 0.0016 | 0.0466 |
| 100 | 0.1137 | 0.2311 | 0.9466 | 0.6291 | 0.1005 | 0.5102 |
| 101 | 0.2485 | 0.2999 | 0.6493 | 0.5695 | 0.4757 | 0.7453 |
| 102 | 0.1453 | 0.2422 | 0.1714 | 0.3733 | 0.9239 | 0.8691 |
| 103 | 0.4127 | 0.3838 | 0.4558 | 0.5230 | 0.9401 | 0.8691 |
| 105 | 0.3363 | 0.3473 | 0.7033 | 0.5824 | 0.5560 | 0.7770 |
| 107 | 0.7779 | 0.5212 | 0.6755 | 0.5775 | 0.4855 | 0.7453 |
| 113 | 0.1309 | 0.2311 | 0.1766 | 0.3736 | 0.0075 | 0.1289 |
| 114 | 0.7008 | 0.4913 | 0.1085 | 0.2848 | 0.2116 | 0.6023 |
| 117 | 0.4347 | 0.3960 | 0.3941 | 0.4991 | 0.1109 | 0.5146 |
| 119 | 0.0000 | 0.0000 | 0.0059 | 0.0770 | 0.0000 | 0.0000 |
| 120 | 0.3416 | 0.3473 | 0.6244 | 0.5695 | 0.1567 | 0.5562 |
| 121 | 0.2413 | 0.2964 | 0.8079 | 0.6041 | 0.1615 | 0.5562 |
| 122 | 0.4630 | 0.4136 | 0.8773 | 0.6181 | 0.5606 | 0.7770 |
| 126 | 0.3134 | 0.3388 | 0.9179 | 0.6254 | 0.2684 | 0.6409 |
| 137 | 0.4537 | 0.4086 | 0.2240 | 0.3875 | 0.0571 | 0.4034 |
| 138 | 0.6950 | 0.4913 | 0.0519 | 0.2360 | 0.0229 | 0.2599 |
| 150 | 0.0678 | 0.1925 | 0.6914 | 0.5790 | 0.0301 | 0.2992 |
| 154 | 0.1614 | 0.2443 | 1.0000 | 0.6499 | 0.1614 | 0.5562 |
| 180 | 0.8101 | 0.5274 | 0.8403 | 0.6048 | 0.6592 | 0.8268 |
| 181 | 0.7774 | 0.5212 | 0.4219 | 0.5036 | 0.2816 | 0.6480 |
| 191 | 0.1771 | 0.2595 | 0.2268 | 0.3879 | 0.8807 | 0.8620 |
| 210 | 0.7774 | 0.5212 | 0.5512 | 0.5606 | 0.7526 | 0.8380 |
| 217 | 0.2425 | 0.2964 | 0.6882 | 0.5790 | 0.4347 | 0.7283 |
| 221 | 0.6866 | 0.4905 | 0.4818 | 0.5299 | 0.2734 | 0.6411 |
| 227 | 0.0570 | 0.1757 | 0.0395 | 0.2100 | 0.8559 | 0.8610 |
| 241 | 0.2015 | 0.2715 | 0.6268 | 0.5695 | 0.4182 | 0.7283 |
| 254 | 0.0078 | 0.0610 | 0.0000 | 0.0068 | 0.0000 | 0.0000 |
| 261 | 0.6739 | 0.4870 | 0.8377 | 0.6041 | 0.5328 | 0.7770 |
| 263 | 0.4187 | 0.3872 | 0.3589 | 0.4766 | 0.9109 | 0.8681 |
| 265 | 0.8984 | 0.5563 | 0.5609 | 0.5622 | 0.4794 | 0.7453 |
| 273 | 0.7334 | 0.5011 | 0.1088 | 0.2848 | 0.1975 | 0.5917 |
| 280 | 0.0391 | 0.1566 | 0.3214 | 0.4661 | 0.2478 | 0.6228 |
| 296 | 0.1886 | 0.2645 | 0.8972 | 0.6233 | 0.2328 | 0.6153 |
| 299 | 0.2279 | 0.2893 | 0.9055 | 0.6254 | 0.1876 | 0.5850 |
| 300 | 0.2365 | 0.2953 | 0.5503 | 0.5606 | 0.5469 | 0.7770 |
| 301 | 0.0108 | 0.0724 | 0.1225 | 0.3029 | 0.2442 | 0.6224 |
| 303 | 0.7027 | 0.4913 | 0.6393 | 0.5695 | 0.9302 | 0.8691 |
| 306 | 0.9759 | 0.5766 | 0.7557 | 0.5925 | 0.7787 | 0.8418 |
| 311 | 0.0015 | 0.0272 | 0.0376 | 0.2039 | 0.1616 | 0.5562 |
| 312 | 0.5547 | 0.4482 | 0.1987 | 0.3759 | 0.4748 | 0.7453 |
| 318 | 0.8247 | 0.5300 | 0.6009 | 0.5693 | 0.7619 | 0.8380 |
| 321 | 0.0378 | 0.1538 | 0.1191 | 0.3026 | 0.5578 | 0.7770 |
| 323 | 0.6526 | 0.4749 | 0.9420 | 0.6284 | 0.7055 | 0.8380 |
| 326 | 0.9918 | 0.5795 | 0.3433 | 0.4761 | 0.3484 | 0.7016 |
| 328 | 0.6245 | 0.4679 | 0.0968 | 0.2845 | 0.2275 | 0.6153 |
| 332 | 0.2433 | 0.2964 | 0.8078 | 0.6041 | 0.3507 | 0.7016 |
| 333 | 0.0003 | 0.0076 | 0.0134 | 0.1146 | 0.1008 | 0.5102 |
| 334 | 0.4757 | 0.4222 | 0.7546 | 0.5925 | 0.6862 | 0.8380 |
| 337 | 0.0047 | 0.0517 | 0.0052 | 0.0717 | 0.9615 | 0.8691 |
| 342 | 0.1942 | 0.2690 | 0.6750 | 0.5775 | 0.0922 | 0.5044 |
| 343 | 0.4133 | 0.3838 | 0.3604 | 0.4766 | 0.9210 | 0.8691 |
| 349 | 0.1327 | 0.2311 | 0.1766 | 0.3736 | 0.8693 | 0.8610 |
| 351 | 0.0404 | 0.1585 | 0.0266 | 0.1631 | 0.8416 | 0.8610 |
| 353 | 0.1294 | 0.2311 | 0.4200 | 0.5036 | 0.4572 | 0.7415 |
| 362 | 0.8135 | 0.5274 | 0.3491 | 0.4761 | 0.2450 | 0.6224 |
| 363 | 0.0229 | 0.1162 | 0.7891 | 0.6001 | 0.0128 | 0.1680 |
| 364 | 0.4589 | 0.4111 | 0.5792 | 0.5622 | 0.2021 | 0.5984 |
| 365 | 0.1078 | 0.2298 | 0.0720 | 0.2551 | 0.8312 | 0.8558 |
| 367 | 0.5179 | 0.4340 | 0.1322 | 0.3205 | 0.3730 | 0.7152 |
| 369 | 0.0000 | 0.0004 | 0.5749 | 0.5622 | 0.0000 | 0.0009 |
| 371 | 0.9686 | 0.5743 | 0.4009 | 0.4995 | 0.4228 | 0.7283 |
| 372 | 0.6384 | 0.4708 | 0.7492 | 0.5914 | 0.4324 | 0.7283 |
| 373 | 0.1835 | 0.2616 | 0.5921 | 0.5688 | 0.4146 | 0.7283 |
| 375 | 0.6029 | 0.4610 | 0.2477 | 0.4074 | 0.5154 | 0.7653 |
| 379 | 0.9052 | 0.5567 | 0.8506 | 0.6098 | 0.7587 | 0.8380 |
| 380 | 0.8005 | 0.5274 | 0.4689 | 0.5230 | 0.3318 | 0.6976 |
| 381 | 0.5163 | 0.4340 | 0.3312 | 0.4749 | 0.1132 | 0.5146 |
| 382 | 0.3435 | 0.3473 | 0.0004 | 0.0215 | 0.0000 | 0.0026 |
| 383 | 0.6292 | 0.4691 | 0.6280 | 0.5695 | 0.3376 | 0.6981 |
| 386 | 0.0570 | 0.1757 | 0.6894 | 0.5790 | 0.1221 | 0.5308 |
| 387 | 0.7305 | 0.5006 | 0.5623 | 0.5622 | 0.8128 | 0.8519 |
| 392 | 0.1278 | 0.2311 | 0.0025 | 0.0487 | 0.0001 | 0.0026 |
| 397 | 0.1012 | 0.2257 | 0.6055 | 0.5695 | 0.2466 | 0.6228 |
| 399 | 0.1239 | 0.2311 | 0.8032 | 0.6041 | 0.1910 | 0.5863 |

TABLE 4E-continued

| | Sp/ABX | | GF/ABX | | GF/Sp | |
|---|---|---|---|---|---|---|
| PSO | p-value | q-value | p-value | q-value | p-value | q-value |
| 405 | 0.9950 | 0.5795 | 0.6737 | 0.5775 | 0.6691 | 0.8314 |
| 410 | 0.6520 | 0.4749 | 0.1169 | 0.2991 | 0.2514 | 0.6228 |
| 411 | 0.2790 | 0.3161 | 0.8906 | 0.6233 | 0.3420 | 0.7014 |
| 412 | 0.4963 | 0.4305 | 0.2211 | 0.3875 | 0.5750 | 0.7827 |
| 418 | 0.3217 | 0.3454 | 0.4188 | 0.5036 | 0.8508 | 0.8610 |
| 421 | 0.5870 | 0.4576 | 0.7796 | 0.5988 | 0.7911 | 0.8447 |
| 426 | 0.6146 | 0.4647 | 0.8137 | 0.6041 | 0.7879 | 0.8447 |
| 429 | 0.2543 | 0.2999 | 0.5647 | 0.5622 | 0.5630 | 0.7782 |
| 430 | 0.0292 | 0.1325 | 0.0875 | 0.2729 | 0.5868 | 0.7858 |
| 436 | 0.0058 | 0.0536 | 0.0112 | 0.1024 | 0.7702 | 0.8418 |
| 438 | 0.9896 | 0.5795 | 0.9261 | 0.6282 | 0.9364 | 0.8691 |
| 439 | 0.2011 | 0.2715 | 0.8897 | 0.6233 | 0.2513 | 0.6228 |
| 442 | 0.1372 | 0.2318 | 0.0766 | 0.2639 | 0.7533 | 0.8380 |
| 443 | 0.6099 | 0.4633 | 0.5663 | 0.5622 | 0.9489 | 0.8691 |
| 445 | 0.1297 | 0.2311 | 0.1574 | 0.3616 | 0.9125 | 0.8681 |
| 446 | 0.4198 | 0.3872 | 0.6980 | 0.5811 | 0.2376 | 0.6213 |
| 447 | 0.0065 | 0.0556 | 0.0007 | 0.0251 | 0.3406 | 0.7013 |
| 451 | 0.3489 | 0.3474 | 0.7264 | 0.5835 | 0.2037 | 0.5984 |
| 454 | 0.4529 | 0.4086 | 0.3514 | 0.4761 | 0.1009 | 0.5102 |
| 456 | 0.1567 | 0.2443 | 0.4118 | 0.5036 | 0.0317 | 0.2992 |
| 459 | 0.0066 | 0.0556 | 0.0718 | 0.2551 | 0.2715 | 0.6409 |
| 460 | 0.7922 | 0.5254 | 0.2051 | 0.3759 | 0.1305 | 0.5309 |
| 461 | 0.3841 | 0.3681 | 0.5082 | 0.5413 | 0.8310 | 0.8558 |
| 465 | 0.0773 | 0.2022 | 0.3118 | 0.4633 | 0.4192 | 0.7283 |
| 467 | 0.1101 | 0.2298 | 0.0435 | 0.2196 | 0.6344 | 0.8251 |
| 468 | 0.2810 | 0.3162 | 0.0624 | 0.2508 | 0.3968 | 0.7283 |
| 469 | 0.0594 | 0.1764 | 0.3463 | 0.4761 | 0.3133 | 0.6797 |
| 471 | 0.9604 | 0.5715 | 0.1405 | 0.3366 | 0.1532 | 0.5562 |
| 472 | 0.5430 | 0.4464 | 0.7291 | 0.5835 | 0.7917 | 0.8447 |
| 473 | 0.2141 | 0.2800 | 0.0205 | 0.1413 | 0.2321 | 0.6153 |
| 474 | 0.1243 | 0.2311 | 0.1644 | 0.3649 | 0.8736 | 0.8620 |
| 475 | 0.1726 | 0.2541 | 0.1588 | 0.3616 | 0.9610 | 0.8691 |
| 476 | 0.3067 | 0.3362 | 0.7248 | 0.5835 | 0.4969 | 0.7557 |
| 477 | 0.9531 | 0.5691 | 0.7816 | 0.5988 | 0.8270 | 0.8551 |
| 478 | 0.0872 | 0.2155 | 0.1477 | 0.3488 | 0.7731 | 0.8418 |
| 479 | 0.1962 | 0.2703 | 0.7802 | 0.5988 | 0.1209 | 0.5307 |
| 480 | 0.9258 | 0.5621 | 0.8309 | 0.6041 | 0.7593 | 0.8380 |
| 756 | 0.1600 | 0.2443 | 0.5439 | 0.5598 | 0.4098 | 0.7283 |
| 929 | 0.0303 | 0.1333 | 1.0000 | 0.6499 | 0.0303 | 0.2992 |
| 955 | 0.0930 | 0.2167 | 0.0001 | 0.0117 | 0.0000 | 0.0002 |
| 958 | 0.5888 | 0.4576 | 0.0053 | 0.0717 | 0.0178 | 0.2172 |
| 959 | 0.1041 | 0.2278 | 0.1597 | 0.3616 | 0.8112 | 0.8519 |
| 965 | 0.0316 | 0.1372 | 0.0461 | 0.2206 | 0.8557 | 0.8610 |
| 967 | 0.5598 | 0.4491 | 0.6986 | 0.5811 | 0.3360 | 0.6976 |
| 972 | 0.2604 | 0.3026 | 0.1420 | 0.3376 | 0.7150 | 0.8380 |
| 973 | 0.3242 | 0.3458 | 0.0951 | 0.2834 | 0.4671 | 0.7420 |
| 974 | 0.5643 | 0.4500 | 0.1966 | 0.3759 | 0.4621 | 0.7415 |
| 975 | 0.3391 | 0.3473 | 0.2258 | 0.3879 | 0.7897 | 0.8447 |
| 978 | 0.1822 | 0.2616 | 0.0926 | 0.2797 | 0.7048 | 0.8380 |
| 981 | 0.0036 | 0.0444 | 0.1025 | 0.2848 | 0.1295 | 0.5309 |
| 982 | 0.0918 | 0.2167 | 0.0954 | 0.2834 | 0.9838 | 0.8791 |
| 983 | 0.8477 | 0.5385 | 0.7611 | 0.5929 | 0.6205 | 0.8150 |
| 984 | 0.9778 | 0.5766 | 0.9290 | 0.6282 | 0.9069 | 0.8681 |
| 986 | 0.1900 | 0.2653 | 0.3179 | 0.4661 | 0.7430 | 0.8380 |
| 993 | 0.0640 | 0.1838 | 0.5981 | 0.5693 | 0.1695 | 0.5655 |
| 994 | 0.5374 | 0.4428 | 0.0337 | 0.1949 | 0.1141 | 0.5146 |
| 995 | 0.6207 | 0.4661 | 0.7094 | 0.5835 | 0.3890 | 0.7252 |
| 997 | 0.8871 | 0.5563 | 0.6314 | 0.5695 | 0.5352 | 0.7770 |
| 1018 | 0.0004 | 0.0121 | 0.0111 | 0.1024 | 0.1772 | 0.5832 |
| 1020 | 0.3512 | 0.3477 | 0.4874 | 0.5345 | 0.8075 | 0.8519 |
| 1023 | 0.0592 | 0.1764 | 0.2002 | 0.3759 | 0.5070 | 0.7596 |
| 1024 | 0.2063 | 0.2747 | 0.4318 | 0.5036 | 0.6198 | 0.8150 |
| 1028 | 0.2556 | 0.2999 | 0.8764 | 0.6181 | 0.1992 | 0.5933 |
| 1030 | 0.1493 | 0.2443 | 0.6480 | 0.5695 | 0.3124 | 0.6797 |
| 1033 | 0.4107 | 0.3838 | 0.4982 | 0.5368 | 0.8820 | 0.8620 |
| 1073 | 0.1032 | 0.2278 | 0.0201 | 0.1413 | 0.4227 | 0.7283 |
| 1078 | 0.1526 | 0.2443 | 0.6473 | 0.5695 | 0.3188 | 0.6817 |
| 1079 | 0.6450 | 0.4735 | 0.1106 | 0.2871 | 0.2436 | 0.6224 |
| 1080 | 0.0941 | 0.2167 | 0.0973 | 0.2845 | 0.9859 | 0.8794 |
| 1090 | 0.2351 | 0.2947 | 0.1609 | 0.3616 | 0.8190 | 0.8519 |
| 1099 | 0.8154 | 0.5274 | 0.9431 | 0.6284 | 0.7606 | 0.8380 |
| 1104 | 0.3839 | 0.3681 | 0.3514 | 0.4761 | 0.9497 | 0.8691 |
| 1108 | 0.5927 | 0.4576 | 0.1820 | 0.3746 | 0.4113 | 0.7283 |
| 1109 | 0.0585 | 0.1764 | 0.8297 | 0.6041 | 0.0889 | 0.4997 |
| 1111 | 0.2407 | 0.2964 | 0.1232 | 0.3029 | 0.6933 | 0.8380 |
| 1115 | 0.1584 | 0.2443 | 0.4610 | 0.5230 | 0.4836 | 0.7453 |

TABLE 4E-continued

| | Sp/ABX | | GF/ABX | | GF/Sp | |
|---|---|---|---|---|---|---|
| PSO | p-value | q-value | p-value | q-value | p-value | q-value |
| 1116 | 0.7075 | 0.4931 | 0.4940 | 0.5353 | 0.7552 | 0.8380 |
| 1123 | 0.1154 | 0.2311 | 0.1488 | 0.3493 | 0.8866 | 0.8632 |
| 1127 | 0.4971 | 0.4305 | 0.5922 | 0.5688 | 0.8843 | 0.8626 |
| 1131 | 0.8069 | 0.5274 | 0.5793 | 0.5622 | 0.4268 | 0.7283 |
| 1132 | 0.0729 | 0.2002 | 0.0373 | 0.2039 | 0.7397 | 0.8380 |
| 1138 | 0.6885 | 0.4905 | 0.4302 | 0.5036 | 0.2396 | 0.6213 |
| 1149 | 0.6889 | 0.4905 | 0.6836 | 0.5790 | 0.9942 | 0.8795 |
| 1150 | 0.8072 | 0.5274 | 0.6913 | 0.5790 | 0.8779 | 0.8620 |
| 1152 | 0.9386 | 0.5646 | 0.5432 | 0.5598 | 0.4941 | 0.7538 |
| 1157 | 0.5546 | 0.4482 | 0.3481 | 0.4761 | 0.7227 | 0.8380 |
| 1163 | 0.8336 | 0.5336 | 0.5247 | 0.5509 | 0.6685 | 0.8314 |
| 1165 | 0.2018 | 0.2715 | 0.6608 | 0.5743 | 0.3923 | 0.7252 |
| 1166 | 0.6943 | 0.4913 | 0.5138 | 0.5441 | 0.3003 | 0.6708 |
| 1167 | 0.8192 | 0.5274 | 0.9094 | 0.6254 | 0.9085 | 0.8681 |
| 1169 | 0.1645 | 0.2464 | 0.7169 | 0.5835 | 0.0852 | 0.4957 |
| 1179 | 0.5044 | 0.4333 | 0.4052 | 0.5016 | 0.8663 | 0.8610 |
| 1181 | 0.1688 | 0.2495 | 0.1840 | 0.3746 | 0.9593 | 0.8691 |
| 1183 | 0.7897 | 0.5248 | 0.0049 | 0.0717 | 0.0026 | 0.0693 |
| 1201 | 0.4051 | 0.3805 | 0.8535 | 0.6107 | 0.5146 | 0.7653 |
| 1203 | 0.0926 | 0.2167 | 0.8176 | 0.6041 | 0.1411 | 0.5562 |
| 1204 | 0.3659 | 0.3590 | 0.9672 | 0.6353 | 0.3452 | 0.7016 |
| 1205 | 0.6329 | 0.4691 | 0.1569 | 0.3616 | 0.0646 | 0.4168 |
| 1217 | 0.1501 | 0.2443 | 0.2233 | 0.3875 | 0.8128 | 0.8519 |
| 1218 | 0.1080 | 0.2298 | 0.0339 | 0.1949 | 0.5582 | 0.7770 |
| 1223 | 0.2420 | 0.2964 | 0.5336 | 0.5566 | 0.5736 | 0.7827 |
| 1225 | 0.0787 | 0.2041 | 0.0797 | 0.2676 | 0.9945 | 0.8795 |
| 1236 | 0.1101 | 0.2298 | 0.5744 | 0.5622 | 0.2840 | 0.6489 |
| 1239 | 0.6055 | 0.4610 | 0.5774 | 0.5622 | 0.9673 | 0.8695 |
| 1244 | 0.1255 | 0.2311 | 0.3290 | 0.4736 | 0.5563 | 0.7770 |
| 1247 | 0.3954 | 0.3754 | 0.1727 | 0.3733 | 0.5914 | 0.7891 |
| 1253 | 0.1372 | 0.2318 | 0.6101 | 0.5695 | 0.3151 | 0.6797 |
| 1258 | 0.0050 | 0.0517 | 0.0012 | 0.0339 | 0.5403 | 0.7770 |
| 1259 | 0.0444 | 0.1640 | 0.0234 | 0.1513 | 0.7605 | 0.8380 |
| 1260 | 0.1095 | 0.2298 | 0.0511 | 0.2355 | 0.6935 | 0.8380 |
| 1264 | 0.0974 | 0.2214 | 0.0499 | 0.2355 | 0.7313 | 0.8380 |
| 1265 | 0.0330 | 0.1393 | 0.1052 | 0.2848 | 0.5594 | 0.7770 |
| 1267 | 0.3399 | 0.3473 | 0.1785 | 0.3736 | 0.6814 | 0.8357 |
| 1269 | 0.0297 | 0.1325 | 0.0655 | 0.2508 | 0.6994 | 0.8380 |
| 1270 | 0.1142 | 0.2311 | 0.0842 | 0.2676 | 0.8706 | 0.8610 |
| 1271 | 0.3725 | 0.3622 | 0.2997 | 0.4575 | 0.8804 | 0.8620 |
| 1272 | 0.3467 | 0.3473 | 0.3642 | 0.4776 | 0.9722 | 0.8705 |
| 1273 | 0.2251 | 0.2893 | 0.5853 | 0.5661 | 0.4938 | 0.7538 |
| 1274 | 0.1353 | 0.2318 | 0.2172 | 0.3866 | 0.7808 | 0.8418 |
| 1276 | 0.0703 | 0.1968 | 0.0760 | 0.2639 | 0.9679 | 0.8695 |
| 1277 | 0.2702 | 0.3106 | 0.3804 | 0.4867 | 0.8150 | 0.8519 |
| 1351 | 0.0246 | 0.1231 | 0.2014 | 0.3759 | 0.2807 | 0.6480 |
| 1355 | 0.8160 | 0.5274 | 0.6748 | 0.5775 | 0.8512 | 0.8610 |
| 1359 | 0.8479 | 0.5385 | 0.7363 | 0.5835 | 0.5979 | 0.7958 |
| 1360 | 0.7865 | 0.5248 | 0.1928 | 0.3759 | 0.2960 | 0.6642 |
| 1363 | 0.9411 | 0.5646 | 0.3941 | 0.4991 | 0.3555 | 0.7016 |
| 1372 | 0.0768 | 0.2022 | 0.7786 | 0.5988 | 0.1297 | 0.5309 |
| 1430 | 0.6811 | 0.4891 | 0.2009 | 0.3759 | 0.3760 | 0.7182 |
| 1446 | 0.0908 | 0.2167 | 0.0161 | 0.1236 | 0.4043 | 0.7283 |
| 1449 | 0.4880 | 0.4290 | 0.2339 | 0.3921 | 0.6081 | 0.8054 |
| 1452 | 0.0057 | 0.0536 | 0.0207 | 0.1413 | 0.5657 | 0.7798 |
| 1480 | 0.0876 | 0.2155 | 0.0158 | 0.1236 | 0.4103 | 0.7283 |
| 1482 | 0.8932 | 0.5563 | 0.2034 | 0.3759 | 0.1623 | 0.5562 |
| 1483 | 0.5727 | 0.4527 | 0.9634 | 0.6339 | 0.5422 | 0.7770 |
| 1485 | 0.0448 | 0.1640 | 0.0022 | 0.0478 | 0.1862 | 0.5850 |
| 1487 | 0.3523 | 0.3477 | 0.5522 | 0.5606 | 0.7317 | 0.8380 |
| 1488 | 0.0481 | 0.1705 | 0.0145 | 0.1190 | 0.5732 | 0.7827 |
| 1495 | 0.0265 | 0.1275 | 0.0006 | 0.0251 | 0.1077 | 0.5131 |
| 1496 | 0.0027 | 0.0354 | 0.0032 | 0.0542 | 0.9359 | 0.8691 |
| 1498 | 0.0049 | 0.0517 | 0.0313 | 0.1861 | 0.4069 | 0.7283 |
| 1499 | 0.0012 | 0.0250 | 0.0002 | 0.0150 | 0.4594 | 0.7415 |
| 1500 | 0.0120 | 0.0774 | 0.1777 | 0.3736 | 0.1868 | 0.5850 |
| 1501 | 0.0060 | 0.0536 | 0.0000 | 0.0068 | 0.0398 | 0.3434 |
| 1503 | 0.1279 | 0.2311 | 0.0034 | 0.0550 | 0.0992 | 0.5102 |
| 1504 | 0.0042 | 0.0494 | 0.0007 | 0.0251 | 0.4521 | 0.7415 |
| 1506 | 0.0071 | 0.0583 | 0.0002 | 0.0150 | 0.1233 | 0.5308 |
| 1517 | 0.0021 | 0.0325 | 0.3098 | 0.4633 | 0.0216 | 0.2516 |
| 1518 | 0.2135 | 0.2800 | 0.1219 | 0.3029 | 0.7443 | 0.8380 |
| 1519 | 0.1253 | 0.2311 | 0.0672 | 0.2508 | 0.7404 | 0.8380 |
| 1521 | 0.9421 | 0.5646 | 0.7271 | 0.5835 | 0.7821 | 0.8418 |
| 1522 | 0.0752 | 0.2002 | 0.0032 | 0.0542 | 0.1574 | 0.5562 |
| 1523 | 0.0186 | 0.0987 | 0.0112 | 0.1024 | 0.8197 | 0.8519 |

TABLE 4E-continued

| PSO | Sp/ABX p-value | Sp/ABX q-value | GF/ABX p-value | GF/ABX q-value | GF/Sp p-value | GF/Sp q-value |
|---|---|---|---|---|---|---|
| 1524 | 0.0012 | 0.0250 | 0.0541 | 0.2376 | 0.1008 | 0.5102 |
| 1527 | 0.6329 | 0.4691 | 0.7653 | 0.5937 | 0.8571 | 0.8610 |
| 1528 | 0.9839 | 0.5782 | 0.3664 | 0.4776 | 0.3561 | 0.7016 |
| 1529 | 0.9418 | 0.5646 | 0.9150 | 0.6254 | 0.8574 | 0.8610 |
| 1536 | 0.2549 | 0.2999 | 0.0457 | 0.2206 | 0.3492 | 0.7016 |
| 1537 | 0.3395 | 0.3473 | 0.8190 | 0.6041 | 0.4640 | 0.7418 |
| 1539 | 0.6187 | 0.4657 | 0.0239 | 0.1518 | 0.0079 | 0.1319 |
| 1541 | 0.3704 | 0.3613 | 0.6673 | 0.5775 | 0.6364 | 0.8251 |
| 1542 | 0.3291 | 0.3473 | 0.3550 | 0.4766 | 0.9579 | 0.8691 |
| 1547 | 0.5510 | 0.4474 | 0.0349 | 0.1980 | 0.0095 | 0.1438 |
| 1565 | 0.0995 | 0.2247 | 0.1886 | 0.3753 | 0.7181 | 0.8380 |
| 1567 | 0.0514 | 0.1713 | 0.1082 | 0.2848 | 0.7006 | 0.8380 |
| 1582 | 0.6160 | 0.4647 | 0.9628 | 0.6339 | 0.6489 | 0.8251 |
| 1711 | 0.2539 | 0.2999 | 0.5787 | 0.5622 | 0.5486 | 0.7770 |
| 1718 | 0.5919 | 0.4576 | 0.1954 | 0.3759 | 0.4361 | 0.7283 |
| 1721 | 0.1512 | 0.2443 | 0.6197 | 0.5695 | 0.3348 | 0.6976 |
| 1731 | 0.9262 | 0.5621 | 0.9144 | 0.6254 | 0.9881 | 0.8795 |
| 1732 | 0.4243 | 0.3886 | 0.4206 | 0.5036 | 0.9947 | 0.8795 |
| 1744 | 0.5087 | 0.4333 | 0.5348 | 0.5566 | 0.9676 | 0.8695 |
| 1753 | 0.2935 | 0.3257 | 0.5427 | 0.5598 | 0.1050 | 0.5131 |
| 1754 | 0.0014 | 0.0272 | 0.4012 | 0.4995 | 0.0100 | 0.1466 |
| 1782 | 0.0594 | 0.1764 | 0.1090 | 0.2848 | 0.7514 | 0.8380 |
| 1783 | 0.5924 | 0.4576 | 0.7553 | 0.5925 | 0.3999 | 0.7283 |
| 1784 | 0.0174 | 0.0987 | 0.2076 | 0.3788 | 0.2118 | 0.6023 |
| 1786 | 0.0000 | 0.0007 | 0.0004 | 0.0215 | 0.1142 | 0.5146 |
| 1788 | 0.2512 | 0.2999 | 0.7611 | 0.5929 | 0.1518 | 0.5562 |
| 1789 | 0.2869 | 0.3217 | 0.7359 | 0.5835 | 0.4608 | 0.7415 |
| 1790 | 0.0089 | 0.0665 | 0.1755 | 0.3736 | 0.1507 | 0.5562 |
| 1791 | 0.8874 | 0.5563 | 0.3204 | 0.4661 | 0.2587 | 0.6316 |
| 1792 | 0.5911 | 0.4576 | 0.0275 | 0.1661 | 0.0819 | 0.4886 |
| 1793 | 0.0000 | 0.0008 | 0.0089 | 0.0919 | 0.0000 | 0.0000 |
| 1811 | 0.2616 | 0.3026 | 0.8182 | 0.6041 | 0.1804 | 0.5850 |
| 1815 | 0.6708 | 0.4860 | 0.8005 | 0.6041 | 0.8626 | 0.8610 |
| 1827 | 0.2900 | 0.3230 | 0.6911 | 0.5790 | 0.5020 | 0.7580 |
| 1828 | 0.5922 | 0.4576 | 0.5475 | 0.5606 | 0.2612 | 0.6345 |
| 1829 | 0.0363 | 0.1496 | 0.3586 | 0.4766 | 0.2069 | 0.5984 |
| 1831 | 0.3354 | 0.3473 | 0.8571 | 0.6114 | 0.4304 | 0.7283 |
| 1834 | 0.1364 | 0.2318 | 0.9269 | 0.6282 | 0.1602 | 0.5562 |
| 1837 | 0.2408 | 0.2964 | 0.7994 | 0.6041 | 0.1581 | 0.5562 |
| 1841 | 0.0260 | 0.1275 | 0.4799 | 0.5295 | 0.1075 | 0.5131 |
| 1845 | 0.2742 | 0.3117 | 0.7228 | 0.5835 | 0.4534 | 0.7415 |
| 1851 | 0.7175 | 0.4958 | 0.1004 | 0.2848 | 0.1904 | 0.5863 |
| 1866 | 0.4976 | 0.4305 | 0.2195 | 0.3875 | 0.0643 | 0.4168 |
| 1867 | 0.5923 | 0.4576 | 0.3013 | 0.4575 | 0.1241 | 0.5308 |
| 1870 | 0.1911 | 0.2658 | 0.5162 | 0.5450 | 0.0577 | 0.4034 |
| 1878 | 0.5989 | 0.4592 | 0.3385 | 0.4761 | 0.1454 | 0.5562 |
| 1884 | 0.5446 | 0.4466 | 0.0735 | 0.2580 | 0.2178 | 0.6063 |
| 1889 | 0.4130 | 0.3838 | 0.0684 | 0.2522 | 0.2887 | 0.6507 |
| 1892 | 0.0105 | 0.0719 | 0.7495 | 0.5914 | 0.0051 | 0.1021 |
| 1902 | 0.2507 | 0.2999 | 0.0530 | 0.2376 | 0.3927 | 0.7252 |
| 1903 | 0.0020 | 0.0325 | 0.9348 | 0.6284 | 0.0024 | 0.0680 |
| 1907 | 0.1561 | 0.2443 | 0.8592 | 0.6114 | 0.2104 | 0.6023 |
| 1945 | 0.9674 | 0.5743 | 0.4211 | 0.5036 | 0.4446 | 0.7345 |
| 1948 | 0.2513 | 0.2999 | 0.7634 | 0.5935 | 0.1528 | 0.5562 |
| 1949 | 0.5600 | 0.4491 | 0.1070 | 0.2848 | 0.2865 | 0.6507 |
| 1950 | 0.0497 | 0.1713 | 0.2671 | 0.4245 | 0.3546 | 0.7016 |
| 1953 | 0.3117 | 0.3380 | 0.4666 | 0.5230 | 0.7705 | 0.8418 |
| 1955 | 0.3568 | 0.3511 | 0.0674 | 0.2508 | 0.3336 | 0.6976 |
| 1962 | 0.9114 | 0.5574 | 0.1815 | 0.3746 | 0.2181 | 0.6063 |
| 1970 | 0.4974 | 0.4305 | 0.1732 | 0.3733 | 0.4791 | 0.7453 |
| 1974 | 0.3480 | 0.3474 | 0.0505 | 0.2355 | 0.2760 | 0.6423 |
| 1975 | 0.1455 | 0.2422 | 0.2588 | 0.4219 | 0.7282 | 0.8380 |
| 1976 | 0.0216 | 0.1120 | 0.4143 | 0.5036 | 0.1128 | 0.5146 |
| 1979 | 0.1612 | 0.2443 | 0.3770 | 0.4841 | 0.5873 | 0.7858 |
| 1982 | 0.3398 | 0.3473 | 0.1021 | 0.2848 | 0.4705 | 0.7431 |
| 1985 | 0.0467 | 0.1693 | 0.5029 | 0.5402 | 0.1661 | 0.5616 |
| 2016 | 0.6755 | 0.4870 | 0.8330 | 0.6041 | 0.8348 | 0.8578 |
| 2021 | 0.9932 | 0.5795 | 0.6421 | 0.5695 | 0.6482 | 0.8251 |
| 2024 | 0.5150 | 0.4340 | 0.4712 | 0.5230 | 0.9437 | 0.8691 |
| 2034 | 0.1335 | 0.2311 | 0.9181 | 0.6254 | 0.1599 | 0.5562 |
| 2052 | 0.5201 | 0.4340 | 0.1615 | 0.3616 | 0.4337 | 0.7283 |
| 2067 | 0.6403 | 0.4711 | 0.3621 | 0.4766 | 0.6517 | 0.8251 |
| 2072 | 0.1572 | 0.2443 | 0.1039 | 0.2848 | 0.8171 | 0.8519 |
| 2105 | 0.1672 | 0.2483 | 0.7675 | 0.5941 | 0.2704 | 0.6409 |
| 2106 | 0.0634 | 0.1838 | 0.3699 | 0.4799 | 0.3070 | 0.6785 |
| 2107 | 0.1812 | 0.2616 | 0.5744 | 0.5622 | 0.4250 | 0.7283 |

TABLE 4E-continued

| PSO | Sp/ABX p-value | Sp/ABX q-value | GF/ABX p-value | GF/ABX q-value | GF/Sp p-value | GF/Sp q-value |
|---|---|---|---|---|---|---|
| 2113 | 0.1153 | 0.2311 | 0.4629 | 0.5230 | 0.3799 | 0.7228 |
| 2115 | 0.1968 | 0.2703 | 0.8429 | 0.6055 | 0.2700 | 0.6409 |
| 2118 | 0.9029 | 0.5563 | 0.4954 | 0.5353 | 0.4230 | 0.7283 |
| 2136 | 0.7034 | 0.4913 | 0.4358 | 0.5066 | 0.6869 | 0.8380 |
| 2157 | 0.1619 | 0.2443 | 0.6697 | 0.5775 | 0.3201 | 0.6817 |
| 2164 | 0.3501 | 0.3476 | 0.6313 | 0.5695 | 0.1642 | 0.5589 |
| 2165 | 0.5508 | 0.4474 | 0.6280 | 0.5695 | 0.9098 | 0.8681 |
| 2166 | 0.2437 | 0.2964 | 0.6778 | 0.5782 | 0.4447 | 0.7345 |
| 2168 | 0.8103 | 0.5274 | 0.3486 | 0.4761 | 0.4818 | 0.7453 |
| 2179 | 0.1591 | 0.2443 | 0.2351 | 0.3921 | 0.8139 | 0.8519 |
| 2192 | 0.2607 | 0.3026 | 0.3177 | 0.4661 | 0.8957 | 0.8681 |
| 2193 | 0.0433 | 0.1640 | 0.1861 | 0.3748 | 0.4394 | 0.7305 |
| 2194 | 0.8745 | 0.5533 | 0.7578 | 0.5929 | 0.6416 | 0.8251 |
| 2199 | 0.2222 | 0.2893 | 0.0840 | 0.2676 | 0.5829 | 0.7858 |
| 2203 | 0.2282 | 0.2893 | 0.4013 | 0.4995 | 0.7039 | 0.8380 |
| 2206 | 0.7021 | 0.4913 | 0.6515 | 0.5695 | 0.4072 | 0.7283 |
| 2209 | 0.7281 | 0.5004 | 0.6080 | 0.5695 | 0.3927 | 0.7252 |
| 2211 | 0.3753 | 0.3628 | 0.7981 | 0.6041 | 0.5246 | 0.7740 |
| 2217 | 0.0942 | 0.2167 | 0.0646 | 0.2508 | 0.8445 | 0.8610 |
| 2310 | 0.1841 | 0.2616 | 0.1950 | 0.3759 | 0.9724 | 0.8705 |
| 2311 | 0.0447 | 0.1640 | 0.2344 | 0.3921 | 0.3707 | 0.7146 |
| 2312 | 0.5323 | 0.4420 | 0.2612 | 0.4221 | 0.0883 | 0.4997 |
| 2313 | 0.5651 | 0.4500 | 0.6088 | 0.5695 | 0.2823 | 0.6480 |
| 2314 | 0.1623 | 0.2443 | 0.3326 | 0.4750 | 0.6520 | 0.8251 |
| 2318 | 0.2100 | 0.2772 | 0.1137 | 0.2931 | 0.7236 | 0.8380 |
| 2327 | 0.2886 | 0.3225 | 0.3721 | 0.4811 | 0.8613 | 0.8610 |
| 2343 | 0.7723 | 0.5212 | 0.2678 | 0.4245 | 0.1673 | 0.5618 |
| 2345 | 0.2277 | 0.2893 | 0.0415 | 0.2154 | 0.3614 | 0.7037 |
| 2347 | 0.9766 | 0.5766 | 0.0877 | 0.2729 | 0.0927 | 0.5044 |
| 2348 | 0.1321 | 0.2311 | 0.2274 | 0.3879 | 0.7487 | 0.8380 |
| 2350 | 0.9394 | 0.5646 | 0.8270 | 0.6041 | 0.7685 | 0.8418 |
| 2351 | 0.0549 | 0.1757 | 0.1667 | 0.3679 | 0.5529 | 0.7770 |
| 2356 | 0.3408 | 0.3473 | 0.2658 | 0.4245 | 0.8675 | 0.8610 |
| 2357 | 0.5479 | 0.4474 | 0.8603 | 0.6114 | 0.6696 | 0.8314 |
| 2360 | 0.6340 | 0.4691 | 0.6009 | 0.5693 | 0.9622 | 0.8691 |
| 2361 | 0.4778 | 0.4222 | 0.7888 | 0.6001 | 0.6561 | 0.8251 |
| 2364 | 0.4396 | 0.3992 | 0.6469 | 0.5695 | 0.7497 | 0.8380 |
| 2371 | 0.1537 | 0.2443 | 0.8214 | 0.6041 | 0.2242 | 0.6097 |
| 2374 | 0.0871 | 0.2155 | 0.3760 | 0.4841 | 0.3822 | 0.7245 |
| 2375 | 0.7645 | 0.5185 | 0.8326 | 0.6041 | 0.9295 | 0.8691 |
| 2376 | 0.8157 | 0.5274 | 0.7779 | 0.5988 | 0.9608 | 0.8691 |
| 2379 | 0.9018 | 0.5563 | 0.5705 | 0.5622 | 0.6562 | 0.8251 |
| 2381 | 0.4894 | 0.4290 | 0.5093 | 0.5413 | 0.1840 | 0.5850 |
| 2383 | 0.1840 | 0.2616 | 0.3225 | 0.4661 | 0.7214 | 0.8380 |
| 2394 | 0.1243 | 0.2311 | 0.2913 | 0.4492 | 0.6084 | 0.8054 |
| 2395 | 0.0130 | 0.0808 | 0.6430 | 0.5695 | 0.0354 | 0.3175 |
| 2407 | 0.9444 | 0.5650 | 0.4218 | 0.5036 | 0.4623 | 0.7415 |
| 2411 | 0.8949 | 0.5563 | 0.6834 | 0.5790 | 0.7823 | 0.8418 |
| 2413 | 0.0095 | 0.0696 | 0.1895 | 0.3753 | 0.1468 | 0.5562 |
| 2416 | 0.2734 | 0.3117 | 0.4735 | 0.5240 | 0.6964 | 0.8380 |
| 2418 | 0.0128 | 0.0808 | 0.5694 | 0.5622 | 0.0435 | 0.3453 |
| 2419 | 0.1246 | 0.2311 | 0.0914 | 0.2784 | 0.8665 | 0.8610 |
| 2420 | 0.5868 | 0.4576 | 0.4232 | 0.5036 | 0.7935 | 0.8449 |
| 2422 | 0.0734 | 0.2002 | 0.0104 | 0.1024 | 0.3603 | 0.7037 |
| 2423 | 0.1282 | 0.2311 | 0.0007 | 0.0251 | 0.0270 | 0.2876 |
| 2426 | 0.0076 | 0.0609 | 0.1055 | 0.2848 | 0.2171 | 0.6063 |
| 2429 | 0.6126 | 0.4643 | 0.4182 | 0.5036 | 0.7580 | 0.8380 |
| 2431 | 0.1221 | 0.2311 | 0.3934 | 0.4991 | 0.4665 | 0.7420 |
| 2432 | 0.0181 | 0.0987 | 0.3080 | 0.4633 | 0.1423 | 0.5562 |
| 2442 | 0.2232 | 0.2893 | 0.9776 | 0.6396 | 0.2334 | 0.6153 |
| 2443 | 0.6514 | 0.4749 | 0.9108 | 0.6254 | 0.5737 | 0.7827 |
| 2445 | 0.2344 | 0.2947 | 0.2646 | 0.4245 | 0.9384 | 0.8691 |
| 2448 | 0.9076 | 0.5571 | 0.0461 | 0.2206 | 0.0582 | 0.4034 |
| 2449 | 0.5356 | 0.4425 | 0.0595 | 0.2435 | 0.1866 | 0.5850 |
| 2474 | 0.8804 | 0.5560 | 0.6482 | 0.5695 | 0.5452 | 0.7770 |
| 2480 | 0.3736 | 0.3623 | 0.0830 | 0.2676 | 0.3713 | 0.7146 |
| 2481 | 0.5681 | 0.4508 | 0.0567 | 0.2376 | 0.0170 | 0.2130 |
| 2488 | 0.1556 | 0.2443 | 0.0031 | 0.0542 | 0.0738 | 0.4614 |
| 2491 | 0.3989 | 0.3757 | 0.4702 | 0.5230 | 0.1257 | 0.5309 |
| 2493 | 0.7144 | 0.4948 | 0.3117 | 0.4633 | 0.1742 | 0.5773 |
| 2498 | 0.5980 | 0.4592 | 0.2048 | 0.3759 | 0.0796 | 0.4860 |
| 2499 | 0.9211 | 0.5621 | 0.6360 | 0.5695 | 0.7077 | 0.8380 |
| 2513 | 0.0751 | 0.2002 | 0.0559 | 0.2376 | 0.8802 | 0.8620 |
| 2514 | 0.3463 | 0.3473 | 0.3045 | 0.4599 | 0.0572 | 0.4034 |
| 2517 | 0.5486 | 0.4474 | 0.0832 | 0.2676 | 0.2391 | 0.6213 |
| 2518 | 0.3423 | 0.3473 | 0.6378 | 0.5695 | 0.6262 | 0.8182 |

TABLE 4E-continued

| PSO | Sp/ABX p-value | Sp/ABX q-value | GF/ABX p-value | GF/ABX q-value | GF/Sp p-value | GF/Sp q-value |
|---|---|---|---|---|---|---|
| 2520 | 0.4220 | 0.3875 | 0.7001 | 0.5811 | 0.6725 | 0.8315 |
| 2522 | 0.3457 | 0.3473 | 0.8662 | 0.6127 | 0.2692 | 0.6409 |
| 2523 | 0.9294 | 0.5621 | 0.5386 | 0.5590 | 0.4826 | 0.7453 |
| 2525 | 0.9111 | 0.5574 | 0.4665 | 0.5230 | 0.4024 | 0.7283 |
| 2543 | 0.6767 | 0.4870 | 0.9625 | 0.6339 | 0.7112 | 0.8380 |
| 2547 | 0.1665 | 0.2483 | 0.5764 | 0.5622 | 0.0588 | 0.4034 |
| 2549 | 0.6467 | 0.4737 | 0.0817 | 0.2676 | 0.1866 | 0.5850 |
| 2561 | 0.8192 | 0.5274 | 0.9742 | 0.6388 | 0.8444 | 0.8610 |
| 2563 | 0.1241 | 0.2311 | 0.9291 | 0.6282 | 0.1453 | 0.5562 |
| 2564 | 0.3928 | 0.3742 | 0.7265 | 0.5835 | 0.2336 | 0.6153 |
| 2565 | 0.3303 | 0.3473 | 0.2933 | 0.4503 | 0.9358 | 0.8691 |
| 2566 | 0.8272 | 0.5305 | 0.5797 | 0.5622 | 0.7361 | 0.8380 |
| 2567 | 0.0922 | 0.2167 | 0.9478 | 0.6291 | 0.1042 | 0.5131 |
| 2568 | 0.1188 | 0.2311 | 0.5943 | 0.5688 | 0.0421 | 0.3453 |
| 2569 | 0.7019 | 0.4913 | 0.3509 | 0.4761 | 0.5772 | 0.7827 |
| 2570 | 0.0943 | 0.2167 | 0.3472 | 0.4761 | 0.4366 | 0.7283 |
| 2575 | 0.5220 | 0.4345 | 0.3582 | 0.4766 | 0.7757 | 0.8418 |
| 2577 | 0.2102 | 0.2772 | 0.4688 | 0.5230 | 0.5844 | 0.7858 |
| 2579 | 0.4349 | 0.3960 | 0.2238 | 0.3875 | 0.6515 | 0.8251 |
| 2580 | 0.0542 | 0.1757 | 0.4499 | 0.5197 | 0.2169 | 0.6063 |
| 2581 | 0.1288 | 0.2311 | 0.4892 | 0.5349 | 0.3895 | 0.7252 |
| 2583 | 0.0863 | 0.2155 | 0.9790 | 0.6396 | 0.0907 | 0.5044 |
| 2588 | 0.2704 | 0.3106 | 0.6243 | 0.5695 | 0.5320 | 0.7770 |
| 2591 | 0.1471 | 0.2433 | 0.4643 | 0.5230 | 0.0355 | 0.3175 |
| 2592 | 0.7752 | 0.5212 | 0.0881 | 0.2729 | 0.0504 | 0.3818 |
| 2594 | 0.6856 | 0.4905 | 0.8129 | 0.6041 | 0.5226 | 0.7738 |
| 2610 | 0.0753 | 0.2002 | 0.6346 | 0.5695 | 0.1788 | 0.5847 |
| 2624 | 0.1982 | 0.2712 | 0.6000 | 0.5693 | 0.0771 | 0.4764 |
| 2625 | 0.4206 | 0.3872 | 0.5346 | 0.5566 | 0.1614 | 0.5562 |
| 2649 | 0.0059 | 0.0536 | 0.0562 | 0.2376 | 0.3034 | 0.6748 |
| 2652 | 0.5148 | 0.4340 | 0.2860 | 0.4447 | 0.0938 | 0.5048 |
| 2669 | 0.0280 | 0.1320 | 0.1059 | 0.2848 | 0.5070 | 0.7596 |
| 3453 | 0.6988 | 0.4913 | 0.2050 | 0.3759 | 0.3697 | 0.7146 |
| 3454 | 0.9582 | 0.5712 | 0.1073 | 0.2848 | 0.1181 | 0.5242 |
| 3455 | 0.8397 | 0.5354 | 0.0643 | 0.2508 | 0.0428 | 0.3453 |
| 3456 | 0.4812 | 0.4241 | 0.1233 | 0.3029 | 0.0306 | 0.2992 |
| 3458 | 0.0267 | 0.1275 | 0.0016 | 0.0422 | 0.2238 | 0.6097 |
| 3461 | 0.1794 | 0.2616 | 0.7325 | 0.5835 | 0.3086 | 0.6785 |
| 3462 | 0.7023 | 0.4913 | 0.0904 | 0.2777 | 0.0425 | 0.3453 |
| 3464 | 0.0047 | 0.0517 | 0.0841 | 0.2676 | 0.1882 | 0.5850 |
| 3466 | 0.2729 | 0.3117 | 0.5765 | 0.5622 | 0.1056 | 0.5131 |
| 3471 | 0.0565 | 0.1757 | 0.0212 | 0.1420 | 0.6393 | 0.8251 |
| 3472 | 0.7507 | 0.5113 | 0.2731 | 0.4282 | 0.4303 | 0.7283 |
| 3473 | 0.0162 | 0.0939 | 0.3477 | 0.4761 | 0.1119 | 0.5146 |
| 3474 | 0.0016 | 0.0282 | 0.0172 | 0.1295 | 0.3091 | 0.6785 |
| 3478 | 0.7286 | 0.5004 | 0.3977 | 0.4995 | 0.6140 | 0.8107 |
| 3479 | 0.8920 | 0.5563 | 0.0659 | 0.2508 | 0.0503 | 0.3818 |
| 3480 | 0.5085 | 0.4333 | 0.8352 | 0.6041 | 0.6488 | 0.8251 |
| 3485 | 0.3407 | 0.3473 | 0.8628 | 0.6114 | 0.2632 | 0.6364 |
| 3495 | 0.1476 | 0.2433 | 0.9375 | 0.6284 | 0.1285 | 0.5309 |
| 3498 | 0.3963 | 0.3754 | 0.8121 | 0.6041 | 0.5384 | 0.7770 |
| 3505 | 0.4588 | 0.4111 | 0.1039 | 0.2848 | 0.3543 | 0.7016 |
| 3507 | 0.3431 | 0.3473 | 0.7293 | 0.5835 | 0.5422 | 0.7770 |
| 3508 | 0.1538 | 0.2443 | 0.0806 | 0.2676 | 0.7243 | 0.8380 |
| 3513 | 0.1333 | 0.2311 | 0.1841 | 0.3746 | 0.8522 | 0.8610 |
| 3514 | 0.1222 | 0.2311 | 0.2607 | 0.4221 | 0.6530 | 0.8251 |
| 3516 | 0.5175 | 0.4340 | 0.9399 | 0.6284 | 0.4708 | 0.7431 |
| 3522 | 0.1013 | 0.2257 | 0.3453 | 0.4761 | 0.4614 | 0.7415 |
| 3528 | 0.4692 | 0.4181 | 0.4296 | 0.5036 | 0.1383 | 0.5562 |
| 3530 | 0.8917 | 0.5563 | 0.6426 | 0.5695 | 0.7424 | 0.8380 |
| 3533 | 0.7342 | 0.5011 | 0.0145 | 0.1190 | 0.0303 | 0.2992 |
| 3534 | 0.7285 | 0.5004 | 0.0019 | 0.0462 | 0.0042 | 0.0925 |
| 3535 | 0.1140 | 0.2311 | 0.2034 | 0.3759 | 0.7393 | 0.8380 |
| 3537 | 0.7091 | 0.4932 | 0.6344 | 0.5695 | 0.9177 | 0.8691 |
| 3541 | 0.2248 | 0.2893 | 0.1794 | 0.3736 | 0.8911 | 0.8658 |
| 3542 | 0.8063 | 0.5274 | 0.2310 | 0.3905 | 0.1534 | 0.5562 |
| 3547 | 0.3238 | 0.3458 | 0.0066 | 0.0842 | 0.0572 | 0.4034 |
| 3548 | 0.0742 | 0.2002 | 0.0070 | 0.0854 | 0.2742 | 0.6411 |
| 3549 | 0.0183 | 0.0987 | 0.4057 | 0.5016 | 0.1008 | 0.5102 |
| 3550 | 0.0631 | 0.1838 | 0.8948 | 0.6233 | 0.0484 | 0.3787 |
| 3552 | 0.1138 | 0.2311 | 0.1875 | 0.3753 | 0.0068 | 0.1213 |
| 3563 | 0.0294 | 0.1325 | 0.6125 | 0.5695 | 0.0820 | 0.4886 |
| 3565 | 0.5592 | 0.4491 | 0.8370 | 0.6041 | 0.7038 | 0.8380 |
| 3566 | 0.1183 | 0.2311 | 0.7143 | 0.5835 | 0.0588 | 0.4034 |
| 3567 | 0.1998 | 0.2715 | 0.8892 | 0.6233 | 0.2500 | 0.6228 |
| 3568 | 0.6043 | 0.4610 | 0.0084 | 0.0919 | 0.0265 | 0.2876 |

TABLE 4E-continued

| PSO | Sp/ABX p-value | Sp/ABX q-value | GF/ABX p-value | GF/ABX q-value | GF/Sp p-value | GF/Sp q-value |
|---|---|---|---|---|---|---|
| 3572 | 0.1181 | 0.2311 | 0.2684 | 0.4245 | 0.6263 | 0.8182 |
| 3573 | 0.3454 | 0.3473 | 0.4205 | 0.5036 | 0.0888 | 0.4997 |
| 3576 | 0.6347 | 0.4691 | 0.9016 | 0.6245 | 0.7246 | 0.8380 |
| 3577 | 0.1196 | 0.2311 | 0.0177 | 0.1305 | 0.3492 | 0.7016 |
| 3578 | 0.7635 | 0.5185 | 0.3616 | 0.4766 | 0.2298 | 0.6153 |
| 3579 | 0.9242 | 0.5621 | 0.6417 | 0.5695 | 0.5758 | 0.7827 |
| 3580 | 0.3075 | 0.3362 | 0.7120 | 0.5835 | 0.5088 | 0.7600 |
| 3585 | 0.0947 | 0.2167 | 0.6588 | 0.5739 | 0.2063 | 0.5984 |
| 3587 | 0.0564 | 0.1757 | 0.0088 | 0.0919 | 0.3910 | 0.7252 |
| 3588 | 0.2554 | 0.2999 | 0.8628 | 0.6114 | 0.1933 | 0.5864 |
| 3589 | 0.3985 | 0.3757 | 0.8302 | 0.6041 | 0.5259 | 0.7740 |
| 3598 | 0.3169 | 0.3414 | 0.0399 | 0.2100 | 0.2552 | 0.6290 |
| 3599 | 0.1514 | 0.2443 | 0.4277 | 0.5036 | 0.5029 | 0.7580 |
| 3602 | 0.1067 | 0.2298 | 0.4316 | 0.5036 | 0.3860 | 0.7252 |
| 3603 | 0.5341 | 0.4424 | 0.8982 | 0.6233 | 0.4548 | 0.7415 |
| 3607 | 0.0136 | 0.0833 | 0.0083 | 0.0919 | 0.8241 | 0.8538 |
| 3608 | 0.0293 | 0.1325 | 0.0657 | 0.2508 | 0.6931 | 0.8380 |
| 3624 | 0.9279 | 0.5621 | 0.9314 | 0.6284 | 0.9965 | 0.8795 |
| 3627 | 0.1279 | 0.2311 | 0.8037 | 0.6041 | 0.1964 | 0.5917 |
| 3628 | 0.9903 | 0.5795 | 0.7214 | 0.5835 | 0.7305 | 0.8380 |
| 3636 | 0.3080 | 0.3362 | 0.8352 | 0.6041 | 0.4134 | 0.7283 |
| 3641 | 0.0142 | 0.0854 | 0.5193 | 0.5467 | 0.0033 | 0.0776 |
| 3643 | 0.0023 | 0.0325 | 0.1619 | 0.3616 | 0.0001 | 0.0031 |
| 3644 | 0.0087 | 0.0665 | 0.6521 | 0.5695 | 0.0031 | 0.0771 |
| 3648 | 0.3678 | 0.3597 | 0.2309 | 0.3905 | 0.7567 | 0.8380 |
| 3649 | 0.0801 | 0.2064 | 0.9139 | 0.6254 | 0.0650 | 0.4168 |
| 3650 | 0.7836 | 0.5240 | 0.4937 | 0.5353 | 0.6798 | 0.8357 |
| 3651 | 0.0112 | 0.0738 | 0.2116 | 0.3803 | 0.0006 | 0.0192 |
| 3653 | 0.0149 | 0.0877 | 0.0261 | 0.1631 | 0.7961 | 0.8458 |
| 3654 | 0.8166 | 0.5274 | 0.0201 | 0.1413 | 0.0121 | 0.1630 |
| 3656 | 0.5640 | 0.4500 | 0.6367 | 0.5695 | 0.9158 | 0.8691 |
| 3658 | 0.2269 | 0.2893 | 0.1717 | 0.3733 | 0.8661 | 0.8610 |
| 3662 | 0.2810 | 0.3162 | 0.2413 | 0.4006 | 0.9217 | 0.8691 |
| 3663 | 0.1609 | 0.2443 | 0.3205 | 0.4661 | 0.6665 | 0.8314 |
| 3664 | 0.0570 | 0.1757 | 0.0158 | 0.1236 | 0.5441 | 0.7770 |
| 3667 | 0.1378 | 0.2318 | 0.2031 | 0.3759 | 0.8206 | 0.8519 |
| 3668 | 0.4944 | 0.4305 | 0.5523 | 0.5606 | 0.9280 | 0.8691 |
| 3670 | 0.0837 | 0.2140 | 0.1951 | 0.3759 | 0.6368 | 0.8251 |
| 3694 | 0.0023 | 0.0325 | 0.5766 | 0.5622 | 0.0085 | 0.1331 |
| 3698 | 0.3311 | 0.3473 | 0.3420 | 0.4761 | 0.0629 | 0.4168 |
| 3714 | 0.0104 | 0.0719 | 0.0090 | 0.0919 | 0.9463 | 0.8691 |
| 3715 | 0.0704 | 0.1968 | 0.3434 | 0.4761 | 0.3581 | 0.7028 |
| 3718 | 0.1859 | 0.2619 | 0.4513 | 0.5197 | 0.5542 | 0.7770 |
| 3727 | 0.5952 | 0.4584 | 0.0421 | 0.2154 | 0.1184 | 0.5242 |
| 3728 | 0.5890 | 0.4576 | 0.8945 | 0.6233 | 0.5022 | 0.7580 |
| 3751 | 0.2320 | 0.2930 | 0.0020 | 0.0462 | 0.0312 | 0.2992 |
| 3754 | 0.4775 | 0.4222 | 0.1407 | 0.3366 | 0.0353 | 0.3175 |
| 3757 | 0.0036 | 0.0444 | 1.0000 | 0.6499 | 0.0036 | 0.0827 |
| 3771 | 0.8174 | 0.5274 | 0.7150 | 0.5835 | 0.5524 | 0.7770 |
| 3978 | 0.3288 | 0.3473 | 0.2446 | 0.4041 | 0.8450 | 0.8610 |
| 4000 | 0.0480 | 0.1705 | 0.0082 | 0.0919 | 0.4183 | 0.7283 |
| 4079 | 0.1101 | 0.2298 | 0.0023 | 0.0479 | 0.0850 | 0.4957 |
| 4108 | 0.0005 | 0.0121 | 0.2899 | 0.4489 | 0.0059 | 0.1143 |
| 4131 | 0.6703 | 0.4860 | 0.6994 | 0.5811 | 0.4197 | 0.7283 |
| 4144 | 0.0446 | 0.1640 | 0.3567 | 0.4766 | 0.2443 | 0.6224 |
| 4221 | 0.0001 | 0.0019 | 0.0450 | 0.2206 | 0.0082 | 0.1319 |
| 4246 | 0.0000 | 0.0015 | 0.0216 | 0.1420 | 0.0110 | 0.1537 |
| 4274 | 0.0052 | 0.0517 | 0.3017 | 0.4575 | 0.0004 | 0.0158 |
| 4363 | 0.0892 | 0.2167 | 0.4952 | 0.5353 | 0.2879 | 0.6507 |
| 4756 | 0.2067 | 0.2747 | 0.7881 | 0.6001 | 0.3141 | 0.6797 |
| 4832 | 0.0326 | 0.1393 | 0.0580 | 0.2403 | 0.7786 | 0.8418 |
| 4835 | 0.0010 | 0.0234 | 0.4269 | 0.5036 | 0.0064 | 0.1195 |
| 4899 | 0.0440 | 0.1640 | 0.1216 | 0.3029 | 0.0012 | 0.0380 |
| 4926 | 1.0000 | 0.5814 | 0.0051 | 0.0717 | 0.0051 | 0.1021 |
| 4930 | 0.0000 | 0.0007 | 0.5097 | 0.5413 | 0.0001 | 0.0026 |
| 4971 | 0.0559 | 0.1757 | 0.0703 | 0.2551 | 0.9080 | 0.8681 |

Example 9: Table 5 for Examples 1-3, Provided as Parts Tables 5A Though 5F

Tables 5A through 5F (collectively "Table 5") relate to the top 22 maternal serum and fetal brain metabolites down-regulated in GF and ABX relative to SPF and Sp. The cells can be classified from the given data based on $p<0.05$ or $0.05<p<0.10$, as well as based on the mean values being significantly higher or not for each comparison. In addition, the biochemicals found unpregulated in SPF and Sp compared to ABX and GF in both serum and brain can be extracted from the provided data (imidazole propionate; N,N,N-trimethyl-5-aminovalerate; 3-indoxyl sulfate; trimethylamine N-oxide; biotin; hippurate; stachydrine; pyrraline).

Tables 5A through 5C provide data for maternal serum, whereas Tables 5D through 5F provide data for fetal brain. Tables 5A and 5D provide "fold of change," and the remaining sub-tables of Table 5 provide the ANOVA contrasts.

TABLE 5A

| Biochemical Name | Sp/SPF | ABX/SPF | GF/SPF | Sp/ABX | GF/ABX | GF/Sp |
|---|---|---|---|---|---|---|
| alpha-ketoglutaramate* | 1.37 | 0.61 | 0.49 | 2.23 | 0.81 | 0.36 |
| imidazole propionate | 2.40 | 0.35 | 0.22 | 6.90 | 0.62 | 0.09 |
| N,N,N-trimethyl-5-aminovalerate | 2.37 | 0.13 | 0.19 | 18.06 | 1.45 | 0.08 |
| indolepropionate | 0.70 | 0.01 | 0.00 | 54.72 | 0.24 | 0.00 |
| 3-indoxyl sulfate | 0.52 | 0.43 | 0.00 | 1.20 | 0.00 | 0.00 |
| trimethylamine N-oxide | 0.36 | 0.16 | 0.02 | 2.33 | 0.10 | 0.04 |
| beta-muricholate | 6.42 | 0.01 | 0.01 | 676.89 | 1.27 | 0.00 |
| alpha-muricholate | 8.04 | 0.04 | 0.04 | 221.52 | 1.00 | 0.00 |
| deoxycholate | 1.69 | 0.01 | 0.02 | 115.92 | 1.05 | 0.01 |
| taurodeoxycholate | 0.07 | 0.00 | 0.00 | 21.07 | 1.00 | 0.05 |
| ursodeoxycholate | 3.73 | 0.02 | 0.02 | 201.13 | 1.00 | 0.00 |
| taurohyodeoxycholic acid | 0.16 | 0.01 | 0.00 | 17.84 | 0.47 | 0.03 |
| 7-ketodeoxycholate | 3.31 | 0.00 | 0.00 | 717.10 | 1.00 | 0.00 |
| biotin | 1.50 | 0.44 | 0.44 | 3.41 | 0.99 | 0.29 |
| hippurate | 0.47 | 0.02 | 0.02 | 23.99 | 0.78 | 0.03 |
| p-cresol sulfate | 0.59 | 0.02 | 0.02 | 30.11 | 1.04 | 0.03 |
| phenylpropionylglycine | 0.60 | 0.01 | 0.01 | 72.57 | 1.00 | 0.01 |
| 3-(3-hydroxyphenyl)propionate sulfate | 0.07 | 0.01 | 0.01 | 7.24 | 1.00 | 0.14 |
| 2-(4-hydroxyphenyl)propionate | 0.99 | 0.06 | 0.06 | 16.71 | 1.00 | 0.06 |
| 3-phenylpropionate (hydrocinnamate) | 1.72 | 0.07 | 0.12 | 25.21 | 1.72 | 0.07 |
| stachydrine | 0.92 | 0.63 | 0.59 | 1.45 | 0.94 | 0.65 |
| pyrraline | 1.03 | 0.59 | 0.44 | 1.73 | 0.74 | 0.43 |

TABLE 5B

| | Sp/SPF | | ABX/SPF | | GF/SPF | |
|---|---|---|---|---|---|---|
| Biochemical Name | p-value | q-value | p-value | q-value | p-value | q-value |
| alpha-ketoglutaramate* | 0.1410 | 0.7037 | 0.0422 | 0.2485 | 0.0048 | 0.0281 |
| imidazole propionate | 0.0014 | 0.0451 | 0.0001 | 0.0021 | 0.0000 | 0.0000 |
| N,N,N-trimethyl-5-aminovalerate | 0.0001 | 0.0038 | 0.0000 | 0.0000 | 0.0000 | 0.0000 |
| indolepropionate | 0.4484 | 0.9734 | 0.0000 | 0.0000 | 0.0000 | 0.0000 |
| 3-indoxyl sulfate | 0.1140 | 0.6811 | 0.0350 | 0.2157 | 0.0000 | 0.0000 |
| trimethylamine N-oxide | 0.0259 | 0.3001 | 0.0001 | 0.0010 | 0.0000 | 0.0000 |
| beta-muricholate | 0.0245 | 0.2975 | 0.0000 | 0.0000 | 0.0000 | 0.0000 |
| alpha-muricholate | 0.0457 | 0.3999 | 0.0010 | 0.0117 | 0.0010 | 0.0068 |
| deoxycholate | 0.3135 | 0.9011 | 0.0000 | 0.0000 | 0.0000 | 0.0000 |
| taurodeoxycholate | 0.0263 | 0.3001 | 0.0000 | 0.0000 | 0.0000 | 0.0000 |
| ursodeoxycholate | 0.0259 | 0.3001 | 0.0000 | 0.0000 | 0.0000 | 0.0000 |
| taurohyodeoxycholic acid | 0.2745 | 0.8757 | 0.0000 | 0.0007 | 0.0000 | 0.0000 |
| 7-ketodeoxycholate | 0.1494 | 0.7164 | 0.0000 | 0.0000 | 0.0000 | 0.0000 |
| biotin | 0.0342 | 0.3258 | 0.0001 | 0.0011 | 0.0001 | 0.0007 |
| hippurate | 0.1238 | 0.7020 | 0.0000 | 0.0000 | 0.0000 | 0.0000 |
| p-cresol sulfate | 0.3343 | 0.9196 | 0.0000 | 0.0000 | 0.0000 | 0.0000 |
| phenylpropionylglycine | 0.2613 | 0.8757 | 0.0000 | 0.0000 | 0.0000 | 0.0000 |
| 3-(3-hydroxyphenyl)propionate sulfate | 0.0000 | 0.0000 | 0.0000 | 0.0000 | 0.0000 | 0.0000 |
| 2-(4-hydroxyphenyl)propionate | 0.3603 | 0.9196 | 0.0000 | 0.0000 | 0.0000 | 0.0000 |
| 3-phenylpropionate (hydrocinnamate) | 0.8014 | 1.0000 | 0.0000 | 0.0000 | 0.0000 | 0.0000 |
| stachydrine | 0.6362 | 0.9975 | 0.0247 | 0.1690 | 0.0090 | 0.0468 |
| pyrraline | 0.8498 | 1.0000 | 0.0673 | 0.3424 | 0.0002 | 0.0014 |

TABLE 5C

| Biochemical Name | Sp/ABX | | GF/ABX | | GF/Sp | |
|---|---|---|---|---|---|---|
| | p-value | q-value | p-value | q-value | p-value | q-value |
| alpha-ketoglutaramate* | 0.0009 | 0.0093 | 0.3789 | 0.9355 | 0.0001 | 0.0005 |
| imidazole propionate | 0.0000 | 0.0000 | 0.0451 | 0.4249 | 0.0000 | 0.0000 |
| N,N,N-trimethyl-5-aminovalerate | 0.0000 | 0.0000 | 0.0781 | 0.5552 | 0.0000 | 0.0000 |
| indolepropionate | 0.0000 | 0.0000 | 0.3756 | 0.9355 | 0.0000 | 0.0000 |
| 3-indoxyl sulfate | 0.5737 | 0.6872 | 0.0000 | 0.0000 | 0.0000 | 0.0000 |
| trimethylamine N-oxide | 0.0369 | 0.1821 | 0.0000 | 0.0000 | 0.0000 | 0.0000 |
| beta-muricholate | 0.0000 | 0.0000 | 0.6005 | 1.0000 | 0.0000 | 0.0000 |
| alpha-muricholate | 0.0000 | 0.0000 | 1.0000 | 1.0000 | 0.0000 | 0.0000 |
| deoxycholate | 0.0000 | 0.0000 | 0.8840 | 1.0000 | 0.0000 | 0.0000 |
| taurodeoxycholate | 0.0000 | 0.0003 | 1.0000 | 1.0000 | 0.0000 | 0.0002 |
| ursodeoxycholate | 0.0000 | 0.0000 | 1.0000 | 1.0000 | 0.0000 | 0.0000 |
| taurohyodeoxycholic acid | 0.0011 | 0.0112 | 0.3075 | 0.9193 | 0.0000 | 0.0005 |
| 7-ketodeoxycholate | 0.0000 | 0.0000 | 1.0000 | 1.0000 | 0.0000 | 0.0000 |
| biotin | 0.0000 | 0.0000 | 0.9763 | 1.0000 | 0.0000 | 0.0000 |
| hippurate | 0.0000 | 0.0000 | 0.4182 | 0.9628 | 0.0000 | 0.0000 |
| p-cresol sulfate | 0.0000 | 0.0000 | 0.9657 | 1.0000 | 0.0000 | 0.0000 |
| phenylpropionylglycine | 0.0000 | 0.0000 | 1.0000 | 1.0000 | 0.0000 | 0.0000 |
| 3-(3-hydroxyphenyl)propionate sulfate | 0.0000 | 0.0000 | 1.0000 | 1.0000 | 0.0000 | 0.0000 |
| 2-(4-hydroxyphenyl)propionate | 0.0000 | 0.0000 | 1.0000 | 1.0000 | 0.0000 | 0.0000 |
| 3-phenylpropionate (hydrocinnamate) | 0.0000 | 0.0000 | 0.2181 | 0.8254 | 0.0000 | 0.0000 |
| stachydrine | 0.0706 | 0.2607 | 0.6835 | 1.0000 | 0.0288 | 0.0948 |
| pyrraline | 0.0448 | 0.2021 | 0.0280 | 0.3460 | 0.0001 | 0.0008 |

TABLE 5D

| Biochemical Name | Sp/SPF | ABX/SPF | GF/SPF | Sp/ABX | GF/ABX | GF/Sp |
|---|---|---|---|---|---|---|
| glutamine | 0.86 | 0.70 | 0.67 | 1.23 | 0.96 | 0.78 |
| alpha-ketoglutaramate* | 1.87 | 0.77 | 0.63 | 2.42 | 0.81 | 0.34 |
| pyroglutamine* | 0.97 | 0.73 | 0.51 | 1.34 | 0.70 | 0.52 |
| imidazole propionate | 1.60 | 0.33 | 0.33 | 4.81 | 0.99 | 0.20 |
| anserine | 0.82 | 0.40 | 0.42 | 2.04 | 1.04 | 0.51 |
| N2-acetyllysine | 0.88 | 0.49 | 0.58 | 1.80 | 1.18 | 0.66 |
| N6-methyllysine | 0.86 | 0.64 | 0.57 | 1.35 | 0.89 | 0.66 |
| N,N,N-trimethyl-5-aminovalerate | 1.79 | 0.09 | 0.16 | 19.45 | 1.71 | 0.09 |
| 3-indoxyl sulfate | 0.56 | 0.31 | 0.08 | 1.79 | 0.25 | 0.14 |
| 3-sulfo-L-alanine | 0.92 | 0.37 | 0.40 | 2.49 | 1.08 | 0.43 |
| phenylacetylglycine | 0.80 | 0.45 | 0.45 | 1.79 | 1.00 | 0.56 |
| arachidoylcarnitine (C20)* | 1.03 | 0.75 | 0.83 | 1.36 | 1.10 | 0.80 |
| trimethylamine N-oxide | 0.38 | 0.08 | 0.04 | 4.61 | 0.48 | 0.10 |
| sphingomyelin (d18:1/20:0, d16:1/22:0)* | 0.84 | 0.68 | 0.69 | 1.24 | 1.02 | 0.83 |
| trigonelline (N'-methylnicotinate) | 0.90 | 0.58 | 0.55 | 1.55 | 0.95 | 0.61 |
| pantothenate | 0.98 | 0.80 | 0.72 | 1.22 | 0.90 | 0.74 |
| biotin | 0.81 | 0.37 | 0.44 | 2.17 | 1.17 | 0.54 |
| hippurate | 0.42 | 0.24 | 0.24 | 1.72 | 1.00 | 0.58 |
| homostachydrine* | 0.72 | 0.38 | 0.46 | 1.91 | 1.24 | 0.65 |
| stachydrine | 0.77 | 0.44 | 0.57 | 1.75 | 1.28 | 0.73 |
| pyrraline | 0.98 | 0.46 | 0.40 | 2.14 | 0.87 | 0.41 |
| O-sulfo-L-tyrosine | 0.95 | 0.47 | 0.58 | 2.01 | 1.22 | 0.61 |

TABLE 5E

| Biochemical Name | Sp/SPF | | ABX/SPF | | GF/SPF | |
|---|---|---|---|---|---|---|
| | p-value | q-value | p-value | q-value | p-value | q-value |
| glutamine | 0.0903 | 0.0627 | 0.0010 | 0.0037 | 0.0003 | 0.0015 |
| alpha-ketoglutaramate* | 0.0006 | 0.0059 | 0.1065 | 0.0509 | 0.0061 | 0.0089 |
| pyroglutamine* | 0.9870 | 0.3040 | 0.0347 | 0.0252 | 0.0001 | 0.0006 |
| imidazole propionate | 0.0121 | 0.0243 | 0.0000 | 0.0001 | 0.0000 | 0.0001 |
| anserine | 0.5221 | 0.1970 | 0.0042 | 0.0068 | 0.0025 | 0.0052 |
| N2-acetyllysine | 0.3313 | 0.1431 | 0.0010 | 0.0038 | 0.0049 | 0.0076 |
| N6-methyllysine | 0.1851 | 0.0975 | 0.0010 | 0.0037 | 0.0001 | 0.0006 |
| N,N,N-trimethyl-5-aminovalerate | 0.0019 | 0.0111 | 0.0000 | 0.0000 | 0.0000 | 0.0000 |
| 3-indoxyl sulfate | 0.0326 | 0.0377 | 0.0000 | 0.0005 | 0.0000 | 0.0000 |
| 3-sulfo-L-alanine | 0.5338 | 0.2006 | 0.0000 | 0.0000 | 0.0000 | 0.0001 |
| phenylacetylglycine | 0.5433 | 0.2032 | 0.0079 | 0.0096 | 0.0079 | 0.0107 |

TABLE 5E-continued

| | Sp/SPF | | ABX/SPF | | GF/SPF | |
|---|---|---|---|---|---|---|
| Biochemical Name | p-value | q-value | p-value | q-value | p-value | q-value |
| arachidoylcarnitine (C20)* | 0.7317 | 0.2468 | 0.0046 | 0.0069 | 0.0445 | 0.0332 |
| trimethylamine N-oxide | 0.0018 | 0.0110 | 0.0000 | 0.0000 | 0.0000 | 0.0000 |
| sphingomyelin (d18:1/20:0, d16:1/22:0)* | 0.1795 | 0.0960 | 0.0045 | 0.0069 | 0.0048 | 0.0076 |
| trigonelline (N'-methylnicotinate) | 0.4532 | 0.1780 | 0.0025 | 0.0055 | 0.0005 | 0.0022 |
| pantothenate | 0.6854 | 0.2376 | 0.0044 | 0.0069 | 0.0002 | 0.0014 |
| biotin | 0.4864 | 0.1893 | 0.0004 | 0.0025 | 0.0017 | 0.0038 |
| hippurate | 0.0000 | 0.0008 | 0.0000 | 0.0000 | 0.0000 | 0.0000 |
| homostachydrine* | 0.0336 | 0.0377 | 0.0000 | 0.0001 | 0.0000 | 0.0004 |
| stachydrine | 0.0223 | 0.0321 | 0.0000 | 0.0000 | 0.0000 | 0.0003 |
| pyrraline | 0.8733 | 0.2799 | 0.0036 | 0.0064 | 0.0003 | 0.0016 |
| O-sulfo-L-tyrosine | 0.7093 | 0.2411 | 0.0004 | 0.0025 | 0.0027 | 0.0053 |

TABLE 5F

| | Sp/ABX | | GF/ABX | | GF/Sp | |
|---|---|---|---|---|---|---|
| Biochemical Name | p-value | q-value | p-value | q-value | p-value | q-value |
| glutamine | 0.0500 | 0.1713 | 0.5935 | 0.5688 | 0.0161 | 0.2066 |
| alpha-ketoglutaramate* | 0.0000 | 0.0007 | 0.1850 | 0.3746 | 0.0000 | 0.0001 |
| pyroglutamine* | 0.0359 | 0.1496 | 0.0114 | 0.1024 | 0.0001 | 0.0026 |
| imidazole propionate | 0.0000 | 0.0000 | 0.9507 | 0.6291 | 0.0000 | 0.0000 |
| anserine | 0.0181 | 0.0987 | 0.8231 | 0.6041 | 0.0111 | 0.1537 |
| N2-acetyllysine | 0.0100 | 0.0718 | 0.5070 | 0.5413 | 0.0423 | 0.3453 |
| N6-methyllysine | 0.0217 | 0.1120 | 0.2581 | 0.4219 | 0.0016 | 0.0466 |
| N,N,N-trimethyl-5-aminovalerate | 0.0000 | 0.0000 | 0.0059 | 0.0770 | 0.0000 | 0.0000 |
| 3-indoxyl sulfate | 0.0078 | 0.0610 | 0.0000 | 0.0068 | 0.0000 | 0.0000 |
| 3-sulfo-L-alanine | 0.0000 | 0.0004 | 0.5749 | 0.5622 | 0.0000 | 0.0009 |
| phenylacetylglycine | 0.0303 | 0.1333 | 1.0000 | 0.6499 | 0.0303 | 0.2992 |
| arachidoylcarnitine (C20)* | 0.0021 | 0.0325 | 0.3098 | 0.4633 | 0.0216 | 0.2516 |
| trimethylamine N-oxide | 0.0000 | 0.0008 | 0.0089 | 0.0919 | 0.0000 | 0.0000 |
| sphingomyelin (d18:1/20:0, d16:1/22:0)* | 0.0863 | 0.2155 | 0.9790 | 0.6396 | 0.0907 | 0.5044 |
| trigonelline (N'-methylnicotinate) | 0.0142 | 0.0854 | 0.5193 | 0.5467 | 0.0033 | 0.0776 |
| pantothenate | 0.0112 | 0.0738 | 0.2116 | 0.3803 | 0.0006 | 0.0192 |
| biotin | 0.0023 | 0.0325 | 0.5766 | 0.5622 | 0.0085 | 0.1331 |
| hippurate | 0.0036 | 0.0444 | 1.0000 | 0.6499 | 0.0036 | 0.0827 |
| homostachydrine* | 0.0005 | 0.0121 | 0.2899 | 0.4489 | 0.0059 | 0.1143 |
| stachydrine | 0.0001 | 0.0019 | 0.0450 | 0.2206 | 0.0082 | 0.1319 |
| pyrraline | 0.0052 | 0.0517 | 0.3017 | 0.4575 | 0.0004 | 0.0158 |
| O-sulfo-L-tyrosine | 0.0010 | 0.0234 | 0.4269 | 0.5036 | 0.0064 | 0.1195 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method of promoting healthy neural development in an unborn baby, the method comprising administering to a maternal subject gestating the unborn baby a composition comprising trimethylamine N-oxide (TMAO), 5-aminovalerate (5-AV), imidazole propionate (IP), and hippurate (HIP).

2. The method of claim 1, wherein said healthy neural development comprises healthy thalamocortical axon growth.

3. The method of claim 1, wherein said healthy neural development comprises healthy netrin-Gla+ thalamocortical axogenesis.

4. The method of claim 1, wherein the maternal subject and the unborn baby are mammals.

5. The method of claim 1, wherein the maternal subject and the unborn baby are humans.

6. The method of claim 5, wherein the method comprises administering the composition at least once during the first trimester of the gestating maternal subject's gestation period.

7. The method of claim 6, wherein the method comprises administering the composition at least once during a period that runs from the start of the third week after conception to the end of the eighth week after conception.

8. The method of claim 6, wherein the method comprises administering the composition at least once during a period that runs from the $17^{th}$ day post conception (dpc) to the $52^{nd}$ dpc.

9. The method of claim 5, wherein the method comprises administering the composition at least once during the second trimester of the gestating maternal subject's gestation period.

10. The method of claim 5, wherein the method comprises administering the composition at least once during the third trimester of the gestating maternal subject's gestation period.

11. The method of claim 1, wherein the unborn baby is an offspring of the maternal subject.

12. A method of conditioning a female subject for fostering healthy neural development in offspring, the method comprising administering to the female subject a composition comprising trimethylamine N-oxide (TMAO), 5-aminovalerate (5-AV), imidazole propionate (IP), and hippurate (HIP), wherein the composition is administered at least once during a period that runs from the first day of an expected-but-missed menstruation to a day that is two months after said first day.

13. The method of claim 12, wherein the composition is administered at least once during a period that runs from the second day of the expected-but-missed menstruation to a day that is 37 days after said second day.

14. The method of claim 12, wherein said healthy neural development comprises healthy tactile sensory development.

15. A method of reducing adverse effects of antibiotic treatment on an unborn baby in a pregnant subject, the method comprising administering to the pregnant subject, conjointly with the antibiotic treatment, a composition comprising trimethylamine N-oxide (TMAO), 5-aminovalerate (5-AV), imidazole propionate (IP), and hippurate (HIP).

* * * * *